US007470669B2

(12) United States Patent
Yen et al.

(10) Patent No.: US 7,470,669 B2
(45) Date of Patent: Dec. 30, 2008

(54) ISOLATED POLYPEPTIDE COMPRISING A LEPTIN FRAGMENT

(75) Inventors: Frances Yen, Vandoeuvre-les-Nancy (FR); Mary Ruth Erickson, San Diego, CA (US); Joachim Fruebis, Redmond, WA (US); Bernard Bihain, Cancale (FR)

(73) Assignee: Serono Genetics Institute, S.A., Evry (FR)

( * ) Notice: Subject to any disclaimer, the term of this patent is extended or adjusted under 35 U.S.C. 154(b) by 197 days.

(21) Appl. No.: 11/236,198

(22) Filed: Sep. 27, 2005

(65) Prior Publication Data

US 2006/0030530 A1    Feb. 9, 2006

Related U.S. Application Data

(63) Continuation of application No. 09/668,558, filed on Sep. 22, 2000, now abandoned.

(60) Provisional application No. 60/155,506, filed on Sep. 22, 1999.

(51) Int. Cl.
*A61K 38/00* (2006.01)
*C12Q 1/00* (2006.01)
(52) U.S. Cl. .............................. 514/12; 435/4; 435/7.1; 530/324
(58) Field of Classification Search ...................... None
See application file for complete search history.

(56) References Cited

U.S. PATENT DOCUMENTS

| | | | | |
|---|---|---|---|---|
| 5,827,734 A | * | 10/1998 | Weigle et al. | ............... 435/325 |
| 5,935,810 A | | 8/1999 | Friedman et al. | |
| 6,344,441 B1 | | 2/2002 | Bihain et al. | |
| 6,635,431 B1 | * | 10/2003 | Bihain et al. | ............... 435/7.21 |

FOREIGN PATENT DOCUMENTS

| | | |
|---|---|---|
| FR | 2767135 A1 | 2/1999 |
| WO | WO 96/30400 A1 | 10/1996 |
| WO | WO 96/39429 A2 | 12/1996 |
| WO | WO 97/06816 A1 | 2/1997 |
| WO | WO 97/46585 A2 | 12/1997 |
| WO | WO 98/12224 A1 | 3/1998 |

OTHER PUBLICATIONS

Verploegen et al., FEBS Letters 405, 237-240, 1997.*
Mickle et al., Med. Clin. North Am., 2000, vol. 84(3), p. 597-607.*
Grasso et al., Endocrinol. 138: 1413-1418, 1997.*
Rohner-Jearnrenaud et al., The New Eng. J. Med., 334: 324-325, 1996.*
Campfield et al., Science 280: 1383-1387, 1998.*
Baskin, D.G. et al. "Leptin Receptor mRNA Identifies a Subpopulation of Neuropeptide Y Neurons Activated By Fasting in Ray Hypothalamus" *Diabetes*, Apr. 1999, pp. 828-833, vol. 48.
Bays, H. "Current and Investigational Antiobesity Agents and Obesity Therapeutic Treatment Targets" *Obesity Research*, Aug. 2004, pp. 1197-1210, vol. 12, No. 8.
Bihain, B.E. et al. "The Lipolysis Stimulated Receptor: A Gene at Last" *Curr. Opinion in Lip.*, Jun. 1998, pp. 221-224, vol. 9, No. 3.
Campfield, L.A. et al. "Recombinant Mouse OB Protein: Evidence for a Peripheral Signal Linking Adiposity and Central Neural Networks" *Science*, 1995, pp. 546-549, vol. 269, No. 5223.
Cheung, C.C. et al. "Proopiomelanocortin Neurons are Directed Targets for Leptin in the Hypothalamus" *Endocrinology*, 1997, pp. 4489-4492, vol. 138, No. 10.
Considine, R.V. et al. "Serum Immunoreactive-Leptin Concentrations in Normal-Weight and Obese Humans" *New Eng. J. Med*, Feb. 1, 1996, pp. 292-295, vol. 334.
Ghebrehiwet, B. et al. "Isolation, cDNA Cloning and Overexpression of a 33-kD Cell Surface Glycoprotein that binds to the Globular 'Heads' of C1q" *J. Exp. Med.*, Jun. 1994, pp. 1809-1821, vol. 179, The Rockefeller University Press.
Hayward, C.P.M. et al. "The cDNA Sequence of Human Endothelial Cell Multimerin" *J. Biol. Chem.*, Aug. 4, 1995, pp. 18246-18251, vol. 270, No. 31.
Hu, E. et al. "AdipoQ is a Novel Adipose-Specific Gene Dysregulated in Obesity" *J. Biol. Chem.*, May 3, 1996, pp. 10697-10703, vol. 271, No. 18.
Kopelman, P.G. "Obesity as a Medical Problem" *Nature*, Apr. 6, 2000, pp. 635-643, vol. 404.
Maeda, K. et al. "cDNA Cloning and Expression of a Novel Adipose Specific Collagen-Like Factor, apM1 (Adipose Most Abundant Gene Transcript 1)" *Biochem. and Biophys. Research Comm.*, 1996, pp. 286-289, vol. 221.
Mann, C.J. et al. "Mechanism of Activation and Functional Significance of the Lipolysis-Stimulated Receptor. Evidence for a Role as Chylomicron Remnant Receptor" *Biochemistry*, 1995, pp. 10421-10431, vol. 34, No. 33.
Mann, C.J. et al. "ApoCIII Inhibits the Binding of Triglyceride-Rich Lipoproteins to the Lipolysis Stimulated Receptor" *Inserm Unit 391*, 1996, Rennes, France, abstract only.
Schwartz, M.W. et al. "Central Nervous System Control of Food Intake" *Nature*, Apr. 6, 2000, pp. 661-671, vol. 404.
Schwartz, M.W. et al. "Cerebrospinal Fluid Leptin Levels: Relationship to Plasma Levels and to Adiposity in Humans" *Nature Med.*, May 1, 1996, pp. 589-593, vol. 2.

(Continued)

*Primary Examiner*—Robert Landsman
*Assistant Examiner*—Gyan Chandra
(74) *Attorney, Agent, or Firm*—Saliwanchik, Lloyd & Saliwanchik

(57) ABSTRACT

The present invention is drawn to methods of screening for new compounds for the treatment of obesity and obesity-related diseases and disorders, as well as methods of treating obesity-related diseases and disorders, based on the discovery of the role of the leptin-LSR interaction in obesity.

17 Claims, 54 Drawing Sheets

OTHER PUBLICATIONS

Sellar, C.G. et al. "Characterization and Organization of the Genes Encoding the A-, B- and C-Chains of Human Complement Subcomponent C1q. The Complete Derived Amino Acid Sequence of Human C1q" *Biochemical Journal,* 1991, pp. 481-490, vol. 274.

Troussard, A.A. et al. "Inhibitory Effect on the Lipolysis-Stimulated Receptor of the 39-kDa Receptor-Associated Protein" *J. Biol. Chem.,* Jul. 21, 1995, pp. 17068-17071, vol. 270, No. 29.

Urade, Y. et al. "Precerebellin is a Cerebellum-Specific Protein with Similarity to the Globular Domain of Complement C1q B Chain" *Proc. Natl. Sci. USA,* Feb. 1991, pp. 1069-1073, vol. 88.

Weigle, D.S. et al. "Recombinant OB Protein Reduces Feeding and Body Weight in the OB/OB Mouse" *J. Clin. Invest,* Oct. 1995, pp. 2065-2070, vol. 96, No. 4.

Zhang, Y. et al. "Positional Cloning of the Mouse Obese Gene and Its Human Homologue" *Nature,* 1994, pp. 425-432, vol. 372.

* cited by examiner

Effect of test meal with and without leptin injection on postheparin lipolytic activity in $db^{Pas}/db^{Pas}$ mice

|  | Postheparin lipolytic activities in $db^{Pas}/db^{Pas}$ (μmol FFA/ml/h) |
|---|---|
| No high-fat test meal | 11.7 ± 2.4 |
| High-fat test meal | 19.5 ± 9.2 ns |
| High-fat test meal + 50 μg leptin | 12.2 ± 2.7 ns | ns = not significant).

Figure 12

Table

Characteristics of recombinant ZFPs directed toward LSR sequences.

| ID# | ZFP | Fold Activation | Kd (nM) | Target Sequence |
|---|---|---|---|---|
| 5182 | 2B-1A | 21.5 | 0.10 | AAGGTCGCCtatGGTGCAGAC (SEQ ID NO:102) |
| 5183 | 4A-3A | 8.7 | 0.05 | GTGGGAGCCcgGGGGCTGGA (SEQ ID NO:103) |
| 5185 | 6A-5A | 8.4 | 0.02 | TGGGGGTGGGCGGCGGGG (SEQ ID NO:104) |
| 5186 | 8A-7B | 6.5 | 0.02 | CCGGGAGTGcgCAGGGGGTA (SEQ ID NO:105) |
| 5205 | 1A-7B | 29.7 | 0.30 | GTGGCTGCACAAGGTCGCC (SEQ ID NO:106) |

Figure 25

```
LOCUS       pSBS5182-N    6319 bp    DNA    CIRCULAR SYN
DEFINITION  Ligation of 5182 into NVF (KpnI, BamHI)
ACCESSION   pSBS5182-N
REFERENCE   1  (bases 1 to 6319)
FEATURES             Location/Qualifiers
     CDS             956..1003
                     /gene="NLS"
                     /product="Nuclear Localization Signal"
     CDS             1004..1597
                     /gene="ZFP"
                     /product="LSR 2B-1A"
     CDS             1598..1840
                     /gene="VP16"
                     /product="VP16 activation domain"
     CDS             1841..1867
                     /gene="FLAG"
                     /product="FLAG epitope"
     CDS             3064..3947
                     /gene="Neo"
                     /product="neomycin resistance"
     CDS             complement (5321..6181)
                     /gene="Amp "
                     /product="Ampcillin resistance"
BASE COUNT     1451 a   1683 c   1651 g   1534 t
ORIGIN
        1 GACGGATCGG GAGATCTCCC GATCCCCTAT GGTCGACTCT CAGTACAATC TGCTCTGATG
       61 CCGCATAGTT AAGCCAGTAT CTGCTCCCTG CTTGTGTGTT GGAGGTCGCT GAGTAGTGCG
      121 CGAGCAAAAT TTAAGCTACA ACAAGGCAAG GCTTGACCGA CAATTGCATG AAGAATCTGC
      181 TTAGGGTTAG GCGTTTTGCG CTGCTTCGCG ATGTACGGGC CAGATATACG CGTTGACATT
      241 GATTATTGAC TAGTTATTAA TAGTAATCAA TTACGGGGTC ATTAGTTCAT AGCCCATATA
      301 TGGAGTTCCG CGTTACATAA CTTACGGTAA ATGGCCCGCC TGGCTGACCG CCCAACGACC
      361 CCCGCCCATT GACGTCAATA ATGACGTATG TTCCCATAGT AACGCCAATA GGGACTTTCC
      421 ATTGACGTCA ATGGGTGGAC TATTTACGGT AAACTGCCCA CTTGGCAGTA CATCAAGTGT
      481 ATCATATGCC AAGTACGCCC CCTATTGACG TCAATGACGG TAAATGGCCC GCCTGGCATT
      541 ATGCCCAGTA CATGACCTTA TGGGACTTTC CTACTTGGCA GTACATCTAC GTATTAGTCA
      601 TCGCTATTAC CATGGTGATG CGGTTTTGGC AGTACATCAA TGGGCGTGGA TAGCGGTTTG
      661 ACTCACGGGG ATTTCCAAGT CTCCACCCCA TTGACGTCAA TGGGAGTTTG TTTTGGCACC
      721 AAAATCAACG GGACTTTCCA AAATGTCGTA ACAACTCCGC CCCATTGACG CAAATGGGCG
      781 GTAGGCGTGT ACGGTGGGAG GTCTATATAA GCAGAGCTCT CTGGCTAACT AGAGAACCCA
      841 CTGCTTACTG GCTTATCGAA ATTAATACGA CTCACTATAG GGAGACCCAA GCTGGCTAGC
      901 GTTTAAACTT AAGCTGATCC ACTAGTCCAG TGTGGTGGAA TTCGCTAGCG CCACCATGGC
      961 CCCCAAGAAG AAGAGGAAGG TGGGAATCCA TGGGGTACCG GCAAGAAGA AGCAGCACAT
     1021 CTGCCACATC CAGGGCTGTG GTAAAGTTTA CGGCGACCGC TCCAACCTGA CCCGCCACCT
     1081 GCGCTGGCAC ACCGGCGAGA GGCCTTTCAT GTGTACATGG TCCTACTGTG GTAAACGCTT
     1141 CACCCAGTCC GGCGACCTGA CCCGCCACAA GCGTACCCAC ACCGGTGAGA AGAAATTTGC
     1201 TTGTCCGGAA TGTCCGAAGC GCTTCATGAT GTCCCACCAC CTGTCCCGCC ACATCAAGAC
     1261 CCACCAGAAC AAGAAGGGTG GATCTGGTGA TGGTGGCCGT CGCGGTGCCG GTTCTGGCAA
     1321 GAAGAAGCAG CACATCTGCC ACATCCAGGG CTGTGGTAAA GTTTACGGCG AGCGCGGCGA
     1381 CCTGACCCGC CACCTGCGCT GGCACACCGG CGAGAGGCCT TTCATGTGTA CATGGTCCTA
     1441 CTGTGGTAAA CGCTTCACCG ACCCGGGCGC CCTGGTGCGC CACAAGCGTA CCCACACCGG
```

Figure 26F

```
1501 TGAGAAGAAA TTTGCTTGTC CGGAATGTCC GAAGCGCTTC ATGCGCTCCG ACAACCTGAC
1561 CCAGCACATC AAGACCCACC AGAACAAGAA GGGTGGATCC GCCCCCCCGA CCGATGTCAG
1621 CCTGGGGGAC GAGCTCCACT TAGACGGCGA GGACGTGGCG ATGGCGCATG CCGACGCGCT
1681 AGACGATTTC GATCTGGACA TGTTGGGGGA CGGGGATTCC CCGGGGCCGG GATTTACCCC
1741 CCACGACTCC GCCCCCTACG GCGCTCTGGA TATGGCCGGC TTCGAGTTTG AGCAGATGTT
1801 TACCGATGCC CTTGGAATTG ACGAGTACGG TGGGGCAGC GACTACAAGG ACGACGATGA
1861 CAAGTAAGCT TCTCGAGTCT AGAGGGCCCG TTTAAACCCG CTGATCAGCC TCGACTGTGC
1921 CTTCTAGTTG CCAGCCATCT GTTGTTTGCC CCTCCCCCGT GCCTTCCTTG ACCCTGGAAG
1981 GTGCCACTCC CACTGTCCTT TCCTAATAAA ATGAGGAAAT TGCATCGCAT TGTCTGAGTA
2041 GGTGTCATTC TATTCTGGGG GGTGGGGTGG GGCAGGACAG CAAGGGGGAG GATTGGGAAG
2101 ACAATAGCAG GCATGCTGGG GATGCGGTGG GCTCTATGGC TTCTGAGGCG GAAAGAACCA
2161 GCTGGGGCTC TAGGGGGTAT CCCCACGCGC CCTGTAGCGG CGCATTAAGC GCGGCGGGTG
2221 TGGTGGTTAC GCGCAGCGTG ACCGCTACAC TTGCCAGCGC CCTAGCGCCC GCTCCTTTCG
2281 CTTTCTTCCC TTCCTTTCTC GCCACGTTCG CCGGCTTTCC CCGTCAAGCT CTAAATCGGG
2341 GCATCCCTTT AGGGTTCCGA TTTAGTGCTT TACGGCACCT CGACCCCAAA AAACTTGATT
2401 AGGGTGATGG TTCACGTAGT GGGCCATCGC CCTGATAGAC GGTTTTCGC CCTTTGACGT
2461 TGGAGTCCAC GTTCTTTAAT AGTGGACTCT TGTTCCAAAC TGGAACAACA CTCAACCCTA
2521 TCTCGGTCTA TTCTTTTGAT TTATAAGGGA TTTTGGGGAT TTCGGCCTAT TGGTTAAAAA
2581 ATGAGCTGAT TTAACAAAAA TTTAACGCGA ATTAATTCTG TGGAATGTGT GTCAGTTAGG
2641 GTGTGGAAAG TCCCCAGGCT CCCCAGGCAG GCAGAAGTAT GCAAAGCATG CATCTCAATT
2701 AGTCAGCAAC CAGGTGTGGA AAGTCCCCAG GCTCCCCAGC AGGCAGAAGT ATGCAAAGCA
2761 TGCATCTCAA TTAGTCAGCA ACCATAGTCC CGCCCCTAAC TCCGCCCATC CCGCCCCTAA
2821 CTCCGCCCAG TTCCGCCCAT TCTCCGCCCC ATGGCTGACT AATTTTTTTT ATTTATGCAG
2881 AGGCCGAGGC CGCCTCTGCC TCTGAGCTAT TCCAGAAGTA GTGAGGAGGC TTTTTTGGAG
2941 GCCTAGGCTT TTGCAAAAAG CTCCCGGGAG CTTGTATATC CATTTTCGGA TCTGATCAAG
3001 AGACAGGATG AGGATCGTTT CGCATGATTG AACAAGATGG ATTCACGCA GGTTCTCCGG
3061 CCGCTTGGGT GGAGAGGCTA TTCGGCTATG ACTGGGCACA ACAGACAATC GGCTGCTCTG
3121 ATGCCGCCGT GTTCCGGCTG TCAGCGCAGG GCGCCCGGT TCTTTTTGTC AAGACCGACC
3181 TGTCCGGTGC CCTGAATGAA CTGCAGGACG AGGCAGCGCG GCTATCGTGG CTGGCCACGA
3241 CGGGCGTTCC TTGCGCAGCT GTGCTCGACG TTGTCACTGA AGCGGGAAGG GACTGGCTGC
3301 TATTGGGCGA AGTGCCGGGG CAGGATCTCC TGTCATCTCA CCTTGCTCCT GCCGAGAAAG
3361 TATCCATCAT GGCTGATGCA ATGCGGCGGC TGCATACGCT TGATCCGGCT ACCTGCCCAT
3421 TCGACCACCA AGCGAAACAT CGCATCGAGC GAGCACGTAC TCGGATGGAA GCCGGTCTTG
3481 TCGATCAGGA TGATCTGGAC GAAGAGCATC AGGGGCTCGC GCCAGCCGAA CTGTTCGCCA
3541 GGCTCAAGGC GCGCATGCCC GACGGCGAGG ATCTCGTCGT GACCCATGGC GATGCCTGCT
3601 TGCCGAATAT CATGGTGGAA AATGGCCGCT TTTCTGGATT CATCGACTGT GGCCGGCTGG
3661 GTGTGGCGGA CCGCTATCAG GACATAGCGT TGGCTACCCG TGATATTGCT GAAGAGCTTG
3721 GCGGCGAATG GGCTGACCGC TTCCTCGTGC TTTACGGTAT CGCCGCTCCC GATTCGCAGC
3781 GCATCGCCTT CTATCGCCTT CTTGACGAGT TCTTCTGAGC GGGACTCTGG GGTTCGAAAT
3841 GACCGACCAA GCGACGCCCA ACCTGCCATC ACGAGATTTC GATTCCACCG CCGCCTTCTA
3901 TGAAAGGTTG GGCTTCGGAA TCGTTTTCCG GACGCCGGC TGGATGATCC TCCAGCGCGG
3961 GGATCTCATG CTGGAGTTCT TCGCCCACCC CAACTTGTTT ATTGCAGCTT ATAATGGTTA
4021 CAAATAAAGC AATAGCATCA CAAATTTCAC AAATAAAGCA TTTTTTTCAC TGCATTCTAG
4081 TTGTGGTTTG TCCAAACTCA TCAATGTATC TTATCATGTC TGTATACCGT CGACCTCTAG
4141 CTAGAGCTTG GCGTAATCAT GGTCATAGCT GTTTCCTGTG TGAAATTGTT ATCCGCTCAC
4201 AATTCCACAC AACATACGAG CCGGAAGCAT AAAGTGTAAA GCCTGGGGTG CCTAATGAGT
4261 GAGCTAACTC ACATTAATTG CGTTGCGCTC ACTGCCCGCT TTCCAGTCGG GAAACCTGTC
4321 GTGCCAGCTG CATTAATGAA TCGGCCAACG CGCGGGGAGA GGCGGTTTGC GTATTGGGCG
4381 CTCTTCCGCT TCCTCGCTCA CTGACTCGCT GCGCTCGGTC GTTCGGCTGC GGCGAGCGGT
```

Figure 26G

```
4441 ATCAGCTCAC TCAAAGGCGG TAATACGGTT ATCCACAGAA TCAGGGGATA ACGCAGGAAA
4501 GAACATGTGA GCAAAAGGCC AGCAAAAGGC CAGGAACCGT AAAAAGGCCG CGTTGCTGGC
4561 GTTTTTCCAT AGGCTCCGCC CCCTGACGA GCATCACAAA AATCGACGCT CAAGTCAGAG
4621 GTGGCGAAAC CCGACAGGAC TATAAAGATA CCAGGCGTTT CCCCCTGGAA GCTCCCTCGT
4681 GCGCTCTCCT GTTCCGACCC TGCCGCTTAC CGGATACCTG TCCGCCTTTC TCCCTTCGGG
4741 AAGCGTGGCG CTTTCTCAAT GCTCACGCTG TAGGTATCTC AGTTCGGTGT AGGTCGTTCG
4801 CTCCAAGCTG GGCTGTGTGC ACGAACCCCC CGTTCAGCCC GACCGCTGCG CCTTATCCGG
4861 TAACTATCGT CTTGAGTCCA ACCCGGTAAG ACACGACTTA TCGCCACTGG CAGCAGCCAC
4921 TGGTAACAGG ATTAGCAGAG CGAGGTATGT AGGCGGTGCT ACAGAGTTCT TGAAGTGGTG
4981 GCCTAACTAC GGCTACACTA GAAGGACAGT ATTTGGTATC TGCGCTCTGC TGAAGCCAGT
5041 TACCTTCGGA AAAAGAGTTG GTAGCTCTTG ATCCGGCAAA CAAACCACCG CTGGTAGCGG
5101 TGGTTTTTTT GTTTGCAAGC AGCAGATTAC GCGCAGAAAA AAAGGATCTC AAGAAGATCC
5161 TTTGATCTTT TCTACGGGGT CTGACGCTCA GTGGAACGAA AACTCACGTT AAGGGATTTT
5221 GGTCATGAGA TTATCAAAAA GGATCTTCAC CTAGATCCTT TTAAATTAAA AATGAAGTTT
5281 TAAATCAATC TAAAGTATAT ATGAGTAAAC TTGGTCTGAC AGTTACCAAT GCTTAATCAG
5341 TGAGGCACCT ATCTCAGCGA TCTGTCTATT TCGTTCATCC ATAGTTGCCT GACTCCCCGT
5401 CGTGTAGATA ACTACGATAC GGGAGGGCTT ACCATCGGC CCCAGTGCTG CAATGATACC
5461 GCGAGACCCA CGCTCACCGG CTCCAGATTT ATCAGCAATA AACCAGCCAG CCGGAAGGGC
5521 CGAGCGCAGA AGTGGTCCTG CAACTTTATC CGCCTCCATC CAGTCTATTA ATTGTTGCCG
5581 GGAAGCTAGA GTAAGTAGTT CGCCAGTTAA TAGTTTGCGC AACGTTGTTG CCATTGCTAC
5641 AGGCATCGTG GTGTCACGCT CGTCGTTTGG TATGGCTTCA TTCAGCTCCG GTTCCCAACG
5701 ATCAAGGCGA GTTACATGAT CCCCCATGTT GTGCAAAAAA GCGGTTAGCT CCTTCGGTCC
5761 TCCGATCGTT GTCAGAAGTA AGTTGGCCGC AGTGTTATCA CTCATGGTTA TGGCAGCACT
5821 GCATAATTCT CTTACTGTCA TGCCATCCGT AAGATGCTTT TCTGTGACTG GTGAGTACTC
5881 AACCAAGTCA TTCTGAGAAT AGTGTATGCG GCGACCGAGT TGCTCTTGCC CGGCGTCAAT
5941 ACGGGATAAT ACCGCGCCAC ATAGCAGAAC TTTAAAAGTG CTCATCATTG GAAAACGTTC
6001 TTCGGGGCGA AAACTCTCAA GGATCTTACC GCTGTTGAGA TCCAGTTCGA TGTAACCCAC
6061 TCGTGCACCC AACTGATCTT CAGCATCTTT TACTTTCACC AGCGTTTCTG GGTGAGCAAA
6121 AACAGGAAGG CAAAATGCCG CAAAAAAGGG AATAAGGGCG ACACGGAAAT GTTGAATACT
6181 CATACTCTTC CTTTTTCAAT ATTATTGAAG CATTTATCAG GGTTATTGTC TCATGAGCGG
6241 ATACATATTT GAATGTATTT AGAAAAATAA ACAAATAGGG GTTCCGCGCA CATTTCCCCG
6301 AAAAGTGCCA CCTGACGTC
//
```

Figure 26H

```
LOCUS       pSBS5183-N    6319 bp    DNA    CIRCULAR SYN
DEFINITION  Ligation of 5183 into NVF (KpnI, BamHI)
ACCESSION   pSBS5183-N
REFERENCE   1  (bases 1 to 6319)
FEATURES             Location/Qualifiers
     CDS             956..1003
                     /gene="NLS"
                     /product="Nuclear Localization Signal"
     CDS             1004..1597
                     /gene="ZFP"
                     /product="LSR 4A-3A"
     CDS             1598..1840
                     /gene="VP16"
                     /product="VP16 activation domain"
     CDS             1841..1867
                     /gene="FLAG"
                     /product="FLAG epitope"
     CDS             3064..3947
                     /gene="Neo"
                     /product="neomycin resistance"
     CDS             complement (5321..6181)
                     /gene="Amp "
                     /product="Ampcillin resistance"
BASE COUNT     1446 a    1683 c    1655 g    1535 t
ORIGIN
        1 GACGGATCGG GAGATCTCCC GATCCCCTAT GGTCGACTCT CAGTACAATC TGCTCTGATG
       61 CCGCATAGTT AAGCCAGTAT CTGCTCCCTG CTTGTGTGTT GGAGGTCGCT GAGTAGTGCG
      121 CGAGCAAAAT TTAAGCTACA ACAAGGCAAG GCTTGACCGA CAATTGCATG AAGAATCTGC
      181 TTAGGGTTAG GCGTTTTGCG CTGCTTCGCG ATGTACGGGC CAGATATACG CGTTGACATT
      241 GATTATTGAC TAGTTATTAA TAGTAATCAA TTACGGGGTC ATTAGTTCAT AGCCCATATA
      301 TGGAGTTCCG CGTTACATAA CTTACGGTAA ATGGCCCGCC TGGCTGACCG CCCAACGACC
      361 CCCGCCCATT GACGTCAATA ATGACGTATG TTCCCATAGT AACGCCAATA GGGACTTTCC
      421 ATTGACGTCA ATGGGTGGAC TATTTACGGT AAACTGCCCA CTTGGCAGTA CATCAAGTGT
      481 ATCATATGCC AAGTACGCCC CCTATTGACG TCAATGACGG TAAATGGCCC GCCTGGCATT
      541 ATGCCCAGTA CATGACCTTA TGGGACTTTC CTACTTGGCA GTACATCTAC GTATTAGTCA
      601 TCGCTATTAC CATGGTGATG CGGTTTTGGC AGTACATCAA TGGGCGTGGA TAGCGGTTTG
      661 ACTCACGGGG ATTTCCAAGT CTCCACCCCA TTGACGTCAA TGGGAGTTTG TTTTGGCACC
      721 AAAATCAACG GGACTTTCCA AAATGTCGTA ACAACTCCGC CCCATTGACG CAAATGGGCG
      781 GTAGGCGTGT ACGGTGGGAG GTCTATATAA GCAGAGCTCT CTGGCTAACT AGAGAACCCA
      841 CTGCTTACTG GCTTATCGAA ATTAATACGA CTCACTATAG GGAGACCCAA GCTGGCTAGC
      901 GTTTAAACTT AAGCTGATCC ACTAGTCCAG TGTGGTGGAA TTCGCTAGCG CCACCATGGC
      961 CCCCAAGAAG AAGAGGAAGG TGGGATCCA TGGGGTACCG GCAAGAAGA AGCAGCACAT
     1021 CTGCCACATC CAGGGCTGTG GTAAAGTTTA CGGCCAGTCC GGCCACCTGG CCCGCCACCT
     1081 GCGCTGGCAC ACCGGCGAGA GGCCTTTCAT GTGTACATGG TCCTACTGTG GTAAACGCTT
     1141 CACCACCTCC GGCGAGCTGG TGCGCCACAA GCGTACCCAC ACCGGTGAGA GAAATTTGC
     1201 TTGTCCGGAA TGTCCGAAGC GCTTCATGCG TTCCGACCAC CTGTCCCGTC ACATCAAGAC
     1261 CCACCAGAAC AAGAAGGGTG GATCTGGTGA TGGTGGCCGT CGCGGTGGCG GTTCTGGCAA
     1321 GAAGAAGCAG CACATCTGCC ACATCCAGGG CTGTGGTAAA GTTACGGCG AGCGCGGCGA
     1381 CCTGACCCGC CACCTGCGCT GGCACACCGG CGAGAGGCCT TCATGTGTA CATGGTCCTA
```

```
1441 CTGTGCTAAA CGCTTCACCC AGCGCGCCCA CCTGGAGCGC CACAAGCGTA CCCACACCGG
1501 TGAGAAGAAA TTTGCTTGTC CGGAATGTCC GAAGCGCTTC ATGCGCTCCG ACGCCCTGAC
1561 CCGCCACATC AAGACCCACC AGAACAAGAA GGGTGGATCC GCCCCCCCGA CCGATGTCAG
1621 CCTGGGGGAC GAGCTCCACT TAGACGGCGA GGACGTGGCG ATGGCGCATG CCGACGCGCT
1681 AGACGATTTC GATCTGGACA TGTTGGGGGA CGGGGATTCC CCGGGGCCGG GATTTACCCC
1741 CCACGACTCC GCCCCCTACG GCGCTCTGGA TATGGCCGGC TTCGAGTTTG AGCAGATGTT
1801 TACCGATGCC CTTGGAATTG ACGAGTACGG TGGGGGCAGC GACTACAAGG ACGACGATGA
1861 CAAGTAAGCT TCTCGAGTCT AGAGGGCCCG TTTAAACCCG CTGATCAGCC TCGACTGTGC
1921 CTTCTAGTTG CCAGCCATCT GTTGTTTGCC CCTCCCCCGT GCCTTCCTTG ACCCTGGAAG
1981 GTGCCACTCC CACTGTCCTT TCCTAATAAA ATGAGGAAAT TGCATCGCAT TGTCTGAGTA
2041 GGTGTCATTC TATTCTGGGG GGTGGGGTGG GGCAGGACAG CAAGGGGGAG GATTGGGAAG
2101 ACAATAGCAG GCATGCTGGG GATGCGGTGG GCTCTATGGC TTCTGAGGCG GAAAGAACCA
2161 GCTGGGGCTC TAGGGGGTAT CCCCACGCGC CCTGTAGCGG CGCATTAAGC GCGGCGGGTG
2221 TGGTGGTTAC GCGCAGCGTG ACCGCTACAC TTGCCAGCGC CCTAGCGCCC GCTCCTTTCG
2281 CTTTCTTCCC TTCCTTTCTC GCCACGTTCG CCGGCTTTCC CCGTCAAGCT CTAAATCGGG
2341 GCATCCCTTT AGGGTTCCGA TTTAGTGCTT TACGGCACCT CGACCCCAAA AAACTTGATT
2401 AGGGTGATGG TTCACGTAGT GGGCCATCGC CCTGATAGAC GGTTTTCGC CCTTTGACGT
2461 TGGAGTCCAC GTTCTTTAAT AGTGGACTCT TGTTCCAAAC TGGAACAACA CTCAACCCTA
2521 TCTCGGTCTA TTCTTTTGAT TTATAAGGGA TTTTGGGGAT TTCGGCCTAT TGGTTAAAAA
2581 ATGAGCTGAT TTAACAAAAA TTTAACGCGA ATTAATTCTG TGGAATGTGT GTCAGTTAGG
2641 GTGTGGAAAG TCCCCAGGCT CCCCAGGCAG GCAGAAGTAT GCAAAGCATG CATCTCAATT
2701 AGTCAGCAAC CAGGTGTGGA AAGTCCCCAG GCTCCCCAGC AGGCAGAAGT ATGCAAAGCA
2761 TGCATCTCAA TTAGTCAGCA ACCATAGTCC CGCCCCTAAC TCCGCCCATC CCGCCCCTAA
2821 CTCCGCCCAG TTCCGCCCAT TCTCCGCCCC ATGGCTGACT AATTTTTTTT ATTTATGCAG
2881 AGGCCGAGGC CGCCTCTGCC TCTGAGCTAT TCCAGAAGTA GTGAGGAGGC TTTTTTGGAG
2941 GCCTAGGCTT TTGCAAAAAG CTCCCGGGAG CTTGTATATC CATTTTCGGA TCTGATCAAG
3001 AGACAGGATG AGGATCGTTT CGCATGATTG AACAAGATGG ATTGCACGCA GGTTCTCCGG
3061 CCGCTTGGGT GGAGAGGCTA TTCGGCTATG ACTGGGCACA ACAGACAATC GGCTGCTCTG
3121 ATGCCGCCGT GTTCCGGCTG TCAGCGCAGG GGCGCCCGGT TCTTTTTGTC AAGACCGACC
3181 TGTCCGGTGC CCTGAATGAA CTGCAGGACG AGGCAGCGCG GCTATCGTGG CTGGCCACGA
3241 CGGGCGTTCC TTGCGCAGCT GTGCTCGACG TTGTCACTGA AGCGGGAAGG GACTGGCTGC
3301 TATTGGGCGA AGTGCCGGGG CAGGATCTCC TGTCATCTCA CCTTGCTCCT GCCGAGAAAG
3361 TATCCATCAT GGCTGATGCA ATGCGGCGGC TGCATACGCT TGATCCGGCT ACCTGCCCAT
3421 TCGACCACCA AGCGAAACAT CGCATCGAGC GAGCACGTAC TCGGATGGAA GCCGGTCTTG
3481 TCGATCAGGA TGATCTGGAC GAAGAGCATC AGGGGCTCGC GCCAGCCGAA CTGTTCGCCA
3541 GGCTCAAGGC GCGCATGCCC GACGGCGAGG ATCTCGTCGT GACCCATGGC GATGCCTGCT
3601 TGCCGAATAT CATGGTGGAA AATGGCCGCT TTTCTGGATT CATCGACTGT GGCCGGCTGG
3661 GTGTGGCGGA CCGCTATCAG GACATAGCGT TGGCTACCCG TGATATTGCT GAAGAGCTTG
3721 GCGGCGAATG GGCTGACCGC TTCCTCGTGC TTTACGGTAT CGCCGCTCCC GATTCGCAGC
3781 GCATCGCCTT CTATCGCCTT CTTGACGAGT TCTTCTGAGC GGGACTCTGG GGTTCGAAAT
3841 GACCGACCAA GCGACGCCCA ACCTGCCATC ACGAGATTTC GATTCCACCG CCGCCTTCTA
3901 TGAAAGGTTG GGCTTCGGAA TCGTTTTCCG GACGCCGGC TGGATGATCC TCCAGCGCGG
3961 GGATCTCATG CTGGAGTTCT TCGCCCACCC CAACTTGTTT ATTGCAGCTT ATAATGGTTA
4021 CAAATAAAGC AATAGCATCA CAAATTTCAC AAATAAAGCA TTTTTTTCAC TGCATTCTAG
4081 TTGTGGTTTG TCCAAACTCA TCAATGTATC TTATCATGTC TGTATACCGT CGACCTCTAG
4141 CTAGAGCTTG GCGTAATCAT GGTCATAGCT GTTTCCTGTG TGAAATTGTT ATCCGCTCAC
4201 AATTCCACAC AACATACGAG CCGGAAGCAT AAAGTGTAAA GCCTGGGGTG CCTAATGAGT
4261 GAGCTAACTC ACATTAATTG CGTTGCGCTC ACTGCCCGCT TTCCAGTCGG GAAACCTGTC
4321 GTGCCAGCTG CATTAATGAA TCGGCCAACG CGCGGGGAGA GGCGGTTTGC GTATTGGGCG
4381 CTCTTCCGCT TCCTCGCTCA CTGACTCGCT GCGCTCGGTC GTTCGGCTGC GGCGAGCGGT
4441 ATCAGCTCAC TCAAAGGCGG TAATACGGTT ATCCACAGAA TCAGGGGATA ACGCAGGAAA
```

Figure 26J

```
4501 GAACATGTGA GCAAAAGGCC AGCAAAAGGC CAGGAACCGT AAAAAGGCCG CGTTGCTGGC
4561 GTTTTTCCAT AGGCTCCGCC CCCCTGACGA GCATCACAAA AATCGACGCT CAAGTCAGAG
4621 GTGGCGAAAC CCGACAGGAC TATAAAGATA CCAGGCGTTT CCCCCTGGAA GCTCCCTCGT
4681 GCGCTCTCCT GTTCCGACCC TGCCGCTTAC CGGATACCTG TCCGCCTTTC TCCCTTCGGG
4741 AAGCGTGGCG CTTTCTCAAT GCTCACGCTG TAGGTATCTC AGTTCGGTGT AGGTCGTTCG
4801 CTCCAAGCTG GGCTGTGTGC ACGAACCCCC CGTTCAGCCC GACCGCTGCG CCTTATCCGG
4861 TAACTATCGT CTTGAGTCCA ACCCGGTAAG ACACGACTTA TCGCCACTGG CAGCAGCCAC
4921 TGGTAACAGG ATTAGCAGAG CGAGGTATGT AGGCGGTGCT ACAGAGTTCT TGAAGTGGTG
4981 GCCTAACTAC GGCTACACTA GAAGGACAGT ATTTGGTATC TGCGCTCTGC TGAAGCCAGT
5041 TACCTTCGGA AAAAGAGTTG GTAGCTCTTG ATCCGGCAAA CAAACCACCG CTGGTAGCGG
5101 TGGTTTTTTT GTTTGCAAGC AGCAGATTAC GCGCAGAAAA AAAGGATCTC AAGAAGATCC
5161 TTTGATCTTT TCTACGGGGT CTGACGCTCA GTGGAACGAA AACTCACGTT AAGGGATTTT
5221 GGTCATGAGA TTATCAAAAA GGATCTTCAC CTAGATCCTT TTAAATTAAA AATGAAGTTT
5281 TAAATCAATC TAAAGTATAT ATGAGTAAAC TTGGTCTGAC AGTTACCAAT GCTTAATCAG
5341 TGAGGCACCT ATCTCAGCGA TCTGTCTATT TCGTTCATCC ATAGTTGCCT GACTCCCCGT
5401 CGTGTAGATA ACTACGATAC GGGAGGGCTT ACCATCTGGC CCCAGTGCTG CAATGATACC
5461 GCGAGACCCA CGCTCACCGG CTCCAGATTT ATCAGCAATA AACCAGCCAG CCGGAAGGGC
5521 CGAGCGCAGA AGTGGTCCTG CAACTTTATC CGCCTCCATC CAGTCTATTA ATTGTTGCCG
5581 GGAAGCTAGA GTAAGTAGTT CGCCAGTTAA TAGTTTGCGC AACGTTGTTG CCATTGCTAC
5641 AGGCATCGTG GTGTCACGCT CGTCGTTTGG TATGGCTTCA TTCAGCTCCG GTTCCCAACG
5701 ATCAAGGCGA GTTACATGAT CCCCCATGTT GTGCAAAAAA GCGGTTAGCT CCTTCGGTCC
5761 TCCGATCGTT GTCAGAAGTA AGTTGGCCGC AGTGTTATCA CTCATGGTTA TGGCAGCACT
5821 GCATAATTCT CTTACTGTCA TGCCATCCGT AAGATGCTTT TCTGTGACTG GTGAGTACTC
5881 AACCAAGTCA TTCTGAGAAT AGTGTATGCG GCGACCGAGT TGCTCTTGCC CGGCGTCAAT
5941 ACGGGATAAT ACCGCGCCAC ATAGCAGAAC TTTAAAAGTG CTCATCATTG GAAAACGTTC
6001 TTCGGGGCGA AAACTCTCAA GGATCTTACC GCTGTTGAGA TCCAGTTCGA TGTAACCCAC
6061 TCGTGCACCC AACTGATCTT CAGCATCTTT TACTTTCACC AGCGTTTCTG GGTGAGCAAA
6121 AACAGGAAGG CAAAATGCCG CAAAAAAGGG AATAAGGGCG ACACGGAAAT GTTGAATACT
6181 CATACTCTTC CTTTTTCAAT ATTATTGAAG CATTTATCAG GGTTATTGTC TCATGAGCGG
6241 ATACATATTT GAATGTATTT AGAAAAATAA ACAAATAGGG GTTCCGCGCA CATTTCCCCG
6301 AAAAGTGCCA CCTGACGTC
```

Figure 26K

```
LOCUS       pSBS5185-N    6295 bp    DNA    CIRCULAR SYN
DEFINITION  Ligation of 5185 into NVF (KpnI, BamHI)
ACCESSION   pSBS5185-N
REFERENCE   1  (bases 1 to 6295)
FEATURES            Location/Qualifiers
     CDS            956..1003
                    /gene="NLS"
                    /product="Nuclear Localization Signal"
     CDS            1004..1573
                    /gene="ZFP"
                    /product="LSR 6A-5A"
     CDS            1574..1816
                    /gene="VP16"
                    /product="VP16 activation domain"
     CDS            1817..1843
                    /gene="FLAG"
                    /product="FLAG epitope"
     CDS            3040..3923
                    /gene="Neo"
                    /product="neomycin resistance"
     CDS            complement (5297..6157)
                    /gene="Amp "
                    /product="Ampcillin resistance"
BASE COUNT     1452 a    1682 c    1635 g    1526 t
ORIGIN
     1 GACGGATCGG GAGATCTCCC GATCCCCTAT GGTCGACTCT CAGTACAATC TGCTCTGATG
    61 CCGCATAGTT AAGCCAGTAT CTGCTCCCTG CTTGTGTGTT GGAGGTCGCT GAGTAGTGCG
   121 CGAGCAAAAT TTAAGCTACA ACAAGGCAAG GCTTGACCGA CAATTGCATG AAGAATCTGC
   181 TTAGGGTTAG GCGTTTTGCG CTGCTTCGCG ATGTACGGGC CAGATATACG CGTTGACATT
   241 GATTATTGAC TAGTTATTAA TAGTAATCAA TTACGGGGTC ATTAGTTCAT AGCCCATATA
   301 TGGAGTTCCG CGTTACATAA CTTACGGTAA ATGGCCCGCC TGGCTGACCG CCCAACGACC
   361 CCCGCCCATT GACGTCAATA ATGACGTATG TTCCCATAGT AACGCCAATA GGGACTTTCC
   421 ATTGACGTCA ATGGGTGGAC TATTTACGGT AAACTGCCCA CTTGGCAGTA CATCAAGTGT
   481 ATCATATGCC AAGTACGCCC CCTATTGACG TCAATGACGG TAAATGGCCC GCCTGGCATT
   541 ATGCCCAGTA CATGACCTTA TGGGACTTTC CTACTTGGCA GTACATCTAC GTATTAGTCA
   601 TCGCTATTAC CATGGTGATG CGGTTTTGGC AGTACATCAA TGGGCGTGGA TAGCGGTTTG
   661 ACTCACGGGG ATTTCCAAGT CTCCACCCCA TTGACGTCAA TGGGAGTTTG TTTTGGCACC
   721 AAAATCAACG GGACTTTCCA AAATGTCGTA ACAACTCCGC CCCATTGACG CAAATGGGCG
   781 GTAGGCGTGT ACGGTGGGAG GTCTATATAA GCAGAGCTCT CTGGCTAACT AGAGAACCCA
   841 CTGCTTACTG GCTTATCGAA ATTAATACGA CTCACTATAG GGAGACCCAA GCTGGCTAGC
   901 GTTTAAACTT AAGCTGATCC ACTAGTCCAG TGTGGTGGAA TTCGCTAGCG CCACCATGGC
   961 CCCCAAGAAG AAGAGGAAGG TGGGAATCCA TGGGGTACCG GGCAAGAAGA AGCAGCACAT
  1021 CTGCCACATC CAGGGCTGTG GTAAAGTTTA CGGCCGCTCC GACCACCTGG CCCGCCACCT
  1081 GCGCTGGCAC ACCGGCGAGA GGCCTTTCAT GTGTACATGG TCCTACTGTG GTAAACGCTT
  1141 CACCCGCTCC GACGAGCTGC AGCGCCACAA GCGTACCCAC ACCGGTGAGA AGAAATTTGC
  1201 TTGTCCGGAA TGTCCGAAGC GCTTCATGCG CTCCGACGAG CGCAAGCGCC ACATCAAGAC
  1261 CCACCAGAAC AAGAAGGGTG GATCTGGTGA TGGCAAGAAG AAGCAGCACA TCTGCCACAT
  1321 CCAGGGCTGT GGTAAAGTTT ACGGCCGCTC CGACCACCTG ACCACCCACC TGCGCTGGCA
  1381 CACCGGCGAG AGGCCTTTCA TGTGTACATG GTCCTACTGT GGTAAACGCT TCACCCGCTC
```

Figure 26L

```
1441 CGACCACCTG ACCCGCCACA AGCGTACCCA CACCGGTGAG AAGAAATTTG CTTGTCCGGA
1501 ATGTCCGAAG CGCTTCATGC GCTCCGACCA CCTGACCACC CACATCAAGA CCCACCAGAA
1561 CAAGAAGGGT GGATCCGCCC CCCCGACCGA TGTCAGCCTG GGGGACGAGC TCCACTTAGA
1621 CGGCGAGGAC GTGGCGATGG CGCATGCCGA CGCGCTAGAC GATTTCGATC TGGACATGTT
1681 GGGGGACGGG GATTCCCCGG GGCCGGGATT TACCCCCCAC GACTCCGCCC CCTACGGCGC
1741 TCTGGATATG GCCGGCTTCG AGTTTGAGCA GATGTTTACC GATGCCCTTG GAATTGACGA
1801 GTACGGTGGG GGCAGCGACT ACAAGGACGA CGATGACAAG TAAGCTTCTC GAGTCTAGAG
1861 GGCCCGTTTA AACCCGCTGA TCAGCCTCGA CTGTGCCTTC TAGTTGCCAG CCATCTGTTG
1921 TTTGCCCCTC CCCCGTGCCT TCCTTGACCC TGGAAGGTGC CACTCCCACT GTCCTTTCCT
1981 AATAAAATGA GGAAATTGCA TCGCATTGTC TGAGTAGGTG TCATTCTATT CTGGGGGGTG
2041 GGGTGGGGCA GGACAGCAAG GGGGAGGATT GGGAAGACAA TAGCAGGCAT GCTGGGGATG
2101 CGGTGGGCTC TATGGCTTCT GAGGCGGAAA GAACCAGCTG GGGCTCTAGG GGGTATCCCC
2161 ACGCGCCCTG TAGCGGCGCA TTAAGCGCGG CGGGTGTGGT GGTTACGCGC AGCGTGACCG
2221 CTACACTTGC CAGCGCCCTA GCGCCCGCTC CTTTCGCTTT CTTCCCTTCC TTTCTCGCCA
2281 CGTTCGCCGG CTTTCCCCGT CAAGCTCTAA ATCGGGGCAT CCCTTTAGGG TTCCGATTTA
2341 GTGCTTTACG GCACCTCGAC CCCAAAAAAC TTGATTAGGG TGATGGTTCA CGTAGTGGGC
2401 CATCGCCCTG ATAGACGGTT TTTCGCCCTT TGACGTTGGA GTCCACGTTC TTTAATAGTG
2461 GACTCTTGTT CCAAACTGGA ACAACACTCA ACCCTATCTC GGTCTATTCT TTTGATTTAT
2521 AAGGGATTTT GGGGATTTCG GCCTATTGGT TAAAAAATGA GCTGATTTAA CAAAAATTTA
2581 ACGCGAATTA ATTCTGTGGA ATGTGTGTCA GTTAGGGTGT GGAAAGTCCC CAGGCTCCCC
2641 AGGCAGGCAG AAGTATGCAA AGCATGCATC TCAATTAGTC AGCAACCAGG TGTGGAAAGT
2701 CCCCAGGCTC CCCAGCAGGC AGAAGTATGC AAAGCATGCA TCTCAATTAG TCAGCAACCA
2761 TAGTCCCGCC CCTAACTCCG CCCATCCCGC CCTAACTCC GCCCAGTTCC GCCCATTCTC
2821 CGCCCCATGG CTGACTAATT TTTTTATTT ATGCAGAGGC CGAGGCCGCC TCTGCCTCTG
2881 AGCTATTCCA GAAGTAGTGA GGAGGCTTTT TTGGAGGCCT AGGCTTTTGC AAAAAGCTCC
2941 CGGGAGCTTG TATATCCATT TTCGGATCTG ATCAAGAGAC AGGATGAGGA TCGTTTCGCA
3001 TGATTGAACA AGATGGATTG CACGCAGGTT CTCCGGCCGC TTGGGTGGAG AGGCTATTCG
3061 GCTATGACTG GGCACAACAG ACAATCGGCT GCTCTGATGC CGCCGTGTTC CGGCTGTCAG
3121 CGCAGGGGCG CCCGGTTCTT TTTGTCAAGA CCGACCTGTC CGGTGCCCTG AATGAACTGC
3181 AGGACGAGGC AGCGCGGCTA TCGTGGCTGG CCACGACGGG CGTTCCTTGC GCAGCTGTGC
3241 TCGACGTTGT CACTGAAGCG GGAAGGGACT GGCTGCTATT GGGCGAAGTG CCGGGGCAGG
3301 ATCTCCTGTC ATCTCACCTT GCTCCTGCCG AGAAAGTATC CATCATGGCT GATGCAATGC
3361 GGCGGCTGCA TACGCTTGAT CCGGCTACCT GCCCATTCGA CCACCAAGCG AAACATCGCA
3421 TCGAGCGAGC ACGTACTCGG ATGGAAGCCG GTCTTGTCGA TCAGGATGAT CTGGACGAAG
3481 AGCATCAGGG GCTCGCGCCA GCCGAACTGT TCGCCAGGCT CAAGGCGCGC ATGCCCGACG
3541 GCGAGGATCT CGTCGTGACC CATGGCGATG CCTGCTTGCC GAATATCATG GTGGAAAATG
3601 GCCGCTTTTC TGGATTCATC GACTGTGGCC GGCTGGGTGT GGCGGACCGC TATCAGGACA
3661 TAGCGTTGGC TACCCGTGAT ATTGCTGAAG AGCTTGGCGG CGAATGGGCT GACCGCTTCC
3721 TCGTGCTTTA CGGTATCGCC GCTCCCGATT CGCAGCGCAT CGCCTTCTAT CGCCTTCTTG
3781 ACGAGTTCTT CTGAGCGGGA CTCTGGGGTT CGAAATGACC GACCAAGCGA CGCCCAACCT
3841 GCCATCACGA GATTTCGATT CCACCGCCGC CTTCTATGAA AGGTTGGGCT TCGGAATCGT
3901 TTTCCGGGAC GCCGGCTGGA TGATCCTCCA GCGCGGGGAT CTCATGCTGG AGTTCTTCGC
3961 CCACCCCAAC TTGTTTATTG CAGCTTATAA TGGTTACAAA TAAAGCAATA GCATCACAAA
4021 TTTCACAAAT AAAGCATTTT TTTCACTGCA TTCTAGTTGT GGTTTGTCCA AACTCATCAA
4081 TGTATCTTAT CATGTCTGTA TACCGTCGAC CTCTAGCTAG AGCTTGGCGT AATCATGGTC
4141 ATAGCTGTTT CCTGTGTGAA ATTGTTATCC GCTCACAATT CCACACAACA TACGAGCCGG
4201 AAGCATAAAG TGTAAAGCCT GGGGTGCCTA ATGAGTGAGC TAACTCACAT TAATTGCGTT
4261 GCGCTCACTG CCCGCTTTCC AGTCGGGAAA CCTGTCGTGC CAGCTGCATT AATGAATCGG
4321 CCAACGCGCG GGGAGAGGCG GTTTGCGTAT TGGGCGCTCT TCCGCTTCCT CGCTCACTGA
4381 CTCGCTGCGC TCGGTCGTTC GGCTGCGGCG AGCGGTATCA GCTCACTCAA AGGCGGTAAT
4441 ACGGTTATCC ACAGAATCAG GGGATAACGC AGGAAAGAAC ATGTGAGCAA AAGGCCAGCA
```

Figure 26M

```
4501 AAAGGCCAGG AACCGTAAAA AGGCCGCGTT GCTGGCGTTT TTCCATAGGC TCCGCCCCCC
4561 TGACGAGCAT CACAAAAATC GACGCTCAAG TCAGAGGTGG CGAAACCCGA CAGGACTATA
4621 AAGATACCAG GCGTTTCCCC CTGGAAGCTC CCTCGTGCGC TCTCCTGTTC CGACCCTGCC
4681 GCTTACCGGA TACCTGTCCG CCTTTCTCCC TTCGGGAAGC GTGGCGCTTT CTCAATGCTC
4741 ACGCTGTAGG TATCTCAGTT CGGTGTAGGT CGTTCGCTCC AAGCTGGGCT GTGTGCACGA
4801 ACCCCCCGTT CAGCCCGACC GCTGCGCCTT ATCCGGTAAC TATCGTCTTG AGTCCAACCC
4861 GGTAAGACAC GACTTATCGC CACTGGCAGC AGCCACTGGT AACAGGATTA GCAGAGCGAG
4921 GTATGTAGGC GGTGCTACAG AGTTCTTGAA GTGGTGGCCT AACTACGGCT ACACTAGAAG
4981 GACAGTATTT GGTATCTGCG CTCTGCTGAA GCCAGTTACC TTCGGAAAAA GAGTTGGTAG
5041 CTCTTGATCC GGCAAACAAA CCACCGCTGG TAGCGGTGGT TTTTTTGTTT GCAAGCAGCA
5101 GATTACGCGC AGAAAAAAAG GATCTCAAGA AGATCCTTTG ATCTTTTCTA CGGGGTCTGA
5161 CGCTCAGTGG AACGAAAACT CACGTTAAGG GATTTTGGTC ATGAGATTAT CAAAAAGGAT
5221 CTTCACCTAG ATCCTTTTAA ATTAAAAATG AAGTTTTAAA TCAATCTAAA GTATATATGA
5281 GTAAACTTGG TCTGACAGTT ACCAATGCTT AATCAGTGAG GCACCTATCT CAGCGATCTG
5341 TCTATTTCGT TCATCCATAG TTGCCTGACT CCCCGTCGTG TAGATAACTA CGATACGGGA
5401 GGGCTTACCA TCTGGCCCCA GTGCTGCAAT GATACCGCGA GACCCACGCT CACCGGCTCC
5461 AGATTTATCA GCAATAAACC AGCCAGCCGG AAGGGCCGAG CGCAGAAGTG GTCCTGCAAC
5521 TTTATCCGCC TCCATCCAGT CTATTAATTG TTGCCGGGAA GCTAGAGTAA GTAGTTCGCC
5581 AGTTAATAGT TTGCGCAACG TTGTTGCCAT TGCTACAGGC ATCGTGGTGT CACGCTCGTC
5641 GTTTGGTATG GCTTCATTCA GCTCCGGTTC CCAACGATCA AGGCGAGTTA CATGATCCCC
5701 CATGTTGTGC AAAAAAGCGG TTAGCTCCTT CGGTCCTCCG ATCGTTGTCA GAAGTAAGTT
5761 GGCCGCAGTG TTATCACTCA TGGTTATGGC AGCACTGCAT AATTCTCTTA CTGTCATGCC
5821 ATCCGTAAGA TGCTTTTCTG TGACTGGTGA GTACTCAACC AAGTCATTCT GAGAATAGTG
5881 TATGCGGCGA CCGAGTTGCT CTTGCCCGGC GTCAATACGG GATAATACCG CGCCACATAG
5941 CAGAACTTTA AAAGTGCTCA TCATTGGAAA ACGTTCTTCG GGGCGAAAAC TCTCAAGGAT
6001 CTTACCGCTG TTGAGATCCA GTTCGATGTA ACCCACTCGT GCACCCAACT GATCTTCAGC
6061 ATCTTTTACT TTCACCAGCG TTTCTGGGTG AGCAAAAACA GGAAGGCAAA ATGCCGCAAA
6121 AAAGGGAATA AGGGCGACAC GGAAATGTTG AATACTCATA CTCTTCCTTT TTCAATATTA
6181 TTGAAGCATT TATCAGGGTT ATTGTCTCAT GAGCGGATAC ATATTTGAAT GTATTTAGAA
6241 AAATAAACAA ATAGGGGTTC CGCGCACATT TCCCCGAAAA GTGCCACCTG ACGTC
//
```

Figure 26N

```
LOCUS       pSBS5186-N    6319 bp    DNA    CIRCULAR SYN
DEFINITION  Ligation of 5186 into NVF (KpnI, BamHI)
ACCESSION   pSBS5186-N
REFERENCE   1  (bases 1 to 6319)
FEATURES             Location/Qualifiers
     CDS             956..1003
                     /gene="NLS"
                     /product="Nuclear Localization Signal"
     CDS             1004..1597
                     /gene="ZFP"
                     /product="LSR 8A-7B"
     CDS             1598..1840
                     /gene="VP16"
                     /product="VP16 activation domain"
     CDS             1841..1867
                     /gene="FLAG"
                     /product="FLAG epitope"
     CDS             3064..3947
                     /gene="Neo"
                     /product="neomycin resistance"
     CDS             complement (5321..6181)
                     /gene="Amp "
                     /product="Ampcillin resistance"
BASE COUNT      1449 a    1687 c    1651 g    1532 t
ORIGIN
        1 GACGGATCGG GAGATCTCCC GATCCCCTAT GGTCGACTCT CAGTACAATC TGCTCTGATG
       61 CCGCATAGTT AAGCCAGTAT CTGCTCCCTG CTTGTGTGTT GGAGGTCGCT GAGTAGTGCG
      121 CGAGCAAAAT TTAAGCTACA ACAAGGCAAG CTTGACCGA CAATTGCATG AAGAATCTGC
      181 TTAGGGTTAG GCGTTTTGCG CTGCTTCGCG ATGTACGGGC CAGATATACG CGTTGACATT
      241 GATTATTGAC TAGTTATTAA TAGTAATCAA TTACGGGGTC ATTAGTTCAT AGCCCATATA
      301 TGGAGTTCCG CGTTACATAA CTTACGGTAA ATGGCCCGCC TGGCTGACCG CCCAACGACC
      361 CCCGCCCATT GACGTCAATA ATGACGTATG TTCCCATAGT AACGCCAATA GGGACTTTCC
      421 ATTGACGTCA ATGGGTGGAC TATTTACGGT AAACTGCCCA CTTGGCAGTA CATCAAGTGT
      481 ATCATATGCC AAGTACGCCC CCTATTGACG TCAATGACGG TAAATGGCCC GCCTGGCATT
      541 ATGCCCAGTA CATGACCTTA TGGGACTTTC CTACTTGGCA GTACATCTAC GTATTAGTCA
      601 TCGCTATTAC CATGGTGATG CGGTTTTGGC AGTACATCAA TGGGCGTGGA TAGCGGTTTG
      661 ACTCACGGGG ATTTCCAAGT CTCCACCCCA TTGACGTCAA TGGGAGTTTG TTTTGGCACC
      721 AAAATCAACG GGACTTTCCA AAATGTCGTA ACAACTCCGC CCCATTGACG CAAATGGGCG
      781 GTAGGCGTGT ACGGTGGGAG GTCTATATAA GCAGAGCTCT CTGGCTAACT AGAGAACCCA
      841 CTGCTTACTG GCTTATCGAA ATTAATACGA CTCACTATAG GGAGACCCAA GCTGGCTAGC
      901 GTTTAAACTT AAGCTGATCC ACTAGTCCAG TGTGGTGGAA TTCGCTAGCC CACCATGGC
      961 CCCAAGAAG AAGAGGAAGG TGGAATCCA TGGGGTACCG GCAAGAAGA AGCAGCACAT
     1021 CTGCCACATC CAGGGCTGTG GTAAAGTTTA CGGCCAGTCC GGCGCCCTGA CCCGCCACCT
     1081 GCGCTGGCAC ACCGGCGAGA GGCCTTTCAT GTGTACATGG TCCTACTGTG GTAAACGCTT
     1141 CACCCGCTCC GACCACCTGA CCCGCCACAA GCGTACCCAC ACCGGTGAGA AGAAATTTGC
     1201 TTGTCCGGAA TGTCCGAAGC GCTTCATGCG CTCCGACAAC CTGCGCGAGC ACAACAAGAC
     1261 CCACCAGAAC AAGAAGGGTG GATCTGGTGA TGGTGGCCGT CGCGGTGGCG GTTCTGGCAA
     1321 GAAGAAGCAG CACATCTGCC ACATCCAGGG CTGTGGTAAA GTTTACGGCC GCTCCTCCGC
```

Figure 26O

```
1381 CCTGACCCGC CACCTGCGCT GGCACACCGG CGAGAGGCCT TTCATGTGTA CATGGTCCTA
1441 CTGTGGTAAA CGCTTCACCC AGCGCGCCCA CCTGGAGCGC CACAAGCGTA CCCACACCGG
1501 TGAGAAGAAA TTTGCTTGTC CGGAATGTCC GAAGCGCTTC ATGCGCTCCG ACACCCTGCG
1561 CGAGCACATC AAGACCCACC AGAACAAGAA GGGTGGATCC GCCCCCCCGA CCGATGTCAG
1621 CCTGGGGGAC GAGCTCCACT TAGACGGCGA GGACGTGGCG ATGGCGCATG CCGACGCGCT
1681 AGACGATTTC GATCTGGACA TGTTGGGGGA CGGGGATTCC CCGGGGCCGG GATTTACCCC
1741 CCACGACTCC GCCCCCTACG GCGCTCTGGA TATGGCCGGC TTCGAGTTTG AGCAGATGTT
1801 TACCGATGCC CTTGGAATTG ACGAGTACGG TGGGGGCAGC GACTACAAGG ACGACGATGA
1861 CAAGTAAGCT TCTCGAGTCT AGAGGGCCCG TTTAAACCCG CTGATCAGCC TCGACTGTGC
1921 CTTCTAGTTG CCAGCCATCT GTTGTTTGCC CCTCCCCGT GCCTTCCTTG ACCCTGGAAG
1981 GTGCCACTCC CACTGTCCTT TCCTAATAAA ATGAGGAAAT TGCATCGCAT TGTCTGAGTA
2041 GGTGTCATTC TATTCTGGGG GGTGGGGTGG GGCAGGACAG CAAGGGGGAG GATTGGGAAG
2101 ACAATAGCAG GCATGCTGGG GATGCGGTGG GCTCTATGGC TTCTGAGGCG GAAAGAACCA
2161 GCTGGGCTC TAGGGGGTAT CCCCACGCGC CCTGTAGCGG CGCATTAAGC GCGGCGGGTG
2221 TGGTGGTTAC GCGCAGCGTG ACCGCTACAC TTGCCAGCGC CCTAGCGCCC GCTCCTTTCG
2281 CTTTCTTCCC TTCCTTTCTC GCCACGTTCG CCGGCTTTCC CCGTCAAGCT CTAAATCGGG
2341 GCATCCCTTT AGGGTTCCGA TTTAGTGCTT TACGGCACCT CGACCCCAAA AAACTTGATT
2401 AGGGTGATGG TTCACGTAGT GGGCCATCGC CCTGATAGAC GGTTTTCGC CCTTTGACGT
2461 TGGAGTCCAC GTTCTTTAAT AGTGGACTCT TGTTCCAAAC TGGAACAACA CTCAACCCTA
2521 TCTCGGTCTA TTCTTTTGAT TTATAAGGGA TTTTGGGGAT TTCGGCCTAT TGGTTAAAAA
2581 ATGAGCTGAT TTAACAAAAA TTTAACGCGA ATTAATTCTG TGGAATGTGT GTCAGTTAGG
2641 GTGTGGAAAG TCCCCAGGCT CCCCAGGCAG GCAGAAGTAT GCAAAGCATG CATCTCAATT
2701 AGTCAGCAAC CAGGTGTGGA AAGTCCCCAG GCTCCCCAGC AGGCAGAAGT ATGCAAAGCA
2761 TGCATCTCAA TTAGTCAGCA ACCATAGTCC CGCCCCTAAC TCCGCCCATC CGCCCCTAA
2821 CTCCGCCCAG TTCCGCCCAT TCTCCGCCCC ATGGCTGACT AATTTTTTTT ATTTATGCAG
2881 AGGCCGAGGC CGCCTCTGCC TCTGAGCTAT TCCAGAAGTA GTGAGGAGGC TTTTTTGGAG
2941 GCCTAGGCTT TTGCAAAAAG CTCCCGGGAG CTTGTATATC CATTTTCGGA TCTGATCAAG
3001 AGACAGGATG AGGATCGTTT CGCATGATTG AACAAGATGG ATTGCACGCA GGTTCTCCGG
3061 CCGCTTGGGT GGAGAGGCTA TTCGGCTATG ACTGGGCACA ACAGACAATC GGCTGCTCTG
3121 ATGCCGCCGT GTTCCGGCTG TCAGCGCAGG GGCGCCCGGT TCTTTTTGTC AAGACCGACC
3181 TGTCCGGTGC CCTGAATGAA CTGCAGGACG AGGCAGCGCG GCTATCGTGG CTGGCCACGA
3241 CGGGCGTTCC TTGCGCAGCT GTGCTCGACG TTGTCACTGA AGCGGGAAGG GACTGGCTGC
3301 TATTGGGCGA AGTGCCGGGG CAGGATCTCC TGTCATCTCA CCTTGCTCCT GCCGAGAAAG
3361 TATCCATCAT GGCTGATGCA ATGCGGCGGC TGCATACGCT TGATCCGGCT ACCTGCCCAT
3421 TCGACCACCA AGCGAAACAT CGCATCGAGC GAGCACGTAC TCGGATGGAA GCCGGTCTTG
3481 TCGATCAGGA TGATCTGGAC GAAGAGCATC AGGGGCTCGC GCCAGCCGAA CTGTTCGCCA
3541 GGCTCAAGGC GCGCATGCCC GACGGCGAGG ATCTCGTCGT GACCCATGGC GATGCCTGCT
3601 TGCCGAATAT CATGGTGGAA AATGGCCGCT TTTCTGGATT CATCGACTGT GGCCGGCTGG
3661 GTGTGGCGGA CCGCTATCAG GACATAGCGT TGGCTACCCG TGATATTGCT GAAGAGCTTG
3721 GCGGCGAATG GGCTGACCGC TTCCTCGTGC TTTACGGTAT CGCCGCTCCC GATTCGCAGC
3781 GCATCGCCTT CTATCGCCTT CTTGACGAGT TCTTCTGAGC GGGACTCTGG GGTTCGAAAT
3841 GACCGACCAA GCGACGCCCA ACCTGCCATC ACGAGATTTC GATTCCACCG CCGCCTTCTA
3901 TGAAAGGTTG GGCTTCGGAA TCGTTTTCCG GGACGCCGGC TGGATGATCC TCCAGCGCGG
3961 GGATCTCATG CTGGAGTTCT TCGCCCACCC CAACTTGTTT ATTGCAGCTT ATAATGGTTA
4021 CAAATAAAGC AATAGCATCA CAAATTTCAC AAATAAAGCA TTTTTTTCAC TGCATTCTAG
4081 TTGTGGTTTG TCCAAACTCA TCAATGTATC TTATCATGTC TGTATACCGT CGACCTCTAG
4141 CTAGAGCTTG GCGTAATCAT GGTCATAGCT GTTTCCTGTG TGAAATTGTT ATCCGCTCAC
4201 AATTCCACAC AACATACGAG CCGGAAGCAT AAAGTGTAAA GCCTGGGGTG CCTAATGAGT
4261 GAGCTAACTC ACATTAATTG CGTTGCGCTC ACTGCCCGCT TTCCAGTCGG GAAACCTGTC
4321 GTGCCAGCTG CATTAATGAA TCGGCCAACG CGCGGGGAGA GGCGGTTTGC GTATTGGGCG
```

Figure 26P

```
4381 CTCTTCCGCT TCCTCGCTCA CTGACTCGCT GCGCTCGGTC GTTCGGCTGC GGCGAGCGGT
4441 ATCAGCTCAC TCAAAGGCGG TAATACGGTT ATCCACAGAA TCAGGGGATA ACGCAGGAAA
4501 GAACATGTGA GCAAAAGGCC AGCAAAAGGC CAGGAACCGT AAAAAGGCCG CGTTGCTGGC
4561 GTTTTTCCAT AGGCTCCGCC CCCTGACGA GCATCACAAA AATCGACGCT CAAGTCAGAG
4621 GTGGCGAAAC CCGACAGGAC TATAAAGATA CCAGGCGTTT CCCCCTGGAA GCTCCCTCGT
4681 GCGCTCTCCT GTTCCGACCC TGCCGCTTAC CGGATACCTG TCCGCCTTTC TCCCTTCGGG
4741 AAGCGTGGCG CTTTCTCAAT GCTCACGCTG TAGGTATCTC AGTTCGGTGT AGGTCGTTCG
4801 CTCCAAGCTG GGCTGTGTGC ACGAACCCCC CGTTCAGCCC GACCGCTGCG CCTTATCCGG
4861 TAACTATCGT CTTGAGTCCA ACCCGGTAAG ACACGACTTA TCGCCACTGG CAGCAGCCAC
4921 TGGTAACAGG ATTAGCAGAG CGAGGTATGT AGGCGGTGCT ACAGAGTTCT TGAAGTGGTG
4981 GCCTAACTAC GGCTACACTA GAAGGACAGT ATTTGGTATC TGCGCTCTGC TGAAGCCAGT
5041 TACCTTCGGA AAAAGAGTTG GTAGCTCTTG ATCCGGCAAA CAAACCACCG CTGGTAGCGG
5101 TGGTTTTTTT GTTTGCAAGC AGCAGATTAC GCGCAGAAAA AAAGGATCTC AAGAAGATCC
5161 TTTGATCTTT TCTACGGGGT CTGACGCTCA GTGGAACGAA AACTCACGTT AAGGGATTTT
5221 GGTCATGAGA TTATCAAAAA GGATCTTCAC CTAGATCCTT TTAAATTAAA AATGAAGTTT
5281 TAAATCAATC TAAAGTATAT ATGAGTAAAC TTGGTCTGAC AGTTACCAAT GCTTAATCAG
5341 TGAGGCACCT ATCTCAGCGA TCTGTCTATT TCGTTCATCC ATAGTTGCCT GACTCCCCGT
5401 CGTGTAGATA ACTACGATAC GGGAGGGCTT ACCATCTGGC CCCAGTGCTG CAATGATACC
5461 GCGAGACCCA CGCTCACCGG CTCCAGATTT ATCAGCAATA AACCAGCCAG CCGGAAGGGC
5521 CGAGCGCAGA AGTGGTCCTG CAACTTTATC CGCCTCCATC CAGTCTATTA ATTGTTGCCG
5581 GGAAGCTAGA GTAAGTAGTT CGCCAGTTAA TAGTTTGCGC AACGTTGTTG CCATTGCTAC
5641 AGGCATCGTG GTGTCACGCT CGTCGTTTGG TATGGCTTCA TTCAGCTCCG GTTCCCAACG
5701 ATCAAGGCGA GTTACATGAT CCCCCATGTT GTGCAAAAAA GCGGTTAGCT CCTTCGGTCC
5761 TCCGATCGTT GTCAGAAGTA AGTTGGCCGC AGTGTTATCA CTCATGGTTA TGGCAGCACT
5821 GCATAATTCT CTTACTGTCA TGCCATCCGT AAGATGCTTT TCTGTGACTG GTGAGTACTC
5881 AACCAAGTCA TTCTGAGAAT AGTGTATGCG GCGACCGAGT TGCTCTTGCC CGGCGTCAAT
5941 ACGGGATAAT ACCGCGCCAC ATAGCAGAAC TTTAAAAGTG CTCATCATTG GAAAACGTTC
6001 TTCGGGGCGA AAACTCTCAA GGATCTTACC GCTGTTGAGA TCCAGTTCGA TGTAACCCAC
6061 TCGTGCACCC AACTGATCTT CAGCATCTTT TACTTTCACC AGCGTTTCTG GGTGAGCAAA
6121 AACAGGAAGG CAAAATGCCG CAAAAAAGGG AATAAGGGCG ACACGGAAAT GTTGAATACT
6181 CATACTCTTC CTTTTTCAAT ATTATTGAAG CATTTATCAG GGTTATTGTC TCATGAGCGG
6241 ATACATATTT GAATGTATTT AGAAAAATAA ACAAATAGGG GTTCCGCGCA CATTTCCCCG
6301 AAAAGTGCCA CCTGACGTC
//
```

Figure 26Q

```
LOCUS       pSBS5205-N    6295 bp    DNA    CIRCULAR SYN
DEFINITION  Ligation of 5205 into NVF (KpnI, BamHI)
ACCESSION   pSBS5205-N
REFERENCE   1  (bases 1 to 6295)
FEATURES             Location/Qualifiers
    CDS              956..1003
                     /gene="NLS"
                     /product="Nuclear Localization Signal"
    CDS              1004..1573
                     /gene="ZFP"
                     /product="LSR 1A-7B"
    CDS              1574..1816
                     /gene="VP16"
                     /product="VP16 activation domain"
    CDS              1817..1843
                     /gene="FLAG"
                     /product="FLAG epitope"
    CDS              3040..3923
                     /gene="Neo"
                     /product="neomycin resistance"
    CDS              complement (5297..6157)
                     /gene="Amp "
                     /product="Ampcillin resistance"
BASE COUNT     1448 a   1677 c   1643 g   1527 t
ORIGIN
        1 GACGGATCGG GAGATCTCCC GATCCCCTAT GGTCGACTCT CAGTACAATC TGCTCTGATG
       61 CCGCATAGTT AAGCCAGTAT CTGCTCCCTG CTTGTGTGTT GGAGGTCGCT GAGTAGTGCG
      121 CGAGCAAAAT TTAAGCTACA ACAAGGCAAG GCTTGACCGA CAATTGCATG AAGAATCTGC
      181 TTAGGGTTAG GCGTTTTGCG CTGCTTCGCG ATGTACGGGC CAGATATACG CGTTGACATT
      241 GATTATTGAC TAGTTATTAA TAGTAATCAA TTACGGGGTC ATTAGTTCAT AGCCCATATA
      301 TGGAGTTCCG CGTTACATAA CTTACGGTAA ATGGCCCGCC TGGCTGACCG CCCAACGACC
      361 CCCGCCCATT GACGTCAATA ATGACGTATG TTCCCATAGT AACGCCAATA GGGACTTTCC
      421 ATTGACGTCA ATGGGTGGAC TATTTACGGT AAACTGCCCA CTTGGCAGTA CATCAAGTGT
      481 ATCATATGCC AAGTACGCCC CCTATTGACG TCAATGACGG TAAATGGCCC GCCTGGCATT
      541 ATGCCCAGTA CATGACCTTA TGGGACTTTC CTACTTGGCA GTACATCTAC GTATTAGTCA
      601 TCGCTATTAC CATGGTGATG CGGTTTTGGC AGTACATCAA TGGGCGTGGA TAGCGGTTTG
      661 ACTCACGGGG ATTTCCAAGT CTCCACCCCA TTGACGTCAA TGGGAGTTTG TTTTGGCACC
      721 AAAATCAACG GGACTTTCCA AAATGTCGTA CAACTCCGCC CCATTGACG CAAATGGGCG
      781 GTAGGCGTGT ACGGTGGGAG GTCTATATAA GCAGAGCTCT CTGGCTAACT AGAGAACCCA
      841 CTGCTTACTG GCTTATCGAA ATTAATACGA CTCACTATAG GGAGACCCAA GCTGGCTAGC
      901 GTTTAAACTT AAGCTGATCC ACTAGTCCAG TGTGGTGGAA TTCGCTAGCG CCACCATGGC
      961 CCCCAAGAAG AAGAGGAAGG TGGGAATCCA TGGGGTACCG GGCAAGAAGA AGCAGCACAT
     1021 CTGCCACATC CAGGGCTGTG GTAAAGTTTA CGGCGAGCGC GGCGACCTGA CCCGCCACCT
     1081 GCGCTGGCAC ACCGGCGAGA GGCCTTTCAT GTGTACATGG TCCTACTGTG GTAAACGCTT
     1141 CACCGACCCG GGCGCCCTGG TGCGCCACAA GCGTACCCAC ACCGGTGAGA GAAATTTGC
     1201 TTGTCCGGAA TGTCCGAAGC GCTTCATGCG CTCCGACAAC CTGACCCAGC ACATCAAGAC
     1261 CCACCAGAAC AAGAAGGGTG GATCTGGTGA TGGCAAGAAG AAGCAGCACA TCTGCCACAT
     1321 CCAGGGCTGT GGTAAAGTTT ACGGCCAGTC CGGCACCCTG ACCCGCCACC TGCGCTGGCA
```

Figure 26R

```
1381 CACCGGCGAG AGGCCTTTCA TGTGTACATG GTCCTACTGT GGTAAACGCT TCACCCAGTC
1441 CTCCGACCTG CAGCGCCACA AGCGTACCCA CACCGGTGAG AAGAAATTTG CTTGTCCGGA
1501 ATGTCCGAAG CGCTTCATGC GCTCCGACGC CCTGGCCCGC CACATCAAGA CCCACCAGAA
1561 CAAGAAGGGT GGATCCGCCC CCCCGACCGA TGTCAGCCTG GGGGACGAGC TCCACTTAGA
1621 CGGCGAGGAC GTGGCGATGG CGCATGCCGA CGCGCTAGAC GATTTCGATC TGGACATGTT
1681 GGGGGACGGG GATTCCCCGG GGCCGGGATT TACCCCCCAC GACTCCGCCC CCTACGGCGC
1741 TCTGGATATG GCCGGCTTCG AGTTTGAGCA GATGTTTACC GATGCCCTTG GAATTGACGA
1801 GTACGGTGGG GGCAGCGACT ACAAGGACGA CGATGACAAG TAAGCTTCTC GAGTCTAGAG
1861 GGCCCGTTTA AACCCGCTGA TCAGCCTCGA CTGTGCCTTC TAGTTGCCAG CCATCTGTTG
1921 TTTGCCCCTC CCCCGTGCCT TCCTTGACCC TGGAAGGTGC CACTCCCACT GTCCTTTCCT
1981 AATAAAATGA GGAAATTGCA TCGCATTGTC TGAGTAGGTG TCATTCTATT CTGGGGGGTG
2041 GGGTGGGGCA GGACAGCAAG GGGGAGGATT GGAAGACAA TAGCAGGCAT GCTGGGGATG
2101 CGGTGGGCTC TATGGCTTCT GAGGCGGAAA GAACCAGCTG GGGCTCTAGG GGGTATCCCC
2161 ACGCGCCCTG TAGCGGCGCA TTAAGCGCGG CGGGTGTGGT GGTTACGCGC AGCGTGACCG
2221 CTACACTTGC CAGCGCCCTA GCGCCCGCTC CTTTCGCTTT CTTCCCTTCC TTTCTCGCCA
2281 CGTTCGCCGG CTTTCCCCGT CAAGCTCTAA ATCGGGGCAT CCCTTTAGGG TTCCGATTTA
2341 GTGCTTTACG GCACCTCGAC CCCAAAAAAC TTGATTAGGG TGATGGTTCA CGTAGTGGGC
2401 CATCGCCCTG ATAGACGGTT TTTCGCCCTT TGACGTTGGA GTCCACGTTC TTTAATAGTG
2461 GACTCTTGTT CCAAACTGGA ACAACACTCA ACCCTATCTC GGTCTATTCT TTTGATTTAT
2521 AAGGGATTTT GGGGATTTCG GCCTATTGGT TAAAAAATGA GCTGATTTAA CAAAAATTTA
2581 ACGCGAATTA ATTCTGTGGA ATGTGTGTCA GTTAGGGTGT GGAAAGTCCC CAGGCTCCCC
2641 AGGCAGGCAG AAGTATGCAA AGCATGCATC TCAATTAGTC AGCAACCAGG TGTGGAAAGT
2701 CCCCAGGCTC CCCAGCAGGC AGAAGTATGC AAAGCATGCA TCTCAATTAG TCAGCAACCA
2761 TAGTCCCGCC CCTAACTCCG CCCATCCCGC CCTAACTCC GCCCAGTTCC GCCCATTCTC
2821 CGCCCCATGG CTGACTAATT TTTTTATTT ATGCAGAGGC CGAGGCCGCC TCTGCCTCTG
2881 AGCTATTCCA GAAGTAGTGA GGAGGCTTTT TTGGAGGCCT AGGCTTTTGC AAAAAGCTCC
2941 CGGGAGCTTG TATATCCATT TTCGGATCTG ATCAAGAGAC AGGATGAGGA TCGTTTCGCA
3001 TGATTGAACA AGATGGATTG CACGCAGGTT CTCCGGCCGC TTGGGTGGAG AGGCTATTCG
3061 GCTATGACTG GGCACAACAG ACAATCGGCT GCTCTGATGC CGCCGTGTTC CGGCTGTCAG
3121 CGCAGGGGCG CCCGGTTCTT TTTGTCAAGA CCGACCTGTC CGGTGCCCTG AATGAACTGC
3181 AGGACGAGGC AGCGCGGCTA TCGTGGCTGG CCACGACGGG CGTTCCTTGC GCAGCTGTGC
3241 TCGACGTTGT CACTGAAGCG GGAAGGGACT GGCTGCTATT GGGCGAAGTG CCGGGGCAGG
3301 ATCTCCTGTC ATCTCACCTT GCTCCTGCCG AGAAAGTATC CATCATGGCT GATGCAATGC
3361 GGCGGCTGCA TACGCTTGAT CCGGCTACCT GCCCATTCGA CCACCAAGCG AAACATCGCA
3421 TCGAGCGAGC ACGTACTCGG ATGGAAGCCG GTCTTGTCGA TCAGGATGAT CTGGACGAAG
3481 AGCATCAGGG GCTCGCGCCA GCCGAACTGT TCGCCAGGCT CAAGGCGCGC ATGCCCGACG
3541 GCGAGGATCT CGTCGTGACC CATGGCGATG CCTGCTTGCC GAATATCATG GTGGAAAATG
3601 GCCGCTTTTC TGGATTCATC GACTGTGGCC GGCTGGGTGT GGCGGACCGC TATCAGGACA
3661 TAGCGTTGGC TACCCGTGAT ATTGCTGAAG AGCTTGGCGG CGAATGGGCT GACCGCTTCC
3721 TCGTGCTTTA CGGTATCGCC GCTCCCGATT CGCAGCGCAT CGCCTTCTAT CGCCTTCTTG
3781 ACGAGTTCTT CTGAGCGGGA CTCTGGGGTT CGAAATGACC GACCAAGCGA CGCCCAACCT
3841 GCCATCACGA GATTTCGATT CCACCGCCGC CTTCTATGAA AGGTTGGGCT TCGGAATCGT
3901 TTTCCGGGAC GCCGGCTGGA TGATCCTCCA GCGCGGGGAT CTCATGCTGG AGTTCTTCGC
3961 CCACCCCAAC TTGTTTATTG CAGCTTATAA TGGTTACAAA TAAAGCAATA GCATCACAAA
4021 TTTCACAAAT AAAGCATTTT TTTCACTGCA TTCTAGTTGT GGTTTGTCCA AACTCATCAA
4081 TGTATCTTAT CATGTCTGTA TACCGTCGAC CTCTAGCTAG AGCTTGGCGT AATCATGGTC
4141 ATAGCTGTTT CCTGTGTGAA ATTGTTATCC GCTCACAATT CCACACAACA TACGAGCCGG
4201 AAGCATAAAG TGTAAAGCCT GGGGTGCCTA ATGAGTGAGC TAACTCACAT TAATTGCGTT
4261 GCGCTCACTG CCCGCTTTCC AGTCGGGAAA CCTGTCGTGC CAGCTGCATT AATGAATCGG
4321 CCAACGCGCG GGGAGAGGCG GTTTGCGTAT TGGGCGCTCT TCCGCTTCCT CGCTCACTGA
```

Figure 26S

```
4381 CTCGCTGCGC TCGGTCGTTC GGCTGCGGCG AGCGGTATCA GCTCACTCAA AGGCGGTAAT
4441 ACGGTTATCC ACAGAATCAG GGGATAACGC AGGAAAGAAC ATGTGAGCAA AAGGCCAGCA
4501 AAAGGCCAGG AACCGTAAAA AGGCCGCGTT GCTGGCGTTT TTCCATAGGC TCCGCCCCCC
4561 TGACGAGCAT CACAAAAATC GACGCTCAAG TCAGAGGTGG CGAAACCCGA CAGGACTATA
4621 AAGATACCAG GCGTTTCCCC CTGGAAGCTC CCTCGTGCGC TCTCCTGTTC CGACCCTGCC
4681 GCTTACCGGA TACCTGTCCG CCTTTCTCCC TTCGGGAAGC GTGGCGCTTT CTCAATGCTC
4741 ACGCTGTAGG TATCTCAGTT CGGTGTAGGT CGTTCGCTCC AAGCTGGGCT GTGTGCACGA
4801 ACCCCCCGTT CAGCCCGACC GCTGCGCCTT ATCCGGTAAC TATCGTCTTG AGTCCAACCC
4861 GGTAAGACAC GACTTATCGC CACTGGCAGC AGCCACTGGT AACAGGATTA GCAGAGCGAG
4921 GTATGTAGGC GGTGCTACAG AGTTCTTGAA GTGGTGGCCT AACTACGGCT ACACTAGAAG
4981 GACAGTATTT GGTATCTGCG CTCTGCTGAA GCCAGTTACC TTCGGAAAAA GAGTTGGTAG
5041 CTCTTGATCC GGCAAACAAA CCACCGCTGG TAGCGGTGGT TTTTTGTTT GCAAGCAGCA
5101 GATTACGCGC AGAAAAAAAG GATCTCAAGA AGATCCTTTG ATCTTTTCTA CGGGGTCTGA
5161 CGCTCAGTGG AACGAAAACT CACGTTAAGG GATTTTGGTC ATGAGATTAT CAAAAAGGAT
5221 CTTCACCTAG ATCCTTTTAA ATTAAAAATG AAGTTTTAAA TCAATCTAAA GTATATATGA
5281 GTAAACTTGG TCTGACAGTT ACCAATGCTT AATCAGTGAG GCACCTATCT CAGCGATCTG
5341 TCTATTTCGT TCATCCATAG TTGCCTGACT CCCCGTCGTG TAGATAACTA CGATACGGGA
5401 GGGCTTACCA TCTGGCCCCA GTGCTGCAAT GATACCGCGA GACCCACGCT CACCGGCTCC
5461 AGATTTATCA GCAATAAACC AGCCAGCCGG AAGGGCCGAG CGCAGAAGTG GTCCTGCAAC
5521 TTTATCCGCC TCCATCCAGT CTATTAATTG TTGCCGGGAA GCTAGAGTAA GTAGTTCGCC
5581 AGTTAATAGT TTGCGCAACG TTGTTGCCAT TGCTACAGGC ATCGTGGTGT CACGCTCGTC
5641 GTTTGGTATG GCTTCATTCA GCTCCGGTTC CCAACGATCA AGGCGAGTTA CATGATCCCC
5701 CATGTTGTGC AAAAAAGCGG TTAGCTCCTT CGGTCCTCCG ATCGTTGTCA GAAGTAAGTT
5761 GGCCGCAGTG TTATCACTCA TGGTTATGGC AGCACTGCAT AATTCTCTTA CTGTCATGCC
5821 ATCCGTAAGA TGCTTTTCTG TGACTGGTGA GTACTCAACC AAGTCATTCT GAGAATAGTG
5881 TATGCGGCGA CCGAGTTGCT CTTGCCCGGC GTCAATACGG GATAATACCG CGCCACATAG
5941 CAGAACTTTA AAAGTGCTCA TCATTGGAAA ACGTTCTTCG GGGCGAAAAC TCTCAAGGAT
6001 CTTACCGCTG TTGAGATCCA GTTCGATGTA ACCCACTCGT GCACCCAACT GATCTTCAGC
6061 ATCTTTTACT TTCACCAGCG TTTCTGGGTG AGCAAAAACA GGAAGGCAAA ATGCCGCAAA
6121 AAAGGGAATA AGGGCGACAC GGAAATGTTG AATACTCATA CTCTTCCTTT TTCAATATTA
6181 TTGAAGCATT TATCAGGGTT ATTGTCTCAT GAGCGGATAC ATATTTGAAT GTATTTAGAA
6241 AAATAAACAA ATAGGGGTTC CGCGCACATT TCCCCGAAAA GTGCCACCTG ACGTC
//
```

Figure 26T

ISOLATED POLYPEPTIDE COMPRISING A LEPTIN FRAGMENT

RELATED APPLICATIONS

This application is a continuation of U.S. application Ser. No. 09/668,558, filed Sep. 22, 2000, which claims priority to U.S. provisional application Ser. No. 60/155,506, filed Sep. 22, 1999, which are hereby incorporated by reference herein in their entireties including any figures, drawings, sequence listing, or tables.

FIELD OF THE INVENTION

The present invention relates to the field of obesity research, in particular methods of screening for new compounds for the treatment of obesity and obesity-related diseases and disorders, as well as methods of treating obesity-related diseases and disorders. To this end, the characterization of the interaction between a new complex receptor polypeptide, LSR (Lipolysis Stimulated Receptor), and one of its ligands, leptin, is described. The obesity-related diseases or disorders envisaged to be treated by the methods of the invention include, but are not limited to, anorexia, hyperlipidemias, atherosclerosis, diabetes, hypertension and syndrome X. In addition, and more generally, the various pathologies associated with abnormalities in the metabolism of cytokines, may be treated by the methods of the invention.

BACKGROUND OF THE INVENTION

The following discussion is intended to facilitate the understanding of the invention, but is not intended nor admitted to be prior art to the invention.

Obesity is a public health problem that is serious, widespread, and increasing. In the United States, 20 percent of the population is obese; in Europe, a slightly lower percentage is obese (Friedman (2000) Nature 404:632-634). Obesity is associated with increased risk of hypertension, cardiovascular disease, diabetes, and cancer as well as respiratory complications and osteoarthritis (Kopelman (2000) Nature 404: 635-643). Even modest weight loss ameliorates these associated conditions.

While still acknowledging that lifestyle factors including environment, diet, age and exercise play a role in obesity, twin studies, analyses of familial aggregation, and adoption studies all indicate that obesity is largely the result of genetic factors (Barsh et al (2000) Nature 404:644-651). In agreement with these studies, is the fact that an increasing number of obesity-related genes are being identified. Some of the more extensively studied genes include those encoding leptin (ob) and its receptor (db), pro-opiomelanocortin (Pomc), melanocortin-4-receptor (Mc4r), agouti protein ($A^y$), carboxypeptidase E (fat), 5-hydroxytryptamine receptor 2C (Htr2c), nescient basic helix-loop-helix 2 (Nhlh2), prohormone convertase 1 IPCSK1), and tubby protein (tubby) (rev'd in Barsh et al (2000) Nature 404:644-651).

The gene encoding leptin, one of the most widely studied obesity genes, is involved in the mechanisms of satiety (rev'd in Schwartz et al (2000) Nature 404:661-671). Leptin is a plasma protein of 16 kDa produced by adipocytes (Zhang et al ((1994) Nature 372:425-432). Mice with an autosomal recessive mutation in this gene (ob/ob mice) are obese and hyperphagic. Similarly, mice with an autosomal recessive mutation of the leptin receptor (db/db mice, for example) are also obese (Campfield et al (1995) Science 269:546-549). Administration of leptin to ob/ob, but not db/db, mice corrects their relative hyperphagia and allows normalization of their weight (Weigle (1995) J. Clin. Invest. 96:2065-2070).

Leptin circulates in the body at levels proportional to body fat content (Considine et al (1996) New Eng J Med 334:292-295) and enters the central nervous system (CNS) at levels proportional to the plasma level (Schwartz et al (1996) Nature Med 2:589-593). Leptin receptors are expressed by brain neurons involved in energy intake (Baskin et al (1999) Diabetes 48:828-833; Cheung et al (1997) Endocrinology 138: 4489-4492) and administration of leptin into the brain reduces food intake (Weigle (1995) J. Clin. Invest. 96:2065-2070; Campfield et al (1995) Science 269:546-549), whereas its deficiency increases food intake (Zhang et al (1994) Nature 372:425-432).

Despite this clear evidence of leptin's role as an adiposity signal, with only a few exceptions the genes encoding leptin or its ob receptor have proved to be normal in obese human subjects (Kopelman et al (2000) Nature 404:635-643). Furthermore, and paradoxically, the plasma concentrations of leptin, are abnormally high in most obese human subjects (Considine et al (1996) New Eng J Med 334:292-295).

SUMMARY OF THE INVENTION

The present invention results from a focusing of the research effort on the discovery of the mechanisms of leptin elimination. The most widely accepted working hypothesis is that the plasma levels of leptin are high in obese subjects because this hormone is produced by adipose tissue which is increased in obese subjects. In contrast, although not wishing to be limited by any particular theory, the inventors postulated that the concentrations of leptin are increased in obese individuals because the clearance of this hormone is reduced. The resulting high levels of leptin cause a leptin resistance syndrome. Thus, the treatment of obese subjects should not be based on increasing leptin levels, but in normalizing leptin levels.

The lipolysis stimulated receptor (LSR) displays a high affinity for unmodified triglyceride-rich lipoproteins and is involved in the partitioning of dietary lipids among the liver, adipose tissue and muscle. The instant invention stems inter alia from studies of the role of LSR in modulating obesity. As part of the instant invention, leptin and the leptin fragment described herein were found to diminish the postprandial lipemic response in $db^{Pas}/db^{Pas}$ mice which lack the leptin OB receptor, thereby showing that leptin signaling can be independent of the OB receptor. Further, the instant invention stems from the discovery that leptin increases the activity of LSR, binds directly to LSR, and that leptin binding leads to leptin degradation. Although not wishing to be bound by a particular theory, the link between leptin signaling and LSR suggests the post-prandial lipemic response in $db^{Pas}/db^{Pas}$ mice is modulated through this pathway.

In addition, the inventors have discovered that LSR is actually at least two receptors, one for triglyceride-rich lipoproteins, and one for leptin. The three subunits that make up LSR, $\alpha$, $\beta$, and $\alpha'$, actually combine in at least two ways: (1) $\alpha$ and $\beta$ together make up the LSR receptor for triglyceride-rich lipoproteins, and (2) $\alpha'$ is a necessary part of the LSR receptor for leptin, that may include $\beta$ as well. Thus, it is now clear that assays can be designed for identifying modulators or receptors/binding partners/signaling cascade members that are specific for the triglyceride-related activity of LSR or for the leptin-related activity of LSR or both.

Further, the invention features the discovery of a 22 amino acid region of human leptin that modulates LSR activity in vitro and in vivo in the same way as the intact human leptin, thus allowing the use of only this critical region in assays for modulators of the leptin-LSR interaction, and new leptin receptors and binding partners. The new leptin fragment can also be used in disease treatment since it is active in mice at a physiologically-relevant level. In addition, the homologous region from mouse leptin was found to inhibit LSR activity in the human system, and is thus an LSR antagonist of the invention as well as being a powerful tool for identifying further modulators (both inhibitory and stimulatory) of LSR activity.

In a preferred aspect, the invention features a leptin polypeptide fragment that modulates the activity of LSR, comprising at least 4, but not more than 50 contiguous amino acids of any one of the leptin polypeptide sequences set forth in FIG. 13, wherein said at least 4 and not more than 50 contiguous amino acids comprise the leptin fragment central sequence. In preferred embodiments, the leptin polypeptide fragment comprises at least 10 but not more than 50, at least 20 but not more than 40, or at least 20 but not more than 30 contiguous amino acids.

Alternatively, the invention features a variant of a leptin polypeptide fragment that modulates the activity of LSR, consisting of a 22 contiguous amino acid sequence that is at least 75% identical to the leptin fragment variable region of any one of the leptin polypeptide sequences set forth in FIG. 13. In preferred embodiments, the variant of a leptin polypeptide fragment is 85% identical, or 95% identical to the leptin fragment variable region. Preferably the leptin fragments and variants are from human or mouse leptin.

In a second aspect, the invention features, a chimeric oligonucleotide, comprising at least 9 contiguous nucleotides from a sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:15, and SEQ ID NO:16, wherein said at least 9 contiguous nucleotides comprise at least one amino acid codon selected from the group consisting of TTA, TTG, TCA, TCG, TAU, TAC, TGT, TGC, TGG, CAA, CAG, AGA, GAA, GAG, and GGA, and wherein a point mutation is present in said codon such that said codon is a stop codon. Alternatively, the chimeric oligonucleotide comprises at least 9 contiguous nucleotides of SEQ ID NO:1, wherein said at least 9 contiguous nucleotides comprise a single nucleotide polymorphism selected from the group consisting of A1 to A32.

In a third aspect, the invention features a zinc finger protein, comprising a DNA binding domain that binds specifically to 18 nucleotides of a sequence at least 50% homologous to SEQ ID NO:1, wherein said 18 nucleotides comprise two fragments of 9 contiguous nucleotides, and wherein said fragments are separated by 0, 1, 2, or 3 nucleotides. In preferred embodiments, said sequence is at least 50% homologous to intronic sequences selected from the group consisting of 2357 to 3539, 3885 to 12162, 12283 to 15143, 15201 to 17764, 15912 to 19578, 19753 to 19898, 19959 to 20055, 20188 to 20328, and 20958 to 21046 of SEQ ID NO:1, preferably to residues 2357 to 3539 of SEQ ID NO:1, or alternatively 5' untranslated regions such as the sequence 1 to 2356 of SEQ ID NO:1. In preferred embodiments, said protein further comprises a functional domain selected from the group consisting of a transcription repressor and a transcription initiator; preferably said repressor is a KRAB repressor and said initiator is a VP16 initiator. In other preferred embodiments, said protein further comprises a small molecule regulatory system, preferably said system is selected from the group consisting of a Tet system, RU486, and ecdysone.

In a fourth aspect, the invention features polynucleotides encoding the leptin polypeptide fragments and variants of the invention, or polynucleotides encoding a zinc finger protein of the invention.

In a fifth aspect, the invention features recombinant vectors comprising the polynucleotides encoding the leptin polypeptide fragments and variants of the invention, or polynucleotides or recombinant vectors encoding a zinc finger protein of the invention. In preferred embodiments, said vector is an adenovirus associated virus.

In a sixth aspect, the invention features recombinant cells comprising the polynucleotides and recombinant vectors encoding the leptin polypeptide fragments and variants of the invention, or polynucleotides and recombinant vectors encoding zinc finger proteins of the invention. In preferred embodiments, the recombinant cell comprising the polynucleotides and recombinant vectors encoding leptin fragments and variants and zinc finger polypeptides of the invention, are transfected with at least one LSR polypeptide comprising a sequence at least 75% identical to an amino acid sequence selected from the group consisting of SEQ ID NO:3, SEQ ID NO:5, SEQ ID NO:7, SEQ ID NO:9, SEQ ID NO:11, SEQ ID NO:13, SEQ ID NO:17, SEQ ID NO:18, and SEQ ID NO:19. Preferably, said transfected cell is stably transfected. Preferably, said cell is selected from the group consisting of PLC, CHO-K1, Hep3B, Hepa 1-6, and HepG2.

In a seventh embodiment, the invention features a pharmaceutical composition comprising the leptin polypeptide fragments and variants of the invention, or polynucleotides or recombinant vectors encoding a zinc finger protein of the invention, or chimeraplasts of the invention.

In an eighth aspect, the invention features non-human mammals comprising polynucleotides and recombinant vectors encoding zinc finger proteins of the invention. Preferably, said vector is an adenovirus associated virus.

In a ninth aspect, the invention features a method of treating or preventing an obesity-related disease or disorder comprising providing to an individual in need of such treatment a pharmaceutical composition comprising the leptin polypeptide fragments and variants of the invention. Preferably, said disease is congenital generalized lipodystrophy. Alternatively, the patient is provided a chimeric oligonucleotide of the invention or a polynucleotide or recombinant vector encoding a zinc finger protein of the invention. Preferably, said providing comprises a liposome, and preferably said vector is an adenovirus associated virus. In preferred embodiments, the obesity related disease or disorder is selected from the group consisting of obesity, anorexia, cachexia, cardiac insufficiency, coronary insufficiency, stroke, hypertension, atheromatous disease, atherosclerosis, high blood pressure, non-insulin-dependent diabetes, hyperlipidemia, hyperuricemia, and Syndrome X. Preferably the individual is an animal, preferably a mammal, most preferably a human.

In a tenth aspect, the invention features a method of designing mimetics of a leptin fragment that modulates an activity of LSR, comprising: identifying critical interactions between one or more amino acids of said leptin fragment and LSR; designing potential mimetics to comprise said critical interactions; and testing said potential mimetics ability to modulate said activity as a means for designing said mimetics. Preferably, the leptin fragment consists of the leptin fragment variable region or the leptin fragment central sequence of any one of the leptin polypeptide sequences set forth in FIG. 13. Alternatively, the leptin fragment is any one of the leptin fragments or variants of the invention. Preferably, the leptin fragment or variant is from human or mouse leptin. In preferred embodiments, the activity of ISR is selected from the group consisting of leptin binding, leptin uptake, leptin degradation, triglyceride binding, triglyceride uptake, and triglyceride degradation. Preferably the critical interactions are selected from the group consisting of hydrogen bonding, covalent bonding, Van der Waals forces, steric hindrances, and hydrophobic interactions, and are identified using assays selected from the group consisting of NMR, X-ray crystallography, and computer modeling.

In an eleventh aspect, the invention features a method of inhibiting the expression of at least one subunit of LSR, comprising providing to a cell a chimeric oligonucleotide of the invention that changes a amino acid codon to a stop codon. Preferably, the cell is selected from the group consisting of PLC, CHO-K1, HepG2, Hepa 1-6, and Hep3B. Alternatively the cell is in a mammal, preferably a mouse, more preferably in a human, and is provided using a liposome.

In a related aspect, the invention features a method of modulating the expression of at least one subunit of LSR, comprising providing to a cell a polynucleotide encoding a zinc finger protein of the invention. Preferably, said cell is selected from the group consisting of PLC, CHO-K1, HepG2, Hepa 1-6, and Hep3B. Alternatively, said cell is in an animal, preferably a mammal, and preferably said mammal is a mouse or a human.

In a twelfth aspect, the invention features a method for selecting a compound useful for the treatment or prevention of an obesity-related disease or disorder, comprising: contacting a recombinant cell comprising a polynucleotide or recombinant vector encoding a zinc finger protein of the invention, and that optionally further comprises at least one LSR polypeptide comprising a sequence at least 75% identical to an amino acid sequence selected from the group consisting of SEQ ID NO:3, SEQ ID NO:5, SEQ ID NO:7, SEQ ID NO:9, SEQ ID NO:11, SEQ ID NO:13, SEQ ID NO:17, SEQ ID NO:18, and SEQ ID NO:19, with a candidate compound; and detecting a result selected from the group consisting of a modulation of an activity of the Lipolysis Stimulated Receptor and modulation of expression of the Lipolysis Stimulated Receptor; as a means for selecting said compound useful for the treatment or prevention of said obesity-related disease or disorder. In preferred embodiments, said contacting is in the presence of a ligand of said Lipolysis Stimulated Receptor. Preferably, said ligand is selected from the group consisting of cytokine, lipoprotein, free fatty acids, Apm1, and C1q. Most preferably said cytokine is leptin, or a leptin polypeptide fragment or variant of the invention. Alternatively said free fatty acid is oleate.

In preferred embodiments, said LSR activity is selected from the group consisting of binding of lipoproteins, uptake of lipoproteins, degradation of lipoproteins, binding of leptin, uptake of leptin, and degradation of leptin. Preferably said modulation is an increase in said activity, alternatively a decrease in activity. In other preferred embodiments, said expression is on the surface of said cell, and preferably said detecting comprises FACS. Preferably, said detecting further comprises antibodies that bind specifically to said LSR, wherein said LSR comprises an amino acid sequence at least 75% homologous to at least one of the sequences selected from the group consisting of SEQ ID NO:3, SEQ ID NO:5, SEQ ID NO:7, SEQ ID NO:9, SEQ ID NO:11, SEQ ID NO:13, SEQ ID NO:17, SEQ ID NO:18, and SEQ ID NO:19 Most preferably, said antibodies bind specifically to a region of said LSR selected from the group consisting of an amino terminus, a carboxy terminus, a splice site, a cytokine binding site, a fatty acid binding site, a clathrin binding site, an apoprotein ligand binding site, a LI/LL motif, a RSRS motif, and a hydrophobic region. Preferably, said cell is selected from the group consisting of PLC, CHO-K1, Hep3B, Hepa 1-6, and HepG2.

In other preferred embodiments, said candidate compound is selected from the group consisting of peptides, peptide libraries, non-peptide libraries, peptoids, fatty acids, lipoproteins, medicaments, antibodies, and small molecules. Preferably, said obesity-related diseases and disorders are selected from the group consisting of obesity, anorexia, cachexia, cardiac insufficiency, coronary insufficiency, stroke, hypertension, atheromatous disease, atherosclerosis, high blood pressure, non-insulin-dependent diabetes, hyperlipidemia, hyperuricemia, and Syndrome X.

In a thirteenth aspect, the invention features a method of selecting for genes that modulate an activity of the Lipolysis Stimulated Receptor, comprising: providing a retroviral gene library to cells that express said Lipolysis Stimulated Receptor; contacting said cells with a ligand of said Lipolysis Stimulated Receptor; detecting a change in said activity of the Lipolysis Stimulated Receptor as a means for selecting for said genes. In preferred embodiments, said retroviral gene library comprises a cDNA library from tissues selected from the group consisting of liver and adipose. Preferably, said retroviral gene library further comprises a detectable marker protein selected from the group consisting of GFP, truncated CD2, and truncated CD4. In other preferred embodiments, the invention further comprises selecting said cells comprising the retroviral gene library for moderate expression of GFP; preferably said selecting of cells is by FACS.

In other preferred embodiments, said ligand is selected from the group consisting of cytokine, lipoprotein, free fatty acids, Apm1, and C1q. Most preferably said cytokine is leptin, or a leptin polypeptide fragment or variant of the invention. Alternatively said free fatty acid is oleate.

In yet other preferred embodiments, preferably said detecting a change in said activity comprises FACS. Preferably, said detecting further comprises antibodies that bind specifically to said LSR, wherein said LSR comprises an amino acid sequence at least 75% homologous to at least one of the sequences selected from the group consisting of SEQ ID NO:3, SEQ ID NO:5, SEQ ID NO:7, SEQ ID NO:9, SEQ ID NO:1, SEQ ID NO:13, SEQ ID NO:17, SEQ ID NO:18, and SEQ ID NO:19 Most preferably, said antibodies bind specifically to a region of said LSR selected from the group consisting of an amino terminus, a carboxy terminus, a splice site, a cytokine binding site, a fatty acid binding site, a clathrin binding site, an apoprotein ligand binding site, a LI/LL motif, a RSRS motif, and a hydrophobic region. Preferably, said cell is selected from the group consisting of PLC, CHO-K1, Hep3B, Hepa 1-6, and HepG2.

DETAILED DESCRIPTION OF THE INVENTION

LSR (Lipolysis Stimulated Receptor), which is described in PCT publication No WO IB98/01257 (hereby incorporated by reference herein in its entirety including any figures, tables, or drawings), is expressed on the surface of hepatic cells, and is involved in the partitioning of dietary lipids between the liver and peripheral tissues, including muscles and adipose tissue. The LSR gene encodes, by alternative splicing, three types of subunits, LSR $\alpha$, LSR $\alpha'$, and LSR $\beta$. The $\alpha'$ subunit specifically binds a cytokine, leptin, which activates LSR and is taken up and degraded. The invention is drawn inter alia to compounds that modulate the interaction between LSR and leptin useful in the treatment or prevention of obesity-related diseases and disorders.

Definitions

Before describing the invention in greater detail, the following definitions are set forth to illustrate and define the meaning and scope of the terms used to describe the invention herein.

As used interchangeably herein, the terms "oligonucleotides", and "polynucleotides" include RNA, DNA, or RNA/DNA hybrid sequences of more than one nucleotide in either single chain or duplex form. The terms "nucleotide", "nucleotide sequence" and "nucleic acid" are used herein consistently with their use in the art, including to encompass "modified nucleotides" which comprise at least one modification, including by way of example and not limitation: (a) an alternative linking group, (b) an analogous form of purine, (c) an analogous form of pyrimidine, or (d) an analogous sugar. For examples of analogous linking groups, purines, pyrimidines, and sugars see for example PCT publication No. WO 95/04064. The polynucleotide sequences of the invention may be prepared by any known method, including synthetic, recombinant, ex vivo generation, or a combination thereof, as well as utilizing any purification methods known in the art.

The terms polynucleotide construct, recombinant polynucleotide and recombinant polypeptide are used herein consistently with their use in the art. The terms "upstream" and "downstream" are also used herein consistently with their use in the art. The terms "base paired" and "Watson & Crick base paired" are used interchangeably herein and consistently with their use in the art. Similarly, the terms "complementary", "complement thereof", "complement", "complementary polynucleotide", "complementary nucleic acid" and "complementary nucleotide sequence" are used interchangeably herein and consistently with their use in the art.

The term "purified" is used herein to describe a polynucleotide or polynucleotide vector of the invention that has been separated from other compounds including, but not limited to, other nucleic acids, carbohydrates, lipids and proteins (such as the enzymes used in the synthesis of the polynucleotide). Purified can also refer to the separation of covalently closed polynucleotides from linear polynucleotides, or vice versa, for example. A polynucleotide is substantially pure when at least about 50%, 60%, 75%, or 90% of a sample contains a single polynucleotide sequence. In some cases this involves a determination between conformations (linear versus covalently closed). A substantially pure polynucleotide typically comprises about 50, 60, 70, 80, 90, 95, 99% weight/weight of a nucleic acid sample. Polynucleotide purity or homogeneity may be indicated by a number of means well known in the art, such as agarose or polyacrylamide gel electrophoresis of a sample, followed by visualizing a single polynucleotide band upon staining the gel. For certain purposes higher resolution can be provided by using HPLC or other means well known in the art.

Similarly, the term "purified" is used herein to describe a polypeptide of the invention that has been separated from other compounds including, but not limited to, nucleic acids, lipids, carbohydrates and other proteins. In some preferred embodiments, a polypeptide is substantially pure when at least about 50%, 60%, 75%, 85%, 90%, or 95% of a sample exhibits a single polypeptide sequence. In some preferred embodiments, a substantially pure polypeptide typically comprises about 50%, 60%, 70%, 80%, 90% 95%, or 99% weight/weight of a protein sample. Polypeptide purity or homogeneity is indicated by a number of methods well known in the art, such as agarose or polyacrylamide gel electrophoresis of a sample, followed by visualizing a single polypeptide band upon staining the gel. For certain purposes higher resolution can be provided by using HPLC or other methods well known in the art.

Further, as used herein, the term "purified" does not require absolute purity; rather, it is intended as a relative definition. Purification of starting material or natural material to at least one order of magnitude, preferably two or three orders, and more preferably four or five orders of magnitude is expressly contemplated. Alternatively, purification may be expressed as "at least" a percent purity relative to heterologous polynucleotides (DNA, RNA or both) or polypeptides. As a preferred embodiment, the polynucleotides or polypeptides of the present invention are at least; 10%, 20%, 30%, 40%, 50%, 60%, 70%, 80%, 90%, 95%, 96%, 97%, 98%, 99%, or 100% pure relative to heterologous polynucleotides or polypeptides. As a further preferred embodiment the polynucleotides or polypeptides have an "at least" purity ranging from any number, to the thousandth position, between 90% and 100% (e.g., at least 99.995% pure) relative to heterologous polynucleotides or polypeptides. Additionally, purity of the polynucleotides or polypeptides may be expressed as a percentage (as described above) relative to all materials and compounds other than the carrier solution. Each number, to the thousandth position, may be claimed as individual species of purity.

The term "isolated" requires that the material be removed from its original environment (e.g., the natural environment if it is naturally occurring). For example, a naturally-occurring polynucleotide or polypeptide present in a living animal is not isolated, but the same polynucleotide or DNA or polypeptide, separated from some or all of the coexisting materials in the natural system, is isolated. Such polynucleotide could be part of a vector and/or such polynucleotide or polypeptide could be part of a composition, and still be isolated in that the vector or composition is not part of its natural environment.

Specifically excluded from the definition of "isolated" are: naturally occurring chromosomes (e.g., chromosome spreads), artificial chromosome libraries, genomic libraries, and cDNA libraries that exist either as an in vitro nucleic acid preparation or as a transfected/transformed host cell preparation, wherein the host cells are either an in vitro heterogeneous preparation or plated as a heterogeneous population of single colonies. Also specifically excluded are the above libraries wherein a 5' EST makes up less than 5% of the number of nucleic acid inserts in the vector molecules. Further specifically excluded are whole cell genomic DNA or whole cell RNA preparations (including said whole cell preparations which are mechanically sheared or enzymatically digested). Further specifically excluded are the above whole cell preparations as either an in vitro preparation or as a heterogeneous mixture separated by electrophoresis (including blot transfers of the same) wherein the polynucleotide of the invention have not been further separated from the heterologous polynucleotides in the electrophoresis medium (e.g., further separating by excising a single band from a heterogeneous band population in an agarose gel or nylon blot).

The term "primer" denotes a specific oligonucleotide sequence which is complementary to a target nucleotide sequence and used to hybridize to the target nucleotide sequence. A primer serves as an initiation point for nucleotide polymerization catalyzed by DNA polymerase, RNA polymerase, or reverse transcriptase.

The term "probe" denotes a defined nucleic acid segment (or nucleotide analog segment, e.g., PNA as defined hereinbelow) which can be used to identify a specific polynucleotide sequence present in a sample, said nucleic acid segment comprising a nucleotide sequence complementary to the specific polynucleotide sequence to be identified.

The term "polypeptide" refers to a polymer of amino acids without regard to the length of the polymer. Thus, peptides, oligopeptides, and proteins are included within the definition of polypeptide. This term also does not specify or exclude post-expression modifications of polypeptides. For example, polypeptides that include the covalent attachment of glycosyl groups, acetyl groups, phosphate groups, lipid groups and the like are expressly encompassed by the term polypeptide. Also included within the definition are polypeptides which contain one or more analogs of an amino acid (including, for example, non-naturally occurring amino acids, amino acids which only occur naturally in an unrelated biological system, modified amino acids from mammalian systems etc.), polypeptides with substituted linkages, as well as other modifications known in the art, both naturally occurring and non-naturally occurring.

Without being limited by theory, the compounds/polypeptides of the invention are believed to treat "diseases involving the partitioning of dietary lipids between the liver and peripheral tissues". The term "peripheral tissues" is meant to include muscle and adipose tissue. In preferred embodiments, the compounds/polypeptides of the invention partition the dietary lipids toward the muscle. In alternative preferred embodiments, the dietary lipids are partitioned toward the adipose tissue. In other preferred embodiments, the dietary lipids are partitioned toward the liver. In yet other preferred embodiments, the compounds/polypeptides of the invention increase or decrease the oxidation of dietary lipids, preferably free fatty acids (FFA) by the muscle. Dietary lipids include, but are not limited to triglycerides and free fatty acids.

Preferred diseases believed to involve the partitioning of dietary lipids include obesity and obesity-related diseases and disorders such as atherosclerosis, heart disease, insulin resistance, hypertension, stroke, Syndrome X, and Type II diabetes. Type II diabetes-related complications to be treated by the methods of the invention include microangiopathic lesions, ocular lesions, and renal lesions. Heart disease includes, but is not limited to, cardiac insufficiency, coronary insufficiency, and high blood pressure. Other obesity-related disorders to be treated by compounds of the invention include hyperlipidemia and hyperuricemia. Yet other obesity-related diseases or disorders of the invention include cachexia, wasting, AIDS-related weight loss, neoplasia-related weight loss, anorexia, and bulimia.

The term "obesity" as used herein is defined in the WHO classifications of weight (Kopelman (2000) Nature 404:635-643). Underweight is less than 18.5 (thin); Healthy is 18.5-24.9 (normal); grade 1 overweight is 25.0-29.9 (overweight); grade 2 overweight is 30.0-39.0 (obesity); grade 3 overweight is greater than or equal to 40.0 BMI (morbid obesity). BMI is body mass index and is $kg/m^2$. Waist circumference can also be used to indicate a risk of metabolic complications where in men a circumference of greater than or equal to 94 cm indicates an increased risk, and greater than or equal to 102 cm indicates a substantially increased risk. Similarly for women, greater than or equal to 88 cm indicates an increased risk, and greater than or equal to 88 cm indicates a substantially increased risk. The waist circumference is measured in cm at midpoint between lower border of ribs and upper border of the pelvis. Other measures of obesity include, but are not limited to, skinfold thickness which is a measurement in cm of skinfold thickness using calipers, and bioimpedance, which is based on the principle that lean mass conducts current better than fat mass because it is primarily an electrolyte solution; measurement of resistance to a weak current (impedance) applied across extremities provides an estimate of body fat using an empirically derived equation.

The term "agent acting on the partitioning of dietary lipids between the liver and peripheral tissues" refers to a compound or polypeptide of the invention that modulates the partitioning of dietary lipids between the liver and the peripheral tissues as previously described. Preferably, the agent increases or decreases the oxidation of dietary lipids, preferably free fatty acids (FFA) by the muscle. Preferably the agent decreases or increases the body weight of individuals or is used to treat or prevent an obesity-related disease or disorder such as atherosclerosis, heart disease, insulin resistance, hypertension, stroke, Syndrome X, and Type II diabetes. Type II diabetes-related complications to be treated by the methods of the invention include, but are not limited to, microangiopathic lesions, ocular lesions, and renal lesions. Heart disease includes, but is not limited to, cardiac insufficiency, coronary insufficiency, and high blood pressure. Other obesity-related disorders to be treated by compounds of the invention include hyperlipidemia and hyperuricemia. Yet other obesity-related diseases or disorders of the invention include cachexia, wasting, AIDS-related weight loss, anorexia, and bulimia.

The terms "response to an agent acting on the partitioning of dietary lipids between the liver and peripheral tissues" refer to drug efficacy, including but not limited to, ability to metabolize a compound, to the ability to convert a pro-drug to an active drug, and to the pharmacokinetics (absorption, distribution, elimination) and the pharmacodynamics (receptor-related) of a drug in an individual.

The terms "side effects to an agent acting on the partitioning of dietary lipids between the liver and peripheral tissues" refer to adverse effects of therapy resulting from extensions of the principal pharmacological action of the drug or to idiosyncratic adverse reactions resulting from an interaction of the drug with unique host factors. "Side effects to an agent acting on the partitioning of dietary lipids between the liver and peripheral tissues" can include, but are not limited to, adverse reactions such as dermatologic, hematologic or hepatologic toxicities and further includes gastric and intestinal ulceration, disturbance in platelet function, renal injury, nephritis, vasomotor rhinitis with profuse watery secretions, angioneurotic edema, generalized urticaria, and bronchial asthma to laryngeal edema and bronchoconstriction, hypotension, and shock.

As used herein, the term "antibody" refers to a polypeptide or group of polypeptides which are comprised of at least one binding domain, where an antibody binding domain is formed from the folding of variable domains of an antibody molecule to form three-dimensional binding spaces with an internal surface shape and charge distribution complementary to the features of an antigenic determinant of an antigen, and that allows an immunological reaction with the antigen. Antibodies include recombinant proteins comprising the antibody binding domains, as well as fragments, including Fab, Fab', $F(ab)_2$, and $F(ab')_2$ fragments.

As used herein, an "antigenic determinant" is the portion of an antigen molecule, in this case an LSR polypeptide, that determines the specificity of the antigen-antibody reaction. An "epitope" refers to an antigenic determinant of a polypeptide. An epitope can comprise as few as 3 amino acids in a spatial conformation which is unique to the epitope. Generally an epitope consists of at least 6 such amino acids, and more usually at least 8-10 such amino acids. Methods for determining the amino acids which make up an epitope include x-ray crystallography, 2-dimensional nuclear magnetic resonance, and epitope mapping e.g. the Pepscan method described by H. Mario Geysen et al. 1984. Proc. Natl.

Acad. Sci. U.S.A. 81:3998-4002; PCT Publication No. WO 84/03564; and PCT Publication No. WO 84/03506.

The term "compound" as used herein refers to molecules, either organic or inorganic, that can be tested for activity in an assay. Preferably, compounds have a low molecular weight of less than 500 kda, some compounds can have a molecular weight between 500 and 1500, other compounds may have a molecular weight of at least 1500 kda. In addition, compounds of interest preferably have a desired activity at a low concentration, e.g. a compound that is active at a concentration of 1 ng/mL or less, is generally preferred over one that is active at 1 ng/mL to 100 ng/mL, or one that is active only at concentrations greater than 100 ng/mL. Examples of compounds to be tested in the assays herein include: peptides, peptide libraries, non-peptide libraries, antibodies, and peptoids.

The term "activity" as used herein refers to a measurable result of the interaction of molecules. For example, some LSR activities include leptin binding, leptin uptake, leptin degradation, as well as triglyceride binding, triglyceride uptake, and triglyceride degradation. Some exemplary methods of measuring these activities are provided herein.

The term "modulate" as used herein refers to the ability of a compound to change an activity in some measurable way as compared to an appropriate control. As a result of the presence of compounds in the assays, activities can increase (e.g. there could be increased levels of leptin binding), or "decrease" (e.g. there could be decreased levels of leptin binding) as compared to controls in the absence of these compounds. Preferably, an increase in activity is at least 25%, more preferably at least 50%, most preferably at least 100% compared to the level of activity in the absence of the compound. Similarly, a decrease in activity is preferably at least 25%, more preferably at least 50%, most preferably at least 100% compared to the level of activity in the absence of the compound. A compound that increases a known activity is an "agonist". One that decreases, or prevents, a known activity is an "antagonist".

The term "monitoring" as used herein refers to any method in the art by which an activity can be measured. For each of the activities in the assays of the invention, exemplary methods are provided in the Examples section.

The term "providing" as used herein refers to any means of adding a compound or molecule to something known in the art. Examples of providing can include the use of pipets, pipettmen, syringes, needles, tubing, guns, etc. This can be manual or automated. It can include transfection by any mean or any other means of providing nucleic acids to dishes, cells, tissue, cell-free systems and can be in vitro or in vivo. Methods are provided in the Examples section as examples.

The term "LSR-related diseases and disorders" as used herein refers to any disease or disorder or condition comprising an aberrant functioning of LSR, or a subunit(s) of LSR, to include aberrant levels of expression of LSR, or a subunit(s) of LSR (either increased or decreased), aberrant activity of LSR (either increased or decreased), and aberrant interactions with ligands or binding partners (either increased or decreased). By "aberrant" is meant a change from the type, or level of activity seen in normal cells, tissues, or individuals, or seen previously in the cell, tissue, or individual prior to the onset of the illness.

The term "cosmetic treatments" is meant to include treatments with compounds or polypeptides of the invention that increase or decrease the body mass of an individual where the individual is not clinically obese or clinically thin. Thus, these individuals have a body mass index (BMI) below the cut-off for clinical obesity (e.g. below 25 kg/m$^2$) and above the cut-off for clinical thinness (e.g. above 18.5 kg/m$^2$). In addition, these individuals are preferably healthy (e.g. do not have an obesity-related disease or disorder of the invention). "Cosmetic treatments" are also meant to encompass, in some circumstances, more localized increases in adipose tissue, for example, gains or losses specifically around the waist or hips, or around the hips and thighs, for example. These localized gains or losses of adipose tissue can be identified by increases or decreases in waist or hip size, for example.

The term "preventing" as used herein refers to administering a compound prior to the onset of clinical symptoms of a disease or conditions so as to prevent a physical manifestation of aberrations associated with obesity or LSR.

The term "treating" as used herein refers to administering a compound after the onset of clinical symptoms.

The term "in need of treatment" as used herein refers to a judgment made by a caregiver (e.g. physician, nurse, nurse practitioner, etc in the case of humans; veterinarian in the case of animals, including non-human mammals) that an individual or animal requires or will benefit from treatment. This judgment is made based on a variety of factors that are in the realm of a care giver's expertise, but that include the knowledge that the individual or animal is ill, or will be ill, as the result of a condition that is treatable by the compounds of the invention.

The term "perceives a need for treatment" refers to a subclinical determination that an individual desires to reduce weight for cosmetic reasons as discussed under "cosmetic treatment" above. The term "perceives a need for treatment" in other embodiments can refer to the decision that an owner of an animal makes for cosmetic treatment of the animal.

The term "individual" as used herein refers to a mammal, including animals, preferably mice, rats, other rodents, rabbits, dogs, cats, swine, cattle, sheep, horses, or primates, most preferably humans.

The term "non-human animal" refers to any non-human vertebrate, birds and more usually mammals, preferably primates, animals such as swine, goats, sheep, donkeys, horses, cats, dogs, rabbits or rodents, more preferably rats or mice. Both the terms "animal" and "mammal" expressly embrace human subjects unless preceded with the term "non-human".

The terms "percentage of sequence identity" and "percentage homology" are used interchangeably herein to refer to comparisons among polynucleotides and polypeptides, and are determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Homology is evaluated using any of the variety of sequence comparison algorithms and programs known in the art. Such algorithms and programs include, but are by no means limited to, TBLASTN, BLASTP, FASTA, TFASTA, and CLUSTALW (Pearson and Lipman, 1988, Proc. Natl. Acad. Sci. USA 85(8):2444-2448; Altschul et al., 1990, J. Mol. Biol. 215(3):403-410) Thompson et al., 1994, Nucleic Acids Res. 22(2):4673-4680; Higgins et al., 1996, Methods Enzymol. 266:383-402; Altschul et al., 1990, J. Mol. Biol. 215(3):403-410; Altschul et al., 1993, Nature Genetics 3:266-272). In a particularly preferred embodiment, protein and nucleic acid sequence homologies are evaluated using the Basic Local Alignment Search Tool ("BLAST") which is well known in the art (see e.g., Karlin and Altschul, 1990, Proc. Natl. Acad. Sci. USA 87:2267-2268; Altschul et al., 1990. J. Mol. Biol. 215:403-410; Altschul et al., 1993, Nature Genetics 3:266-272; Altschul et al., 1997, Nuc. Acids Res. 25:3389-3402. In particular, five specific BLAST programs are used to perform the following task:

(1) BLASTP and BLAST3 compare an amino acid query sequence against a protein sequence database;

(2) BLASTN compares a nucleotide query sequence against a nucleotide sequence database;

(3) BLASTX compares the six-frame conceptual translation products of a query nucleotide sequence (both strands) against a protein sequence database;

(4) TBLASTN compares a query protein sequence against a nucleotide sequence database translated in all six reading frames (both strands); and (5) TBLASTX compares the six-frame translations of a nucleotide query sequence against the six-frame translations of a nucleotide sequence database.

The BLAST programs identify homologous sequences by identifying similar segments, which are referred to herein as "high-scoring segment pairs," between a query amino or nucleic acid sequence and a test sequence which is preferably obtained from a protein or nucleic acid sequence database. High-scoring segment pairs are preferably identified (i.e., aligned) by means of a scoring matrix, many of which are known in the art. Preferably, the scoring matrix used is the BLOSUM62 matrix (Gonnet et al., 1992, Science 256:1443-1445; Henikoff and Henikoff, 1993, Proteins 17:49-61. Less preferably, the PAM or PAM250 matrices may also be used (see, e.g., Schwartz and Dayhoff, eds., 1978, Matrices for Detecting Distance Relationships: Atlas of Protein Sequence and Structure, Washington: National Biomedical Research Foundation). The BLAST programs evaluate the statistical significance of all high-scoring segment pairs identified, and preferably selects those segments which satisfy a user-specified threshold of significance, such as a user-specified percent homology. Preferably, the statistical significance of a high-scoring segment pair is evaluated using the statistical significance formula of Karlin (see, e.g., Karlin and Altschul, 1990, Proc. Natl. Acad. Sci. USA 87:2267-2268).

By way of example and not limitation, procedures using conditions of high stringency are as follows: Prehybridization of filters containing DNA is carried out for 8 h to overnight at 65° C. in buffer composed of 6×SSC, 50 mM Tris-HCl (pH 7.5), 1 mM EDTA, 0.02% PVP, 0.02% Ficoll, 0.02% BSA, and 500 µg/mL denatured salmon sperm DNA. Filters are hybridized for 48 h at 65° C., the preferred hybridization temperature, in prehybridization mixture containing 100 µg/mL denatured salmon sperm DNA and 5-20×10$^6$ cpm of $^{32}$P-labeled probe. Alternatively, the hybridization step can be performed at 65° C. in the presence of SSC buffer, 1×SSC corresponding to 0.15 M NaCl and 0.05 M Na citrate. Subsequently, filter washes can be done at 37° C. for 1 h in a solution containing 2×SSC, 0.01% PVP, 0.01% Ficoll, and 0.01% BSA, followed by a wash in 0.1×SSC at 50° C. for 45 min. Alternatively, filter washes can be performed in a solution containing 2×SSC and 0.1% SDS, or 0.5×SSC and 0.1% SDS, or 0.1×SSC and 0.1% SDS at 68° C. for 15 minute intervals. Following the wash steps, the hybridized probes are detectable by autoradiography. Other conditions of high stringency that may be used are well known in the art (see, for example, Sambrook et al., 1989; and Ausubel et al., 1989, both of which are hereby incorporated by reference herein in their entirety). These hybridization conditions are suitable for a nucleic acid molecule of about 20 nucleotides in length. A person of ordinary skill in the art will realize that the hybridization conditions described above are to be adapted according to the length of the desired nucleic acid following techniques well known to the one skilled in the art. Suitable hybridization conditions may for example be adapted according to the teachings disclosed in the book of Hames and Higgins (1985) or in Sambrook et al. (1989).

Variants

It will be recognized by one of ordinary skill in the art that some amino acids of the polypeptide sequences of the present invention can be varied without significant effect on the structure or function of the protein; there will be critical amino acids in the polypeptide sequence that determine activity. Thus, the invention further includes variants of polypeptides. Such variants include polypeptide sequences with one or more amino acid deletions, insertions, inversions, repeats, and substitutions either from natural mutations or human manipulation selected according to general rules known in the art so as to have little effect on activity. Guidance concerning how to make phenotypically silent amino acid substitutions is provided below.

There are two main approaches for studying the tolerance of an amino acid sequence to change (See, Bowie, J. U. et al. 1990). The first method relies on the process of evolution, in which mutations are either accepted or rejected by natural selection. The second approach uses genetic engineering to introduce amino acid changes at specific positions of a cloned gene and selections or screens to identify sequences that maintain functionality.

These studies have revealed that proteins are surprisingly tolerant of amino acid substitutions and indicate which amino acid changes are likely to be permissive at a certain position of the protein. For example, most buried amino acid residues require nonpolar side chains, whereas few features of surface side chains are generally conserved. Other such phenotypically silent substitutions are described by Bowie et al. (supra) and the references cited therein.

Typically seen as conservative substitutions are the replacements, one for another, among the aliphatic amino acids Ala, Val, Leu and Phe; interchange of the hydroxyl residues Ser and Thr; exchange of the acidic residues Asp and Glu; substitution between the amide residues Asn and Gln; exchange of the basic residues Lys and Arg; and replacements among the aromatic residues Phe, Tyr. In addition, the following groups of amino acids generally represent equivalent changes: (1) Ala, Pro, Gly, Glu, Asp, Gln, Asn, Ser, Thr; (2) Cys, Ser, Tyr, Thr; (3) Val, Ile, Leu, Met, Ala, Phe; (4) Lys, Arg, His; (5) Phe, Tyr, Trp, His.

Similarly, amino acids in polypeptide sequences of the invention that are essential for function can also be identified by methods known in the art, such as site-directed mutagenesis or alanine-scanning mutagenesis (See, e.g., Cunningham et al. 1989). The latter procedure introduces single alanine mutations at every residue in the molecule. The resulting mutant molecules are then tested for obesity-related activity using assays as described above. Of special interest are substitutions of charged amino acids with other charged or neutral amino acids that may produce proteins with highly desirable improved characteristics, such as less aggregation. Aggregation may not only reduce activity but also be problematic when preparing pharmaceutical formulations, because aggregates can be immunogenic, (See, e.g., Pinckard, et al., 1967; Robbins, et al., 1987; and Cleland, et al., 1993).

Thus, the fragment, derivative, analog, or homolog of the polypeptide of the present invention may be, for example: (i) one in which one or more of the amino acid residues are substituted with a conserved or non-conserved amino acid residue (preferably a conserved amino acid residue) and such substituted amino acid residue may or may not be one encoded by the genetic code: or (ii) one in which one or more of the amino acid residues includes a substituent group: or (iii) one in which the polypeptide is fused with another compound, such as a compound to increase the half-life of the polypeptide (for example, polyethylene glycol): or (iv) one in which the additional amino acids are fused to the above form of the polypeptide, such as an IgG Fc fusion region peptide or leader or secretory sequence or a sequence which is employed for purification of the above form of the polypeptide or a pro-protein sequence. Such fragments, derivatives and analogs are deemed to be within the scope of those skilled in the art from the teachings herein.

A further embodiment of the invention relates to a polypeptide which comprises the amino acid sequence of a polypeptide having an amino acid sequence which contains at least one conservative amino acid substitution, but not more than 50 conservative amino acid substitutions, not more than 40 conservative amino acid substitutions, not more than 30 conservative amino acid substitutions, and not more than 20 conservative amino acid substitutions. Also provided are polypeptides which comprise the amino acid sequence of polypeptide, having at least one, but not more than 10, 9, 8, 7, 6, 5, 4, 3, 2 or 1 conservative amino acid substitutions.

Another specific embodiment of a modified polypeptide of the invention is a polypeptide that is resistant to proteolysis, for example a polypeptide in which a —CONH— peptide bond is modified and replaced by one or more of the following: a (CH2NH) reduced bond; a (NHCO) retro inverso bond; a (CH2-O) methylene-oxy bond; a (CH2-S) thiomethylene bond; a (CH2CH2) carba bond; a (CO—CH2) cetomethylene bond; a (CHOH—CH2) hydroxyethylene bond); a (N—N) bound; a E-alcene bond; or a —CH=CH— bond. Thus, the invention also encompasses a polypeptide or a fragment or a variant thereof in which at least one peptide bond has been modified as described above.

In addition, amino acids have chirality within the body of either L or D. In some embodiments it is preferable to alter the chirality of the amino acids in the polypeptides of the invention in order to extend half-life within the body. Thus, in some embodiments, one or more of the amino acids are preferably in the L configuration. In other embodiments, one or more of the amino acids are preferably in the D configuration.

I. Leptin Polynucleotides of the Invention

Polynucleotides have been designed that encode a LSR-binding/activating/modulating portion of the leptin protein. This region was identified by a comparison of the human and murine amino acid sequences, and its activity was confirmed in vitro and in vivo (See Examples 1-8). The recombinant polynucleotide encoding the LSR-activating leptin fragment can be used in a variety of ways, including: (1) to express the polypeptide in recombinant cells so as to be purified and used as described below, (2) to express the polypeptide in cells as part of an assay system to discover modulators of the leptin/LSR interaction, and (3) as part of a gene surgery where the fragment itself can be used in treatment and/or prevention of obesity-related diseases and disorders and modulating body mass.

The invention relates to the polynucleotides encoding a leptin polypeptide fragment described in the Examples (7 & 8), and variants and fragments thereof as described herein in Leptin Polypeptides of the Invention (section II), as well as to variants and fragments of the polynucleotides that encode these polypeptides. Preferably, polynucleotides are purified, isolated and/or recombinant.

In other preferred embodiments, variants of the leptin polynucleotides encoding leptin polypeptides as described herein in Leptin Polypeptides of the Invention are envisioned. Variants of polynucleotides, as the term is used herein, are polynucleotides whose sequence differs from a reference polynucleotide. A variant of a polynucleotide may be a naturally occurring variant such as a naturally occurring allelic variant, or it may be a variant that is not known to occur naturally. Such non-naturally occurring variants of the polynucleotide may be made by mutagenesis techniques, including those applied to polynucleotides, cells or organisms. Generally, differences are limited so that the nucleotide sequences of the reference and the variant are closely similar overall and, in many regions, identical.

Variants of leptin polynucleotides according to the invention may include, without being limited to, nucleotide sequences which are at least 90% (preferably at least 95%, more preferably at least 99%, and most preferably at least 99.5%) identical to a polynucleotide that encodes a leptin polypeptide of the invention, or to any polynucleotide fragment of at least 8 (preferably at least 15, more preferably at least 25, and most preferably at least 45) consecutive nucleotides of a polynucleotide that encodes a polypeptide of the invention.

Nucleotide changes present in a variant polynucleotide are preferably silent, which means that they do not alter the amino acids encoded by the polynucleotide. However, nucleotide changes may also result in amino acid substitutions, additions, deletions, fusions and truncations in the polypeptide encoded by the reference sequence. The substitutions, deletions or additions may involve one or more nucleotides. Alterations in the leptin coding regions of the invention may produce conservative or non-conservative amino acid substitutions, deletions or additions in the encoded protein. Preferably, the nucleotide substitutions result in non-conservative amino acid changes and more preferably in conservative amino acid changes in the encoded polypeptide.

In cases where the nucleotide substitutions result in one or more amino acid changes, preferred leptin polypeptides include those that retain the same activities and activity levels as the leptin polypeptide encoded by the reference polynucleotide sequence, as well as those where the level of one or more activities is increased, and alternatively where the level of one or more activities is decreased or even absent. Leptin polypeptide activities of the invention are described herein in the Examples in more detail (1-8, 10 & 14), but include LSR binding leading to the uptake and degradation of leptin, as well as the upregulation of LSR receptors that bind, uptake and degrade triglycerides. Examples of assays to determine the presence or absence of specific leptin activities and the level of the activity(s) are also described herein.

By "retain the same activities" is meant that the activity measured using the polypeptide encoded by the variant leptin polynucleotide in assays is at least 75% (preferably at least 85%, more preferably at least 95%, most preferably at least 98%) and not more than 125% (preferably not more than 115%, more preferably not more than 105%, most preferably not more than 102%) of the activity measured using the leptin polypeptide encoded by the reference sequence.

By the activity being "increased" is meant that the activity measured using the polypeptide encoded by the variant leptin polynucleotide in assays is at least 125% (preferably at least 150%, more preferably at least 200%, most preferably at least 500%) of the activity measured using the leptin polypeptide encoded by the reference sequence.

By the activity being "decreased" is meant that the activity measured using the polypeptide encoded by the variant leptin polynucleotide in assays is not more than 75% (preferably not more than 50%, more preferably not more than 25%, most preferably not more than 10%) of the activity measured using the leptin polypeptide encoded by the reference sequence.

By the activity being "absent" is meant that the activity measured using the polypeptide encoded by the variant leptin polynucleotide in assays is less than 25%, alternatively less than 10% (preferably less than 5%, more preferably less than 2%, most preferably less than 1%) of the activity measured using the leptin polypeptide encoded by the reference sequence.

A polynucleotide fragment is a polynucleotide having a sequence that entirely is the same as part, but not all, of a given nucleotide sequence, preferably the nucleotide sequence encoding a leptin polypeptide that binds and activates LSR, and variants thereof as described above, and the complements of these polynucleotides. Such fragments may be "free-standing", i.e. not part of or fused to other polynucleotides, or they may be comprised within a single larger non-leptin polynucleotide of which they form a part or region. However, several fragments may be comprised within a single larger polynucleotide.

Optionally, such fragments may consist of a contiguous span that ranges in length from 8, 10, 12, 15, 18 or 20 to 25, 35, 40, 50, 60, 70, 80, 90, 100, 110, 120, 130, 140, or 150 nucleotides, or be specified as being 12, 15, 18, 20, 25, 35, 40, 50, 60, 70, 80, 90, 10, 110, 120, 130, 140, or 150 nucleotides in length.

A preferred embodiment of the invention includes isolated, purified, or recombinant polynucleotides consisting of a contiguous span of at least 12, 15, 18, 20, 25, 30, 35, 40, 50, 60, 70, 80, 90, 100, 110, 120, 130, 140, or 150 nucleotides encoding a leptin polypeptide of the invention, or the complements thereof, wherein said contiguous span encodes a fragment of leptin that retains the same activities and activity levels as the leptin polypeptide encoded by the reference polynucleotide sequence, or encodes a fragment of leptin where the level of one or more activities is increased, or alternatively where the level of one or more activities is decreased or even absent as described above.

An additional preferred embodiment of the invention includes isolated, purified, or recombinant polynucleotides consisting of a contiguous span of 8 to 50 nucleotides of a leptin polypeptide of the invention, or their variants, or the complements thereof, wherein said contiguous span encodes a fragment of leptin that retains the same activities and activity levels as the leptin polypeptide encoded by the reference polynucleotide sequence, or encodes a fragment of leptin where the level of one or more activities is increased, or alternatively where the level of one or more activities is decreased or even absent as described above. Any of the above-described fragments may be comprised within a larger non-leptin polynucleotide fragment.

II. Leptin Polypeptide Fragments of the Invention

Leptin polypeptide fragments that bind/activate/modulate LSR have been identified (Examples 1-8). This region was identified by a comparison of the human and murine leptin amino acid sequences, and its activity confirmed in vitro and in vivo (See Examples 1-8). The advantages to having identified a leptin fragment responsible for leptin activity, include its use (1) as part of an assay system to discover leptin receptors and binding partners (in association with LSR for example), (2) as a lead molecule for the design of other compounds able to modulate LSR activity, and (3) as part of a treatment and/or prevention for obesity-related diseases and disorders. Knowledge of specific polypeptides involved is especially useful since it allows its use in assay systems (rather than the entire protein) and keeps the cost down (easily synthesized). In addition, a peptide can be expected to easily crystallize in the correct conformation to allow structure-function studies to design other small molecule activators. Finally, use of just the active portion in treatment should increase the chances of the peptide remaining active and potentially decreasing side-effects.

Furthermore, in the process of identifying the "active" portion of human leptin for human cells, a corresponding inhibitory portion of mouse leptin for human cells was identified. Comparisons between the two highly similar fragments will enable the identification of important residues for both increasing the activity of LSR and inhibiting the activity of LSR. This will be useful both in competitive assays for inhibitors and activators of LSR, and also for treatments in mammals and animals where inhibition of LSR is desired.

The invention relates to leptin polypeptides as well as to variants, fragments, analogs and derivatives of the leptin polypeptides described herein, including modified leptin polypeptides. Preferred embodiments of the invention feature a leptin polypeptide that consists of a sequence described in Example 10, or variants, fragments, analogs, or derivatives thereof. Preferably the polypeptides are, purified, isolated and/or recombinant.

In other preferred embodiments, the invention features a leptin polypeptide fragment that modulates the activity of LSR, comprising at least 4, but not more than 50 contiguous amino acids of any one of the leptin polypeptide sequences set forth in FIG. 13, wherein said at least 4 and not more than 50 contiguous amino acids comprise the leptin fragment central sequence. By the "leptin fragment central sequence" as used herein is meant the four variable amino acids of the active leptin peptide identified in Example 10 by sequence comparisons and molecular modeling. These residues comprise ETLD (SEQ ID NO:40) and QKPE (SEQ ID NO:41) for the human and mouse sequences, respectively, in FIG. 13. Preferably, the leptin polypeptide fragment comprises at least 10, but not more than 50, more preferably at least 15 but not more than 40, or at least 20 and not more than 40, or most preferably at least 15 but not more than 30, or 20 but not more than 30 contiguous amino acids of any one of the leptin polypeptide sequences set forth in FIG. 13, wherein said contiguous amino acids comprise the leptin polypeptide variable region. Preferably the leptin polypeptide fragment is human or mouse, but most preferably human, or a derivative or variant thereof.

Variant leptin polypeptides of the invention may be 1) ones in which one or more of the amino acid residues are substituted with a conserved or non-conserved amino acid residue and such substituted amino acid residue may or may not be one encoded by the genetic code, or 2) ones in which one or more of the amino acid residues includes a substituent group, or 3) ones in which a modified leptin polypeptide is fused with another compound, such as a compound to increase the half-life of the polypeptide (for example, polyethylene glycol), or 4) ones in which the additional amino acids are fused to a modified leptin polypeptide, such as a leader or secretory sequence or a sequence which is employed for purification of the modified leptin polypeptide or a pre-protein sequence. Such variants are deemed to be within the scope of those skilled in the art.

Amino acid changes present in a variant polypeptide may be non-conservative amino acid changes but more preferably are conservative amino acid changes. In cases where there are one or more amino acid changes, preferred leptin polypeptides include those that retain the same activities and activity levels as the reference leptin polypeptide sequence, as well as those where the level of one or more activities is increased, and alternatively where the level of one or more activities is decreased or even absent. Assays for determining leptin polypeptide activities of the invention are described herein in the Examples (1-8 & 13) in more detail, but include LSR binding leading to the uptake and degradation of leptin, as well as the upregulation of LSR receptors that bind, uptake and degrade triglyceride-rich lipoproteins. Examples of assays to determine the presence or absence of specific leptin activities and the level of the activity(s) are also described herein. Definitions of activities are provided in "Leptin Polynucleotides of the Invention" (section I).

In preferred embodiments, the invention features a variant of a leptin polypeptide fragment that modulates the activity of LSR, consisting of a 22 contiguous amino acid sequence that is at least 75% identical to the leptin fragment variable region of any one of the leptin polypeptide sequences set forth in FIG. 13. By the "leptin fragment variable region" as used herein is meant the region of 22 amino acids that is shaded in FIG. 13 for all the species in the alignment. Preferably, the 22 contiguous amino acid sequence is at least 85% identical to the leptin fragment variable region of any one of the leptin polypeptide sequences set forth in FIG. 13, more preferably 90% identical, most preferably 95% identical and optionally 100% identical. Preferably the sequence is human or mouse, and most preferably human.

In yet other preferred embodiments, the invention features a variant of a leptin polypeptide fragment that modulates the activity of LSR, consisting of a 22 contiguous amino acid sequence, wherein at least 16 of the 22 amino acids are identical to the leptin fragment variable region of any one of the leptin polypeptide sequences set forth in FIG. 13. Preferably, at least 18 of the 22 amino acids are identical to the leptin fragment variable region of any one of the leptin polypeptide sequences set forth in FIG. 13, more preferably 20 of the 22 are identical, most preferably all of the amino acids are identical. Preferably the sequence is human or mouse, and most preferably human.

A polypeptide fragment is a polypeptide having a sequence that is entirely the same as part, but not all, of a given polypeptide sequence, preferably a polypeptide encoded by a leptin gene and variants thereof. Such fragments may be "free-standing", i.e. not part of or fused to other polypeptides, or they may be comprised within a single larger non-leptin polypeptide of which they form a part or region. However, several fragments may be comprised within a single larger polypeptide. As representative examples of polypeptide fragments of the invention, there may be mentioned those which have from about 4, 5, 6, 7, 8, 9 or 10 to 15, 10 to 20, 15 to 40, or 30 to 55 amino acids long. Preferred are those fragments containing at least one amino acid substitution or deletion in a leptin polypeptide.

The present invention is particularly focused on a set of variant leptin polypeptides and the fragments thereof. A preferred set of polypeptides of the invention include isolated, purified, or recombinant polypeptides comprising a contiguous span of at least 3 (preferably at least 6, more preferably at least 10, most preferably at least 15) amino acids of any of the leptin fragment variable regions of the sequences provided in FIG. 13.

III. Zinc Finger Proteins of the Invention

Zinc finger proteins of the Cys2His2 type are malleable DNA binding proteins that can be designed to bind diverse sequences, and that typically contain 3 zinc finger domains. The inventors contemplate the use of any zinc finger protein engineered to bind the DNA of interest, specifically. Although six-fingered proteins have been described to target unique sites within the genome (International Publication WO 98/54311, hereby incorporated herein by reference in its entirety including any figures, tables and drawings) proteins with different numbers of fingers that are engineered to bind specifically to the genome are also included in the invention. The six-fingered proteins described in WO 98/54311, bind two 9 contiguous base pair fragments (separated by 0, 1, 2, or 3 nucleotides) of DNA or RNA in a sequence specific fashion, and can be used to regulate gene transcription. The zinc finger proteins of the invention also include those that are designed to bind sequences a greater distance apart and thereby confer greater specificity with fewer (or the same number, or more) "fingers". Methods for designing the zinc finger proteins of the invention, as well as for determining the sequences to which the zinc finger proteins bind, are described in International Publication WO 98/54311 entitled "Zinc Finger Protein Derivatives and Methods Therefor".

For one embodiment of the invention, zinc finger proteins have been designed that will bind to the 5' regulatory regions and selected introns of LSR and thereby inhibit or augment the transcription of endogenous LSR as described herein (Example 12). Exogenous LSR that is introduced into the cell without these regulatory regions or introns (cDNA) will be expressed normally. This can be useful in vitro both as a research tool to study the role of the various LSR components in leptin signaling and triglyceride-rich lipoprotein uptake and degradation, for example, and as part of an assay to discover modulators of LSRlep and LSRtg activity. Therefore, in currently preferred embodiments, zinc finger proteins are not designed to bind to the exons of LSR. However, in circumstances where no endogenous nor exogenously-introduced LSR activity is desired in a cell, for example, zinc finger proteins designed to bind to LSR exons could be useful.

The invention features a zinc finger protein, comprising a DNA binding domain that binds specifically to 18 nucleotides of a sequence at least 50% homologous to SEQ ID NO:1, wherein said 18 nucleotides comprise two fragments of 9 contiguous nucleotides, and wherein said fragments are separated by 0, 1, 2, or 3 nucleotides. In preferred embodiments, the zinc finger protein binds to sequences that are at least 50% homologous to the sequence of the introns of SEQ ID NO:1. Preferably, the sequence is at least 50% homologous to the sequence of the first intron of SEQ ID NO:1. In other preferred embodiments, the zinc finger protein binds specifically to 18 nucleotides of a sequence that is 75% identical, 80%, 85%, or 90% identical, or most preferably 99 to 100% identical to SEQ ID NO:1, the introns of SEQ ID NO:1, or preferably the first intron of SEQ ID NO:1.

In preferred embodiments of the invention, the zinc finger protein of the invention further comprises a functional domain selected from the group consisting of a transcription repressor and a transcription initiator. These repressors and initiators can be any that are known in the art. Preferably, the repressor is a KRAB repressor and the initiator is a VP16 initiator. In highly preferred embodiments, the protein further comprises a small molecule regulatory system that can be any known in the art; however, the system is preferably selected from the group consisting of a Tet system, RU486, and ecdysone.

It is envisioned that zinc finger proteins could be designed to bind to any 18 or more contiguous base pairs of a sequence at least 50%, preferably 75%, more preferably 90%, most preferably 95% identical to the 5' regulatory region (for example, residues 1-2000 of SEQ ID NO:1) or any of the introns of LSR (for example, 2357 to 3539, 3885 to 12162, 12283 to 15143, 15201 to 17764, 15912 to 19578, 19753 to 19898, 19959 to 20055, 20188 to 20328, and 20958 to 21046 of SEQ ID NO:1), and more preferably residues 2357 to 3539 of SEQ ID NO:1. In particular, introns within 3,000 base pairs of the LSR start site are preferred, for example introns 1 through 3.

Guidance is available for determining optimal base pair stretches for zinc finger protein binding, and for determining what zinc finger amino acids will bind to what DNA sequences (WO 98/54311). This information has been used to design an algorithm for designing zinc finger proteins available from Sangamo BioSciences. However, as described in WO 98/54311, zinc finger proteins for binding a given piece of DNA can be identified by screening or "panning" libraries of zinc finger proteins with the DNA sequence. Zinc finger libraries can be made, for example, by randomly mutating genes encoding known zinc finger proteins (WO 98/54311). The effectiveness of the zinc finger protein identified by the panning procedure can then be assessed in the *E. coli* method described in WO 98/54311 (co-transfection of genes encoding the zinc finger protein and the gene of which the DNA sequence makes up a part). The effectiveness of the zinc finger protein for inhibiting LSR expression can be further tested using the assay systems described in the Examples (1-8); in particular the use of FACS following staining with an LSR specific antibody and quantitative PCR will be useful.

In preferred embodiments, addition of the zinc finger protein preferably inhibits LSR transcription completely, or inhibits LSR translation completely. By "inhibits transcription completely" is meant that the level of transcription following addition of the zinc finger protein is preferably below the level of detection by the assay used as compared to control cells. The assay used may be a Northern blot, or any other assay that measures RNA expression, such as quantitative PCR. Alternatively, the level of transcription of LSR may be significantly reduced. By "significantly reduced" is meant that the amount of RNA is preferably reduced at least 2-fold, more preferably at least 5-fold, and most preferably at least 10-fold compared to the level RNA prior to the addition of the zinc finger protein, or the level in control cells.

Similarly, by "inhibits translation completely" is meant that LSR protein is preferably below the level of detection by the assay used compared with control cells. The assay used may be a Western blot, or dot blot, or other type of immunoassay for example, or any other assay known in the art to be used to measure or detect the presence of proteins, such as FACS with fluorescent antibodies to LSR. Alternatively, the level of translation of LSR may be significantly reduced. By "significantly reduced" is meant the amount of protein present is preferably reduced at least 2-fold, more preferably at least 5-fold, most preferably at least 10-fold compared to the level of protein present prior to the addition of zinc finger protein, or in control cells.

Highly preferred sequences to be used for designing zinc finger proteins include, residues 1841 to 1860, 1880 to 1898, 1918 to 1945, 1951 to 1973, and 3362 to 3382 of human LSR (SEQ ID NO:1) and of the homologous regions in genes coding for LSR proteins of other species, preferably including mouse and rat LSR. The genomic sequences encoding LSR from other species can be identified by methods well-known in the art.

These zinc finger proteins can also be useful in vivo both as part of an assay system in animal models to discover modulators of LSRlep (at least $\alpha'$, may include $\beta$ and/or $\alpha$) and LSRtg (at least $\alpha$, may include $\beta$ and/or $\alpha'$) activity, as well as in gene surgery in which transcription of endogenous LSR is inhibited as part of the treatment for an obesity-related disease or disorder. This could be useful in a case where the LSR message was being over-expressed, or incorrectly expressed (mutated), for example. A potential therapy would include providing this zinc finger protein alone, in cases of simple over-expression, or in conjunction with other appropriate components of LSR if the cellular LSR was mutated. These proteins could be targeted to the appropriate cells (those with LSR) by using liposomes, for example, with leptin or another LSR binding protein in the liposome membrane.

In an alternative embodiment of the invention, zinc finger proteins are designed to bind to the 5' regulatory regions of LSR and thereby increase the transcription of endogenous LSR. Typically, within the 5' regulatory region of genes are promoters as well as other regulatory elements. Binding of zinc finger proteins to certain regions of the DNA may serve to facilitate binding of the initiation complex and thus transcription of the gene. For instance, where some unusual folding prevents access to the promoter region, if a zinc finger protein were to bind the DNA upstream such that the folding were prevented, then the promoter would have greater access and enhanced transcription should result. Alternatively, it may be possible to design a zinc finger protein that binds the promoter region directly, thereby initiating transcription.

In these and other circumstances, zinc finger binding proteins designed to bind stretches of DNA in the 5' regulatory region as described above can be tested for their ability to enhance transcription of LSR. Thus, in preferred embodiments, addition of the zinc finger protein preferably significantly increases LSR transcription, or significantly increases LSR translation. By "significantly increases LSR transcription" is meant that the level of transcription following addition of the zinc finger protein is preferably increased at least 2-fold, more preferably at least 5-fold, and most preferably at least 10-fold compared to the level RNA prior to the addition of the zinc finger protein. The assay used may be a Northern blot, or any other assay that measures RNA expression. Alternatively, if the starting level of RNA transcription is below the level of detection by the assay used, "significantly increases LSR transcription" may mean that the level of transcription of LSR may become detectable on the addition of the zinc finger binding protein.

Similarly, by "significantly increases LSR translation" is meant that the level of translation following addition of the zinc finger protein is preferably increased at least 2-fold, more preferably at least 5-fold, and most preferably at least 10-fold compared to the level of translation prior to the addition of the zinc finger protein. The assay used may be a Western blot, or dot blot, or other type of immunoassay for example, or any other assay known in the art to be used to measure or detect the presence of proteins. Alternatively, if the starting level of LSR protein is below the level of detection by the assay used, "significantly increases LSR translation" may mean that LSR protein may become detectable after the addition of the zinc finger binding protein.

These zinc finger proteins can be useful in vivo in gene surgery in which transcription of endogenous LSR is enhanced as part of the treatment for an obesity-related disease or disorder. This can be envisioned in a situation where higher levels of the LSR protein are thought to be advantageous for the patient clinically. For example, increased expression of LSR could be advantageous when the LSR gene is normal, but is expressed at lower than normal levels, or when it is expressed at normal levels, but does not function as efficiently as it should in clearing triglycerides from the bloodstream, or when some other abnormality results in abnormally high levels of triglycerides and an increased amount of LSR protein is necessary to clear them.

In a further alternative embodiment of the invention, zinc finger proteins are designed to bind to any sequence of 18 or more contiguous base pairs of LSR mRNA and thereby inhibit translation of LSR. In preferred embodiments, expression of all three forms of LSR are inhibited by the zinc finger protein. In an alternative embodiment, zinc finger proteins are designed to specifically inhibit expression of the LSR α, α', or β subunit individually, or to inhibit both the LSR α and α' subunits. All three forms of LSR can be inhibited by zinc finger proteins targeted to mRNA fragments transcribed from exons one through 3 and exon 6 to the end. The α subunit can be targeted with zinc finger proteins designed to bind in exon 4. The α' subunit can be targeted with zinc finger proteins designed to bind to the splice site between exon 3 and exon 5. The β subunit can be targeted with zinc finger proteins designed to bind to the splice site between exon 3 and exon 6. Both the α and α' subunits can be targeted with zinc finger proteins designed to bind to exon 5.

These zinc finger proteins would be useful for many of the uses previously described for zinc finger proteins binding to and inhibiting or increasing transcription of LSR DNA. Similarly the definitions for inhibiting or increasing LSR transcription and tests for the desired zinc finger proteins and methods for designing and making them would be as previously described. In addition, for all of the zinc fingers described, it should be remembered that the system can be further controlled by addition of a small molecule control system (for example the Tet-responsive system, or RU486, or ecdysone) to the cell. This allows greater control/greater finesse for an in vitro assay system, in particular, but can be used in vivo as well. The basic idea is to provide the zinc finger with part of the Tet system integrated upstream such that transcription of the zinc finger protein can be regulated by the addition of an outside element, for example Dox or Tc. These methods are well-known to those in the art.

IV. Polynucleotides Encoding Zinc Finger Polypeptides of the Invention

The invention also features polynucleotides that encode the zinc finger polypeptides of the invention described above. In one method of identifying the desired zinc finger polypeptides of the invention, libraries are screened (panned) for those clones expressing a zinc finger protein that binds to the desired nucleotide sequence. Frequently, multiple clones are identified that express zinc finger proteins that bind to the nucleotide sequence. All the variant polynucleotides that code for the zinc finger polypeptide(s) that bind to the desired sequence are also part of the present invention.

Variants of polynucleotides, as the term is used here, are polynucleotides whose sequence differs from a reference polynucleotide; in this case a reference polynucleotide is the polynucleotide that is ultimately chosen to be used. Thus, the variant of the polynucleotide would frequently be the result of mutagenesis techniques as described in WO 98/54311. Generally, differences are limited so that the nucleotide sequences of the reference and the variant are closely similar overall and, in many regions, identical.

Nucleotide changes present in a variant polynucleotide are preferably silent, which means that they do not alter the amino acids encoded by the polynucleotide. However, nucleotide changes may also result in amino acid substitutions, additions, deletions, fusions and truncations in the polypeptide encoded by the reference sequence. The substitutions, deletions or additions may involve one or more nucleotides. Alterations in the zinc finger polypeptide coding regions of the invention may produce conservative or non-conservative amino acid substitutions, deletions or additions in the encoded protein. Preferably, the nucleotide substitutions result in non-conservative amino acid changes and more preferably in conservative amino acid changes in the encoded polypeptide.

In cases where the nucleotide substitutions result in one or more amino acid changes, preferred zinc finger polypeptides include those that retain the same activities and activity levels as the zinc finger polypeptide encoded by the reference polynucleotide sequence, as well as those where the level of one or more activities is increased, and alternatively where the level of one or more activities is decreased or even absent. Zinc finger polypeptide activities of the invention and methods for testing are described above.

A polynucleotide fragment is a polynucleotide having a sequence that entirely is the same as part, but not all, of a given nucleotide sequence, preferably the nucleotide sequence encoding a zinc finger polypeptide, and variants thereof, as described above, and the complements of these polynucleotides. Such fragments may be "free-standing", i.e. not part of or fused to other polynucleotides, or they may be comprised within a single larger polynucleotide of which they form a part or region. However, several fragments may be comprised within a single larger polynucleotide. Optionally, such fragments may consist of a contiguous span that ranges in length from 8, 10, 12, 15, 18 or 20 to 25, 35, 40, 50, or 60 nucleotides, or be specified as being 12, 15, 18, 20, 25, 35, 40, 50, or 60 nucleotides in length.

V. Chimeric Oligonucleotides of the Invention

Chimeraplasty is a technique used to change the nucleotide sequence of DNA of cells and of animals (Science 285:316-318 (1999)). It can be used to create or to correct mutations, usually point mutations, that have an effect on the protein coding sequence. The technique relies on hybrid molecules of DNA and RNA called chimeras that contain DNA with a mutation in its sequence (compared to the target sequence in the cell) flanked by RNA that perfectly mirrors the flanking target gene sequence. The target gene sequence is thought to be modified through the action of the cell's DNA repair machinery as a result of the pairing of the target DNA with the chimera containing the mutated sequence.

In the present invention, the advantages to using chimeraplasty to modify LSR include: (1) case of creating cells lacking LSR polypeptides for use in assays or gene surgery; (2) specifically blocking production of the α subunit or the α and α' subunits for use in assays or in gene surgery; and (3) the ability to correct defects in the LSR gene in cells in vitro and in vivo for use in gene surgery. Chimeraplasty has been shown to be effective for correcting (or creating) mutations in cells in vitro and in vivo in animals (Cole-Strauss, et al. Science 273: 13861389 (1996); Alexeev and Yoon Nature Biotechnology 16:1343-1346 (1998); Kren et al Nature Medicine 4: 285-290 (1998); Yoon et al Proc Natl. Acad. Sci. USA 93: 2071-2076 (1996); Xiang et al J Mol Med 75: 829-825 (1997), hereby incorporated by reference herein in their entirety including any figures, drawings, or tables). Chimeraplasty is particularly useful in cases of point mutations that need to be corrected to allow either expression or function of the protein.

Chimeraplasty apparently works through the cell's own DNA repair system to correct the targeted gene. Although the gene is not corrected in 100% of the cells following transfection in vitro or introduction into the animal in vivo, the genes in enough of the cells have been found to be changed to permit a clinically detectable change. This could, in fact, be beneficial in the LSR system where it is unlikely that you would ever want to completely prevent LSR expression. However, reduction in LSR expression might be advantageous in some obesity-related diseases and disorders. In particular, specific reduction in any one or more of the α, α', or β subunits could be advantageous.

The invention features a chimeric oligonucleotide, comprising at least 9 contiguous nucleotides from a sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:15, and SEQ ID NO:16, wherein said at least 9 contiguous nucleotides comprise at least one amino acid codon selected from the group consisting of TTA, TTG, TCA, TCG, TAU, TAC, TGT, TGC, TGG, CAA, CAG, AGA, GAA, GAG, and GGA, and wherein a point mutation is present in said codon such that said codon is a stop codon. In preferred embodiments, the sequence is selected from the group consisting of Exon 1, Exon 4 and Exon 5 from SEQ ID NO:1 and homologous sequences from mouse or rat, preferably mouse.

Another embodiment of the invention features chimeraplast LSR polynucleotides, where the polynucleotide comprises at least 7 (preferably at least 13, more preferably at least 25, most preferably at least 35 nucleotides of the LSR gene (or its complement), and where the DNA portion of the chimera comprises a point mutation such that instead of coding for an amino acid, it now codes for a termination codon. Thus, substitution of this nucleotide for the nucleotide present in the endogenous LSR gene, results in a stop codon being created al the site. The other nucleotides present in both the DNA and RNA portions of the chimera arc 100% complementary to the flanking regions of the endogenous TSR gene. The DNA portion of the chimera is at least 3 consecutive nucleotides in length, preferably at least 5 consecutive nucleotides in length, optionally at least 7 or at least 11 nucleotides in length. The point mutation is preferably the middle nucleotide (n; alternatively n+1, or n−1; less preferably n+2, or n−2; n+3, or n−3, etc.) of the DNA part of the chimera when the DNA portion has an odd number of nucleotides (AGnCT, AnGCT, AGCnT, for example), or the n+1 or n−1 positions (less preferably n+2, or n−2; n+3, or n−3, etc.) when the sequence has an even number of nucleotides (AnCT, AcnT, for example). The RNA portion of the chimera is at least 4 consecutive nucleotides in length, preferably at least 10 consecutive nucleotides in length, more preferably at least 20 consecutive nucleotides in length, and most preferably at least 30 consecutive nucleotides in length. The RNA portion of the chimera flanks the DNA portion of the chimera, preferably with an equal number of nucleotides on each side of the DNA sequence (x; when the number on RNA residues is even), less preferably with x+1 on the upstream side and x−1 on the downstream side or alternatively x+1 on the downstream side and x−1 on the upstream side; even less preferably with x+2 on the upstream side and x−2 on the downstream side or alternatively x+2 on the downstream side and x−2 on the upstream side, and so on. Similarly, when the number of RNA residues is odd, there are either x+1 on the upstream side and x−1 on the downstream side or alternatively x+1 on the downstream side and x−1 on the upstream side of the DNA; less preferably there are x+2 on the upstream side and x−2 on the downstream side or alternatively x+2 on the downstream side and x−2 on the upstream side, and so on. In some cases, particularly when the point mutation is not in the center of the DNA part of the chimera, the number of residues of RNA flanking the DNA is preferably not equal on both sides. In some cases it is preferred that there are more RNA residues on one side than the other so as to have the point mutation be located at the center of the chimera, or at least n+1 or n−1 from the center of the chimera, less preferably n+2, or n−2 from the center, etc. Sequences that encode stop codons include TAA, TAG, and TGA. Therefore, sequences encoding the amino acids leucine (TTA or TTG), serine (TCA or TCG), tyrosine (TAU or TAC), cysteine (TGT or TGC), tryptophan (TGG), glutamine (CAA or CAG), arginine (AGA), glutamate (GAA or GAG), or glycine (GGA), for example, can be changed to one of the stop codons by a single polynucleotide exchange. The preferred stop codon is TGA. The exact design of the chimeras will depend on the particular sequence to be mutated, but guidance has been given in the papers listed above and in the Examples herein. In general, however, the sequence should be at least 14 nucleotides in length (preferably 18, more preferably 25, most preferably 30) to ensure specificity to the desired sequence. Preferably, the amino acid to be mutated to a termination codon is located at the 5' end of the coding sequence, preferably within the first exon, and preferably is the first amino acid that can be mutated in this way after the first ATG or most preferably the second ATG. Amino acids to be mutated to stop all LSR expression should not be selected from Exon 4 or Exon 5, since exon 4 is not present in the α' subunit, and neither Exon 4 nor Exon 5 is present in the β subunit. The success of a chimeraplast in preventing LSR expression can be tested using the techniques described herein, to include screens for the presence of the mRNA by Northern blot, for example, and for the protein by Western blot, for example.

Alternatively, in some preferred embodiments it is preferable to stop expression of the LSR α subunit only. To do this, the amino acid to be mutated is preferably located in Exon 4 of LSR, since this Exon is not present in the α' or β subunits. In other preferred embodiments it is preferable to prevent expression of both α and α' subunits, but not the β subunit. To do this, the amino acid to be mutated is preferably located in Exon 5 of LSR, since this exon is present in both α and α' subunits, but not the β subunit.

In another embodiment, the invention features chimeraplast LSR polynucleotides, where the polynucleotide comprises at least 7 (preferably at least 13, more preferably at least 25, most preferably at least 35 nucleotides of the LSR gene (or its complement), and where the DNA portion of the chimera comprises one of the alleles of the single nucleotide polymorphisms (SNPs) described in U.S. Provisional Application No. 60/119,592, entitled "Polymorphic Markers of the LSR Gene" by Blumenfeld, Bougueleret, and Bihain, filed Feb. 10, 1999 and indicated in Table A. Preferably, the SNP's are selected from the group consisting of A1, A2, A3, A4, A5, A6, A7, A8, A9, A10, A11, A12, A13, A14, A15, A16, A17, A18, A19, A20, A21, A22, A23, A24, A25, A26, A27, A28, A29, A30, A31, AND A32. The SNPs may be in either coding or non-coding regions of the LSR gene. Some SNPs in the coding region result in amino acid changes that may affect the activity of LSR. However, the majority of the SNPs do not code for amino acid changes. These nucleotide changes can also modulate the activity of LSR in a variety of ways, for example by interfering with the binding of a regulatory molecule that influences the splicing of the introns, particularly where there is differential splicing depending on the subunit to be expressed or by affecting the binding of promoters or the function of other regulatory sequences in the 5' and 3' regions of the gene. Changes in the expression of various subunits, or the levels of expression of LSR in general, can have profound effects on the obesity of patients.

VI. Recombinant Vectors of the Invention

The term "vector" is used herein to designate either a circular or a linear DNA or RNA molecule, that is either double-stranded or single-stranded, and that comprises at least one polynucleotide of interest that is sought to be transferred in a cell host or in a unicellular or multicellular host organism.

The present invention relates to recombinant vectors comprising any one of the polynucleotides described herein.

The present invention encompasses a family of recombinant vectors that comprise polynucleotides encoding leptin polypeptides of the invention, polynucleotides encoding zinc finger proteins of the invention, and chimeraplastic polynucleotides of the invention as described herein.

In a first preferred embodiment, a recombinant vector of the invention is used to amplify the inserted polynucleotide in a suitable cell host, this polynucleotide being amplified every time that the recombinant vector replicates. The inserted polynucleotide can be one that encodes leptin polypeptides of the invention or zinc finger polypeptides of the invention, or a chimeraplast polynucleotide.

A second preferred embodiment of the recombinant vectors according to the invention, consists of expression vectors comprising either a polynucleotide encoding leptin polypeptides of the invention or zinc finger proteins of the invention, or both. Within certain embodiments, expression vectors are employed to express a leptin polypeptide of the invention, preferably a modified leptin polypeptide described in the present invention, which can be then purified and, for example, be used in screening assays or as a treatment for obesity-related diseases. In other embodiments, expression vectors are employed to express a zinc finger protein of the invention, preferably one that inhibits LSR expression or expression of specific subunits of LSR as described in the present invention, which can be then purified and, for example, be used in screening assays or as a treatment for obesity-related diseases. In other embodiments, the expression vectors are used for constructing transgenic animals and also for gene surgery, in particular, expression vectors containing a polynucleotide encoding zinc finger proteins of the invention.

Expression requires that appropriate signals are provided in the vectors, said signals including various regulatory elements, such as enhancers/promoters from both viral and mammalian sources, that drive expression of the genes of interest in host cells. Dominant drug selection markers for establishing permanent, stable, cell clones expressing the products are generally included in the expression vectors of the invention, as they are elements that link expression of the drug selection markers to expression of the polypeptide.

More particularly, the present invention relates to expression vectors which include nucleic acids encoding a leptin polypeptide fragment of the invention, or a modified leptin polypeptide as described herein, or variants or fragments thereof, under the control of a regulatory sequence selected among the leptin regulatory polynucleotides, or alternatively under the control of an exogenous regulatory sequence. The present also relates to expression vectors which include nucleic acids encoding a zinc finger polypeptide of the invention, or a modified zinc finger polypeptide as described herein, or variants or fragments thereof, under the control of an exogenous regulatory sequence.

Consequently, preferred expression vectors of the invention are selected from the group consisting of: (a) a leptin regulatory sequence and driving the expression of a coding polynucleotide operably linked thereto; (b) a leptin polypeptide coding sequence of the invention, operably linked to regulatory sequences allowing its expression in a suitable cell host and/or host organism. Other preferred expression vectors of the invention comprise a zinc finger polypeptide coding sequence of the invention, operably linked to regulatory sequences allowing its expression in a suitable cell host and/or host organism.

Some of the elements which can be found in the vectors of the present invention are described in further detail in the following sections.

1) General Features of the Expression Vectors of the Invention:

A recombinant vector according to the invention comprises, but is not limited to, a YAC (Yeast Artificial Chromosome), a BAC (Bacterial Artificial Chromosome), a phage, a phagemid, a cosmid, a plasmid, or even a linear DNA molecule which may consist of a chromosomal, non-chromosomal, semi-synthetic or synthetic DNA. Such a recombinant vector can comprise a transcriptional unit comprising an assembly of:

(1) a genetic element or elements having a regulatory role in gene expression, for example promoters or enhancers. Enhancers are cis-acting elements of DNA, usually from about 10 to 300 bp in length that act on the promoter to increase the transcription.

(2) a structural or coding sequence which is transcribed into mRNA and eventually translated into a polypeptide, said structural or coding sequence being operably linked to the regulatory elements described in (1); and (3) appropriate transcription initiation and termination sequences. Structural units intended for use in yeast or eukaryotic expression systems preferably include a leader sequence enabling extracellular secretion of translated protein by a host cell. Alternatively, when a recombinant protein is expressed without a leader or transport sequence, it may include a N-terminal residue. This residue may or may not be subsequently cleaved from the expressed recombinant protein to provide a final product.

Generally, recombinant expression vectors will include origins of replication, selectable markers permitting transformation of the host cell, and a promoter derived from a highly expressed gene to direct transcription of a downstream structural sequence. The heterologous structural sequence is assembled in appropriate phase with translation initiation and termination sequences, and preferably a leader sequence capable of directing secretion of the translated protein into the periplasmic space or the extracellular medium. In a specific embodiment wherein the vector is adapted for transfecting and expressing desired sequences in mammalian host cells, preferred vectors will comprise an origin of replication in the desired host, a suitable promoter and enhancer, and also any necessary ribosome binding sites, polyadenylation sites, splice donor and acceptor sites, transcriptional termination sequences, and 5'-flanking non-transcribed sequences. DNA sequences derived from the SV40 viral genome, for example SV40 origin, early promoter, enhancer, splice and polyadenylation sites may be used to provide the required non-transcribed genetic elements.

2) Regulatory Elements

Promoters

The suitable promoter regions used in the expression vectors according to the present invention are chosen taking into account the cell host in which the heterologous gene has to be expressed. The particular promoter employed to control the expression of a nucleic acid sequence of interest is not believed to be important, so long as it is capable of directing the expression of the nucleic acid in the targeted cell. Thus, where a human cell is targeted, it is preferable to position the nucleic acid coding region adjacent to and under the control of a promoter that is capable of being expressed in a human cell, such as, for example, a human or a viral promoter.

A suitable promoter may be heterologous with respect to the nucleic acid for which it controls the expression or alternatively can be endogenous to the native polynucleotide containing the coding sequence to be expressed. Additionally, the promoter is generally heterologous with respect to the recombinant vector sequences within which the construct promoter/coding sequence has been inserted.

Promoter regions can be selected from any desired gene using, for example, CAT (chloramphenicol transferase) vectors and more preferably pKK232-8 and pCM7 vectors. Preferred bacterial promoters are the LacI, LacZ, the T3 or T7 bacteriophage RNA polymerase promoters, the gpt, lambda PR, PL and trp promoters (EP 0036776), the polyhedrin promoter, or the p10 protein promoter from baculovirus (Kit Novagen) (Smith et al. (1983) *Mol. Cell. Biol.* 3:2156-2165; O'Reilly et al., 1992, Baculovirus expression vectors: a Laboratory Manual. W.H. Freeman and Co., New York the lambda PR promoter or also the trc promoter.

Eukaryotic promoters include CMV immediate early, HSV thymidine kinase, early and late SV40, LTRs from retrovirus, and mouse metallothionein-L. Selection of a convenient vector and promoter is well within the level of ordinary skill in the art.

The choice of a promoter is well within the ability of a person skilled in the field of genetic engineering. For example, one may refer to the book or (Sambrook, J., Fritsch, E. F., and T. Maniatis. (1989), *Molecular Cloning: A Laboratory Manual.* 2ed. Cold Spring Harbor Laboratory, Cold Spring Harbor, N.Y.)) or also to the procedures described by (Fuller S. A. et al. (1996) *Immunology in Current Protocols in Molecular Biology*, Ausubel et al., Eds, John Wiley & Sons, Inc., USA).

Other Regulatory Elements

Where a cDNA insert is employed, one will typically desire to include a polyadenylation signal to effect proper polyadenylation of the gene transcript. The nature of the polyadenylation signal is not believed to be crucial to the successful practice of the invention, and any such sequence may be employed such as human growth hormone and SV40 polyadenylation signals. Also contemplated as an element of the expression cassette is a terminator. These elements can serve to enhance message levels and to minimize read through from the cassette into other sequences.

The vector containing the appropriate DNA sequence as described above, more preferably LSR gene inhibitory or activating polynucleotide, a polynucleotide encoding a leptin polypeptide or both of them, can be utilized to transform an appropriate host to allow the expression of the desired polypeptide or polynucleotide.

3) Selectable Markers

Such markers would confer an identifiable change to the cell permitting easy identification of cells containing the expression construct. The selectable marker genes for selection of transformed host cells are preferably dihydrofolate reductase or zeocin, hygromycin or neomycin resistance for eukaryotic cell culture, TRP1 for *S. cerevisiae* or tetracycline, rifampicin or ampicillin resistance in *E. coli*, or levan saccharase for mycobacteria, this latter marker being a negative selection marker.

4) Preferred Vectors

Bacterial Vectors

As a representative but non-limiting example, useful expression vectors for bacterial use can comprise a selectable marker and a bacterial origin of replication derived from commercially available plasmids comprising genetic elements of pBR322 (ATCC 37017). Such commercial vectors include, for example, pKK223-3 (Pharmacia, Uppsala, Sweden), and GEM1 (Promega Biotec, Madison, Wis., USA).

Large numbers of other suitable vectors are known to those of skill in the art, and are commercially available, such as the following bacterial vectors: pQE70, pQE60, pQE-9 (Qiagen), pbs, pD10, phagescript, psiX174, pbluescript SK, pbsks, pNH8A, pNH16A, pNH18A, pNH46A (Stratagene); ptrc99a, pKK223-3, pKK233-3, pDR540, pRIT5 (Pharmacia); pWLNEO, pSV2CAT, pOG44, pXT1, pSG (Stratagene); pSVK3, pBPV, pMSG, pSVL (Pharmacia); pQE-30 (QIAexpress).

Baculovirus Vectors

A suitable vector for the expression polypeptides of the invention is a baculovirus vector that can be propagated in insect cells and in insect cell lines. A specific suitable host vector system is the pVL1392/1393 baculovirus transfer vector (Pharmingen) that is used to transfect the SF9 cell line (ATCC No. CRL 1711) which is derived from *Spodoptera frugiperda*.

Other suitable vectors for the expression of a leptin polypeptide in a baculovirus expression system include those described by (Chai H. et al. (1993), *Biotechnol. Appl. Biochem.* 18:259-273; Vlasak R. et al. (1983), *Eur. J. Biochem.* 135:123-126; Lenhard T. et al. (1996), *Gene.* 169:187-190).

Viral Vectors

In one specific embodiment, the vector is derived from an adenovirus. Preferred adenovirus vectors according to the invention are those described by Feldman and Steg (1996) or Ohno et al. (1994). Another preferred recombinant adenovirus according to this specific embodiment of the present invention is the human adenovirus type 2 or 5 (Ad 2 or Ad 5) or an adenovirus of animal origin (French patent application No. FR-93.05954).

Retrovirus vectors and adeno-associated virus vectors are generally understood to be the recombinant gene delivery systems of choice for the transfer of exogenous polynucleotides in vivo, particularly to mammals, including humans. These vectors provide efficient delivery of genes into cells, and the transferred nucleic acids are stably integrated into the chromosomal DNA of the host. Particularly preferred retroviruses for the preparation or construction of retroviral in vitro or in vitro gene delivery vehicles of the present invention include retroviruses selected from the group consisting of Mink-Cell Focus Inducing Virus, Murine Sarcoma Virus, Reticuloendotheliosis virus and Rous Sarcoma virus. Particularly preferred Murine Leukemia Viruses include the 4070A and the 1504A viruses, Abelson (ATCC No VR-999), Friend (ATCC No VR-245), Gross (ATCC No VR-590), Rauscher (ATCC No VR-998) and Moloney Murine Leukemia Virus (ATCC No VR-190; PCT Application No WO 94/24298). Particularly preferred Rous Sarcoma Viruses include Bryan high titer (ATCC Nos VR-334, VR-657, VR-726, VR-659 and VR-728). Other preferred retroviral vectors are those described in Roth J. A. et al. (1996), *Nature Medicine.* 2(9): 985-991 PCT Application No WO 93/25234, PCT Application No WO 94/06920, Roux et al., 1989, *Proc. Natl. Acad. Sci. USA*, 86: 9079-9083, Julan et al., 1992, *J. Gen. Virol.*, 73: 3251-3255 Neda et al., 1991, *J. Biol. Chem.*, 266: 14143-14146.

Yet another viral vector system that is contemplated by the invention consists of the adeno-associated virus (AAV). The adeno-associated virus is a naturally occurring defective virus that requires another virus, such as an adenovirus or a herpes virus, as a helper virus for efficient replication and a productive life cycle (Muzyczka et al., 1992, *Curr. Topics in Micro.*

*and Immunol.*, 158: 97-129). It is also one of the few viruses that may integrate its DNA into non-dividing cells, and exhibits a high frequency of stable integration (Flotte et al., 1992, *Am. J. Respir. Cell Mol. Biol.*, 7:349-356; Samulski et al., 1989, *J. Virol.*, 63: 3822-3828;

McLaughlin B. A. et al. (1996), *Am. J. Hum. Genet.* 59:561-569. One advantageous feature of AAV derives from its reduced efficacy for transducing primary cells relative to transformed cells.

5) Delivery of the Recombinant Vectors

In order to effect expression of the polynucleotides of the invention, these constructs must be delivered into a cell. This delivery may be accomplished in vitro, as in laboratory procedures for transforming cell lines, or in vivo or ex vivo, as in the treatment of certain disease states.

One mechanism is viral infection where the expression construct is encapsulated in an infectious viral particle.

Several non-viral methods for the transfer of polynucleotides into cultured mammalian cells are also contemplated by the present invention, and include, without being limited to, calcium phosphate precipitation (Graham et al. (1973), *Virology*. 52:456-457; Chen et al., 1987, Mol. Cell. Biol., 7: 2745-2752;), DEAE-dextran (Gopal, 1985, Mol. Cell. Biol., 5: 1188-1190 electroporation (Tur-Kaspa et al. (1986), *Mol. Cell. Biol.* 6:716-718; Potter et al., 1984, Proc Natl Acad Sci USA. 81(22):7161-5) direct microinjection (Harland et al., 1985, J. Cell. Biol., 101:1094-1095) DNA-loaded liposomes (Nicolau et al., 1982, Biochim. Biophys. Acta, 721:185-190; Fraley et al., 1979, Proc. Natl. Acad. Sci. USA, 76: 3348-3352 and receptor-mediate transfection (Wu and Wu, 1987, J. Biol. Chem, 262: 4429-4432; Wu and Wu, 1988, Biochemistry, 27:887-892). Some of these techniques may be successfully adapted for in vivo or ex vivo use.

Once the expression polynucleotide has been delivered into the cell, it may be stably integrated into the genome of the recipient cell. This integration may be in the cognate location and orientation via homologous recombination (gene replacement) or it may be integrated in a random, non specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle.

One specific embodiment for a method for delivering a protein or peptide to the interior of a cell of a vertebrate in vivo comprises the step of introducing a preparation comprising a physiologically acceptable carrier and a naked polynucleotide operatively coding for the polypeptide of interest into the interstitial space of a tissue comprising the cell, whereby the naked polynucleotide is taken up into the interior of the cell and has a physiological effect. This is particularly applicable for transfer in vitro but it may be applied to in vivo as well.

Compositions for use in vitro and in vivo comprising a "naked" polynucleotide are described in PCT application No. WO 90/11092 (Vical Inc.) and also in PCT application No. WO 95/11307 (Institut Pasteur, INSERM, Université d'Ottawa) as well as in the articles of Tacson et al. (1996) *Nature Medicine.* 2(8):888-892 and Huygen et al. (1996) *Nature Medicine.* 2(8):893-898.

In still another embodiment of the invention, the transfer of a naked polynucleotide of the invention, including a polynucleotide construct of the invention, into cells may be proceeded with a particle bombardment (biolistic), said particles being DNA-coated microprojectiles accelerated to a high velocity allowing them to pierce cell membranes and enter cells without killing them, such as described by Klein et al. (1987) *Nature.* 327:70-73.

In a further embodiment, the polynucleotide of the invention may be entrapped in a liposome (Ghosh and Bacchawat, 1991, *Targeting of liposomes to hepatocytes*, IN: *Liver Diseases, Targeted diagnosis and therapy using specific receptors and ligands*. Wu et al. Eds., Marcel Dekeker, New York, pp. 87-104; Wong et al., 1980, Gene, 10: 87-94; Nicolau C. et al. (1987), *Methods Enzymol.* 149:157-76). These liposomes may further be targeted to cells expressing LSR by incorporating leptin, triglycerides, Acrp30, or other known LSR ligands into the liposome membrane.

In a specific embodiment, the invention provides a composition for the in vivo production of a leptin polypeptide, or a zinc finger protein, described herein. It comprises a naked polynucleotide operatively coding for this polypeptide, in solution in a physiologically acceptable carrier, and suitable for introduction into a tissue to cause cells of the tissue to express the said polypeptide.

The amount of vector to be injected to the desired host organism varies according to the site of injection. As an indicative dose, it will be injected between 0.1 and 100 μg of the vector in an animal body, preferably a mammal body, for example a mouse body.

In another embodiment of the vector according to the invention, it may be introduced in vitro in a host cell, preferably in a host cell previously harvested from the animal to be treated and more preferably a somatic cell such as a muscle cell. In a subsequent step, the cell that has been transformed with the vector coding for the desired leptin polypeptide or the desired fragment thereof is reintroduced into the animal body in order to deliver the recombinant protein within the body either locally or systemically.

VI. Recombinant Cells of the Invention

The invention is in part based on the surprising and unexpected discovery that the different subunits of LSR interact to form at least two very different receptors: LSR-lep and LSR-tg. The LSR-lep receptor requires at least α'. In some embodiments a combination with β and/or α as well as α' is preferred. The LSR-tg receptor requires a combination of at least α and β. In some embodiments a combination with β and/or α as well as α' is preferred. Based on this novel and unexpected finding, it has become critical to engineer cells lacking endogenous LSR activity/expression (e.g. as a result of a classical knock-out, chimeraplasty, or zinc finger protein inhibition), and then to re-transfect the subunits of interest in various combinations and at various levels. This will allow not only the study of these receptors in isolation, but also the design of specific inhibitors for the different receptors, and the assessment of what genes may act to regulate or modulate the receptors, or to transmit the intracellular signals from or for each receptor. Although LSR-lep and LSR-tg have been identified, it is possible that other LSR receptors with other activities also exist and can be identified by these methods.

Recombinant cells have been designed that are useful in many situations, including: (1) the study of the role of the various LSR components in isolation and together with and without interference from endogenous LSR, (2) as part of an assay system to discover modulators of the leptin/LSR interaction, for example, using known components of the LSR system (and in some cases no endogenous LSR components; see above), and (3) to produce various polypeptides of the invention (see above). To this end, in preferred embodiments, a recombinant cell is transiently, or preferably stably, transfected with one or more LSR subunits selected from the group consisting of α, α' and β. Preferably, the two or more subunits are expressed in pairwise ratios to each other of from 1:1 to 1:5. For example, if α and β are present in a cell, cells with ratios of 1:1, 1:2, 1:3, 1:4, 1:5, 5:1, 4:1, 3:1, 2:1, as well as 2:3, 3:2, 3:4, 4:3, 3:5, 5:3, 4:5, and 5:4, etc. are preferred. Similar ratios are desired for cells containing α' and β. When all three subunits are present, cells with all possible combinations of ratios are preferred. These are most easily obtained by screening cells (wild-type, transfected, or knockout, for example) for their expression levels of the various subunits. Preferably, the one or more LSR components are α' and β, and preferably the recombinant cells are cultured PLC cells. However, the cells can be selected from any of the cells in the ATCC bank. The LSR polypeptides, the polynucleotides encoding LSR, and the vectors to transfer the polynucleotides encoding LSR between cells and tissues have been described previously (U.S. National phase application Ser. No. 09/269,939, hereby incorporated herein by reference in its entirety including any figures, drawings or tables).

Another object of the invention consists of host cells that have been transformed or transfected with one of the polynucleotides described herein, and more precisely a polynucleotide comprising: a polynucleotide encoding a leptin polypeptide of the invention, or a polynucleotide encoding a zinc finger protein of the invention. These polynucleotides can be present in the same cell or in a different cell, and can be present in cells transiently or stably transfected with any combination of the components of LSR.

In another embodiment, the invention features cells that lack expression of at least one of the LSR subunits. These can be cells identified by screening processes, but they are preferably recombinant cells that have had the gene for LSR knocked-out by traditional techniques well known in the art; a cell in which a polynucleotide encoding a zinc finger protein of the invention has been transfected that either constitutively suppresses the expression of at least one subunit of LSR or whose suppression of LSR can be regulated by the Tet On/Off system, for example; or a cell in which the expression of at least one subunit of LSR has been inhibited as the result of the transfection of chimeric oligonucleotides of the invention.

The invention further features either transiently, or preferably stably, transfecting the LSR knockout cells (or zinc finger protein cells) in which expression of at least one, and in some cases all, of the endogenous LSR subunits has been inhibited (or eliminated), with at least one, preferably at least two, and alternatively three, of the LSR subunits and then selecting/screening for cells expressing the various ratios of subunits as described above. Preferably, β, α or α' alone are transfected, or alternatively α' and β, or α and β together are transfected.

The invention includes host cells that are transformed (prokaryotic cells) or that are transfected (eukaryotic cells) with a recombinant vector such as any one of those described in "Recombinant Vectors of the Invention".

Generally, a recombinant host cell of the invention comprises at least one of the polynucleotides or the recombinant vectors of the invention which are described herein, but also includes those cells in which the gene for LSR has been knock-out by traditional recombinant techniques, zinc finger techniques, or using chimeraplast oligonucleotides.

Preferred host cells used as recipients for the recombinant vectors of the invention are the following:

a) Prokaryotic host cells: *Escherichia coli* strains (i.e. DH5-α strain), *Bacillus subtilis, Salmonella typhimurium,* and strains from species like *Pseudomonas, Streptomyces* and *Staphylococcus,* and b) Eukaryotic host cells: HeLa cells (ATCC No. CCL2; No. CCL2.1; No. CCL2.2), Cv 1 cells (ATCC No. CCL70), COS cells (ATCC No. CRL1650; No. 1651), Sf-9 cells (ATCC No. CRL1711), C127 cells (ATCC No. CRL-1804), 3T3 (ATCC No. CRL-6361), CHO (ATCC No. CCL-61), human kidney 293 (ATCC No. 45504; No. CRL-1573), BHK (ECACC No. 84100501; No. 84111301), PLC cells, HepG2, Hepa 1-6, and Hep3B.

The constructs in the host cells can be used in a conventional manner to produce the gene product encoded by the recombinant sequence.

Following transformation of a suitable host and growth of the host to an appropriate cell density, the selected promoter is induced by appropriate means, such as temperature shift or chemical induction, and cells are cultivated for an additional period.

Cells are typically harvested by centrifugation, disrupted by physical or chemical means, and the resulting crude extract retained for further purification.

Microbial cells employed in the expression of proteins can be disrupted by any convenient method, including freeze-thaw cycling, sonication, mechanical disruption, or use of cell lysing agents. Such methods are well known by the skilled artisan.

Further, according to the invention, these recombinant cells can be created in vitro or in vivo in an animal, preferably a mammal, most preferably selected from the group consisting of mice, rats, dogs, pigs, sheep, cattle, and primates, not to include humans. Recombinant cells created in vitro can also be later surgically implanted in an animal, for example. Methods to create recombinant cells in vivo in animals are well-known in the art, and are specifically meant to include the techniques associated with chimeraplasty described herein and known in the art, whereby the chimeraplast oligonucleotides are provided to the cells in the animal by the use of liposomes, preferably liposomes that have targeting molecules for cells containing LSR such as LSR binding proteins or ligands, such as apm1, C1q, or leptin, for example, in the membrane layer.

VIII. Assays for Identifying Modulators of LSR Activity

The surprising and unexpected discovery that the different subunits of LSR interact to form at least two very different receptors (LSR-lep and LSR-tg) with different activities has resulted in the necessity of designing novel assays to identify inhibitors for the different LSR receptors. In particular, these assays will preferably utilize the recombinant cells of the invention, that are engineered to lack endogenous LSR activity/expression (e.g. as a result of a classical knock-out, chimeraplasty, or zinc finger protein inhibition). These cells are then re-transfected with the subunits of interest in various combinations and at various levels. Preferred combinations include those that give rise to the LSR-lep receptor that requires at least α', but may also include combination of α' and β, and the LSR-tg receptor that requires a combination of α and β. Other combinations (and the individual subunits) are also useful to look for other LSR receptor activities and as controls for the activity of compounds (or genes) selected in the other assays.

The invention features methods of screening for one or more compounds that modulate LSR activity in cells, that includes providing potential compounds to be tested to the cells, and where modulation of LSR activity indicates the one or more compounds. In some preferred embodiments, the potential compounds are compounds that have been molecularly designed based on the identified fragment of leptin that binds and activates LSR as described herein.

In a preferred embodiment, the invention features a method for selecting a compound useful for the treatment or prevention of an obesity-related disease or disorder, comprising: contacting a recombinant cell that comprises a zinc finger protein of the invention, or a recombinant vector comprising any of the zinc finger proteins of the invention with a candidate compound; and detecting a result selected from the group consisting of a modulation of an activity of the Lipolysis Stimulated Receptor and modulation of expression of the Lipolysis Stimulated Receptor; as a means for selecting said compound useful for the treatment or prevention of said obesity-related disease or disorder.

In preferred embodiments, said contacting is in the presence of a ligand of said Lipolysis Stimulated Receptor. Preferably, said ligand is selected from the group consisting of cytokine, lipoprotein, free fatty acid, adipoQ (Apm1 and Acrp30), and C1q, and more preferably said cytokine is leptin. Alternatively, said free fatty acid is oleate. In other preferred embodiments, said leptin is a leptin polypeptide fragment that modulates the activity of LSR, comprising at least 4, but not more than 50 contiguous amino acids of any one of the leptin polypeptide sequences set forth in FIG. 13, wherein said at least 4 and not more than 50 contiguous amino acids comprise the leptin fragment central sequence. In other preferred embodiments, said leptin is a variant of a leptin polypeptide fragment that modulates the activity of LSR, consisting of a 22 contiguous amino acid sequence that is at least 75% identical to the leptin fragment variable region of any one of the leptin polypeptide sequences set forth in FIG. 13. Optionally, the leptin fragment is any leptin fragment of the invention described herein.

In other preferred embodiments of the invention, said activity is selected from the group consisting of binding of lipoproteins, uptake of lipoproteins, degradation of lipoproteins, binding of leptin, uptake of leptin, and degradation of leptin. Preferably, said modulation of LSR activity is an increase in said activity, and optionally a decrease in said activity. In other preferred embodiments, said expression is on the surface of said cell, and preferably said detecting comprises FACS, more preferably said detecting further comprises antibodies that bind specifically to said LSR, wherein said LSR comprises an amino acid sequence at least 75% homologous to at least one of the sequences selected from the group consisting of SEQ ID NO:3, SEQ ID NO:5, SEQ ID NO:7, SEQ ID NO:9, SEQ ID NO:11, SEQ ID NO:17, SEQ ID NO:18, and SEQ ID NO:19. In other preferred embodiments, said amino acid sequence is at least 80, 85, 90, 95, or 99 to 100% homologous to at least one of the sequences selected from the group consisting of SEQ ID NO:3, SEQ ID NO:5, SEQ ID NO:7, SEQ ID NO:9, SEQ ID NO:11, SEQ ID NO:17, SEQ ID NO:18, and SEQ ID NO:19. In other preferred embodiments, said antibodies bind specifically to a region of said LSR selected from the group consisting of an amino terminus, a carboxy terminus, a splice site, a cytokine binding site, a fatty acid binding site, a clathrin binding site, an apoprotein ligand binding site, a LULL motif, a RSRS motif, and a hydrophobic region. Preferably, said cell is selected from the group consisting of PLC, CHO-K1, Hep3B, and HepG2, although any cell expressing detectable levels of LSR can be used.

Antibodies to LSR and to the various regions of LSR have been extensively described previously in U.S. National application Ser. No. 09/269,939, filed May 28, 1999 and its related PCT application, both are hereby incorporated herein by reference in their entirety including any figures, drawings or tables. In addition, specific antibodies to LSR are described in the Examples (1-8).

In preferred embodiments, said candidate compound is selected from the group consisting of peptides, peptide libraries, non-peptide libraries, peptoids, fatty acids, lipoproteins, medicaments, antibodies, and small molecules, and optionally can include leptin mimetics designed by methods of the invention. The compounds may be active in vitro or in vivo. The activity may be increased or decreased; the compounds may be antagonists or agonists.

Preferably, said obesity-related diseases and disorders are selected from the group consisting of obesity, anorexia, cachexia, cardiac insufficiency, coronary insufficiency, stroke, hypertension, atheromatous disease, atherosclerosis, high blood pressure, non-insulin-dependent diabetes, hyperlipidemia, and hyperuricemia. The compounds may also modulate body mass. Most preferably, the diseases include congenital generalized lipodystrophy.

In other highly preferred embodiments of the invention, the cells used in the above-describe assays cells have been modified to express none, or a subset, of the LSR subunits. The recombinant cells containing zinc finger proteins of the invention are also transfected with at least one polynucleotide encoding a LSR polypeptide comprising a sequence at least 75% identical to an amino acid sequence selected from the group consisting of SEQ ID NO:3, SEQ ID NO:5, SEQ ID NO:7, SEQ ID NO:9, SEQ ID NO:11, SEQ ID NO:17, SEQ ID NO:18, and SEQ ID NO:19. Preferably the LSR subunit is stably transfected. Preferably the cell is selected from the group consisting of PLC, CHO-K1, Hep3B, Hepa 1-6, and HepG2. However, other cells available from the ATCC, for example, may also be used. In addition, cells with the endogenous LSR gene "knocked out" by methods well-known in the art are also expressly contemplated (as an option to the use of the zinc finger proteins of the invention, or to the use of the chimeraplasts of the invention.). Cells, preferably modified cells, are transfected with one or more LSR components that may include one, part, or all, of $\alpha'$, $\alpha$, and $\beta$, most preferably $\alpha'$ and $\beta$. Recombinant cells useful for assays to identify modulators of the leptin-LSR interaction include those described in the "Recombinant Cells of the Invention". In particular, cells expressing a range of ratios of the subunits are desired, including 1:1, 1:2, 1:3, 1:4, 1:5, 5:1, 4:1, 3:1, 2:1, as well as 2:3, 3:2, 3:4, 4:3, 3:5, 5:3, 4:5, and 5:4, etc. for $\alpha'$ to $\beta$ or $\alpha$ to $\beta$, or even $\alpha$ to $\alpha'$, for example. In addition, the various combinations where all three subunits are present in a cell are also envisioned to be useful in assays for modulators of LSR activity.

In highly preferred embodiments of the invention, cells with endogenous LSR activity knocked-out and transfected with the $\alpha'$ alone, or $\alpha'$ and $\beta$ LSR subunits together are used to screen for modulators of the LSR-leptin interaction. In other preferred embodiments, the $\alpha$ and $\beta$ LSR subunits are used to screen for modulators of triglyceride-rich lipoprotein binding, uptake, and degradation. Cells with all three LSR subunits are useful to screen for modulators of the effect of leptin binding uptake and degradation on triglyceride-rich lipoprotein binding, uptake and degradation. Similarly, these cells would be useful for screening molecules arising from the active leptin fragment molecular modeling described herein.

IX. Methods for Designing Leptin Polypeptide Fragment Mimetics

Following the discovery of the differential results of human and mouse leptin on human and rodent LSR, the region of amino acid sequence sharing the least homology between the two homologs was identified and was found to stimulate rodent and human LSR activity differentially (Examples 1-8). Identification of the differences between these two highly similar peptides allows the design of small molecule activators or inhibitors of LSR. Methods of determining the differences are well known in the art and include, but are not limited to techniques such as molecular dynamic assays, X-ray crystallography, and NMR. Previously, these kinds of techniques for creating inhibitors/activators of enzymes have been used successfully in the art. Potential small molecule activators/inhibitors designed or identified by these methods can be tested in the assays described herein. Those that function in these assays can then be tested for their effectiveness for treatment of obesity-related disorders and diseases, as described herein, for activity in modulating body mass, and for activity in treating congenital generalized lipodystrophy (Example 14).

The invention features a method of designing mimetics of a leptin fragment that modulates an activity of LSR, comprising: identifying critical interactions between one or more amino acids of said leptin fragment and LSR; designing potential mimetics to comprise said critical interactions; and testing said potential mimetics ability to modulate said activity as a means for designing said mimetics. By "designing mimetics" as used herein is meant comparing and combining known molecules to obtain a molecule that is able to mimic some or all of the activities modulated by leptin, or to preferentially increase or decrease some of the activities normally modulated by leptin. These activities include, but are not limited to those activities selected from the group consisting of leptin binding, leptin uptake, leptin degradation, triglyceride binding, triglyceride uptake, and triglyceride degradation. The methods of comparing and combining use molecular modeling, X-Ray crystallography and other techniques well-known in the art to identify the critical interactions. These critical interactions include, but are not limited to those selected from the group consisting of hydrogen bonding, covalent bonding, Van der Waal s forces, steric hindrances, and hydrophobic interactions. These critical interactions are identified using assays that include, but are not limited to, those selected from the group consisting of NMR, X-ray crystallography, and computer modeling. Preferably the now-leptin compounds that are identified or designed by these means include, but are not limited to, small molecules (molecular weight <500, alternatively between 500 and 1000 MW, or >1,000 MW), peptides, peptide libraries, non-peptide molecules, non-peptide libraries and peptoids.

In preferred embodiments, the leptin fragment to be mimicked consists of the leptin fragment variable region of any one of the leptin polypeptide sequences set forth in FIG. 13, preferably the human or mouse sequence, most preferably the human sequence. In other embodiments, the leptin fragment consists of the leptin fragment central sequence of any one of the leptin polypeptide sequences set forth in FIG. 13, preferably the human or mouse sequence, most preferably the human sequence.

Methods of studying the structure of enzyme-substrate complexes are well known in the art. X-Ray crystallography allows the determination of the precise three-dimensional positions of most of the atoms in a protein molecule. To do this, a source of x-rays, a protein crystal, and a detector are needed. Obtaining the crystal is necessary because the techniques requires that all the molecules are precisely positioned. Methods to produce crystals are well-known in the art. X-rays going through the protein crystal are scattered by electrons, thus the amplitude of the wave scattered by an atom is proportional to its number of electrons. The scattered waves then recombine, either reinforcing one another on the film or cancelling each other out, depending on the atomic arrangement. From this information, the image is formed by applying a mathematical relation called a Fourier transform, and from here an electron-density map can be calculated, and then interpreted. The limiting resolution for a protein with a good crystal is typically 2 A.

Two methods important for enzyme-ligand interactions include (1) the difference Fourier method, and (2) production of stable complexes. In the Fourier method, the enzyme is crystallized (in this case LSR) and then the X-ray diffraction of the crystallized protein in solvent is compared with the X-ray diffraction of the crystallized protein in the presence of ligand (in this case the 22 amino acid leptin peptide). Provided that there are no drastic changes in the structure or packing of the protein when it binds the ligand, the structure of the complex can be solved by comparing the differences between the diffraction patterns. This allows the electron density of the bound ligand and minor changes in the protein structure to be obtained without starting from scratch.

Alternatively, the X-ray diffraction pattern of a stably bound complex can be used to determine the protein-ligand interactions. Sometimes this is done using an inhibitor of the ligand, but can also be achieved under unreactive conditions such as: (1) weakly reactive conditions due to pH conditions, ionic state, or very low temperature, (2) using a chemically modified protein or ligand in which important residues are modified, or (3) under conditions in which the equilibrium conditions are shifted.

X-ray crystallography can be complemented by nuclear magnetic resonance (NMR) spectroscopy, which can reveal the structure of macromolecules in solution. Certain atomic nuclei such as hydrogen are intrinsically magnetic. The spinning of the positively charged proton, generates a magnetic moment. This moment can take either of two orientations when an external magnetic field is applied. The flow of electrons around a magnetic nucleus generates a small local magnetic field that opposes the external field. Under different environments the energy is absorbed at different resonance frequencies, an effect termed a chemical shift. Comparison of the shifts and spin-spin couplings, as well as the nuclear Overhauser effect (NOESY spectra) leads to the identification of pairs of protons that are less than 5 A apart. Overlapping peaks in NOESY spectra can be further resolved by obtaining NMR spectra of proteins labelled with 15N and 13C (multidimensional NMR spectroscopy). Typically highly concentrated solutions of proteins are required (1 mM or 15 mg/ml for a 15 kd protein) and the size is generally limited to 30 kd.

Molecular modelling by computer is also used extensively to augment, supplement and integrate the information gained by X-Ray crystallography, NMR, EPR and other techniques. In particular, computer programs such as DOCK allow the prediction, identification, and three-D testing of inhibitors and activators of enzymes. This methodology has been used successfully previously to identify inhibitors. Basically, using the information gained from X-ray crystallography, NMR, and direct modelling, computer programs can now predict the residues that are important for the ligand-protein interactions and can predict structures that can perform the same interactions and test compounds proposed to be able to perform the same interactions. Through this interplay, molecules can be designed and identified to activate LSR in the manner of the leptin peptide, or to inhibit this interaction. The advantages to designing a molecule in this way include the ability to use compounds that the body cannot metabolize as rapidly as a peptide, that are less expensive to make, and that hopefully lack any unwanted leptin-associated side-effects.

X. Pharmaceutical Compositions of the Invention

The identified compounds can be administered to a mammal, including a human patient, alone or in pharmaceutical compositions where they are mixed with suitable carriers or excipient(s) at therapeutically effective doses to treat or ameliorate a variety of disorders associated with lipid metabolism. A therapeutically effective dose further refers to that amount of the compound sufficient to result in amelioration of symptoms of obesity-related diseases or disorders as determined by the methods described herein. Thus, a therapeutically effective dosage of a leptin polypeptide fragment of the invention, or an antagonist or agonist of the leptin-LSR interaction, or a leptin fragment mimetic designed from molecular modeling studies, will be that dosage of the compound that is adequate to promote reduced or increased triglyceride-rich lipoprotein levels following a high-fat meal and that will promote weight loss or weight gain with continued periodic use or administration. Similarly, a therapeutically effective dosage of a chimeric oligonucleotide of the invention or a polynucleotide encoding a zinc finger protein of the invention will be that dosage of the compound that is adequate to increase or reduce triglyceride-rich lipoprotein levels following a high-fat meal and that will promote weight loss or weight gain with continued periodic use or administration. Techniques for formulation and administration of the compounds of the instant application may be found in "Remington's Pharmaceutical Sciences," Mack Publishing Co., Easton, Pa., latest edition.

Additional aspects of the invention feature the use of the compounds, chimeric oligonucleotides and zinc fingers, described throughout the application as modulators of LSR activity in the making of medicaments for the treatment of diseases and disorders described in the following section as well as throughout the application. These diseases or disorders include, but are not limited to, anorexia, cachexia, AIDS-related weight loss, neoplasia-related weight loss, or obesity-related atherosclerosis, obesity-related insulin resistance, obesity-related hypertension, microangiopathic lesions resulting from obesity-related Type II diabetes, ocular lesions caused by microangiopathy in obese individuals with Type II diabetes, and renal lesions caused by microangiopathy in obese individuals with Type II diabetes. Modulators of body mass are also expressly included, as are compounds (such as the leptin fragments of the invention) for treating congenital generalized lipodystrophy.

Routes of Administration.

Suitable routes of administration include oral, rectal, transmucosal, or intestinal administration, parenteral delivery, including intramuscular, subcutaneous, intramedullary injections, as well as intrathecal, direct intraventricular, intravenous, intraperitoneal, intranasal or intraocular injections. A particularly useful method of administering compounds for promoting weight loss involves surgical implantation, for example into the abdominal cavity of the recipient, of a device for delivering the compound over an extended period of time. Sustained release formulations of the invented medicaments particularly are contemplated.

Composition/Formulation

Pharmaceutical compositions and medicaments for use in accordance with the present invention may be formulated in a conventional manner using one or more physiologically acceptable carriers comprising excipients and auxiliaries. Proper formulation is dependent upon the route of administration chosen.

Certain of the medicaments described herein will include a pharmaceutically acceptable carrier and at least one polypeptide that is a leptin polypeptide of the invention. In addition to medicaments that include leptin polypeptides of the invention, non-protein compounds designed based on molecular modeling of the active leptin polypeptide of the invention also will find utility as modulators of LSR activity, both in vitro and in vivo. Further, antagonists and agonists of the leptin-LSR interaction, including leptin and/or triglyceride-rich lipoprotein binding, uptake and degradation will also find utility in modulating LSR activity and/or stimulating a reduction of plasma lipoproteins and/or promoting weight loss.

For injection, the agents of the invention may be formulated in aqueous solutions, preferably in physiologically compatible buffers such as Hanks's solution, Ringer's solution, or physiological saline buffer such as a phosphate or bicarbonate buffer. For transmucosal administration, penetrants appropriate to the barrier to be permeated are used in the formulation. Such penetrants are generally known in the art.

Pharmaceutical preparations that can be taken orally include push-fit capsules made of gelatin, as well as soft, sealed capsules made of gelatin and a plasticizer, such as glycerol or sorbitol. The push-fit capsules can contain the active ingredients in admixture with fillers such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable gaseous propellant, e.g., carbon dioxide. In the case of a pressurized aerosol the dosage unit may be determined by providing a valve to deliver a metered amount. Capsules and cartridges of, e.g., gelatin, for use in an inhaler or insufflator, may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in aqueous vehicles, and may contain formulatory agents such as suspending, stabilizing and/or dispersing agents.

Pharmaceutical formulations for parenteral administration include aqueous solutions of the active compounds in water-soluble form. Aqueous suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Alternatively, the active ingredient may be in powder or lyophilized form for constitution with a suitable vehicle, such as sterile pyrogen-free water, before use.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Additionally, the compounds may be delivered using a sustained-release system, such as semipermeable matrices of solid hydrophobic polymers containing the therapeutic agent. Various sustained release materials have been established and are well known by those skilled in the art. Sustained-release capsules may, depending on their chemical nature, release the compounds for a few weeks up to over 100 days.

Depending on the chemical nature and the biological stability of the therapeutic reagent, additional strategies for protein stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Effective Dosage.

Pharmaceutical compositions suitable for use in the present invention include compositions wherein the active ingredients are contained in an effective amount to achieve their intended purpose. More specifically, a therapeutically effective amount means an amount effective to prevent development of or to alleviate the existing symptoms of the subject being treated. Determination of the effective amounts is well within the capability of those skilled in the art, especially in light of the detailed disclosure provided herein.

For any compound used in the method of the invention, the therapeutically effective dose can be estimated initially from cell culture assays. For example, a dose can be formulated in animal models to achieve a circulating concentration range that includes or encompasses a concentration point or range shown to effect enhanced or inhibited LSR activity in an in vitro system. Such information can be used to more accurately determine useful doses in humans.

A therapeutically effective dose refers to that amount of the compound that results in amelioration of symptoms in a patient. Toxicity and therapeutic efficacy of such compounds can be determined by standard pharmaceutical procedures in cell cultures or experimental animals, e.g., for determining the LD50, (the dose lethal to 50% of the test population) and the ED50 (the dose therapeutically effective in 50% of the population). The dose ratio between toxic and therapeutic effects is the therapeutic index and it can be expressed as the ratio between LD50 and ED50. Compounds that exhibit high therapeutic indices are preferred.

The data obtained from these cell culture assays and animal studies can be used in formulating a range of dosage for use in human. The dosage of such compounds lies preferably within a range of circulating concentrations that include the ED50, with little or no toxicity. The dosage may vary within this range depending upon the dosage form employed and the route of administration utilized. The exact formulation, route of administration and dosage can be chosen by the individual physician in view of the patient's condition. (See, e.g., Fingl et al., 1975, in "The Pharmacological Basis of Therapeutics", Ch. 1).

Dosage amount and interval may be adjusted individually to provide plasma levels of the active compound which are sufficient to maintain the LSR modulating effects. Dosages necessary to achieve the LSR modulating effect will depend on individual characteristics and route of administration.

Dosage intervals can also be determined using the value for the minimum effective concentration. Compounds should be administered using a regimen that maintains plasma levels above the minimum effective concentration for 10-90% of the time, preferably between 30-90%; and most preferably between 50-90%. In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

A preferred dosage range for the amount of a leptin polypeptide of the invention, or compound designed based on its molecular modeling, or an antagonist or agonist of its activity with LSR, that can be administered on a daily or regular basis to achieve desired results, including a reduction in levels of circulating plasma triglyceride-rich lipoproteins, range from 0.1-50 mg/kg body mass. A more preferred dosage range is from 0.2-25 mg/kg. A still more preferred dosage range is from 1.0-20 mg/kg, while the most preferred range is from 2.0-10 mg/kg. Of course, these daily dosages can be delivered or administered in small amounts periodically during the course of a day.

XI. Methods of Preventing or Treating Obesity-Related Diseases and Disorders

A method of preventing or treating obesity-related diseases and disorders comprising providing a patient in need of such treatment with a leptin polypeptide fragment or a leptin mimetic of the invention. Preferably, the leptin polypeptide fragment or mimetic modulates the activity of LSR, more preferably increases the activity of LSR, and optionally decreases the activity of LSR either in vitro or in vivo. Preferably the leptin polypeptide fragment or mimetic is provided to the patient in a pharmaceutical composition that is preferably taken orally. Preferably the patient is a mammal, and most preferably a human. In preferred embodiments, the obesity-related disease or disorder is selected from the group consisting of anorexia, cachexia, AIDS-related weight loss, neoplasia-related weight loss, or obesity-related atherosclerosis, obesity-related insulin resistance, obesity-related hypertension, microangiopathic lesions resulting from obesity-related Type II diabetes, ocular lesions caused by microangiopathy in obese individuals with Type II diabetes, and renal lesions caused by microangiopathy in obese individuals with Type II diabetes. Modulators of body mass (weight gain or loss) are also expressly included, as are compounds (such as the leptin fragments of the invention) for treating congenital generalized lipodystrophy.

Alternatively, the invention features a method of preventing or treating obesity-related diseases and disorders comprising providing a patient in need of such treatment with a compound identified by assays of the invention. Preferably these compounds antagonize or agonize the interaction of leptin and LSR. In other embodiments, the compounds are those created as a result of the molecular modeling of the active leptin polypeptide and are non-peptide mimetics that function in the same manner as the active leptin polypeptide of the invention. Preferably, the compound is provided to the patient in a pharmaceutical composition that is preferably taken orally. Preferably the patient is a mammal, and most preferably a human. In preferred embodiments, the obesity-related disease or disorder is selected from the group consisting of anorexia, cachexia, AIDS-related weight loss, neoplasia-related weight loss, or obesity-related atherosclerosis, obesity-related insulin resistance, obesity-related hypertension, microangiopathic lesions resulting from obesity-related Type II diabetes, ocular lesions caused by microangiopathy in obese individuals with Type II diabetes, and renal lesions caused by microangiopathy in obese individuals with Type II diabetes. Modulators of body mass are also expressly included, as are compounds (such as the leptin fragments of the invention) for treating congenital generalized lipodystrophy.

The invention also features a method for treating or preventing obesity-related diseases or disorders involving gene surgery. To this end, it is advantageous in some conditions to either express more or less LSR, or alternatively to express more or less of one or more LSR subunits. Using the methods described herein, it is possible to modulate the levels of expression of LSR, or of some LSR subunits using zinc finger polypeptides of the invention or chimeric oligonucleotides of the invention. Preferably, the zinc finger polypeptides are provided to an individual in need of such treatment by polynucleotides encoding the zinc finger polypeptides of the invention. Preferably the zinc finger polynucleotides of the invention are present in a recombinant vector, preferably a retroviral vector, more preferably AAV. Preferably the chimeric oligonucleotides are provided to a patient in need of such treatment using liposomes. Preferably the liposomes are constructed such that molecules targeting the liposomes to cells containing LSR are present in the membrane. Preferably the molecules include leptin, apm1, and C1q, for example. Alternatively they may have compounds that target them to the liver, such as glucose, for example, or alternatively to adipose tissue. Preferably the patient is a mammal and the obesity-related disease or disorder is selected from the group consisting of anorexia, cachexia, AIDS-related weight loss, neoplasia-related weight loss, or obesity-related atherosclerosis, obesity-related insulin resistance, obesity-related hypertension, microangiopathic lesions resulting from obesity-related Type II diabetes, ocular lesions caused by microangiopathy in obese individuals with Type II diabetes, and renal lesions caused by microangiopathy in obese individuals with Type II diabetes. Modulators of body mass are also expressly included, as are compounds (such as the leptin fragments of the invention) for treating congenital generalized lipodystrophy.

Still another aspect of the invention relates to the use of chimeric oligonucleotides to specifically alter single nucleotide polymorphisms in a patient in need of such treatment. Single polymorphisms associated with the LSR gene and with obesity have been described in U.S. provisional application No. 60/119,592, entitled "Polymorphic Markers of the LSR gene" by Blumenfeld et al, filed Feb. 10, 1999, which is hereby incorporated by reference herein in its entirety including any drawings, figures, or tables, and shown in Table A. In one embodiment, this medicament can be used for reducing food intake in obese individuals, reducing the levels of free fatty acids in obese individuals, decreasing the body weight of obese individuals, or treating an obesity related condition selected from the group consisting of obesity-related atherosclerosis, obesity-related insulin resistance, obesity-related hypertension, microangiopathic lesions resulting from obesity-related Type II diabetes, ocular lesions caused by microangiopathy in obese individuals with Type II diabetes, and renal lesions caused by microangiopathy in obese individuals with Type II diabetes. Modulators of body mass are also expressly included, as are compounds (such as the leptin fragments of the invention) for treating congenital generalized lipodystrophy.

TABLE A

| Biallelic Marker | Marker Name | Localization In LSR Gene | Polymorphism | Frequency Of Allele 2 | AA Change | Marker Position |
|---|---|---|---|---|---|---|
| 99-14410/373 | A1 | 5'regulatory region | Allele 1: C<br>Allele 2: T | | | 373 of SEQ ID No 2 |
| 99-14424/353 | A2 | 5'regulatory region | Allele 1: A<br>Allele 2: G | | | 353 of SEQ ID No 3 |
| 99-14418/322 | A3 | 5'regulatory region | Allele 1: A<br>Allele 2: G | | | 322 of SEQ ID No 4 |
| 99-14417/126 | A4 | 5'regulatory region | Allele 1: C<br>Allele 2: T | | | 126 of SEQ ID No 5 |
| 99-14417/334 | A5 | 5'regulatory region | Allele 1: C<br>Allele 2: T | | | 334 of SEQ ID No 5 |
| 99-14415/106 | A6 | 5'regulatory region | Allele 1: C<br>Allele 2: T | | | 106 of SEQ ID No 6 |
| 99-14413/250 | A7 | 5'regulatory region | Allele 1: A<br>Allele 2: C | | | 250 of SEQ ID No 7 |
| 99-14413/383 | A8 | 5'regulatory region | Allele 1: G<br>Allele 2: T | | | 383 of SEQ ID No 7 |
| 99-4575/226 | A9 | 5'regulatory region | Allele 1: T<br>Allele 2: C | 25% | | 226 of SEQ ID No 8 |
| 9-19/148 | A10 | 5'regulatory region | Allele 1: C<br>Allele 2: T | 15% | | 1243 of SEQ ID No 1 |
| 9-19/307 | A11 | 5'regulatory region | Allele 1: A<br>Allele 2: T | 12% | | 1401 of SEQ ID No 1 |
| 9-19/442 | A12 | 5'regulatory region | Allele 1: C<br>Allele 2: Del C | | | 1535 of SEQ ID No 1 |
| 9-20/187 | A13 | 5'regulatory region | Allele 1: A<br>Allele 2: C | | | 1788 of SEQ ID No 1 |
| 9-1/308 | A14 | Intron 1 | Allele 1: C<br>Allele 2: G | 24% | | 2391 of SEQ ID No 1 |
| 9-3/324 | A15 | Exon 2 | Allele 1: C<br>Allele 2: T | 29% | | 3778 of SEQ ID No 1; 595 of SEQ ID Nos 13, 15, and 17 |
| 99-14419/424 | A16 | Intron 2 | Allele 1: C<br>Allele 2: A | 22% | | 4498 of SEQ ID No 1 |
| 9-24/260 | A17 | Intron 3 | Allele 1: A<br>Allele 2: G | 35% | | 15007 of SEQ ID No 1 |

TABLE A-continued

| Biallelic Marker | Marker Name | Localization In LSR Gene | Polymorphism | Frequency Of Allele 2 | AA Change | Marker Position |
|---|---|---|---|---|---|---|
| 9-24/486 | A18 | Intron 4 | Allele 1: G<br>Allele 2: A | 15% | | 15233 of SEQ ID No 1 |
| 9-6/187 | A19 | Exon 5 | Allele 1: C<br>Allele 2: T | 1% | | 15826 of SEQ ID No 1;<br>940 of SEQ ID No 13;<br>883 of SEQ ID No 15 |
| 9-7/148 | A20 | Intron 5 | Allele 1: G<br>Allele 2: A | 35% | | 19567 of SEQ ID No 1 |
| 9-7/325 | A21 | Exon 6 | Allele 1: G<br>Allele 2: A | 14% | S→N | 19744 of SEQ ID No 1;<br>1191 of SEQ ID No 13;<br>1134 of SEQ ID No 15;<br>987 of SEQ ID No 17 |
| 9-7/367 | A22 | Intron 6 | Allele 1: A<br>Allele 2: C | | | 19786 of SEQ ID No 1 |
| 9-9/246 | A23 | Exon 8 | Allele 1: C<br>Allele 2: G | 0.5% | P→R | 20158 of SEQ ID No 1;<br>1362 of SEQ ID No 13;<br>1305 of SEQ ID No 15;<br>1158 of SEQ ID No 17 |
| LSRX9-BM (17-1/240) | A24 | Exon 9 | Allele 1: AGG<br>Allele 2: Del AGG | Del 26% | Del R | 20595 of SEQ ID No 1;<br>1658 of SEQ ID No 13;<br>1601 of SEQ ID No 15;<br>1454 of SEQ ID No 17 |
| LSRX10-BM | A25 | Exon 10 | Allele 1: T<br>Allele2: G | | | 21108 of SEQ ID No 1;<br>2079 of SEQ ID No 13;<br>2022 of SEQ ID No 15;<br>1875 of SEQ ID No 17 |
| 99-4580/296 | A26 | 3'regulatory region | Allele 1: A<br>Allele 2: G | 24% | | 296 of SEQ ID No 9 |
| 99-4567/424 | A27 | 3'regulatory region | Allele 1: C<br>Allele 2: T | | | 424 of SEQ ID No 10 |
| 99-14420/477 | A28 | 3'regulatory region | Allele 1: G<br>Allele 2: T | | | 477 of SEQ ID No 11 |
| 99-4582/62 | A29 | 3'regulatory region | Allele 1: A<br>Allele 2: G | | | 62 of SEQ ID No 12 |
| 99-4582/359 | A30 | 3'regulatory region | Allele 1: G<br>Allele 2: T | 24% | | 359 of SEQ ID No 12 |
| 17-2/297 | A31 | 5'regulatory region | Allele 1: C<br>Allele 2: G | 48% | | 818 of SEQ ID No 1 |
| 9-19/256 | A32 | 5'regulatory region | Allele 1: A<br>Allele 2: G | | | 1374 of SEQ ID No 1 |

XII: Methods for Selecting Genes that Modulate LSR Expression

Another aspect of the invention features a method for selecting for genes that modulate the expression of LSR. This method relies on the use of a retroviral vector to provide cells of choice (those that express LSR naturally or recombinantly, and in any combination of subunits and subunit levels) with genes of interest at a moderate level. By "a moderate level" is meant a level that is intermediary between high and low, as based on the level of expression of GFP. Neither high nor low expression is desired since low levels might result in undetectable effects on LSR activity and high levels might co-opt the use of the cell machinery such that LSR isn't made simply for this reason. These moderate levels are easily detected and selected for by FACS analysis as described in the Examples. This method also relies on the use of FACS to detect changes in the activity of LSR as judged by detecting the expression of LSR, or LSR subunits on the surface of the cells, or alternatively intracellularly as well. This can be done by using two antibodies that bind specifically to different regions of LSR, for example the 81B and 93A antibodies.

Thus, in a preferred embodiment, the invention features a method of selecting for genes that modulate an activity of the Lipolysis Stimulated Receptor, comprising: providing a retroviral gene library to cells that express said Lipolysis Stimulated Receptor; contacting said cells with a ligand of said Lipolysis Stimulated Receptor; and detecting a change in said activity of the Lipolysis Stimulated Receptor as a means for selecting for said genes. Preferably, said retroviral gene library comprises a cDNA library from tissues selected from the group consisting of liver, brain, muscle, and adipose, and preferably further comprises a detectable marker protein selected from the group consisting of GFP, truncated CD2, and truncated CD4. In preferred embodiments, the method further comprises selecting said cells transfected with the retroviral vector for moderate expression of GFP. Preferably, said selecting of cells is by FACS.

In other preferred embodiments, said ligand is selected from the group consisting of cytokine, free fatty acid, lipoprotein, adipoQ (Acrp30, Apm1), and C1q, and preferably said cytokine is leptin. Preferably said free fatty acid is oleate. More preferably, said leptin is a leptin polypeptide fragment that modulates the activity of LSR, comprising at least 4, but not more than 50 contiguous amino acids of any one of the leptin polypeptide sequences set forth in FIG. 13, wherein said at least 4 and not more than 50 contiguous amino acids comprise the leptin fragment central sequence. Optionally, said leptin is a variant of a leptin polypeptide fragment that modulates the activity of LSR, consisting of a 22 contiguous amino acid sequence that is at least 75% identical to the leptin fragment variable region of any one of the leptin polypeptide sequences set forth in FIG. 13.

In other preferred embodiments, said detecting a change in said activity is by FACS, preferably said detecting further comprises fluorescent antibodies that bind specifically to said LSR, wherein said LSR comprises an amino acid sequence at least 75% homologous to at least one of the sequences selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:15, and SEQ ID NO:16. More preferably, said antibodies bind specifically to a region of said LSR selected from the group consisting of an amino terminus, a carboxy terminus, a splice site, a cytokine binding site, a fatty acid binding site, a clathrin binding site, an apoprotein ligand binding site, a LI/LL motif, a RSRS motif, and a hydrophobic region.

Antibodies to LSR and to the various regions of LSR have been extensively described previously in U.S. National application Ser. No. 09/269,939, filed May 28, 1999 and its related PCT application, both are hereby incorporated herein by reference in their entirety including any figures, drawings or tables. In addition, specific antibodies to LSR are described in the Examples (1-8).

In other preferred embodiments said cell is selected from the group consisting of PLC, CHO-K1, Hep3B, and HepG2. In some of these embodiments, said cell has had the endogenous LSR activity inhibited by either a traditional "knockout" of the gene encoding LSR, alternatively said cell has had the expression of endogenous LSR inhibited by transfection of a polynucleotide encoding a zinc linger protein of the invention, or by providing a chimeric oligonucleotide of the invention to the cell.

Other characteristics and advantages of the invention are described in the Brief Description of the Figures and the Examples. These are meant to be exemplary only, and not to limit the invention in any way. Throughout this application, various publications, patents and published patent applications are cited. The disclosures of these publications, patents and published patent specifications referenced in this application are hereby incorporated by reference into the present disclosure to more fully describe the state of the art to which this invention pertains.

BRIEF DESCRIPTION OF THE FIGURES

FIG. 4C is a schematic diagram of the motifs found from the predicted protein sequence of LSR α cDNA. A corresponding Kyte-Doolittle hydrophilicity plot (Lasergene, DNAstar, Madison, Wis.) is shown underneath. For FIG. 4D, PLC cell aliquots were prepared and incubated with irrelevant, 93A or 81B antibodies. After washing and incubation with goat-anti-rabbit FITC-conjugated antibody, the cells were fixed and analyzed by flow cytometry using a FACSCalibur (Becton Dickinson).

FIG. 12 contains a Table that presents results showing the effect of test meal with and without leptin injection on postheparin lipolytic activity in db$^{Pas}$/db$^{Pas}$ mice. Animals were gavaged with the test-meal and injected at the same time with 50 µg leptin or physiological saline as described previously (t=0 h). After 1 h, the mice were injected with heparin and blood samples were taken at the peak of postprandial triglyceridemia (t=2 h). Lipase activity was measured in the postheparin plasma as described in the Examples section herein, and is reported here as the mean±SEM (n=3 animals for each condition; ns=not significant).

FIGS. 20A and 20 B show graphs of the relative levels of LSR isotype expression in mouse liver.

FIGS. 24A and 24B show graphs of LSR mRNA levels (24A) and cell surface expression (24B) in PLC (GG) and HepG2 (AG) cells by quantitative PCR and FACS, respectively. FIGS. 24C, 24D, and 24E show graphs of the oleate-induced $^{125}$I-LDL bound (A), internalized (B), and degraded (C) in confluent monolayers of PLC (■) and HepG2 (▲) that were incubated 3 h at 37° C. with the indicated concentrations of oleate and 20 µg/mL $^{125}$I-LDL. The cells were then washed and the amounts of $^{125}$I-LDL bound, internalized and degraded were measured as described previously.

FIG. 25 shows a table of the characteristics of recombinant ZFPs directed toward LSR sequences. The first column is the identification number of the plasmid expressing a specifically engineered ZFP. The ZFP column represents different zinc finger "cassettes" designed to recognize the 9 bp regions of the target sequence. These "cassettes" have then been linked together (see WO 98/54311) to create the ZFP for the final 18 bp target sequence listed in the final column. Sangamo determined the data on the fold activation and binding constant. The target sequences are located 5' to the translation start site in the mouse LSR gene sequence.

FIGS. 26A, 26B, 26C, 26D, 26E, 26F-H (SEQ ID NO:107), 26I-K (SEQ ID NO:108), 26L-N (SEQ ID NO:109), 26O-Q (SEQ ID NO:110), and 26R-T (SEQ ID NO:111) show schematics and nucleotide sequence of the LSR zinc finger plasmids pSBS5182-NVF (26A), pSBS5183-NVF (26B), pSBS5185-NVF (26C), pSBS5186-NVF (26D), and pSBS5205-NVF (26E). The locations of the ampicillin gene (Amp), neomycin gene (Neo) CMV promoter NLS, ZEP, VP16, FLAG, bGHpA as well as various restriction sites are shown in the schematics.

In FIG. 35A, PLC monolayers were incubated 24 h at 37° C. with (o) or without (n) 200 ng/mL human recombinant leptin. After washing with PBS, cells were incubated 30 min at 37° C. with increasing concentrations of human leptin, followed by a 2 h incubation at 37° C. with 0.8 mM oleate and 20 µg/mL $^{125}$I-LDL. Cells were washed, and the amount of oleate-induced $^{125}$I-LDL binding was measured as described previously. Results are shown as the mean of triplicate determinations. In FIG. 35B, PLC monolayers were incubated 24 h at 37° C. with 0, 200, or 400 ng/mL human recombinant leptin. After washing with PBS, the cells were harvested. Total RNA was prepared from the cell pellets, and Northerns were performed to detect LSR mRNA, using GAPDH probe as loading control as described previously. Northern blots were scanned on the Phosphorimager (Molecular Dynamics, Sunnyvale, Calif.). Densitometric analysis of the images was performed using the software ImageQuant. Results are shown as the amount of LSR signal relative to that of GAPDH (mean±SD, n=3/condition).

EXAMPLES

The following Examples are provided for illustrative purposes and not as a means of limitation. One of ordinary skill in the art would be able to design equivalent assays and methods based on the disclosure herein all of which form part of the instant invention.

General Materials and Methods

Materials

Figure 1:
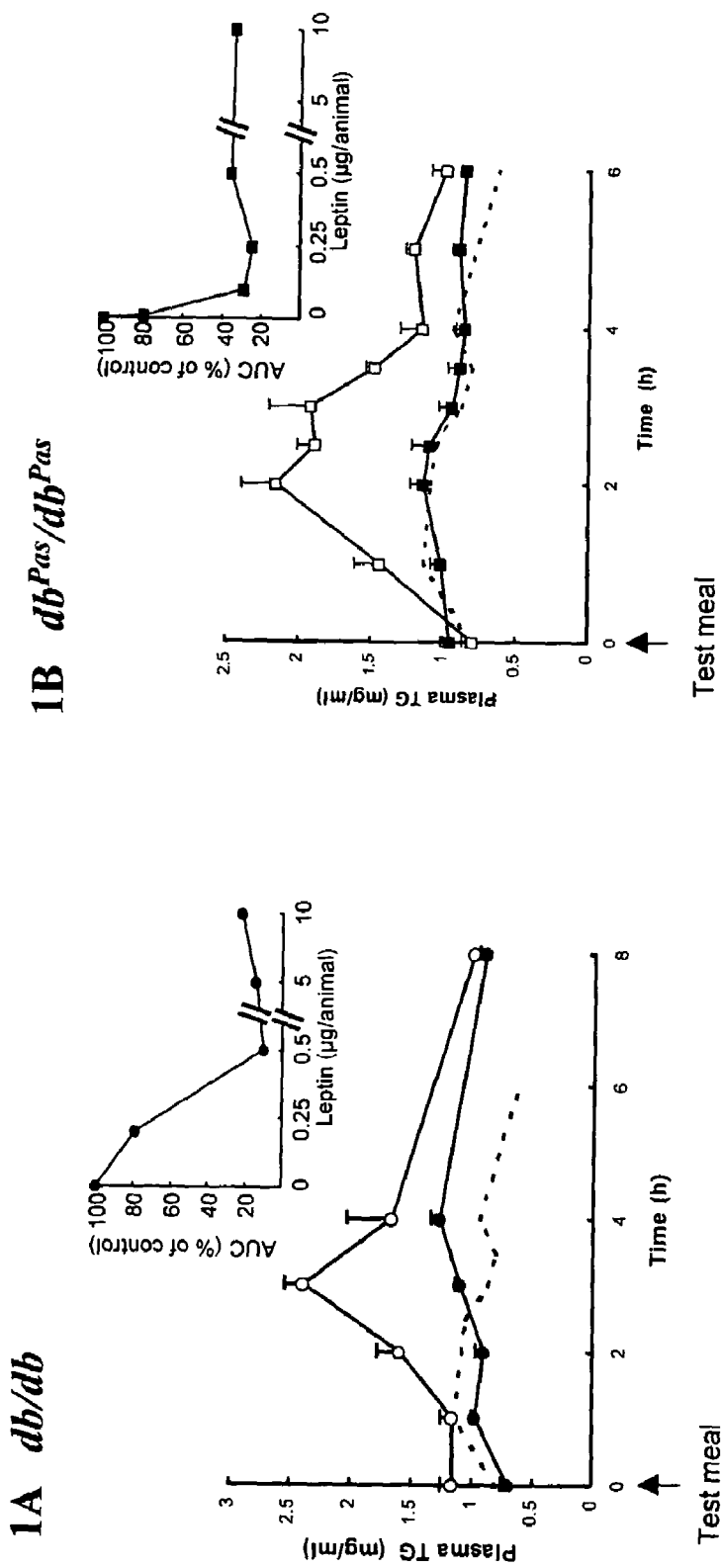
FIGS. 1A and 1B show the effect of leptin on postprandial plasma TG response in db/db and $db^{Pas}/db^{Pas}$ mice. Overnight-fasted db/db (A), $db^{Pas}/db^{Pas}$ (B) mice were gavage-fed a high-fat test meal and immediately injected intravenously (db/db) or intraperitoneally ($db^{Pas}/db^{Pas}$) with saline (open symbols) or 50 μg mouse recombinant leptin (closed symbols). At the indicated times, blood was collected from the tail (A) or orbital (B) vein, plasma was separated by centrifugation, and plasma TG concentrations were determined using an enzymatic kit. Each point represents the mean±SEM (db/db: saline, n=4, leptin, n=3; $db^{Pas}/db^{Pas}$: saline, n=6, leptin, n=7). The average plasma lipid response in 10 control C57BL6 mice is shown as a dotted line in both A and B. In a separate experiment, shown as an inset for each strain of mice, overnight fasted db/db (●) or $db^{Pas}/db^{Pas}$ (■) mice were gavage-fed the test meal and immediately injected intravenously with increasing concentrations of leptin. The plasma lipid response was then measured as in A and B. The area under the response curve (AUC) was then calculated using a triangulation method on Microsoft Excel between 0 and 4 hr (mg TG·h/mL). Values are presented as % of control value (test meal alone obtained in A or B). Each point represents the mean of at least 3 mice.

Na $^{125}$I was purchased from Amersham-Pharmacia (Piscataway, N.J.; Les Ulis, France). Oleic acid, bovine serum albumin (A2153) (BSA), were obtained from Sigma (St. Louis, Mo.; St. Quentin Fallavier, France). Sodium heparin was purchased from Choay laboratories (Gentilly, France). Fugene was purchased from Roche Boehringer Mannheim (Indianapolis, Ind.), and Superfect from Qiagen (Valencia, Calif.). Zeocin was obtained from Invitrogen (Carlsbad, Calif.). Suramin was a gift from Bayer Pharmaceuticals (Puteaux, France). Enzymatic kits for the determination of TG and FFA were obtained from Roche-Boehringer Mannheim (Meylan, France) and WAKO (Richmond, Va.; Unipath, Dardilly, France), respectively. Dulbecco's modified Eagle's medium (DMEM), trypsin, penicillin-streptomycin, glutamine, and fetal bovine serum (FBS) were purchased from Life Technologies, Inc (Grand Island, N.Y.; Eragny, France). RIA kits for plasma leptin measurements were obtained from Linco (St. Louis, Mo.). Experiments in FIGS. 1 (db/db only), 2 and 6 were performed using recombinant mouse leptin prepared in the laboratory as described previously (Yen F. T., Masson M., Clossais-Besnard N., Andre P., Grosset J. M., Bougueleret L., Dumas J. B., Guerassimenko, O., and Bihain B. E. (1999). J Biol Chem 274, 13390-13398). The remainder of the experiments were performed using commercial preparations of recombinant human or mouse leptin (Sigma and Calbiochem, Meudon, France). $\alpha_2$-Macroglobulin-methylamine was a kind gift from Dr. D. Strickland (American Red Cross, Rockville, Md.).

Animals

Male wild-type and C57BL/Ks db/db (db) mice were purchased from R. Janvier Breeding Center (Le Genest St. Isle, France), while male db$^{Pas}$/db$^{Pas}$ were kindly made available by Prof. J. L. Guenet (Institut Pasteur, Paris, France). Female ob/ob mice were obtained from The Jackson Laboratory (Bar Harbor, Me.). All animals were housed in an animal facility on a 12 h light/dark cycle and were allowed water and rodent chow (No. 113, UAR, Epinay-sur-Orge, France) ad libitum. Mean body weights at the time of the experiment for wild-type, db/db, db$^{Pas}$/db$^{Pas}$, and ob/ob mice were 27.8±1.4, 33.8±9, 74.6±11.4 g, and 49.4±5.49 g, respectively. The research protocol was in accordance with French Ministry of Agriculture, section of Health and Animal Protection and the established institutional guidelines.

Cells

Primary cultures of rat hepatocytes were prepared as described previously (Yen, F. T., Mann, C. J., Guermani, L. M., Hannouche, N. F., Hubert, N., Hornick, C. A., Bordeau, V. N., Agnani, G., and Bihain, B. E. (1994). Biochemistry 33, 1172-1180) using overnight-fasted 150-200 g Sprague-Dawley male rats (R. Janvier Breeding Center) or obtained commercially (In Vitro Technologies, Baltimore, Md.). Cells were used in experiments 48 h after plating. The PLC liver hepatoma (CRL-8024) and Chinese hamster ovary (CHO-K1, CRL 9618) cell lines were obtained from the ATCC repository (CRL-8024; Manasass, Va.). The PLC line was maintained in tissue culture with MEM containing 10% (v/v) FBS, 2 mM glutamine, sodium pyruvate, non-essential amino acids, 100 units/mL penicillin, and 100 units/mL streptomycin. CHO-K1 cells were grown in Ham's-F12 containing 10% (v/v) FBS, 2 mM glutamine and 100 units/mL each of penicillin and streptomycin.

Anti-LSR Antibodies and Peptides

The preparation of antibodies directed against rat LSR protein, and anti-LSR peptide 170 antibodies was as described previously (Yen F. T., Masson M., Clossais-Besnard N., Andre P., Grosset J. M., Bougueleret L., Dumas J. B., Guerassimenko, O., and Bihain B. E. (1999). J Biol Chem 274, 13390-13398. Synthetic peptides 81B and 93A with sequences corresponding to human LSR α residues 35-45 of SEQ ID NO:3 (FGRDARARRAQ) and 613-627 of SEQ ID NO:3 (EEAYYPPAPPPYSET), respectively, were obtained commercially. Polyclonal antibodies directed against this synthetic peptide conjugated to KLH were prepared, and the IgG fraction was purified as described previously (Yen F. T., Masson M., Clossais-Besnard N., Andre P., Grosset J. M., Bougueleret L. Dumas J. B., Guerassimenko, O., and Bihain B. E. (1999). J Biol Chem 274, 13390-13398.) Synthetic peptides corresponding to residues 117-138 of SEQ ID NO:34 of mouse leptin (CSLPQTSGLQKPESLDGVLEAS) as well as the corresponding fragment of human leptin were commercially prepared (Research Genetics, Huntsville, Ala.).

In Vivo Methods

Measurement of Plasma Lipid Response in Mice

Mice that were fasted for 2-3 hours were gavage-fed 300 µL of a test meal consisting of 60% fat (37% saturated, 27% mono-, and 36% polyunsaturated fatty acids), 20% protein and 20% carbohydrate, and providing 56 kcal of energy/kg (1.5 g butter, 1.5 g sunflower oil, 2.5 g nonfat dry milk, 2.5 g sucrose and 3 ml water). Immediately after the meal, the animals were injected intravenously (db/db) or intraperitoneally (db$^{Pas}$/db$^{Pas}$) with either 200 µL physiological saline or 200 µL of the same solution containing recombinant mouse leptin. At selected time intervals, 20 µL of blood were collected from the orbital (db$^{Pas}$/db$^{Pas}$) or tail (db/db) vein into ice-cold microfuge tubes containing 4 mmol/L EDTA. Plasma was obtained by centrifugation at 2500 rpm for 20 min at 4° C., and was frozen as aliquots at −80° C. before analysis. TG concentrations were determined using a commercially available enzymatic kit with controls included in each assay (Precinorm L, Roche-Boehringer Mannheim; Lyotrol N, BioMérieux).

Measurement of Postheparin Lipolytic Activity

Mice were gavage-fed and injected with leptin or control solutions as described above. At t=1 h, the mice were injected subcutaneously with heparin (100 IU/kg body weight). At t=2 h, the animals were bled and the plasma was immediately separated by centrifugation. Lipase activity was determined according to Iverius and Brunzell (1985) using 20% Lipoven (Fresenius France Pharma, Louviers, France) as the source of TG. The assay was performed using 25 µL postheparin plasma in 0.15 M NaCl (200 µL total volume), and in the presence of 10 µL heat-inactivated (56° C., 30 min) human plasma as a source of apoC's. Before and at the end of the incubation, FFA concentrations were determined using an enzymatic kit.

Cell Culture Studies

Lipoprotein Receptor Studies

LSR activity was measured as the oleate-induced binding, uptake, and degradation of $^{125}$I-low density lipoprotein (LDL) in cells following the method described in detail previously (, B. E., and Yen, F. T. (1992). Free fatty acids activate a high-affinity saturable pathway for degradation of low-density lipoproteins in fibroblasts from a subject homozygous for familial hypercholesterolemia. Biochemistry 31, 4628-4636; Yen, F. T., Mann, C. J., Guermani, L. M. Hannouche, N. F., Hubert, N., Hornick, C. A., Bordeau, V. N., Agnani, G., and Bihain, B. E (1994). Biochemistry 33, 1172-1180); Yen F. T., Masson M., Clossais-Besnard N., Andre P., Grosset J. M., Bougueleret L., Dumas J. B., Guerassimenko, O., and Bihain B. E. (1999). J Biol Chem 274, 13390-13398). Modifications of the standard protocols are described in the Brief Description of the Drawings.

Identification of LSR Protein

Western Blotting

Confluent monolayers of cells were washed in PBS, and lysed in 20 mM Tris containing 2 mM EDTA and 0.5% (w/v) SDS and an protease inhibitors (0.1 mg/mL PMSF, 2 µg/mL leupeptin and 1.9 µg/mL aprotinin). The lysate was then separated on 10% SDS-PAGE under denaturing conditions. After transfer to nitrocellulose, the strips were probed with anti-LSR peptide anti-serum. Bands were revealed after incubations with secondary goat anti-rabbit IgG conjugated to alkaline phosphatase. After washing in PBS containing 0.5% (v/v) Tween 20, the bands were revealed by incubation with substrate.

Immunoprecipitation

Confluent monolayers of PLC cells were lysed in PBS containing 1% (w/v) Triton X-100, and then were incubated with the specified anti-LSR antibodies, as described previously (Yen F. T., Masson M., Clossais-Besnard N., Andre P., Grosset J. M., Bougueleret L., Dumas J. B., Guerassimenko, O., and Bihain B. E. (1999). J Biol Chem 274, 13390-13398). Immunoprecipitates were separated on 10% SDS-polyacrylamide gels under nondenaturing conditions, and then transferred onto nitrocellulose.

Ligand Blotting

Partially purified rat LSR (240 kDa band complex) was obtained as described previously (Yen F. T., Masson M., Clossais-Besnard N., Andre P., Grosset J. M., Bougueleret L., Yen F. T., Masson M., Clossais-Besnard N., Andre P., Grosset J. M., Bougueleret L., Dumas J. B., Guerassimenko, O., and Bihain B. E. (1999). J Biol Chem 274, 13390-13398.) The band was separated on non-denaturing 4-12% gradient SDS polyacrylamide gel, and was transferred to nitrocellulose by semi-dry transfer (Biorad, 18 V, 25 mm). The nitrocellulose strip was incubated at room temperature with PBS containing 3% BSA, and then incubated at 37° C. for 1 h with 200 ng/mL 125I-leptin in PBS containing 0.2% BSA, pH 7.4. After six 10 mm washes in PBS containing 0.5% TritonX-100, the strip was air-dried and exposed on a phosphor screen for analysis.

Preparation of Lipoproteins

Human LDL (1.025<d<1.055 g/mL) were isolated by sequential ultracentrifugation of fresh plasma obtained from the local blood bank (Havel, R., and Kane, J. P. (1995). In The Metabolic and Molecular Basis of Inherited Disease, vol. II, Scriver, C. R., Beaudet, A. L., Sly, W. S., and Valle, D., eds. (New York, N.Y.: McGraw-Hill, Inc), pp. 1841-1851.

Rat chylomicrons were prepared from overnight-fasted male Sprague-Dawley rats (300-400 g) given a high-fat liquid meal similar to that given to mice (2 mL per animal). After 45 min, the animals were anesthetized and catheters were inserted in the main abdominal lymph duct. Lymph was collected over 2 hours, and the chylomicrons were isolated. Contaminating albumin was removed by incubation for 30 min at room temperature with an equivalent volume of swollen Blue Sepharose CL-6B gel (Amersham Pharmacia Biotech) (Mann, C. J., Troussard, A. A., Yen, F. T., Hannouche, N., Najib, J., Fruchart, J.-C., Lotteau, V., André, P., and Bihain, B. E. (1997). J. Biol. Chem. 272, 31348-31354). All lipoproteins were stored in the dark at 4° C. under $N_2$ and used within 2 weeks (LDL) or 3 days (chylomicrons) of their isolation Radiolabelling Lipoproteins were radioiodinated using Bilheimer's modification of the McFarlane's procedure (Bilheimer, D. W., et al. (1972). Biochim. Biophys. Acta 260, 212-221), and used no more than 1 week after radiolabeling. $^{125}$I-LDL was filtered (0.2 µm, Gelman, Ann Arbor, Mich.) on the day of the experiment.

Leptin was iodinated using Iodobeads (Pierce) according to the manufacturer's instructions.

Cloning of Full Length cDNA Human LSR

Human homologous sequences of rat LSR cDNA were found with 2 partially overlapping human genomic sequences (Genbank accession nos: AD000684 and AC002128). ESTs generated on the basis of these sequences were used to screen a human BAC library. A single clone was isolated and sequenced. Analysis of this sequence revealed several variations from the public sequence. A revised LSR sequence is currently available in Genbank (accession numbers TBA).

An 805 bp fragment was obtained by PCR amplification of human liver mRNA (Sense primer: 5'-CTACAAC-CCCTACGTCGAGT (SEQ ID NO:22), antisense primer: 5'-AGGCGGAGATCGCCAGTCGT (SEQ ID NO:23)), and subcloned into the TA cloning vector (Invitrogen, Carlsbad, Calif.). The cloned insert was isolated by digestion with EcoR1, was purified (GenClean kit, Bio 101, Vista, Calif.), and the DNA was labeled with α-$^{33}$P-dCTP (NEN, Boston, Mass.) using the random primers labeling system (Life Technologies). The labelled fragment was used to screen the cDNA library (Superscript, Life Technologies), from which we obtained a partial α' clone (clone 18251), lacking 161 bp of the 5' region.

The missing 5' region was obtained by PCR amplification (AmpliTaq, Promega, Madison, Wis.) from a first strand cDNA prepared from human liver total RNA (Clonetech, Palo Alto, Calif.) (both oligo dT and random primers were used). The primers for PCR were sense 5'CCTTTGTC-CACGTCGTTTACGCTC-3' (SEQ ID NO:24) and antisense 5'-TCACAGCGTTGCCCTGCTTG-3' (SEQ ID NO:25). The PCR was performed with annealing temperature of 65° C. and 35 cycles. The fragment was cloned into pGEMT-Easy Vector (Promega).

Fragments corresponding to the α forms and β were cloned into pGEMT-Easy Vector and then used to replace the appropriate region in the LSR α' clone. The full-length LSR α, α', and β clones were reconstructed in pTracer-CMV2 vector (Invitrogen) using EcoRI/Xba I.

PCR Analysis of Human LSR

Figure 3:
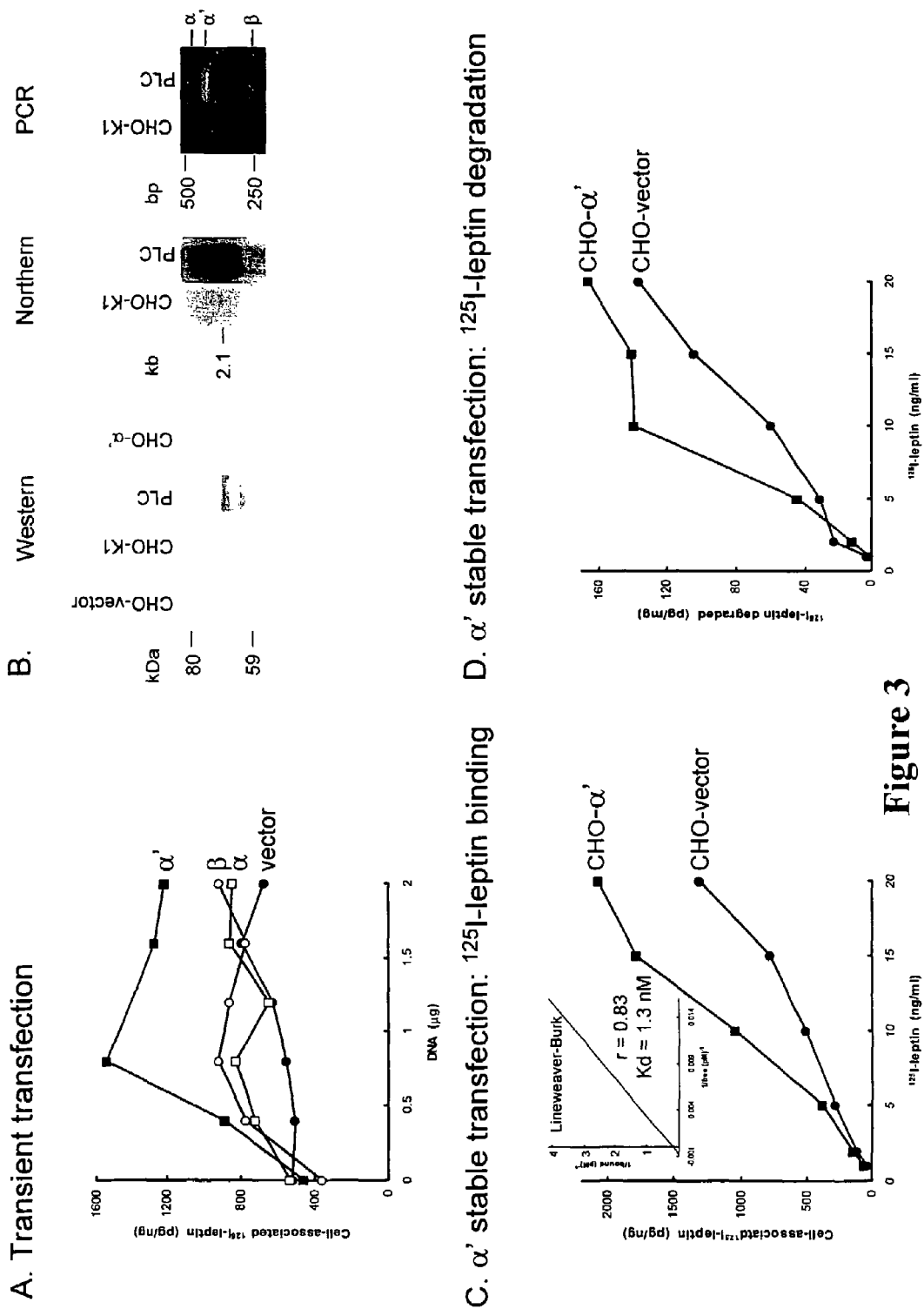
FIGS. 3A, 3B, 3C, and 3D show the effect of LSR subunit transfection on leptin binding and degradation in CHO-K1 cells. For FIG. 3A, CHO-K1 cells were transfected with increasing concentrations of the α, (□), α' (■) or β (○) LSR plasmid, or vector alone (●) using Fugene transfection reagent. After 48 h, the cells were washed once in PBS and incubated at 37° C. for 2 h with 10 ng/mL of $^{125}$I-leptin in DMEM containing 0.2% (w/v) BSA, 2 mM $CaCl_2$ and 5 mM HEPES, pH 7.4 (Buffer A). The monolayers were washed and lysed with 0.1 N NaOH containing 0.24 mM EDTA, and the lysates were counted. The results are shown as the amount of cell-associated $^{125}$I-leptin. For FIG. 3B, lysates were prepared from CHO-K1 wild type, stable transfectants of vector or LSR α' subunit, and PLC, and separated on a 10% SDS-polyacrylamide gel under denaturing and reduced conditions. After transfer to nitrocellulose, Western blots were performed using anti-LSR 170 antibody (can also be done with the human equivalent, 93A). Northern blots were done to detect LSR mRNA in CHO-K1 wild-type versus PLC. RT-PCR analysis was also done in CHO-K1 as compared to PLC. For FIGS. 3C and 3D, confluent monolayers of stable-transfected cell lines expressing LSR α' subunit (■) or vector alone (●) were washed once in PBS and incubated at 37° C. for 2 h with increasing concentrations of $^{125}$I-leptin in Buffer A. The amount of cell-associated (FIG. 3C) and degraded (FIG. 3D) $^{125}$I-leptin was then measured as described herein. Results are shown as the mean of triplicate determinations.

Similarly to previous results with rat LSR (Yen F. T., Masson M., Clossais-Besnard N., Andre P., Grosset J. M., Bougueleret L., Dumas J. B., Guerassimenko, O., and Bihain B. E. (1999). J Biol Chem 274, 13390-13398), two splice variants of LSR were detected by RT-PCR analysis of human hepatocyte cDNA. In FIG. 3B, sense and antisense primers were designed to yield three products, of which two were the splice variants. The primer sequences were: sense, 5'-TTACTGCTCCGTGGTCTCAGC-3' (SEQ ID NO:26) and antisense, 5' AGCTACTCCTGTCAACGTCTCC-3' (SEQ ID NO:27). Identities of each band were confirmed by sequencing.

Northern Blotting

Northern blots were performed as described previously using as a probe clone 18251 described above (Yen F. T., Masson M., Clossais-Besnard N., Andre P., Grosset J. M., Bougueleret L., Dumas J. B., Guerassimenko, O., and Bihain B. E. (1999). J Biol Chem 274, 13390-13398).

In Vitro Translation

In vitro translation products were obtained using $^{35}$S-methionine (Amersham) and the T7 coupled transcription/translation kit from Promega.

Transient Transfection Studies

CHO-K1 cells were plated at a density of 300,000 cells/36 mm dish the day before transfection. After 24 h, plasmid preincubated with Fugene transfection reagent was added to the cells, which were further incubated at 37° C. Cells were used 48 h after transfection as described in the Brief Description of the Figures.

Stable Transfections

Stable transfectants were prepared from CHO-K1 cells using Superfect according to the manufacturer's instructions. After introduction of the plasmid into the cell with Superfect, the cells were grown in the presence of 750 μg/mL zeocin. After elimination of untransfected cells, the antibiotic concentration was reduced to 500 μg/mL. Clones were isolated using cloning cylinders, and maintained in tissue culture media containing 100 μg/mL zeocin.

FACS Analysis

Flow cytometry is a laser-based technology that is used to measure characteristics of biological particles. The underlying principle of flow cytometry is that light is scattered and fluorescence is emitted as light from the excitation source strikes the moving particles.

Assay 1: PLC cell suspensions were obtained using non-enzymatic dissociation solution (Sigma), and then were incubated for 1 h at 4° C. with a 1:200 dilution of anti-LSR 81B or irrelevant anti-serum in PBS containing 1% (w/v) BSA. After washing twice with the same buffer, goat anti-rabbit FITC-conjugated antibody (Rockland, Gilbertsville, Pa.) was added to the cells, followed by a further incubation for 30 min at 4° C. After washing, the cells were fixed in 2% formalin. Flow cytometry analysis was done on a FACSCalibur cytometer (Becton-Dickinson, Franklin Lakes, N.J.).

Assay 2: Cells are cultured in a T175 flasks according to manufacturer's instructions for 48 hours prior to analysis.

Cells are washed once with FACs buffer (1×PBS/2% FBS, filter sterilized), and manually scraped from the flask in 10 mLs of FACs buffer. The cell suspension is transferred to a 15 mL conical tube and centrifuged at 1200 rpm, 4° C. for 5 minutes. Supernatant is discarded and cells are resuspended in 10 mL FACs buffer chilled to 4° C. A cell count is performed and the cell density adjusted with FACs buffer to a concentration of 1×10$^6$ cells/mL. One milliliter of cell suspension was added to each well of a 48 well plate for analysis. Cells are centrifuged at 1200 rpm for 5 minutes at 4° C. Plates are checked to ensure that cells are pelleted, the supernatant is removed and cells resuspended by running plate over a vortex mixer. One milliliter of FACs buffer is added to each well, followed by centrifugation at 1200 rpm for 5 minutes at 4° C. This described cell washing was performed a total of 3 times.

Primary antibody, titered in screening experiments to determine proper working dilutions (for example 1:25, 1:50, 1:100, 1:200, 1:400, 1:500, 1:800, 1:1000, 1:2000, 1:4000, 1:5000, or 1:10000), is added to cells in a total volume of 50 μL FACs buffer. Plates are incubated for 1 h at 4° C. protected from light. Following incubation, cells are washed 3 times as directed above. Appropriate secondary antibody, titered in screening experiments to determine proper working dilutions (for example 1:25, 1:50, 1:100, 1:200, 1:400, 1:500, 1:800, 1:1000, 1:2000, 1:4000, 1:5000, or 1:10000), is added to cells in a total volume of 50 μL FACs buffer. Plates are incubated for 1 h at 4° C. protected from light. Following incubation, cells are washed 3 times as directed above. Upon final wash, cells are resuspended in 500 μL FACs buffer and transferred to a FACs acquisition tube. Samples are placed on ice protected from light and analyzed within 1 hour.

Protein Determinations

Protein concentrations were determined using Markwell's modified Lowry procedure (1981) or BCA protein assay (Pierce Chemical Co, Rockford, Ill.) and BSA as standard.

Statistical Analysis

Results were analyzed using unpaired Student's t-test.

Example 1

Effect of Leptin on Postprandial Plasma TG Response

Transient hypertriglyceridemia seen after administration of a test meal in two strains of obese mice with defects of the Ob-Receptor (OB-R) is shown in FIGS. 1A and 1B (open symbols). The db/db mice present a mutation of the Ob-Rb isoform, preventing signaling to the JAK and Stat system, while the db$^{Pas}$/db$^{Pas}$ lack any leptin signaling capacity through the Ob-R. Similar to what is observed in most obese human subjects (Lewis, G. F., O'Meara, N. M., Soltys, P. A., Blackman, J. D., Iverius, P. H., Druetzler, A. F., Getz, G. S., and Polonsky, K. S. (1990) J. Clin. Endocrinol. Metab. 71, 1041-105o; Vansant, G., Mertens, A., and Muls, E. (1999) Intl. J. Obesity 23, 14-21) postprandial plasma lipid levels were elevated in both strains of obese mice when compared to lean controls (shown as dotted lines). A single bolus injection of 50 μg leptin at the time of the meal decreased the amplitude of the triglyceride response (FIGS. 1A and 1B, closed symbols); this effect could not be attributed to a reduction in food intake since the meal was administered by intragastric cannulation.

A significant reduction of the area under the TG curve was observed with 250 ng of leptin per animal (FIGS. 1A, 1B, insets). It can be estimated (average body weight of $db^{Pas}/db^{Pas}$, 74.6±11.4 g; plasma volume 45 mL per kg) that this dose cannot cause more than a two-fold increase of the concentration of circulating leptin (86.7±12.2 ng/mL) in $db^{Pas}/db^{Pas}$. Maximum effect of leptin was achieved with 500 ng per animal which decreased by >80% and >65% the area under the postprandial TG curve in db/db and $db^{Pas}/db^{Pas}$, respectively. This dose of leptin (7 µg per kg body weight) is 15-fold lower than that used to achieve 30 to 40% reduction of food intake after peripheral administration of leptin (Campfield, L. A., Smith, F. J., Guisez, Y., Devos, R., and Burn, P. (1995) *Science* 269, 546-549; Halaas et al, 1995; Halaas, J. L., Gajiwala, K. S., Maffei, M., Cohen, S. L., Chait, B. T., Rabinowitz, D., Lallone, R. L., Burley, S. K., and, J. M. (1995) *Science* 269, 543-546; Pelleymounter, M. A., Cullen, M. J., Baker, M. B., Hecht, R., Winters, D., Boone, T., and Collins, F. (1995) *Science* 269, 540-543). These data establish that leptin can control the exogenous lipoprotein pathway and that this regulation occurs in $db^{Pas}/db^{Pas}$ in spite of the complete defect of the Ob-R.

Example 2

Leptin Binding to Rat LSR

Figure 2:
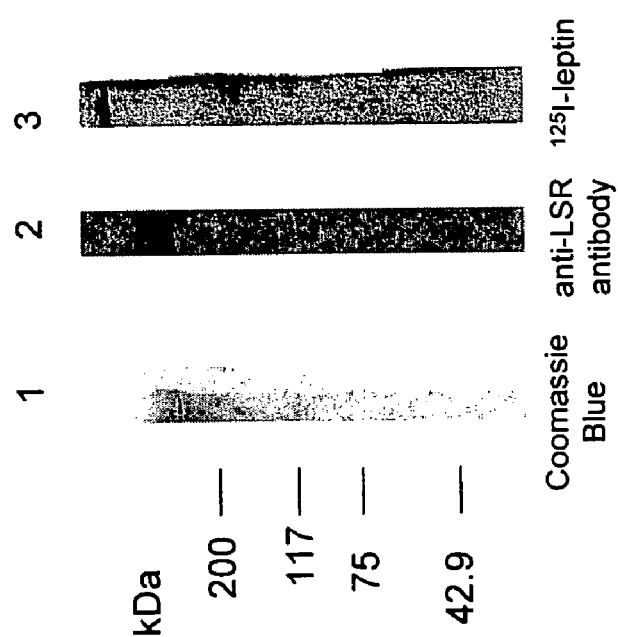
FIG. 2 shows $^{125}$I-Leptin binding to partially purified rat LSR. Aliquots (72 μg) of partially purified rat liver LSR were separated on a 4%-12% SDS-gradient polyacrylamide gel, and transferred to nitrocellulose as described previously (Yen F. T., Masson M., Clossais-Besnard N., Andre P., Grosset J. M., Bougueleret L., Dumas J. B., Guerassimenko, O., and Bihain B. E. (1999). J Biol Chem 274, 13390-13398) a gel strip stained with Coomassie blue is shown in lane 1. The nitrocellulose strips were washed, blocked, and incubated with anti-rat LSR protein antiserum (1:1000 dilution) (lane 2), or with 200 ng/mL $^{125}$I-leptin (lane 3). The strips were washed and bands were detected as described herein. Image analysis of lane 3 was performed on a Phosphorimager (Molecular Dynamics).

The binding of leptin to LSR was tested using partially purified rat LSR multimeric complexes. Complexes separated by SDS electrophoresis (FIG. 2, lane 1) and transferred to nitrocellulose, bound $^{125}$I-leptin (FIG. 2, lane 3). The same bands were recognized by polyclonal anti-rat LSR antibodies (FIG. 2, lane 2). The specificity of these antibodies has been described previously (Yen F. T., Masson M., Clossais-Besnard N., Andre P., Grosset J. M., Bougueleret L., Dumas J. B., Guerassimenko, O., and Bihain B. E. (1999). J Biol Chem 274, 13390-13398).

Example 3

Effect of LSR Subunit Transfection

To determine which of the LSR subunits is responsible for leptin binding, CHO-K1 cells were transiently transfected with increasing concentrations of each of the 3 human LSR plasmids (FIG. 3A). CHO-K1 cells were selected because they had the lowest level of endogenous LSR expression of the different cell lines tested. This level is far lower than that of a human hepatocyte cell line (PLC) used to systematically characterize human LSR activity (FIG. 3B). The data showed that only transfection with the LSR α' plasmid increased the binding of leptin to CHO-K1 cells (FIG. 3A). Leptin binding to CHO-K1 cells transfected with LSR β or α remained at levels similar to those seen with the vector alone. Analysis of the expression of co-transfected green fluorescent protein (GFP) estimated transfection efficiency at ±25% for all 3 transiently transfected plasmids.

CHO-K1 cells stably expressing LSR α' were also obtained and were determined to have an increased $^{125}$I-leptin binding and uptake (FIG. 3C). The apparent molecular mass of human LSR α' in stable CHO-K1 transfectant cells corresponded to that of the smallest LSR subunit (~70 kDa) in PLC cells (FIG. 3B). Lineweaver-Burk transformation of leptin binding to CHO-K1 cells expressing LSR α' yielded an estimated Kd of 1.3 nM (FIG. 3C, inset), ~2 fold that of the Ob-R (Kd=0.7 nM; Tartaglia et al, 1995). Leptin binding to LSR α' led to its internalization and proteolytic degradation consistent with this leptin binding reflecting a biologically relevant process (FIG. 3D).

Similar to what is observed in cells transfected with the Ob-Ra or Ob-Rb (Uotani, S., Bjørbærk, C., Tornøe, J., and Flier, J. S. (1999). Diabetes 48, 279-286.) the amount of $^{125}$I-leptin degraded by CHO-K1 cells transfected with LSR α' represented only 16% of that bound and internalized by the cells. These rates of $^{125}$I-leptin degradation are much lower than those observed with receptors mediating rapid endocytosis (Goldstein, J. L., Basu, S. K., Brown, M. S. (1983). 98, 241-260). For instance, after 2 h incubation, the amount of $^{125}$I-LDL degraded through LSR represents 4-5 times the amount bound to the cell surface (Bihain, B. E., and Yen, F. T. (1992). Although not intending to be limited by any particular theory, the simplest explanation is that LSR α' lacks the di-leucine routing signal known to trigger rapid lysosomal delivery. The LSR α contains such a signal, consistent with previous observations that the α subunit is a critical element allowing LSR to function as lipoprotein receptor (Yen F. T., Masson M., Clossais-Besnard N., Andre P., Grosset J. M., Bougueleret L., Dumas J. B., Guerassimenko, O., and Bihain B. E. (1999). J Biol Chem 274, 13390-13398).

Similar experiments are performed in the other stable cell lines expressing the subunits of LSR alone or in all combinations (see table, below). These cell lines are useful for screening small molecules or any potential agonist or antagonist for activity against either the leptin or triglyceride (or both) activity of LSR. In addition, they can be employed in receptor binding assays using FACS analysis or radiolabelled ligands to identify additional ligands of LSR.

| LSR stable-transfectant Cell Lines |
| --- |
| CHO LSR alpha |
| CHO LSR alpha' |
| CHO LSR beta |
| CHO LSR alpha'/beta |
| CHO LSR alpha/beta |
| CHO LSR alpha/alpha' |
| CHO LSR alpha/alpha'/beta |

Example 4

Effect of 81B Anti-LSR Antibody on LSR Binding and Degradation of Leptin

Figure 4:
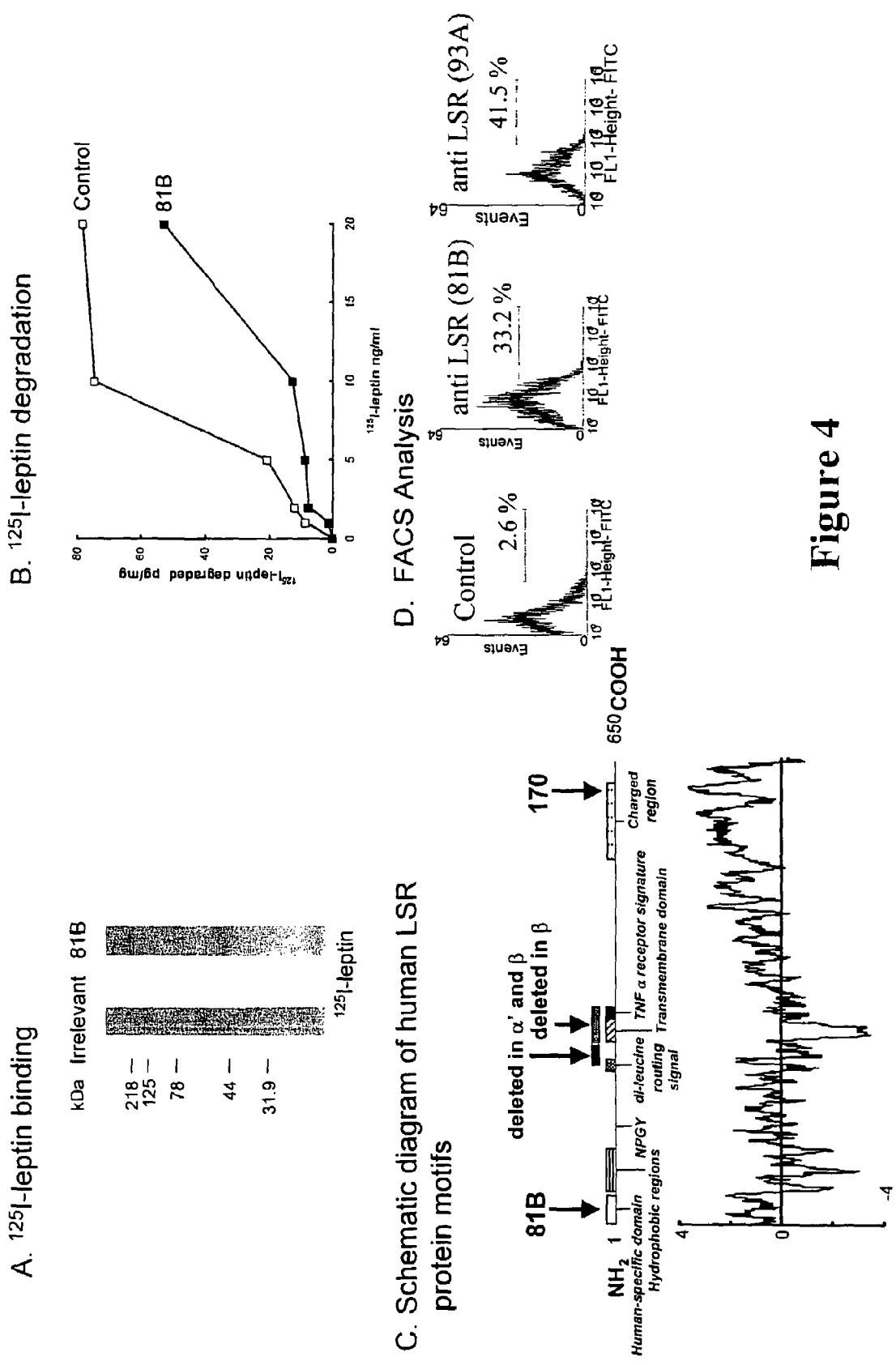
FIGS. 4A, 4B, 4C, and 4D show LSR binding and degradation of $^{125}$I-leptin in human hepatocytes, and the effect of 81B anti-LSR antibody. For FIG. 4A, PLC cells were lysed (3-T175 cm$^2$ flasks per condition) and immunoprecipitated with irrelevant or 81B anti-serum. The immunoprecipitates were washed, were separated on 10% SDS-polyacrylamide gels under nondenaturing conditions, and were transferred to nitrocellulose. Ligand blots using $^{125}$I-leptin were then performed as described in FIG. 2. For FIG. 4B, confluent monolayers of PLC cells were incubated at 37° C. for 30 min with 100 nM insulin, were washed, and then were incubated for 30 min at room temperature in the presence of anti-LSR peptide 81B antibody (■), or irrelevant (□) IgG. After this, the cells were incubated at 37° C. for 2 h with increasing concentrations of $^{125}$I-leptin in Buffer A. The monolayers were washed, and the amount of $^{125}$I-leptin degraded was determined as described herein. Results are shown as the mean of duplicate (irrelevant IgG) or triplicate (anti-LSR peptide IgG) determinations.

To test whether in nontransfected cells leptin binds to LSR, PLC cell lysates were immunoprecipitated with an antibody directed against a synthetic peptide with a sequence identical to LSR residues 35-45 (81B). Ligand blotting showed that $^{125}$I-leptin binds directly to the multimeric complexes (apparent molecular masses of 200 and 230 kDa) precipitated by the 81B antibody (FIG. 4A). These complexes are of a size similar to that of rat LSR multimeric complexes (Yen F. T., Masson M., Clossais-Besnard N., Andre P., Grosset J. M., Bougueleret L., Dumas J. B., Guerassimenko, O., and Bihain B. E. (1999). J Biol Chem 274, 13390-13398). Significant amounts of TCA-soluble chloroform-insoluble $^{125}$I-leptin degradation products were found in the incubation media after 2 h incubation of PLC cells with increasing concentrations of $^{125}$I-leptin (FIG. 4B, □). The dose response curve indicated that the process saturated for leptin concentrations ≧10 ng/mL (FIG. 4B). The amount of leptin degraded per mg of PLC cell protein is about half as much as that degraded by CHO-K1 LSR α'stable transfectants (FIG. 3D).

Chloroquine (50 µM) inhibited $^{125}$I-leptin degradation by more than 60%, while increasing the amount of cell-associated $^{125}$I-leptin (2-4 fold). This is consistent with $^{125}$I-leptin degradation occurring in lysosomes after receptor-mediated endocytosis. The 81B antibody that immunoprecipitated LSR multimeric complexes had a profound inhibitory effect on leptin degradation in PLC cells (FIG. 4B, ■). This effect was maximal with 10 ng/mL of leptin and 200 µg/mL of antibody and was partially competed off by increasing leptin concentrations at 20 ng/mL. Because immunoprecipitation data revealed no interaction of the 81B antibody with the Ob-R or any other protein (FIG. 4A), the inhibitory effect of this antibody on leptin degradation indicates that in cells of liver origin, the LSR is quantitatively the primary mechanism for leptin degradation. FACS analysis confirmed that the 81B anti-LSR antibody binds to non-permeabilized PLC cells (FIG. 4D). This indicates that the amino-terminal is exposed on the cell surface.

Leptin binding to LSR does not require the presence of FFA and is inhibited by the 81B antibody directed towards the LSR sequence located near the amino terminal end Immunoinhibition studies previously showed that the cluster of charged residues found at the carboxyl terminal end most likely represents the rat LSR lipoprotein binding site (Yen, F. T., Masson M., Clossais-Besnard N., Andre P., Grosset J. M., Bougueleret L., Dumas J. B., Guerassimenko, O., and Bihain B. E. (1999). J Biol Chem 274, 13390-13398). Accordingly, LSR was classified as a type II membrane receptor. FACS analysis using the 170 antibody, directed towards a synthetic peptide with a sequence corresponding to that of LSR's carboxyl terminal end, is consistent with this interpretation (FIG. 4D).

While not wishing to be limited by any theory, the observation that the 81B antibody inhibits leptin binding to LSR and binds to intact PLC cells (FACS analysis, FIG. 4D), suggests that LSR amino terminal ends are also exposed on the external side of the plasma membrane. LSR contains a typical 28 amino acid transmembrane spanning domain located between residues 259-286 (FIG. 4C). In addition, a cluster consisting of 3 stretches of hydrophobic amino acids is located towards the amino terminal end. Each of these hydrophobic clusters is too short to allow crossing of the plasma membrane, but since the three hydrophobic elements are in close proximity with only two short hydrophilic separating clusters, a transmembrane spanning region could be constituted. In this case, the two separating hydrophilic domains would be oriented inwardly to minimize interaction with the hydrophobic moieties of the phospholipid bilayers. According to this model, LSR α and α' could cross the plasma membrane twice, with both carboxyl and amino terminal ends protruding extracellularly. LSR β would be limited to a single crossing of the membrane.

Example 5

Effect of Leptin on LSR Activity

Figure 5:
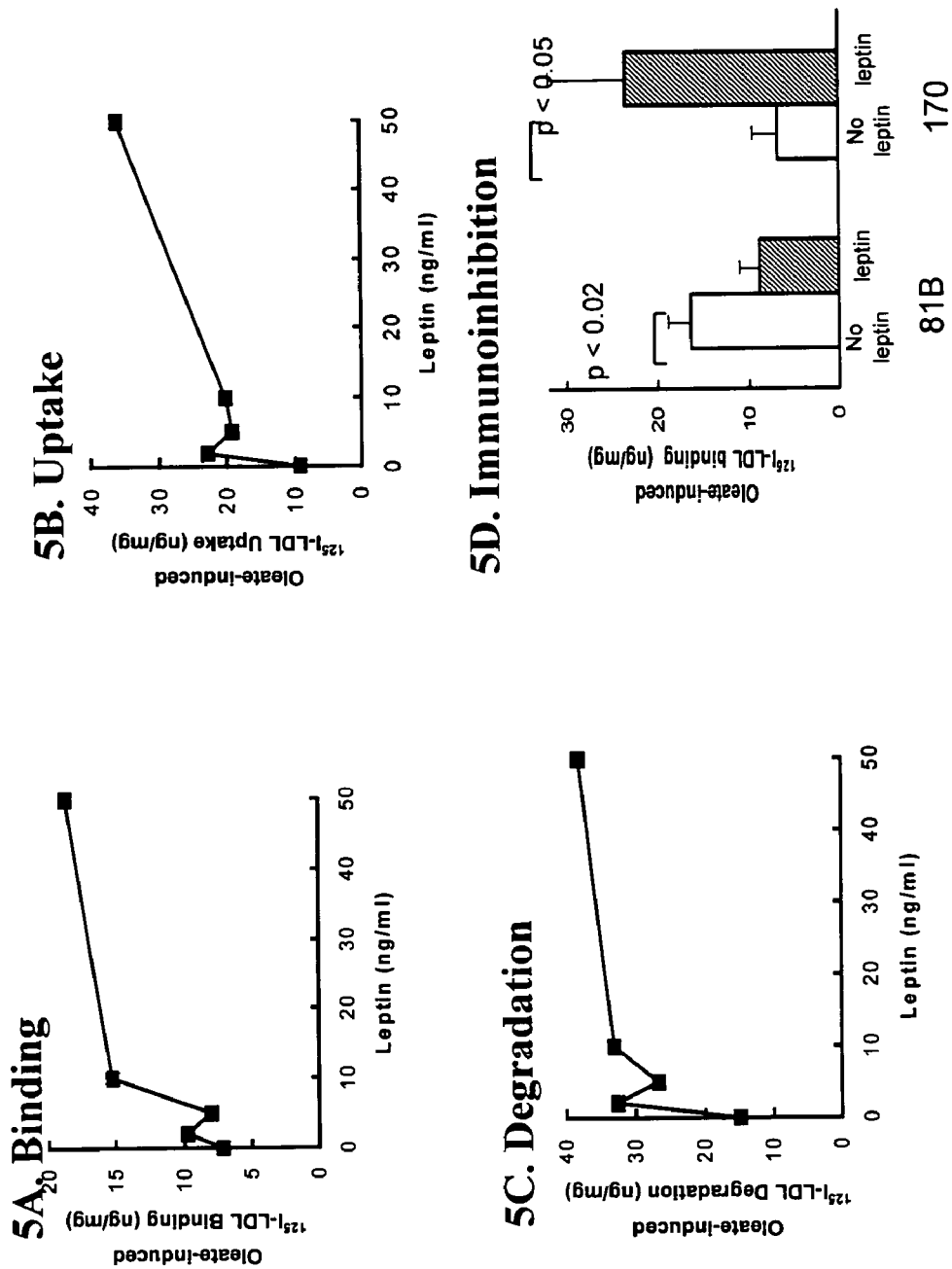
FIGS. 5A, 5B, 5C, and 5D show the stimulatory effect of leptin on LSR activity in PLC and suppression of this effect by 81B antibody. For FIGS. 5A, 5B, and 5C, cultured PLC cells were incubated at 37° C. for 30 min with increasing concentrations of human recombinant leptin in Buffer A. After this, 0.5 mM oleate and 20 µg/mL $^{125}$I-LDL were added, and cells were further incubated at 37° C. for 2 h. Cells were washed, and the amount of oleate-induced $^{125}$I-LDL bound (5A), internalized (5B) and degraded (5C) were measured. For FIG. 5D, PLC cells were incubated at room temperature for 30 min with 200 µg/mL anti-LSR peptide 81B or 170 antibody, followed by incubation at 37° C. for 30 min without (open bar) or with (hatched bar) 10 ng/mL human leptin. Oleate (0.5 mM) and $^{125}$I-LDL (20 µg/mL) were added, and the monolayers were left at 37° C. for 3 h. After washing, the amount of $^{125}$I-LDL binding was determined, and is shown here as the mean±SD of triplicate determinations.

The effect of leptin on the activity of LSR with respect to its ability to bind, internalize and degrade lipoproteins was also studied. Leptin directly increased the oleate-induced LSR binding uptake and degradation of $^{125}$I-LDL in a dose-dependent manner (FIG. 5A, 5B, 5C). The effect was observed at leptin concentrations ≧10 ng/mL.

The specificity of leptin's stimulatory effect upon LSR was further established by the observation that leptin at concentrations of up to 2 µg/mL had no detectable effect on the degradation of LDL by the LDL-receptor nor on that of activated $α_2$-macroglobulin, the preferred LRP ligand.

The stimulatory effect of leptin on LSR activity as a lipoprotein receptor was suppressed by the 81B antibody (FIG. 5D). The antibody 170 directed against a rat LSR sequence located towards the carboxyl terminal end was used as a control. Although the 170 antibody had an inhibitory effect on the oleate-induced $^{125}$I-LDL binding in human PLC incubated without leptin, it did not prevent the leptin stimulatory effect on LSR activity (FIG. 5D).

The stimulatory effect of leptin on LSR activity as lipoprotein receptor was seen not only in cells of human origin, but also in rodent hepatocytes. A brief, 30 min, preincubation of rat hepatocytes with 20 ng/mL mouse recombinant leptin at 37° C. increased oleate-induced $^{125}$I-LDL binding to the cell surface in subsequent incubations at 4° C. (FIG. 6A), indicating that this stimulatory effect of leptin occurred rapidly. Northern blots showed that this leptin treatment did not increase mRNA levels significantly. Further, inhibition of cell protein synthesis (50 µM cycloheximide) did not suppress the stimulatory effect of leptin, while microfilament inhibitors (50 µM cytochalasin B) reduced leptin stimulation by more than 80%. While not wishing to be limited by any particular theory, these results are consistent with the stimulatory effect of leptin on LSR activity resulting primarily from mobilization of a cryptic pool of receptors to the cell surface.

Figure 6:
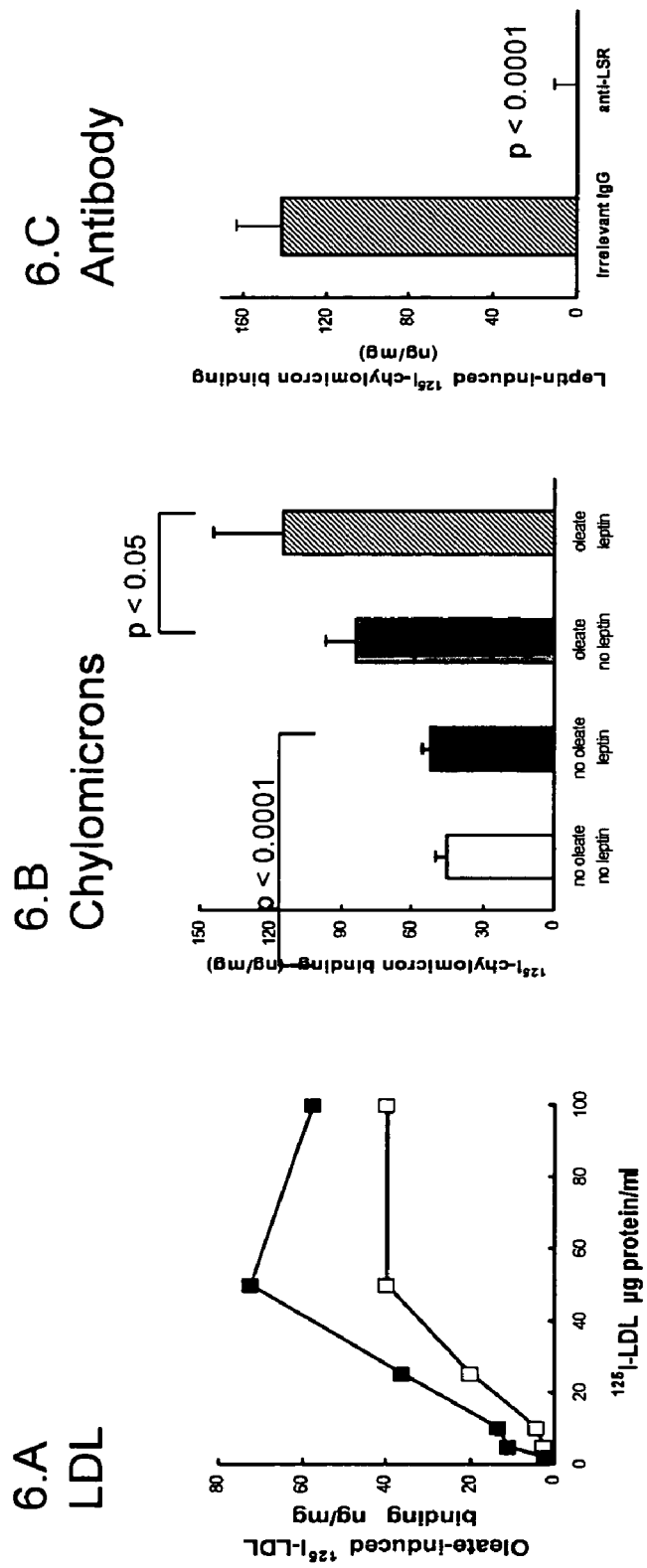
FIGS. 6A, 6B, and 6C show the effect of leptin on $^{125}$I-LDL and $^{125}$I-chylomicron binding to LSR in primary cultures of rat hepatocytes. For FIG. 6A, primary cultures of rat hepatocytes (48 hours after plating) were incubated at 37° C. for 30 min in the absence (□) or presence (■) of 50 ng/mL leptin in Buffer A, followed by a 20 min incubation at 37° C. with 0.5 mM oleate. The cells were then washed with ice-cold PBS, precooled for 10 min, and then incubated for 1 h at 4° C. with increasing concentrations of $^{125}$I-LDL in Buffer A. Cells were washed, were lysed in 0.1 N NaOH and were counted for radioactivity. Results are shown as the mean of duplicate determinations. For FIG. 6B, primary cultures of rat hepatocytes were incubated at 37° C. for 30 min with or without 20 ng/mL leptin followed by incubation at 37° C. for 4 h with 6 µg protein/mL $^{125}$I-chylomicrons in the absence or presence of 0.5 mM oleate in Buffer A. The cells were then washed and the $^{125}$I-chylomicrons bound to the cell surface were released into the media by incubation with 10 mM suramin. The media was recovered and the radioactivity was measured. Results are shown as the mean±SD of six determinations. Fir FIG. 6C, after incubation at 37° C. for 30 min with 50 ng/mL leptin, the cells were incubated at room temperature for 30 min with 200 µg IgG/mL antibodies directed against rat LSR protein or irrelevant IgG. The amount of $^{125}$I-chylomicrons bound was determined, and results are shown as means±SD of triplicate (irrelevant) or quadruplicate (anti-LSR) determinations.

FIG. 6B shows the additive stimulatory effect of leptin and oleate on the binding of chylomicrons to rat hepatocytes. This leptin and oleate-induced binding of chylomicrons to rat hepatocytes was suppressed by specific polyclonal anti-LSR antibodies (FIG. 6C). Thus, the stimulatory effect of leptin on LSR is not limited to LDL, but extends to TG-rich lipoproteins that are directly responsible for the transport of dietary lipid. The data show that physiological amounts of leptin acutely regulate the removal of dietary TG by the liver, and that in vitro, the same concentrations of leptin regulate LSR activity in hepatocytes while leaving that of other lipoprotein receptors unchanged.

The inhibition of the intestinal absorption of dietary lipids by leptin was also investigated. Overnight-fasted ob/ob mice were gavage-fed a high fat test meal. Immediately after the test meal (time=0 h), the mice were injected intravenously with 200 µL saline containing either no supplement, 0.5 µg recombinant mouse leptin, 2.5 mg lactoferrin, or a mixture of 0.5 µg leptin and 2.5 mg lactoferrin. Blood samples were taken at 2 and 3 h after the test meal, and plasma TG concentrations were measured (see Table, below). Values for these 2 time points were pooled and are presented as means±SD of quadruplicate determinations obtained in 2 different animals for each condition (*$p<0.02$ (saline versus leptin; ¶$p<0.01$ saline versus lactoferrin; §NS (lactoferrin versus leptin+lactoferrin)).

TABLE

Effect of lactoferrin and/or leptin on the plasma lipid response of ob/ob mice

| | Plasma TG 2-3 hours nafter test meal (mg/mL) |
|---|---|
| Saline | 1.04 ± 0.08 |
| Leptin | 0.79 ± 0.1* |
| Lactoferrin | 2.02 ± 0.26¶ |
| Leptin + Lactoferrin | 1.96 ± 0.42§ |

The amplitude of postprandial lipemia is determined by both the rate of intestinal lipid absorption and the rate of lipid clearance. To distinguish between these two possible sites of leptin regulation, we used lactoferrin, a milk protein that inhibits the removal of dietary lipid by the liver (Huettinger, M., Retzek, H., Eder, M. and Goldenberg, H. (1988). Clin. Biochem. 21, 87-92). As shown in the Table, injection of lactoferrin in ob/ob mice caused a doubling of plasma TG measured during the postprandial stage. Further, leptin caused a decrease in postprandial plasma TG when injected without lactoferrin, but was unable to achieve a significant effect in mice simultaneously treated with lactoferrin. Although not wishing to be bound by a particular theory, this suggested that most of leptin's regulatory effect was due to stimulation of dietary lipid removal by the liver. Lactoferin has been shown previously to be an inhibitor of LSR at the concentration used (Yen, F. T., Mann, C. J., Guermani, L. M., Hannouche, N. F., Hubert, N., Hornick, C. A., Bordeau, V. N., Agnani, G., and Bihain, B. E. (1994) Biochemistry 33, 1172-1180; Mann, C. J., Khallou, J., Chevreuil, O., Troussard, A. A., Guermani, L. M., Launay K., Delplanque, B., Yen, F. T., and Bihain, B. E. (1995) *Biochemistry* 34, 10421-10431).

The effect of leptin injection on the activity of lipolytic enzymes that are involved in the hydrolysis of plasma TG was also examined. Injections of leptin (50 μg/animal) did not significantly modify lipase activity released in serum of $db^{Pas}/db^{Pas}$ after heparin injections (FIG. 12). If anything, leptin decreased, although not significantly, the lipase activity when compared to the effect of administering the test meal alone. These data ruled out the possibility that leptin regulates postprandial lipemia by directly controlling the activity of lipolytic enzymes.

Example 6

Comparison of the Effect of Human and Mouse Leptin

Figure 7:
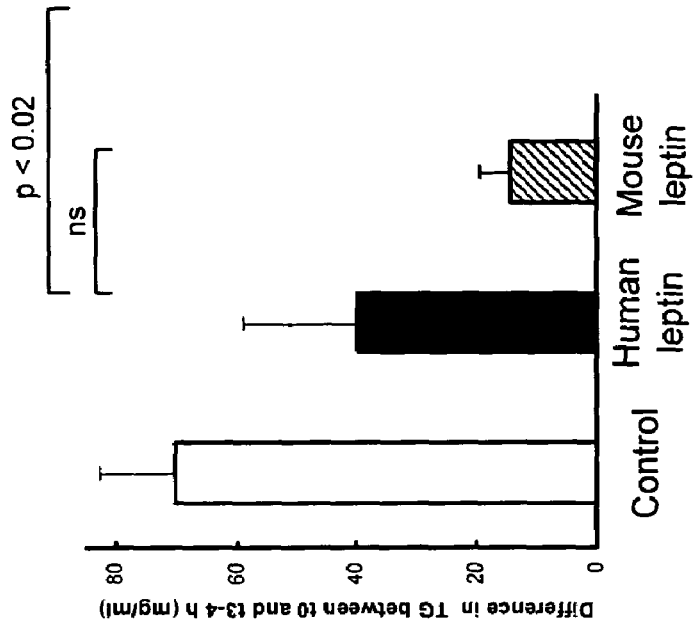
FIGS. 7A and 7B show a comparison of the effect of human and mouse leptin on LSR activity in rat hepatocytes and on postprandial increase in plasma TG in db$^{Pas}$/db$^{Pas}$ mice. For FIG. 7A, primary cultures of rat hepatocytes were incubated 30 min at 37° C. without (open bar) or with 10 ng/mL recombinant human (solid bar) or mouse (hatched bar) leptin in Buffer A. Oleate (0.5 mM) and $^{125}$I-LDL (20 µg/mL) were added and the cells were incubated 2 h at 37° C. The media were removed and were analyzed for TCA-soluble degradation products. The mean of duplicate determinations is shown. For FIG. 7B, db$^{Pas}$/db$^{Pas}$ mice were given a test meal as previously described, followed immediately by injection i.p. of saline (open bar, n=4), human leptin (1 µg/animal; solid bar, n=3) or mouse leptin (0.25 µg/animal; hatched bar; n=3). The data represent the difference in TG concentrations measured at t=0 and the average of the concentrations at 3 and 4 hours. Results are shown as mean±SEM.
Figure 7:
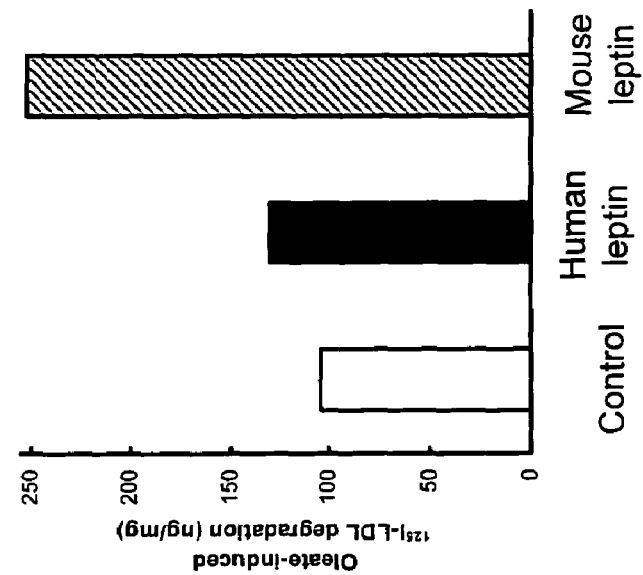
Figure 8:
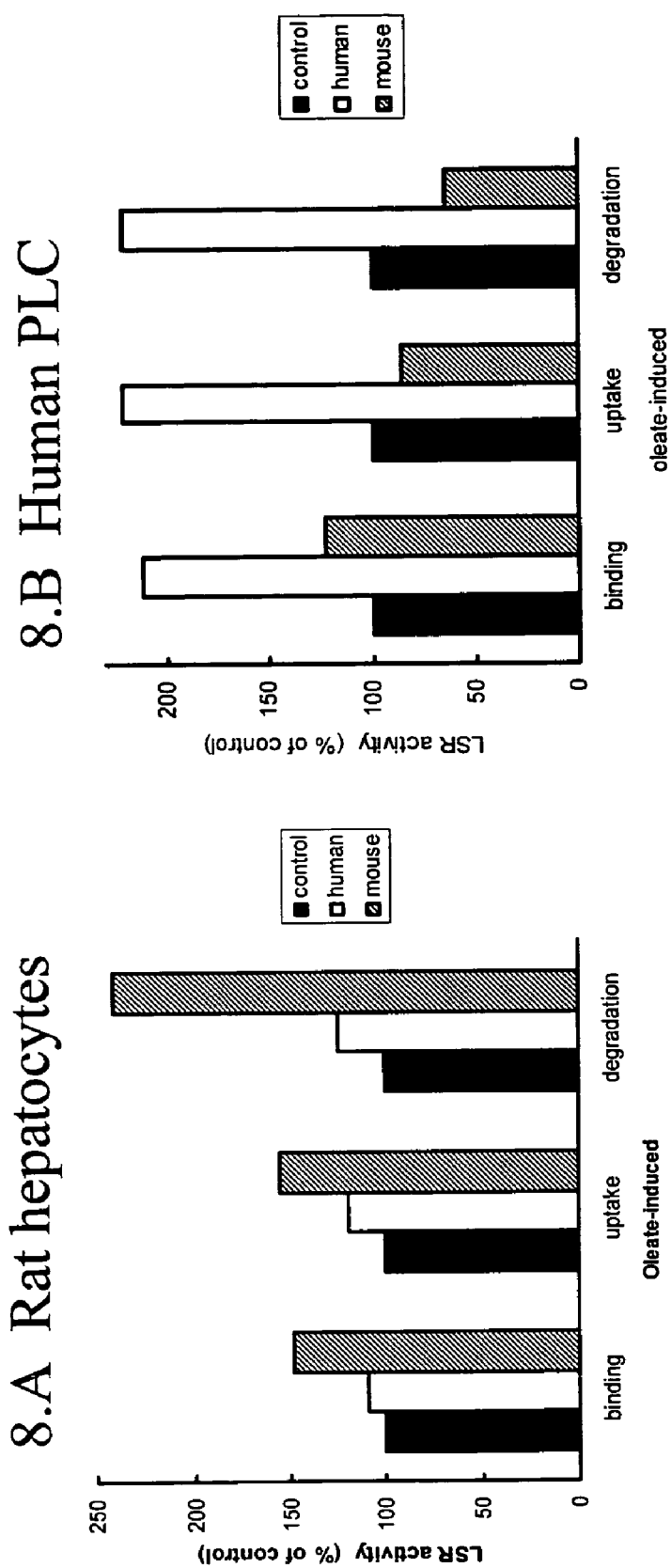
FIGS. 8A and 8B show the effect of mouse or human leptin on LSR activity in primary cultures of rat hepatocytes or a human liver cell line (PLC). Primary cultured rat hepatocytes were obtained commercially (In Vitro Tech). The PLC cell line was obtained from ATCC repository and maintained in culture. Rat hepatocytes 72 h after plating (8A) or confluent monolayers of PLC (8B) were incubated 30 min at 37° C. with 0 (closed bar) or 10 ng/mL of human (open bar) or mouse (hatched bar) recombinant leptin. Following this, 0.5 mM oleate and 20 µg/mL $^{125}$I-LDL were added and the cells were further incubated for 2 h at 37° C. The cells were washed, and the amount of oleate-induced $^{125}$I-LDL bound, internalized and degraded was measured as described previously (Bihain, B. E., and Yen, F. T. (1992). Free fatty acids activate a high-affinity saturable pathway for degradation of low-density lipoproteins in fibroblasts from a subject homozygous for familial hypercholesterolemia. Biochemistry 31, 4628-4636. Results here are shown as % of control values obtained in the absence of leptin.

To establish a link between leptin control of postprandial lipemia in mice and its stimulation of LSR in cultured cells, the species specificity in the ability of mouse and human leptin to activate LSR in cultured cells was utilized. Mouse leptin was more efficient than human leptin in stimulating LSR-mediated LDL degradation in primary cultures of rat hepatocytes (FIG. 7A); binding and uptake of $^{125}$I-LDL followed a pattern superimposable to that of $^{125}$I-LDL degradation. Conversely, human leptin was more efficient in stimulating LSR activity in human PLC cells than mouse leptin (FIG. 8B).

The effect of human (1 μg/animal) and mouse (0.25 μg/animal) leptin on plasma TG response of $db^{Pas}/db^{Pas}$ mice was also compared. The data showed that human leptin slightly reduced the postprandial plasma TG response (FIG. 7B, closed bar), but the effect did not reach statistical significance. This is consistent with the relative inability of human leptin to stimulate rodent LSR activity in cultured cells (FIG. 7A, closed bar). Mouse leptin injected at a 4-fold lower dose had a pronounced effect on postprandial plasma TG (FIG. 7B, hatched bar), consistent with its profound stimulatory effect on LSR in cultured cells (FIG. 7A, hatched bar). Thus, the effects of human and mouse leptin on postprandial TG response in obese mice paralleled their ability to stimulate LSR activity as lipoprotein receptor in cultured cells. Such species specificity has not been shown for the Ob-R.

Example 7

Differential Effect of Mouse and Human Leptin and Leptin Peptide in Cells

Species specificity has been observed with respect to leptin's ability to increase LSR activity in rodent or human liver cells (FIGS. 8A and 8B). Mouse leptin increases LSR activity more in rat hepatocytes, and human leptin increases LSR activity more in human cells. In human cells the mouse leptin is inactive and almost approaches an inhibitory effect.

Figure 9:
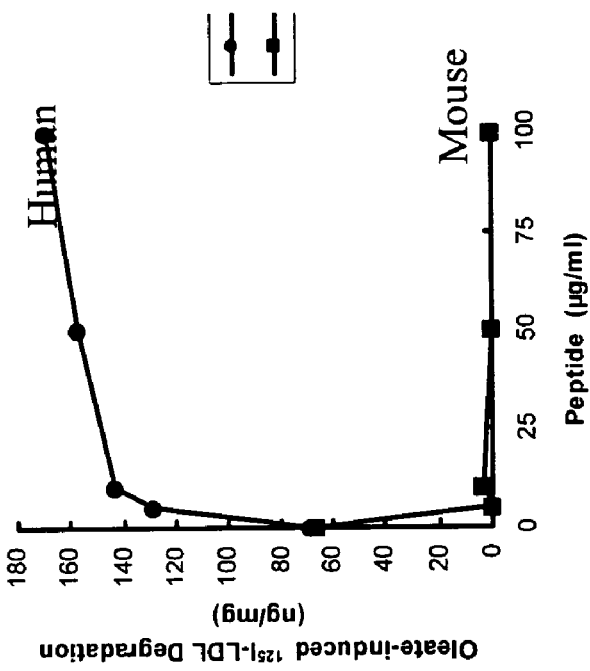
FIG. 9 shows the effect of mouse or human leptin peptide on LSR activity in PLC. Confluent PLC monolayers were incubated 30 min at 37° C. with increasing concentrations of mouse (■) or human (●) leptin peptide. Following this, 0.5 mM oleate and 20 µg/mL $^{125}$I-LDL were added and the cells were further incubated for 2 h at 37° C. The cells were washed, and the amount of oleate-induced $^{125}$I-LDL bound and degraded was measured as described previously (Bihain, B. E., and Yen, F. T. (1992). Free fatty acids activate a high-affinity saturable pathway for degradation of low density lipoproteins in fibroblasts from a subject homozygous for familial hypercholesterolemia. *Biochemistry* 31, 4628-4636.
Figure 9:
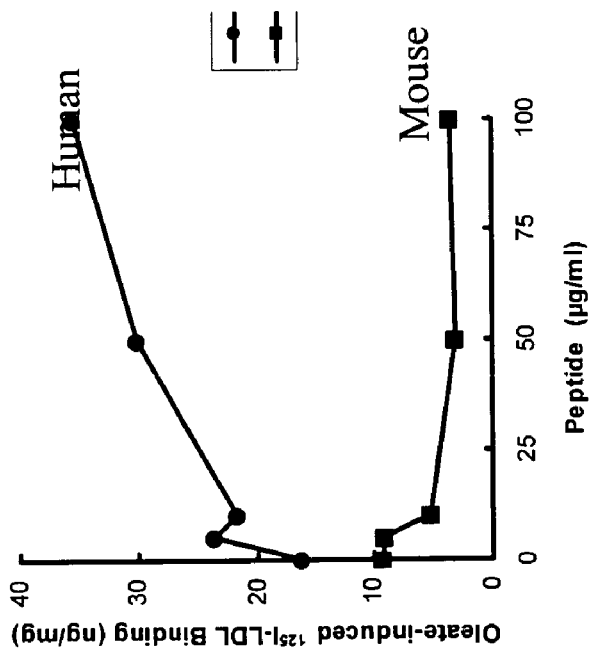
Figure 10:
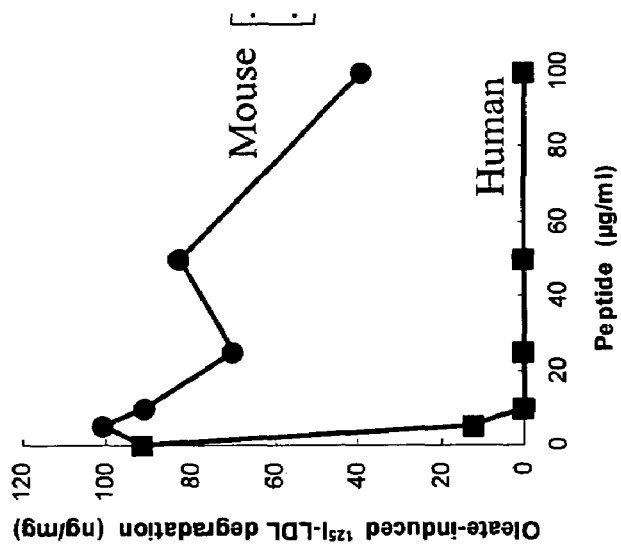
FIG. 10 shows the effect of mouse or human leptin peptide on LSR activity in primary cultured rat hepatocytes. Cells were incubated 30 min at 37° C. with increasing concentrations of mouse (■) or human (●) leptin peptide. Following this, 0.5 mM oleate and 20 µg/mL $^{125}$I-LDL were added and the cells were further incubated for 2 h at 37° C. The cells were washed, and the amount of oleate-induced $^{125}$I-LDL bound and degraded was measured as described previously (Bihain, B. E., and Yen, F. T. (1992). Free fatty acids activate a high-affinity saturable pathway for degradation of low-density lipoproteins in fibroblasts from a subject homozygous for familial hypercholesterolemia. *Biochemistry* 31, 4628-4636).
Figure 10:
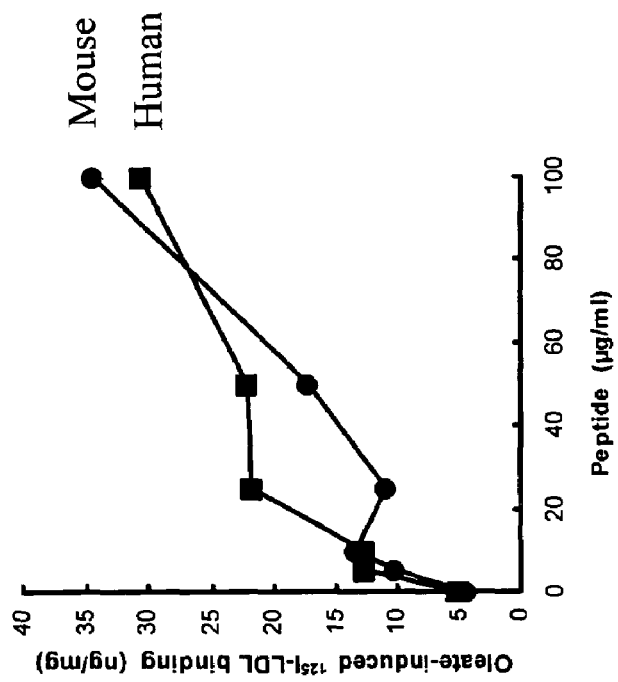
Figure 13:
FIG. 13 shows a multiple sequence alignment of leptin polypeptides from various species including: *Homo sapiens* (SEQ ID NO:32), *Mus musculus* (SEQ ID NO:34), *Rattus norvegicus* (SEQ ID NO:38), *Sus scrofa* (SEQ ID NO:39), *Bos Taurus* (SEQ ID NO:28), *Gallus gallus* (SEQ ID NO:30), *Ovus aries* (SEQ ID NO:35), *Canis familiaris* (SEQ ID NO:29), *Gorilla gorilla gorilla* (SEQ ID NO:31), *Macaca mulatta* (SEQ ID NO:33), *Pan troglodytes* (SEQ ID NO:36), and *Pongo pygmaeus* (SEQ ID NO:37). Divergent residues (from the consensus sequence) are boxed. The 22 amino acid region of the exemplary active leptin peptide is shaded for all species in the alignment. Residues 10-13 of the shaded region make up the "leptin fragment central sequence".

An internal segment of the leptin polypeptide that is near the carboxy terminus was found to differ significantly in different species (See shaded area in FIG. 13). The mouse and human sequence of this segment was synthesized as a 22-mer peptide and tested for activity in cells (FIGS. 9 & 10). The human peptide was agonistic for LSR activity in human cells, while the mouse peptide was antagonist for LSR activity in human cells. Thus, the human leptin peptide has a complete signaling capacity in human cells (FIG. 9). In primary cultures of rat hepatocytes, both peptides increased oleate-induced LDL binding, though not to the same extent (at concentrations <50 μg/mL). However, there was an inhibitory effect on oleate-induced LDL degradation, indicating that these peptides do not completely mimic the activity of leptin in the rat system (FIG. 10).

Example 8

Effect of Mouse Leptin or Leptin Peptide on the Post-Prandial Response

The apparent Kd of LSR for leptin is in the same range as that of the Ob-receptor, suggesting that the regulation of LSR activity by leptin could represent a physiologically relevant process. To address this issue, the variation in plasma leptin concentration that occurs after administration of a test meal to normal mice was measured. Leptin concentrations of 1.9±0.7 and 4.5±0.2 ng/mL (p<0.007, n=4) were measured before and 2 h after the meal. However, in normal mice, the postprandial increase in plasma TG remained small and transient, even when massive amounts of dietary lipid were provided by intragastric cannulation. This reflects the fact that in normal mice, the rate of lipid clearance is adapted to that of intestinal absorption.

Imbalance of this system appears to occur only in obese mice. However, $db^{Pas}/db^{Pas}$ mice are not a satisfactory model to test the physiological effect of leptin. The plasma leptin levels of these animals are extremely high (86.7±12.2 ng/mL) and furthermore, do not detectably vary after administration of a test meal. Two hours after the test meal, leptin concentrations were measured as 86.6±18.9 ng/mL (NS, n=5). Therefore, ob/ob mice that lack leptin were used to test whether administration of a physiological dose of leptin modulates postprandial lipemia.

Figure 11:
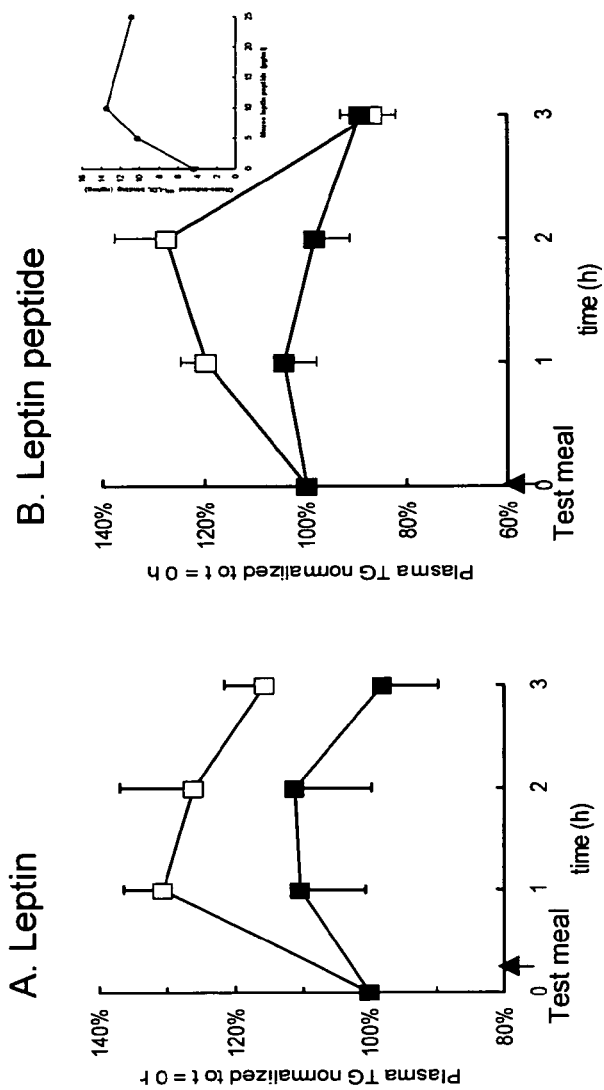
FIGS. 11A and 11B show the effect of mouse leptin (FIG. 11A) or leptin peptide (FIG. 11B) on postprandial plasma TG response in ob/ob mice. A single dose of 50 ng mouse leptin (A, ■), leptin peptide (B, ■), or a comparable volume of saline (□) was injected subcutaneously at t=0 h (8:30 AM) directly following gavage of a high fat meal (0.5 mL). Postprandial triglyceridemia was measured as described previously. Each point represents the mean±SEM (A: saline, n=8, leptin, n=7; leptin peptide: saline, n=8, leptin, n=8). The insert to FIG. 11B shows the effect of mouse leptin on LSR activity in primary cultures of rat hepatocytes. Primary cultures of rat hepatocytes were incubated 30 min at 37° C. with increasing concentrations of mouse leptin peptide. Oleate (0.5 mM) and $^{125}$I-LDL (20 µg/mL) were added and the cells were incubated 2 h at 37° C. After washing, the amount of 125I-LDL bound to the cell surface was measured as described in the Examples section herein.

As seen in FIG. 11A, a single subcutaneous injection of 50 ng of leptin in ob/ob mice decreases the postprandial lipemic response. This injection caused a transient increase in plasma leptin concentrations up to 3.25±0.03 ng/mL at 2 h; baseline values were recorded 4 h after injection. The dose of leptin that is needed to control postprandial lipemia in ob/ob mice is 5-10 fold lower than those used in leptin-resistant db/db mice. In ob/ob mice, the signaling effect of leptin could result either from interaction with the Ob-receptor or the LSR.

A synthetic peptide with a sequence identical to that of mouse leptin between residues 117-138 was obtained and found to stimulate the oleate-induced binding of $^{125}$I-LDL in primary cultures of rat hepatocytes (FIG. 11B, insert). Daily subcutaneous injections of 25 μg of this synthetic leptin peptide to ob/ob mice had no effect on the food intake over a 12 day period (7.6±0.4 g/day in ob/ob receiving saline and 6.7±0.3 g/day in ob/ob receiving peptide; n=4, NS). Daily injections of 25 μg of mouse leptin caused a reduction of food intake to 4.7±0.5 g/day (n=3; p<0.003 versus controls). Thus, the synthetic peptide that activates LSR in vitro does not influence food intake by activating the Ob-receptor. Injection of 50 ng of this synthetic peptide reduced the postprandial lipemic response in ob/ob mice (FIG. 11B).

Example 9

Relevance to Disease States

The instant invention has shown that leptin regulates cellular functions in the absence of functional Ob-R. A myriad of peripheral regulatory effects of leptin have been identified and attributed to leptin signaling through the Ob-R, even when the targeted tissues lack the long isoform of the Ob-R, i.e., the sole isoform with a clearly established signaling capacity (Friedman, J. M., and Halaas, J. L. (1998). Nature 395, 763-770). The characterization of a leptin receptor distinct from the Ob-R and controlling the entry of exogenous TG into the liver opens the possibility that leptin controls other aspects of cell metabolism independently of the Ob-R. Although not wishing to be limited to a particular theory, one hypothesis is that leptin resistance is due to desensitization of the signaling pathway through which leptin binding to LSR leads to mobilization of the receptor to the cell surface.

Leptin regulation of the exogenous lipoprotein pathway opens new perspectives towards the understanding of the relationship between obesity, hypertriglyceridemia and cardiovascular disease. Indeed, accumulation in plasma of the residues of chylomicrons has been shown to increase the risk of cardiovascular disease due to the formation of atherosclerotic plaque (Karpe et al, 1998 Atherosclerosis 141, 307-314). Hypertriglyceridemia is also considered an independent predictor of cardiovascular disease in obese subjects with Type II diabetes (Feeman, 1998 Ann. Intern. Med. 128, 73-74).

By increasing the contribution of the liver to the removal of plasma TG, leptin prevents deposition of dietary lipid in adipose tissue in excess of their FFA-releasing capacity. Thus the liver plays a critical but underestimated role in the pathogeny of obesity.

Example 10

Molecular Modeling of an Active Leptin Fragment of the Invention

The amino acid sequence for the human leptin fragment with activity is: NH$_2$-CHLPWASGLETLDSLGGVLEAS-COOH (SEQ ID NO:57; residues 117-138). The amino acid sequence of the mouse leptin fragment with inhibitory activity in the human system is: NH$_2$-CSLPQTSGLQK-PESLDGVLEAS-COOH (SEQ ID NO:67).

A molecular dynamic assay (MD) was performed on both the human and the mouse 22aa peptides. MDs were performed under AMBER force field, in vacuo, with a dielectric constant proportional to 4r, a switched cutoff with inner radius of 10 A outer radius of 14 A, a heating phase of 20 ps from 0 to 300K by steps of 50K, and a production phase of 120 ps at 300K. At the end of the 120 ps MDs, both peptides have lost their short helical part, and have shrunk to a more compact conformation.

The main difference between the human and mouse 22aa peptides in the packed conformations is the presence of a residue with higher accessibility (namely L133, before the 2 Glycines of the end sequence LGGVLEAS (SEQ ID NO: 129)) in the human 22aa peptide.

In order to decipher which amino acid is important among the 126-129 amino acid residues, which differ significantly between human and mouse, the following in-silico combinatorial mutational assay was performed.

Each residue in positions 126-129 of the 22aa human peptide (conformation extracted from the human leptin) was mutated, resulting in 16 mutated peptide models. Each model was minimized until reaching an rms gradient of 0.1 Kcal/mol (within the AMBER force field). Then, each minimized model was used as the starting conformation of ultra-short molecular dynamics (MD) assay (heating phase from 0K to 300K of 20 ps, and production phase at 300K of 20 ps, in vacuo, under the same conditions as described above). The final MD snapshots were re-minimized, and the corresponding energies are given in the following HTML table, as well as the sequence of the spontaneously formed alpha helices.

| Central Sequence | LD | LE | PE | PD |
|---|---|---|---|---|
| ET | −87.4<br>LDSLGG<br>(SEQ ID NO:42) | −79.3 | −83.9 | −69.3<br>TPDSL<br>(SEQ ID NO:46) |
| QT | −66.0<br>GLQTLDSLG<br>(SEQ ID NO:47) | −83.3<br>GGVLE<br>(SEQ ID NO:48) | −68.0 | −65.4<br>TPDSLG<br>(SEQ ID NO:49) |
| EK | −82.5<br>SLGGVLEAS<br>(SEQ ID NO:50) | −93.1<br>PESLGG<br>(SEQ ID NO:51) | −92.2<br>PDSLGG<br>(SEQ ID NO:52) | −92.2 |
| QK | −83.3<br>LGGVLEA<br>(SEQ ID NO:53) | −85.2 | −90.2 | −84.2 |

Energies of 16 Mutated Human 22aa Leptin Peptides

Left column: first 2 aa residues of the mutated ETLD (SEQ ID NO:40) human motif. First line: last 2aa residues of the mutated ETLD (SEQ ID NO:40) human motif. Information available in each cell: energy of the minimized 20 ps snapshot (Kcal/mol), and alpha helix sequence if present in the 20 ps snapshot. Peptides containing ETLD (SEQ ID NO:40; human motif) and QKPE (SEQ ID NO:41; mouse motif) are in italic.

Under these conditions, the EKLE (SEQ ID NO:43), EKPE (SEQ ID NO:44) and EKPD (SEQ ID NO:45) containing peptides are the most favorable ones and have an alpha helix. QKPE (SEQ ID NO:41; mouse motif) and ETLD (SEQ ID NO:40; human motif) containing peptides are the next favorable conformations, with an alpha helix for ETLD (SEQ ID NO:40). Since the residue composition of each peptide is different, both composition and conformation energies form part of the comparison, and not only conformation energies.

Other peptides of the invention that can be tested in the assays described herein or other comparable assays for LSR agonistic or antagonistic activity include the following:

TABLE

| Position | Sequence | SEQUENCE ID NUMBER |
|---|---|---|
| Human Leptin Peptide Fragments | | |
| 117-138 | CHLPWASGLETLDSLGGVLEAS | SEQ ID NO:57 |
| 122-143 | ASGLETDSLGGVLEASGYSTE | SEQ ID NO:60 |
| 127-148 | TLDSLGGVLEASGYSTEVVALS | SEQ ID NO:62 |
| 132-153 | GGVLEASGYSTEVVALSRGQGS | SEQ ID NO:63 |
| 112-133 | AFSKSCHLPWASGLETLDSLGG | SEQ ID NO:56 |
| 107-128 | LLHVLAFSKSCHLPWASGLETL | SEQ ID NO:55 |
| 102-123 | ENLRDLLHVLAFSKSCHLPWAS | SEQ ID NO:54 |
| 119-136 | LPWASGLETLDSLGGVLE | SEQ ID NO:58 |
| 121-134 | WASGLETLDSLGGV | SEQ ID NO:59 |
| 123-132 | SGLETLDSLG | SEQ ID NO:61 |
| Mouse Leptin Peptide Fragments | | |
| 117-138 | CSLPQTSGLQKPESLDGVLEAS | SEQ ID NO:67 |
| 122-143 | TSGLQKPESLDGVLEASLYSTE | SEQ ID NO:70 |
| 127-148 | KPESLDGVLEASLYSTEVVALS | SEQ ID NO:72 |
| 132-153 | DGVLEASLYSTEVVALSRLQGS | SEQ ID NO:73 |
| 112-133 | AFSKSCSLPQTSGLQKPESLDG | SEQ ID NO:66 |
| 107-128 | LLHLLAFSKSCSLPQTSGLQKP | SEQ ID NO:65 |
| 102-123 | ENLRDLLHLLAFSKSCSLPQTS | SEQ ID NO:64 |
| 119-136 | LPQTSGLQKPESLDGVLE | SEQ ID NO:68 |
| 121-134 | QTSGLQKPESLDGV | SEQ ID NO:69 |
| 123-132 | SGLQKPESLD | SEQ ID NO:71 |

Example 11

Inhibition of the Expression of Endogenous LSR Using Chimeraplasty

Chimeraplasty experiments to inhibit the expression of cellular LSR are designed based on publications by Cole-Strauss et al. (Science 273:1386-1389 (1996)) and Alexeev and Yoon (Nature Biotech. 16:1343-1346 (1998)). The following Example is exemplary only. Other sites in LSR can be targeted using the same approach to achieve either inhibition of expression, or to change base pairs to study the importance of various residues (both protein coding and within regulatory regions, intronic, or 5' or 3' to the coding region) for LSR functioning in vitro and in vivo. Similarly, chimeric oligonucleotides can be designed to modify LSR amino acids either in the coding or non-coding regions in experimental animals and for treatment of diseases in humans.

There are two ATG codons in human LSR. The second ATG corresponds to the ATGs present in mouse and rat LSR. The first ATG is used as the start site for at least some of the forms at least some of the time, since the N-terminal antibody 81B is specific for this region of the LSR protein (See other Examples). Therefore, chimeric oligonucleotides were designed for the region after the first ATG and before the second ATG, and the region after the second ATG.

The first step was to identify regions of LSR where changing a single base pair results in the creation of a stop codon. Although there are three stop codons, TAG (amber), TAA (ochre) and TGA (stop), TGA is preferred for giving a complete stop (complete inhibition of LSR expression). Two regions were identified (one after the first ATG and one after the second ATG) where changing a single base pair would result in a TGA stop codon, and chimeric oligonucleotides were designed for the appropriate sequences (FIG. 9). Chimeric oligonucleotides are designed such that they will basically form a double-stranded sequence with two sets of 4T's at the bends and a GC-clamp (typically 5 bases in length) at one end and the mutated sequence and its wild-type complement forming the main part of the double-stranded part (typically 25 bases in length). Flanking the mutated sequence (typically 5 DNA bases) is 2'-o-methyl RNA sequence (typically 10 bases on either side).

Primers and probes were also designed for these regions for use in an allelic discrimination assay (PE Applied Biosystems, "Allelic Discrimination Using 5' Nuclease Assays": see Worldwide Website: perkin-elmer.com/ab/apply/dr/dra1b4.html). The use of fluorogenic probes in a 5' nuclease assay combines PCR amplification and allele detection into a single step. Hybridization probes for the endogenous and mutant forms of the allele are included in the PCR amplification reaction. The hybridization probes are cleaved by the 5' nuclease activity of Taq DNA polymerase only if the probe's target sequence is being amplified. By using a fluorogenic probe, cleavage of the probe can be detected without post-PCR processing. The fluorogenic probe comprises an oligonucleotide labeled with both a fluorescent reporter dye (typically 5') and a quencher dye (typically 3'). In the intact probe, the proximity of the quencher reduces the fluorescent signal from the reporter dye. Cleavage liberates the reporter dye allowing an increase in its fluorescent activity. The essence of the technique is that it can detect single nucleotide mismatches since these interfere with the ability of Taq DNA polymerase to cleave the probe.

Probe placement is dictated by the location of the polymorphism. Generally, the polymorphic site should be near the center of the probe, since mismatches at the ends are not typically as disruptive to hybridization. A separate probe is synthesized for each allele, and each is labeled differently (FAM and TET or JOE, for example). The main criterion for probe selection is that it be long enough to hybridize at the annealing/extension temperature used in the PCR amplification. Calculation of the annealing/extension temperature is routine for those of ordinary skill in the art. Typically a probe Tm (melting temperature) of 65-67 C works well at an annealing temperature of 60-62 C. Therefore, the length of each probe is typically adjusted so that both probes have an estimated Tm of 65-67 C. In addition, there can be no G at the 5' end, since a G adjacent to the reporter dye quenches fluorescence somewhat even after cleavage. The probes can be for either strand; the strand with more C's than G's generally performs better in the 5' nuclease assay.

Primers are chosen based primarily of estimated Tms as well as small amplicon size. Primers with Tms of 58-60 C (approximately 5 C below the probe Tm) generally work well at annealing/extension temperatures of 60-62 C. Generally, primers that are unstable at their 3' ends are preferred, as this seems to reduce non-specific priming. Therefore, primers with only one to two Gs and Cs within the last 5 nucleotides of the 3' end are preferred. In addition, primers should be placed as close as possible to the probe location without overlapping the probes. This generally results in amplicons of less than 100 bp, which is advantageous for PCR amplification success.

First ATG:

Chimeric oligonucleotides. DNA is in capital letters; 2'-o-methyl RNA is in small letters; mutated base is underlined:

```
                                              (SEQ ID NO:74)
5'-ATGCAACAGGACGGACTTGGAGTAGTTTTcuacuccaagTCAGT ccuguugcauGCGCGTTTCGCGC-3'
```

Allelic Discrimination Assay:

```
Forward Primer: TGTCCACGTCGTTTACGCTC   (SEQ ID NO:75)

Reverse Primer: TCCCACTTCCGTTCCTTGTC   (SEQ ID NO:76)

(SEQ ID NO:77)
Probes (endogenous/mutant): 3'-CCTACTCCAAGTC(C/A)

GTCCTGTTGCATT-5'
```

Second ATG:

Chimeric oligonucleotides. DNA is in capital letters; 2' o-methyl RNA is in small letters; mutated base is underlined):

```
                                              (SEQ ID NO:78)
5'-GACCCTGCCCTGTACCTACCTACCAGATGTTTTcaucugguagGT TCAggggcagggucGCGCGTTTT-3'
```

Allelic Discrimination Assay:

```
                                       (SEQ ID NO:79)
Forward Primer: GTGGTGATCCTCTTCCAGCCT Reverse Primer: CCAGATGACGATGGGTTGC    (SEQ ID NO:80)

(SEQ ID NO:81)
Probes (endogenous/mutant): 5'-ACCCTGCCCTG(T/A)CCT

ACCAGATGAC-3'
```

The chimeric oligonucleotides are also made fluorescently labeled to allow tests for transfection efficiency.

Following synthesis of the chimeric oligonucleotides and the primers and probes for the allelic discrimination assay, the fluorescein-labeled chimeric oligonucleotides are transfected into PLC cells using standard methodology (other Examples), and the transfection efficiency determined by fluorescence. The proportion of cells that are fluorescent (successful transfection) is compared with the total number of cells by techniques that are standard in the art. If the transfection efficiency is low, various parameters of the transfection methodology may be modified to increase the transfection efficiency. These parameters are well-known in the art.

Following a successful transfection of the fluorescently-labeled chimeric oligonucleotides, the unlabeled chimeric oligonucleotides are transfected into PLC cells, and the cells are sorted using FACS (fluorescent activated cell sorter) after labeling cells with a first anti-LSR antibody followed by a fluorescently-labeled second antibody that binds the first antibody using methods standard in the art. The first antibody can be the N-terminal specific 81B antibody to sort cells for LSR expression following mutation of the site after the first ATG, but needs to be a more C-terminal specific antibody (such as the 170 antibody (to mouse carboxy terminus) or 93A (to same region of human carboxy terminus)) to sort cells for LSR expression tested for creation of the stop codon and expression of LSR expression following mutation of the site after the second ATG.

The cells in both groups with the lower LSR expression are collected to enrich for cells with the stop codon in at least one of the copies of LSR. The cells are then cultured and checked for the presence of the stop codon mutations using allelic discrimination. An exemplary reaction set-up and procedure is as follows:

| REAGENT | FINAL CONC. | (µL) |
|---|---|---|
| 10× TaqMan Buffer A | 1× | 2.5 |
| 25 mM MgCl$_2$ | 5 mM | 5 |
| dATP | 200 µM | 0.5 |
| dCTP | 200 µM | 0.5 |
| dGTP | 200 µM | 0.5 |
| dUTP | 400 µM | 0.5 |
| AmpliTaq Gold (5 U/µL) | 1 U | 0.2 |
| AmpErase UNG (1 U/µL) | 0.25 U | 0.25 |
| DEPC H$_2$O | | 2.55 |
| TOTAL VOLUME | | 12.5 µL |

The primer concentrations can vary from 100 nM to 300 nM. Probe concentrations can vary from 50 nM to 200 nM. Template concentrations can vary from 0.1-100 ng/reaction.

Steps
1. 50 C for 2 min.
2. 95 C for 10 min.
3. 95 C for 15 sec.
4. 58 to 65 C for one min.
5. hold at 4 C Repeat steps 3 & 4 for 40 cycles.

Following testing, the cells are retransfected with the chimeric oligonucleotides and again sorted for LSR expression using FACS. The cells that are expressing the lowest amounts of LSR (or none) are selected, cultured to form a homogeneous population, and rechecked using allelic discrimination to identify cell clones that no longer express LSR. These cells can then be used in assays to study the role of the various LSR subunits and the interaction of compounds with particular subunits, as well as for screening for modulators of specific LSR activities (modulated by the different subunits, for example). In addition, the above-described techniques can be used on other cells, (including those in the ATCC databank and in animals or humans) to create other kinds of cells lacking LSR activity. As well as the uses as a research and compound screening tool, the technique is also useful for treatment of diseases related to obesity in vivo.

Chimeric oligonucleotides were also designed to specifically inhibit either the α subunit of LSR, or both the α and the α' subunits of LSR, by targeting either Exon 4 or Exon 5, specifically.

Exon 4

Chimeric oligonucleotides. DNA is in capital letters; 2' o-methyl RNA is in small letters; mutated base is underlined):

```
                                         (SEQ ID NO:82)
5'-TGGCTGAGCTCTTACCTGGTTTTCATTTTtgaaaaccagGTCAGag ctcagccaGCGCGTTTTCGCGC-3'
```

Allelic Discrimination Assay:

```
Forward Primer: GAGCTCATCGTCCTTGGGAG    (SEQ ID NO:83)

Reverse Primer: AGTGTTCTATGGGCCCCGC     (SEQ ID NO:84)

(SEQ ID NO:85)
Probes (endogenous/mutant): 3' CACCGACTCGAGA(A/C)T

GGACCAAAAGTC 5'
```

Exon 5

Chimeric oligonucleotides. DNA is in capital letters; 2' o-methyl RNA is in small letters; mutated base is underlined):

```
                                         (SEQ ID NO:86)
5'-GGTTGTGGTATGCCTGGCTGGGTTCTTTTgaaggcagccAGTCAta ccacaaccGCGCGTTTTCGCGC-3'
```

Allelic Discrimination Assay:

```
Forward Primer: ACGCAGAGCTCATCGTCCTT    (SEQ ID NO:87)

Reverse Primer: GATGCCCAGGAGGAGGAAGA    (SEQ ID NO:88)

(SEQ ID NO:89)
Probes (endogenous/mutant): 3'-CAACACCATAC(G/T)GAC

CGACGGAA-5'
```

For both, use FAM as the dye for the endogenous nucleotide (A and G, respectively), and JOE as the dye for the changed nucleotide (C and T, respectively).

Example 12
Use of Zinc Finger Polypeptides for LSR Modulation

A method for specifically binding DNA of choice and repressing or initiating its transcription has been described recently in WO 98/54311. The repression or initiation can be constitutive in the presence of the vector carrying the zinc finger, or it can be placed under the control of a small molecule switch, for example the TET system, where the expression of the repressor/initiator-bound zinc finger can be regulated. This is especially important in systems where complete absence of a gene at certain developmental stages, for example, is lethal, or where it's overexpression is toxic (Massie B, Couture F, Lamoureux L, Mosser D D, Guilbault C, Jolicoeur P, Belanger F, Langelier Y Inducible overexpression of a toxic protein by an adenovirus vector with a tetracycline-regulatable expression cassette. J Virol 1998 March; 72(3):2289-96 hereby incorporated by reference herein in its entirety including any figures, tables, or drawings).

Zinc finger polypeptides are designed to specifically bind to LSR genomic DNA, and then are linked with the KRAB repressor to inhibit LSR expression. Sequences identified for use in making the zinc finger polypeptides are

```
1936 to 1927 of SEQ ID NO:1    TAG GGG TGA GCG GCG GGG        (SEQ ID NO:91)

1947 to 1936 of SEQ ID NO:1    GAG GGC TGG NNN TAG GGG TGA    (SEQ ID NO:92)

1946 to 1936 of SEQ ID NO:1    AGG GCT GGG NN TAG GGG TGA     (SEQ ID NO:93)

1956 to 1947 of SEQ ID NO:1    GTG GGA GCC GAG GGC TGG        (SEQ ID NO:94)

1956 to 1946 of SEQ ID NO:1    GTG GGA GCC N AGG GCT GGG      (SEQ ID NO:95)

2304 to 2295 of SEQ ID NO:1    GCG GCG GCC GGG TGG GAG        (SEQ ID NO:96)

1778 to 1787 of SEQ ID NO:1    TTG GCC GGA GCA GAT GGG        (SEQ ID NO:97)

1787 to 1798 of SEQ ID NO:1    GCA GAT GGG NN CCG GAA GGG     (SEQ ID NO:98)

1946 to 1934 of SEQ ID NO:1    AGG GCT GGG NNN AGG GGT GAG    (SEQ ID NO:99)

1934 to 1922 of SEQ ID NO:1    AGG GGT GAG NNN CGG GGA GGG    (SEQ ID NO:100)

1740 to 1749 of SEQ ID NO:1    AAG TGG GTC TCG GTT GCA        (SEQ ID NO:101)
```

The sequences to be bound by zinc finger polypeptides are provided to Sangamo, where the actual zinc finger proteins are synthesized and are linked to the KRAB domain, a transcription repressor (Pengue G, Calabro V, Bartoli P C, Pagliuca A, Lania L Repression of transcriptional activity at a distance by the evolutionarily conserved KRAB domain present in a subfamily of zinc finger proteins. Nucleic Acids Res 1994 Aug. 11; 22(15):2908-14) hereby incorporated by reference herein in its entirety including any figures, tables, or drawings), are synthesized. The DNA binding domain can also be linked to transcription initiators (such as VP16; Proceedings of the National Academy of Sciences USA 94:5525 (1997) hereby incorporated by reference herein in its entirety including any figures, tables, or drawings) or a small molecule switch system, that is used to turn on or off the zinc finger protein linked to the repressor or initiator. Examples of small molecule switches that are effective in cells and in animals include, the Tet system, RU486, and ecdysone.

The zinc finger proteins are delivered as plasmids suitable for transfection into cells using standard techniques (Fugene, is a method of choice). The cells used include, but are not limited to, the human cell lines HepG2, PLC, Hep3B, C3A, and 293 and the mouse cell lines taoBpRcl, BpRcl, and Hepa1-6. All cells are available from ATCC. Following transient transfection, the cells are tested for LSR expression and activity using standard techniques described in this application, that may include FACS analysis to look for LSR expression on the cell surface, quantitative PCR to look at whether the message is being made, and various binding, uptake and degradation experiments to study LSR activity.

Following a determination of which zinc finger proteins are the most effective in inhibiting LSR expression, stably tranfected cell lines are created, using the techniques described in this application. These cell lines are used to then study the activity of the subunits of LSR separately and in combination by co-transfecting them into the cells either stably or transiently, or by turning on and off endogenous LSR genes. These cell lines are the basis of assays for agonists and antagonists of LSR generally and the subunits separately and in any combination.

The zinc finger proteins are also provided as part of a supernatant associated virus, or retroviral adenovirus (for example adeno-associated viral (AAV)). These are effective gene transfer vectors for use in cells or in animals, as well as humans. Upon receipt, the AAV supernatant is amplified using techniques well-known in the art and examples are described in Xiao et al. J. Virology 72:2224-2232 (1998), hereby incorporated by reference herein in its entirety including any figures, tables or drawings) and can include the use of helper plasmids as described in Collaco et al (Gene (1999) 238:397-405, hereby incorporated by reference herein in its entirety including any figures, tables or drawings). Following amplification, the supernatant is used to infect cells or preferably mice using standard techniques in the art some examples of which are provided by Snyder et al. (Nature Medicine 5:64-69 (1999) and Teramoto et al. J. Virol. 72:8904-8912 (1998), both of which are hereby incorporated by reference herein in their entirety including any figures, tables, or drawings.

Following infection, the cells are tested as described above; the mice are tested for effects on fasting and post-prandial levels of triglycerides, free fatty acids, cholesterol, leptin, glucose, insulin, and adipoQ (Acrp30, Apm1) as well as fragments thereof, for example, before and after feedings as described herein. Similarly to plasmids, constructs in AAV gene transfer vectors can be co-infected. Thus, mice or cells can be co-infected with constructs containing cDNA encoding the $\alpha$, $\alpha'$, or $\beta$ subunits either alone or in combination to study their role in vivo and to test the effects of agonists/antagonists on specific subunits, or subunit combinations, in animals or cells.

LSR Zinc Finger Proteins

Sangamo's Universal GeneTools technology platform enables the rational design and rapid generation of highly specific ZFP transcription factors that can selectively recognize and regulate/modulate transcription of any target gene or DNA sequence. Expression of the ZFP's as fusions to activation (herpes simplex virus VP16) or repression (Kruppel-associated box A domain/KRAB-A) domains allows transcription to be specifically up or down modulated within cells. FIG. 25 contains a table with a summary of the five sets of plasmids encoding ZFPs targeted to the LSR gene. Each set contains the ZFP target sequence fused to the VP16 domain (NVF), or the KRAB-A domain (NKF). The sequences for the NVF versions of these plasmids are listed in FIG. 26. These engineered ZFP's are being used for the functional analysis of LSR in both cell-based assays and in animal models.

Cell Based Assays:

To determine the effect of these engineered on LSR expression, mouse hepatocytes were transfected and assayed for LSR mRNA by Northern analysis. Hepa1-6 cells transfected with ZFP-NVF constructs, were harvested 24 and 48 hours post transfection for total RNA isolation (Qiagen RNeasy mini kit). Standard protocols were followed for Northern gels and blotting. Blots were probed with the full length mouse LSR alpha cDNA (EcoRI fragment from pTracer clone) and G3PDH DNA (Clontech). Probes were prepared using Prime-IT II random primer labeling kit (Stratagene) and $^{32}$P dCTP. Quantitation of the Northern bands was done using Gel-Pro software.

Figure 27:
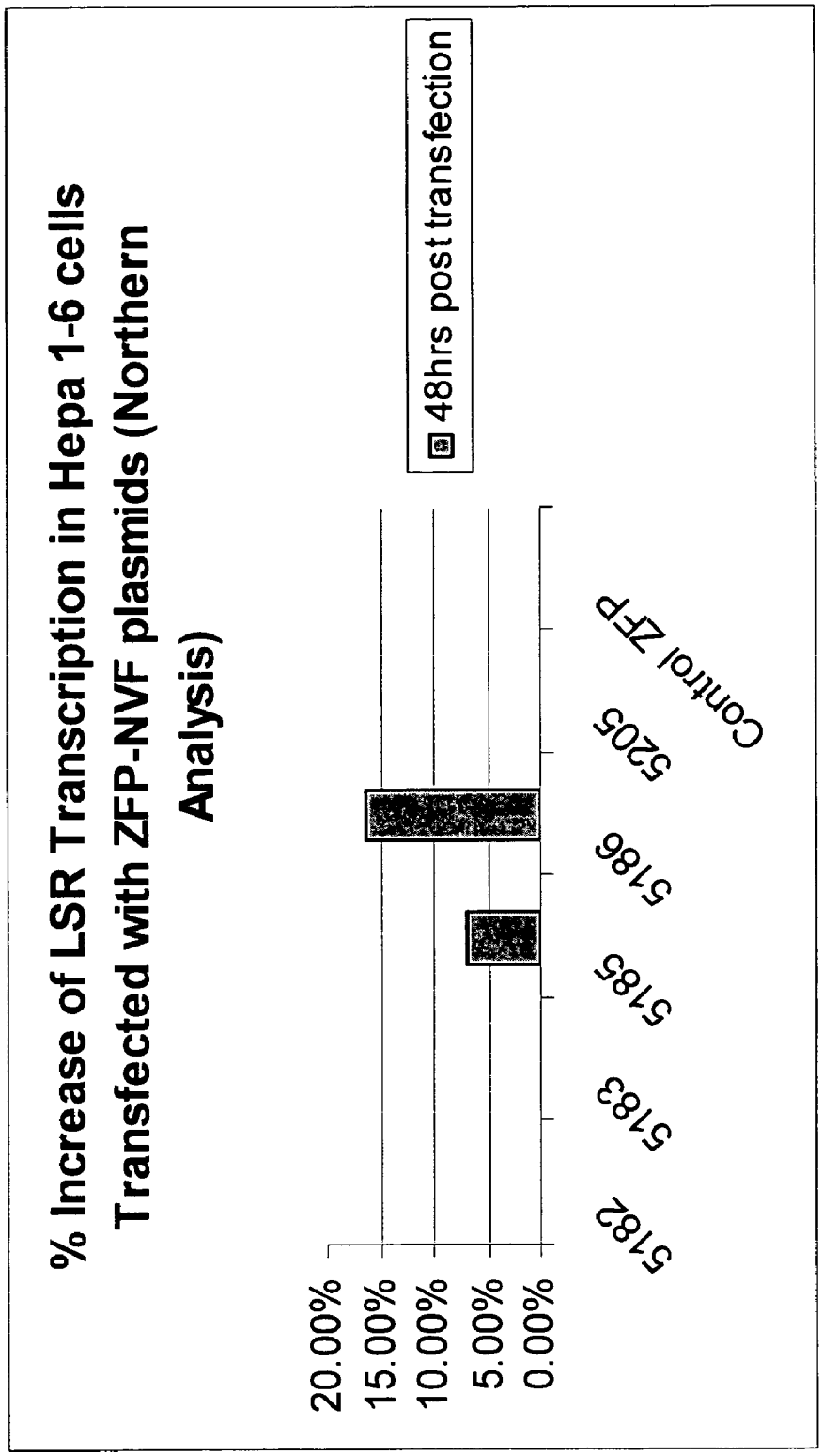
FIG. 27 shows a Northern Analysis of LSR zinc finger mRNA expression. Numbers are shown as percent of control plasmid. Only the results from 48 hrs are shown.

FIG. 27 shows an analysis of all 5 candidate ZFPs linked to VP16. Only 2 of these plasmids, 5185 and 5186, exhibited any increase in expression, 6% and 16%, respectively, at 48 hours post-transfection. Since this increase was not very large, a more detailed analysis of these 2 ZFPs by Northern and QPCR was used to confirm the up-regulation of LSR by 5185 and 5186.

Figure 28:
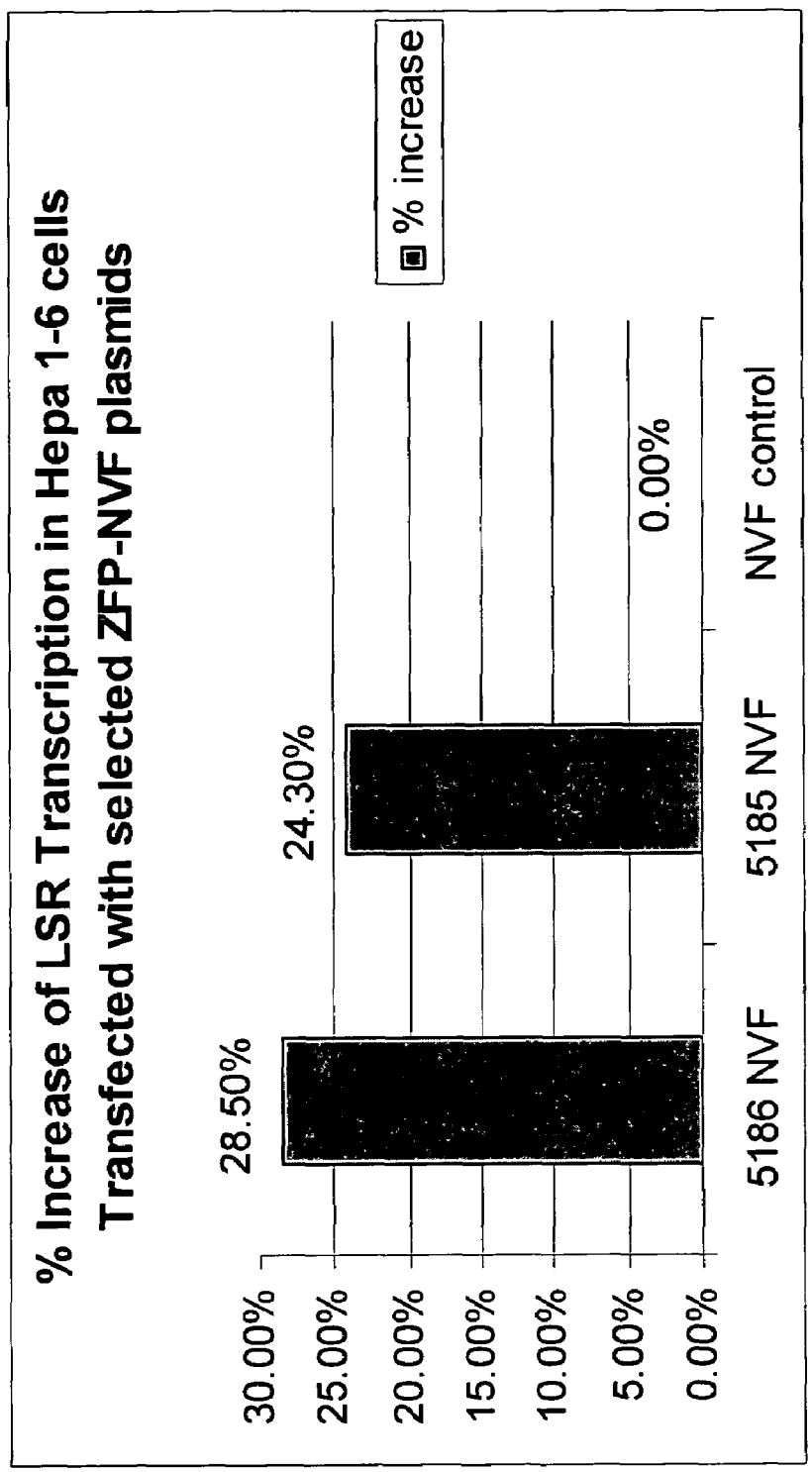
FIG. 28 shows a more detailed Northern analysis of LSR zinc finger mRNA expression. Numbers are shown as percent of control plasmid. Only the results from 48 hrs are shown.

Hepa1-6 cells transfected with ZFP-NVF constructs in triplicate, were harvested 24 and 48 hours post transfection for total RNA isolation (Qiagen RNeasy mini kit). Standard protocols were followed for Northern gels and blotting. Blots were probed with the full length mouse LSR alpha cDNA (EcoRI fragment from pTracer clone) and G3PDH DNA (Clontech). Probes were prepared using Prime-IT II random primer labeling kit (Stratagene) and $^{32}$P dCTP. Quantitation of the Northern bands was done using Gel-Pro software. The results show an average of 28% mRNA increase with 5186 and a 24% increase with 5185 (FIG. 28). It should be noted that there was no significant increase in LSR mRNA on either Northern at the 24-hour time point.

Figure 29:
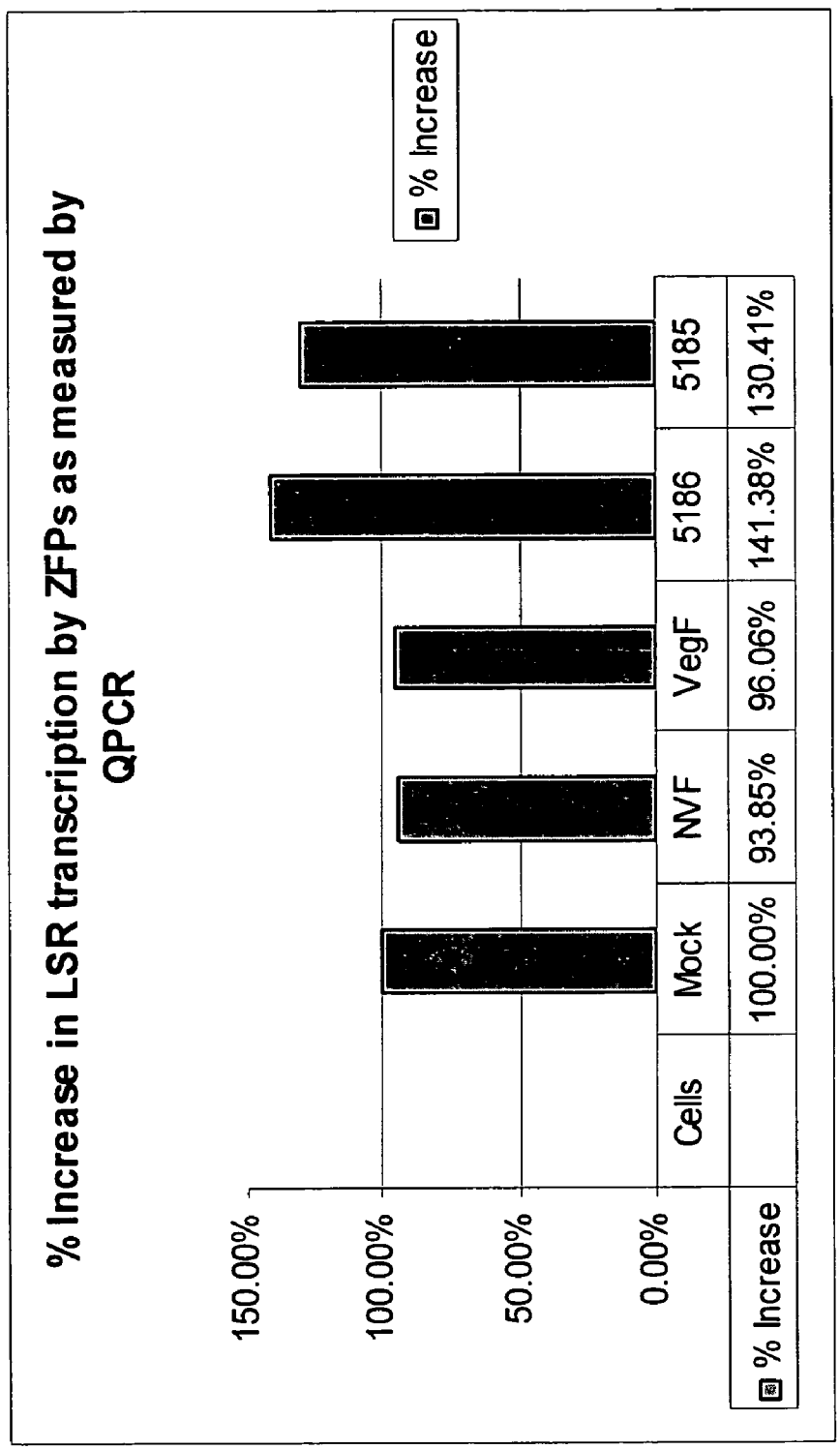
FIG. 29 shows a quantitative PCR Analysis of Hepa1-6 cells transfected with ZFP-NVF constructs.

Since the Northern analysis is not quite as sensitive as QPCR, the transcriptional increase was confirmed using QPCR. Cells were harvested 48 hours post transfection for Total RNA isolation (Ambion RNaqueous Kit). RNA was then reverse transcribed to generate cDNA for PCR analysis. Primer and Probe sets directed toward the mouse LSR and control GAPDH sequences were used to quantitate levels of transcription in ZFP transfected cells. As shown in FIG. 29, QPCR results indicate a 41% increase in LSR transcription when Hepa 1-6 cells are transfected with ZFP plasmid 5186-NVF and a 30% increase with ZFP plasmid 5185-NVF. These results indicate that both 5185 and 5186 plasmids were functioning in cells.

Binding-Uptake-Degradation (BUD) studies were used to assay the ability of these plasmids to increase the cells ability to process $^{125}$I-LDL. Cultures of Hepa1-6 mouse hepatocytes were transfected with ZFP's plasmids 24 hrs after plating. Cells were transfected with 1 μg plasmid/well in a 6 well plate, using Lipofectamine (Gibco BRL) according to manufacturer's instructions. Forty-eight hours post transfection, Oleate-induced $^{125}$I-LDL binding, uptake, and degradation was measured as described herein.

Figure 30:
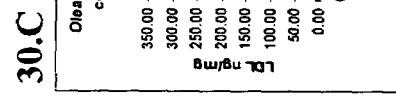
FIGS. 30A, 30B, 30C, 30D, 30E, and 30F show binding, uptake and degradation (BUD) data from ZFPs. The following ZFP's were examined: 5185-NVF, 5186-NVF, and control plasmid VegF-NVF (a non related ZFP). Results are corrected for total protein in A-C and for β-gal in D-F.
Figure 30:
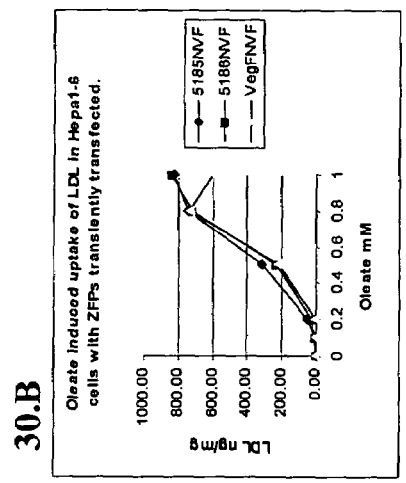
Figure 30:
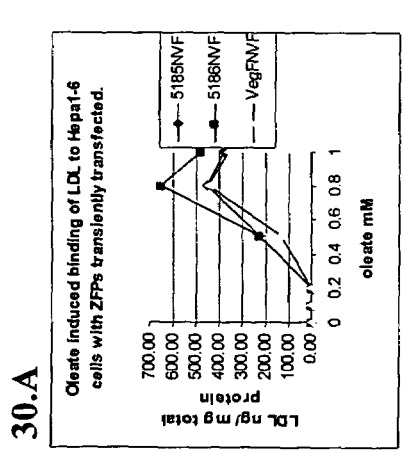
Figure 30:
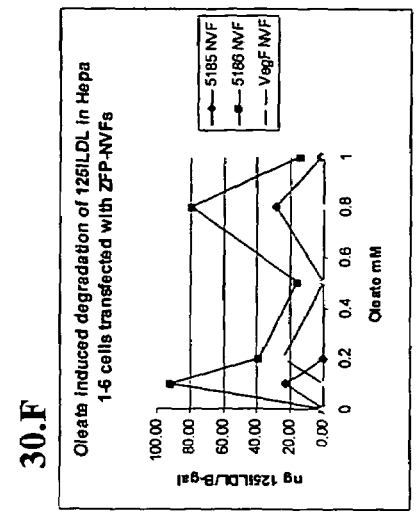
Figure 30:
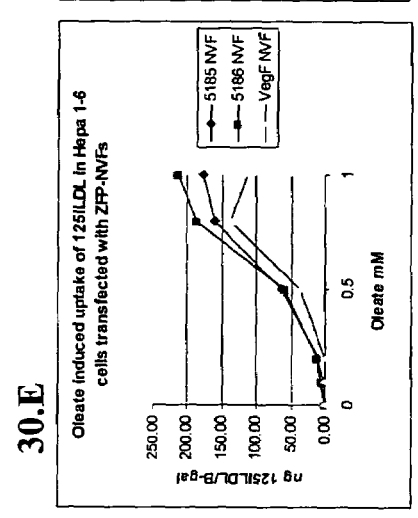
Figure 30:
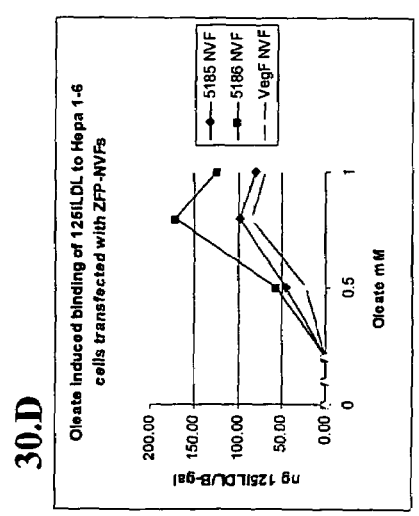

Results of the BUD studies indicate increased binding and uptake of labeled LDL when Hepa1-6 cells are transfected with ZFP's 5186-NVF and 5185-NVF when compared to control transfected cells. The data in FIG. 30 have been corrected either for total protein (30A-30C) or for β-gal (30D-30F), which is a crude measure of the transfection efficiency. BUD data supports a role for ZFP 5186-NVF and 5185-NVF in the transcriptional activation of LSR and confirms a corresponding increase in functional activity.

The increase in LDL binding and uptake suggests an increase in expression of LSR at the cell surface. To prove this, cells transfected with the ZFPs were analyzed by Flow cytometry (FACs) Analysis. FACs analysis (described above) allows for direct estimation of the proportion of positive cells in a population, as well as an indirect measure of the level of receptor on the cell surface (mean fluorescence intensity).

Hepa1-6 cells were transfected with ZFP-NVF constructs 5186 and 5185, along with control plasmids. Forty-eight hours post transfection, cells were analyzed for cell surface expression of LSR in the presence/absence of Leptin (20 ng/mL). Staining of Hepa1-6 cells involved incubation with primary antibodies, generated in rabbits against mouse LSR NH2 terminal sequence CPDRASAIQ (SEQ ID NO:112), or mouse COOH terminal sequence EEGHYPPAPPYSET (SEQ ID NO:113), followed by detection with a fluorescent-labeled secondary antibody against IgG rabbit (Sigma).

Results indicate that in the presence of Leptin, Hepa1-6 transfected with plasmid 5185-NVF had a 50% increase in the level of LSR on the cell surface when compared to controls. While cells transfected with 5186-NVF had a 35% increase in LSR at the cell surface. These findings support a functional role for ZFP 5185-NVF and 5186-NVF in the transcriptional up-regulation of LSR and concomitant increase of LSR on the cell surface.

Analogous experiments are used to assess the efficacy of ZFP-NKFs for repressing LSR transcription.

Example 13

Retroviral Library Screening by FACS

In order to identify more genes involved in the regulation of LSR and in ligand signaling through LSR (leptin, C1q, AdipoQ (Acrp30, Apm1), triglyceride-rich lipoproteins, etc) a retroviral library screening assay has been designed. In its most basic form, cells expressing LSR (PLC or HepG2, for example) are transfected with a retroviral library. Following sorting for expression of a marker protein, the cells are treated with a LSR ligand (leptin, for example) and assayed for LSR expression by FACS following staining with an antibody to LSR. Cells of interest, are those that either express more LSR or less LSR than is expressed following leptin stimulation of the same cells without the retroviral library.

Figure 14:
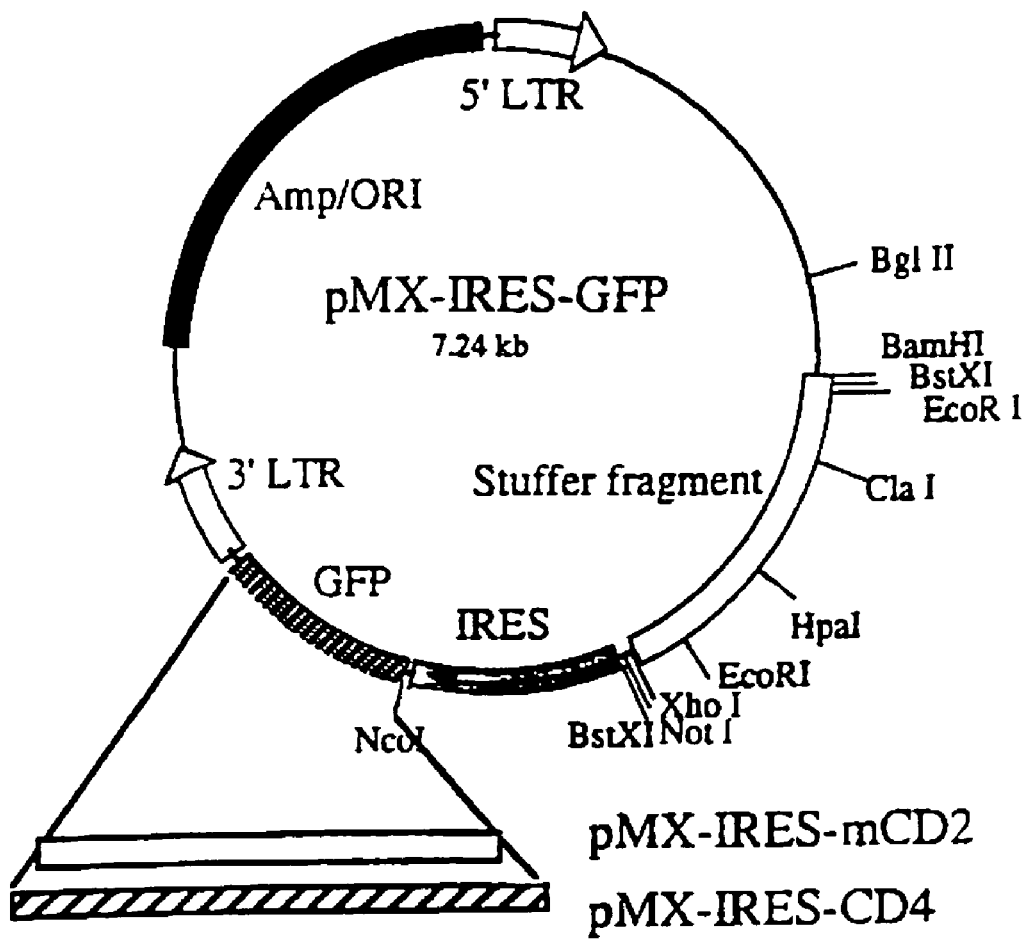
FIG. 14 shows a schematic diagram of an exemplary retroviral vector. The vector pMX-IRES-GFP contains the murine Moloney virus LTR and a packaging signal (Onishi et al. Exp. Hematol. 24: 324-329 (1996)); the EMCV IRES is placed between the polylinker/stuffer and a cDNA encoding a selectable marker protein. Three exemplary marker proteins are GFP, murine CD2 and human CD4. The IRES sequence is indicated as a shaded box with an arrow indicating the direction of translation. The segment containing the bacterial origin of replication and ampicillin resistant gene is indicated by a black box. The stippled box represents sequence encoding the green fluorescent protein; alternatively it can contain the truncated CD2 or CD4 sequences. Open boxes with arrows indicate the viral LTR sequences. The open box indicates a stuffer fragment containing multiple cloning sites.

The assay takes advantage of a retroviral vector developed by Lodish at the Whitehead Institute for Biomedical Research that takes advantage of the spectrum of expression levels of cloned cDNAs while simultaneously maintaining the high efficiency of retroviral gene transfer. The vectors employ an encephalomyocarditis virus IRES (Jang et al. J. Virol. 62:2636-2643 (1988)), followed by quantitative selection marker, such as green fluorescent protein (GFP) or a cell surface marker protein, that are detectable by intrinsic fluorescence or by staining live cells with a fluorescent antibody, respectively (FIG. 14). Because expression of the two reading frames is strongly correlated, FACS sorting based on the GFP or cell surface marker protein can be used to sort the cells for those cells expressing the unknown protein at a desired level-high, low, or moderate. For the proposed assay, the cells would preferentially be sorted for moderate expression, to allow a detectable, but not overwhelming effect.

The individual members of the gene library are placed upstream of the IRES (FIG. 14). Genes of interest for screening for their effect on LSR expression on the cell surface include cDNA libraries from liver or adipose cells. Cells expressing LSR (such as Hep3B, HepG2, PLC) would be transfected by the library using standard techniques so as to achieve approximately 1 clone (gene) per cell. The cells would then be screened, and those with moderate expression of GFP would be selected for. Cells where endogenous LSR expression has been knocked out either by traditional methods, or using the Sangamo (zinc finger proteins) or chimeraplasty techniques described herein could also be used by co-transfecting various subunits of LSR (from 1-3 and any combination thereof), or in cells stably expressing recombinant LSR subunits, or combinations.

In the GLUT 4 system, described by Lodish (Whitehead), the GLUT4 gene was linked to 7 c-myc epitope tags and then GFP fused in frame at the carboxy terminus. This allows the quantity of the gene to be studied in the cell compartment where it is sequestered by comparing overall fluorescence with the GFP to cell surface fluorescence with anti-myc antibodies. A similar assay is envisioned for LSR where LSR could be fused to GFP (in this case the library would have to be linked to CD2 or CD4). Alternatively, the amount of LSR sequestered in a cellular compartment could be determined using the 81B antibody, for example, and the amount of LSR on the cell surface could be determined using the 93A antibody, for example.

Once infected cells expressing moderate amounts of GFP are obtained, the cells can be treated with leptin, for example, (or any other LSR ligand of interest) and the difference in LSR levels in the compartment versus the cell surface, or simply on the cell surface can be determined by FACS (after antibody staining). Populations that have decreased LSR or increased LSR levels could be selected for. Optionally, the cells could be re-selected and then the retroviral DNA from the cells PCR'd and sequenced. Samples that appeared to be interesting by homologies or locations, for example, could then be cloned and re-transfected for further study. This would allow the other genes that interact with this system to be discovered. The genes are likely to encode proteins whose modulation could have a direct impact on the regulation of obesity.

Example 14

Effect of the Leptin Peptide in Mice with Congenital Lipodystrophy

Congenital generalized lipodystrophy (CGL) is a rare autosomal recessive disorder characterized by a paucity of adipose tissue which is evident at birth and is accompanied by a severe resistance to insulin, leading to hyperinsulinemia, hyperglycemia, and enlarged fatty liver (Seip et al Acta Pediatr Supp. 413:2-28 (1996)). Leptin has been shown to reverse insulin resistance and diabetes mellitus in mice with congenital lipodystrophy (Shimomura et al. *Nature* 401:73-76 (1999)). These mice have extremely low levels of leptin in plasma. However, the authors do not link the effect of leptin with LSR. The instant invention includes the use of the leptin peptides of the invention for treatment of lipodystrophy and for use in this mouse model.

Leptin peptide will be provided to transgenic mice expressing SREBP-1c436 in adipose tissue under the control of the adipocyte-specific aP2 promoter/enhancer (Shimomura et al. Genes Dev. 12:3182-3194 (1998)). The levels used are similar to those described for the ob/ob mice herein, a range around 50 ng per mouse. Leptin is provided daily for 12 days, either by injection, or using micro-osmotic pumps. Plasma glucose will be measured using a glucose (Trinder)-100 kit, plasma insulin by an anti-rat insulin radioimmunoassay (linco), and plasma leptin and triglyceride by standard methods described previously. A similar experiment is performed where the food intake is restricted to a level that is consumed completely by all animals.

Example 15

Effect of Truncated Human LSR on Binding, Uptake & Degradation of LDL

Truncated forms of the LSR receptor were made and tested for their ability to function as either dominant positive (i.e. increase the activity of the receptor) or dominant negative proteins (i.e. interfere with the activity of the receptor), when over-expressed in cultured cells.

Figure 15:
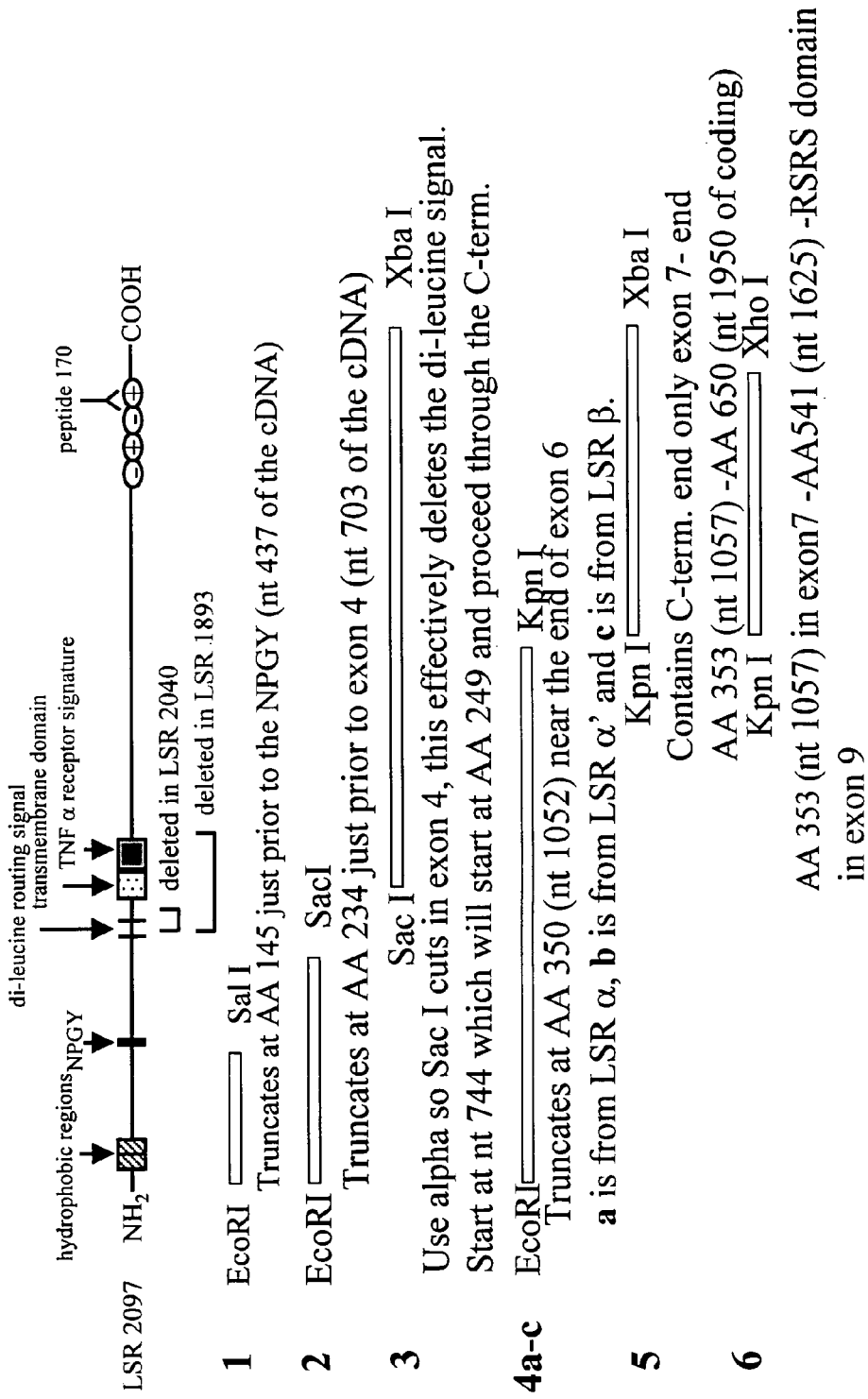
FIG. 15 shows a schematic of a plan to create truncated LSR constructs.

Materials:
Human LSR cDNAs α, α' and β from constructs made in pTracer CMV2.
pcDNA/HisMax vector from Invitrogen
Appropriate restriction enzymes, T4 DNA polymerase I and Klenow, and T4 DNA ligase.
Standard cloning procedures from "Molecular Cloning" by Sambrook et al.
Follow construct plan (FIG. 15).

Method of Cloning & Testing.
1. Digest Human LSR plasmids with enzymes of interest under appropriate conditions. Separate the appropriate insert fragment from the vector using agarose gel electrophoresis and Qiaquick gel extraction columns. Note: For constructs 1, 2, 3, 4a, 5, and 6 pTracerCMV2 LSR α was used as the source for the insert. For construct 4b, pTracerCMV2 LSR α' was used as the source for the insert. For 4c, pTracerCMV2 LSR β was used as the source for the insert.
2. Digest the pcDNA/HisMax vector in the appropriate reading frame with the enzymes of interest. Purify using agarose gel electrophoresis and Qiaquick gel extraction columns.
3. If necessary, treat insert fragments with Klenow DNA polymerase or T4 DNA polymerase I to blunt 3' overhangs. Purify DNA from the reaction using Qiaquick PCR purification kit.
4. Ligate inserts into vector according to Sambrook et al. using a 3-5 M excess of insert to vector.
5. Transform plasmids into competent *E. coli*—XL1blue from Stratagene. Follow manufacturer's instructions.
6. Isolate colonies with correct plasmids by either PCR or Qiagen miniprep analysis.
7. Verify correct clones by having them sequenced to ensure that they are in the proper reading frame and that there are no amino acid changes.
8. Grow and harvest DNA from large-scale cultures using Qiagen endotoxin free maxi preps.
9. Analyze constructs by transfecting them into human cells and assaying LDL binding using the standard BUD protocol.

BUD Assay Materials:
DNA from LSR truncated constructs at approximately 1 mg/mL.
Lipofectamine Plus transfection reagent—Life Technologies Cat. No 10964-013
PLC cells plated at $0.3 \times 10^6$ cells/well in a 6 well plate.
$^{125}$I-LDL
10 mM suramin (70 mL PBS per 1 g suramin)
100 mM oleate in isopropanol, freshly prepared from a 400 mM stock solution
DMEM (without $CaCl_2$) containing 0.2% (w/v) BSA, 5 mM Hepes, 2 mM $CaCl_2$, pH 7.5, and 3.7 g/L $NaHCO_3$ (this media should be prepared before the experiment, stored at 4° C., and used for up to 1 week)
PBS, pH 7.4
PBS containing 0.2% (w/v) BSA
0.1 N NaOH containing 0.24 mM EDTA BUD Assay Methods:
1. Cells (adherent) in 6-well plates seeded at $3 \times 10^5$ cells 3 days prior to the BUD.
   Transfect the cells using lipofectamine plus reagent, according to the manufacturer's instructions, the day after the cells are seeded. Confluence should be between 50-80% when transfected.
   Let cells go about 48 hrs (2 days) after transfection before BUD analysis.
2. Wash cells once with PBS (room temperature), 2 mL/well
3. Add DMEM/0.2% BSA (950 µL)
4. Add oleate, (0 to 1 mM oleate, e.g. 0, 0.1 mM 0.2 mM, 0.5 mM, 0.8 mM and 1 mL, from 100 mM stock)
   never exceed 10 µL isopropanol per mL DMEM
   It is necessary to include wells with no oleate as a control for background. This control allows one to calculate the amount of oleate-induced $^{125}$I-LDL metabolized.
5. Add appropriate concentration of $^{125}$I-LDL to each well (50 µL of each dilution).
6. Incubate cells for 90 min to 4 hours at 37° C. in a $CO_2$ incubator. In these experiments, 3 hrs was the incubation time.
7. Transfer media from wells into 5 mL polycarbonate tubes. Store at 4° C. overnight for degradation analysis (see below).
8. Wash cells at 4° C. (on ice):
   Wash 2 times consecutively with ice-cold PBS/0.2% BSA
   Wash once with ice-cold PBS/0.2% BSA
   Wash 2 times consecutively with ice-cold PBS
9. Add 1 mL/well 10 mM suramin and incubate at 4° C. for 1 hour.
10. Remove suramin into gamma counter tubes, and count for radioactivity. This represents the amount of $^{125}$I-LDL bound to the cell surface.
11. Add 0.1 N NaOH/0.24 mM EDTA (1 mL/well) and incubate at room temperature for a minimum of 30 min. to lyse the cells.
12. Recover the cell lysates into gamma counter tubes and count for radioactivity. This represents the amount of $^{125}$I-LDL internalized. Alternatively, the suramin step may be omitted (LSR as leptin receptor) and the cells lysed immediately after washing. This would represent the amount of cell-associated $^{125}$I-LDL or $^{125}$I-leptin.
13. After cell lysates have been counted, determine the protein concentration per mL so that data can be reported as ng $^{125}$I-LDL bound/mg of total protein. Protein is determined using the BCA assay from Pierce according to the manufacturer's instructions. Alternatively, data can be corrected for β-Gal units by transfecting extra wells and collecting them for the β-Gal assay at the time the BUD is done. For this protocol, see β-Gal protocol, below.

Degradation of $^{125}$I-LDL
1.) After leaving overnight at 4° C., add 1 mL ice-cold 40% TCA to the pre-cooled media. Do not Vortex.
2.) Incubate 1 hour at 4° C.
3.) Centrifuge at 3000 rpm (Beckman Allegra centrifuge), 30 min @ 4° C. (If the precipitate is floating, it is necessary to break the air-water interface by gently shaking the tubes before pelleting.
4.) Transfer 1 mL supernatant to 5 mL glass tubes.
5.) Add 40 µL 30% $H_2O_2$ and vortex briefly.

6.) Add 1 mL chloroform and vortex briefly. Let tubes sit for 15 minutes to allow separation of the 2 phases.
7.) Transfer 0.5 mL to gamma counter tubes, and count for radioactivity.
8.) For the calculation of the amount degraded, the dilution factor is 4.16. Corresponding plates without cells serve as controls to define the level of the background.

B-Gal Assay

1). Transfect cells with test construct+⅛$^{th}$ the amount of β-gal expressing plasmid.
2). Harvest cells in lysis buffer (250 μL/well of a 6 well plate). Pull through a syringe several times before transferring into an eppendorf tube.
3). Freeze cells at −80° C. until ready to perform the assay.
4). Thaw cells of interest and spin at 14K in a microfuge at 4° C. for 5 min.
5). Transfer 10 μL of each lysate to a clear PP 96 well plate:

Example

| | | | Example | | | | | | | | |
|---|---|---|---|---|---|---|---|---|---|---|---|
| 1 | 2 | 3 | 4 | 5 | 6 | 7 | 8 | 9 | 10 | 11 | 12 |
| A Blank 10 μL | Blank 10 μL | empty | Sample 2 10 μL | Sample 2 10 μL | Sample 2 10 μL | Etc ... | | | | | |
| B Control *100 μL | Control *100 μL | empty | Sample 3 10 μL | Sample 3 10 μL | Sample 3 10 μL | | | | | | |
| C Sample 1 10 μL | Sample 1 10 μL | Sample 1 10 μL | Sample 4 10 μL | Sample 4 10 μL | Sample 4 10 μL | | | | | | |

*Control = reference standard
Blank = reaction buffer only

6). Add Fluo-Reporter β-gal substrate (Molecular Probes cat #F-2905) to β-gal reaction buffer. (275 μL CUG substrate to [componet A] 9.73 mL of reaction buffer) NOTE: need 10 mL for a 96 well plate, but if you don't use it all it can be stored at −20° C. for at least 6 months.
7). Add 100 μL of Reaction buffer with substrate to each well.
8). Incubate at room temp. for 30 min.
9). Add 50 μL of stop mix (0.2 M Na$_2$CO$_3$)
10). Read on Cytoflour plate reader with excitation at 360 and emission at 460. Gain should be set around 30.

| | | [Final] |
|---|---|---|
| β-gal reaction buffer: | | |
| 0.5 M NaPhosphate pH 7.3 | 40 mL | 0.1 M |
| 1 M MgCl$_2$ | 0.2 mL | 1 mM |
| 14.3 M β-mercaptoethanol | 629 μL | 45 mM |
| ddH$_2$O | 159.171 mL | 200 mL |
| Lysis Buffer: | | |
| Buffer II | 9.875 mL | |
| 100% TritonX100 | 100 μL | 1% |
| 400 mM DTT | 25 μL | 1 mM |
| Buffer II | | |
| 1 M Tris-Ac pH 7.8 | 50 mL | 100 mM |
| 1 M MgAc | 5 mL | 10 mM |
| 0.5 M EDTA | 1 mL | 1 mM |
| ddH$_2$O | 439 mL | 500 mL |

Figure 16:
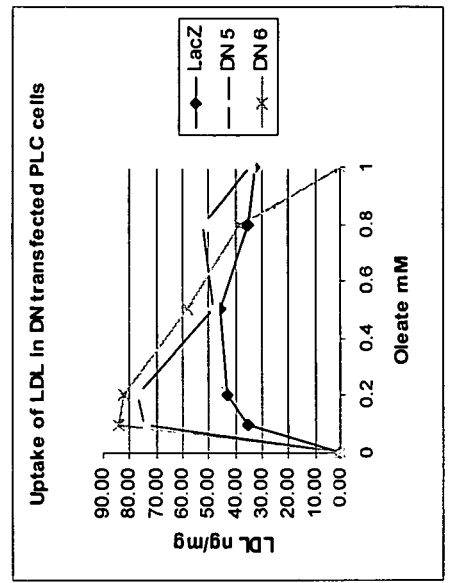
FIGS. 16A, 16B, and 16C show that the transfection of a truncated form of LSR (DN5+6) increases $^{125}$I-LDL binding (A), uptake (B) and degradation (C) in PLC cells in reference to protein concentration. All points are done in triplicate.
Figure 16:
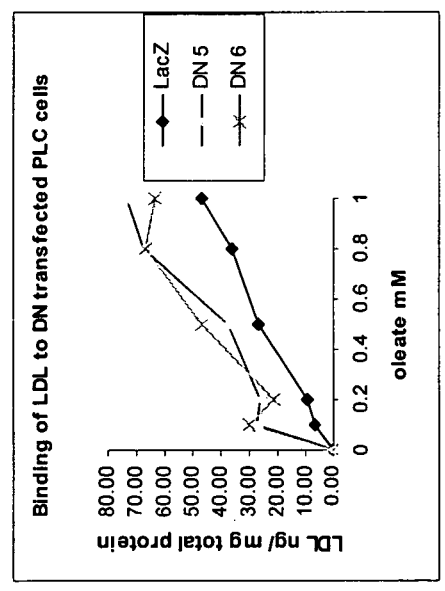
Figure 16:
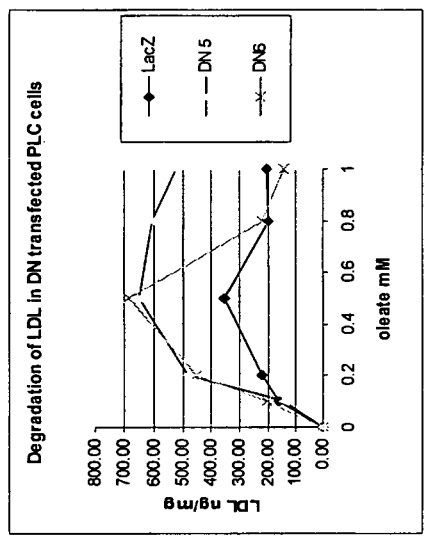
Figure 17:
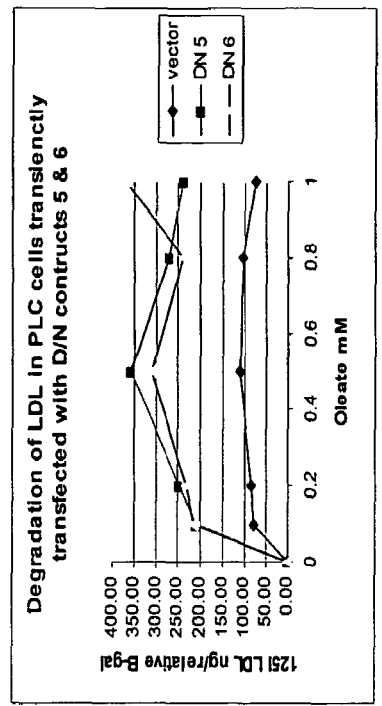
FIGS. 17A, 17B, and 17C show that the transfection of a truncated form of LSR (DN5+6) increases $^{125}$I-LDL binding (A), uptake (B) and degradation (C) in PLC cells correcting for transfection efficiency using β-gal as a reference. All points are done in triplicate.
Figure 17:
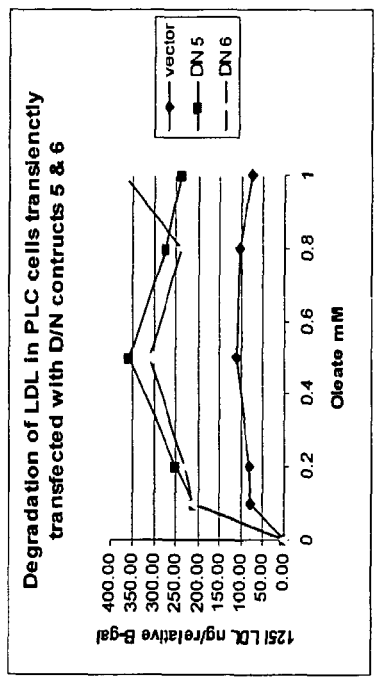
Figure 17:
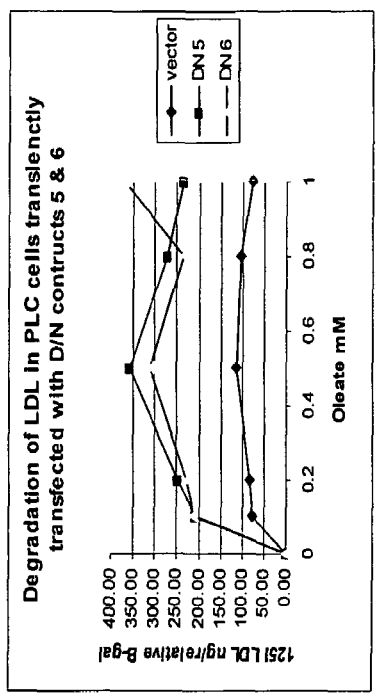

Results of BUD Assay:

Addition of the C-terminal portion of LSR increased $^{125}$I-LDL binding (a), uptake (b) and degradation (c) in PLC cells (FIG. 16). $^{125}$I-LDL degradation is increased almost 2 fold at 0.5 mM oleate. Data in this experiment is corrected for protein only. The transfection efficiency was not monitored. All points were done in triplicate. In a separate experiment, addition of the C-terminal portion of LSR also increased $^{125}$I-LDL binding (a), uptake (b) and degradation (c) in PLC cells (FIG. 17). $^{125}$I-LDL degradation was increased 2-3 fold at 0.5 mM oleate. Data in this experiment was corrected for transfection efficiency only. All points are in triplicate.

The C-terminal portion of LSR from AA353 to 650 (the last AA) as well as the C-terminal portion from AA 353 to 541 are able to increase the binding, uptake and degradation of $^{125}$labelled LDL in vitro (FIGS. 16 & 17). The increase is on the order of 2-3 fold for all 3 measurements when corrected for transfection efficiency using the β-Gal reporter as a carrier in the test DNA. The increase in LDL metabolism is still on the order of 2 fold when data are corrected for total protein, depending on the oleate concentration. These constructs can be cloned into a vector to allow expression and testing in vivo for this dominant positive effect in animals using methods well known to those in the art.

Example 16

LSR Gene Expression in Liver and Brain of Lean and Obese Mice

LSR gene expression was determined by quantitative PCR (QPCR) in liver and brain tissue of 7 different mouse models: normal and high fat diet-fed C57BL/6J mice (C57), C57BL6/J ob/ob (ob/ob), C57BLK/S, C57BLK/S db/db (db/db), NZB and NZO mice. The normal diet was obtained from Harlan Teklad (Teklad Certified LM-485 mouse/rat 7011C), the high fat diet, also called cafeteria diet was from Research Diets (D12331, Rat Diet 58 kcal % fat and sucrose). The cause of obesity in the different models is high fat diet in the obese C57 mice, leptin deficiency in ob/ob mice, deficiency in functional leptin receptor in db/db mice. The cause of obesity in the NZO mouse is currently unknown (Lit 1-3). C57BLK/S and NZB mice are both lean and were used as controls since they represent the corresponding background strain of db/db and NZO mice, respectively.

The qPCR results for the different LSR levels in the livers of different mouse strains are supported by immunohistochemistry result using methods well-known to persons of ordinary skill in the art.

Reverse Transcriptase—Polymerase Chain Reaction

Liver and whole brain were isolated from mice following perfusion with ice-cold saline containing 10 mM EDTA. Tissues were stored in RNAlater (Ambion, Austin) at 4° C. for 1 day and then at −20° C. Liver total RNA was isolated using RNAqueous (Ambion, Austin) following the manufacturer's protocol. The amount of RNA was determined by absorption at 260 nm. The quality of the isolated RNA was verified by the ratio 260/280 nm (between 1.9 and 2.1 is good) and by denaturing agarose gel electrophoresis.

RNA was reverse transcribed to cDNA using oligo dT plus an LSR specific primer and Superscript II (Gibco BRL) according to manufacturer's instructions. The LSR specific primer is in exon 6 of the LSR gene (5'ACGCATGGGAAT-CATGGC; SEQ ID NO:90). Plasmids containing mouse LSR-α/α'/β sequence were obtained by cloning RT-PCR tration. The forward and reverse GAPDH and LSR primers used are shown in Table 1. PCR reaction conditions were 50° C. for 2 minutes, 95° C. for 10 minutes, followed by 40 cycles at 95° C. for 15 seconds and 1 minute at 60° C. PCR was performed in 96 well reaction plates with optical caps and fluorescence was continuously followed for each reaction. cDNA corresponding to 15 ng of total RNA were used per PCR reaction.

Quantification of LSR expression was obtained using a standard curve of the corresponding LSR plasmid covering a concentration range between $5 \times 10^{-6}$ and $5 \times 10^{-10}$ M (approximately $10^6$ to $10^2$ copies). A standard curve of mouse (C56BL/6J) total liver RNA between 200 and 0.1 ng RNA was used to determine relative levels of GAPDH expression. Amplification plots were analyzed using SDS software (PE Biosystems).

TABLE 1

PCR primers and probes used to determine the expression level of mouse GAPDH and mouse LSR isoforms.

| Target Gene | Forward Primer | Reverse Primer | Probe |
|---|---|---|---|
| GAPDH | AACGACCCCTTCATTGACCTC (SEQ ID NO:114) | CTTCCCATTCTCGGCCTTG (SEQ ID NO:115) | ACTCACGGCAAATTTCAACGGCACAG (SEQ ID NO:116) |
| LSR complete | GGCAGGAGAATCACCATCACA (SEQ ID NO:117) | GATCTTGGGCTGAGACCACG (SEQ ID NO:118) | TGCTGGCCTGACCTTCGAGCAGAC (SEQ ID NO:119) |
| LSR alpha | GCCCTTGGAAGATTGGCTCT (SEQ ID NO:120) | ATGCTTGGCACACCTGAGGT (SEQ ID NO:121) | CCAGTGCTGTCCCCACACCTGCT (SEQ ID NO:122) |
| LSR alpha' | ACCAGGGCAGGAGAATCACC (SEQ ID NO:123) | GGAGGAAGAAGAGGAGGCTTG (SEQ ID NO:124) | AGCTCATTGTCCTTGATTGGCTCTTTGTG (SEQ ID NO:125) |
| LSR beta | TTGTCCTTGTTTATGCTGCTGG (SEQ ID NO:126) | CAGGAGAGAGGTGGGTATAGATGC (SEQ ID NO:127) | AGCAGCCACCTCAGGTGTGCCAA (SEQ ID NO:128) | products produced from mouse liver total RNA into pGEM-T easy (Promega). The sequence of the plasmid was confirmed by cycle sequencing on a ABI Prism 377 DNA Sequencer.

Quantitative PCR was performed on a ABI Prism 7700 Sequence Detection System using TaqMan technology (PE Biosystems). TaqMan assay primers and probes were designed using Primer Express software (PE Biosystems) and were synthesized by Genset, La Jolla. Each probe was double labeled with the fluorescent reporter dye 6-carboxyfluorescein (FAM) covalently linked to the 5' end of the probe and the quencher dye 6-carboxytetramethylrhodamine (TAMRA) attached to the 3' end. Uracil-N-glycosylase technology (PE Biosystems) was used to prevent contamination with PCR product.

PCR was performed using the following reagent concentrations: 25 mM MgCl2, dNTPs at 200 µM, except for dUTP at 400 µM, 1 U of AmpliTaq Gold, 0.25 U AmpErase UNG. Primers were added at 300 nM and probes at 200 nM concen- Quantification by TaqMan technology is based on determining the threshold cycle of amplification, which was determined for each unknown sample and for the standard dilutions using 0.1 fluorescence units as a threshold (maximum fluorescence>1.5). The amount of unknown cDNA was calculated using the corresponding standard curve. LSR expression was given as absolute copy numbers and also normalized for GAPDH expression (by dividing the determined absolute copy number by the relative level of GAPDH for each individual animal). Each determination was done in triplicate and was repeated at least once; very similar results (SD<5%) were obtained.

All data were confirmed by standard Northern analysis. 16 µg total RNA was pooled from 4 mice per group and tissue and analyzed by Northern. Although this type of analysis is semi-quantitative at best and LSR isoforms can not be differentiated, relative levels of gene expression show the same trends as measured by QPCR.

Results
LSR Expression in Liver

TABLE 1

LSR gene expression in liver of lean and obese mice (copy numbers in 15 ng total liver RNA)

|  |  | LSR-alpha | LSR-alpha' | LSR-beta | LSR (sum of isoforms) | GAPDH | LSR total |
|---|---|---|---|---|---|---|---|
| C57 normal | ave | 93966 | 110334 | 18454 | 222754 | 2.8 | 281654 |
|  | SEM | 21760 | 16682 | 2790 | 39779 | 0.4 | 83220 |
|  | ave | 42.2% | 49.5% | 8.3% |  |  |  |
|  | SEM | 2.5% | 2.4% | 0.3% |  |  |  |
| C57 obese | ave | 82814 | 44084 | 17280 | 144177 | 6.0 | 161206 |
|  | SEM | 12274 | 8073 | 2344 | 22521 | 1.7 | 21161 |
|  | ave | 57.4% | 30.6% | 12.0% |  |  |  |
|  | SEM | 1.2% | 1.3% | 0.4% |  |  |  |
| C57 ob/ob | ave | 49898 | 51056 | 21126 | 122079 | 9.1 | 120026 |
|  | SEM | 5928 | 10469 | 1758 | 15113 | 1.0 | 32474 |
|  | ave | 40.9% | 41.8% | 17.3% |  |  |  |
|  | SEM | 0.7% | 4.2% | 3.9% |  |  |  |
| C57BLK/S | ave | 49029 | 68379 | 41340 | 158749 | 3.9 | 163060 |
|  | SEM | 3862 | 3721 | 2043 | 5903 | 0.4 | 94537 |
|  | ave | 30.9% | 43.1% | 26.0% |  |  |  |
|  | SEM | 1.3% | 1.6% | 1.8% |  |  |  |
| C57BLK/S db/db | ave | 30625 | 48504 | 18683 | 97811 | 9.2 | 79745 |
|  | SEM | 1953 | 12021 | 3123 | 10819 | 1.0 | 26413 |
|  | ave | 31.3% | 49.6% | 19.1% |  |  |  |
|  | SEM | 1.7% | 7.0% | 5.4% |  |  |  |
| NZB normal | ave | 98455 | 387287 | 54079 | 539822 | 3.1 | 588656 |
|  | SEM | 44.46 | 13253 | 6740 | 21241 | 0.7 | 27993 |
|  | ave | 18.2% | 71.7% | 10.0% |  |  |  |
|  | SEM | 0.6% | 0.8% | 0.9% |  |  |  |
| NZO obese | ave | 57497 | 225574 | 23377 | 306448 | 1.8 | 333271 |
|  | SEM | 4595 | 11767 | 1091 | 15948 | 0.3 | 11416 |
|  | ave | 18.8% | 73.6% | 7.6% |  |  |  |
|  | SEM | 0.9% | 1.1% | 0.2% |  |  |  |

LSR Expression in Brain of Lean and Obese Mice

TABLE 2

LSR gene expression in brain of lean and obese mice (copy numbers in 15 ng total liver RNA)

|  |  | LSR-alpha | LSR-alpha' | LSR-beta | LSR (sum of isoforms) | GAPDH | LSR total |
|---|---|---|---|---|---|---|---|
| C57 normal | ave | 1192 | 6443 | 7731 | 15365 | 36.2 | 10653 |
|  | SEM | 155 | 1512 | 443 | 1717 | 3.0 | 1933 |
|  | ave | 7.8% | 41.9% | 50.3% |  |  |  |
|  | SEM | 0.5% | 6.0% | 6.3% |  |  |  |
| C57 obese | ave | 1496 | 10472 | 7418 | 19387 | 20.8 | 14118 |
|  | SEM | 155 | 1295 | 716 | 1998 | 5.7 | 805 |
|  | ave | 7.7% | 54.0% | 38.3% |  |  |  |
|  | SEM | 0.5% | 1.9% | 2.2% |  |  |  |
| C57 ob/ob | ave | 1293 | 6502 | 6158 | 13954 | 34.2 | 14034 |
|  | SEM | 190 | 797 | 475 | 863 | 5.2 | 1939 |
|  | ave | 9.3% | 46.6% | 44.1% |  |  |  |
|  | SEM | 1.0% | 3.4% | 4.4% |  |  |  |
| C57BLK/S | ave | 1918 | 5585 | 6456 | 13958 | 26.7 | 10458 |
|  | SEM | 206 | 354 | 1024 | 1087 | 5.3 | 980 |
|  | ave | 13.7% | 40.0% | 46.3% |  |  |  |
|  | SEM | 1.7% | 2.8% | 4.2% |  |  |  |
| C57BLK/S db/db | ave | 1834 | 5195 | 8189 | 15217 | 35.0 | 10912 |
|  | SEM | 199 | 297 | 789 | 1117 | 4.5 | 670 |
|  | ave | 12.0% | 34.1% | 53.8% |  |  |  |
|  | SEM | 0.7% | 2.0% | 1.4% |  |  |  |
| NZB normal | ave | 654 | 1019 | 5463 | 7135 | 17.0 | 4430 |
|  | SEM | 159 | 321 | 929 | 1051 | 4.7 | 926 |
|  | ave | 9.2% | 14.3% | 76.6% |  |  |  |
|  | SEM | 1.7% | 5.1% | 6.8% |  |  |  |
| NZO obese | ave | 168 | 320 | 2715 | 3202 | 13.4 | 1446 |
|  | SEM | 112 | 52 | 37 | 1638 | 4.5 | 1008 |
|  | ave | 5.2% | 10.0% | 84.8% |  |  |  |
|  | SEM | 12.9% | 5.6% | 16.8% |  |  |  |

C57BL6/J, C57BLK/S, db/db, ob/ob Mice

Figure 18:
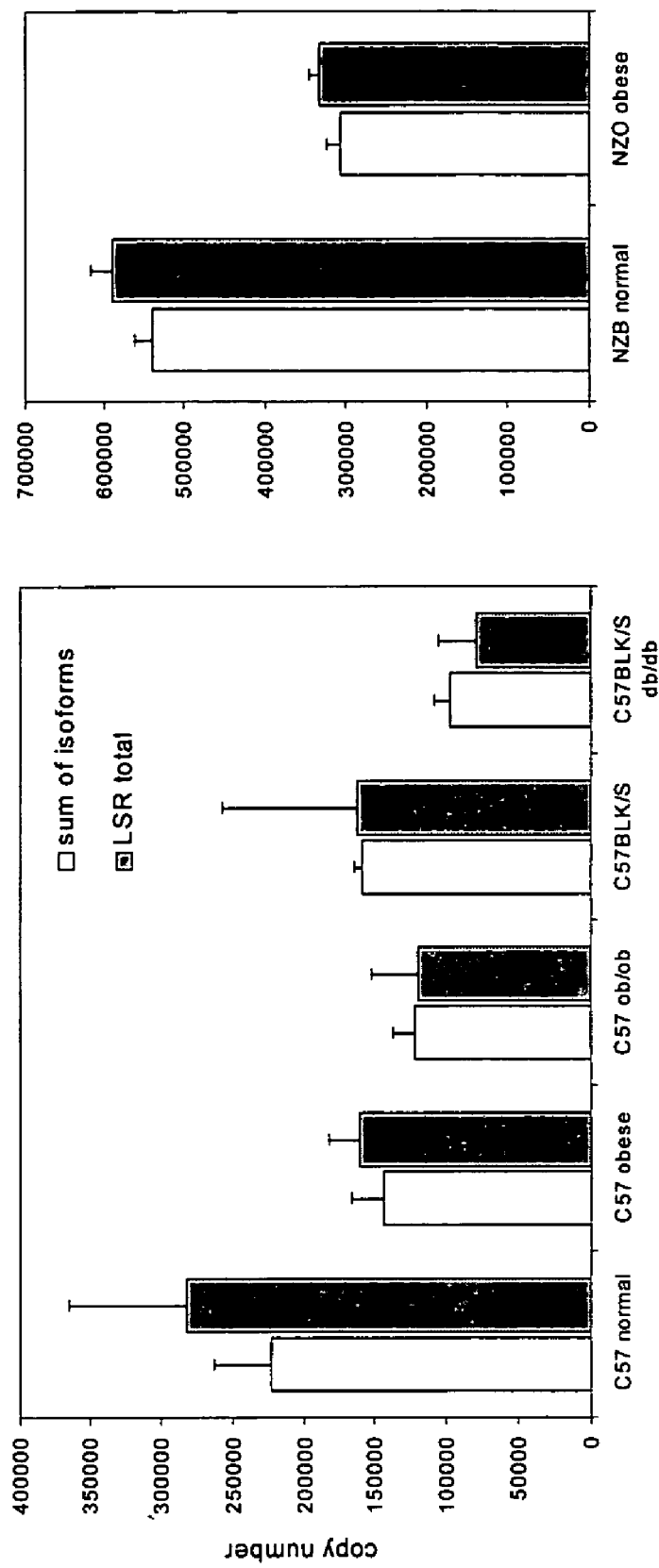
FIGS. 18A and 18B show graphs of the total LSR expression in mouse liver determined by Quantitative PCR.
Figure 21:
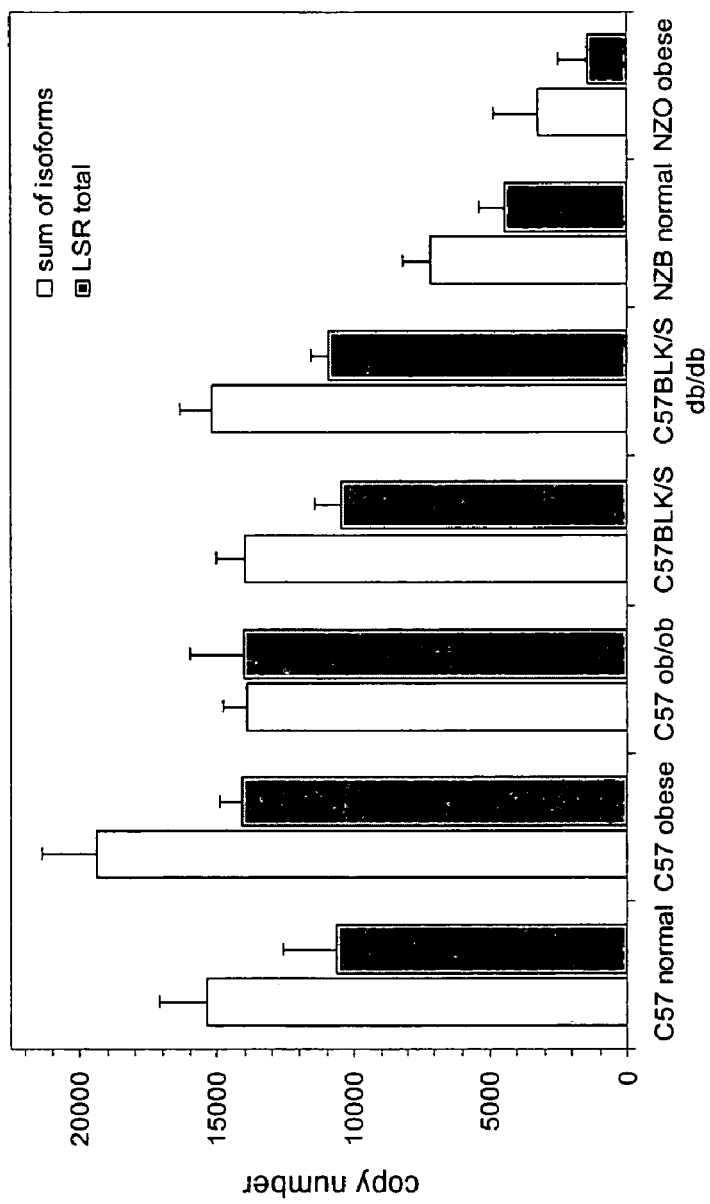
FIG. 21 shows a graph of total LSR expression in mouse brain determined by Quantitative PCR.

LSR expression in the liver of obese animals is significantly lower than in lean control animals (FIG. 18). In general, the expression of LSR in brain tissue is much lower than in liver. However, unlike in liver, obesity does not cause further downregulation (FIG. 21).

Figure 19:
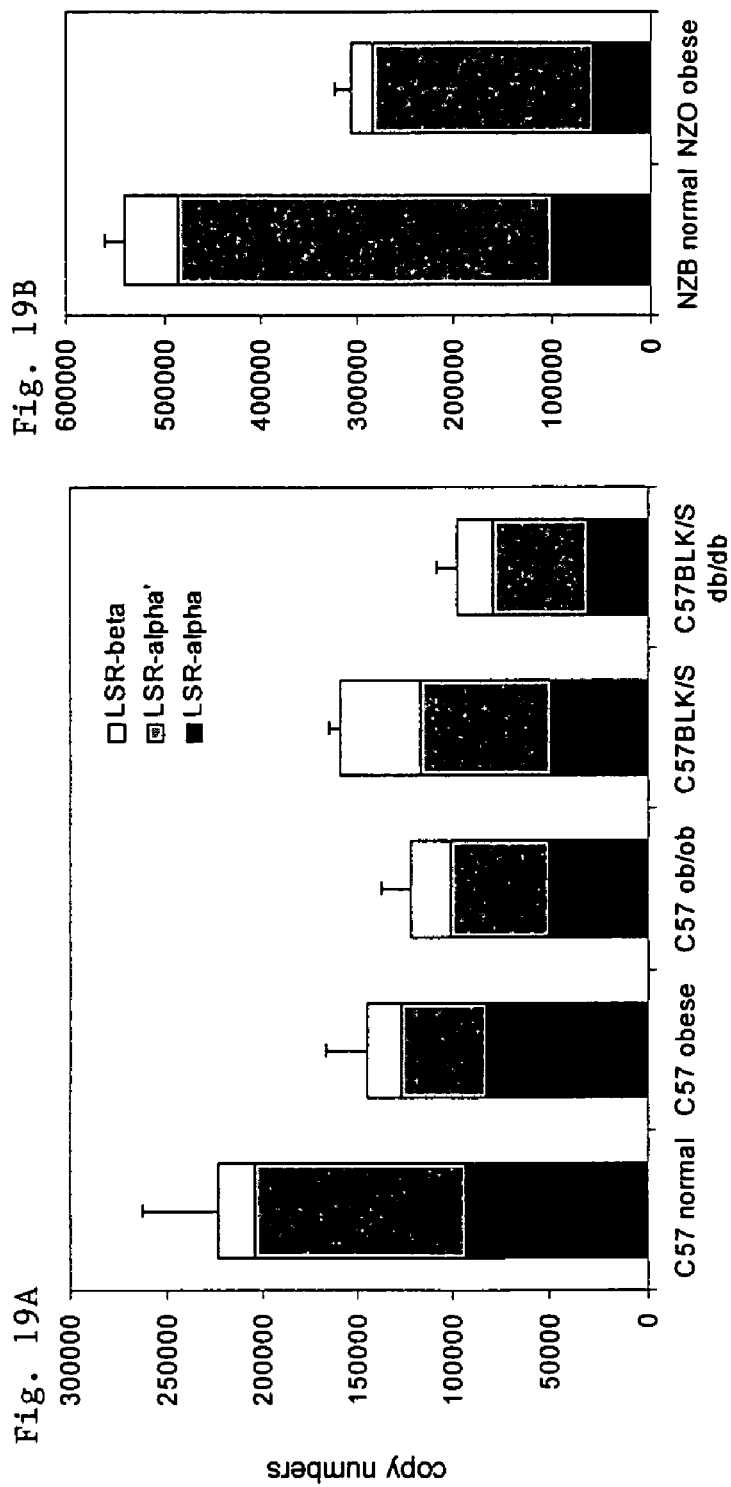
FIGS. 19A and 19B show graphs of the expression of LSR isotypes in mouse liver.
Figure 20:
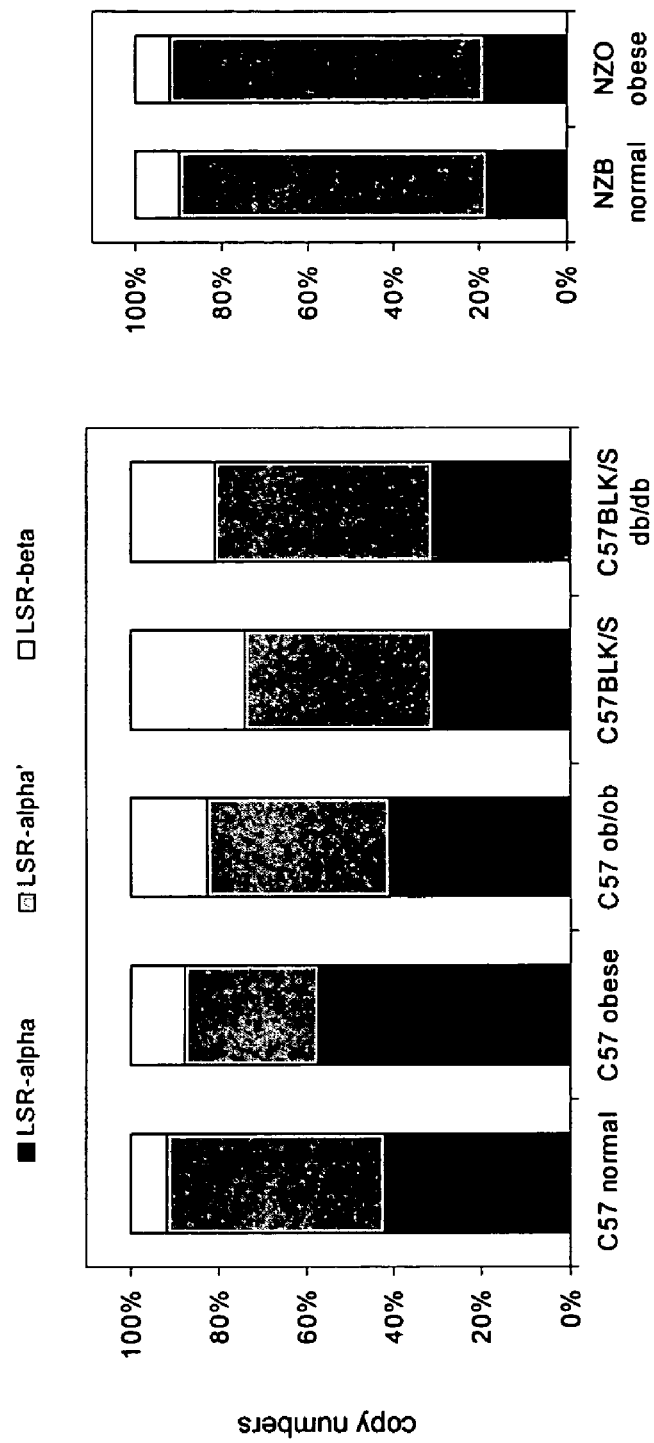

No significant differences in isotype patterns were found in liver samples from the different mouse models. LSR alpha and alpha' contribute equally and account for almost all of the total LSR expression. LSR beta contributes only a small percentage (FIG. 19 and FIG. 20).

Figure 22:
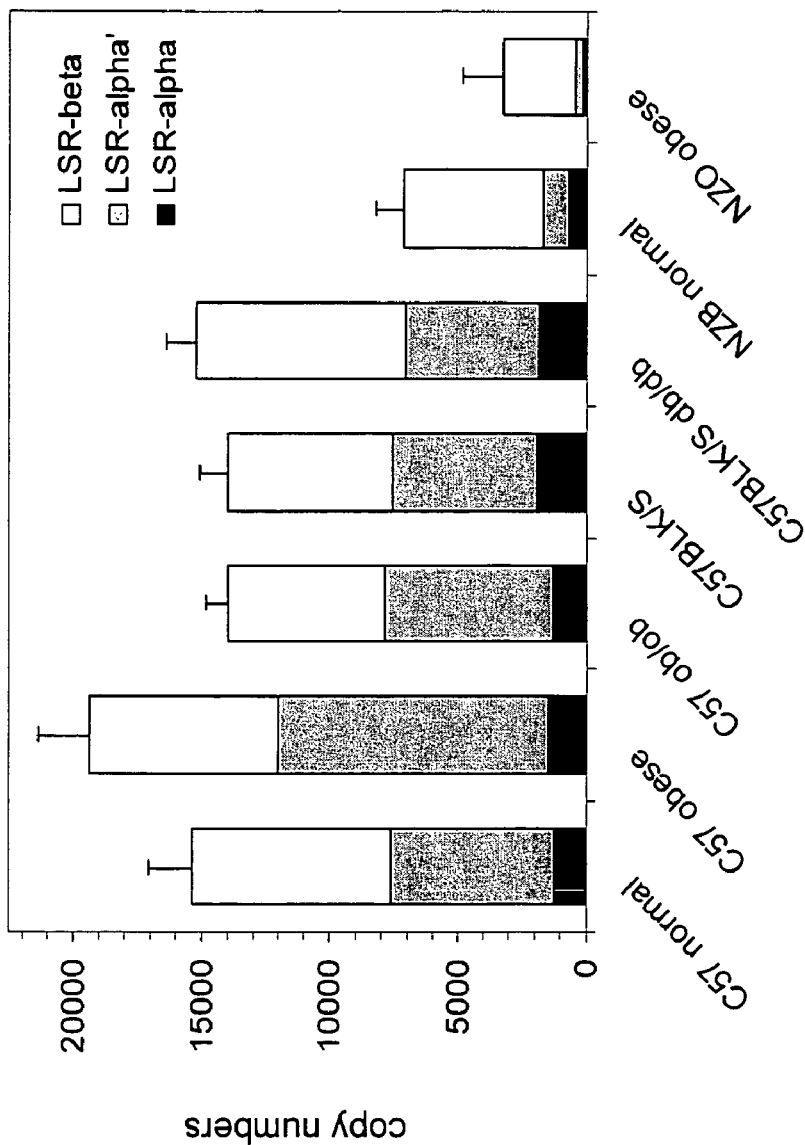
FIG. 22 shows a graph of the expression of LSR isotypes in mouse brain.
Figure 23:
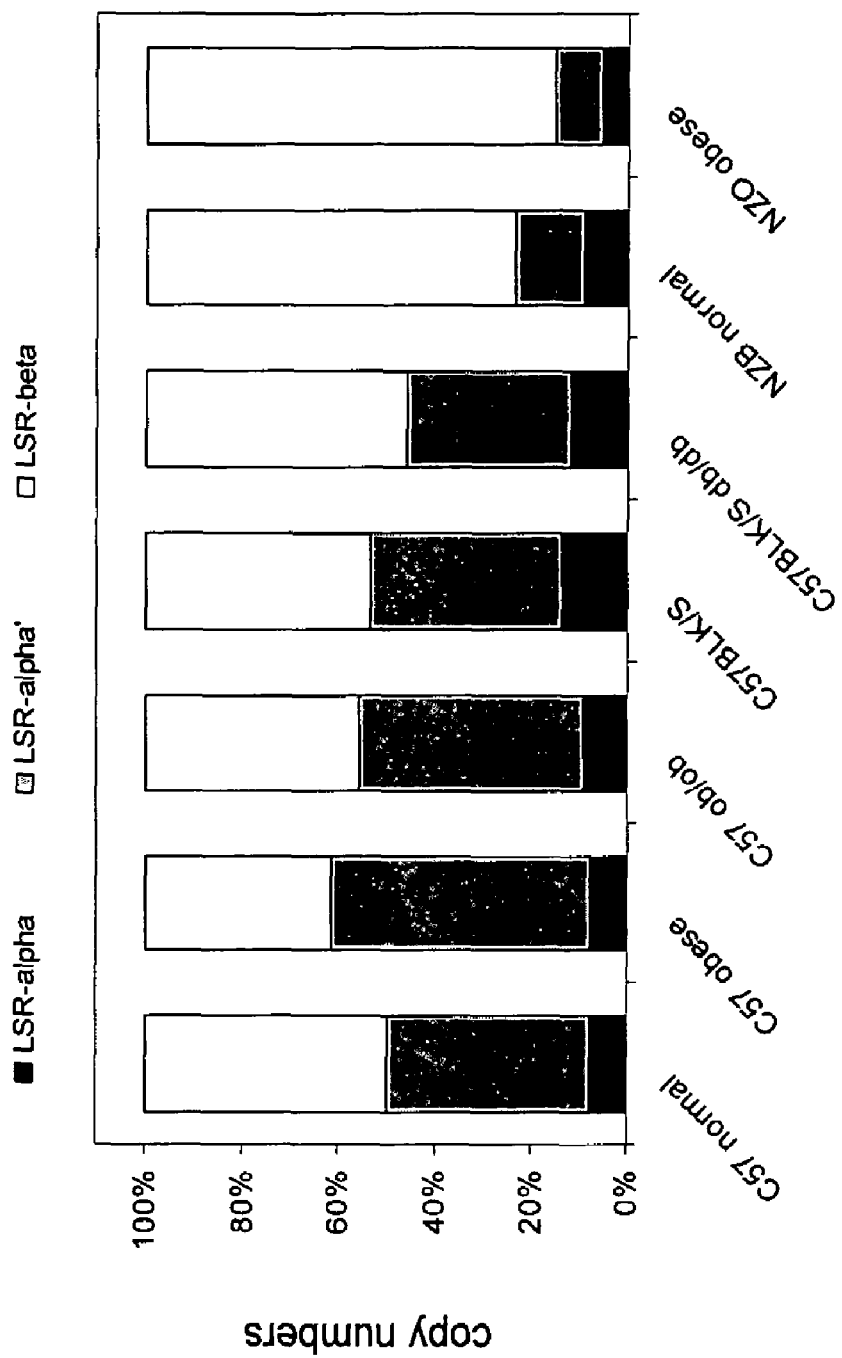
FIG. 23 shows a graph of the relative levels of LSR isotype expression in mouse brain.

In contrast, LSR alpha' and beta are the major contributors to overall LSR expression in brain, accounting in equal proportions for about 90% of total LSR message. No significant levels of LSR alpha were seen in any of the studied models (FIG. 22 and FIG. 23).

The downregulation of LSR seems to be strongly associated with obesity independent of the cause of obesity (dietary as well as different genetic defects are the causes in the used models). One might expect that upregulation of liver LSR expression in obese individuals would be beneficial.

NZB and NZO Mice

LSR expression in liver tissue of NZB mice is 2-fold higher than in normal C57 mice. Obesity (in the NZO) again leads to strong downregulation, however, this level is still significantly higher than in other obese mice (FIG. 18). In contrast, LSR expression in the brain of NZB and even more so in brain tissue of NZO, is significantly lower than in the other 5 models (FIG. 21).

Distribution of LSR isotypes in NZB and NZO mice was very different from the previously described 5 models. The dramatic increase in liver LSR expression seen in NZB (and in NZO) mice was found to be mainly LSR alpha'. This form accounted for 80% of total LSR (FIG. 19 and FIG. 20). The complete opposite was seen in brain tissue. NZB mice have very low expression of LSR alpha and alpha' with LSR beta being the dominant isoform. This picture is even more pronounced in NZO mice. Brain LSR in these animals is almost exclusively LSR beta and some animals had virtually no alpha or alpha' expression (FIG. 22 and FIG. 23).

The fact that NZO mice respond to intracerebroventricular injection of leptin but not to peripheral injection (Halaas J L, et al., Proc. Natl. Acad. Sci. USA, 94, 8878-8883, 1997) suggests a transport defect. Since LSR alpha' has been shown to bind leptin, and since LSR alpha' levels are reduced in NZO mice, the implication is that the genetic defect in NZO mice causing obesity might be deficiency in brain LSR alpha' expression resulting in non-functioning leptin transport across the blood brain barrier. This conclusion is further supported by the discovery that some NZO mice that do not become obese have LSR alpha' expressed at significant levels in brain.

Example 17

Effect of a Ser→Asn Substitution on LSR Activity in Human Hepatocytes

Previously, we described a frequent (allele frequency 12%) G→A mutation of cDNA base pair 1088 (LSR exon 6), which results in a Ser→Asn mutation at amino acid position 363, presumably in the extra-cellular domain of the receptor.

In a group of 34 obese adolescent girls, this coding mutation significantly increased fasting and postprandial plasma triglyceride response to a high fat test meal. In a larger population of 154 obese adolescent girls, the same coding mutation significantly and selectively influenced fasting plasma triglyceride levels and increased 3.5 fold the risk of hypertriglyceridemia. This data suggested that LSR plays a significant role in the clearance of triglyceride-rich lipoproteins. Interestingly, even individuals heterozygous at this locus showed the effect.

An in vitro model was obtained after sequence analysis of LSR in 2 cell lines, PLC and HepG2, revealed that PLC cells are homozygous for the G allele, while HepG2 cells are heterozygous, having both the G and A allele.

Methods:

The oleate-induced $^{125}$I-LDL binding, uptake and degradation was measured in HepG2 and PLC according to the method described previously (Bihain, B. E., and Yen, F. T. (1992). Free fatty acids activate a high-affinity saturable pathway for degradation of low-density lipoproteins in fibroblasts from a subject homozygous for familial hypercholesterolemia. Biochemistry 31, 4628-4636.). Briefly, confluent monolayers of cells were washed once in phosphate buffered saline (PBS), and then incubated 3 h at 37° C. with increasing concentrations of oleate (as indicated) and 20 µg/mL $^{125}$I-LDL. At the end of the incubation, cells were placed on ice and washed twice with PBS containing 0.2% BSA, once with the same buffer, and then twice with PBS alone. The amounts of $^{125}$I-LDL bound, internalized and degraded were then measured according to the method of Bihain, B. E., and Yen, F. T. (1992). Free fatty acids activate a high-affinity saturable pathway for degradation of low-density lipoproteins in fibroblasts from a subject homozygous for familial hypercholesterolemia. Biochemistry 31, 4628-4636.

Figure 24:
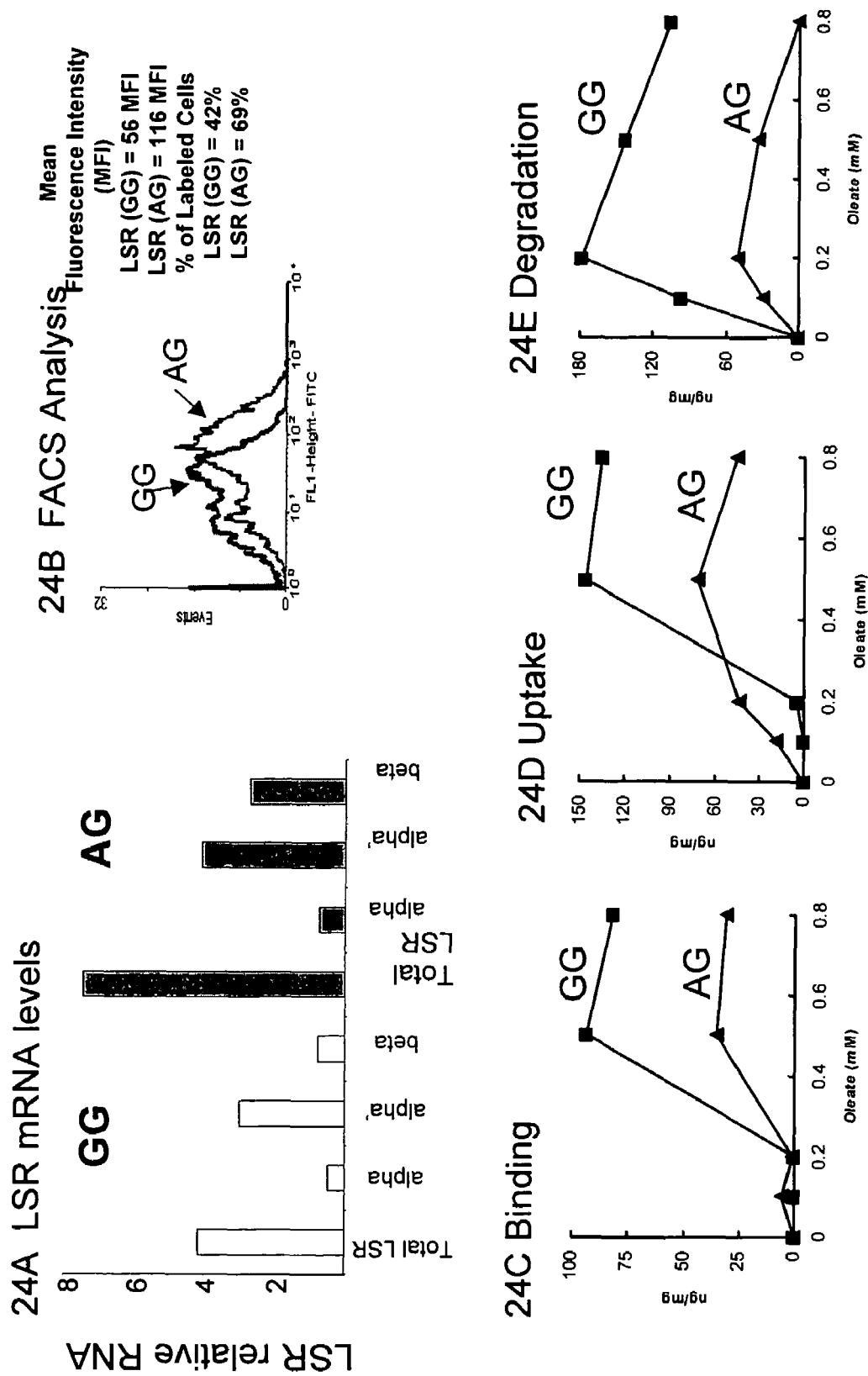
FIGS. 24A, 24B, 24C, 24D, and 24E show the difference in LSR expression and activity in 2 cultured human hepatocyte cell lines.
Figure 26A:
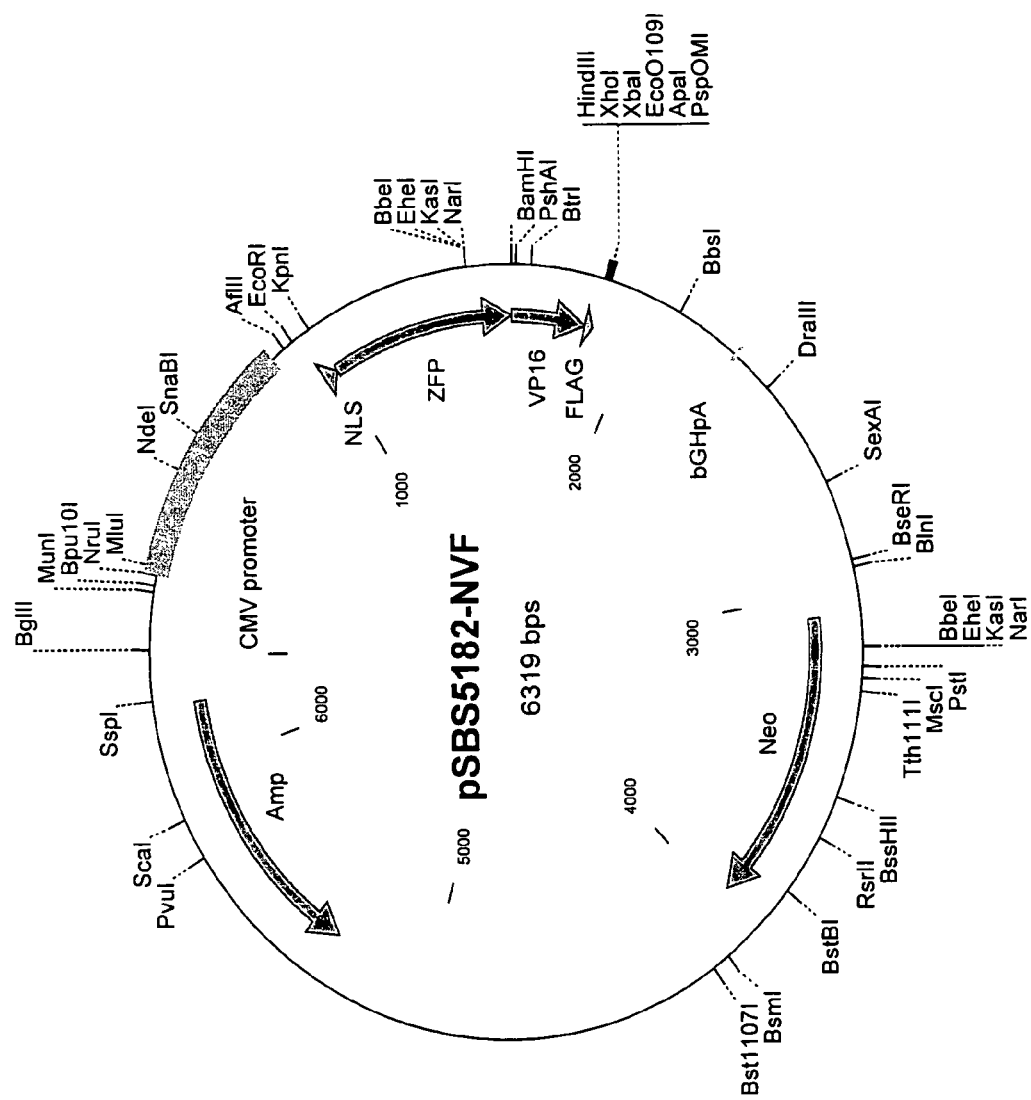
Figure 26B:
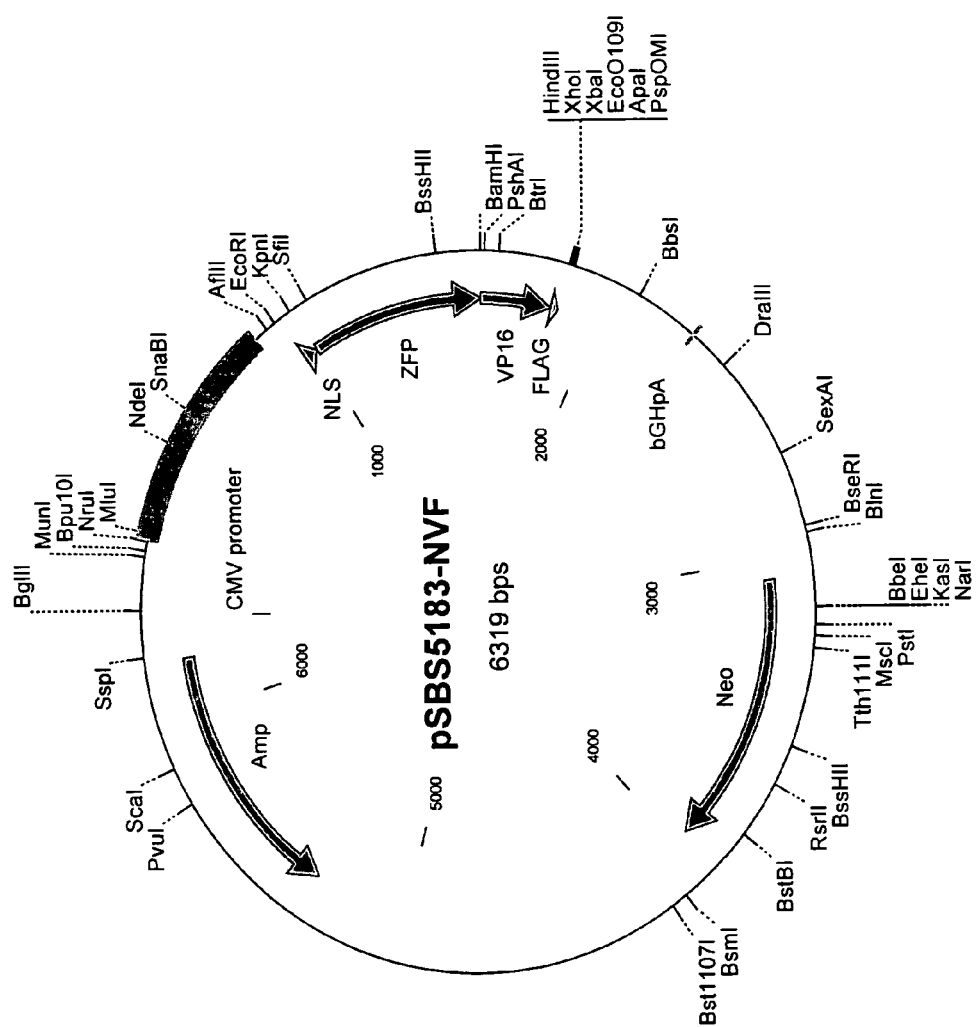
Figure 26C:
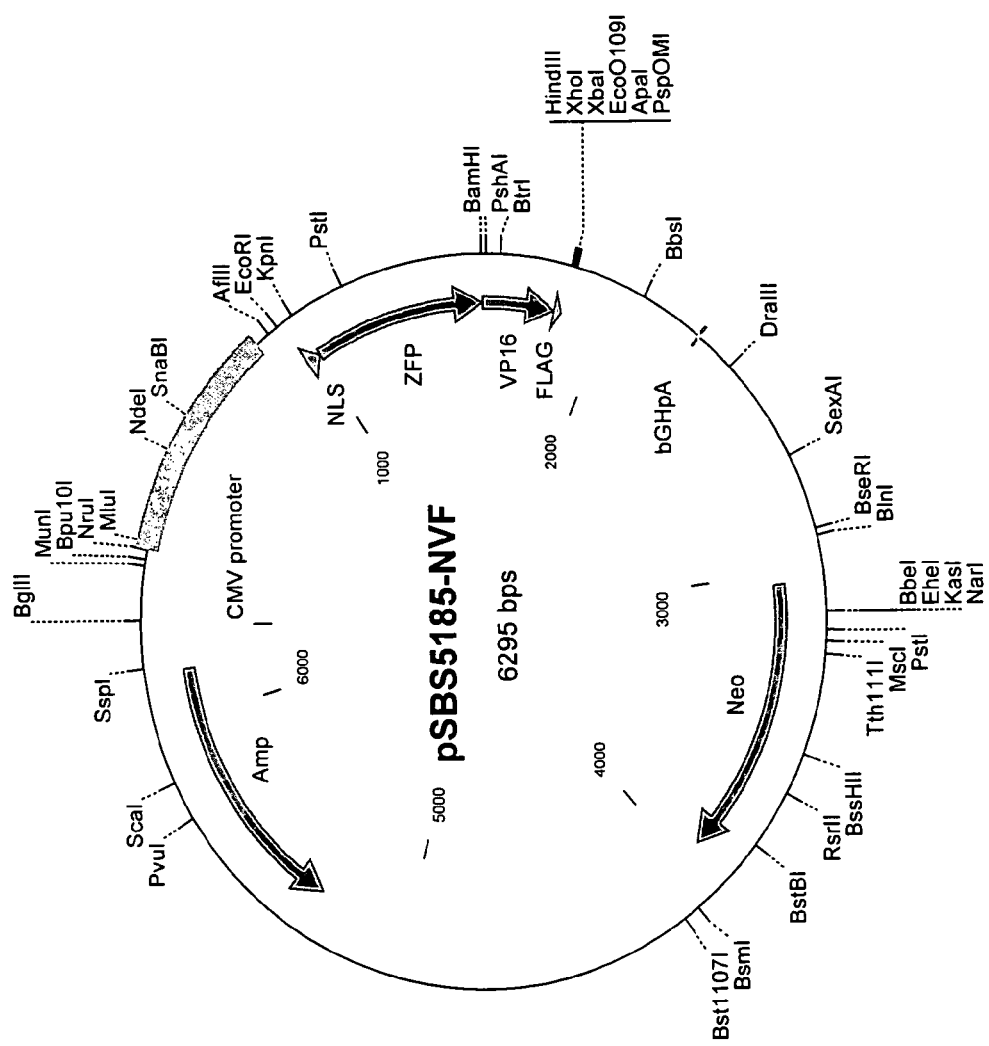
Figure 26D:
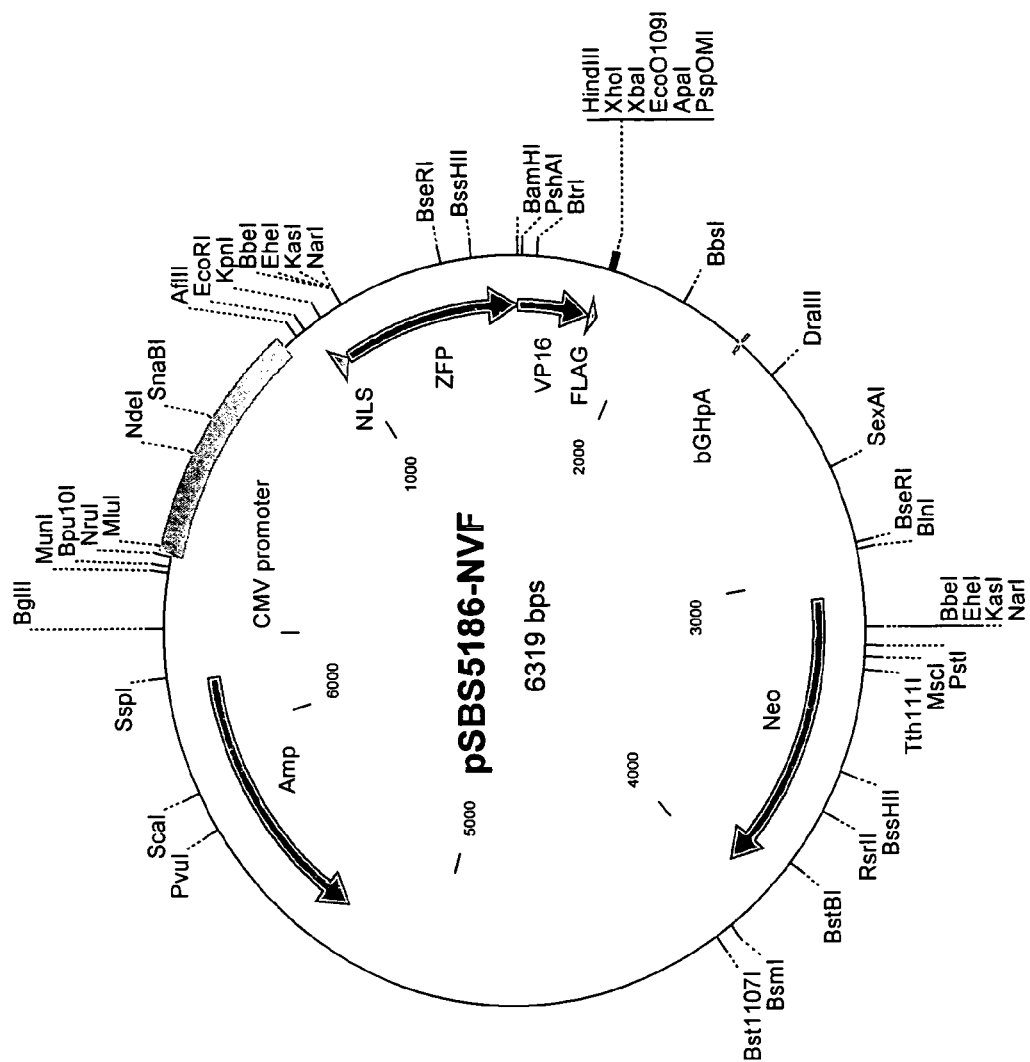
Figure 26E:
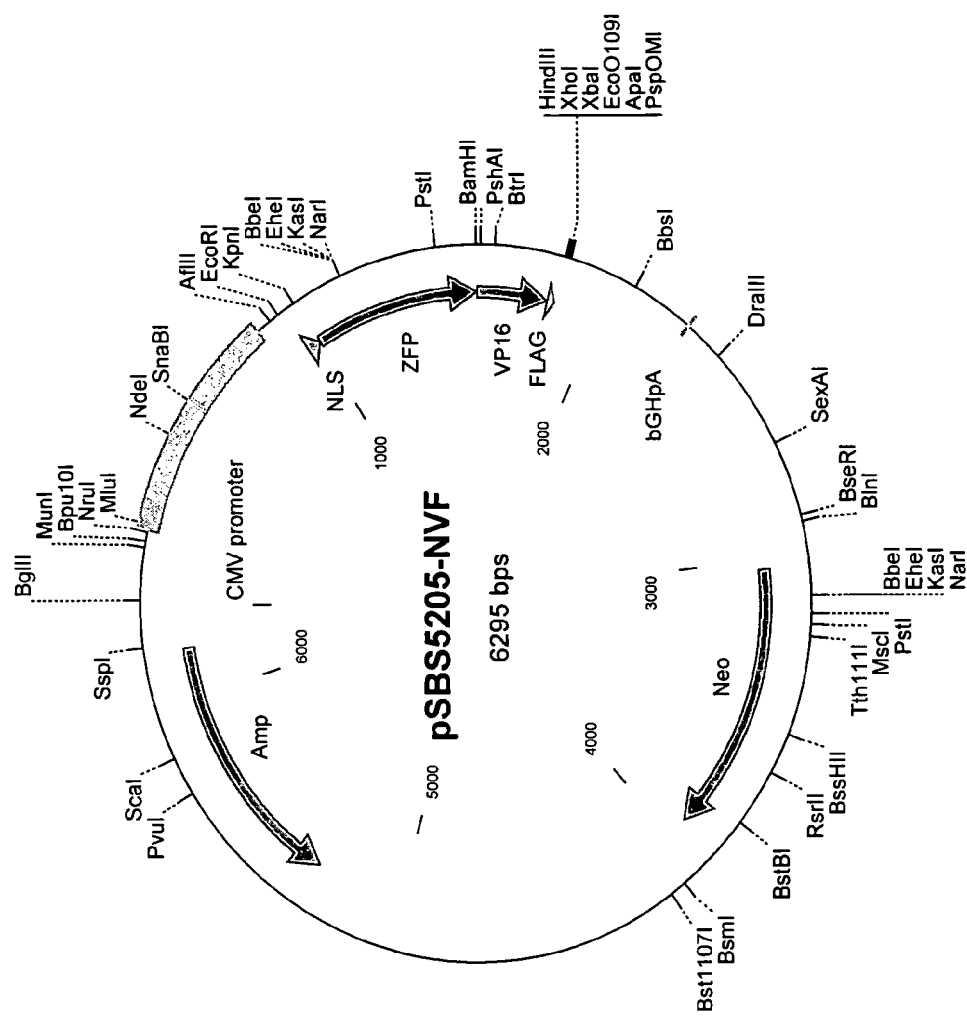

Results:

The PLC cell line displayed a much greater capacity to bind, internalize and degrade $^{125}$I-LDL in the presence of increasing concentrations of oleate, as compared to the HepG2 cell line (FIG. 24). This is most marked in the degradation. The decrease in degradation observed with >0.5 mM oleate concentrations is thought to be due to the accumulation of oleate as triglycerides in the cells. This increase in lipid in the cells decreases proteolytic degradation at the lysosomal level.

Quantitative PCR and facs data indicates that LSR expression is almost 50% higher in HepG2 cells than in PLC cells. This would be consistent with the notion of compensation for the lower activity of the receptor in the cells.

These in vitro data suggest that a person with a G/G genotype (hence Ser) would display a greater ability to clear triglycerides during the postprandial stage as compared to one with a G/A genotype. Since we have postulated a rate-limiting role of LSR in the removal of dietary lipid, these data could explain the significant association found between low postprandial triglyceride levels and G/G genotype. In contrast to G/G homozygotes, G/A heterozygotes with lower LSR activity would have a lesser capacity of removing dietary lipid, thus increasing their time in the circulation. This would in turn cause a change in the partitioning of lipid between the liver and the adipose tissue, leading to a greater deposition of fat in the adipose tissue.

This example indicates the potential use of this polymorphism, as a marker to detect people with a propensity towards obesity. It also supports the hypothesis that LSR is a potential pharmaceutical target for the development of compounds aimed at targeting lipids away from the adipose tissue and towards the liver.

Example 18

Leptin Transport Through the Blood Brain Barrier

Figure 31:
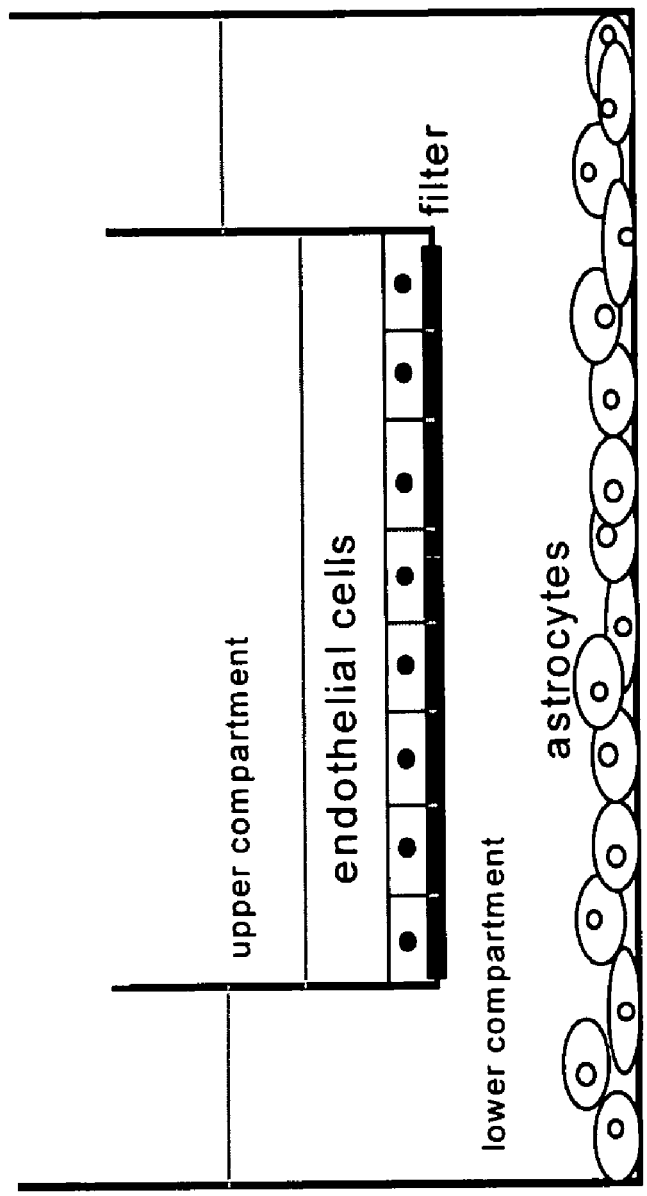
FIG. 31 shows a diagram of the coculture system. Endothelial cells are plated in the upper compartment on the filter and astrocytes in the lower compartment on the plastic of the Petri dish.

Human leptin transport through the blood-brain barrier (BBB) is studied using an in vitro model (Dehouck, et al J Neurochem 54:1798-801, 1990 hereby incorporated herein by reference in its entirety including any figures, tables, or drawings). This model closely mimics the in vivo situation with regard to the selective passage of nutrients and drugs through the cerebro-vascular endothelium. The presence of tight junctions that prevent non-specific diffusion, the expression of specific receptors such as LDL receptor and transferrin receptor, and the expression of P-glycoprotein in brain capillary endothelial cells in vitro demonstrates that this model is a useful system to study the selective transport through the BBB. Briefly, this model consists of a co-culture of bovine brain capillary endothelial cells (ECs) and rat astrocytes (FIG. 31). The astrocytes are seeded on the plastic of a six-well dish and grown for 3 weeks. A collagen-coated filter is then set in each dish and bovine ECs are plated on the upper-side of the filter. ECs form a confluent monolayer in 5 days and they are used for experiments after 16 days of coculture with astrocytes.

Methods

Leptin transcytosis: Experiments were performed on brain capillary endothelial cells in coculture with astrocytes for 16 days. On the day of the experiment, ECs were transferred to a clean 6-well plate containing 2 mL of Ringer-Hepes buffer (see, FIG. 32). At time 0, 1 mL Ringer Hepes containing $^{125}$I-leptin was placed in the upper compartment. After 30, 60, 120, or 180 min incubation at 37° C. on a rocking platform, the insert was transferred into another well of a six-well plate to minimize the possible passage of substances from the lower to the upper compartment. At the end of the experiment, the amount of radioactivity of each well was counted. The transcytosis was performed over 3 h with 1) 10 ng/mL $^{125}$I-leptin (10,000 dpm/ng), 2) 10 ng/mL $^{125}$I-leptin+1 µg/mL of cold leptin, 3) 10 ng/mL $^{125}$I-leptin+50 µg/mL peptides or 4) 10 ng/mL $^{125}$I-leptin+2 mg/mL lactoferrin. The synthetic peptides studied include the human (HP) and mouse (MP) leptin peptide fragments:
CHLPWASGLETLDSLGGVLEAS (SEQ ID NO:57) and CSLPQTSGLQKPESLDGVLEAS (SEQ ID NO:67), respectively.

Sucrose and inulin permeability studies: The [$^{14}$C]-sucrose (342 Da) and [$^3$H]-inulin (57000 Da) are hydrosoluble molecules which pass through the BBB through non-receptor mediated processes. The transport is nonspecific and primarily through tight junctions. These serve as markers for the integrity of the BBB and hence toxicity of the added compounds on the cerebral endothelium.

Figure 32:
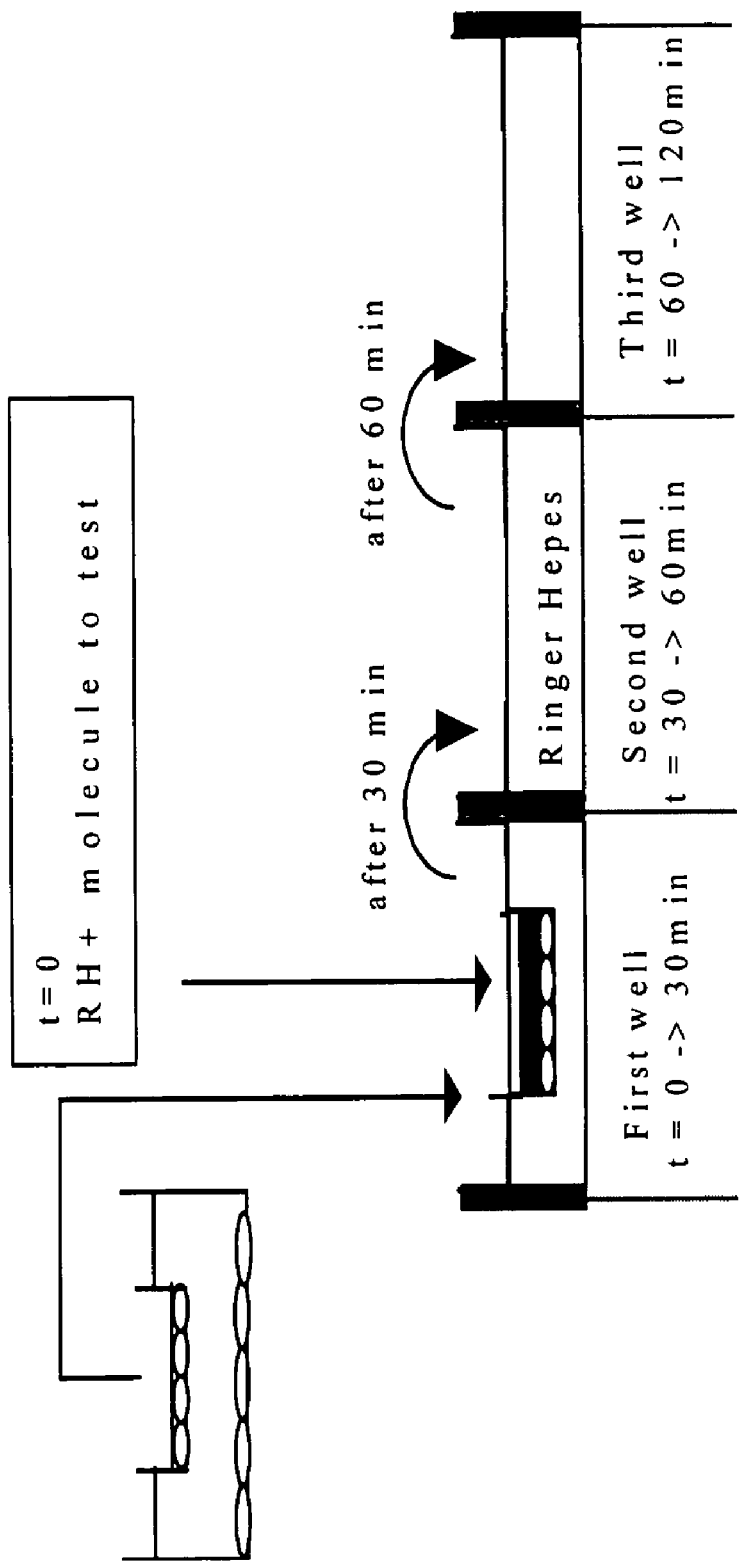
FIG. 32 shows a diagram of transcytosis and permeability studies.

After 16 days of coculture, permeability studies were performed as described in FIG. 32. On the day of the experiment, ECs were transferred to a new 6-well plate containing 2 mL of Ringer-Hepes. At time 0, 1 mL Ringer Hepes containing [$^{14}$C]-sucrose, [$^3$H]-inulin and cold leptin were placed in the upper compartment. Sucrose and inulin permeability studies were performed in the presence of 10 ng/mL leptin, 5 µg/mL leptin, 10 µg/mL leptin or without leptin as a control. The effect of peptides was also tested by the addition of 10 ng/mL leptin+50 µg/mL mouse peptide (MP), 10 ng/mL leptin+50 µg/mL human peptide (HP), or 10 ng/mL leptin+2 mg/mL lactoferrin (lacto). At the end of the experiment, an aliquot from each well was placed in a scintillation vial, and radioactivity was determined.

The transport of molecules through the endothelial monolayer was determined for each time point as % passage: % passage of radiolabelled molecule through the endothelium: dpm found in the lower compartment at a time point divided by the initial dpm found in the upper compartment: % transport at 30 min=(lower dpm t30/upper dpm)*100.

Results

Figure 33:
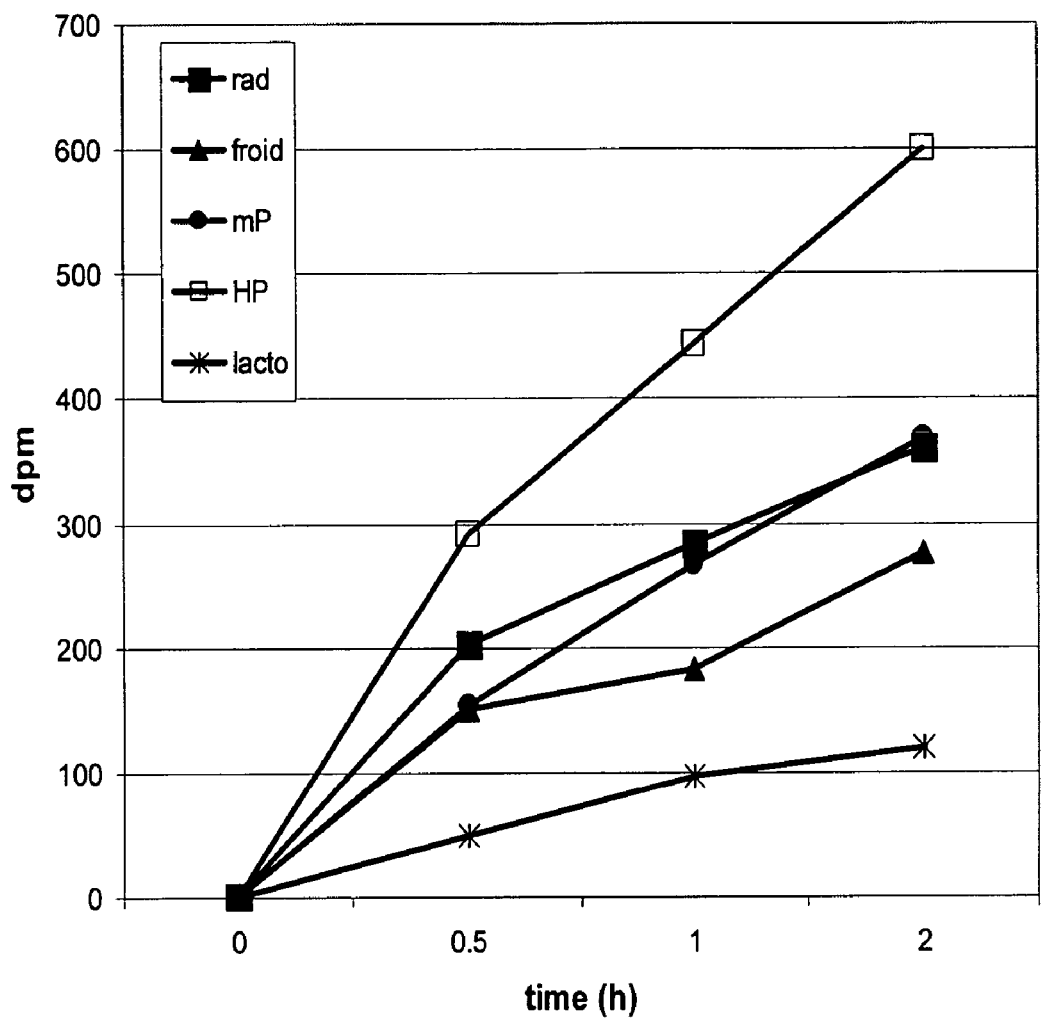
FIG. 33 shows a graph of leptin transcytosis in BBB in vitro model. Cells were incubated with $^{125}$I-leptin alone (10,000 dpm/ng) (closed squares), with 1 µg/mL unlabelled leptin (triangles), 50 µg/mL MP (circles), 50 µg/mL HP (open squares), or 2 mg/mL lactoferrin (asterisks).

FIG. 33 shows an increased transport of radiolabelled leptin over time through the endothelium monolayer after 16 days of coculture. The addition of unlabelled leptin reduced the amount of leptin by approximately 30%, indicating that there is a specific component involved in the transport of leptin across the EC monolayer. A higher concentration of unlabelled leptin is needed to decrease the effect of nonspecific processes. The specific component involved in leptin transport is associated with the complete differentiation and formation of the BBB.

Lactoferrin, an inhibitor of LSR, significantly inhibited the amount of leptin transported. The mouse leptin peptide fragment had no significant effect on leptin transport. However, the addition of human leptin peptide fragment caused a significant increase in the amount of leptin transcytosis. This same peptide fragment increases LSR activity in human hepatocytes.

Figure 34:
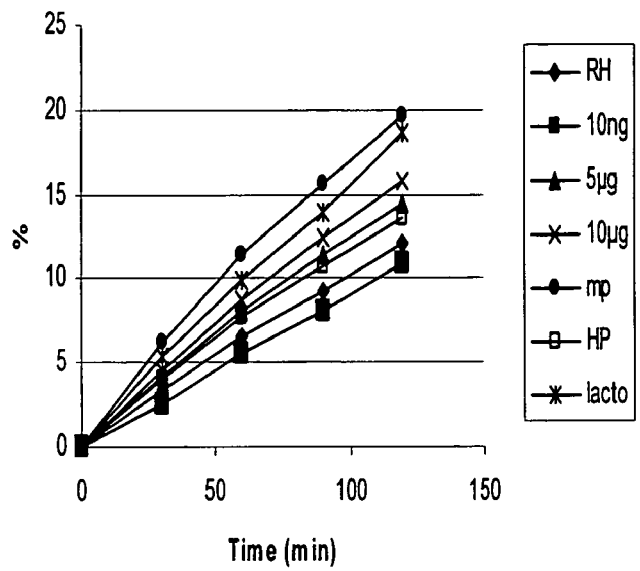
FIGS. 34A and 34B show graphs of the effect of leptin, MP, HP, and lactoferrin on the permeability of the EC monolayer. Sucrose (34A) and inulin (34B) permeability studies were performed in the absence (diamonds) or presence of 10 ng/mL leptin (squares), 5 µg/mL leptin (triangles), 10 µg/mL leptin (crosses). The effect of peptides were also tested by the addition of 10 ng/mL leptin+50 µg/mL mouse peptide (MP, circles) or 10 ng/mL leptin+50 µg/mL human peptide (HP, open squares) or 10 ng/mL leptin+2 mg/mL lactoferrin (lacto, asterisks).
Figure 34:
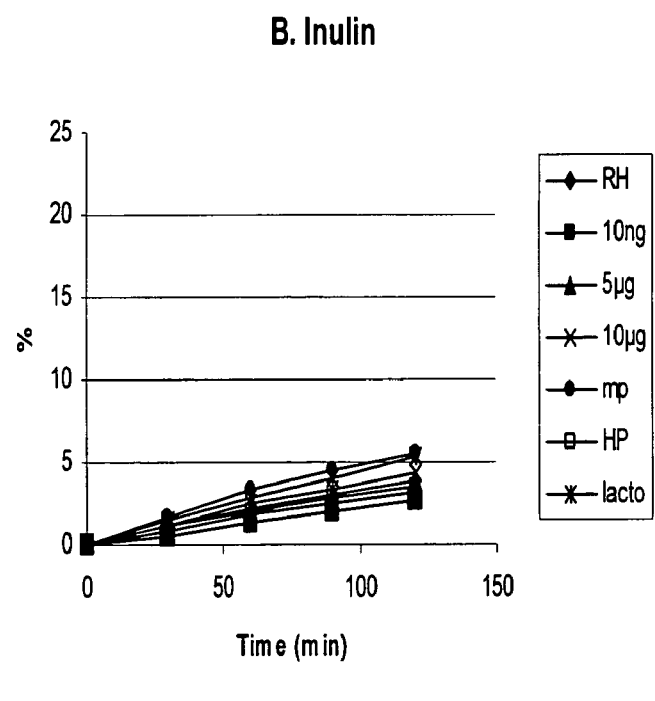

The integrity of the BBB was tested using sucrose and inulin (FIGS. 34A and 34B). It is clear that the integrity of the BBB was not significantly compromised by the addition of leptin, the peptides, or lactoferrin. Hence, we can conclude that the trancytosis measured in FIG. 33 represents active processes, and is not due to disintegration of the EC monolayer.

Thus the invention is drawn to inhibitors and activators of LSR as a means for controlling the transport of leptin across the blood brain barrier. Agents directed towards activation or inhibition of brain LSR regulate leptin transport into the CNS where it acts as satiety factor.

While preferred embodiments of the invention has been illustrated and described, it will be appreciated that various changes can be made by one skilled in the art without departing from the spirit and scope of the invention.

Example 19

Effect Long-term Exposure to High Levels of Leptin on LSR Activity

Figure 35:
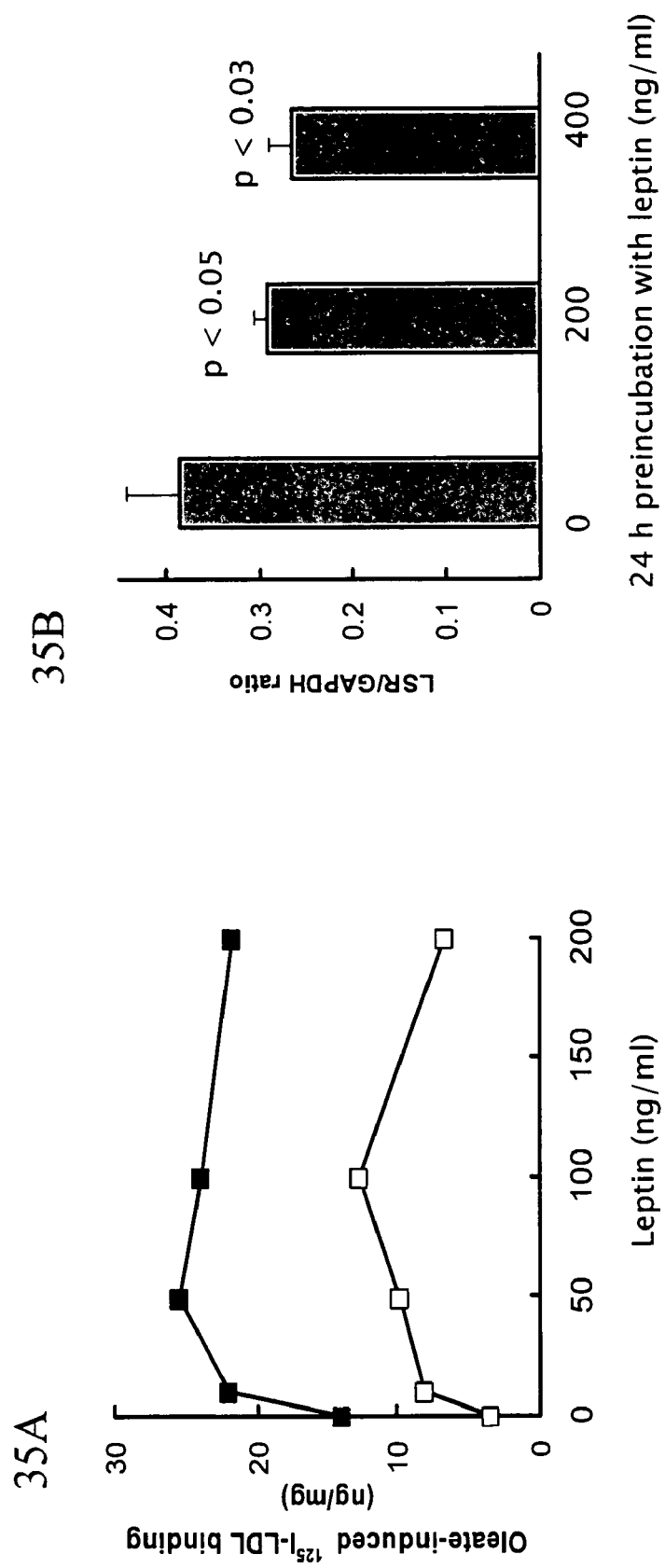
FIGS. 35A and 35B show graphs of LSR activity and mRNA expression measured in PLC cells preincubated 24 h with leptin.

Human liver cells preincubated with 200 ng/mL human recombinant leptin for 24 h had a markedly reduced LSR activity (FIG. 35A, □), as compared to those not preincubated with leptin (FIG. 35A, ■). Leptin retained its ability to acutely increase oleate-induced $^{125}$I-LDL binding to LSR in a subsequent short incubation (FIG. 35A, □). However, the maximal stimulatory effect was reduced by about 50%, and was achieved only with higher leptin concentrations (100 ng/mL). In hepatocytes preincubated for 24 h with high doses of leptin (200-400 ng/mL), a 25-35% decrease of hepatocyte LSR mRNA relative to GAPDH was observed, as compared to control cells (FIG. 35B).

Although not wishing to be limited by any particular theory, these data suggest that the consistently elevated leptin levels in db/db mice cause a decrease in LSR expression, as well as cause a reduction in leptin's ability to acutely stimulate the receptor. This, and the fact that plasma leptin did not increase in db$^{Pas}$/db$^{Pas}$ after the test meal could explain the massively-elevated postprandial lipemic response observed in this strain. However, because leptin signaling to LSR proceeds independent of the Ob-R, acute increase in plasma leptin concentrations obtained with injection of 500-50,000 ng of leptin in db/db mice could accelerate the removal of lipid by activating LSR.

Based on these observations, it is likely that 1) the reduced LSR activity, caused by the constantly high levels of circulating leptin, and 2) the lack of increase in plasma leptin levels during the postprandial stage, contribute to elevated postprandial plasma TG levels in db/db. It should be noted that the dose of leptin regulating postprandial lipemia in ob/ob is ~500 fold lower than those typically used to reduce food intake (2). In db/db mice, leptin doses 10 fold greater than those used in ob/ob mice were needed to achieve maximal regulation of postprandial lipemia. Thus, the regulation of postprandial lipemia in db/db mice appears partially leptin-resistant, despite the fact that leptin signaling effect occurs independently of the Ob-R.

REFERENCES

Aalto-Setala, K., Fisher, E. A., Chen, X., Chajek-Shaul, T., Hayek, T., Zechner, R., Walsh, A., Ramakrishnan, R., Ginsberg, H. N., and Breslow, J. L. (1992). J Clin Invest. 90, 1889-1900.

Alexeev and Yoon (Nature Biotech. 16 :1343-1346 (1998).

Beisiegel, U., Weber, W., Ihrke, G., Herz, J., and Stanley, K. K. (1989). Nature 341, 162-164.

Bihain, B. E., and Yen, F. T. (1992). Free fatty acids activate a high-affinity saturable pathway for degradation of low-density lipoproteins in fibroblasts from a subject homozygous for familial hypercholesterolemia. Biochemistry 31, 4628-4636.

Bihain, B. E., Deckelbaum, R. J., Yen, F. T., Gleeson, A. M., Carpentier, Y. A., Witte, L. D. (1989) J. Biol. Chem. 264, 17316-17321.

Bihain, B. E., and Yen, F. T. (1998). Curr. Opin. Lipidol. 9, 221-224. Bilheimer, D. W., Eisenberg, S., and Levy, R. I. (1972). Biochim. Biophys. Acta 260, 212-221.

Bilheimer, D. W., Eisenberg, S., and Levy, R. I. (1972). The metabolism of very low density lipoprotein proteins. I. Preliminary in vitro and in vivo observations. Biochim. Biophys. Acta 260, 212-221.

Breslow, J. L. (1985). Adv Exp Med Biol 183,121-124.

Brown, M. S. and Goldstein, J. L. (1986). Science 232, 34-47.

Bruce, C., Chouinard, R. A. Jr., and Tall, A. R. (1998). Annu. Rev. Nutr. 18,297-330.

Campfield, L. A., Smith, F. J., Guisez, Y., Devos, R. and Burn, P. (1995). Science 269, 546-549.

Chai H. et al. (1993), *Biotechnol. Appl. Biochem.* 18:259-273.

Charron, M. J., Katz, E. B., and Olson, A. L. (1999). J. Biol. Chem. 274, 3253-3256.

Chen et al., 1987, Mol. Cell. Biol., 7: 2745-2752.

Cherif, D., Julier, C., Delattre, O., Derré, J., Lathrop, G. M., and Berger, R. (1990). Proc. Natl. Acad. Sci. USA 87, 6639-6643.

Cole-Strauss et al. (Science 273:1386-1389 (1996).

Cooper, A. D. (1997). *J. Lipid Res.* 38, 2173-2192.

Costet, P., Legendre, C., More, J., Edgar, A., Galtier, P., and Pineau, T. (1998). J. Biol. Chem. 273, 29577-29585.

Dehouck, et al *J Neurochem* 54:1798-801, 1990.

Everhart, J. E., Lombardero, M., Lake, J. R., Wiesner, R. H., Zetterman, R. K., and Hoofnagle, J. H. (1998). Liver Transpl. Surg. 4,285-296.

Feeman, W. E., Jr. (1998) Ann. Intern. Med. 128, 73-74.

Friedman, J M (2000) Nature 404:632-634).

Friedman, J. M., and Halaas, J. L. (1998). Nature 395, 763-770.

Fuller S. A. et al. (1996) *Immunology in Current Protocols in Molecular Biology*, Ausubel et al., Eds, John Wiley & Sons, Inc., USA Ghosh and Bacchawat, 1991, *Targeting of liposomes to hepatocytes,* IN: *Liver Diseases, Targeted diagnosis and therapy using specific receptors and ligands*. Wu et al. Eds., Marcel Dekeker, New York, pp. 87-104.

Ginsberg, H. N., Le, N. A., Goldberg, I. J., Gibson, J. C., Rubinstein, A., Wang-Iverson, P., Norum, R., and Brown, W. V. (1986). J. Clin. Invest. 78, 1287-1295.

Goldberg, I. J. (1996). J. Lipid Res. 37, 693-707.

Goldstein, J. L., Basu, S. K., Brown, M. S. (1983). 98, 241-260.

Goldstein, J. L., Hobbs, H. H., and Brown, M. S. (1995). In The Metabolic and Molecular Basis of Inherited Disease, vol. II, Scriver, C. R., Beaudet, A. L., Sly, W. S., and Valle, D., eds. (New York, N.Y.: McGraw-Hill, Inc), pp. 1981-2030.

Gopal, 1985, Mol. Cell. Biol., 5: 1188-1190

Graham et al. (1973), *Virology.* 52:456-457.

Guven, S., El-Bershawi, A., Sonnenberg, G. E., Wilson, C. R., Hoffmann, R. G., Krakower, G. R., and Kissebah, A. H. (1999). Diabetes 48, 347-352.

Halaas, J. L., Gajiwala, K. S., Maffei, M., Cohen, S. L., Chait, B. T., Rabinowitz, D., Lallone, R. L., Burley, S. K., and Friedman, J. M 1995. Science 269, 543-546.

Halaas J L, Boozer C, Blair-West J, Fidahusein N, Denton D A, Friedman J M; Physiological response to long-term peripheral and central leptin infusion in lean and obese mice. Proc. Natl. Acad. Sci. USA, 94, 8878-8883, 1997

Halaas J L, et al., Proc. Natl. Acad. Sci. USA, 94, 8878-8883, 1997.

Havel, P. J. (1998). Am. J. Clin. Nutr. 67, 355-356.

Havel, R. J., Eder, H. A. and Bragdon, J. H. (1955). J. Clin. Invest. 34, 1345-1353.

Havel, R., and Kane, J. P. (1995). In The Metabolic and Molecular Basis of Inherited Disease, vol. II, Scriver, C. R., Beaudet, A. L., Sly, W. S., and Valle, D., eds. (New York, N.Y.: McGraw-Hill, Inc), pp. 1841-1851.

Huygen et al. (1996) *Nature Medicine.* 2(8):893-898.

Huettinger, M., Retzek, H., Eder, M. and Goldenberg, H. (1988). Clin. Biochem. 21, 87-92.

Igel M, Becker W, Herberg L, Jost H G; Hyperleptinemia, Leptin Resistance, and Polymorphic Leptin Receptor in the New Zealand Obese Mouse. Endocrinology, 138, 4234-4239, 1997.

Ito, Y., Azrolan, N., O'Connell, A., Walsh, A., Breslow, J. L. (1990). Science 249, 790-793.

Iverius P. H., and Brunzell, J. D. (1985). Am. J. Physiol. 249, E107-E114

Johnson, C. P., Gallagher-Lepak, S., Zhu, Y. R., Porth, C., Kelber, S., Roza, A. M., and Adams, M. B. (1993). Transplantation 56,822-827.

Jang et al J. Virol. 62:2636-2643 (1988).

Jong, M. C., Hofker, M. H., and Havekes, L. M. (1999). Arterioscler. Thromb. Vasc. Biol. 19, 472-484.

Kandror, K. V., Stephens, J. M., and Pilch, P. F. (1995). J. Cell Biol. 129, 999-1006.

Karpe, F., de Faire, U., Mercuri, M., Bond, M. G., Hellenius, M. L., and Hamsten, A. (1998) Atherosclerosis 141, 307-314.

Kersten, S., Seydoux, J., Peters, J. M., Gonzalez, F. J., Desvergne, B., and Wahli, W. (1999). J. Clin. Invest. 103, 1489-1498.

Klein et al. (1987) *Nature.* 327:70-73.

Komaromy, M. C., Schotz, M. C. (1987). Proc. Natl. Acad. Sci. USA 84, 1526-1529.

Kopelman et al. (2000) Nature 404:635-643.

Lenhard T. et al. (1996), *Gene*. 169:187-190.

Levitt, R. C., Liu, Z., Nouri, N., Meyers, D. A., Brandriff, B., and Mohrenweiser, H. M. (1995). Cytogenet. Cell Genet. 69, 211-214.

Lewis, G. F., O'Meara, N. M., Soltys, P. A., Blackman, J. D., Iverius, P. H., Druetzler, A. F., Getz, G. S., and Polonsky, K. S. (1990) *J. Clin. Endocrinol. Metab.* 71, 1041-1050.

Li, C., Ioffe, E., Fidahusein, N., Connolly, E., and Friedman, J. M. (1998). J. Biol. Chem. 273, 10078-10082.

Liu Q, Segal D J, Ghiara J B, Barbas C F 3$^{rd}$ Design of polydactyl zinc-finger proteins for unique addressing within complex genomes. Proc Natl Acad Sci USA 1997 May 27; 94(11):5525-30.

Mann, C. J., Khallou, J., Chevreuil, O., Troussard, A. A., Guermani, L. M., Launay, K., Delplanque, B., Yen, F. T., and Bihain, B. E. (1995). Biochemistry 34, 10421-10431.

Mann, C. J., Troussard, A. A., Yen, F. T., Hannouche, N., Najib, J., Fruchart, J.-C., Lotteau, V., André, P., and Bihain, B. E. (1997). J. Biol. Chem. 272, 31348-31354.

Markwell, M. A. K., Haas, S. M., Rolbert, N. E. and Bieber, L. L. (1981). Methods Enzymol. 72,296-30

Massie B, Couture F, Lamoureux L, Mosser D D, Guilbault C, Jolicoeur P, Belanger F, Langelier Y Inducible overexpression of a toxic protein by an adenovirus vector with a tetracycline-regulatable expression cassette. J Virol 1998 March; 72(3):2289-96.

Pelleymounter, M. A., Cullen, M. J., Baker, M. B., Hecht, R., Winters, D., Boone, T., and Collins, F. (1995) *Science* 269, 540-543.

Pengue G. Calabro V, Bartoli P C, Pagliuca A, Lania L Repression of transcriptional activity at a distance by the evolutionarily conserved KRAB domain present in a subfamily of zinc finger proteins. Nucleic Acids Res 1994 Aug. 11; 22(15):2908-14.

Perusse, L., Chagnon, Y. C., Weisnagel, J., and Bouchard, C. (1999). Obes. Res. 7,111-29.

Picard, F., Richard, D., Huang, Q., and Deshaies, Y. (1998). Int. J. Obes. Relat. Metab. Disord. 22, 1088-1095.

Rohlmann, A., Gotthardt, M., Hammer, R. E., and Herz, J. (1998). J Clin Invest 101, 689-695.

Romana, S. P., Tachdjian, G., Druart, L., Cohen, D., Berger, R., and Cherif D. (1993). Eur. J. Hum. Genet. 1, 245-251.

Roth J. A. et al. (1996), *Nature Medicine*. 2(9):985-991.

Sambrook, J., Fritsch, E. F., and T. Maniatis. (1989), *Molecular Cloning: A Laboratory Manual*. 2ed. Cold Spring Harbor Laboratory, Cold Spring Harbor, N.Y.

Seip et al Acta Pediatr Supp. 413:2-28 (1996).

Shimabukuro, M., Koyama, K., Chen, G., Wang, M.-Y., Trieu, F., Lee, Y., Newgard, C. B., and Unger, R. H. (1997). Proc. Natl. Acad. Sci. USA 94, 4637-4641.

Shimomura et al. Genes Dev. 12:3182-3194 (1998)

Shimomura et al. Nature 401:73-76 (1999).

Silver, D. L., Jiang, X. C., and Tall, A. R. (1999). J. Biol. Chem. 274, 4140-4146.

Sinha, M. K., Opentanova, I., Ohannesian, J. P., Kolaczynski, J. W., Heiman, M. L., Hale, J., Becker, G. W., Bowsher, R. R., Stephens, T. W., and Caro, J. F. (1996). *J. Clin. Invest*. 98, 1277-1282.

Smith et al. (1983) *Mol. Cell. Biol.* 3:2156-2165.

Snyder et al. (Nature Medicine 5:64-69 (1999).

Strickland, D. K., Ashcom, J. D., Williams, S., Burgess, W. H., Migliorini, M., and Argraves, W. S. (1990). J. Biol. Chem. 265, 17401-17404.

Tacson et al. (1996) *Nature Medicine*. 2(8):888-892.

Tartaglia, L. A. (1997). J. Biol. Chem. 272, 6093-6096.

Teramoto et al. J. Virol. 72 :8904-8912 (1998)

Tur-Kaspa et al. (1986), *Mol. Cell. Biol.* 6:716-718.

Uotani, S., Bjørbæk, C., Tornøe, J., and Flier, J. S. (1999). Diabetes 48, 279-286.

Van Heek, M., Mullins, D. E., Wirth, M. A., Graziano, M. P., Fawzi, A. B., Compton, D. S., France, C. F., Hoos, L. M., Casale, R. L., Sybertz, E. J., Strader, C. D., and Davis, H. R., Jr. (1996). Horm. Metabl. Res. 28, 635-658.

Van Heek M, Compton D S, France C F, Tedesco R P, Fawzi A B, Graziano M P, Sybertz E J, Strader C D, Davis H R; Diet-induced obese mice develop peripheral, but not central, resistance to leptin. J. Clin. Invest., 99, 385-390, 1997.

Vansant, G., Mertens, A., and Muls, E. (1999) *Intl. J. Obesity* 23, 14-21.

Virkamäki, A., Ueki, K., and Kahn, C. R. (1999). J. Clin. Invest. 103, 931-943.

Vlasak R. et al. (1983), *Eur. J. Biochem.* 135:123-126.

Wang, D., and Sul, H. S. (1997). J. Biol. Chem. 272, 26367-26374.

Wang, J. L., Chinookoswong, N., Scully, S., Qi, M., and Shi, Z. Q. (1999). Endocrinology 140, 2117-21124.

Ware, C. F., Sanser, S., and Alison, E. (1998). In *The Cytokine Handbook*, Thomson, A., ed. (San Diego, Calif.: Academic Press), pp. 549-592.

Weigle, D. S., Duell, P. B., Connor, W. E., Steiner, R. A., Soules, M. R., and Kuijper, J. L. (1997). Clin. Endocrinol. Metab. 82,561-565.

Willnow, T. E., Sheng, Z., Ishibashi, S., and Herz, J. (1994). Science 264, 1471-1474.

Wong et al., 1980, Gene, 10 : 87-94.

Wu et al. Eds., Marcel Dekeker, New York, pp. 87-104.

Xiao et al. (J. Virology 72 :2224-2232 (1998).

Yen, F. T., Mann, C. J., Guermani, L. M., Hannouche, N. F., Hubert, N., Hornick, C. A., Bordeau, V. N., Agnani, G., and Bihain, B. E. (1994). Biochemistry 33, 1172-1180.

Yen F. T., Masson M., Clossais-Besnard N., Andre P., Grosset J. M., Bougueleret L., Dumas J. B., Guerassimenko, O., and Bihain B. E. (1999). J Biol Chem 274, 13390-13398.

Zhang, Y., Proenca, R., Maffei, M., Barone, M., Leopold, L., and Friedman, J. M. (1994). Nature 372, 425-432.

SEQUENCE LISTING

<160> NUMBER OF SEQ ID NOS: 106

<210> SEQ ID NO 1
<211> LENGTH: 23187
<212> TYPE: DNA
<213> ORGANISM: Homo sapiens
<220> FEATURE:

```
<221> NAME/KEY: exon
<222> LOCATION: 2001..2356
<223> OTHER INFORMATION: exon1
<220> FEATURE:
<221> NAME/KEY: exon
<222> LOCATION: 3540..3884
<223> OTHER INFORMATION: exon2
<220> FEATURE:
<221> NAME/KEY: exon
<222> LOCATION: 12163..12282
<223> OTHER INFORMATION: exon3
<220> FEATURE:
<221> NAME/KEY: exon
<222> LOCATION: 15144..15200
<223> OTHER INFORMATION: exon4
<220> FEATURE:
<221> NAME/KEY: exon
<222> LOCATION: 15765..15911
<223> OTHER INFORMATION: exon5
<220> FEATURE:
<221> NAME/KEY: exon
<222> LOCATION: 19579..19752
<223> OTHER INFORMATION: exon6
<220> FEATURE:
<221> NAME/KEY: exon
<222> LOCATION: 19899..19958
<223> OTHER INFORMATION: exon7
<220> FEATURE:
<221> NAME/KEY: exon
<222> LOCATION: 20056..20187
<223> OTHER INFORMATION: exon8
<220> FEATURE:
<221> NAME/KEY: exon
<222> LOCATION: 20329..20957
<223> OTHER INFORMATION: exon9
<220> FEATURE:
<221> NAME/KEY: exon
<222> LOCATION: 21047..21187
<223> OTHER INFORMATION: exon10
<220> FEATURE:
<221> NAME/KEY: polyA_signal
<222> LOCATION: 21168..21173
<223> OTHER INFORMATION: AATAAA
<220> FEATURE:
<221> NAME/KEY: misc_feature
<222> LOCATION: 1..2000
<223> OTHER INFORMATION: potential 5'regulatory region
<220> FEATURE:
<221> NAME/KEY: misc_feature
<222> LOCATION: 22324..23187
<223> OTHER INFORMATION: homology with USF2 gene in ref: embl
      Y07661
<220> FEATURE:
<221> NAME/KEY: primer_bind
<222> LOCATION: 523..544
<223> OTHER INFORMATION: upstream amplification primer 17-2
<220> FEATURE:
<221> NAME/KEY: primer_bind
<222> LOCATION: 1047..1068
<223> OTHER INFORMATION: downstream amplification primer 17-2 ,
      complement
<220> FEATURE:
<221> NAME/KEY: primer_bind
<222> LOCATION: 946..963
<223> OTHER INFORMATION: upstream amplification primer 99-4576
<220> FEATURE:
<221> NAME/KEY: primer_bind
<222> LOCATION: 1385..1402
<223> OTHER INFORMATION: downstream amplification primer 99-4576 ,
      complement
<220> FEATURE:
<221> NAME/KEY: primer_bind
<222> LOCATION: 1096..1115
<223> OTHER INFORMATION: upstream amplification primer 9-19
<220> FEATURE:
<221> NAME/KEY: primer_bind
<222> LOCATION: 1616..1635
<223> OTHER INFORMATION: downstream amplification primer 9-19 ,
      complement
```

```
<220> FEATURE:
<221> NAME/KEY: primer_bind
<222> LOCATION: 1602..1621
<223> OTHER INFORMATION: upstream amplification primer 9-20
<220> FEATURE:
<221> NAME/KEY: primer_bind
<222> LOCATION: 2074..2093
<223> OTHER INFORMATION: downstream amplification primer 9-20 ,
      complement
<220> FEATURE:
<221> NAME/KEY: primer_bind
<222> LOCATION: 2036..2053
<223> OTHER INFORMATION: upstream amplification primer 99-4557
<220> FEATURE:
<221> NAME/KEY: primer_bind
<222> LOCATION: 2563..2580
<223> OTHER INFORMATION: downstream amplification primer 99-4557 ,
      complement
<220> FEATURE:
<221> NAME/KEY: primer_bind
<222> LOCATION: 2084..2102
<223> OTHER INFORMATION: upstream amplification primer 9-1
<220> FEATURE:
<221> NAME/KEY: primer_bind
<222> LOCATION: 2483..2500
<223> OTHER INFORMATION: downstream amplification primer 9-1 ,
      complement
<220> FEATURE:
<221> NAME/KEY: primer_bind
<222> LOCATION: 2470..2489
<223> OTHER INFORMATION: upstream amplification primer 9-21 ,
      complement
<220> FEATURE:
<221> NAME/KEY: primer_bind
<222> LOCATION: 2062..2081
<223> OTHER INFORMATION: downstream amplification primer 9-21
<220> FEATURE:
<221> NAME/KEY: primer_bind
<222> LOCATION: 3455..3474
<223> OTHER INFORMATION: upstream amplification primer 9-3
<220> FEATURE:
<221> NAME/KEY: primer_bind
<222> LOCATION: 3882..3901
<223> OTHER INFORMATION: downstream amplification primer 9-3 ,
      complement
<220> FEATURE:
<221> NAME/KEY: primer_bind
<222> LOCATION: 3775..3792
<223> OTHER INFORMATION: upstream amplification primer 99-4558
<220> FEATURE:
<221> NAME/KEY: primer_bind
<222> LOCATION: 4336..4356
<223> OTHER INFORMATION: downstream amplification primer 99-4558 ,
      complement
<220> FEATURE:
<221> NAME/KEY: primer_bind
<222> LOCATION: 4902..4920
<223> OTHER INFORMATION: upstream amplification primer 99-14419 ,
      complement
<220> FEATURE:
<221> NAME/KEY: primer_bind
<222> LOCATION: 4444..4463
<223> OTHER INFORMATION: downstream amplification primer 99-14419
<220> FEATURE:
<221> NAME/KEY: primer_bind
<222> LOCATION: 6638..6655
<223> OTHER INFORMATION: upstream amplification primer 99-4577
<220> FEATURE:
<221> NAME/KEY: primer_bind
<222> LOCATION: 7072..7089
<223> OTHER INFORMATION: downstream amplification primer 99-4577 ,
      complement
<220> FEATURE:
<221> NAME/KEY: primer_bind
<222> LOCATION: 7995..8012
<223> OTHER INFORMATION: upstream amplification primer 99-4559
<220> FEATURE:
<221> NAME/KEY: primer_bind
<222> LOCATION: 8576..8593
```

```
<223> OTHER INFORMATION: downstream amplification primer 99-4559 ,
      complement
<220> FEATURE:
<221> NAME/KEY: primer_bind
<222> LOCATION: 9622..9639
<223> OTHER INFORMATION: upstream amplification primer 99-3148
<220> FEATURE:
<221> NAME/KEY: primer_bind
<222> LOCATION: 10023..10040
<223> OTHER INFORMATION: downstream amplification primer 99-3148 ,
      complement
<220> FEATURE:
<221> NAME/KEY: primer_bind
<222> LOCATION: 9964..9981
<223> OTHER INFORMATION: upstream amplification primer 99-4560
<220> FEATURE:
<221> NAME/KEY: primer_bind
<222> LOCATION: 10546..10563
<223> OTHER INFORMATION: downstream amplification primer 99-4560 ,
      complement
<220> FEATURE:
<221> NAME/KEY: primer_bind
<222> LOCATION: 10996..11015
<223> OTHER INFORMATION: upstream amplification primer 99-14411 ,
      complement
<220> FEATURE:
<221> NAME/KEY: primer_bind
<222> LOCATION: 10492..10512
<223> OTHER INFORMATION: downstream amplification primer 99-14411
<220> FEATURE:
<221> NAME/KEY: primer_bind
<222> LOCATION: 11972..11990
<223> OTHER INFORMATION: upstream amplification primer 99-4561
<220> FEATURE:
<221> NAME/KEY: primer_bind
<222> LOCATION: 12481..12501
<223> OTHER INFORMATION: downstream amplification primer 99-4561 ,
      complement
<220> FEATURE:
<221> NAME/KEY: primer_bind
<222> LOCATION: 12005..12023
<223> OTHER INFORMATION: upstream amplification primer 9-4
<220> FEATURE:
<221> NAME/KEY: primer_bind
<222> LOCATION: 12417..12436
<223> OTHER INFORMATION: downstream amplification primer 9-4 ,complement
<220> FEATURE:
<221> NAME/KEY: primer_bind
<222> LOCATION: 14102..14119
<223> OTHER INFORMATION: upstream amplification primer 99-4562
<220> FEATURE:
<221> NAME/KEY: primer_bind
<222> LOCATION: 14543..14563
<223> OTHER INFORMATION: downstream amplification primer 99-4562 ,
      complement
<220> FEATURE:
<221> NAME/KEY: primer_bind
<222> LOCATION: 14431..14448
<223> OTHER INFORMATION: upstream amplification primer 99-3149
<220> FEATURE:
<221> NAME/KEY: primer_bind
<222> LOCATION: 14848..14865
<223> OTHER INFORMATION: downstream amplification primer 99-3149 ,
      complement
<220> FEATURE:
<221> NAME/KEY: primer_bind
<222> LOCATION: 14748..14767
<223> OTHER INFORMATION: upstream amplification primer 9-22
<220> FEATURE:
<221> NAME/KEY: primer_bind
<222> LOCATION: 15198..15218
<223> OTHER INFORMATION: downstream amplification primer 9-22 ,
      complement
<220> FEATURE:
<221> NAME/KEY: primer_bind
<222> LOCATION: 14748..14767
<223> OTHER INFORMATION: upstream amplification primer 9-24
<220> FEATURE:
<221> NAME/KEY: primer_bind
```

```
<222> LOCATION: 15333..15351
<223> OTHER INFORMATION: downstream amplification primer 9-24 ,
      complement
<220> FEATURE:
<221> NAME/KEY: primer_bind
<222> LOCATION: 15002..15019
<223> OTHER INFORMATION: upstream amplification primer 9-5
<220> FEATURE:
<221> NAME/KEY: primer_bind
<222> LOCATION: 15333..15351
<223> OTHER INFORMATION: downstream amplification primer 9-5 ,
      complement
<220> FEATURE:
<221> NAME/KEY: primer_bind
<222> LOCATION: 15640..15657
<223> OTHER INFORMATION: upstream amplification primer 9-6
<220> FEATURE:
<221> NAME/KEY: primer_bind
<222> LOCATION: 16072..16089
<223> OTHER INFORMATION: downstream amplification primer 9-6 ,
      complement
<220> FEATURE:
<221> NAME/KEY: primer_bind
<222> LOCATION: 15800..15817
<223> OTHER INFORMATION: upstream amplification primer 99-4563
<220> FEATURE:
<221> NAME/KEY: primer_bind
<222> LOCATION: 16179..16199
<223> OTHER INFORMATION: downstream amplification primer 99-4563 ,
      complement
<220> FEATURE:
<221> NAME/KEY: primer_bind
<222> LOCATION: 19295..19312
<223> OTHER INFORMATION: upstream amplification primer 99-3150
<220> FEATURE:
<221> NAME/KEY: primer_bind
<222> LOCATION: 19729..19746
<223> OTHER INFORMATION: downstream amplification primer 99-3150 ,
      complement
<220> FEATURE:
<221> NAME/KEY: primer_bind
<222> LOCATION: 19420..19438
<223> OTHER INFORMATION: upstream amplification primer 9-7
<220> FEATURE:
<221> NAME/KEY: primer_bind
<222> LOCATION: 19824..19841
<223> OTHER INFORMATION: downstream amplification primer 9-7 ,
      complement
<220> FEATURE:
<221> NAME/KEY: primer_bind
<222> LOCATION: 19798..19815
<223> OTHER INFORMATION: upstream amplification primer 9-8
<220> FEATURE:
<221> NAME/KEY: primer_bind
<222> LOCATION: 20137..20155
<223> OTHER INFORMATION: downstream amplification primer 9-8 ,
      complement
<220> FEATURE:
<221> NAME/KEY: primer_bind
<222> LOCATION: 19913..19931
<223> OTHER INFORMATION: upstream amplification primer 9-9
<220> FEATURE:
<221> NAME/KEY: primer_bind
<222> LOCATION: 20329..20346
<223> OTHER INFORMATION: downstream amplification primer 9-9 ,
      complement
<220> FEATURE:
<221> NAME/KEY: primer_bind
<222> LOCATION: 20139..20157
<223> OTHER INFORMATION: upstream amplification primer 99-4564
<220> FEATURE:
<221> NAME/KEY: primer_bind
<222> LOCATION: 20582..20599
<223> OTHER INFORMATION: downstream amplification primer 99-4564 ,
      complement
<220> FEATURE:
<221> NAME/KEY: primer_bind
<222> LOCATION: 20238..20256
<223> OTHER INFORMATION: upstream amplification primer 9-10
```

-continued

```
<220> FEATURE:
<221> NAME/KEY: primer_bind
<222> LOCATION: 20645..20662
<223> OTHER INFORMATION: downstream amplification primer 9-10 ,
      complement
<220> FEATURE:
<221> NAME/KEY: primer_bind
<222> LOCATION: 20410..20424
<223> OTHER INFORMATION: upstream amplification primer 9-26
<220> FEATURE:
<221> NAME/KEY: primer_bind
<222> LOCATION: 20690..20706
<223> OTHER INFORMATION: downstream amplification primer 9-26 ,
      complement
<220> FEATURE:
<221> NAME/KEY: primer_bind
<222> LOCATION: 20569..20588
<223> OTHER INFORMATION: upstream amplification primer 9-23
<220> FEATURE:
<221> NAME/KEY: primer_bind
<222> LOCATION: 21243..21262
<223> OTHER INFORMATION: downstream amplification primer 9-23 ,
      complement
<220> FEATURE:
<221> NAME/KEY: primer_bind
<222> LOCATION: 20583..20604
<223> OTHER INFORMATION: upstream amplification primer 9-11
<220> FEATURE:
<221> NAME/KEY: primer_bind
<222> LOCATION: 21015..21034
<223> OTHER INFORMATION: downstream amplification primer 9-11 ,
      complement
<220> FEATURE:
<221> NAME/KEY: primer_bind
<222> LOCATION: 20584..20601
<223> OTHER INFORMATION: upstream amplification primer 99-15285 ,
      complement
<220> FEATURE:
<221> NAME/KEY: primer_bind
<222> LOCATION: 20139..20158
<223> OTHER INFORMATION: downstream amplification primer 99-15285
<220> FEATURE:
<221> NAME/KEY: primer_bind
<222> LOCATION: 20642..20659
<223> OTHER INFORMATION: upstream amplification primer 99-15287 ,
      complement
<220> FEATURE:
<221> NAME/KEY: primer_bind
<222> LOCATION: 20207..20227
<223> OTHER INFORMATION: downstream amplification primer 99-15287
<220> FEATURE:
<221> NAME/KEY: primer_bind
<222> LOCATION: 20691..20709
<223> OTHER INFORMATION: upstream amplification primer 99-15286 ,
      complement
<220> FEATURE:
<221> NAME/KEY: primer_bind
<222> LOCATION: 20238..20257
<223> OTHER INFORMATION: downstream amplification primer 99-15286
<220> FEATURE:
<221> NAME/KEY: primer_bind
<222> LOCATION: 20943..20960
<223> OTHER INFORMATION: upstream amplification primer 9-2
<220> FEATURE:
<221> NAME/KEY: primer_bind
<222> LOCATION: 21295..21312
<223> OTHER INFORMATION: downstream amplification primer 9-2 ,complement
<220> FEATURE:
<221> NAME/KEY: primer_bind
<222> LOCATION: 21013..21031
<223> OTHER INFORMATION: upstream amplification primer 99-15284 ,
      complement
<220> FEATURE:
<221> NAME/KEY: primer_bind
<222> LOCATION: 20582..20602
<223> OTHER INFORMATION: downstream amplification primer 99-15284
<220> FEATURE:
<221> NAME/KEY: primer_bind
<222> LOCATION: 21019..21038
```

-continued

```
<223> OTHER INFORMATION: upstream amplification primer 99-14407 ,
      complement
<220> FEATURE:
<221> NAME/KEY: primer_bind
<222> LOCATION: 20571..20589
<223> OTHER INFORMATION: downstream amplification primer 99-14407
<220> FEATURE:
<221> NAME/KEY: primer_bind
<222> LOCATION: 21079..21097
<223> OTHER INFORMATION: upstream amplification primer 99-15283 ,
      complement
<220> FEATURE:
<221> NAME/KEY: primer_bind
<222> LOCATION: 20638..20655
<223> OTHER INFORMATION: downstream amplification primer 99-15283
<220> FEATURE:
<221> NAME/KEY: primer_bind
<222> LOCATION: 21013..21032
<223> OTHER INFORMATION: upstream amplification primer LSRi9f15s
<220> FEATURE:
<221> NAME/KEY: primer_bind
<222> LOCATION: 21195..21214
<223> OTHER INFORMATION: downstream amplification primer LSRi10r14s ,
      complement
<220> FEATURE:
<221> NAME/KEY: primer_bind
<222> LOCATION: 20354..20372
<223> OTHER INFORMATION: upstream amplification primer LSRx9f13s
<220> FEATURE:
<221> NAME/KEY: primer_bind
<222> LOCATION: 20570..20591
<223> OTHER INFORMATION: upstream amplification primer LSRx9f14s
<220> FEATURE:
<221> NAME/KEY: primer_bind
<222> LOCATION: 20811..20832
<223> OTHER INFORMATION: downstream amplification primer LSRx9r13s ,
      complement
<220> FEATURE:
<221> NAME/KEY: allele
<222> LOCATION: 818
<223> OTHER INFORMATION: 17-2-297 :  polymorphic  base  G  or  C
<220> FEATURE:
<221> NAME/KEY: allele
<222> LOCATION: 1243
<223> OTHER INFORMATION: 9-19-148 :  polymorphic  base  C  or  T
<220> FEATURE:
<221> NAME/KEY: allele
<222> LOCATION: 1374
<223> OTHER INFORMATION: 9-19-256 :  polymorphic  base  A  or  G
<220> FEATURE:
<221> NAME/KEY: allele
<222> LOCATION: 1401
<223> OTHER INFORMATION: 9-19-307 :  polymorphic  base  A  or  T
<220> FEATURE:
<221> NAME/KEY: allele
<222> LOCATION: 1535
<223> OTHER INFORMATION: 9-19-442 :  polymorphic  base  deletion  of  C
<220> FEATURE:
<221> NAME/KEY: allele
<222> LOCATION: 1788
<223> OTHER INFORMATION: 9-20-187 :  polymorphic  base  A  or  C
<220> FEATURE:
<221> NAME/KEY: allele
<222> LOCATION: 2391
<223> OTHER INFORMATION: 9-1-308 :  polymorphic  base  G  or  C
<220> FEATURE:
<221> NAME/KEY: allele
<222> LOCATION: 3778
<223> OTHER INFORMATION: 9-3-324 :  polymorphic  base  C  or  T
<220> FEATURE:
<221> NAME/KEY: allele
<222> LOCATION: 4498
<223> OTHER INFORMATION: 99-14419-424 :  polymorphic  base  T  or  G
<220> FEATURE:
<221> NAME/KEY: allele
<222> LOCATION: 15007
<223> OTHER INFORMATION: 9-24-260 :  polymorphic  base  A  or  G
<220> FEATURE:
<221> NAME/KEY: allele
```

```
<222> LOCATION: 15233
<223> OTHER INFORMATION: 9-24-486 : polymorphic base A or G
<220> FEATURE:
<221> NAME/KEY: allele
<222> LOCATION: 15826
<223> OTHER INFORMATION: 9-6-187 : polymorphic base C or T
<220> FEATURE:
<221> NAME/KEY: allele
<222> LOCATION: 19567
<223> OTHER INFORMATION: 9-7-148 : polymorphic base A or G
<220> FEATURE:
<221> NAME/KEY: allele
<222> LOCATION: 19744
<223> OTHER INFORMATION: 9-7-325 : polymorphic base A or G
<220> FEATURE:
<221> NAME/KEY: allele
<222> LOCATION: 19786
<223> OTHER INFORMATION: 9-7-367 : polymorphic base A or C
<220> FEATURE:
<221> NAME/KEY: allele
<222> LOCATION: 20158
<223> OTHER INFORMATION: 9-9-246 : polymorphic base G or C
<220> FEATURE:
<221> NAME/KEY: allele
<222> LOCATION: 20595
<223> OTHER INFORMATION: LSRX9-BM (17-1-240) : polymorphic base
      deletion of AGG
<220> FEATURE:
<221> NAME/KEY: allele
<222> LOCATION: 21108
<223> OTHER INFORMATION: LSRX10-BM : polymorphic base T or G
<220> FEATURE:
<221> NAME/KEY: allele
<222> LOCATION: 606
<223> OTHER INFORMATION: potential polymorphic base C or T
<220> FEATURE:
<221> NAME/KEY: allele
<222> LOCATION: 5141
<223> OTHER INFORMATION: potential polymorphic base insertion of G
<220> FEATURE:
<221> NAME/KEY: allele
<222> LOCATION: 7428
<223> OTHER INFORMATION: potential polymorphic base insertion of C
<220> FEATURE:
<221> NAME/KEY: allele
<222> LOCATION: 8394
<223> OTHER INFORMATION: potential polymorphic base C or G
<220> FEATURE:
<221> NAME/KEY: allele
<222> LOCATION: 8704
<223> OTHER INFORMATION: potential polymorphic base T or C
<220> FEATURE:
<221> NAME/KEY: allele
<222> LOCATION: 9028
<223> OTHER INFORMATION: potential polymorphic base G or A
<220> FEATURE:
<221> NAME/KEY: allele
<222> LOCATION: 9950
<223> OTHER INFORMATION: potential polymorphic base deletion of
      GAATGAAA
<220> FEATURE:
<221> NAME/KEY: allele
<222> LOCATION: 9977
<223> OTHER INFORMATION: potential polymorphic base T or C
<220> FEATURE:
<221> NAME/KEY: allele
<222> LOCATION: 10021
<223> OTHER INFORMATION: potential polymorphic base A or G
<220> FEATURE:
<221> NAME/KEY: allele
<222> LOCATION: 11878
<223> OTHER INFORMATION: potential polymorphic base C or T
<220> FEATURE:
<221> NAME/KEY: allele
<222> LOCATION: 19040
<223> OTHER INFORMATION: potential polymorphic base deletion of G
<220> FEATURE:
<221> NAME/KEY: allele
<222> LOCATION: 21363
```

```
<223> OTHER INFORMATION: potential polymorphic base A or G
<220> FEATURE:
<221> NAME/KEY: allele
<222> LOCATION: 21449
<223> OTHER INFORMATION: potential polymorphic base C or T
<220> FEATURE:
<221> NAME/KEY: allele
<222> LOCATION: 21451
<223> OTHER INFORMATION: potential polymorphic base G or C
<220> FEATURE:
<221> NAME/KEY: allele
<222> LOCATION: 21454
<223> OTHER INFORMATION: potential polymorphic base A or G
<220> FEATURE:
<221> NAME/KEY: allele
<222> LOCATION: 21455
<223> OTHER INFORMATION: potential polymorphic base G or A
<220> FEATURE:
<221> NAME/KEY: allele
<222> LOCATION: 21569
<223> OTHER INFORMATION: potential polymorphic base T or A
<220> FEATURE:
<221> NAME/KEY: allele
<222> LOCATION: 21683
<223> OTHER INFORMATION: potential polymorphic base deletion of C
<220> FEATURE:
<221> NAME/KEY: allele
<222> LOCATION: 21694
<223> OTHER INFORMATION: potential polymorphic base insertion of T
<220> FEATURE:
<221> NAME/KEY: allele
<222> LOCATION: 21728
<223> OTHER INFORMATION: potential polymorphic base deletion of G
<220> FEATURE:
<221> NAME/KEY: misc_binding
<222> LOCATION: 799..817
<223> OTHER INFORMATION: 17-2-297.mis1
<220> FEATURE:
<221> NAME/KEY: misc_binding
<222> LOCATION: 819..837
<223> OTHER INFORMATION: complement 17-2-297.mis2
<220> FEATURE:
<221> NAME/KEY: misc_binding
<222> LOCATION: 1224..1242
<223> OTHER INFORMATION: 9-19-148.mis1
<220> FEATURE:
<221> NAME/KEY: misc_binding
<222> LOCATION: 1244..1262
<223> OTHER INFORMATION: complement 9-19-148.mis2
<220> FEATURE:
<221> NAME/KEY: misc_binding
<222> LOCATION: 1330..1373
<223> OTHER INFORMATION: 9-19-256.mis1
<220> FEATURE:
<221> NAME/KEY: misc_binding
<222> LOCATION: 1375..1393
<223> OTHER INFORMATION: complement 9-19-256.mis2
<220> FEATURE:
<221> NAME/KEY: misc_binding
<222> LOCATION: 1382..1400
<223> OTHER INFORMATION: 9-19-307.mis1
<220> FEATURE:
<221> NAME/KEY: misc_binding
<222> LOCATION: 1402..1420
<223> OTHER INFORMATION: complement 9-19-307.mis2
<220> FEATURE:
<221> NAME/KEY: misc_binding
<222> LOCATION: 1516..1534
<223> OTHER INFORMATION: 9-19-442.mis1
<220> FEATURE:
<221> NAME/KEY: misc_binding
<222> LOCATION: 1769..1787
<223> OTHER INFORMATION: 9-20-187.mis1
<220> FEATURE:
<221> NAME/KEY: misc_binding
<222> LOCATION: 1789..1807
<223> OTHER INFORMATION: complement 9-20-187.mis2
<220> FEATURE:
<221> NAME/KEY: misc_binding
```

```
<222> LOCATION: 2372..2390
<223> OTHER INFORMATION: 9-1-308.mis1
<220> FEATURE:
<221> NAME/KEY: misc_binding
<222> LOCATION: 2392..2410
<223> OTHER INFORMATION: complement 9-1-308.mis2
<220> FEATURE:
<221> NAME/KEY: misc_binding
<222> LOCATION: 3759..3777
<223> OTHER INFORMATION: 9-3-324.mis1
<220> FEATURE:
<221> NAME/KEY: misc_binding
<222> LOCATION: 3779..3797
<223> OTHER INFORMATION: complement 9-3-324.mis2
<220> FEATURE:
<221> NAME/KEY: misc_binding
<222> LOCATION: 4979..4997
<223> OTHER INFORMATION: 99-14419-424.mis2
<220> FEATURE:
<221> NAME/KEY: misc_binding
<222> LOCATION: 4999..5017
<223> OTHER INFORMATION: complement 99-14419-424.mis1
<220> FEATURE:
<221> NAME/KEY: misc_binding
<222> LOCATION: 14988..15006
<223> OTHER INFORMATION: 9-24-260.mis1
<220> FEATURE:
<221> NAME/KEY: misc_binding
<222> LOCATION: 15008..15026
<223> OTHER INFORMATION: complement 9-24-260.mis2
<220> FEATURE:
<221> NAME/KEY: misc_binding
<222> LOCATION: 15214..15232
<223> OTHER INFORMATION: 9-24-486.mis1
<220> FEATURE:
<221> NAME/KEY: misc_binding
<222> LOCATION: 15234..15252
<223> OTHER INFORMATION: complement 9-24-486.mis2
<220> FEATURE:
<221> NAME/KEY: misc_binding
<222> LOCATION: 15807..15825
<223> OTHER INFORMATION: 9-6-187.mis1
<220> FEATURE:
<221> NAME/KEY: misc_binding
<222> LOCATION: 15827..15845
<223> OTHER INFORMATION: complement 9-6-187.mis2
<220> FEATURE:
<221> NAME/KEY: misc_binding
<222> LOCATION: 19548..19566
<223> OTHER INFORMATION: 9-7-148.mis1
<220> FEATURE:
<221> NAME/KEY: misc_binding
<222> LOCATION: 19568..19586
<223> OTHER INFORMATION: complement 9-7-148.mis2
<220> FEATURE:
<221> NAME/KEY: misc_binding
<222> LOCATION: 19725..19743
<223> OTHER INFORMATION: 9-7-325.mis1
<220> FEATURE:
<221> NAME/KEY: misc_binding
<222> LOCATION: 19745..19763
<223> OTHER INFORMATION: complement 9-7-325.mis2
<220> FEATURE:
<221> NAME/KEY: misc_binding
<222> LOCATION: 19767..19785
<223> OTHER INFORMATION: 9-7-367.mis1
<220> FEATURE:
<221> NAME/KEY: misc_binding
<222> LOCATION: 19787..19805
<223> OTHER INFORMATION: complement 9-7-367.mis2
<220> FEATURE:
<221> NAME/KEY: misc_binding
<222> LOCATION: 20139..20157
<223> OTHER INFORMATION: 9-9-246.mis1
<220> FEATURE:
<221> NAME/KEY: misc_binding
<222> LOCATION: 20159..20177
<223> OTHER INFORMATION: complement 9-9-246.mis2
<220> FEATURE:
```

```
<221> NAME/KEY: misc_binding
<222> LOCATION: 20576..20594
<223> OTHER INFORMATION: LSRX9-BM.mis1(17-1-240)
<220> FEATURE:
<221> NAME/KEY: misc_binding
<222> LOCATION: 20596..20614
<223> OTHER INFORMATION: complement LSRX9-BM.mis2(17-1-240)
<220> FEATURE:
<221> NAME/KEY: misc_binding
<222> LOCATION: 21089..21107
<223> OTHER INFORMATION: LSRX10-BM.mis1
<220> FEATURE:
<221> NAME/KEY: misc_binding
<222> LOCATION: 21109..21127
<223> OTHER INFORMATION: complement LSRX10-BM.mis2
<220> FEATURE:
<221> NAME/KEY: misc_binding
<222> LOCATION: 587..605
<223> OTHER INFORMATION: potentialsite606.mis1  potential
<220> FEATURE:
<221> NAME/KEY: misc_binding
<222> LOCATION: 607..625
<223> OTHER INFORMATION: complement potentialsite606.mis2  potential
<220> FEATURE:
<221> NAME/KEY: misc_binding
<222> LOCATION: 5122..5140
<223> OTHER INFORMATION: potentialsite5141.mis1  potential
<220> FEATURE:
<221> NAME/KEY: misc_binding
<222> LOCATION: 5142..5160
<223> OTHER INFORMATION: complement potentialsite5141.mis2  potential
<220> FEATURE:
<221> NAME/KEY: misc_binding
<222> LOCATION: 7409..7427
<223> OTHER INFORMATION: potentialsite7428.mis1  potential
<220> FEATURE:
<221> NAME/KEY: misc_binding
<222> LOCATION: 7429..7447
<223> OTHER INFORMATION: complement potentialsite7428.mis2  potential
<220> FEATURE:
<221> NAME/KEY: misc_binding
<222> LOCATION: 8375..8393
<223> OTHER INFORMATION: potentialsite8394.mis1  potential
<220> FEATURE:
<221> NAME/KEY: misc_binding
<222> LOCATION: 8395..8413
<223> OTHER INFORMATION: complement potentialsite8394.mis2  potential
<220> FEATURE:
<221> NAME/KEY: misc_binding
<222> LOCATION: 8685..8703
<223> OTHER INFORMATION: potentialsite8704.mis1  potential
<220> FEATURE:
<221> NAME/KEY: misc_binding
<222> LOCATION: 8705..8723
<223> OTHER INFORMATION: complement potentialsite8704.mis2  potential
<220> FEATURE:
<221> NAME/KEY: misc_binding
<222> LOCATION: 9009..9027
<223> OTHER INFORMATION: potentialsite9028.mis1  potential
<220> FEATURE:
<221> NAME/KEY: misc_binding
<222> LOCATION: 9029..9047
<223> OTHER INFORMATION: complement potentialsite9028.mis2  potential
<220> FEATURE:
<221> NAME/KEY: misc_binding
<222> LOCATION: 9931..9949
<223> OTHER INFORMATION: potentialsite9950.mis1  potential
<220> FEATURE:
<221> NAME/KEY: misc_binding
<222> LOCATION: 9951..9969
<223> OTHER INFORMATION: complement potentialsite9950.mis2  potential
<220> FEATURE:
<221> NAME/KEY: misc_binding
<222> LOCATION: 9958..9976
<223> OTHER INFORMATION: potentialsite9977.mis1  potential
<220> FEATURE:
<221> NAME/KEY: misc_binding
<222> LOCATION: 9978..9996
<223> OTHER INFORMATION: complement potentialsite9977.mis2  potential
```

```
<220> FEATURE:
<221> NAME/KEY: misc_binding
<222> LOCATION: 10002..10020
<223> OTHER INFORMATION: potentialsite10021.mis1  potential
<220> FEATURE:
<221> NAME/KEY: misc_binding
<222> LOCATION: 10022..10040
<223> OTHER INFORMATION: complement potentialsite10021.mis2  potential
<220> FEATURE:
<221> NAME/KEY: misc_binding
<222> LOCATION: 11859..11877
<223> OTHER INFORMATION: potentialsite11878.mis1  potential
<220> FEATURE:
<221> NAME/KEY: misc_binding
<222> LOCATION: 11879..11897
<223> OTHER INFORMATION: complement potentialsite11878.mis2  potential
<220> FEATURE:
<221> NAME/KEY: misc_binding
<222> LOCATION: 19021..19039
<223> OTHER INFORMATION: potentialsite19040.mis1  potential
<220> FEATURE:
<221> NAME/KEY: misc_binding
<222> LOCATION: 19041..19059
<223> OTHER INFORMATION: complement potentialsite19040.mis2  potential
<220> FEATURE:
<221> NAME/KEY: misc_binding
<222> LOCATION: 21344..21362
<223> OTHER INFORMATION: potentialsite21363.mis1  potential
<220> FEATURE:
<221> NAME/KEY: misc_binding
<222> LOCATION: 21364..21382
<223> OTHER INFORMATION: complement potentialsite21363.mis2  potential
<220> FEATURE:
<221> NAME/KEY: misc_binding
<222> LOCATION: 21430..21448
<223> OTHER INFORMATION: potentialsite21449.mis1  potential
<220> FEATURE:
<221> NAME/KEY: misc_binding
<222> LOCATION: 21450..21468
<223> OTHER INFORMATION: complement potentialsite21449.mis2  potential
<220> FEATURE:
<221> NAME/KEY: misc_binding
<222> LOCATION: 21432..21450
<223> OTHER INFORMATION: potentialsite21451.mis1  potential
<220> FEATURE:
<221> NAME/KEY: misc_binding
<222> LOCATION: 21452..21470
<223> OTHER INFORMATION: complement potentialsite21451.mis2  potential
<220> FEATURE:
<221> NAME/KEY: misc_binding
<222> LOCATION: 21435..21453
<223> OTHER INFORMATION: potentialsite21454.mis1  potential
<220> FEATURE:
<221> NAME/KEY: misc_binding
<222> LOCATION: 21455..21473
<223> OTHER INFORMATION: complement potentialsite21454.mis2  potential
<220> FEATURE:
<221> NAME/KEY: misc_binding
<222> LOCATION: 21436..21454
<223> OTHER INFORMATION: potentialsite21455.mis1  potential
<220> FEATURE:
<221> NAME/KEY: misc_binding
<222> LOCATION: 21456..21474
<223> OTHER INFORMATION: complement potentialsite21455.mis2  potential
<220> FEATURE:
<221> NAME/KEY: misc_binding
<222> LOCATION: 21550..21568
<223> OTHER INFORMATION: potentialsite21569.mis1  potential
<220> FEATURE:
<221> NAME/KEY: misc_binding
<222> LOCATION: 21570..21588
<223> OTHER INFORMATION: complement potentialsite21569.mis2  potential
<220> FEATURE:
<221> NAME/KEY: misc_binding
<222> LOCATION: 21664..21682
<223> OTHER INFORMATION: potentialsite21683.mis1  potential
<220> FEATURE:
<221> NAME/KEY: misc_binding
<222> LOCATION: 21684..21702
```

```
<223> OTHER INFORMATION: complement potentialsite21683.mis2  potential
<220> FEATURE:
<221> NAME/KEY: misc_binding
<222> LOCATION: 21675..21693
<223> OTHER INFORMATION: potentialsite21694.mis1  potential
<220> FEATURE:
<221> NAME/KEY: misc_binding
<222> LOCATION: 21695..21713
<223> OTHER INFORMATION: complement potentialsite21694.mis2  potential
<220> FEATURE:
<221> NAME/KEY: misc_binding
<222> LOCATION: 21709..21727
<223> OTHER INFORMATION: potentialsite21728.mis1  potential
<220> FEATURE:
<221> NAME/KEY: misc_binding
<222> LOCATION: 21729..21747
<223> OTHER INFORMATION: complement potentialsite21728.mis2  potential
<220> FEATURE:
<221> NAME/KEY: misc_feature
<222> LOCATION: 22113,22122,22227,22264,22268
<223> OTHER INFORMATION: n=a, g, c or t

<400> SEQUENCE: 1
ccataatcaa gaaaatggat aataagtttt ggtggggatg tggagaaatt ggaatcctcc      60
gtgcattgct ggtgggaatg tacaatagtg cagtcattgg ggaaaacagt ttggcagttc     120
ctcaaaaggt taaaaataga actaccaagt cacccagcaa ttccattctt aggcatatat     180
tcaaaagaaa tgaaagcaga tatttgtaca ccagtgttca cagctgcact atttacaata     240
gtcaaaaggt agaaacaacc taggtccatc cacaaatgaa tggataaata aaacgtagca     300
tatacataca atggtacact agtccgctgt aaaaagaaat tttgatctta ctgcatgcta     360
catggcttcg acatactaca acatggatgg accttgaaaa cattattctt tgtgaaataa     420
actagacaca ggacaaatgt tagacgattc cacttatatg aggcacctag aatgggcaat     480
ttggtaagca agtagaata gaaattacta ggggcacagg tagcagggaa tggggagtta     540
ctgtttaatg gtcacagagt ttatgttggg gatgatgaaa cagtttcggg gataaagagt     600
ggtgactggt acacgacatt gtgaatatac ttaatgccac tgaattttac acttgaagtg     660
gttaaagcga taaatattat agtttgcata tttatcata aaaatatttt tttaaacgat      720
gaagggacgt gaacgggttg aaatttatat aaaagtggcc agggaaggtg tcactgcaat     780
ggtgtcctac aggaggagga agatcatgtg gacatctscg ggaagggtgt tctggcagag     840
ggagtagcac gggcgatggc tctgaggact gtgagaagta tagttggaaa cagcgaggag     900
gccagggtgt ccgaagctga gtaagccaga gagagtggga ggaggtgaga taagagggg      960 aaggtcagtt tctgctgaga gtgaggagga gccacaggag ggctgtgagc aggtggacgt    1020
gatctggctt gagttttaac agggccagta gaacaaagca cgcctgggta ccgaaaccag    1080
ccactggcca gttggcaacc tggggagtc taacgcgagg aagcgcccag ggttccccca     1140
ggatgcgctt tccctcgccg ccacctggag acagcagagt cacgcccagc gctgcgcagg    1200
ctgatcgccg cgccgcgccc ccgccctcgg tcgcaggtgg ctygttccgg gaattcctaa    1260
gcggaaaccg gtcccaagcc ccgcgccttc gctcggcccc tttaagagcc agaatttccg    1320
gagggctgac ccggggctag ggatgcccag gggccgaacc acaagttggg aacrggtggg    1380
ggaggtggcg aaaacttccg wagtggaatt ccaactttc ctggccctga ttcccttgg     1440 gcatccctga gggggcagag cttcccttcc ggggacttta gagggttcct caggtcatct    1500
aactgggaga cacaggaggc ccgaagcgcc cccctccac ccgtccgga ggaacccag       1560 tggaagtgga gaagtcaggc gccaccaaca agcctctccc agccaggact ttgcttagac    1620
tcgctcctcc cggcagggcg cacctaggcg ggtccatcgc cagccgggga gagggttttg    1680
```

```
ggcagggagg gaacaggtgc gcggcgggac ccgccctatc tcaacaggtg aatcgctcca    1740
agtgggtctc ggttgcatgg atctcggtgc gcttggtttg gccggagmag atgggggccg    1800
gaagggacct gtggtccgca ggcgccctcc cagcgggcca gtcacttggt tcgggccctg    1860
ggggacggag cgcacctggg tcagcccact tccggggagg gaggcagagg aaccccctccc   1920 cgccgctcac ccctaagccc agccctcggc tcccacccct tgtgtacctgg gccgaaccat   1980 tcaccggagc gcgcagcggg tggagtgtgg ctcggaggac cgcggcgggt caagcacctt    2040
tctcccccat atctgaaagc atgccctttg tccacgtcgt ttacgctcat taaaacttcc    2100
agaatgcaac aggacggact tggagtaggg acaaggaacg gaagtgggaa ggggaggagc    2160
gtgcacccct cctggccttg gtgcgcgccg cgcccctaa ggtactttgg aagggacgcg     2220
cgggccagac gcgcccagac ggccgcgatg gcgctgttgg ccggcgggct ctccagaggg    2280
ctgggctccc accggccgc cgcaggccgg gacgcgtcg tcttcgtgtg gcttctgctt      2340
agcacctggt gcacaggtac ggggcacggg gcctctgacg ctgcgaacg scggagggaa     2400 ctgtagaggg ggatggatgg agttggaggc ggcgggaagc gggaagcggg ggtctcagag    2460
gctgggacct tccgatcccc tgggtcttgg gcgatctgtt gcgcgcggga gtgagaggaa    2520
ttccccattt gtgccgggga gcgctccccg cgcccttatc tggaagatag caggaagtga    2580
aactccctgg acggtgagac ccggagcggc agggagaatg gaactctttg tggggaggga    2640
gtggaagacc gcccgatctc tgggaaaaga aaagccggga tgggacttgg gcgcacccgg    2700
ggatttctaa gttttggagt aacggggaga gggcacggga gggctggatc agacgcttcc    2760
tagagggaca gagacgaagg aacaatgcct aggcctcggg tgggtgtggg actggggact    2820
ccccatcccc cgcaccccac ccacctcccg cgggctccgg attatacgtg cgtaagagtc    2880
tggtgggatg gatttacgga cttgaaaccg acttctgctg gcaggctttc acctggatgg    2940
gatatttggg tggtgatgag gtcttttccg agacactttt ggttcagtca tttgaaatga    3000
ctttagagta gggtgaggtg gtgggaggct gatggagata ttgtggggc tttagtccct     3060 ccatggcaaa gcagttcagg caaacaactc catggttttc cctccaaatt caaaggccc     3120 cgggtaacct ggaatccttc gtagtcggtt ttgaagtggg gccttgggcg ctgggggcat    3180
caacatggcc atctgggctt gcctgcccag gccacacaga ggccccttgt tgtgggtgaa    3240
tggcaaaggg aagaggggac tggtgtggtt cagaggccac aggctgggaa gagggatggc    3300
gggcgagtcc aaggaaactg gccgtgtcac cgtgcacctg ccacttcagc cccacgggtc    3360
tataaaatgg gcatgattat cgtggctacc tcactggtcc tggcaattaa ggaacaatgt    3420
gtgccaggca ctctgtaaac cacatacttg cgagtgtcaa gctggtgaca ggtggcgttc    3480
ctgttgaagc acctccctga gctcacagca acccttgctg tctctcctct tgccctcagc    3540
tcctgccagg gccatccagg tgaccgtgtc caacccctac cacgtggtga tcctcttcca    3600
gcctgtgacc ctgccctgta cctaccagat gacctcgacc cccacgcaac ccatcgtcat    3660
ctggaagtac aagtctttct gccgggaccg catcgccgat gccttctccc cggccagcgt    3720
cgacaaccag ctcaatgccc agctggcagc cgggaaccca ggctacaacc cctacgtyga    3780
gtgccaggac agcgtgcgca ccgtcagggt cgtggccacc aagcagggca acgctgtgac    3840
cctgggagat tactaccagg gccggaggat taccatcacc ggaagtatgt tgggcagggc    3900
agggggatga ggctgggctt gcccgggtgg tgggactggc gtccttgtgc gggacctgga    3960
gtccccatct gaaagctctt gagtgccagt gtctgaaagg accattgaag ggagcaattc    4020
```

```
ttttttttttt ttttttttgaa gatggagtct tgctctggac tccaggctgg agtgcagtgg    4080
tgcgatctca gctcactgca acctccacct cccaggttca agcaattctc ttgcctcagc    4140
ctcccgagta gctgggactc caggtgcgtg ccaccacgcc cagttaattt ttgtattttt    4200
agtagagatg gggtttcacc atgttggcca ggctggtctc aaactcctga cctcaaatga    4260
tctgcccgcc ttggcctcgc aaagtgctga gagacaccat acccagccta aagggagcga    4320
ttctattcta ctattcttcc ttctgctaat ccttccattc tttaatttaa taacgaagat    4380
tttttgagta cctgtcatat accaggtgct gttctgggcc ctgggaatac agctgttaac    4440
aaaatcatca aaccacttcc ctcgtggagc ccacattgca gtgagagaga caaacackac    4500
acacactctc aagtccttga agataaagaa aactgggtaa cggagagaag aggccagggt    4560
ttgttctata atcattaata acacgagcag taagaagtaa aatttatcta agtaacaact    4620
tataaagggt ctactgtgtg ctaagctctc atccaggttc ccaaggatta actcagacca    4680
cacagtaatt gaatagattc tatcattgtc atcttacaga ggcccagaga gagaaagtga    4740
cttgcctagt gtcatagctg gtaacggggc tgggattcta actcagccac tttgggtcta    4800
gtggccaagc tcctaatccc tttgcttgcc tagggtggtc cgcagaggac tcacagagga    4860
gatggcagga gtgaactgca ggggcaagag agcttaatgg agaaagcctg tgacatgcca    4920
ggaactgcac acatattctc ccattgagtc ctctcctcta ccctcctgac agctgaggca    4980
cagagaggtt accttgttca aatgggtgca taggaagtca aagtctggag ctggggtttg    5040
aacccaggca gccctgagaa ccttgttctt tttttttgag acggagtctc gctctgtcgc    5100
ccaggctgga gtgcagtggc gggatctcgg ctcactgcaa gctccgcctc ccgggttcac    5160
gccattctcc tgcctcagcc tcccaagtag ctgggactac aggcgcccgc cactacgcct    5220
ggctaatttt ttgtattttt agtagagacg gggtttcacc gttttagccg gatggtctc    5280 gatctcctga cctcgtgatc cgcccgcctc ggcctcccaa agtgctggga ttacaggcgt    5340
gagccaccgc gcccggcccc ttgttcttaa ctgtaatgct gcctcctgat aggatgtgcc    5400
tgttgggact aagtaagggg cagtcattca ttcattcatt tggtatttat caagcatcga    5460
ctatgtgtcg ttggtgctgg ggatagaggt gattgggatg gctgaagttt ctgtcgtcaa    5520
ggagatgaca ttctggtgga gtgagactgg cagtaaataa gcagataaag aaagagtatg    5580
agaatttcaa agtctgggca cggtggctca cgtctgtaat ctcagcactt tgggaggcca    5640
aggtgggtgg atcacctgag gtcaggagtt ccagaccagc ctggccaaca tggtgaaacc    5700
ccgtctctac taaaaataca agattagcc aggcatggtg gcacatgcct gtaatcccag    5760
ctactcagga ggctgaggca tgagaatcgc ttgaacccag gaggcagagg ttgcagtgag    5820
ctgagatcgc accactgtac tgcagtctgg gcgacagagt gagactctgt ctcaaaaaaa    5880
aaaaaaaaaa aaaagactcc gtcaaggtat aagaatgtca gagagtacta agtgttgcaa    5940
agaaaataac accaggctgg gtgcattggc tcatgcctgt aaatttcagc actttgggag    6000
gccaaggcag gaggatcact tgagcctagg agtttgagac cagcctggac aacaaaatga    6060
gaccccatgt ctacaaaaat tttaaaaatt taaaaattag ctgggcatgg tggcatgtgc    6120
ctgtggtccc ggctgctcag gaggctgagg tgggaggatt gcttgggctt gagaggtcaa    6180
ggcttcagtg agtcatgatc gtgccactgc attccagcct gggtgacaga gtgagaccct    6240
gtcttgaaat gaaaagaaaa taggctgggc gcagtggctc acacctgtaa tcccagcact    6300 tgggaggcc gaggtgggtg gatcacctga ggtcaggaga tcgagaccag cctggccaac    6360
atggtgaaat cccatctcta ctaaaaatac aaaatttagc cgggcgtggt ggtgggcgcc    6420
```

```
tgtaatccca gctactcggg aggctgaggc aggagaatcg cttgaacctg ggaggcgaag   6480
gttgcggtgc gccaagattg cgccactgca ctctagcctg ggaaacagtg agactccgtc   6540
ttaaaaaaaa aagaaaaaag aaaatagcac tgggtgatgt gctacatgga atgacttggg   6600
ctgtgaatat gatttgagga gggcctgggc ctgggcctta cagaacctag aaggcagaga   6660
ggaaggggag gggcagggtg ccagggatga aggctcacgt acctcatgtc ttagtgtgtg   6720
ttcactgtct taaacaagaa tttaaagttg gcatggggc agagcgggga agggagcatc    6780
cctttgcaga ccccaagaag ccaggaactg gagcacattc tgctagagga tcgatgggaa   6840
gcagggttcc aggggctgag cctatgtcag tcctgtttca gaggaggcac caggcttgct   6900
tgccctgaat ttctgtgggc agctcagcca tgagcatcct actgttattg aggtcacagg   6960
gctgcttagg cccctcctc tctaacccag ggattgtgcc tgcctggacc aggcgtgact    7020
gctaagcttc tgccaggaca agccaaatac tgagggtgct tcctctgctg gacgcaaaag   7080
tccaggatga cccccaggc tctgtctcgg gaaggggcc ctgcatgctc caggggcctc     7140
acaggcctgg gtcttttcaaa ccaccccac ctgggcctgt gtttgatcaa ggccctgagt   7200
gtaaacatcc attgtgtgtg tccttttcagg aaatcccata gccataggag cttcctctgt  7260
ttcagctttg aggatgggga aaagtggact ccccgtggtg ttcctagggt cacccactgt   7320
gctggggttt ttctgttgtt gttgttttttt ttctgttgcc caggctggag tgcagtggtg   7380
caatctcagc tcactgcaac ctctgcctcg caagttcaag tgattctccc gcctcagcct   7440
cctgagtagc tgggattaca ggtgcacacc accacacctg gctaattttt gtatcttttt   7500
ggtagagatg ggatttcgcc atgttggcca ggctggtctc aaactcctga cctcaggtga   7560
tctgcctgcc ttggcctccc aaagttctgg gattacagat gtgagccacc atgcccggcc   7620
tatcctggtt tcaaaagtga aaatagtcct ggataaggta aaggctgtc cactccaggc    7680 atccctccgg tccggtggct cattccctgc tttgtccttc catgctttgg gtgatgacc    7740 agcacctgga caggaggccc tgttccacct cctcgggctc cttggggtcc aagtgccccc    7800
acctccagct gcactgcagc agagagccca tgggacctct gaaatcatga aggtcacctt   7860
tgcggtgtat aaagaaggaa ccagaggttg gagatgtgga ggaggcctgg ctgctgttcc   7920
cactggagac ctggcatctt ctccccgacc taaaacaatg aaagcagtgc tcagcccgga   7980
tgagatcacg gccagcccaa gaccaggaac agggtacgcc ctgcaggaag aaggtgtgcc   8040
cagaccttag gatggatcaa aagaagccgg aaaactatat ttttgtgag ttttgaaaat    8100 gtcagacagg tcaaacaaaa cacagtgagg tccagcctcg gcctacaaga tgccagattt   8160 caaccccctgg cctatatgat ctgtttgcca tggcaggcgg ttcctgtcca cctcttttgt   8220
ttatagcagg gaccagctct tgagctccag tgttgaagag gcacggtcag ggtctgatct   8280
gaagacactg gtggctcatg cctgtaatcc cagcacttca ggaggccgag gcaggaggat   8340
tgcttgagga caggagctgg gagaccagcc tgggcaacac agtgagaccc agacactaca   8400
aaaaaataaa tttagcgggg catgatggca caccctgcta ctctggagat gggaagattg   8460
cttgagccta ggagttcgaa gctgcagtga cccatgatcg caccactgca ctccagcctg   8520
ggcgaccaag ctaggccctc tcaaaaaaga tacaggtgga aaaatgatgg acgaagaggg   8580
cattgtggca aacctgggga tttaggagaa cctagttttgg aattctatga ggattcaatg   8640
aaagaatgtg tgtagagggg cccagcacat agtaagagct caataaacgg tggggggctag   8700 gggtggtggc tcatgcctgt aatcccagca ctttgggagg ctgaggcagg tggatcactt   8760
```

```
gagccctgga gttcaagatc aacctggaca acaaagcaag atcccatctc aaaattaaaa   8820
aacaacacca acaacaaaaa aacagtggct tagatgcctg atcattaggg taagtcgtgt   8880
cctcaacccc ttcacatctg ctctgaaggt caccatatcc ggaagccttc cctggcctcc   8940
ttgtttaaaa tggcacagcc cccactccac gcctggcact ctctgctgtc cctgattcgt   9000
tttctccata cagcttatct ttgtctggta tgtgacatag ttaacatttt atatttgtct   9060
ttctttccta gttagaatct gaactctaga agggcaaggg caaggattta taactcaaag   9120
attccgggct taggcctctt ttatattctt gattttgagg ttaattaaga gctcaggcct   9180
agcgaggtgg ctcatgcctg gaatcccagc actttgggag gccaggcgg gcagatcact   9240
tgaggtcagg agttccagac ctgcctggcc aacacagtga aaaacctgtc tctactaaaa   9300
atacaaaaat tagccagtta tgttggcagg cgcctataat cccagctact caagaggctg   9360
aggcaggaga atcgcttgaa cccaggaggc agaggctgca gtgagccaag atcgtgccac   9420
tgcactccag cctgggcaac agagcgagac tccatctcaa aaaaaaaaaa aaaattaaga   9480
gctcaaagag tttgttttca taggcagcag aatgagaaaa gtttacaaaa tagtttaaat   9540
gacaataaag tcattataga ttaacataaa taaaatacct tttatgaaaa aaataatcat   9600
tttctgaaat cagacaaaac attgtgaatg agaaggtggc atggttttat ttttttgcaa   9660
gtctccgaag cctggctgga tagaagagcc tggcttctca gagctgcttc agtctgttgt   9720
gatatctatt gtatgtcacg tagcctctgg aaaactccac agttagtatt gttgggaaaa   9780
taactttgac ctcaggatct cctgaaaacg tcttggggaa ccccagggtc tagaggctgc   9840
agtttgagaa ctgttgctgt ggtatcccag gtgtctcaaa tactgcctag aacataggtg   9900
gtactcagta attattgttg aaggatgaat gaatgaatga atgaatgaat gaagaaaga   9960
aatgtgtctt tgaatctagc catgtgccca gaatgatgag acagatgaca aaagctaagg   10020
gactttagca tgaggagagg gggttcgttt cctttttttt ctttttttt tgagatggag   10080
tctcactcta ctgcccaggc tagagtgcag tggtgcaatc tcagctcact gcaatctctg   10140
cctcctgagt tcaagcaatt ctcctgcctc agcctccagg gtagctggga ctacaggtgc   10200
gtgccaccat gcctagctaa ttttttacat ttttggtaga gatggggttt taccatgttg   10260
gccgggctgg tctggaactc ctgacctcaa gtgatccacc tgcctcagcc tcccaaagtg   10320
ttaggattac aggtgtgagc caccatgtcc ggccaagagg gtgttcattt ctgctccttg   10380
ccaggtattg tgtcaggcac tggggaccca gcagtggctg agacagacag ggctctgcct   10440
cacggagccc acattttcac caggcaaagg atggtcggcc cctaagctgg gagataagac   10500
ttcagcagtt gggtgggga gccgtgggag aagcccagcc cacaggggga cagtgcaaat   10560
ctagaaccaa ggcgatggca ggggtgaggc tggcacggta gctagagacc acgtcgtgcc   10620
aagggccttg ggaccatgg gactatggga ccttagggaa ggcgtctgga atgctgtagc   10680
cagacactgt tgcaaggagg attttctgt agacatgagg ccttccttat gaagaaagca   10740
agggttcttt cattcctggg ggtgccaggt gctgtggact gcagcacgcg tggttgctgc   10800
cgtcacagag ctgtcatgca ggagggcagc gcgtccttgg gaaggtggca ggcaggtcag   10860
gctaggagga aagaggccgg gaagctgagg gcatttcctg cccgagatgc ccaatgtagc   10920
ctacttctgt ccccagtggc ttaaggcaga gttgctggt aggtgccctg gtcccaccct   10980
ggtgaaaggc tgaaggtatt taattagtgc ctgagaagca gagaggaaac aggatgtgcc   11040
aaaacacttt gatggatggt agagttaaca ggctccttgc ctgcagctgc ttcagacaag   11100
agcgtcccca agccctgggc ctgacctgga atgtgggat ggaagggag ggggaggaac   11160
```

-continued

```
caaggcactg ggagggtaag tctctctctc ccacatagac acacccactc cttatgggtg    11220
cctgggcatc tcctggtacc tagaatctgg cctgtttatc tccacaccca tccctgggt     11280
ctacactagg ccctgtgggt ggcagttcac atcaggggag ttctgacttt ggctctgaga    11340
ggtggttcag agatggctgt aagttgagaa gcacagactg ctgggtgtgg tggttcacgc    11400
ctgtaatccc agcactttgg gaggctgagg tgggggtgga tcacctgagg tctgagttc     11460
aaaaccaact tggtcaacat ggcgaaactc catctctact aaaaatgcaa aaattagcca    11520
ggtgtggtgg caggtgccta atcccagc tacatgggag gctgaggcag gagaatcgct     11580
tgaatctggg aggcgaagat tgtagtgagc cgagattagt tcgcaccatt gcatgccagc    11640
ctgggcaaca agagtgaaac tccgattcaa acaaacaaaa aaaaaagct gggcatggtg     11700
gagtgcctgt agtcctaact actcaggtgg gaggattgct tgagtccagg aggttgaagt    11760
tgcagtgggc tataattaca ccactgcact ccagccaggg ccacagagtg agaccctgtc    11820
tctaaagaaa gaaaaaaaaa acaaacctca ggctccgagg gcaccattac tgctctacac    11880
tgaagagctg tgcagctttt ccagacccga aatgtcatcc acaaaacaga agtgataatg    11940
gtcctgcctc acagacttct tgcagtagtc caggtgttta aacggggtg taaaaggccg     12000
tgtgcccttg gtaggaatct ttgcatatgc atttgatcat ctgcagcctg cccagcccac    12060
tgcttgcccc ctcctgggtg tgctgggaag gggtctttgg ccctccaggg gttaggtgcc    12120
ccagcctcca aggtgccctc acgccttttc atcccgactc agatgctgac ctgacctttg    12180
accagacggc gtgggggggac agtggtgtgt attactgctc cgtggtctca gcccaggacc    12240
tccaggggaa caatgaggcc tacgcagagc tcatcgtcct tggtgagtgg gcctgggaag    12300
ggggaggcat ggcccttcct tttgtccgct tctgttctgt ctgccctccc ctgtgtccgc    12360
cctctgccct ccagcttacc ctctgggctc tgtcgcctgc tctgctctcc cccaggctct    12420
gccagtcact taggctcccc tgtgccctgc accccaggca gggaccactg gcccacagtg    12480
cctccaatca cccaagccaa actaagagaa gagtggagac aattggagac tctgccttt    12540
caaagtctca ttttttaaaaa aaatccagac ttggggtccg ggtgcggtag ttcatgcctg    12600
taatcccagc actttgggag gccgaggcgg gtggatcact tgaggccagg agttcgagac    12660
tagcctggcc aacgtggcaa aatcccgtct ctataaaaaa tataaaagcc aggcgtggtg    12720
gtgcacatgc ctgtaatccc agttactcag aaggctgagg catgaggatt gcttgaacct    12780
gggaggcaga ggatgcagta agccaagatc aagccactgc actccagcct gggcgacaga    12840
gtgagactct gtccaaaaaa aaaaaaaatc cagacgtggt cagagtccat gggcagtgaa    12900
tgaggacagt tgatggtgtg caaaatcgac ccacctcttg ctacatcccc aaggcctcat    12960
ctcacccgag tccctcgcca aagcacagcg gttttgccgt gtgccctgct gggatggcgc    13020
tgcatggcac acacactgtg taagtttgag tgcagctgaa acgaagccga ttccagacac    13080
ccaggggcag ggcggggtgt ccgtgtggct gggaggcctc cttgtgttag ggggatgttg    13140
ccatcggcca ggtgccctgc tgtaagccaa cacatggagt cttgtatgac atgtgctctg    13200
catgagtgat gccgctgggc tgtacactgc catcttcaca tgtgtgaatg agcacgtgac    13260
tggggggtac ttgggctgca agacagagtt catgtgtggg ggatgaaaca cgtgcaccag    13320
tgacccagga acctctgcct gttcttcggt aaaatgcacc atttgcatca gcagttccca    13380
aaattagtct ccaggtctat ttacactcta aaacattatc gagggtctcc aagagctttt    13440
gtttgtttct gtgggttta tgtctatctg ttgcttaaca tattaggaat taaaatgggg    13500
```

```
agatttttcct tttttttttt ttttttttga gatggagtct cgttctgtcg cccaggctgg    13560
agtgcagtgg ctcgatctcg gctcactgca agcttcacct cctgggttca cgccattctc    13620
ctgcctcagc ctcccaagta gctgggacta caggcacccg ccaccacacc cggctaattt    13680
tttttgtatt tttagtagag actgggtttc accatgttag ccaggatggt ctcgatctcc    13740
tgacctcgtg atccacccac ctgggcctcc caaagtgctg ggattacagg catgagccac    13800
tgcccggcct taaaatgggg agattttttca agcccaagat acacaaggaa gactgggcaa    13860
catggcaaga ccctgactct acaaaaaatt ttaaaattaa ccaggcatgg tggcatgcac    13920
ctgtgagccc agcttcttgg gaggctgagg caggagtatc gcttgcaccc aggaggtcaa    13980
ggctgcagtg agccatgact atgctactgc actctagcat gagtgacaga gaccctggct    14040
caagaaacac aaacacacac acacacacac acacgcatat agtccattag gcatcagggc    14100
gatgatggca tcagggagcc tgggaaactc tactggacat tcatgggaga acaagtgaaa    14160
aaggcaaata acatcttagt gttattctaa aatttcttct tttggccttg tggacaggac    14220
cacgctttga gagctgtgac tgacatgcct ctgtcctgtt gcgagggcct atagtgccaa    14280
gtgcatgagc tctggggagg gcttcgtggg tgcagagctg ggcctgtgga gggcccctcag   14340
acacaacact ggtggggctc agagctccag gggcactcga gggaagacaa gaaccggctc    14400
tgagatgcgt gaatgtgaca gtgcatgagt agagatggag accttgtggg tcccagaacc    14460
aggactgcat atgactttca tatgtgggta ttttttgcctt catgggtccc ttcctgtttt    14520
aaaaaaaatg tgtgattatg ttgtcacaaa gagtttattc ctgtatattg tgttaatttg    14580
tgttcagatt tgtaaagtaa aattaaacca tttcagccag gtgtggtgac acatgcctgt    14640
agccctagct acttaccca gaggctgagg tgggaggatc gcctgagccc acgaggttga    14700
agctgcagtg agccatgatc acaccctgc actccagact gggcgacaga gctgagatcc    14760
tatttcgtgg gccctaggtc cctgtgcctg ctggaacagg acatccctat caccgtggtt    14820
ggagcccttt ggggtgctaa gacctatgaa tgagggaaac ttagggtgcc caagctgagg    14880
tagagccctc agaaccccct gggatttgta ttggagccct cgtggcataa acaggtggga    14940
ttatgcaatg ggagtttctt acctataagc acccacatgt gggcgggtgg agggtaggag    15000
ccatgcrcta gggcttcagc ccccagcccc ttcccgcttc agggcacacc ttgcacttgg    15060
ccagcctgga gctgggcttt cggggggtggc acagcctggg ctggctctgg ccagcataat    15120
ctgtttctct tttgtccctc caggaggac ctcaggggtg gctgagctct tacctggttt    15180
tcaggcgggg cccatagaag gtacggggg tggatcctga gttgggcttc tcrggagctc    15240
ccatacatca cctactgctt ctgactctag ttagtatccc cttccccact aaaccctgct    15300
cactgtggac ccctcactaa cctggcctga ctgtggctct gaggcatcta gtggtctggc    15360
gctgggccta ggctaggctg ggctgaggag agcctggggt gcaggccagg gctctgtgac    15420
tggcacctgc ggtgctcttg aggggtgtggc gtctgggcag ctggctctct ctttggtctg    15480
ggggctgcag tctgtctccc tctgtgcagg ctgcctcgtt ttctgccttg tgttttttgc    15540
acctggggga gggccgtaac tggggaatgg ccgggatggt agaatgggga gtgtgctgtg    15600
cccagcctct ggcacaaaaa atccagccag ggctgcaggt tccttggtga gctttgcaaa    15660
tcgtccccga cctcagtgct ggctccgcac catgtacccc tgctgtgccg ttagccctgt    15720
tccctcccag gcctccgggc tcagggcctg ttgtctttct gcagactggc tcttcgtggt    15780
tgtggtatgc ctggctgcct tcctcatctt cctcctcctg ggcatytgct ggtgccagtg    15840
ctgcccgcac acttgctgct gctacgtcag gtgccctgc tgcccagaca agtgctgctg    15900
```

```
ccccgaggcc cgtaagtgtc ccgctcatgg ccaccctggt ttgggcaaca tcctgcatcc   15960
aagggaagga ggtggccatc cacctgcccc caggacagtg gcgttggtct ggagggtgtg   16020
aatttagcca gtggggagaa agtaggctga ggagggtctg ctgtttagat tgtcgtttac   16080
ttcctccaac ttttagttta tttttattta tgttgttctt ttcttttgta agtataatcc   16140
atacacatgg taaaaatgtc caacagtaca agatactagt cacatggaag taaagccctc   16200
taaaaaaacc aaatcttggc taggcgcagt gattacgcct gtaatcccag cactttggga   16260
ggccaagacg agtggatcac ttgaggtcag gagttccaga tcagcctggc caacatggta   16320
aaacccagtt ctctactaaa aatacaaaaa ttagctgggc atggtggtga tcgcctgtaa   16380
tcccagctac tcaggagact gaggcatgag aatcgcttaa acccaagaag tggaggttgc   16440
agtgagctga gatcacgcca ctgcactcca gcctgggcga cagagtgaga ctctgtctca   16500
aaaaaaaaag aaaaaaaaat gttaagtgaa aaagttaaga aaccaaacaa ggtttacaac   16560
actacatgat ttaagcaaaa aaaatttttt ttgttttaga gaaagggtct cattctgtca   16620
tccaggcagt gcagtgcgat catagctctc tgcagcctca aactcccggg ttcaagcagt   16680
cctcccgcct cagcctctgg agcagctggg actgtaggca cacaccacca tgcccagcta   16740 atttttttgat ttttgttttt tgtagagacg gggtctcagt atgttgccca gcctgatctc   16800
aaactcctgg cctcaggtga tcctccgaag tcagcctccc caaagtgctg ggattacagg   16860
catgtgccac catgctggcc aattttttaaa aattttctgt agagacaggg tcttgctatg   16920
ttgcccaggc tggtcttgaa ctcttgacct caagtgatcc tgcctcaggc tcccaaagtg   16980
atgggattac aggcatgaac taccacacct ggccttaaac ttaagcaaat tttttttttt   17040
ttttggagac agtttcactc tgtcgcccag gctggagtaa agtggcgtga tctctgctca   17100
ctgcaacctc cgccccccgg gtttaagcta ttctcctgcc tcagcctccc gagtagctgg   17160
gatataggcg cctgccacca cgcctgacta atttttgtat ttttagtaga dacggggttt   17220
tgccatgttg gccaggctgg tctcgaactc ctgacctcag gcaatccgct ccccgcacc   17280 cctaccttgg cctcccaaag tgttaggact acaggtgtga gccaccatgc ctggccaaat   17340
ttaagcaaat gtttgaaaac atacccac aggaatgctg cacattttac ccagctacta   17400
tgtctagggt cgtatctagc acaccagcat ggctactgtg gagagctggg actgatgtg   17460 agatgagagc taaggggaa gtaagcaaac caagcagggg aaggtaagag aagacagaag   17520
acagagagag agggacctaa ctctatgaga ggagtcagac atgtgcaatt gaaaaagact   17580
tgctcctgtc tctcttctgt gaatgtttgt gaatatccca acgggacact ttcacagagg   17640
agctgattga cgtggtcaca gccatcagcc ttgggacacc agaccacagt gtgtacacta   17700
agtggcactg atggacactt cagcatccct ctagctgctg tcccgtttcc cctcctcggg   17760
gaccacagct gttgccagtc cttggttttcc ttcaggaggg tgtctgggta gaccagcctg   17820
tgtgcacaca gtccaagata catgaacagt gaagtgccag gcaatccttg caagcatggg   17880
caggtggaga gctgaggcct gcttgacacc ttcctgctca gaagcccagt gagcagtttc   17940
cctccctagg gctcagtgtc atcccctata aaatggggct tatggcagag ctcaccacac   18000
tgggtgcatc tggggatttg gcgagctcat gtgcacacca ttgagcatgg gcccaacct   18060 atataaaata ttctacgtct gtcagctgct gggcactgcc actatcagcc tcagtagtga   18120
ctgagggaca gggcaccagt cagagccctg gtgcacacag agtgacccca gagaagcagc   18180
cttccctctc tgagtcctgt ttccttctgt taggtcctga cttcatgggt tgttgttagc   18240
```

```
attaaggaag tcgctggcta attttatagt cattgaagtc agtggtgtgc aacctggttc    18300
ctcaaaggat cacttccctg aaaaaattcc actgctccct ggaggcttat gcaggccatc    18360
ccatcccctc cctcttgttg tgttcagctg acagcttttt gctcagtgag taagtgttag    18420
gtccatttca cagatgggct gcaaccaagt ttgcagtgaa cccactaaga ccagagctag    18480
ggccaggact aaatgctggt cccaatgcca cattccctg tccccacacc acatttcctc     18540
catccggaga ccctgttacc ccaacccagg gccccattaa ctccctggca gaggccctgt    18600
tacatctgct gctgccacag cctccgccca cccttcagga ggcagcaggt cccactgctg    18660
atgataaagt tgcaggctgc ctgagctaat gaagggggctt cctctaggct gtgcacttag   18720
tcttctgctt ccaaaccaaa tcagaggtga ggcaccctct ctgggcccat ctctctcctc    18780
cattttcctg ttgggtccc agggaggaag ccacttgcct agggcccagg aattttgcaa     18840
gcctcttgcc ctagggagga aggaagggag gaggatctta ccttgaactg tcaagcctag    18900
agcctggtgg ggcaggcaga aatgggtgca gtccatgagt tagaaacact agaggagaca    18960
ctttgctgct tggccggggc aggcaagtta attcccgagg ctcctgccac tgcatctcaa    19020
tctggaaggt gaccaggtgg ggcaggaccc acgtctccca gatgactcat tttttctaga    19080
acagggcctt ggctgccaaa gaggatactt gatttcggct tgtggggaca gtggtggacc    19140
cagcatctgg gctttatata aagggcagct ttgttgccct gtaaacacac agaccatggg    19200
tggccacttc ttccagtaag ttagctgggg agttggaagt ttaggtaaaa ccttttgatt    19260
gacaaatgtt ggcgaattac catgctgtta aatgaaacat tgttctgcca ccctgggggct   19320
gtgggtgcct gcgtgcaccc tctgaaaaat cacacaggaa gtggggtggg gtctctgtga    19380
agctggtgtc ccccagcctc agggatgctg cagaaatgga atgaggacca acagggactc    19440
agatgtccaa ggaagctcta cagcggagag gacggcttgg gaaggaggtc caggcccagg    19500
tccctccgga acccaatggg tatggggcag cctggctcct gcctcatccc ccttctcctg    19560
ttgattrtgt cctcacagtg tatgccgccg gcaaagcagc cacctcaggt gttcccagca    19620
tttatgcccc cagcacctat gcccacctgt ctcccgccaa gaccccaccc ccaccagcta    19680
tgattcccat gggccctgcc tacaacgggt accctggagg ataccctgga gacgttgaca    19740
ggartagctc aggtgaggcc gggggaagca ggaacagctg gtgggmgtgt gctgggcatc    19800
tggacactga ggggcagggg ctggaaggaa gagtgtcttg ggagccgagg aggggctctg    19860
ctcctggtgc gcggccactg acagccactc tcccccagct ggtggccaag gctcctatgt    19920
accccctgctt cgggacacgg acagcagtgt ggcctctggt gagaatccat cgtcccgaag   19980
ttggatgtgc ctgtaaggga gaggggtggg ccaggatcca tcctcccaaa ccgaccacca    20040
cccccctgtc cctagaagtc cgcagtggct acaggattca ggccagccag caggacgact    20100
ccatgcgggt cctgtactac atggagaagg agctggccaa cttcgaccct tctcgacstg    20160
gcccccccag tggccgtgtg gagcggggta agcaggagcc ttggggtctg agggcttta     20220
aggtggggg gtgaaacatg tctccctgat acctgccgca gggactcttg gtgcaaaccc     20280
tggacccgg gctcctccag cagtcagtga cacccccctt ccctgcagcc atgagtgaag     20340
tcacctccct ccacgaggac gactggcgat ctcggccttc cggggccct gccctcaccc     20400
cgatccggga tgaggagtgg ggtggccact cccccggag tccagggga tgggaccagg      20460
agcccgccag ggagcaggca ggcggggggct ggcgggccag gcggcccgg gccgctccg     20520
tggacgccct ggacgacctc accccgccga gcaccgccga gtcagggagc aggtctccca    20580
cgagtaatgg tgggaggaga agccgggcct acatgccccc gcggagccgc agccgggacg    20640
```

```
acctctatga ccaagacgac tcgagggact tcccacgctc ccgggacccc cactacgacg   20700
acttcaggtc tcgggagcgc cctcctgccg accccaggtc ccaccaccac cgtacccggg   20760
accctcggga caacggctcc aggtccgggga acctcccta tgatgggcgg ctactggagg   20820
aggctgtgag gaagaagggg tcggaggaga ggaggagacc ccacaaggag gaggaggaag   20880
aggcctacta cccgcccgcg ccgccccccgt actcggagac cgactcgcag gcgtcccgag   20940
agcgcaggct caagaaggtg agggccgccc tccctggcgt ccagaccgtc cctgggcccc   21000
cagccggtcc ccgcggctca tacccttctt tctttctccc ttgcagaact tggccctgag   21060
tcgggaaagt ttagtcgtct gatctgacgt tttctacgta gcttttgkat ttttttttttt  21120 aatttgaagg aacactgatg aagccctgcc atacccctcc cgagtctaat aaaacgtata   21180
atcacaagct ctggagagaa ccatttgttc ggccgcgcgg ggcggggac cggggctgct    21240 cccgtatgcg tctgtaaagc gccgcgtccc ggggcaccg gagtccgggg ccggaggaa    21300 gagacccagc ctggcccggc ccgcgcccgc ccgccggcc ggagaacgtg ccccgcgcag    21360
ccaccgcccg cctgcgtgcg cgccccggcc ccgcccaggc gtgcgcatgc gccccggccc   21420
tccgccttcg cgcaccgcag gctggccgcc gggagcgcgc gcgcgctcct ctcccttcc    21480 agcccatccc ccccagcccc ccaccgacct actttactgt ctccaaactc gggcagccca   21540
cctggccccc gacgaccca gcccctgctc cgggtacccc gacgttccat ccagaccgc    21600 gtttcaccag ggcggcgcgc ggcgacctcg cgccccgcgg agccccgggc tcgcgcgcgc   21660
ccgcccgccc ccggagacag acagcgcgcg cgctcccggg ccgcctcccc ccagcgcgcg   21720
tccgccccgg gctcgcgccg ccgccgccgc cgccgccgcg cgcgcgcagc tcaagtaaag   21780
gaggaaaaaa aaaaggggga aaaatagaaa gcggcggcgg ctgcagcagc gatccgccgc   21840
cggactgggc caagccgggc ggcggccgcg cgagccggcg atccagggca ctggcggcgg   21900
ccagccaggg cgggccgtgt tcaaaaaaaa aagtcgcgcc ggcggcggct gctcagggaa   21960
ggaggcctga gggccgcgtg cagcgggcgg gcagctgggt gggctggggg cggccgcgcg   22020
gcgtcccgga gcctcgggcc gcccggagcc ggcgggcggg cggaggcgga ggcggcggcg   22080
gctgcagcgg ctgcaggagc ggcggcggct gcngcggcgg cngcggcatc tcctcctcac   22140 atgacccac tgtttgtccc cgtgatcagc gcgagcggct cccgtatctc ctccgtcccc    22200
tcctgccgcg cggcgtgagc gccgggnctc ggggcccccc cggccgcccg ccccctcccc   22260
tccntccntc ccctccccctc ccctccccccc cgggccccgc gccccccccg ccccgcccc   22320 ccccatggac atgctggacc cgggtctgga tcccgctgcc tcggccaccg ctgctgccgc   22380
cgccaggtaa gatccccggc ccggccgtgc ccccgcgccc cggccccggc ccggccccg    22440 cggcctgcag gccggggccg ccatgatccc gagcggccgc gggccccgct caaaatggag   22500
gccgccggcg cgggggggac ctggcgcctc ccgcccccgg ccccccggcct cggcggcgcc   22560 cccggcctca ggcgcggccg ggtgggactg gggccctgca gctgggcgcg ggggcggggg   22620
cgcgggcgcg ggccgcgctg accctgctcc ctcctgtgcc cctggcagcc acgacaaggg   22680
acccgaggcg gaggagggcg tcgagctgca ggaaggtgag tgcttgccgg gccggccgcg   22740
cccggggagg gctgggggcg ctcggcgcgg ccctgaccgt gccccgaccc tcctcggccc   22800
caggcgggga cgggccagga gcggaggagc agacagcggg ggccatcacc agcgtccagc   22860
aggcggcgtt cggcgaccac aacatccagt accagttccg cacagagaca aatggaggac   22920
aggtgagcgc cgggccgcga gagcgaacgg gcgggcgggc gggcgcgccg ggaaggctcg   22980
```

```
gacctggccc cagcgccggc ctcgccgctc tgccgccccc tgcaggtgac ataccgcgta    23040
gtccaggtga ctgatggtca gctggacggc cagggcgaca cagctggcgc cgtcagcgtc    23100
gtgtccaccg ctgccttcgc gggggggcag caggctgtga cccaggtggg tgtggacggg    23160
gcagcccagc gcccgggccc cgccgct                                         23187

<210> SEQ ID NO 2
<211> LENGTH: 2158
<212> TYPE: DNA
<213> ORGANISM: Homo sapiens
<220> FEATURE:
<221> NAME/KEY: allele
<222> LOCATION: 595
<223> OTHER INFORMATION: 9-3-324 : polymorphic base C or T
<220> FEATURE:
<221> NAME/KEY: allele
<222> LOCATION: 940
<223> OTHER INFORMATION: 9-6-187 : polymorphic base C or T
<220> FEATURE:
<221> NAME/KEY: allele
<222> LOCATION: 1191
<223> OTHER INFORMATION: 9-7-325 : polymorphic base A or G
<220> FEATURE:
<221> NAME/KEY: allele
<222> LOCATION: 1362
<223> OTHER INFORMATION: 9-9-246 : polymorphic base G or C
<220> FEATURE:
<221> NAME/KEY: allele
<222> LOCATION: 1658
<223> OTHER INFORMATION: LSRX9f13-BM : polymorphic base deletion of
      AGG
<220> FEATURE:
<221> NAME/KEY: allele
<222> LOCATION: 2079
<223> OTHER INFORMATION: LSRX9f14-BM : polymorphic base T or G

<400> SEQUENCE: 2
tggagtgtgg ctcggaggac cgcggcgggt caagcacctt tctcccccat atctgaaagc    60
atgccctttg tccacgtcgt ttacgctcat taaaacttcc aga atg caa cag gac    115
                                              Met Gln Gln Asp
                                               1 gga ctt gga gta ggg aca agg aac gga agt ggg aag ggg agg agc gtg    163
Gly Leu Gly Val Gly Thr Arg Asn Gly Ser Gly Lys Gly Arg Ser Val
 5              10                  15                  20 cac ccc tcc tgg cct tgg tgc gcg ccg cgc ccc cta agg tac ttt gga    211
His Pro Ser Trp Pro Trp Cys Ala Pro Arg Pro Leu Arg Tyr Phe Gly
             25                  30                  35 agg gac gcg cgg gcc aga cgc gcc cag acg gcc gcg atg gcg ctg ttg    259
Arg Asp Ala Arg Ala Arg Arg Ala Gln Thr Ala Ala Met Ala Leu Leu
         40                  45                  50 gcc ggc ggg ctc tcc aga ggg ctg ggc tcc cac ccg gcc gcc gca ggc    307
Ala Gly Gly Leu Ser Arg Gly Leu Gly Ser His Pro Ala Ala Ala Gly
     55                  60                  65 cgg gac gcg gtc gtc ttc gtg tgg ctt ctg ctt agc acc tgg tgc aca    355
Arg Asp Ala Val Val Phe Val Trp Leu Leu Leu Ser Thr Trp Cys Thr
 70                  75                  80 gct cct gcc agg gcc atc cag gtg acc gtg tcc aac ccc tac cac gtg    403
Ala Pro Ala Arg Ala Ile Gln Val Thr Val Ser Asn Pro Tyr His Val
 85                  90                  95                 100 gtg atc ctc ttc cag cct gtg acc ctg ccc tgt acc tac cag atg acc    451
Val Ile Leu Phe Gln Pro Val Thr Leu Pro Cys Thr Tyr Gln Met Thr
                105                 110                 115 tcg acc ccc acg caa ccc atc gtc atc tgg aag tac aag tct ttc tgc    499
Ser Thr Pro Thr Gln Pro Ile Val Ile Trp Lys Tyr Lys Ser Phe Cys
            120                 125                 130
```

```
cgg gac cgc atc gcc gat gcc ttc tcc ccg gcc agc gtc gac aac cag      547
Arg Asp Arg Ile Ala Asp Ala Phe Ser Pro Ala Ser Val Asp Asn Gln
        135                 140                 145 ctc aat gcc cag ctg gca gcc ggg aac cca ggc tac aac ccc tac gty      595
Leu Asn Ala Gln Leu Ala Ala Gly Asn Pro Gly Tyr Asn Pro Tyr Val
150                 155                 160 gag tgc cag gac agc gtg cgc acc gtc agg gtc gtg gcc acc aag cag      643
Glu Cys Gln Asp Ser Val Arg Thr Val Arg Val Val Ala Thr Lys Gln
165                 170                 175                 180 ggc aac gct gtg acc ctg gga gat tac tac cag ggc cgg agg att acc      691
Gly Asn Ala Val Thr Leu Gly Asp Tyr Tyr Gln Gly Arg Arg Ile Thr
                185                 190                 195 atc acc gga aat gct gac ctg acc ttt gac cag acg gcg tgg ggg gac      739
Ile Thr Gly Asn Ala Asp Leu Thr Phe Asp Gln Thr Ala Trp Gly Asp
        200                 205                 210 agt ggt gtg tat tac tgc tcc gtg gtc tca gcc cag gac ctc cag ggg      787
Ser Gly Val Tyr Tyr Cys Ser Val Val Ser Ala Gln Asp Leu Gln Gly
        215                 220                 225 aac aat gag gcc tac gca gag ctc atc gtc ctt ggg agg acc tca ggg      835
Asn Asn Glu Ala Tyr Ala Glu Leu Ile Val Leu Gly Arg Thr Ser Gly
        230                 235                 240 gtg gct gag ctc tta cct ggt ttt cag gcg ggg ccc ata gaa gac tgg      883
Val Ala Glu Leu Leu Pro Gly Phe Gln Ala Gly Pro Ile Glu Asp Trp
245                 250                 255                 260 ctc ttc gtg gtt gtg gta tgc ctg gct gcc ttc ctc atc ttc ctc ctc      931
Leu Phe Val Val Val Cys Leu Ala Ala Phe Leu Ile Phe Leu Leu
                265                 270                 275 ctg ggc aty tgc tgg tgc cag tgc tgc ccg cac act tgc tgc tgc tac      979
Leu Gly Ile Cys Trp Cys Gln Cys Cys Pro His Thr Cys Cys Cys Tyr
                280                 285                 290 gtc agg tgc ccc tgc tgc cca gac aag tgc tgc tgc ccc gag gcc ctg     1027
Val Arg Cys Pro Cys Cys Pro Asp Lys Cys Cys Cys Pro Glu Ala Leu
            295                 300                 305 tat gcc gcc ggc aaa gca gcc acc tca ggt gtt ccc agc att tat gcc     1075
Tyr Ala Ala Gly Lys Ala Ala Thr Ser Gly Val Pro Ser Ile Tyr Ala
        310                 315                 320 ccc agc acc tat gcc cac ctg tct ccc gcc aag acc cca ccc cca cca     1123
Pro Ser Thr Tyr Ala His Leu Ser Pro Ala Lys Thr Pro Pro Pro Pro
325                 330                 335                 340 gct atg att ccc atg ggc cct gcc tac aac ggg tac cct gga gga tac     1171
Ala Met Ile Pro Met Gly Pro Ala Tyr Asn Gly Tyr Pro Gly Gly Tyr
                345                 350                 355 cct gga gac gtt gac agg art agc tca gct ggt ggc caa ggc tcc tat     1219
Pro Gly Asp Val Asp Arg Xaa Ser Ser Ala Gly Gly Gln Gly Ser Tyr
            360                 365                 370 gta ccc ctg ctt cgg gac acg gac agc agt gtg gcc tct gaa gtc cgc     1267
Val Pro Leu Leu Arg Asp Thr Asp Ser Ser Val Ala Ser Glu Val Arg
        375                 380                 385 agt ggc tac agg att cag gcc agc cag cag gac gac tcc atg cgg gtc     1315
Ser Gly Tyr Arg Ile Gln Ala Ser Gln Gln Asp Asp Ser Met Arg Val
        390                 395                 400 ctg tac tac atg gag aag gag ctg gcc aac ttc gac cct tct cga cst     1363
Leu Tyr Tyr Met Glu Lys Glu Leu Ala Asn Phe Asp Pro Ser Arg Xaa
405                 410                 415                 420 ggc ccc ccc agt ggc cgt gtg gag cgg gcc atg agt gaa gtc acc tcc     1411
Gly Pro Pro Ser Gly Arg Val Glu Arg Ala Met Ser Glu Val Thr Ser
                425                 430                 435 ctc cac gag gac gac tgg cga tct cgg cct tcc cgg ggc cct gcc ctc     1459
Leu His Glu Asp Asp Trp Arg Ser Arg Pro Ser Arg Gly Pro Ala Leu
            440                 445                 450
```

-continued

```
acc ccg atc cgg gat gag gag tgg ggt ggc cac tcc ccc cgg agt ccc      1507
Thr Pro Ile Arg Asp Glu Glu Trp Gly Gly His Ser Pro Arg Ser Pro
            455                 460                 465 agg gga tgg gac cag gag ccc gcc agg gag cag gca ggc ggg ggc tgg      1555
Arg Gly Trp Asp Gln Glu Pro Ala Arg Glu Gln Ala Gly Gly Gly Trp
        470                 475                 480 cgg gcc agg cgg ccc cgg gcc cgc tcc gtg gac gcc ctg gac gac ctc      1603
Arg Ala Arg Arg Pro Arg Ala Arg Ser Val Asp Ala Leu Asp Asp Leu
485                 490                 495                 500 acc ccg ccg agc acc gcc gag tca ggg agc agg tct ccc acg agt aat      1651
Thr Pro Pro Ser Thr Ala Glu Ser Gly Ser Arg Ser Pro Thr Ser Asn
            505                 510                 515 ggt ggg aga agc cgg gcc tac atg ccc ccg cgg agc cgc agc cgg gac      1699
Gly Gly Arg Ser Arg Ala Tyr Met Pro Pro Arg Ser Arg Ser Arg Asp
        520                 525                 530 gac ctc tat gac caa gac gac tcg agg gac ttc cca cgc tcc cgg gac      1747
Asp Leu Tyr Asp Gln Asp Asp Ser Arg Asp Phe Pro Arg Ser Arg Asp
535                 540                 545 ccc cac tac gac gac ttc agg tct cgg gag cgc cct cct gcc gac ccc      1795
Pro His Tyr Asp Asp Phe Arg Ser Arg Glu Arg Pro Pro Ala Asp Pro
            550                 555                 560 agg tcc cac cac cac cgt acc cgg gac cct cgg gac aac ggc tcc agg      1843
Arg Ser His His His Arg Thr Arg Asp Pro Arg Asp Asn Gly Ser Arg
565                 570                 575                 580 tcc ggg gac ctc ccc tat gat ggg cgg cta ctg gag gag gct gtg agg      1891
Ser Gly Asp Leu Pro Tyr Asp Gly Arg Leu Leu Glu Glu Ala Val Arg
            585                 590                 595 aag aag ggg tcg gag gag agg agg aga ccc cac aag gag gag gag gaa      1939
Lys Lys Gly Ser Glu Glu Arg Arg Arg Pro His Lys Glu Glu Glu Glu
        600                 605                 610 gag gcc tac tac ccg ccc gcg ccg ccc ccg tac tcg gag acc gac tcg      1987
Glu Ala Tyr Tyr Pro Pro Ala Pro Pro Pro Tyr Ser Glu Thr Asp Ser
        615                 620                 625 cag gcg tcc cga gag cgc agg ctc aag aag aac ttg gcc ctg agt cgg      2035
Gln Ala Ser Arg Glu Arg Arg Leu Lys Lys Asn Leu Ala Leu Ser Arg
    630                 635                 640 gaa agt tta gtc gtc tga tctgacgttt tctacgtagc ttttgkattt             2083
Glu Ser Leu Val Val *
645                 650 tttttttaa tttgaaggaa cactgatgaa gccctgccat acccctcccg agtctaataa     2143
aacgtataat cacaa                                                     2158

<210> SEQ ID NO 3
<211> LENGTH: 649
<212> TYPE: PRT
<213> ORGANISM: Homo sapiens
<220> FEATURE:
<221> NAME/KEY: VARIANT
<222> LOCATION: 363
<223> OTHER INFORMATION: 9-7-325: polymorphic amino acid Ser or  Asn
<220> FEATURE:
<221> NAME/KEY: VARIANT
<222> LOCATION: 420
<223> OTHER INFORMATION: 9-9-246 : polymorphic  amino  acid  Pro  or Arg
<220> FEATURE:
<221> NAME/KEY: VARIANT
<222> LOCATION: 519
<223> OTHER INFORMATION: LSRX9f13-BM  : polymorphic  amino  acid
      deletion  of  Arg

<400> SEQUENCE: 3

Met Gln Gln Asp Gly Leu Gly Val Gly Thr Arg Asn Gly Ser Gly Lys
```

-continued

```
1               5               10              15
Gly Arg Ser Val His Pro Ser Trp Pro Trp Cys Ala Pro Arg Pro Leu
            20              25              30

Arg Tyr Phe Gly Arg Asp Ala Arg Ala Arg Arg Ala Gln Thr Ala Ala
            35              40              45

Met Ala Leu Leu Ala Gly Gly Leu Ser Arg Gly Leu Gly Ser His Pro
            50              55              60

Ala Ala Ala Gly Arg Asp Ala Val Val Phe Val Trp Leu Leu Leu Ser
65                      70              75                  80

Thr Trp Cys Thr Ala Pro Ala Arg Ala Ile Gln Val Thr Val Ser Asn
                85              90              95

Pro Tyr His Val Val Ile Leu Phe Gln Pro Val Thr Leu Pro Cys Thr
                100             105             110

Tyr Gln Met Thr Ser Thr Pro Thr Gln Pro Ile Val Ile Trp Lys Tyr
            115             120             125

Lys Ser Phe Cys Arg Asp Arg Ile Ala Asp Ala Phe Ser Pro Ala Ser
            130             135             140

Val Asp Asn Gln Leu Asn Ala Gln Leu Ala Ala Gly Asn Pro Gly Tyr
145                     150             155                 160

Asn Pro Tyr Val Glu Cys Gln Asp Ser Val Arg Thr Val Arg Val Val
                165             170             175

Ala Thr Lys Gln Gly Asn Ala Val Thr Leu Gly Asp Tyr Tyr Gln Gly
                180             185             190

Arg Arg Ile Thr Ile Thr Gly Asn Ala Asp Leu Thr Phe Asp Gln Thr
            195             200             205

Ala Trp Gly Asp Ser Gly Val Tyr Tyr Cys Ser Val Val Ser Ala Gln
            210             215             220

Asp Leu Gln Gly Asn Asn Glu Ala Tyr Ala Glu Leu Ile Val Leu Gly
225                     230             235                 240

Arg Thr Ser Gly Val Ala Glu Leu Leu Pro Gly Phe Gln Ala Gly Pro
                245             250             255

Ile Glu Asp Trp Leu Phe Val Val Val Cys Leu Ala Ala Phe Leu
                260             265             270

Ile Phe Leu Leu Leu Gly Ile Cys Trp Cys Gln Cys Cys Pro His Thr
            275             280             285

Cys Cys Cys Tyr Val Arg Cys Pro Cys Cys Pro Asp Lys Cys Cys Cys
            290             295             300

Pro Glu Ala Leu Tyr Ala Ala Gly Lys Ala Ala Thr Ser Gly Val Pro
305                     310             315                 320

Ser Ile Tyr Ala Pro Ser Thr Tyr Ala His Leu Ser Pro Ala Lys Thr
                325             330             335

Pro Pro Pro Pro Ala Met Ile Pro Met Gly Pro Ala Tyr Asn Gly Tyr
            340             345             350

Pro Gly Gly Tyr Pro Gly Asp Val Asp Arg Ser Ser Ala Gly Gly
            355             360             365

Gln Gly Ser Tyr Val Pro Leu Leu Arg Asp Thr Asp Ser Ser Val Ala
            370             375             380

Ser Glu Val Arg Ser Gly Tyr Arg Ile Gln Ala Ser Gln Gln Asp Asp
385                     390             395                 400

Ser Met Arg Val Leu Tyr Tyr Met Glu Lys Glu Leu Ala Asn Phe Asp
                405             410             415

Pro Ser Arg Pro Gly Pro Pro Ser Gly Arg Val Glu Arg Ala Met Ser
            420             425             430
```

```
Glu Val Thr Ser Leu His Glu Asp Asp Trp Arg Ser Arg Pro Ser Arg
            435                 440                 445

Gly Pro Ala Leu Thr Pro Ile Arg Asp Glu Glu Trp Gly Gly His Ser
        450                 455                 460

Pro Arg Ser Pro Arg Gly Trp Asp Gln Glu Pro Ala Arg Glu Gln Ala
465                 470                 475                 480

Gly Gly Gly Trp Arg Ala Arg Arg Pro Arg Ala Arg Ser Val Asp Ala
                485                 490                 495

Leu Asp Asp Leu Thr Pro Pro Ser Thr Ala Glu Ser Gly Ser Arg Ser
            500                 505                 510

Pro Thr Ser Asn Gly Gly Arg Ser Arg Ala Tyr Met Pro Pro Arg Ser
        515                 520                 525

Arg Ser Arg Asp Asp Leu Tyr Asp Gln Asp Asp Ser Arg Asp Phe Pro
        530                 535                 540

Arg Ser Arg Asp Pro His Tyr Asp Asp Phe Arg Ser Arg Glu Arg Pro
545                 550                 555                 560

Pro Ala Asp Pro Arg Ser His His His Arg Thr Arg Asp Pro Arg Asp
                565                 570                 575

Asn Gly Ser Arg Ser Gly Asp Leu Pro Tyr Asp Gly Arg Leu Leu Glu
            580                 585                 590

Glu Ala Val Arg Lys Lys Gly Ser Glu Arg Arg Pro His Lys
        595                 600                 605

Glu Glu Glu Glu Glu Ala Tyr Tyr Pro Pro Ala Pro Pro Tyr Ser
        610                 615                 620

Glu Thr Asp Ser Gln Ala Ser Arg Glu Arg Leu Lys Lys Asn Leu
625                 630                 635                 640

Ala Leu Ser Arg Glu Ser Leu Val Val
                645

<210> SEQ ID NO 4
<211> LENGTH: 2101
<212> TYPE: DNA
<213> ORGANISM: Homo sapiens
<220> FEATURE:
<221> NAME/KEY: allele
<222> LOCATION: 595
<223> OTHER INFORMATION: 9-3-324  :  polymorphic  base  C  or  T
<220> FEATURE:
<221> NAME/KEY: allele
<222> LOCATION: 883
<223> OTHER INFORMATION: 9-6-187  :  polymorphic  base  C  or  T
<220> FEATURE:
<221> NAME/KEY: allele
<222> LOCATION: 1134
<223> OTHER INFORMATION: 9-7-325  :  polymorphic  base  A  or  G
<220> FEATURE:
<221> NAME/KEY: allele
<222> LOCATION: 1305
<223> OTHER INFORMATION: 9-9-246  :  polymorphic  base  G  or  C
<220> FEATURE:
<221> NAME/KEY: allele
<222> LOCATION: 1601
<223> OTHER INFORMATION: LSRX9f13-BM :polymorphic base deletion of AGG
<220> FEATURE:
<221> NAME/KEY: allele
<222> LOCATION: 2022
<223> OTHER INFORMATION: LSRX9f14-BM  :  polymorphic  base  T  or  G

<400> SEQUENCE: 4
tggagtgtgg ctcggaggac cgcggcgggt caagcacctt tctcccccat atctgaaagc       60 atgcccttttg tccacgtcgt ttacgctcat taaaacttcc aga atg caa cag gac      115
                                                Met Gln Gln Asp
```

-continued

1

| | | | | | | | | | | | | | | | |
|---|---|---|---|---|---|---|---|---|---|---|---|---|---|---|---|
| gga | ctt | gga | gta | ggg | aca | agg | aac | gga | agt | ggg | aag | ggg | agg | agc | gtg | 163 |
| Gly | Leu | Gly | Val | Gly | Thr | Arg | Asn | Gly | Ser | Gly | Lys | Gly | Arg | Ser | Val | |
| 5 | | | | | 10 | | | | | 15 | | | | | 20 | |
| cac | ccc | tcc | tgg | cct | tgg | tgc | gcg | ccg | cgc | ccc | cta | agg | tac | ttt | gga | 211 |
| His | Pro | Ser | Trp | Pro | Trp | Cys | Ala | Pro | Arg | Pro | Leu | Arg | Tyr | Phe | Gly | |
| | | | | 25 | | | | | 30 | | | | | 35 | | |
| agg | gac | gcg | cgg | gcc | aga | cgc | gcc | cag | acg | gcc | gcg | atg | gcg | ctg | ttg | 259 |
| Arg | Asp | Ala | Arg | Ala | Arg | Arg | Ala | Gln | Thr | Ala | Ala | Met | Ala | Leu | Leu | |
| | | 40 | | | | | 45 | | | | | 50 | | | | |
| gcc | ggg | ctc | tcc | aga | ggg | ctg | ggc | tcc | cac | ccg | gcc | gcc | gca | ggc | | 307 |
| Ala | Gly | Gly | Leu | Ser | Arg | Gly | Leu | Gly | Ser | His | Pro | Ala | Ala | Ala | Gly | |
| | 55 | | | | | 60 | | | | | 65 | | | | | |
| cgg | gac | gcg | gtc | gtc | ttc | gtg | tgg | ctt | ctg | ctt | agc | acc | tgg | tgc | aca | 355 |
| Arg | Asp | Ala | Val | Val | Phe | Val | Trp | Leu | Leu | Leu | Ser | Thr | Trp | Cys | Thr | |
| | 70 | | | | | 75 | | | | | 80 | | | | | |
| gct | cct | gcc | agg | gcc | atc | cag | gtg | acc | gtg | tcc | aac | ccc | tac | cac | gtg | 403 |
| Ala | Pro | Ala | Arg | Ala | Ile | Gln | Val | Thr | Val | Ser | Asn | Pro | Tyr | His | Val | |
| 85 | | | | | 90 | | | | | 95 | | | | | 100 | |
| gtg | atc | ctc | ttc | cag | cct | gtg | acc | ctg | ccc | tgt | acc | tac | cag | atg | acc | 451 |
| Val | Ile | Leu | Phe | Gln | Pro | Val | Thr | Leu | Pro | Cys | Thr | Tyr | Gln | Met | Thr | |
| | | | | 105 | | | | | 110 | | | | | 115 | | |
| tcg | acc | ccc | acg | caa | ccc | atc | gtc | atc | tgg | aag | tac | aag | tct | ttc | tgc | 499 |
| Ser | Thr | Pro | Thr | Gln | Pro | Ile | Val | Ile | Trp | Lys | Tyr | Lys | Ser | Phe | Cys | |
| | | | 120 | | | | | 125 | | | | | 130 | | | |
| cgg | gac | cgc | atc | gcc | gat | gcc | ttc | tcc | ccg | gcc | agc | gtc | gac | aac | cag | 547 |
| Arg | Asp | Arg | Ile | Ala | Asp | Ala | Phe | Ser | Pro | Ala | Ser | Val | Asp | Asn | Gln | |
| | | | 135 | | | | | 140 | | | | | 145 | | | |
| ctc | aat | gcc | cag | ctg | gca | gcc | ggg | aac | cca | ggc | tac | aac | ccc | tac | gty | 595 |
| Leu | Asn | Ala | Gln | Leu | Ala | Ala | Gly | Asn | Pro | Gly | Tyr | Asn | Pro | Tyr | Val | |
| | | 150 | | | | | 155 | | | | | 160 | | | | |
| gag | tgc | cag | gac | agc | gtg | cgc | acc | gtc | agg | gtc | gtg | gcc | acc | aag | cag | 643 |
| Glu | Cys | Gln | Asp | Ser | Val | Arg | Thr | Val | Arg | Val | Val | Ala | Thr | Lys | Gln | |
| 165 | | | | | 170 | | | | | 175 | | | | | 180 | |
| ggc | aac | gct | gtg | acc | ctg | gga | gat | tac | tac | cag | ggc | cgg | agg | att | acc | 691 |
| Gly | Asn | Ala | Val | Thr | Leu | Gly | Asp | Tyr | Tyr | Gln | Gly | Arg | Arg | Ile | Thr | |
| | | | | 185 | | | | | 190 | | | | | 195 | | |
| atc | acc | gga | aat | gct | gac | ctg | acc | ttt | gac | cag | acg | gcg | tgg | gga | gac | 739 |
| Ile | Thr | Gly | Asn | Ala | Asp | Leu | Thr | Phe | Asp | Gln | Thr | Ala | Trp | Gly | Asp | |
| | | | 200 | | | | | 205 | | | | | 210 | | | |
| agt | ggt | gtg | tat | tac | tgc | tcc | gtg | gtc | tca | gcc | cag | gac | ctc | cag | ggg | 787 |
| Ser | Gly | Val | Tyr | Tyr | Cys | Ser | Val | Val | Ser | Ala | Gln | Asp | Leu | Gln | Gly | |
| | | 215 | | | | | 220 | | | | | 225 | | | | |
| aac | aat | gag | gcc | tac | gca | gag | ctc | atc | gtc | ctt | gac | tgg | ctc | ttc | gtg | 835 |
| Asn | Asn | Glu | Ala | Tyr | Ala | Glu | Leu | Ile | Val | Leu | Asp | Trp | Leu | Phe | Val | |
| | 230 | | | | | 235 | | | | | 240 | | | | | |
| gtt | gtg | gta | tgc | ctg | gct | gcc | ttc | ctc | atc | ttc | ctc | ctc | ctg | ggc | aty | 883 |
| Val | Val | Val | Cys | Leu | Ala | Ala | Phe | Leu | Ile | Phe | Leu | Leu | Leu | Gly | Ile | |
| 245 | | | | | 250 | | | | | 255 | | | | | 260 | |
| tgc | tgg | tgc | cag | tgc | tgc | ccg | cac | act | tgc | tgc | tgc | tac | gtc | agg | tgc | 931 |
| Cys | Trp | Cys | Gln | Cys | Cys | Pro | His | Thr | Cys | Cys | Cys | Tyr | Val | Arg | Cys | |
| | | | | 265 | | | | | 270 | | | | | 275 | | |
| ccc | tgc | tgc | cca | gac | aag | tgc | tgc | tgc | ccc | gag | gcc | ctg | tat | gcc | gcc | 979 |
| Pro | Cys | Cys | Pro | Asp | Lys | Cys | Cys | Cys | Pro | Glu | Ala | Leu | Tyr | Ala | Ala | |
| | | | 280 | | | | | 285 | | | | | 290 | | | |
| ggc | aaa | gca | gcc | acc | tca | ggt | gtt | ccc | agc | att | tat | gcc | ccc | agc | acc | 1027 |
| Gly | Lys | Ala | Ala | Thr | Ser | Gly | Val | Pro | Ser | Ile | Tyr | Ala | Pro | Ser | Thr | |
| | | 295 | | | | | 300 | | | | | 305 | | | | |
| tat | gcc | cac | ctg | tct | ccc | gcc | aag | acc | cca | ccc | cca | gct | atg | att | | 1075 |

```
                Tyr Ala His Leu Ser Pro Ala Lys Thr Pro Pro Pro Ala Met Ile
                    310                 315                 320 ccc atg ggc cct gcc tac aac ggg tac cct gga gga tac cct gga gac      1123
Pro Met Gly Pro Ala Tyr Asn Gly Tyr Pro Gly Gly Tyr Pro Gly Asp
325                 330                 335                 340 gtt gac agg art agc tca gct ggt ggc caa ggc tcc tat gta ccc ctg      1171
Val Asp Arg Xaa Ser Ser Ala Gly Gly Gln Gly Ser Tyr Val Pro Leu
                345                 350                 355 ctt cgg gac acg gac agc agt gtg gcc tct gaa gtc cgc agt ggc tac      1219
Leu Arg Asp Thr Asp Ser Ser Val Ala Ser Glu Val Arg Ser Gly Tyr
            360                 365                 370 agg att cag gcc agc cag cag gac gac tcc atg cgg gtc ctg tac tac      1267
Arg Ile Gln Ala Ser Gln Gln Asp Asp Ser Met Arg Val Leu Tyr Tyr
        375                 380                 385 atg gag aag gag ctg gcc aac ttc gac cct tct cga cst ggc ccc ccc      1315
Met Glu Lys Glu Leu Ala Asn Phe Asp Pro Ser Arg Xaa Gly Pro Pro
    390                 395                 400 agt ggc cgt gtg gag cgg gcc atg agt gaa gtc acc tcc ctc cac gag      1363
Ser Gly Arg Val Glu Arg Ala Met Ser Glu Val Thr Ser Leu His Glu
405                 410                 415                 420 gac gac tgg cga tct cgg cct tcc cgg ggc cct gcc ctc acc ccg atc      1411
Asp Asp Trp Arg Ser Arg Pro Ser Arg Gly Pro Ala Leu Thr Pro Ile
                425                 430                 435 cgg gat gag gag tgg ggt ggc cac tcc ccc cgg agt ccc agg gga tgg      1459
Arg Asp Glu Glu Trp Gly Gly His Ser Pro Arg Ser Pro Arg Gly Trp
                440                 445                 450 gac cag gag ccc gcc agg gag cag gca ggc ggg ggc tgg cgg gcc agg      1507
Asp Gln Glu Pro Ala Arg Glu Gln Ala Gly Gly Gly Trp Arg Ala Arg
            455                 460                 465 cgg ccc cgg gcc cgc tcc gtg gac gcc ctg gac gac ctc acc ccg ccg      1555
Arg Pro Arg Ala Arg Ser Val Asp Ala Leu Asp Asp Leu Thr Pro Pro
        470                 475                 480 agc acc gcc gag tca ggg agc agg tct ccc acg agt aat ggt ggg aga      1603
Ser Thr Ala Glu Ser Gly Ser Arg Ser Pro Thr Ser Asn Gly Gly Arg
485                 490                 495                 500 agc cgg gcc tac atg ccc ccg cgg agc cgc agc cgg gac gac ctc tat      1651
Ser Arg Ala Tyr Met Pro Pro Arg Ser Arg Ser Arg Asp Asp Leu Tyr
                505                 510                 515 gac caa gac gac tcg agg gac ttc cca cgc tcc cgg gac ccc cac tac      1699
Asp Gln Asp Asp Ser Arg Asp Phe Pro Arg Ser Arg Asp Pro His Tyr
                520                 525                 530 gac gac ttc agg tct cgg gag cgc cct cct gcc gac ccc agg tcc cac      1747
Asp Asp Phe Arg Ser Arg Glu Arg Pro Pro Ala Asp Pro Arg Ser His
            535                 540                 545 cac cac cgt acc cgg gac cct cgg gac aac ggc tcc agg tcc ggg gac      1795
His His Arg Thr Arg Asp Pro Arg Asp Asn Gly Ser Arg Ser Gly Asp
        550                 555                 560 ctc ccc tat gat ggg cgg cta ctg gag gag gct gtg agg aag aag ggg      1843
Leu Pro Tyr Asp Gly Arg Leu Leu Glu Glu Ala Val Arg Lys Lys Gly
565                 570                 575                 580 tcg gag gag agg agg aga ccc cac aag gag gag gag gaa gag gcc tac      1891
Ser Glu Glu Arg Arg Arg Pro His Lys Glu Glu Glu Glu Glu Ala Tyr
                585                 590                 595 tac ccg ccc gcg ccg ccc ccg tac tcg gag acc gac tcg cag gcg tcc      1939
Tyr Pro Pro Ala Pro Pro Pro Tyr Ser Glu Thr Asp Ser Gln Ala Ser
                600                 605                 610 cga gag cgc agg ctc aag aag aac ttg gcc ctg agt cgg gaa agt tta      1987
Arg Glu Arg Arg Leu Lys Lys Asn Leu Ala Leu Ser Arg Glu Ser Leu
            615                 620                 625
```

```
gtc gtc tga tctgacgttt tctacgtagc ttttgkattt ttttttttaa          2036
Val Val *
    630 tttgaaggaa cactgatgaa gccctgccat accctcccg agtctaataa aacgtataat   2096 cacaa                                                             2101

<210> SEQ ID NO 5
<211> LENGTH: 630
<212> TYPE: PRT
<213> ORGANISM: Homo sapiens
<220> FEATURE:
<221> NAME/KEY: VARIANT
<222> LOCATION: 344
<223> OTHER INFORMATION: 9-7-325 : polymorphic amino acid Ser or
      Asn
<220> FEATURE:
<221> NAME/KEY: VARIANT
<222> LOCATION: 401
<223> OTHER INFORMATION: 9-9-246 : polymorphic amino acid Pro or
      Arg
<220> FEATURE:
<221> NAME/KEY: VARIANT
<222> LOCATION: 500
<223> OTHER INFORMATION: LSRX9f13-BM : polymorphic amino acid
      deletion of Arg

<400> SEQUENCE: 5
```

Met Gln Gln Asp Gly Leu Gly Val Gly Thr Arg Asn Gly Ser Gly Lys
1               5                   10                  15

Gly Arg Ser Val His Pro Ser Trp Pro Trp Cys Ala Pro Arg Pro Leu
            20                  25                  30

Arg Tyr Phe Gly Arg Asp Ala Arg Ala Arg Ala Gln Thr Ala Ala
        35                  40                  45

Met Ala Leu Leu Ala Gly Gly Leu Ser Arg Gly Leu Gly Ser His Pro
50                  55                  60

Ala Ala Ala Gly Arg Asp Ala Val Val Phe Val Trp Leu Leu Ser
65                  70                  75                  80

Thr Trp Cys Thr Ala Pro Ala Arg Ala Ile Gln Val Thr Val Ser Asn
                85                  90                  95

Pro Tyr His Val Val Ile Leu Phe Gln Pro Val Thr Leu Pro Cys Thr
            100                 105                 110

Tyr Gln Met Thr Ser Thr Pro Thr Gln Pro Ile Val Ile Trp Lys Tyr
        115                 120                 125

Lys Ser Phe Cys Arg Asp Arg Ile Ala Asp Ala Phe Ser Pro Ala Ser
130                 135                 140

Val Asp Asn Gln Leu Asn Ala Gln Leu Ala Ala Gly Asn Pro Gly Tyr
145                 150                 155                 160

Asn Pro Tyr Val Glu Cys Gln Asp Ser Val Arg Thr Val Arg Val Val
                165                 170                 175

Ala Thr Lys Gln Gly Asn Ala Val Thr Leu Gly Asp Tyr Tyr Gln Gly
            180                 185                 190

Arg Arg Ile Thr Ile Thr Gly Asn Ala Asp Leu Thr Phe Asp Gln Thr
        195                 200                 205

Ala Trp Gly Asp Ser Gly Val Tyr Tyr Cys Ser Val Val Ser Ala Gln
210                 215                 220

Asp Leu Gln Gly Asn Asn Glu Ala Tyr Ala Glu Leu Ile Val Leu Asp
225                 230                 235                 240

Trp Leu Phe Val Val Val Val Cys Leu Ala Ala Phe Leu Ile Phe Leu
                245                 250                 255

```
Leu Leu Gly Ile Cys Trp Cys Gln Cys Cys Pro His Thr Cys Cys Cys
            260                 265                 270
Tyr Val Arg Cys Pro Cys Cys Pro Asp Lys Cys Cys Pro Glu Ala
        275                 280                 285
Leu Tyr Ala Ala Gly Lys Ala Thr Ser Gly Val Pro Ser Ile Tyr
    290                 295                 300
Ala Pro Ser Thr Tyr Ala His Leu Ser Pro Ala Lys Thr Pro Pro Pro
305                 310                 315                 320
Pro Ala Met Ile Pro Met Gly Pro Ala Tyr Asn Gly Tyr Pro Gly Gly
                325                 330                 335
Tyr Pro Gly Asp Val Asp Arg Ser Ser Ala Gly Gln Gly Ser
            340                 345                 350
Tyr Val Pro Leu Leu Arg Asp Thr Asp Ser Ser Val Ala Ser Glu Val
            355                 360                 365
Arg Ser Gly Tyr Arg Ile Gln Ala Ser Gln Gln Asp Asp Ser Met Arg
        370                 375                 380
Val Leu Tyr Tyr Met Glu Lys Glu Leu Ala Asn Phe Asp Pro Ser Arg
385                 390                 395                 400
Pro Gly Pro Pro Ser Gly Arg Val Glu Arg Ala Met Ser Glu Val Thr
                405                 410                 415
Ser Leu His Glu Asp Asp Trp Arg Ser Arg Pro Ser Arg Gly Pro Ala
            420                 425                 430
Leu Thr Pro Ile Arg Asp Glu Glu Trp Gly Gly His Ser Pro Arg Ser
        435                 440                 445
Pro Arg Gly Trp Asp Gln Glu Pro Ala Arg Glu Gln Ala Gly Gly Gly
    450                 455                 460
Trp Arg Ala Arg Arg Pro Arg Ala Arg Ser Val Asp Ala Leu Asp Asp
465                 470                 475                 480
Leu Thr Pro Pro Ser Thr Ala Glu Ser Gly Ser Arg Ser Pro Thr Ser
                485                 490                 495
Asn Gly Gly Arg Ser Arg Ala Tyr Met Pro Pro Arg Ser Arg Ser Arg
            500                 505                 510
Asp Asp Leu Tyr Asp Gln Asp Asp Ser Arg Asp Phe Pro Arg Ser Arg
        515                 520                 525
Asp Pro His Tyr Asp Asp Phe Arg Ser Arg Glu Arg Pro Pro Ala Asp
    530                 535                 540
Pro Arg Ser His His His Arg Thr Arg Asp Pro Arg Asp Asn Gly Ser
545                 550                 555                 560
Arg Ser Gly Asp Leu Pro Tyr Asp Gly Arg Leu Leu Glu Glu Ala Val
                565                 570                 575
Arg Lys Lys Gly Ser Glu Glu Arg Arg Pro His Lys Glu Glu Glu
            580                 585                 590
Glu Glu Ala Tyr Tyr Pro Pro Ala Pro Pro Tyr Ser Glu Thr Asp
        595                 600                 605
Ser Gln Ala Ser Arg Glu Arg Arg Leu Lys Lys Asn Leu Ala Leu Ser
    610                 615                 620
Arg Glu Ser Leu Val Val
625                 630

<210> SEQ ID NO 6
<211> LENGTH: 1954
<212> TYPE: DNA
<213> ORGANISM: Homo sapiens
<220> FEATURE:
<221> NAME/KEY: allele
```

```
<222> LOCATION: 595
<223> OTHER INFORMATION: 9-3-324 : polymorphic base C or T
<220> FEATURE:
<221> NAME/KEY: allele
<222> LOCATION: 987
<223> OTHER INFORMATION: 9-7-325 : polymorphic base A or G
<220> FEATURE:
<221> NAME/KEY: allele
<222> LOCATION: 1158
<223> OTHER INFORMATION: 9-9-246 : polymorphic base G or C
<220> FEATURE:
<221> NAME/KEY: allele
<222> LOCATION: 1454
<223> OTHER INFORMATION: LSRX9f13-BM : polymorphic base deletion of
      AGG
<220> FEATURE:
<221> NAME/KEY: allele
<222> LOCATION: 1875
<223> OTHER INFORMATION: LSRX9f14-BM : polymorphic base T or G

<400> SEQUENCE: 6
```

| | |
|---|---:|
| tggagtgtgg ctcggaggac cgcggcgggt caagcacctt tctcccccat atctgaaagc | 60 |

| | | | | | | | | | | | | | | | | |
|---|---|---|---|---|---|---|---|---|---|---|---|---|---|---|---|---:|
| atgcccttt tccacgtcgt ttacgctcat taaaacttcc | aga | atg | caa | cag | gac | | | | | | | | | | | 115 |
| | Arg | Met | Gln | Gln | Asp | | | | | | | | | | | |
| | | 1 | | | | | | | | | | | | | | |

| | | | | | | | | | | | | | | | |
|---|---|---|---|---|---|---|---|---|---|---|---|---|---|---|---:|
| gga | ctt | gga | gta | ggg | aca | agg | aac | gga | agt | ggg | aag | ggg | agg | agc | gtg | 163 |
| Gly | Leu | Gly | Val | Gly | Thr | Arg | Asn | Gly | Ser | Gly | Lys | Gly | Arg | Ser | Val | |
| 5 | | | | 10 | | | | | 15 | | | | | 20 | | |

| | | | | | | | | | | | | | | | |
|---|---|---|---|---|---|---|---|---|---|---|---|---|---|---|---|---:|
| cac | ccc | tcc | tgg | cct | tgg | tgc | gcg | ccg | cgc | ccc | cta | agg | tac | ttt | gga | 211 |
| His | Pro | Ser | Trp | Pro | Trp | Cys | Ala | Pro | Arg | Pro | Leu | Arg | Tyr | Phe | Gly | |
| | | | 25 | | | | | 30 | | | | | 35 | | | |

| | | | | | | | | | | | | | | | |
|---|---|---|---|---|---|---|---|---|---|---|---|---|---|---|---|---:|
| agg | gac | gcg | cgg | gcc | aga | cgc | gcc | cag | acg | gcc | gcg | atg | gcg | ctg | ttg | 259 |
| Arg | Asp | Ala | Arg | Ala | Arg | Arg | Ala | Gln | Thr | Ala | Ala | Met | Ala | Leu | Leu | |
| | | 40 | | | | | 45 | | | | | 50 | | | | |

| | | | | | | | | | | | | | | | |
|---|---|---|---|---|---|---|---|---|---|---|---|---|---|---|---|---:|
| gcc | ggc | ggg | ctc | tcc | aga | ggg | ctg | ggc | tcc | cac | ccg | gcc | gcc | gca | ggc | 307 |
| Ala | Gly | Gly | Leu | Ser | Arg | Gly | Leu | Gly | Ser | His | Pro | Ala | Ala | Ala | Gly | |
| | 55 | | | | | 60 | | | | | 65 | | | | | |

| | | | | | | | | | | | | | | | |
|---|---|---|---|---|---|---|---|---|---|---|---|---|---|---|---|---:|
| cgg | gac | gcg | gtc | gtc | ttc | gtg | tgg | ctt | ctg | ctt | agc | acc | tgg | tgc | aca | 355 |
| Arg | Asp | Ala | Val | Val | Phe | Val | Trp | Leu | Leu | Leu | Ser | Thr | Trp | Cys | Thr | |
| 70 | | | | | 75 | | | | | 80 | | | | | | |

| | | | | | | | | | | | | | | | |
|---|---|---|---|---|---|---|---|---|---|---|---|---|---|---|---|---:|
| gct | cct | gcc | agg | gcc | atc | cag | gtg | acc | gtg | tcc | aac | ccc | tac | cac | gtg | 403 |
| Ala | Pro | Ala | Arg | Ala | Ile | Gln | Val | Thr | Val | Ser | Asn | Pro | Tyr | His | Val | |
| 85 | | | | 90 | | | | | 95 | | | | | 100 | | |

| | | | | | | | | | | | | | | | |
|---|---|---|---|---|---|---|---|---|---|---|---|---|---|---|---|---:|
| gtg | atc | ctc | ttc | cag | cct | gtg | acc | ctg | ccc | tgt | acc | tac | cag | atg | acc | 451 |
| Val | Ile | Leu | Phe | Gln | Pro | Val | Thr | Leu | Pro | Cys | Thr | Tyr | Gln | Met | Thr | |
| | | | | 105 | | | | | 110 | | | | | 115 | | |

| | | | | | | | | | | | | | | | |
|---|---|---|---|---|---|---|---|---|---|---|---|---|---|---|---|---:|
| tcg | acc | ccc | acg | caa | ccc | atc | gtc | atc | tgg | aag | tac | aag | tct | ttc | tgc | 499 |
| Ser | Thr | Pro | Thr | Gln | Pro | Ile | Val | Ile | Trp | Lys | Tyr | Lys | Ser | Phe | Cys | |
| | | | 120 | | | | | 125 | | | | | 130 | | | |

| | | | | | | | | | | | | | | | |
|---|---|---|---|---|---|---|---|---|---|---|---|---|---|---|---|---:|
| cgg | gac | cgc | atc | gcc | gat | gcc | ttc | tcc | ccg | gcc | agc | gtc | gac | aac | cag | 547 |
| Arg | Asp | Arg | Ile | Ala | Asp | Ala | Phe | Ser | Pro | Ala | Ser | Val | Asp | Asn | Gln | |
| | | 135 | | | | | 140 | | | | | 145 | | | | |

| | | | | | | | | | | | | | | | |
|---|---|---|---|---|---|---|---|---|---|---|---|---|---|---|---|---:|
| ctc | aat | gcc | cag | ctg | gca | gcc | ggg | aac | cca | ggc | tac | aac | ccc | tac | gty | 595 |
| Leu | Asn | Ala | Gln | Leu | Ala | Ala | Gly | Asn | Pro | Gly | Tyr | Asn | Pro | Tyr | Val | |
| | 150 | | | | | 155 | | | | | 160 | | | | | |

| | | | | | | | | | | | | | | | |
|---|---|---|---|---|---|---|---|---|---|---|---|---|---|---|---|---:|
| gag | tgc | cag | gac | agc | gtg | cgc | acc | gtc | agg | gtc | gtg | gcc | acc | aag | cag | 643 |
| Glu | Cys | Gln | Asp | Ser | Val | Arg | Thr | Val | Arg | Val | Val | Ala | Thr | Lys | Gln | |
| 165 | | | | 170 | | | | | 175 | | | | | 180 | | |

| | | | | | | | | | | | | | | | |
|---|---|---|---|---|---|---|---|---|---|---|---|---|---|---|---|---:|
| ggc | aac | gct | gtg | acc | ctg | gga | gat | tac | tac | cag | ggc | cgg | agg | att | acc | 691 |
| Gly | Asn | Ala | Val | Thr | Leu | Gly | Asp | Tyr | Tyr | Gln | Gly | Arg | Arg | Ile | Thr | |
| | | | 185 | | | | | 190 | | | | | 195 | | | |

| | | | | | | | | | | | | | | | |
|---|---|---|---|---|---|---|---|---|---|---|---|---|---|---|---|---:|
| atc | acc | gga | aat | gct | gac | ctg | acc | ttt | gac | cag | acg | gcg | tgg | ggg | gac | 739 |
| Ile | Thr | Gly | Asn | Ala | Asp | Leu | Thr | Phe | Asp | Gln | Thr | Ala | Trp | Gly | Asp | |
| | | 200 | | | | | 205 | | | | | 210 | | | | |

-continued

| | |
|---|---|
| agt ggt gtg tat tac tgc tcc gtg gtc tca gcc cag gac ctc cag ggg<br>Ser Gly Val Tyr Tyr Cys Ser Val Val Ser Ala Gln Asp Leu Gln Gly<br>215                    220                225 | 787 |
| aac aat gag gcc tac gca gag ctc atc gtc ctt gtg tat gcc gcc ggc<br>Asn Asn Glu Ala Tyr Ala Glu Leu Ile Val Leu Val Tyr Ala Ala Gly<br>230                    235                240 | 835 |
| aaa gca gcc acc tca ggt gtt ccc agc att tat gcc ccc agc acc tat<br>Lys Ala Ala Thr Ser Gly Val Pro Ser Ile Tyr Ala Pro Ser Thr Tyr<br>245                    250                255              260 | 883 |
| gcc cac ctg tct ccc gcc aag acc cca ccc cca gct atg att ccc<br>Ala His Leu Ser Pro Ala Lys Thr Pro Pro Pro Ala Met Ile Pro<br>                265                270              275 | 931 |
| atg ggc cct gcc tac aac ggg tac cct gga gga tac cct gga gac gtt<br>Met Gly Pro Ala Tyr Asn Gly Tyr Pro Gly Gly Tyr Pro Gly Asp Val<br>          280                285                290 | 979 |
| gac agg art agc tca gct ggt ggc caa ggc tcc tat gta ccc ctg ctt<br>Asp Arg Xaa Ser Ser Ala Gly Gly Gln Gly Ser Tyr Val Pro Leu Leu<br>             295                300              305 | 1027 |
| cgg gac acg gac agc agt gtg gcc tct gaa gtc cgc agt ggc tac agg<br>Arg Asp Thr Asp Ser Ser Val Ala Ser Glu Val Arg Ser Gly Tyr Arg<br>310                    315                320 | 1075 |
| att cag gcc agc cag cag gac gac tcc atg cgg gtc ctg tac tac atg<br>Ile Gln Ala Ser Gln Gln Asp Asp Ser Met Arg Val Leu Tyr Tyr Met<br>325                    330                335              340 | 1123 |
| gag aag gag ctg gcc aac ttc gac cct tct cga cst ggc ccc ccc agt<br>Glu Lys Glu Leu Ala Asn Phe Asp Pro Ser Arg Xaa Gly Pro Pro Ser<br>             345                350              355 | 1171 |
| ggc cgt gtg gag cgg gcc atg agt gaa gtc acc tcc ctc cac gag gac<br>Gly Arg Val Glu Arg Ala Met Ser Glu Val Thr Ser Leu His Glu Asp<br>          360                365                370 | 1219 |
| gac tgg cga tct cgg cct tcc cgg ggc cct gcc ctc acc ccg atc cgg<br>Asp Trp Arg Ser Arg Pro Ser Arg Gly Pro Ala Leu Thr Pro Ile Arg<br>             375                380              385 | 1267 |
| gat gag gag tgg ggt ggc cac tcc ccc cgg agt ccc agg gga tgg gac<br>Asp Glu Glu Trp Gly Gly His Ser Pro Arg Ser Pro Arg Gly Trp Asp<br>390                    395                400 | 1315 |
| cag gag ccc gcc agg gag cag gca ggc ggg ggc tgg cgg gcc agg cgg<br>Gln Glu Pro Ala Arg Glu Gln Ala Gly Gly Gly Trp Arg Ala Arg Arg<br>405                    410                415              420 | 1363 |
| ccc cgg gcc cgc tcc gtg gac gcc ctg gac gac ctc acc ccg ccg agc<br>Pro Arg Ala Arg Ser Val Asp Ala Leu Asp Asp Leu Thr Pro Pro Ser<br>             425                430              435 | 1411 |
| acc gcc gag tca ggg agc agg tct ccc acg agt aat ggt ggg aga agc<br>Thr Ala Glu Ser Gly Ser Arg Ser Pro Thr Ser Asn Gly Gly Arg Ser<br>          440                445                450 | 1459 |
| cgg gcc tac atg ccc ccg cgg agc cgc agc cgg gac gac ctc tat gac<br>Arg Ala Tyr Met Pro Pro Arg Ser Arg Ser Arg Asp Asp Leu Tyr Asp<br>             455                460              465 | 1507 |
| caa gac gac tcg agg gac ttc cca cgc tcc cgg gac ccc cac tac gac<br>Gln Asp Asp Ser Arg Asp Phe Pro Arg Ser Arg Asp Pro His Tyr Asp<br>470                    475                480 | 1555 |
| gac ttc agg tct cgg gag cgc cct cct gcc gac ccc agg tcc cac cac<br>Asp Phe Arg Ser Arg Glu Arg Pro Pro Ala Asp Pro Arg Ser His His<br>485                    490                495              500 | 1603 |
| cac cgt acc cgg gac cct cgg gac aac ggc tcc agg tcc ggg gac ctc<br>His Arg Thr Arg Asp Pro Arg Asp Asn Gly Ser Arg Ser Gly Asp Leu<br>             505                510              515 | 1651 |
| ccc tat gat ggg cgg cta ctg gag gag gct gtg agg aag aag ggg tcg<br>Pro Tyr Asp Gly Arg Leu Leu Glu Glu Ala Val Arg Lys Lys Gly Ser | 1699 |

-continued

```
                520                 525                 530
gag gag agg agg aga ccc cac aag gag gag gaa gag gcc tac tac      1747
Glu Glu Arg Arg Arg Pro His Lys Glu Glu Glu Glu Ala Tyr Tyr
            535                 540                 545 ccg ccc gcg ccg ccc ccg tac tcg gag acc gac tcg cag gcg tcc cga  1795
Pro Pro Ala Pro Pro Pro Tyr Ser Glu Thr Asp Ser Gln Ala Ser Arg
    550                 555                 560 gag cgc agg ctc aag aag aac ttg gcc ctg agt cgg gaa agt tta gtc  1843
Glu Arg Arg Leu Lys Lys Asn Leu Ala Leu Ser Arg Glu Ser Leu Val
565                 570                 575                 580 gtc tga tctgacgttt tctacgtagc ttttgkattt ttttttttaa tttgaaggaa   1899
Val * cactgatgaa gccctgccat acccctcccg agtctaataa aacgtataat cacaa     1954
```

<210> SEQ ID NO 7
<211> LENGTH: 581
<212> TYPE: PRT
<213> ORGANISM: Homo sapiens
<220> FEATURE:
<221> NAME/KEY: VARIANT
<222> LOCATION: 295
<223> OTHER INFORMATION: 9-7-325 : polymorphic amino acid Ser or Asn
<220> FEATURE:
<221> NAME/KEY: VARIANT
<222> LOCATION: 352
<223> OTHER INFORMATION: 9-9-246 : polymorphic amino acid Pro or Arg
<220> FEATURE:
<221> NAME/KEY: VARIANT
<222> LOCATION: 451
<223> OTHER INFORMATION: LSRX9f13-BM : polymorphic amino acid deletion of Arg

<400> SEQUENCE: 7

```
Met Gln Gln Asp Gly Leu Gly Val Gly Thr Arg Asn Gly Ser Gly Lys
1               5                   10                  15

Gly Arg Ser Val His Pro Ser Trp Pro Trp Cys Ala Pro Arg Pro Leu
            20                  25                  30

Arg Tyr Phe Gly Arg Asp Ala Arg Arg Ala Gln Thr Ala Ala
        35                  40                  45

Met Ala Leu Leu Ala Gly Gly Leu Ser Arg Gly Leu Gly Ser His Pro
    50                  55                  60

Ala Ala Ala Gly Arg Asp Ala Val Val Phe Val Trp Leu Leu Leu Ser
65                  70                  75                  80

Thr Trp Cys Thr Ala Pro Ala Arg Ala Ile Gln Val Thr Val Ser Asn
                85                  90                  95

Pro Tyr His Val Val Ile Leu Phe Gln Pro Val Thr Leu Pro Cys Thr
            100                 105                 110

Tyr Gln Met Thr Ser Thr Pro Thr Gln Pro Ile Val Ile Trp Lys Tyr
        115                 120                 125

Lys Ser Phe Cys Arg Asp Arg Ile Ala Asp Ala Phe Ser Pro Ala Ser
    130                 135                 140

Val Asp Asn Gln Leu Asn Ala Gln Leu Ala Ala Gly Asn Pro Gly Tyr
145                 150                 155                 160

Asn Pro Tyr Val Glu Cys Gln Asp Ser Val Arg Thr Val Arg Val Val
                165                 170                 175

Ala Thr Lys Gln Gly Asn Ala Val Thr Leu Gly Asp Tyr Tyr Gln Gly
            180                 185                 190

Arg Arg Ile Thr Ile Thr Gly Asn Ala Asp Leu Thr Phe Asp Gln Thr
```

```
                195                 200                 205
Ala Trp Gly Asp Ser Gly Val Tyr Tyr Cys Ser Val Ser Ala Gln
    210                 215                 220

Asp Leu Gln Gly Asn Asn Glu Ala Tyr Ala Glu Leu Ile Val Leu Val
225                 230                 235                 240

Tyr Ala Ala Gly Lys Ala Ala Thr Ser Gly Val Pro Ser Ile Tyr Ala
                245                 250                 255

Pro Ser Thr Tyr Ala His Leu Ser Pro Ala Lys Thr Pro Pro Pro
            260                 265                 270

Ala Met Ile Pro Met Gly Pro Ala Tyr Asn Gly Tyr Pro Gly Gly Tyr
                275                 280                 285

Pro Gly Asp Val Asp Arg Ser Ser Ser Ala Gly Gln Gly Ser Tyr
        290                 295                 300

Val Pro Leu Leu Arg Asp Thr Asp Ser Ser Val Ala Ser Glu Val Arg
305                 310                 315                 320

Ser Gly Tyr Arg Ile Gln Ala Ser Gln Gln Asp Ser Met Arg Val
                325                 330                 335

Leu Tyr Tyr Met Glu Lys Glu Leu Ala Asn Phe Asp Pro Ser Arg Pro
                340                 345                 350

Gly Pro Pro Ser Gly Arg Val Glu Arg Ala Met Ser Glu Val Thr Ser
                355                 360                 365

Leu His Glu Asp Asp Trp Arg Ser Arg Pro Ser Arg Gly Pro Ala Leu
        370                 375                 380

Thr Pro Ile Arg Asp Glu Glu Trp Gly His Ser Pro Arg Ser Pro
385                 390                 395                 400

Arg Gly Trp Asp Gln Glu Pro Ala Arg Glu Gln Ala Gly Gly Trp
                405                 410                 415

Arg Ala Arg Arg Pro Arg Ala Arg Ser Val Asp Ala Leu Asp Asp Leu
                420                 425                 430

Thr Pro Pro Ser Thr Ala Glu Ser Gly Ser Arg Ser Pro Thr Ser Asn
            435                 440                 445

Gly Gly Arg Ser Arg Ala Tyr Met Pro Pro Arg Ser Arg Ser Arg Asp
450                 455                 460

Asp Leu Tyr Asp Gln Asp Asp Ser Arg Asp Phe Pro Arg Ser Arg Asp
465                 470                 475                 480

Pro His Tyr Asp Asp Phe Arg Ser Arg Glu Arg Pro Pro Ala Asp Pro
                485                 490                 495

Arg Ser His His His Arg Thr Arg Asp Pro Arg Asp Asn Gly Ser Arg
                500                 505                 510

Ser Gly Asp Leu Pro Tyr Asp Gly Arg Leu Leu Glu Glu Ala Val Arg
            515                 520                 525

Lys Lys Gly Ser Glu Glu Arg Arg Pro His Lys Glu Glu Glu Glu
530                 535                 540

Glu Ala Tyr Tyr Pro Pro Ala Pro Pro Pro Tyr Ser Glu Thr Asp Ser
545                 550                 555                 560

Gln Ala Ser Arg Glu Arg Arg Leu Lys Lys Asn Leu Ala Leu Ser Arg
                565                 570                 575

Glu Ser Leu Val Val
            580

<210> SEQ ID NO 8
<211> LENGTH: 2097
<212> TYPE: DNA
<213> ORGANISM: Rattus norvegicus
```

-continued

```
<400> SEQUENCE: 8
accgctcacc aggtcagttg tccccggaaa gccgaaggca tgagcttcgc ccaagttctt      60
tttatgggtt agaactcctc cagagcgggg gaaaaaggac ttggaatagg ggcgggacgg     120
agcacgcacc cttctccgcc ttggttctcg ccgcgccccc tactctcggg atacttggga    180
ggggacgcgc gggcaccgtc gctgctagac ggccgcg atg gcg ccg gcg gcc ggc     235
                                          Met Ala Pro Ala Ala Gly
                                           1               5 gcg tgt gct ggg gcg cct gac tcc cac cca gct acc gtg gtc ttc gtg     283
Ala Cys Ala Gly Ala Pro Asp Ser His Pro Ala Thr Val Val Phe Val
             10                  15                  20 tgt ctc ttt ctc atc att ttc tgc cca gac cct gcc agt gcc atc cag     331
Cys Leu Phe Leu Ile Ile Phe Cys Pro Asp Pro Ala Ser Ala Ile Gln
         25                  30                  35 gtg act gtg tct gac ccc tac cac gta gtg atc ctg ttc cag cca gtg     379
Val Thr Val Ser Asp Pro Tyr His Val Val Ile Leu Phe Gln Pro Val
     40                  45                  50 acc ctg ccc tgc acc tat cag atg agc aac act ctc aca gtc ccc atc     427
Thr Leu Pro Cys Thr Tyr Gln Met Ser Asn Thr Leu Thr Val Pro Ile
 55                  60                  65                  70 gtg atc tgg aag tac aag tca ttc tgc cgg gac cgt att gcc gat gcc     475
Val Ile Trp Lys Tyr Lys Ser Phe Cys Arg Asp Arg Ile Ala Asp Ala
                 75                  80                  85 ttc tct cct gcc agt gtg gac aac cag cta aat gcc cag ttg gca gct     523
Phe Ser Pro Ala Ser Val Asp Asn Gln Leu Asn Ala Gln Leu Ala Ala
             90                  95                 100 ggc aac ccc ggc tac aac ccc tat gtg gag tgc cag gac agt gta cgc     571
Gly Asn Pro Gly Tyr Asn Pro Tyr Val Glu Cys Gln Asp Ser Val Arg
        105                 110                 115 act gtc agg gtg gtg gcc acc aaa cag ggc aat gcg gtg acc ctg gga     619
Thr Val Arg Val Val Ala Thr Lys Gln Gly Asn Ala Val Thr Leu Gly
    120                 125                 130 gac tac tac caa ggc agg agg atc acc ata aca gga aat gct gac ctg     667
Asp Tyr Tyr Gln Gly Arg Arg Ile Thr Ile Thr Gly Asn Ala Asp Leu
135                 140                 145                 150 acc ttc gag cag aca gcc tgg gga gac agt gga gtg tat tac tgc tct     715
Thr Phe Glu Gln Thr Ala Trp Gly Asp Ser Gly Val Tyr Tyr Cys Ser
                155                 160                 165 gtg gtc tcg gcc caa gat ctg gat gga aac aac gag gcg tac gca gag     763
Val Val Ser Ala Gln Asp Leu Asp Gly Asn Asn Glu Ala Tyr Ala Glu
            170                 175                 180 ctc atc gtc ctt ggc agg acc tca gag gcc cct gag ctc cta cct ggt     811
Leu Ile Val Leu Gly Arg Thr Ser Glu Ala Pro Glu Leu Leu Pro Gly
        185                 190                 195 ttt cgg gcg ggg ccc ttg gaa gat tgg ctc ttt gtg gtc gtg gtc tgc     859
Phe Arg Ala Gly Pro Leu Glu Asp Trp Leu Phe Val Val Val Val Cys
    200                 205                 210 ctg gcg agc ctc ctc ctc ttc ctc ctc ctg ggc atc tgc tgg tgc cag     907
Leu Ala Ser Leu Leu Leu Phe Leu Leu Leu Gly Ile Cys Trp Cys Gln
215                 220                 225                 230 tgc tgt cct cac acc tgc tgc tgc tat gtc cga tgt ccc tgc tgc cca     955
Cys Cys Pro His Thr Cys Cys Cys Tyr Val Arg Cys Pro Cys Cys Pro
                235                 240                 245 gac aag tgc tgt tgc cct gag gct ctt tat gct gct ggc aaa gca gcc    1003
Asp Lys Cys Cys Cys Pro Glu Ala Leu Tyr Ala Ala Gly Lys Ala Ala
            250                 255                 260 acc tca ggt gtc ccg agc atc tat gcc ccc agc atc tat acc cac ctc    1051
Thr Ser Gly Val Pro Ser Ile Tyr Ala Pro Ser Ile Tyr Thr His Leu
```

-continued

```
                265                 270                 275
tca cct gcc aag acc cca cca cct ccg cct gcc atg att ccc atg ggc        1099
Ser Pro Ala Lys Thr Pro Pro Pro Pro Ala Met Ile Pro Met Gly
280                 285                 290 cct ccc tat ggg tac cct gga gac ttt gac aga cat agc tca gtt ggt        1147
Pro Pro Tyr Gly Tyr Pro Gly Asp Phe Asp Arg His Ser Ser Val Gly
295                 300                 305                 310 ggc cac agc tcc caa gta ccc ctg ctg cgt gac gtg gat ggc agt gta        1195
Gly His Ser Ser Gln Val Pro Leu Leu Arg Asp Val Asp Gly Ser Val
            315                 320                 325 tct tca gaa gta cga agt ggc tac agg atc cag gct aac cag caa gat        1243
Ser Ser Glu Val Arg Ser Gly Tyr Arg Ile Gln Ala Asn Gln Gln Asp
330                 335                 340 gac tcc atg agg gtc cta tac tat atg gag aaa gag cta gcc aac ttt        1291
Asp Ser Met Arg Val Leu Tyr Tyr Met Glu Lys Glu Leu Ala Asn Phe
            345                 350                 355 gac cct tcc cga cct ggc cct ccc aat ggc aga gtg gaa cgg gcc atg        1339
Asp Pro Ser Arg Pro Gly Pro Pro Asn Gly Arg Val Glu Arg Ala Met
360                 365                 370 agt gaa gta acc tcc ctc cat gaa gat gac tgg cga tcg agg cct tcc        1387
Ser Glu Val Thr Ser Leu His Glu Asp Asp Trp Arg Ser Arg Pro Ser
375                 380                 385                 390 agg gct cct gcc ctc acc ccc atc agg gat gag gag tgg aat cgc cac        1435
Arg Ala Pro Ala Leu Thr Pro Ile Arg Asp Glu Glu Trp Asn Arg His
            395                 400                 405 tcc cca cag agt ccc aga aca tgg gag cag gaa ccc ctt caa gaa caa        1483
Ser Pro Gln Ser Pro Arg Thr Trp Glu Gln Glu Pro Leu Gln Glu Gln
            410                 415                 420 cca agg ggt ggt tgg ggg tct gga cgc cct cgg gcc cgc tct gtg gat        1531
Pro Arg Gly Gly Trp Gly Ser Gly Arg Pro Arg Ala Arg Ser Val Asp
            425                 430                 435 gct cta gat gat atc aac cgg cct ggc tcc act gaa tca gga cgg tct        1579
Ala Leu Asp Asp Ile Asn Arg Pro Gly Ser Thr Glu Ser Gly Arg Ser
440                 445                 450 tct ccc cca agt agt gga cgg aga gga cgg gcc tat gca cct cca aga        1627
Ser Pro Pro Ser Ser Gly Arg Arg Gly Arg Ala Tyr Ala Pro Pro Arg
455                 460                 465                 470 agt cgc agc cgg gat gac ctc tat gac ccg gac gat cct agg gac ttg        1675
Ser Arg Ser Arg Asp Asp Leu Tyr Asp Pro Asp Asp Pro Arg Asp Leu
            475                 480                 485 cca cat tcc cga gat ccc cac tat tat gac gac atc agg tct aga gat        1723
Pro His Ser Arg Asp Pro His Tyr Tyr Asp Asp Ile Arg Ser Arg Asp
            490                 495                 500 cca cgt gct gac ccc aga tcc cgt cag cga tcc cga gat cct cgg gat        1771
Pro Arg Ala Asp Pro Arg Ser Arg Gln Arg Ser Arg Asp Pro Arg Asp
            505                 510                 515 gct ggc ttc agg tca agg gac cct cag tat gat ggg cga cta tta gaa        1819
Ala Gly Phe Arg Ser Arg Asp Pro Gln Tyr Asp Gly Arg Leu Leu Glu
520                 525                 530 gag gct tta aag aaa aag ggg tcg ggc gag aga agg agg gtt tac agg        1867
Glu Ala Leu Lys Lys Lys Gly Ser Gly Glu Arg Arg Arg Val Tyr Arg
535                 540                 545                 550 gag gaa gaa gag gaa gag gag ggc caa tac ccc cca gca cct cca cct        1915
Glu Glu Glu Glu Glu Glu Glu Gly Gln Tyr Pro Pro Ala Pro Pro Pro
            555                 560                 565 tac tca gag act gac tcg cag gcc tca cgg gag agg agg ctg aaa aag        1963
Tyr Ser Glu Thr Asp Ser Gln Ala Ser Arg Glu Arg Arg Leu Lys Lys
570                 575                 580 aat ttg gcc ctg agt cgg gaa agt tta gtc gtc tga tccacgtttt            2009
```

Asn Leu Ala Leu Ser Arg Glu Ser Leu Val Val *
        585                 590 gtatgtagct tttgtacttt tttttaatt ggaatcaata ttgatgaaac ttcaagccta    2069
ataaaatgtc taatcacaaa aaaaaaaa                                      2097

<210> SEQ ID NO 9
<211> LENGTH: 593
<212> TYPE: PRT
<213> ORGANISM: Rattus norvegicus

<400> SEQUENCE: 9

Met Ala Pro Ala Ala Gly Ala Cys Ala Gly Ala Pro Asp Ser His Pro
1               5                   10                  15

Ala Thr Val Val Phe Val Cys Leu Phe Leu Ile Ile Phe Cys Pro Asp
            20                  25                  30

Pro Ala Ser Ala Ile Gln Val Thr Val Ser Asp Pro Tyr His Val Val
        35                  40                  45

Ile Leu Phe Gln Pro Val Thr Leu Pro Cys Thr Tyr Gln Met Ser Asn
    50                  55                  60

Thr Leu Thr Val Pro Ile Val Ile Trp Lys Tyr Lys Ser Phe Cys Arg
65                  70                  75                  80

Asp Arg Ile Ala Asp Ala Phe Ser Pro Ala Ser Val Asp Asn Gln Leu
                85                  90                  95

Asn Ala Gln Leu Ala Ala Gly Asn Pro Gly Tyr Asn Pro Tyr Val Glu
            100                 105                 110

Cys Gln Asp Ser Val Arg Thr Val Arg Val Ala Thr Lys Gln Gly
        115                 120                 125

Asn Ala Val Thr Leu Gly Asp Tyr Tyr Gln Gly Arg Arg Ile Thr Ile
    130                 135                 140

Thr Gly Asn Ala Asp Leu Thr Phe Glu Gln Thr Ala Trp Gly Asp Ser
145                 150                 155                 160

Gly Val Tyr Tyr Cys Ser Val Ser Ala Gln Asp Leu Asp Gly Asn
                165                 170                 175

Asn Glu Ala Tyr Ala Glu Leu Ile Val Leu Gly Arg Thr Ser Glu Ala
            180                 185                 190

Pro Glu Leu Leu Pro Gly Phe Arg Ala Gly Pro Leu Glu Asp Trp Leu
        195                 200                 205

Phe Val Val Val Cys Leu Ala Ser Leu Leu Phe Leu Leu Leu
    210                 215                 220

Gly Ile Cys Trp Cys Gln Cys Cys Pro His Thr Cys Cys Cys Tyr Val
225                 230                 235                 240

Arg Cys Pro Cys Cys Pro Asp Lys Cys Cys Cys Pro Glu Ala Leu Tyr
                245                 250                 255

Ala Ala Gly Lys Ala Ala Thr Ser Gly Val Pro Ser Ile Tyr Ala Pro
            260                 265                 270

Ser Ile Tyr Thr His Leu Ser Pro Ala Lys Thr Pro Pro Pro Pro
        275                 280                 285

Ala Met Ile Pro Met Gly Pro Tyr Gly Tyr Pro Gly Asp Phe Asp
    290                 295                 300

Arg His Ser Ser Val Gly Gly His Ser Gln Val Pro Leu Leu Arg
305                 310                 315                 320

Asp Val Asp Gly Ser Val Ser Ser Glu Val Arg Ser Gly Tyr Arg Ile
                325                 330                 335

Gln Ala Asn Gln Gln Asp Asp Ser Met Arg Val Leu Tyr Tyr Met Glu

```
                        340                 345                 350
Lys Glu Leu Ala Asn Phe Asp Pro Ser Arg Pro Gly Pro Asn Gly
                355                 360                 365

Arg Val Glu Arg Ala Met Ser Glu Val Thr Ser Leu His Glu Asp Asp
370                 375                 380

Trp Arg Ser Arg Pro Ser Arg Ala Pro Ala Leu Thr Pro Ile Arg Asp
385                 390                 395                 400

Glu Glu Trp Asn Arg His Ser Pro Gln Ser Pro Arg Thr Trp Glu Gln
                405                 410                 415

Glu Pro Leu Gln Glu Gln Pro Arg Gly Gly Trp Gly Ser Gly Arg Pro
            420                 425                 430

Arg Ala Arg Ser Val Asp Ala Leu Asp Asp Ile Asn Arg Pro Gly Ser
                435                 440                 445

Thr Glu Ser Gly Arg Ser Ser Pro Ser Ser Gly Arg Arg Gly Arg
        450                 455                 460

Ala Tyr Ala Pro Pro Arg Ser Arg Ser Arg Asp Asp Leu Tyr Asp Pro
465                 470                 475                 480

Asp Asp Pro Arg Asp Leu Pro His Ser Arg Asp Pro His Tyr Tyr Asp
                485                 490                 495

Asp Ile Arg Ser Arg Asp Pro Arg Ala Asp Pro Arg Ser Arg Gln Arg
            500                 505                 510

Ser Arg Asp Pro Arg Asp Ala Gly Phe Arg Ser Arg Asp Pro Gln Tyr
        515                 520                 525

Asp Gly Arg Leu Leu Glu Glu Ala Leu Lys Lys Gly Ser Gly Glu
            530                 535                 540

Arg Arg Arg Val Tyr Arg Glu Glu Glu Glu Glu Gly Gln Tyr
545                 550                 555                 560

Pro Pro Ala Pro Pro Tyr Ser Glu Thr Asp Ser Gln Ala Ser Arg
                565                 570                 575

Glu Arg Arg Leu Lys Lys Asn Leu Ala Leu Ser Arg Glu Ser Leu Val
            580                 585                 590

Val

<210> SEQ ID NO 10
<211> LENGTH: 2040
<212> TYPE: DNA
<213> ORGANISM: Rattus norvegicus

<400> SEQUENCE: 10
accgctcacc aggtcagttg tccccggaaa gccgaaggca tgagcttcgc ccaagttctt      60
tttatgggtt agaactcctc cagagcgggg gaaaaaggac ttggaatagg ggcgggacgg     120
agcacgcacc cttctccgcc ttggttctcg ccgcgccccc tactctcggg atacttggga     180
ggggacgcgc gggcaccgtc gctgctagac ggccgcg atg gcg ccg gcg gcc ggc     235
                                          Met Ala Pro Ala Ala Gly
                                            1               5 gcg tgt gct ggg gcg cct gac tcc cac cca gct acc gtg gtc ttc gtg     283
Ala Cys Ala Gly Ala Pro Asp Ser His Pro Ala Thr Val Val Phe Val
            10                  15                  20 tgt ctc ttt ctc atc att ttc tgc cca gac cct gcc agt gcc atc cag     331
Cys Leu Phe Leu Ile Ile Phe Cys Pro Asp Pro Ala Ser Ala Ile Gln
        25                  30                  35 gtg act gtg tct gac ccc tac cac gta gtg atc ctg ttc cag cca gtg     379
Val Thr Val Ser Asp Pro Tyr His Val Val Ile Leu Phe Gln Pro Val
    40                  45                  50
```

```
acc ctg ccc tgc acc tat cag atg agc aac act ctc aca gtc ccc atc         427
Thr Leu Pro Cys Thr Tyr Gln Met Ser Asn Thr Leu Thr Val Pro Ile
55                  60                  65                  70 gtg atc tgg aag tac aag tca ttc tgc cgg gac cgt att gcc gat gcc         475
Val Ile Trp Lys Tyr Lys Ser Phe Cys Arg Asp Arg Ile Ala Asp Ala
                75                  80                  85 ttc tct cct gcc agt gtg gac aac cag cta aat gcc cag ttg gca gct         523
Phe Ser Pro Ala Ser Val Asp Asn Gln Leu Asn Ala Gln Leu Ala Ala
            90                  95                  100 ggc aac ccc ggc tac aac ccc tat gtg gag tgc cag gac agt gta cgc         571
Gly Asn Pro Gly Tyr Asn Pro Tyr Val Glu Cys Gln Asp Ser Val Arg
        105                 110                 115 act gtc agg gtg gtg gcc acc aaa cag ggc aat gcg gtg acc ctg gga         619
Thr Val Arg Val Val Ala Thr Lys Gln Gly Asn Ala Val Thr Leu Gly
120                 125                 130 gac tac tac caa ggc agg agg atc acc ata aca gga aat gct gac ctg         667
Asp Tyr Tyr Gln Gly Arg Arg Ile Thr Ile Thr Gly Asn Ala Asp Leu
135                 140                 145                 150 acc ttc gag cag aca gcc tgg gga gac agt gga gtg tat tac tgc tct         715
Thr Phe Glu Gln Thr Ala Trp Gly Asp Ser Gly Val Tyr Tyr Cys Ser
                155                 160                 165 gtg gtc tcg gcc caa gat ctg gat gga aac aac gag gcg tac gca gag         763
Val Val Ser Ala Gln Asp Leu Asp Gly Asn Asn Glu Ala Tyr Ala Glu
            170                 175                 180 ctc atc gtc ctt gat tgg ctc ttt gtg gtc gtg gtc tgc ctg gcg agc         811
Leu Ile Val Leu Asp Trp Leu Phe Val Val Val Val Cys Leu Ala Ser
        185                 190                 195 ctc ctc ctc ttc ctc ctc ctg ggc atc tgc tgg tgc cag tgc tgt cct         859
Leu Leu Leu Phe Leu Leu Leu Gly Ile Cys Trp Cys Gln Cys Cys Pro
200                 205                 210 cac acc tgc tgc tgc tat gtc cga tgt ccc tgc tgc cca gac aag tgc         907
His Thr Cys Cys Cys Tyr Val Arg Cys Pro Cys Cys Pro Asp Lys Cys
215                 220                 225                 230 tgt tgc cct gag gct ctt tat gct gct ggc aaa gca gcc acc tca ggt         955
Cys Cys Pro Glu Ala Leu Tyr Ala Ala Gly Lys Ala Ala Thr Ser Gly
                235                 240                 245 gtc ccg agc atc tat gcc ccc agc atc tat acc cac ctc tca cct gcc        1003
Val Pro Ser Ile Tyr Ala Pro Ser Ile Tyr Thr His Leu Ser Pro Ala
            250                 255                 260 aag acc cca cca cct ccg cct gcc atg att ccc atg ggc cct ccc tat        1051
Lys Thr Pro Pro Pro Pro Pro Ala Met Ile Pro Met Gly Pro Pro Tyr
        265                 270                 275 ggg tac cct gga gac ttt gac aga cat agc tca gtt ggt ggc cac agc        1099
Gly Tyr Pro Gly Asp Phe Asp Arg His Ser Ser Val Gly Gly His Ser
280                 285                 290 tcc caa gta ccc ctg ctc cgt gac gtg gat ggc agt gta tct tca gaa        1147
Ser Gln Val Pro Leu Leu Arg Asp Val Asp Gly Ser Val Ser Ser Glu
295                 300                 305                 310 gta cga agt ggc tac agg atc cag gct aac cag caa gat gac tcc atg        1195
Val Arg Ser Gly Tyr Arg Ile Gln Ala Asn Gln Gln Asp Asp Ser Met
                315                 320                 325 agg gtc cta tac tat atg gag aaa gag cta gcc aac ttt gac cct tcc        1243
Arg Val Leu Tyr Tyr Met Glu Lys Glu Leu Ala Asn Phe Asp Pro Ser
            330                 335                 340 cga cct ggc cct ccc aat ggc aga gtg gaa cgg gcc atg agt gaa gta        1291
Arg Pro Gly Pro Pro Asn Gly Arg Val Glu Arg Ala Met Ser Glu Val
        345                 350                 355 acc tcc ctc cat gaa gat gac tgg cga tcg agg cct tcc agg gct cct        1339
Thr Ser Leu His Glu Asp Asp Trp Arg Ser Arg Pro Ser Arg Ala Pro
360                 365                 370
```

```
gcc ctc acc ccc atc agg gat gag gag tgg aat cgc cac tcc cca cag      1387
Ala Leu Thr Pro Ile Arg Asp Glu Glu Trp Asn Arg His Ser Pro Gln
375                 380                 385                 390 agt ccc aga aca tgg gag cag gaa ccc ctt caa gaa caa cca agg ggt      1435
Ser Pro Arg Thr Trp Glu Gln Glu Pro Leu Gln Glu Gln Pro Arg Gly
                395                 400                 405 ggt tgg ggg tct gga cgc cct cgg gcc cgc tct gtg gat gct cta gat      1483
Gly Trp Gly Ser Gly Arg Pro Arg Ala Arg Ser Val Asp Ala Leu Asp
            410                 415                 420 gat atc aac cgg cct ggc tcc act gaa tca gga cgg tct tct ccc cca      1531
Asp Ile Asn Arg Pro Gly Ser Thr Glu Ser Gly Arg Ser Ser Pro Pro
        425                 430                 435 agt agt gga cgg aga gga cgg gcc tat gca cct cca aga agt cgc agc      1579
Ser Ser Gly Arg Arg Gly Arg Ala Tyr Ala Pro Pro Arg Ser Arg Ser
    440                 445                 450 cgg gat gac ctc tat gac ccg gac gat cct agg gac ttg cca cat tcc      1627
Arg Asp Asp Leu Tyr Asp Pro Asp Asp Pro Arg Asp Leu Pro His Ser
455                 460                 465                 470 cga gat ccc cac tat tat gac gac atc agg tct aga gat cca cgt gct      1675
Arg Asp Pro His Tyr Tyr Asp Asp Ile Arg Ser Arg Asp Pro Arg Ala
                475                 480                 485 gac ccc aga tcc cgt cag cga tcc cga gat cct cgg gat gct ggc ttc      1723
Asp Pro Arg Ser Arg Gln Arg Ser Arg Asp Pro Arg Asp Ala Gly Phe
            490                 495                 500 agg tca agg gac cct cag tat gat ggg cga cta tta gaa gag gct tta      1771
Arg Ser Arg Asp Pro Gln Tyr Asp Gly Arg Leu Leu Glu Glu Ala Leu
        505                 510                 515 aag aaa aag ggg tcg ggc gag aga agg agg gtt tac agg gag gaa gaa      1819
Lys Lys Lys Gly Ser Gly Glu Arg Arg Arg Val Tyr Arg Glu Glu Glu
    520                 525                 530 gag gaa gag gag ggc caa tac ccc cca gca cct cca cct tac tca gag      1867
Glu Glu Glu Glu Gly Gln Tyr Pro Pro Ala Pro Pro Pro Tyr Ser Glu
535                 540                 545                 550 act gac tcg cag gcc tca cgg gag agg agg ctg aaa aag aat ttg gcc      1915
Thr Asp Ser Gln Ala Ser Arg Glu Arg Arg Leu Lys Lys Asn Leu Ala
                555                 560                 565 ctg agt cgg gaa agt tta gtc gtc tga tccacgtttt gtatgtagct            1962
Leu Ser Arg Glu Ser Leu Val Val *
            570                 575 tttgtacttt tttttttaatt ggaatcaata ttgatgaaac ttcaagccta ataaaatgtc   2022
taatcacaaa aaaaaaaa                                                   2040

<210> SEQ ID NO 11
<211> LENGTH: 574
<212> TYPE: PRT
<213> ORGANISM: Rattus norvegicus

<400> SEQUENCE: 11

Met Ala Pro Ala Ala Gly Ala Cys Ala Gly Ala Pro Asp Ser His Pro
1               5                   10                  15

Ala Thr Val Val Phe Val Cys Leu Phe Leu Ile Ile Phe Cys Pro Asp
                20                  25                  30

Pro Ala Ser Ala Ile Gln Val Thr Val Ser Asp Pro Tyr His Val Val
            35                  40                  45

Ile Leu Phe Gln Pro Val Thr Leu Pro Cys Thr Tyr Gln Met Ser Asn
        50                  55                  60

Thr Leu Thr Val Pro Ile Val Ile Trp Lys Tyr Lys Ser Phe Cys Arg
65                  70                  75                  80
```

-continued

```
Asp Arg Ile Ala Asp Ala Phe Ser Pro Ala Ser Val Asp Asn Gln Leu
                85                  90                  95

Asn Ala Gln Leu Ala Ala Gly Asn Pro Gly Tyr Asn Pro Tyr Val Glu
            100                 105                 110

Cys Gln Asp Ser Val Arg Thr Val Arg Val Ala Thr Lys Gln Gly
            115                 120                 125

Asn Ala Val Thr Leu Gly Asp Tyr Tyr Gln Gly Arg Arg Ile Thr Ile
        130                 135                 140

Thr Gly Asn Ala Asp Leu Thr Phe Glu Gln Thr Ala Trp Gly Asp Ser
145                 150                 155                 160

Gly Val Tyr Tyr Cys Ser Val Val Ser Ala Gln Asp Leu Asp Gly Asn
                165                 170                 175

Asn Glu Ala Tyr Ala Glu Leu Ile Val Leu Asp Trp Leu Phe Val Val
            180                 185                 190

Val Val Cys Leu Ala Ser Leu Leu Leu Phe Leu Leu Leu Gly Ile Cys
        195                 200                 205

Trp Cys Gln Cys Cys Pro His Thr Cys Cys Cys Tyr Val Arg Cys Pro
210                 215                 220

Cys Cys Pro Asp Lys Cys Cys Pro Glu Ala Leu Tyr Ala Ala Gly
225                 230                 235                 240

Lys Ala Ala Thr Ser Gly Val Pro Ser Ile Tyr Ala Pro Ser Ile Tyr
                245                 250                 255

Thr His Leu Ser Pro Ala Lys Thr Pro Pro Pro Pro Ala Met Ile
            260                 265                 270

Pro Met Gly Pro Pro Tyr Gly Tyr Pro Gly Asp Phe Asp Arg His Ser
        275                 280                 285

Ser Val Gly Gly His Ser Ser Gln Val Pro Leu Leu Arg Asp Val Asp
    290                 295                 300

Gly Ser Val Ser Ser Glu Val Arg Ser Gly Tyr Arg Ile Gln Ala Asn
305                 310                 315                 320

Gln Gln Asp Asp Ser Met Arg Val Leu Tyr Tyr Met Glu Lys Glu Leu
                325                 330                 335

Ala Asn Phe Asp Pro Ser Arg Pro Gly Pro Pro Asn Gly Arg Val Glu
            340                 345                 350

Arg Ala Met Ser Glu Val Thr Ser Leu His Glu Asp Asp Trp Arg Ser
        355                 360                 365

Arg Pro Ser Arg Ala Pro Ala Leu Thr Pro Ile Arg Asp Glu Glu Trp
    370                 375                 380

Asn Arg His Ser Pro Gln Ser Pro Arg Thr Trp Glu Gln Glu Pro Leu
385                 390                 395                 400

Gln Glu Gln Pro Arg Gly Gly Trp Gly Ser Gly Arg Pro Arg Ala Arg
                405                 410                 415

Ser Val Asp Ala Leu Asp Asp Ile Asn Arg Pro Gly Ser Thr Glu Ser
            420                 425                 430

Gly Arg Ser Ser Pro Pro Ser Ser Gly Arg Arg Gly Arg Ala Tyr Ala
        435                 440                 445

Pro Pro Arg Ser Arg Ser Arg Asp Asp Leu Tyr Asp Pro Asp Asp Pro
    450                 455                 460

Arg Asp Leu Pro His Ser Arg Asp Pro His Tyr Tyr Asp Asp Ile Arg
465                 470                 475                 480

Ser Arg Asp Pro Arg Ala Asp Pro Arg Ser Arg Gln Arg Ser Arg Asp
                485                 490                 495
```

```
Pro Arg Asp Ala Gly Phe Arg Ser Arg Asp Pro Gln Tyr Asp Gly Arg
            500                 505                 510

Leu Leu Glu Glu Ala Leu Lys Lys Gly Ser Gly Glu Arg Arg
            515                 520                 525

Val Tyr Arg Glu Glu Glu Glu Glu Gly Gln Tyr Pro Pro Ala
        530                 535                 540

Pro Pro Pro Tyr Ser Glu Thr Asp Ser Gln Ala Ser Arg Glu Arg Arg
545                 550                 555                 560

Leu Lys Lys Asn Leu Ala Leu Ser Arg Glu Ser Leu Val Val
                565                 570

<210> SEQ ID NO 12
<211> LENGTH: 1893
<212> TYPE: DNA
<213> ORGANISM: Rattus norvegicus

<400> SEQUENCE: 12
```

| | |
|---|---:|
| accgctcacc aggtcagttg tccccggaaa gccgaaggca tgagcttcgc ccaagttctt | 60 |
| tttatgggtt agaactcctc cagagcgggg gaaaaaggac ttggaatagg ggcgggacgg | 120 |
| agcacgcacc cttctccgcc ttggttctcg ccgcgccccc tactctcggg atacttggga | 180 |

```
ggggacgcgc gggcaccgtc gctgctagac ggccgcg atg gcg ccg gcg gcc ggc      235
                                        Met Ala Pro Ala Ala Gly
                                          1               5 gcg tgt gct ggg gcg cct gac tcc cac cca gct acc gtg gtc ttc gtg      283
Ala Cys Ala Gly Ala Pro Asp Ser His Pro Ala Thr Val Val Phe Val
             10                  15                  20 tgt ctc ttt ctc atc att ttc tgc cca gac cct gcc agt gcc atc cag      331
Cys Leu Phe Leu Ile Ile Phe Cys Pro Asp Pro Ala Ser Ala Ile Gln
         25                  30                  35 gtg act gtg tct gac ccc tac cac gta gtg atc ctg ttc cag cca gtg      379
Val Thr Val Ser Asp Pro Tyr His Val Val Ile Leu Phe Gln Pro Val
     40                  45                  50 acc ctg ccc tgc acc tat cag atg agc aac act ctc aca gtc ccc atc      427
Thr Leu Pro Cys Thr Tyr Gln Met Ser Asn Thr Leu Thr Val Pro Ile
55                  60                  65                  70 gtg atc tgg aag tac aag tca ttc tgc cgg gac cgt att gcc gat gcc      475
Val Ile Trp Lys Tyr Lys Ser Phe Cys Arg Asp Arg Ile Ala Asp Ala
                 75                  80                  85 ttc tct cct gcc agt gtg gac aac cag cta aat gcc cag ttg gca gct      523
Phe Ser Pro Ala Ser Val Asp Asn Gln Leu Asn Ala Gln Leu Ala Ala
             90                  95                 100 ggc aac ccc ggc tac aac ccc tat gtg gag tgc cag gac agt gta cgc      571
Gly Asn Pro Gly Tyr Asn Pro Tyr Val Glu Cys Gln Asp Ser Val Arg
        105                 110                 115 act gtc agg gtg gtg gcc acc aaa cag ggc aat gcg gtg acc ctg gga      619
Thr Val Arg Val Val Ala Thr Lys Gln Gly Asn Ala Val Thr Leu Gly
    120                 125                 130 gac tac tac caa ggc agg agg atc acc ata aca gga aat gct gac ctg      667
Asp Tyr Tyr Gln Gly Arg Arg Ile Thr Ile Thr Gly Asn Ala Asp Leu
135                 140                 145                 150 acc ttc gag cag aca gcc tgg gga gac agt gga gtg tat tac tgc tct      715
Thr Phe Glu Gln Thr Ala Trp Gly Asp Ser Gly Val Tyr Tyr Cys Ser
                155                 160                 165 gtg gtc tcg gcc caa gat ctg gat gga aac aac gag gcg tac gca gag      763
Val Val Ser Ala Gln Asp Leu Asp Gly Asn Asn Glu Ala Tyr Ala Glu
            170                 175                 180 ctc atc gtc ctt gtt tat gct gct ggc aaa gca gcc acc tca ggt gtc      811
Leu Ile Val Leu Val Tyr Ala Ala Gly Lys Ala Ala Thr Ser Gly Val
```

```
                185                 190                 195
ccg agc atc tat gcc ccc agc atc tat acc cac ctc tca cct gcc aag      859
Pro Ser Ile Tyr Ala Pro Ser Ile Tyr Thr His Leu Ser Pro Ala Lys
    200                 205                 210 acc cca cca cct ccg cct gcc atg att ccc atg ggc cct ccc tat ggg      907
Thr Pro Pro Pro Pro Pro Ala Met Ile Pro Met Gly Pro Pro Tyr Gly
215                 220                 225                 230 tac cct gga gac ttt gac aga cat agc tca gtt ggt ggc cac agc tcc      955
Tyr Pro Gly Asp Phe Asp Arg His Ser Ser Val Gly Gly His Ser Ser
            235                 240                 245 caa gta ccc ctg ctg cgt gac gtg gat ggc agt gta tct tca gaa gta     1003
Gln Val Pro Leu Leu Arg Asp Val Asp Gly Ser Val Ser Ser Glu Val
        250                 255                 260 cga agt ggc tac agg atc cag gct aac cag caa gat gac tcc atg agg     1051
Arg Ser Gly Tyr Arg Ile Gln Ala Asn Gln Gln Asp Asp Ser Met Arg
    265                 270                 275 gtc cta tac tat atg gag aaa gag cta gcc aac ttt gac cct tcc cga     1099
Val Leu Tyr Tyr Met Glu Lys Glu Leu Ala Asn Phe Asp Pro Ser Arg
280                 285                 290 cct ggc cct ccc aat ggc aga gtg gaa cgg gcc atg agt gaa gta acc     1147
Pro Gly Pro Pro Asn Gly Arg Val Glu Arg Ala Met Ser Glu Val Thr
295                 300                 305                 310 tcc ctc cat gaa gat gac tgg cga tcg agg cct tcc agg gct cct gcc     1195
Ser Leu His Glu Asp Asp Trp Arg Ser Arg Pro Ser Arg Ala Pro Ala
            315                 320                 325 ctc acc ccc atc agg gat gag gag tgg aat cgc cac tcc cca cag agt     1243
Leu Thr Pro Ile Arg Asp Glu Glu Trp Asn Arg His Ser Pro Gln Ser
        330                 335                 340 ccc aga aca tgg gag cag gaa ccc ctt caa gaa caa cca agg ggt ggt     1291
Pro Arg Thr Trp Glu Gln Glu Pro Leu Gln Glu Gln Pro Arg Gly Gly
    345                 350                 355 tgg ggg tct gga cgc cct cgg gcc cgc tct gtg gat gct cta gat gat     1339
Trp Gly Ser Gly Arg Pro Arg Ala Arg Ser Val Asp Ala Leu Asp Asp
360                 365                 370 atc aac cgg cct ggc tcc act gaa tca gga cgg tct tct ccc cca agt     1387
Ile Asn Arg Pro Gly Ser Thr Glu Ser Gly Arg Ser Ser Pro Pro Ser
375                 380                 385                 390 agt gga cgg aga gga cgg gcc tat gca cct cca aga agt cgc agc cgg     1435
Ser Gly Arg Arg Gly Arg Ala Tyr Ala Pro Pro Arg Ser Arg Ser Arg
            395                 400                 405 gat gac ctc tat gac ccg gac gat cct agg gac ttg cca cat tcc cga     1483
Asp Asp Leu Tyr Asp Pro Asp Asp Pro Arg Asp Leu Pro His Ser Arg
        410                 415                 420 gat ccc cac tat tat gac gac atc agg tct aga gat cca cgt gct gac     1531
Asp Pro His Tyr Tyr Asp Asp Ile Arg Ser Arg Asp Pro Arg Ala Asp
    425                 430                 435 ccc aga tcc cgt cag cga tcc cga gat cct cgg gat gct ggc ttc agg     1579
Pro Arg Ser Arg Gln Arg Ser Arg Asp Pro Arg Asp Ala Gly Phe Arg
440                 445                 450 tca agg gac cct cag tat gat ggg cga cta tta gaa gag gct tta aag     1627
Ser Arg Asp Pro Gln Tyr Asp Gly Arg Leu Leu Glu Glu Ala Leu Lys
455                 460                 465                 470 aaa aag ggg tcg ggc gag aga agg agg gtt tac agg gag gaa gaa gag     1675
Lys Lys Gly Ser Gly Glu Arg Arg Arg Val Tyr Arg Glu Glu Glu Glu
            475                 480                 485 gaa gag gag ggc caa tac ccc cca gca cct cca cct tac tca gag act     1723
Glu Glu Glu Gly Gln Tyr Pro Pro Ala Pro Pro Pro Tyr Ser Glu Thr
        490                 495                 500 gac tcg cag gcc tca cgg gag agg agg ctg aaa aag aat ttg gcc ctg     1771
```

```
Asp Ser Gln Ala Ser Arg Glu Arg Arg Leu Lys Lys Asn Leu Ala Leu
        505                 510                 515 agt cgg gaa agt tta gtc gtc tga tccacgtttt gtatgtagct tttgtacttt      1825
Ser Arg Glu Ser Leu Val Val *
        520                 525 tttttaatt ggaatcaata ttgatgaaac ttcaagccta ataaaatgtc taatcacaaa      1885
aaaaaaaa                                                              1893

<210> SEQ ID NO 13
<211> LENGTH: 525
<212> TYPE: PRT
<213> ORGANISM: Rattus norvegicus

<400> SEQUENCE: 13

Met Ala Pro Ala Ala Gly Ala Cys Ala Gly Ala Pro Asp Ser His Pro
1               5                   10                  15

Ala Thr Val Val Phe Val Cys Leu Phe Leu Ile Ile Phe Cys Pro Asp
            20                  25                  30

Pro Ala Ser Ala Ile Gln Val Thr Val Ser Asp Pro Tyr His Val Val
        35                  40                  45

Ile Leu Phe Gln Pro Val Thr Leu Pro Cys Thr Tyr Gln Met Ser Asn
    50                  55                  60

Thr Leu Thr Val Pro Ile Val Trp Lys Tyr Lys Ser Phe Cys Arg
65                  70                  75                  80

Asp Arg Ile Ala Asp Ala Phe Ser Pro Ala Ser Val Asp Asn Gln Leu
                85                  90                  95

Asn Ala Gln Leu Ala Ala Gly Asn Pro Gly Tyr Asn Pro Tyr Val Glu
            100                 105                 110

Cys Gln Asp Ser Val Arg Thr Val Arg Val Val Ala Thr Lys Gln Gly
        115                 120                 125

Asn Ala Val Thr Leu Gly Asp Tyr Tyr Gln Gly Arg Arg Ile Thr Ile
    130                 135                 140

Thr Gly Asn Ala Asp Leu Thr Phe Glu Gln Thr Ala Trp Gly Asp Ser
145                 150                 155                 160

Gly Val Tyr Tyr Cys Ser Val Val Ser Ala Gln Asp Leu Asp Gly Asn
                165                 170                 175

Asn Glu Ala Tyr Ala Glu Leu Ile Val Leu Val Tyr Ala Ala Gly Lys
            180                 185                 190

Ala Ala Thr Ser Gly Val Pro Ser Ile Tyr Ala Pro Ser Ile Tyr Thr
        195                 200                 205

His Leu Ser Pro Ala Lys Thr Pro Pro Pro Pro Ala Met Ile Pro
    210                 215                 220

Met Gly Pro Pro Tyr Gly Tyr Pro Gly Asp Phe Asp Arg His Ser Ser
225                 230                 235                 240

Val Gly Gly His Ser Ser Gln Val Pro Leu Leu Arg Asp Val Asp Gly
                245                 250                 255

Ser Val Ser Ser Glu Val Arg Ser Gly Tyr Arg Ile Gln Ala Asn Gln
            260                 265                 270

Gln Asp Asp Ser Met Arg Val Leu Tyr Tyr Met Glu Lys Glu Leu Ala
        275                 280                 285

Asn Phe Asp Pro Ser Arg Pro Gly Pro Pro Asn Gly Arg Val Glu Arg
    290                 295                 300

Ala Met Ser Glu Val Thr Ser Leu His Glu Asp Asp Trp Arg Ser Arg
305                 310                 315                 320
```

```
                                        -continued

Pro Ser Arg Ala Pro Ala Leu Thr Pro Ile Arg Asp Glu Glu Trp Asn
            325                 330                 335

Arg His Ser Pro Gln Ser Pro Arg Thr Trp Glu Gln Glu Pro Leu Gln
            340                 345                 350

Glu Gln Pro Arg Gly Gly Trp Gly Ser Gly Arg Pro Ala Arg Ser
            355                 360                 365

Val Asp Ala Leu Asp Asp Ile Asn Arg Pro Gly Ser Thr Glu Ser Gly
    370                 375                 380

Arg Ser Pro Pro Ser Ser Gly Arg Gly Arg Ala Tyr Ala Pro
385                 390                 395                 400

Pro Arg Ser Arg Ser Arg Asp Asp Leu Tyr Asp Pro Asp Pro Arg
                405                 410                 415

Asp Leu Pro His Ser Arg Asp Pro His Tyr Tyr Asp Asp Ile Arg Ser
            420                 425                 430

Arg Asp Pro Arg Ala Asp Pro Arg Ser Arg Gln Arg Ser Arg Asp Pro
        435                 440                 445

Arg Asp Ala Gly Phe Arg Ser Arg Asp Pro Gln Tyr Asp Gly Arg Leu
    450                 455                 460

Leu Glu Glu Ala Leu Lys Lys Lys Gly Ser Gly Glu Arg Arg Val
465                 470                 475                 480

Tyr Arg Glu Glu Glu Glu Glu Gly Gln Tyr Pro Pro Ala Pro
                485                 490                 495

Pro Pro Tyr Ser Glu Thr Asp Ser Gln Ala Ser Arg Glu Arg Arg Leu
            500                 505                 510

Lys Lys Asn Leu Ala Leu Ser Arg Glu Ser Leu Val Val
            515                 520                 525

<210> SEQ ID NO 14
<211> LENGTH: 1886
<212> TYPE: DNA
<213> ORGANISM: Mus musculus

<400> SEQUENCE: 14
gcaccgtcgc tgctagacgg ccgcg atg gcg ccg gcg gcc agc gcg tgt gct      52
                            Met Ala Pro Ala Ala Ser Ala Cys Ala
                              1               5 ggg gcg cct ggc tcc cac ccg gcc acc acg atc ttc gtg tgt ctt ttt    100
Gly Ala Pro Gly Ser His Pro Ala Thr Thr Ile Phe Val Cys Leu Phe
 10                  15                  20                  25 ctc atc att tac tgc cca gac cgt gcc agt gcc atc cag gtg acc gtg    148
Leu Ile Ile Tyr Cys Pro Asp Arg Ala Ser Ala Ile Gln Val Thr Val
                 30                  35                  40 cct gac ccc tac cac gta gtg atc ctg ttc cag cca gtg aca cta cac    196
Pro Asp Pro Tyr His Val Val Ile Leu Phe Gln Pro Val Thr Leu His
             45                  50                  55 tgc acc tac cag atg agc aat acc ctc aca gcc cct atc gtg atc tgg    244
Cys Thr Tyr Gln Met Ser Asn Thr Leu Thr Ala Pro Ile Val Ile Trp
         60                  65                  70 aag tat aag tcg ttc tgt cgg gac cgt gtt gcc gac gcc ttc tcc cct    292
Lys Tyr Lys Ser Phe Cys Arg Asp Arg Val Ala Asp Ala Phe Ser Pro
 75                  80                  85 gcc agc gtg gac aac cag ctc aac gcc cag ctg gcg gct ggc aac ccc    340
Ala Ser Val Asp Asn Gln Leu Asn Ala Gln Leu Ala Ala Gly Asn Pro
 90                  95                 100                 105 ggc tac aac ccc tat gtg gag tgc cag gac agc gta cgc act gtc agg    388
Gly Tyr Asn Pro Tyr Val Glu Cys Gln Asp Ser Val Arg Thr Val Arg
                110                 115                 120
```

-continued

| | |
|---|---|
| gtg gtg gcc acc aaa cag ggc aat gct gtg acc ctg gga gac tac tac<br>Val Val Ala Thr Lys Gln Gly Asn Ala Val Thr Leu Gly Asp Tyr Tyr<br>              125                  130                        135 | 436 |
| cag ggc agg aga atc acc atc aca gga aat gct ggc ctg acc ttc gag<br>Gln Gly Arg Arg Ile Thr Ile Thr Gly Asn Ala Gly Leu Thr Phe Glu<br>            140                        145 | 484 |
| cag acg gcc tgg gga gac agt gga gtg tat tac tgc tcc gtg gtc tca<br>Gln Thr Ala Trp Gly Asp Ser Gly Val Tyr Tyr Cys Ser Val Val Ser<br>155                      160                        165 | 532 |
| gcc caa gat ctg gat ggg aac aac gag gcg tac gca gag ctc att gtc<br>Ala Gln Asp Leu Asp Gly Asn Asn Glu Ala Tyr Ala Glu Leu Ile Val<br>170                      175                    180                  185 | 580 |
| ctt ggc agg acc tca gaa gcc cct gag ctc cta cct ggt ttt cgg gcg<br>Leu Gly Arg Thr Ser Glu Ala Pro Glu Leu Leu Pro Gly Phe Arg Ala<br>            190                        195                    200 | 628 |
| ggg ccc ttg gaa gat tgg ctc ttt gtg gtc gtg gtc tgc ctg gca agc<br>Gly Pro Leu Glu Asp Trp Leu Phe Val Val Val Val Cys Leu Ala Ser<br>                205                        210                    215 | 676 |
| ctc ctc ttc ttc ctc ctc ctg ggc atc tgc tgg tgc cag tgc tgt ccc<br>Leu Leu Phe Phe Leu Leu Leu Gly Ile Cys Trp Cys Gln Cys Cys Pro<br>            220                        225                    230 | 724 |
| cac acc tgc tgc tgc tat gtc aga tgt ccc tgc tgc cca gac aag tgc<br>His Thr Cys Cys Cys Tyr Val Arg Cys Pro Cys Cys Pro Asp Lys Cys<br>                235                        240                    245 | 772 |
| tgt tgc cct gag gcc ctt tat gct gct ggc aaa gca gcc acc tca ggt<br>Cys Cys Pro Glu Ala Leu Tyr Ala Ala Gly Lys Ala Ala Thr Ser Gly<br>250                      255                        260                    265 | 820 |
| gtg cca agc atc tat gcc ccc agc atc tat acc cac ctc tct cct gcc<br>Val Pro Ser Ile Tyr Ala Pro Ser Ile Tyr Thr His Leu Ser Pro Ala<br>                      270                        275                    280 | 868 |
| aag act ccg cca cct ccg cct gcc atg att ccc atg cgt cct ccc tat<br>Lys Thr Pro Pro Pro Pro Ala Met Ile Pro Met Arg Pro Pro Tyr<br>                      285                        290                    295 | 916 |
| ggg tac cct gga gac ttt gac agg acc agc tca gtt ggt ggc cac agc<br>Gly Tyr Pro Gly Asp Phe Asp Arg Thr Ser Ser Val Gly Gly His Ser<br>                300                        305                    310 | 964 |
| tcc cag gtg ccc ctg ctg cgt gaa gtg gat ggg agc gta tct tca gaa<br>Ser Gln Val Pro Leu Leu Arg Glu Val Asp Gly Ser Val Ser Ser Glu<br>315                      320                        325 | 1012 |
| gta cga agt ggc tac agg atc cag gct aac cag caa gat gac tcc atg<br>Val Arg Ser Gly Tyr Arg Ile Gln Ala Asn Gln Gln Asp Asp Ser Met<br>330                      335                    340                    345 | 1060 |
| agg gtc cta tac tat atg gag aag gag cta gcc aac ttc gat cct tcc<br>Arg Val Leu Tyr Tyr Met Glu Lys Glu Leu Ala Asn Phe Asp Pro Ser<br>                350                        355                    360 | 1108 |
| cgg cct ggc cct ccc aat ggc cga gtg gaa cgg gcc atg agt gaa gta<br>Arg Pro Gly Pro Pro Asn Gly Arg Val Glu Arg Ala Met Ser Glu Val<br>            365                        370                    375 | 1156 |
| acc tcc ctc cat gaa gat gac tgg cga tct cgg cct tcc agg gct cct<br>Thr Ser Leu His Glu Asp Asp Trp Arg Ser Arg Pro Ser Arg Ala Pro<br>                380                        385                    390 | 1204 |
| gcc ctc aca ccc atc agg gat gag gag tgg aat cgc cac tcc cct cgg<br>Ala Leu Thr Pro Ile Arg Asp Glu Glu Trp Asn Arg His Ser Pro Arg<br>395                      400                        405 | 1252 |
| agt ccc aga aca tgg gag cag gaa ccc ctt caa gaa cag cca agg ggt<br>Ser Pro Arg Thr Trp Glu Gln Glu Pro Leu Gln Glu Gln Pro Arg Gly<br>410                      415                    420                    425 | 1300 |
| ggt tgg ggg tct ggg cgg cct cgg gcc cgc tct gtg gat gct cta gat<br>Gly Trp Gly Ser Gly Arg Pro Arg Ala Arg Ser Val Asp Ala Leu Asp<br>                430                        435                    440 | 1348 |

```
gac atc aac cgg cct ggc tcc act gaa tca gga agg tct tct ccc cca    1396
Asp Ile Asn Arg Pro Gly Ser Thr Glu Ser Gly Arg Ser Ser Pro Pro
        445                 450                 455 agt agt gga cgg aga ggg cgg gcc tat gca cct ccg aga agt cgc agc    1444
Ser Ser Gly Arg Arg Gly Arg Ala Tyr Ala Pro Pro Arg Ser Arg Ser
    460                 465                 470 cgg gat gac ctc tat gac ccc gac gat cct aga gac ttg cca cat tcc    1492
Arg Asp Asp Leu Tyr Asp Pro Asp Asp Pro Arg Asp Leu Pro His Ser
475                 480                 485 cga gat ccc cac tat tat gat gat ttg agg tct agg gat cca cgt gct    1540
Arg Asp Pro His Tyr Tyr Asp Asp Leu Arg Ser Arg Asp Pro Arg Ala
490                 495                 500                 505 gac ccc aga tcc cgt cag cga tcc cac gat cct cgg gat gct ggc ttc    1588
Asp Pro Arg Ser Arg Gln Arg Ser His Asp Pro Arg Asp Ala Gly Phe
                510                 515                 520 agg tca cgg gac cct cag tat gat ggg cga ctc tta gaa gag gct tta    1636
Arg Ser Arg Asp Pro Gln Tyr Asp Gly Arg Leu Leu Glu Glu Ala Leu
            525                 530                 535 aag aaa aaa ggg gct ggg gag aga aga cgc gtt tac agg gag gaa gaa    1684
Lys Lys Lys Gly Ala Gly Glu Arg Arg Arg Val Tyr Arg Glu Glu Glu
        540                 545                 550 gaa gaa gaa gag gag ggc cac tat ccc cca gca cct ccg cct tac tct    1732
Glu Glu Glu Glu Glu Gly His Tyr Pro Pro Ala Pro Pro Pro Tyr Ser
555                 560                 565 gag act gac tcg cag gcc tcg agg gag cgg agg atg aaa aag aat ttg    1780
Glu Thr Asp Ser Gln Ala Ser Arg Glu Arg Arg Met Lys Lys Asn Leu
570                 575                 580                 585 gcc ctg agt cgg gaa agt tta gtc gtc tga tcccacgttt tgttatgtag      1830
Ala Leu Ser Arg Glu Ser Leu Val Val *
                590                 595 cttttatact tttttaattg gaatattgat gaaactcttc accaagccta ataaaa      1886

<210> SEQ ID NO 15
<211> LENGTH: 1829
<212> TYPE: DNA
<213> ORGANISM: Mus musculus

<400> SEQUENCE: 15
gcaccgtcgc tgctagacgg ccgcg atg gcg ccg gcg gcc agc gcg tgt gct     52
                            Met Ala Pro Ala Ala Ser Ala Cys Ala
                            1               5 ggg gcg cct ggc tcc cac ccg gcc acc acg atc ttc gtg tgt ctt ttt    100
Gly Ala Pro Gly Ser His Pro Ala Thr Thr Ile Phe Val Cys Leu Phe
10                  15                  20                  25 ctc atc att tac tgc cca gac cgt gcc agt gcc atc cag gtg acc gtg    148
Leu Ile Ile Tyr Cys Pro Asp Arg Ala Ser Ala Ile Gln Val Thr Val
                30                  35                  40 cct gac ccc tac cac gta gtg atc ctg ttc cag cca gtg aca cta cac    196
Pro Asp Pro Tyr His Val Val Ile Leu Phe Gln Pro Val Thr Leu His
            45                  50                  55 tgc acc tac cag atg agc aat acc ctc aca gcc cct atc gtg atc tgg    244
Cys Thr Tyr Gln Met Ser Asn Thr Leu Thr Ala Pro Ile Val Ile Trp
        60                  65                  70 aag tat aag tcg ttc tgt cgg gac cgt gtt gcc gac gcc ttc tcc cct    292
Lys Tyr Lys Ser Phe Cys Arg Asp Arg Val Ala Asp Ala Phe Ser Pro
    75                  80                  85 gcc agc gtg gac aac cag ctc aac gcc cag ctg gcg gct ggc aac ccc    340
Ala Ser Val Asp Asn Gln Leu Asn Ala Gln Leu Ala Ala Gly Asn Pro
90                  95                  100                 105
```

```
ggc tac aac ccc tat gtg gag tgc cag gac agc gta cgc act gtc agg      388
Gly Tyr Asn Pro Tyr Val Glu Cys Gln Asp Ser Val Arg Thr Val Arg
            110                 115                 120 gtg gtg gcc acc aaa cag ggc aat gct gtg acc ctg gga gac tac tac      436
Val Val Ala Thr Lys Gln Gly Asn Ala Val Thr Leu Gly Asp Tyr Tyr
            125                 130                 135 cag ggc agg aga atc acc atc aca gga aat gct ggc ctg acc ttc gag      484
Gln Gly Arg Arg Ile Thr Ile Thr Gly Asn Ala Gly Leu Thr Phe Glu
            140                 145                 150 cag acg gcc tgg gga gac agt gga gtg tat tac tgc tcc gtg gtc tca      532
Gln Thr Ala Trp Gly Asp Ser Gly Val Tyr Tyr Cys Ser Val Val Ser
        155                 160                 165 gcc caa gat ctg gat ggg aac aac gag gcg tac gca gag ctc att gtc      580
Ala Gln Asp Leu Asp Gly Asn Asn Glu Ala Tyr Ala Glu Leu Ile Val
170                 175                 180                 185 ctt gat tgg ctc ttt gtg gtc gtg gtc tgc ctg gca agc ctc ctc ttc      628
Leu Asp Trp Leu Phe Val Val Val Val Cys Leu Ala Ser Leu Leu Phe
                190                 195                 200 ttc ctc ctc ctg ggc atc tgc tgg tgc cag tgc tgt ccc cac acc tgc      676
Phe Leu Leu Leu Gly Ile Cys Trp Cys Gln Cys Cys Pro His Thr Cys
            205                 210                 215 tgc tgc tat gtc aga tgt ccc tgc tgc cca gac aag tgc tgt tgc cct      724
Cys Cys Tyr Val Arg Cys Pro Cys Cys Pro Asp Lys Cys Cys Cys Pro
            220                 225                 230 gag gcc ctt tat gct gct ggc aaa gca gcc acc tca ggt gtg cca agc      772
Glu Ala Leu Tyr Ala Ala Gly Lys Ala Ala Thr Ser Gly Val Pro Ser
            235                 240                 245 atc tat gcc ccc agc atc tat acc cac ctc tct cct gcc aag act ccg      820
Ile Tyr Ala Pro Ser Ile Tyr Thr His Leu Ser Pro Ala Lys Thr Pro
250                 255                 260                 265 cca cct ccg cct gcc atg att ccc atg cgt cct ccc tat ggg tac cct      868
Pro Pro Pro Pro Ala Met Ile Pro Met Arg Pro Pro Tyr Gly Tyr Pro
                270                 275                 280 gga gac ttt gac agg acc agc tca gtt ggt ggc cac agc tcc cag gtg      916
Gly Asp Phe Asp Arg Thr Ser Ser Val Gly Gly His Ser Ser Gln Val
            285                 290                 295 ccc ctg ctg cgt gaa gtg gat ggg agc gta tct tca gaa gta cga agt      964
Pro Leu Leu Arg Glu Val Asp Gly Ser Val Ser Ser Glu Val Arg Ser
            300                 305                 310 ggc tac agg atc cag gct aac cag caa gat gac tcc atg agg gtc cta     1012
Gly Tyr Arg Ile Gln Ala Asn Gln Gln Asp Asp Ser Met Arg Val Leu
            315                 320                 325 tac tat atg gag aag gag cta gcc aac ttc gat cct tcc cgg cct ggc     1060
Tyr Tyr Met Glu Lys Glu Leu Ala Asn Phe Asp Pro Ser Arg Pro Gly
330                 335                 340                 345 cct ccc aat ggc cga gtg gaa cgg gcc atg agt gaa gta acc tcc ctc     1108
Pro Pro Asn Gly Arg Val Glu Arg Ala Met Ser Glu Val Thr Ser Leu
                350                 355                 360 cat gaa gat gac tgg cga tct cgg cct tcc agg gct cct gcc ctc aca     1156
His Glu Asp Asp Trp Arg Ser Arg Pro Ser Arg Ala Pro Ala Leu Thr
            365                 370                 375 ccc atc agg gat gag gag tgg aat cgc cac tcc cct cgg agt ccc aga     1204
Pro Ile Arg Asp Glu Glu Trp Asn Arg His Ser Pro Arg Ser Pro Arg
            380                 385                 390 aca tgg gag cag gaa ccc ctt caa gaa cag cca agg ggt ggt tgg ggg     1252
Thr Trp Glu Gln Glu Pro Leu Gln Glu Gln Pro Arg Gly Gly Trp Gly
            395                 400                 405 tct ggg cgg cct cgg gcc cgc tct gtg gat gct cta gat gac atc aac     1300
Ser Gly Arg Pro Arg Ala Arg Ser Val Asp Ala Leu Asp Asp Ile Asn
410                 415                 420                 425
```

-continued

```
cgg cct ggc tcc act gaa tca gga agg tct tct ccc cca agt agt gga      1348
Arg Pro Gly Ser Thr Glu Ser Gly Arg Ser Ser Pro Pro Ser Ser Gly
            430                 435                 440 cgg aga ggg cgg gcc tat gca cct ccg aga agt cgc agc cgg gat gac      1396
Arg Arg Gly Arg Ala Tyr Ala Pro Pro Arg Ser Arg Ser Arg Asp Asp
            445                 450                 455 ctc tat gac ccc gac gat cct aga gac ttg cca cat tcc cga gat ccc      1444
Leu Tyr Asp Pro Asp Asp Pro Arg Asp Leu Pro His Ser Arg Asp Pro
            460                 465                 470 cac tat tat gat gat ttg agg tct agg gat cca cgt gct gac ccc aga      1492
His Tyr Tyr Asp Asp Leu Arg Ser Arg Asp Pro Arg Ala Asp Pro Arg
475                 480                 485 tcc cgt cag cga tcc cac gat cct cgg gat gct ggc ttc agg tca cgg      1540
Ser Arg Gln Arg Ser His Asp Pro Arg Asp Ala Gly Phe Arg Ser Arg
490                 495                 500                 505 gac cct cag tat gat ggg cga ctc tta gaa gag gct tta aag aaa aaa      1588
Asp Pro Gln Tyr Asp Gly Arg Leu Leu Glu Glu Ala Leu Lys Lys Lys
                510                 515                 520 ggg gct ggg gag aga aga cgc gtt tac agg gag gaa gaa gaa gaa gaa      1636
Gly Ala Gly Glu Arg Arg Arg Val Tyr Arg Glu Glu Glu Glu Glu Glu
            525                 530                 535 gag gag ggc cac tat ccc cca gca cct ccg cct tac tct gag act gac      1684
Glu Glu Gly His Tyr Pro Pro Ala Pro Pro Pro Tyr Ser Glu Thr Asp
            540                 545                 550 tcg cag gcc tcg agg gag cgg agg atg aaa aag aat ttg gcc ctg agt      1732
Ser Gln Ala Ser Arg Glu Arg Arg Met Lys Lys Asn Leu Ala Leu Ser
555                 560                 565 cgg gaa agt tta gtc gtc tga tcccacgttt tgttatgtag cttttatact         1783
Arg Glu Ser Leu Val Val *
570                 575 ttttttaattg gaatattgat gaaactcttc accaagccta ataaaa                  1829

<210> SEQ ID NO 16
<211> LENGTH: 1682
<212> TYPE: DNA
<213> ORGANISM: Mus musculus

<400> SEQUENCE: 16
gcaccgtcgc tgctagacgg ccgcg atg gcg ccg gcg gcc agc gcg tgt gct       52
                             Met Ala Pro Ala Ala Ser Ala Cys Ala
                               1               5 ggg gcg cct ggc tcc cac ccg gcc acc acg atc ttc gtg tgt ctt ttt      100
Gly Ala Pro Gly Ser His Pro Ala Thr Thr Ile Phe Val Cys Leu Phe
10                  15                  20                  25 ctc atc att tac tgc cca gac cgt gcc agt gcc atc cag gtg acc gtg      148
Leu Ile Ile Tyr Cys Pro Asp Arg Ala Ser Ala Ile Gln Val Thr Val
                30                  35                  40 cct gac ccc tac cac gta gtg atc ctg ttc cag cca gtg aca cta cac      196
Pro Asp Pro Tyr His Val Val Ile Leu Phe Gln Pro Val Thr Leu His
            45                  50                  55 tgc acc tac cag atg agc aat acc ctc aca gcc cct atc gtg atc tgg      244
Cys Thr Tyr Gln Met Ser Asn Thr Leu Thr Ala Pro Ile Val Ile Trp
            60                  65                  70 aag tat aag tcg ttc tgt cgg gac cgt gtt gcc gac gcc ttc tcc cct      292
Lys Tyr Lys Ser Phe Cys Arg Asp Arg Val Ala Asp Ala Phe Ser Pro
75                  80                  85 gcc agc gtg gac aac cag ctc aac gcc cag ctg gcg gct ggc aac ccc      340
Ala Ser Val Asp Asn Gln Leu Asn Ala Gln Leu Ala Ala Gly Asn Pro
90                  95                  100                 105
```

| | | |
|---|---|---|
| ggc tac aac ccc tat gtg gag tgc cag gac agc gta cgc act gtc agg<br>Gly Tyr Asn Pro Tyr Val Glu Cys Gln Asp Ser Val Arg Thr Val Arg<br>110                      115                    120 | | 388 |
| gtg gtg gcc acc aaa cag ggc aat gct gtg acc ctg gga gac tac tac<br>Val Val Ala Thr Lys Gln Gly Asn Ala Val Thr Leu Gly Asp Tyr Tyr<br>            125                    130                    135 | | 436 |
| cag ggc agg aga atc acc atc aca gga aat gct ggc ctg acc ttc gag<br>Gln Gly Arg Arg Ile Thr Ile Thr Gly Asn Ala Gly Leu Thr Phe Glu<br>      140                    145                    150 | | 484 |
| cag acg gcc tgg gga gac agt gga gtg tat tac tgc tcc gtg gtc tca<br>Gln Thr Ala Trp Gly Asp Ser Gly Val Tyr Tyr Cys Ser Val Val Ser<br>155                      160                    165 | | 532 |
| gcc caa gat ctg gat ggg aac aac gag gcg tac gca gag ctc att gtc<br>Ala Gln Asp Leu Asp Gly Asn Asn Glu Ala Tyr Ala Glu Leu Ile Val<br>170                      175                    180                    185 | | 580 |
| ctt gtt tat gct gct ggc aaa gca gcc acc tca ggt gtg cca agc atc<br>Leu Val Tyr Ala Ala Gly Lys Ala Ala Thr Ser Gly Val Pro Ser Ile<br>                  190                    195                    200 | | 628 |
| tat gcc ccc agc atc tat acc cac ctc tct cct gcc aag act ccg cca<br>Tyr Ala Pro Ser Ile Tyr Thr His Leu Ser Pro Ala Lys Thr Pro Pro<br>                  205                    210                    215 | | 676 |
| cct ccg cct gcc atg att ccc atg cgt cct ccc tat ggg tac cct gga<br>Pro Pro Pro Ala Met Ile Pro Met Arg Pro Pro Tyr Gly Tyr Pro Gly<br>220                      225                    230 | | 724 |
| gac ttt gac agg acc agc tca gtt ggt ggc cac agc tcc cag gtg ccc<br>Asp Phe Asp Arg Thr Ser Ser Val Gly Gly His Ser Ser Gln Val Pro<br>235                      240                    245 | | 772 |
| ctg ctg cgt gaa gtg gat ggg agc gta tct tca gaa gta cga agt ggc<br>Leu Leu Arg Glu Val Asp Gly Ser Val Ser Ser Glu Val Arg Ser Gly<br>250                      255                    260                    265 | | 820 |
| tac agg atc cag gct aac cag caa gat gac tcc atg agg gtc cta tac<br>Tyr Arg Ile Gln Ala Asn Gln Gln Asp Asp Ser Met Arg Val Leu Tyr<br>                  270                    275                    280 | | 868 |
| tat atg gag aag gag cta gcc aac ttc gat cct tcc cgg cct ggc cct<br>Tyr Met Glu Lys Glu Leu Ala Asn Phe Asp Pro Ser Arg Pro Gly Pro<br>                  285                    290                    295 | | 916 |
| ccc aat ggc cga gtg gaa cgg gcc atg agt gaa gta acc tcc ctc cat<br>Pro Asn Gly Arg Val Glu Arg Ala Met Ser Glu Val Thr Ser Leu His<br>300                      305                    310 | | 964 |
| gaa gat gac tgg cga tct cgg cct tcc agg gct cct gcc ctc aca ccc<br>Glu Asp Asp Trp Arg Ser Arg Pro Ser Arg Ala Pro Ala Leu Thr Pro<br>315                      320                    325 | | 1012 |
| atc agg gat gag gag tgg aat cgc cac tcc cct cgg agt ccc aga aca<br>Ile Arg Asp Glu Glu Trp Asn Arg His Ser Pro Arg Ser Pro Arg Thr<br>330                      335                    340                    345 | | 1060 |
| tgg gag cag gaa ccc ctt caa gaa cag cca agg ggt ggt tgg ggg tct<br>Trp Glu Gln Glu Pro Leu Gln Glu Gln Pro Arg Gly Gly Trp Gly Ser<br>                  350                    355                    360 | | 1108 |
| ggg cgg cct cgg gcc cgc tct gtg gat gct cta gat gac atc aac cgg<br>Gly Arg Pro Arg Ala Arg Ser Val Asp Ala Leu Asp Asp Ile Asn Arg<br>                  365                    370                    375 | | 1156 |
| cct ggc tcc act gaa tca gga agg tct tct ccc cca agt agt gga cgg<br>Pro Gly Ser Thr Glu Ser Gly Arg Ser Ser Pro Pro Ser Ser Gly Arg<br>                    380                    385                    390 | | 1204 |
| aga ggg cgg gcc tat gca cct ccg aga agt cgc agc cgg gat gac ctc<br>Arg Gly Arg Ala Tyr Ala Pro Pro Arg Ser Arg Ser Arg Asp Asp Leu<br>                  395                    400                    405 | | 1252 |
| tat gac ccc gac gat cct aga gac ttg cca cat tcc cga gat ccc cac<br>Tyr Asp Pro Asp Asp Pro Arg Asp Leu Pro His Ser Arg Asp Pro His<br>410                      415                    420                    425 | | 1300 |

-continued

```
tat tat gat gat ttg agg tct agg gat cca cgt gct gac ccc aga tcc    1348
Tyr Tyr Asp Asp Leu Arg Ser Arg Asp Pro Arg Ala Asp Pro Arg Ser
            430                 435                 440 cgt cag cga tcc cac gat cct cgg gat gct ggc ttc agg tca cgg gac    1396
Arg Gln Arg Ser His Asp Pro Arg Asp Ala Gly Phe Arg Ser Arg Asp
        445                 450                 455 cct cag tat gat ggg cga ctc tta gaa gag gct tta aag aaa aaa ggg    1444
Pro Gln Tyr Asp Gly Arg Leu Leu Glu Glu Ala Leu Lys Lys Lys Gly
    460                 465                 470 gct ggg gag aga aga cgc gtt tac agg gag gaa gaa gaa gaa gag        1492
Ala Gly Glu Arg Arg Arg Val Tyr Arg Glu Glu Glu Glu Glu Glu
475                 480                 485 gag ggc cac tat ccc cca gca cct ccg cct tac tct gag act gac tcg    1540
Glu Gly His Tyr Pro Pro Ala Pro Pro Pro Tyr Ser Glu Thr Asp Ser
490                 495                 500                 505 cag gcc tcg agg gag cgg agg atg aaa aag aat ttg gcc ctg agt cgg    1588
Gln Ala Ser Arg Glu Arg Arg Met Lys Lys Asn Leu Ala Leu Ser Arg
                510                 515                 520 gaa agt tta gtc gtc tga tcccacgttt tgttatgtag cttttatact           1636
Glu Ser Leu Val Val  *
                525 tttttaattg gaatattgat gaaactcttc accaagccta ataaaa                 1682
```

<210> SEQ ID NO 17
<211> LENGTH: 594
<212> TYPE: PRT
<213> ORGANISM: Mus musculus

<400> SEQUENCE: 17

```
Met Ala Pro Ala Ala Ser Ala Cys Ala Gly Ala Pro Gly Ser His Pro
1               5                   10                  15

Ala Thr Thr Ile Phe Val Cys Leu Phe Leu Ile Ile Tyr Cys Pro Asp
            20                  25                  30

Arg Ala Ser Ala Ile Gln Val Thr Val Pro Asp Pro Tyr His Val Val
        35                  40                  45

Ile Leu Phe Gln Pro Val Thr Leu His Cys Thr Tyr Gln Met Ser Asn
    50                  55                  60

Thr Leu Thr Ala Pro Ile Val Ile Trp Lys Tyr Lys Ser Phe Cys Arg
65                  70                  75                  80

Asp Arg Val Ala Asp Ala Phe Ser Pro Ala Ser Val Asp Asn Gln Leu
                85                  90                  95

Asn Ala Gln Leu Ala Ala Gly Asn Pro Gly Tyr Asn Pro Tyr Val Glu
            100                 105                 110

Cys Gln Asp Ser Val Arg Thr Val Arg Val Val Ala Thr Lys Gln Gly
        115                 120                 125

Asn Ala Val Thr Leu Gly Asp Tyr Tyr Gln Gly Arg Arg Ile Thr Ile
    130                 135                 140

Thr Gly Asn Ala Gly Leu Thr Phe Glu Gln Thr Ala Trp Gly Asp Ser
145                 150                 155                 160

Gly Val Tyr Tyr Cys Ser Val Val Ser Ala Gln Asp Leu Asp Gly Asn
                165                 170                 175

Asn Glu Ala Tyr Ala Glu Leu Ile Val Leu Gly Arg Thr Ser Glu Ala
            180                 185                 190

Pro Glu Leu Leu Pro Gly Phe Arg Ala Gly Pro Leu Glu Asp Trp Leu
        195                 200                 205

Phe Val Val Val Val Cys Leu Ala Ser Leu Leu Phe Phe Leu Leu Leu
```

-continued

```
             210                 215                 220
Gly Ile Cys Trp Cys Gln Cys Cys Pro His Thr Cys Cys Cys Tyr Val
225                 230                 235                 240

Arg Cys Pro Cys Pro Asp Lys Cys Cys Pro Glu Ala Leu Tyr
                245                 250                 255

Ala Ala Gly Lys Ala Ala Thr Ser Gly Val Pro Ser Ile Tyr Ala Pro
                260                 265                 270

Ser Ile Tyr Thr His Leu Ser Pro Ala Lys Thr Pro Pro Pro Pro
                275                 280                 285

Ala Met Ile Pro Met Arg Pro Pro Tyr Gly Tyr Pro Gly Asp Phe Asp
290                 295                 300

Arg Thr Ser Ser Val Gly Gly His Ser Ser Gln Val Pro Leu Leu Arg
305                 310                 315                 320

Glu Val Asp Gly Ser Val Ser Ser Glu Val Arg Ser Gly Tyr Arg Ile
                325                 330                 335

Gln Ala Asn Gln Gln Asp Asp Ser Met Arg Val Leu Tyr Tyr Met Glu
                340                 345                 350

Lys Glu Leu Ala Asn Phe Asp Pro Ser Arg Pro Gly Pro Asn Gly
                355                 360                 365

Arg Val Glu Arg Ala Met Ser Glu Val Thr Ser Leu His Glu Asp Asp
                370                 375                 380

Trp Arg Ser Arg Pro Ser Arg Ala Pro Ala Leu Thr Pro Ile Arg Asp
385                 390                 395                 400

Glu Glu Trp Asn Arg His Ser Pro Arg Ser Pro Arg Thr Trp Glu Gln
                405                 410                 415

Glu Pro Leu Gln Glu Gln Pro Arg Gly Gly Trp Gly Ser Gly Arg Pro
                420                 425                 430

Arg Ala Arg Ser Val Asp Ala Leu Asp Asp Ile Asn Arg Pro Gly Ser
                435                 440                 445

Thr Glu Ser Gly Arg Ser Ser Pro Pro Ser Ser Gly Arg Arg Gly Arg
                450                 455                 460

Ala Tyr Ala Pro Pro Arg Ser Arg Ser Arg Asp Asp Leu Tyr Asp Pro
465                 470                 475                 480

Asp Asp Pro Arg Asp Leu Pro His Ser Arg Asp Pro His Tyr Tyr Asp
                485                 490                 495

Asp Leu Arg Ser Arg Asp Pro Arg Ala Asp Pro Arg Ser Arg Gln Arg
                500                 505                 510

Ser His Asp Pro Arg Asp Ala Gly Phe Arg Ser Arg Asp Pro Gln Tyr
                515                 520                 525

Asp Gly Arg Leu Leu Glu Glu Ala Leu Lys Lys Lys Gly Ala Gly Glu
530                 535                 540

Arg Arg Arg Val Tyr Arg Glu Glu Glu Glu Glu Glu Gly His
545                 550                 555                 560

Tyr Pro Pro Ala Pro Pro Tyr Ser Glu Thr Asp Ser Gln Ala Ser
                565                 570                 575

Arg Glu Arg Arg Met Lys Lys Asn Leu Ala Leu Ser Arg Glu Ser Leu
                580                 585                 590

Val Val
```

<210> SEQ ID NO 18
<211> LENGTH: 575
<212> TYPE: PRT
<213> ORGANISM: Mus musculus

```
<400> SEQUENCE: 18

Met Ala Pro Ala Ala Ser Ala Cys Ala Gly Ala Pro Gly Ser His Pro
1               5                   10                  15

Ala Thr Thr Ile Phe Val Cys Leu Phe Leu Ile Ile Tyr Cys Pro Asp
            20                  25                  30

Arg Ala Ser Ala Ile Gln Val Thr Val Pro Asp Pro Tyr His Val Val
        35                  40                  45

Ile Leu Phe Gln Pro Val Thr Leu His Cys Thr Tyr Gln Met Ser Asn
    50                  55                  60

Thr Leu Thr Ala Pro Ile Val Ile Trp Lys Tyr Lys Ser Phe Cys Arg
65                  70                  75                  80

Asp Arg Val Ala Asp Ala Phe Ser Pro Ala Ser Val Asp Asn Gln Leu
                85                  90                  95

Asn Ala Gln Leu Ala Ala Gly Asn Pro Gly Tyr Asn Pro Tyr Val Glu
            100                 105                 110

Cys Gln Asp Ser Val Arg Thr Val Arg Val Val Ala Thr Lys Gln Gly
        115                 120                 125

Asn Ala Val Thr Leu Gly Asp Tyr Tyr Gln Gly Arg Arg Ile Thr Ile
130                 135                 140

Thr Gly Asn Ala Gly Leu Thr Phe Glu Gln Thr Ala Trp Gly Asp Ser
145                 150                 155                 160

Gly Val Tyr Tyr Cys Ser Val Val Ser Ala Gln Asp Leu Asp Gly Asn
                165                 170                 175

Asn Glu Ala Tyr Ala Glu Leu Ile Val Leu Asp Trp Leu Phe Val Val
            180                 185                 190

Val Val Cys Leu Ala Ser Leu Leu Phe Phe Leu Leu Leu Gly Ile Cys
        195                 200                 205

Trp Cys Gln Cys Cys Pro His Thr Cys Cys Cys Tyr Val Arg Cys Pro
210                 215                 220

Cys Cys Pro Asp Lys Cys Cys Cys Pro Glu Ala Leu Tyr Ala Ala Gly
225                 230                 235                 240

Lys Ala Ala Thr Ser Gly Val Pro Ser Ile Tyr Ala Pro Ser Ile Tyr
                245                 250                 255

Thr His Leu Ser Pro Ala Lys Thr Pro Pro Pro Pro Ala Met Ile
            260                 265                 270

Pro Met Arg Pro Pro Tyr Gly Tyr Pro Gly Asp Phe Asp Arg Thr Ser
        275                 280                 285

Ser Val Gly Gly His Ser Gln Val Pro Leu Leu Arg Glu Val Asp
    290                 295                 300

Gly Ser Val Ser Glu Val Arg Ser Gly Tyr Arg Ile Gln Ala Asn
305                 310                 315                 320

Gln Gln Asp Asp Ser Met Arg Val Leu Tyr Tyr Met Glu Lys Glu Leu
                325                 330                 335

Ala Asn Phe Asp Pro Ser Arg Pro Gly Pro Asn Gly Arg Val Glu
            340                 345                 350

Arg Ala Met Ser Glu Val Thr Ser Leu His Glu Asp Asp Trp Arg Ser
        355                 360                 365

Arg Pro Ser Arg Ala Pro Ala Leu Thr Pro Ile Arg Asp Glu Glu Trp
    370                 375                 380

Asn Arg His Ser Pro Arg Ser Pro Arg Thr Trp Glu Gln Glu Pro Leu
385                 390                 395                 400

Gln Glu Gln Pro Arg Gly Gly Trp Gly Ser Gly Arg Pro Arg Ala Arg
                405                 410                 415
```

```
Ser Val Asp Ala Leu Asp Asp Ile Asn Arg Pro Gly Ser Thr Glu Ser
            420                 425                 430

Gly Arg Ser Ser Pro Pro Ser Ser Gly Arg Arg Gly Arg Ala Tyr Ala
            435                 440                 445

Pro Pro Arg Ser Arg Ser Arg Asp Asp Leu Tyr Asp Pro Asp Asp Pro
            450                 455                 460

Arg Asp Leu Pro His Ser Arg Asp Pro His Tyr Tyr Asp Asp Leu Arg
465                 470                 475                 480

Ser Arg Asp Pro Arg Ala Asp Pro Arg Ser Gln Arg Ser His Asp
                485                 490                 495

Pro Arg Asp Ala Gly Phe Arg Ser Arg Asp Pro Gln Tyr Asp Gly Arg
                500                 505                 510

Leu Leu Glu Glu Ala Leu Lys Lys Gly Ala Gly Glu Arg Arg
            515                 520                 525

Val Tyr Arg Glu Glu Glu Glu Glu Glu Gly His Tyr Pro Pro
            530                 535                 540

Ala Pro Pro Pro Tyr Ser Glu Thr Asp Ser Gln Ala Ser Arg Glu Arg
545                 550                 555                 560

Arg Met Lys Lys Asn Leu Ala Leu Ser Arg Glu Ser Leu Val Val
                565                 570                 575

<210> SEQ ID NO 19
<211> LENGTH: 526
<212> TYPE: PRT
<213> ORGANISM: Mus musculus

<400> SEQUENCE: 19

Met Ala Pro Ala Ala Ser Ala Cys Ala Gly Ala Pro Gly Ser His Pro
1               5                   10                  15

Ala Thr Thr Ile Phe Val Cys Leu Phe Leu Ile Ile Tyr Cys Pro Asp
            20                  25                  30

Arg Ala Ser Ala Ile Gln Val Thr Val Pro Asp Pro Tyr His Val Val
            35                  40                  45

Ile Leu Phe Gln Pro Val Thr Leu His Cys Thr Tyr Gln Met Ser Asn
        50                  55                  60

Thr Leu Thr Ala Pro Ile Val Ile Trp Lys Tyr Lys Ser Phe Cys Arg
65                  70                  75                  80

Asp Arg Val Ala Asp Ala Phe Ser Pro Ala Ser Val Asp Asn Gln Leu
                85                  90                  95

Asn Ala Gln Leu Ala Ala Gly Asn Pro Gly Tyr Asn Pro Tyr Val Glu
            100                 105                 110

Cys Gln Asp Ser Val Arg Thr Val Arg Val Val Ala Thr Lys Gln Gly
            115                 120                 125

Asn Ala Val Thr Leu Gly Asp Tyr Tyr Gln Gly Arg Arg Ile Thr Ile
            130                 135                 140

Thr Gly Asn Ala Gly Leu Thr Phe Glu Gln Thr Ala Trp Gly Asp Ser
145                 150                 155                 160

Gly Val Tyr Tyr Cys Ser Val Val Ser Ala Gln Asp Leu Asp Gly Asn
                165                 170                 175

Asn Glu Ala Tyr Ala Glu Leu Ile Val Leu Val Tyr Ala Ala Gly Lys
            180                 185                 190

Ala Ala Thr Ser Gly Val Pro Ser Ile Tyr Ala Pro Ser Ile Tyr Thr
            195                 200                 205

His Leu Ser Pro Ala Lys Thr Pro Pro Pro Pro Ala Met Ile Pro
```

```
        210                 215                 220
Met Arg Pro Pro Tyr Gly Tyr Pro Gly Asp Phe Asp Arg Thr Ser Ser
225                 230                 235                 240

Val Gly Gly His Ser Ser Gln Val Pro Leu Leu Arg Glu Val Asp Gly
            245                 250                 255

Ser Val Ser Ser Glu Val Arg Ser Gly Tyr Arg Ile Gln Ala Asn Gln
            260                 265                 270

Gln Asp Asp Ser Met Arg Val Leu Tyr Tyr Met Glu Lys Glu Leu Ala
        275                 280                 285

Asn Phe Asp Pro Ser Arg Pro Gly Pro Asn Gly Arg Val Glu Arg
290                 295                 300

Ala Met Ser Glu Val Thr Ser Leu His Glu Asp Asp Trp Arg Ser Arg
305                 310                 315                 320

Pro Ser Arg Ala Pro Ala Leu Thr Pro Ile Arg Asp Glu Glu Trp Asn
            325                 330                 335

Arg His Ser Pro Arg Ser Pro Arg Thr Trp Glu Gln Glu Pro Leu Gln
            340                 345                 350

Glu Gln Pro Arg Gly Gly Trp Gly Ser Gly Arg Pro Arg Ala Arg Ser
        355                 360                 365

Val Asp Ala Leu Asp Asp Ile Asn Arg Pro Gly Ser Thr Glu Ser Gly
370                 375                 380

Arg Ser Ser Pro Pro Ser Ser Gly Arg Arg Gly Arg Ala Tyr Ala Pro
385                 390                 395                 400

Pro Arg Ser Arg Ser Arg Asp Asp Leu Tyr Asp Pro Asp Pro Arg
            405                 410                 415

Asp Leu Pro His Ser Arg Asp Pro His Tyr Tyr Asp Asp Leu Arg Ser
            420                 425                 430

Arg Asp Pro Arg Ala Asp Pro Arg Ser Arg Gln Arg Ser His Asp Pro
        435                 440                 445

Arg Asp Ala Gly Phe Arg Ser Arg Asp Pro Gln Tyr Asp Gly Arg Leu
        450                 455                 460

Leu Glu Glu Ala Leu Lys Lys Lys Gly Ala Gly Glu Arg Arg Arg Val
465                 470                 475                 480

Tyr Arg Glu Glu Glu Glu Glu Glu Gly His Tyr Pro Pro Ala
            485                 490                 495

Pro Pro Pro Tyr Ser Glu Thr Asp Ser Gln Ala Ser Arg Glu Arg Arg
            500                 505                 510

Met Lys Lys Asn Leu Ala Leu Ser Arg Glu Ser Leu Val Val
            515                 520                 525

<210> SEQ ID NO 20
<211> LENGTH: 18
<212> TYPE: DNA
<213> ORGANISM: Homo Sapiens
<220> FEATURE:
<221> NAME/KEY: misc_binding
<222> LOCATION: 1..18
<223> OTHER INFORMATION: sequencing oligonucleotide PrimerPU

<400> SEQUENCE: 20
tgtaaaacga cggccagt                                                   18

<210> SEQ ID NO 21
<211> LENGTH: 18
<212> TYPE: DNA
<213> ORGANISM: Homo Sapiens
<220> FEATURE:
```

```
<221> NAME/KEY: misc_binding
<222> LOCATION: 1..18
<223> OTHER INFORMATION: sequencing oligonucleotide PrimerRP

<400> SEQUENCE: 21
caggaaacag ctatgacc                                                   18

<210> SEQ ID NO 22
<211> LENGTH: 20
<212> TYPE: DNA
<213> ORGANISM: Artificial Sequence
<220> FEATURE:
<223> OTHER INFORMATION: oligonucleotide sense primer

<400> SEQUENCE: 22
ctacaacccc tacgtcgagt                                                 20

<210> SEQ ID NO 23
<211> LENGTH: 20
<212> TYPE: DNA
<213> ORGANISM: Artificial Sequence
<220> FEATURE:
<223> OTHER INFORMATION: oligonucleotide anti sense primer

<400> SEQUENCE: 23
aggcggagat cgccagtcgt                                                 20

<210> SEQ ID NO 24
<211> LENGTH: 24
<212> TYPE: DNA
<213> ORGANISM: Artificial Sequence
<220> FEATURE:
<223> OTHER INFORMATION: oligonucleotide sense primer

<400> SEQUENCE: 24
cctttgtcca cgtcgtttac gctc                                            24

<210> SEQ ID NO 25
<211> LENGTH: 20
<212> TYPE: DNA
<213> ORGANISM: Artificial Sequence
<220> FEATURE:
<223> OTHER INFORMATION: oligonucleotide anti sense primer

<400> SEQUENCE: 25
tcacagcgtt gccctgcttg                                                 20

<210> SEQ ID NO 26
<211> LENGTH: 21
<212> TYPE: DNA
<213> ORGANISM: Artificial Sequence
<220> FEATURE:
<223> OTHER INFORMATION: oligonucleotide sense primer

<400> SEQUENCE: 26
ttactgctcc gtggtctcag c                                               21

<210> SEQ ID NO 27
<211> LENGTH: 22
<212> TYPE: DNA
<213> ORGANISM: Artificial Sequence
<220> FEATURE:
<223> OTHER INFORMATION: oligonucleotide anti sense primer

<400> SEQUENCE: 27
agctactcct gtcaacgtct cc                                              22
```

<210> SEQ ID NO 28
<211> LENGTH: 167
<212> TYPE: PRT
<213> ORGANISM: Bos taurus

<400> SEQUENCE: 28

Met Arg Cys Gly Pro Leu Tyr Arg Phe Leu Trp Leu Trp Pro Tyr Leu
1               5                   10                  15

Ser Tyr Val Glu Ala Val Pro Ile Arg Lys Val Gln Asp Asp Thr Lys
            20                  25                  30

Thr Leu Ile Lys Thr Ile Val Thr Arg Ile Asn Asp Ile Ser His Thr
        35                  40                  45

Gln Ser Val Ser Ser Lys Gln Arg Val Thr Gly Leu Asp Phe Ile Pro
    50                  55                  60

Gly Leu His Pro Leu Leu Ser Leu Ser Lys Met Asp Gln Thr Leu Ala
65                  70                  75                  80

Ile Tyr Gln Gln Ile Leu Thr Ser Leu Pro Ser Arg Asn Val Val Gln
                85                  90                  95

Ile Ser Asn Asp Leu Glu Asn Leu Arg Asp Leu Leu His Leu Leu Ala
            100                 105                 110

Ala Ser Lys Ser Cys Pro Leu Pro Gln Val Arg Ala Leu Glu Ser Leu
        115                 120                 125

Glu Ser Leu Gly Val Val Leu Glu Ala Ser Leu Tyr Ser Thr Glu Val
    130                 135                 140

Val Ala Leu Ser Arg Leu Gln Gly Ser Leu Gln Asp Met Leu Arg Gln
145                 150                 155                 160

Leu Asp Leu Ser Pro Gly Cys
                165

<210> SEQ ID NO 29
<211> LENGTH: 146
<212> TYPE: PRT
<213> ORGANISM: Canis familiaris

<400> SEQUENCE: 29

Val Pro Ile Arg Lys Val Gln Asp Asp Thr Lys Thr Leu Ile Lys Thr
1               5                   10                  15

Ile Val Ala Arg Ile Asn Asp Ile Ser His Thr Gln Ser Val Ser Ser
            20                  25                  30

Lys Gln Arg Val Ala Gly Leu Asp Phe Ile Pro Gly Leu Gln Pro Val
        35                  40                  45

Leu Ser Leu Ser Arg Met Asp Gln Thr Leu Ala Ile Tyr Gln Gln Ile
    50                  55                  60

Leu Asn Ser Leu His Ser Arg Asn Val Val Gln Ile Ser Asn Asp Leu
65                  70                  75                  80

Glu Asn Leu Arg Asp Leu Leu His Leu Leu Ala Ser Ser Lys Ser Cys
                85                  90                  95

Pro Leu Pro Arg Ala Arg Gly Leu Glu Thr Phe Glu Ser Leu Gly Gly
            100                 105                 110

Val Leu Glu Ala Ser Leu Tyr Ser Thr Glu Val Val Ala Leu Ser Arg
        115                 120                 125

Leu Gln Ala Ala Leu Gln Asp Met Leu Arg Arg Leu Asp Leu Ser Pro
    130                 135                 140

Gly Cys
145

<210> SEQ ID NO 30
<211> LENGTH: 163
<212> TYPE: PRT
<213> ORGANISM: Gallus gallus

<400> SEQUENCE: 30

Met Cys Trp Arg Pro Leu Cys Arg Leu Trp Ser Tyr Leu Val Tyr Val
1               5                   10                  15

Gln Ala Val Pro Cys Gln Ile Phe Gln Asp Asp Thr Lys Thr Leu Ile
            20                  25                  30

Lys Thr Ile Val Thr Arg Ile Asn Asp Ile Ser His Thr Ser Val Ser
        35                  40                  45

Ala Lys Gln Arg Val Thr Gly Leu Asp Phe Ile Pro Gly Leu His Pro
    50                  55                  60

Ile Leu Ser Leu Ser Lys Met Asp Gln Thr Leu Ala Val Tyr Gln Gln
65                  70                  75                  80

Val Leu Thr Ser Leu Pro Ser Gln Asn Val Leu Gln Ile Ala Asn Asp
                85                  90                  95

Leu Glu Asn Leu Arg Asp Leu Leu His Leu Leu Ala Phe Ser Lys Ser
            100                 105                 110

Cys Ser Leu Pro Gln Thr Ser Gly Leu Gln Lys Pro Glu Ser Leu Asp
        115                 120                 125

Gly Val Leu Glu Ala Ser Leu Tyr Ser Thr Glu Val Val Ala Leu Ser
    130                 135                 140

Arg Leu Gln Gly Ser Leu Gln Asp Ile Leu Gln Gln Leu Asp Ile Ser
145                 150                 155                 160

Pro Glu Cys

<210> SEQ ID NO 31
<211> LENGTH: 146
<212> TYPE: PRT
<213> ORGANISM: Gorilla gorilla

<400> SEQUENCE: 31

Val Pro Ile Gln Lys Val Gln Asp Asp Thr Lys Thr Leu Ile Lys Thr
1               5                   10                  15

Ile Val Thr Arg Ile Ser Asp Ile Ser His Thr Gln Ser Val Ser Ser
            20                  25                  30

Lys Gln Lys Val Thr Gly Leu Asp Phe Ile Pro Gly Leu His Pro Ile
        35                  40                  45

Leu Thr Leu Ser Lys Met Asp Gln Thr Leu Ala Val Tyr Gln Gln Ile
    50                  55                  60

Leu Thr Ser Met Pro Ser Arg Asn Met Ile Gln Ile Ser Asn Asp Leu
65                  70                  75                  80

Glu Asn Leu Arg Asp Leu Leu His Val Leu Ala Phe Ser Lys Ser Cys
                85                  90                  95

His Leu Pro Trp Ala Ser Gly Leu Glu Thr Leu Asp Ser Leu Gly Gly
            100                 105                 110

Val Leu Glu Ala Ser Gly Tyr Ser Thr Glu Val Val Ala Leu Ser Arg
        115                 120                 125

Leu Gln Gly Ser Leu Gln Asp Met Leu Trp Gln Leu Asp Leu Ser Pro
    130                 135                 140

Gly Cys
145

-continued

```
<210> SEQ ID NO 32
<211> LENGTH: 167
<212> TYPE: PRT
<213> ORGANISM: Homo sapiens

<400> SEQUENCE: 32

Met His Trp Gly Thr Leu Cys Gly Phe Leu Trp Leu Trp Pro Tyr Leu
1               5                   10                  15

Phe Tyr Val Gln Ala Val Pro Ile Gln Lys Val Gln Asp Asp Thr Lys
            20                  25                  30

Thr Leu Ile Lys Thr Ile Val Thr Arg Ile Asn Asp Ile Ser His Thr
        35                  40                  45

Gln Ser Val Ser Ser Lys Gln Lys Val Thr Gly Leu Asp Phe Ile Pro
    50                  55                  60

Gly Leu His Pro Ile Leu Thr Leu Ser Lys Met Asp Gln Thr Leu Ala
65                  70                  75                  80

Val Tyr Gln Gln Ile Leu Thr Ser Met Pro Ser Arg Asn Val Ile Gln
                85                  90                  95

Ile Ser Asn Asp Leu Glu Asn Leu Arg Asp Leu Leu His Val Leu Ala
            100                 105                 110

Phe Ser Lys Ser Cys His Leu Pro Trp Ala Ser Gly Leu Glu Thr Leu
        115                 120                 125

Asp Ser Leu Gly Gly Val Leu Glu Ala Ser Gly Tyr Ser Thr Glu Val
    130                 135                 140

Val Ala Leu Ser Arg Leu Gln Gly Ser Leu Gln Asp Met Leu Trp Gln
145                 150                 155                 160

Leu Asp Leu Ser Pro Gly Cys
                165

<210> SEQ ID NO 33
<211> LENGTH: 167
<212> TYPE: PRT
<213> ORGANISM: Macaca mulatta

<400> SEQUENCE: 33

Met Tyr Trp Arg Thr Leu Trp Gly Phe Leu Trp Leu Trp Pro Tyr Leu
1               5                   10                  15

Phe Tyr Ile Gln Ala Val Pro Ile Gln Lys Val Gln Ser Asp Thr Lys
            20                  25                  30

Thr Leu Ile Lys Thr Ile Val Thr Arg Ile Asn Asp Ile Ser His Thr
        35                  40                  45

Gln Ser Val Ser Ser Lys Gln Arg Val Thr Gly Leu Asp Phe Ile Pro
    50                  55                  60

Gly Leu His Pro Val Leu Thr Leu Ser Gln Met Asp Gln Thr Leu Ala
65                  70                  75                  80

Ile Tyr Gln Gln Ile Leu Ile Asn Leu Pro Ser Arg Asn Val Ile Gln
                85                  90                  95

Ile Ser Asn Asp Leu Glu Asn Leu Arg Asp Leu Leu His Leu Leu Ala
            100                 105                 110

Phe Ser Lys Ser Cys His Leu Pro Leu Ala Ser Gly Leu Glu Thr Leu
        115                 120                 125

Glu Ser Leu Gly Asp Val Leu Glu Ala Ser Leu Tyr Ser Thr Glu Val
    130                 135                 140

Val Ala Leu Ser Arg Leu Gln Gly Ser Leu Gln Asp Met Leu Trp Gln
145                 150                 155                 160
```

```
Leu Asp Leu Ser Pro Gly Cys
            165

<210> SEQ ID NO 34
<211> LENGTH: 167
<212> TYPE: PRT
<213> ORGANISM: Mus musculus

<400> SEQUENCE: 34

Met Cys Trp Arg Pro Leu Cys Arg Phe Leu Trp Leu Trp Ser Tyr Leu
1               5                   10                  15

Ser Tyr Val Gln Ala Val Pro Ile Gln Lys Val Gln Asp Asp Thr Lys
            20                  25                  30

Thr Leu Ile Lys Thr Ile Val Thr Arg Ile Asn Asp Ile Ser His Thr
        35                  40                  45

Gln Ser Val Ser Ala Lys Gln Arg Val Thr Gly Leu Asp Phe Ile Pro
    50                  55                  60

Gly Leu His Pro Ile Leu Ser Leu Ser Lys Met Asp Gln Thr Leu Ala
65                  70                  75                  80

Val Tyr Gln Gln Val Leu Thr Ser Leu Pro Ser Gln Asn Val Leu Gln
                85                  90                  95

Ile Ala Asn Asp Leu Glu Asn Leu Arg Asp Leu Leu His Leu Leu Ala
            100                 105                 110

Phe Ser Lys Ser Cys Ser Leu Pro Gln Thr Ser Gly Leu Gln Lys Pro
        115                 120                 125

Glu Ser Leu Asp Gly Val Leu Glu Ala Ser Leu Tyr Ser Thr Glu Val
    130                 135                 140

Val Ala Leu Ser Arg Leu Gln Gly Ser Leu Gln Asp Ile Leu Gln Gln
145                 150                 155                 160

Leu Asp Val Ser Pro Glu Cys
            165

<210> SEQ ID NO 35
<211> LENGTH: 146
<212> TYPE: PRT
<213> ORGANISM: Ovus aries

<400> SEQUENCE: 35

Val Pro Ile Arg Lys Val Gln Asp Asp Thr Lys Thr Leu Ile Lys Thr
1               5                   10                  15

Ile Val Thr Arg Ile Asn Asp Ile Ser His Thr Gln Ser Val Ser Ser
            20                  25                  30

Lys Gln Arg Val Thr Gly Leu Asp Phe Ile Pro Gly Leu His Pro Leu
        35                  40                  45

Leu Ser Leu Ser Lys Met Asp Gln Thr Leu Ala Ile Tyr Gln Gln Ile
    50                  55                  60

Leu Ala Ser Leu Pro Ser Arg Asn Val Ile Gln Ile Ser Asn Asp Leu
65                  70                  75                  80

Glu Asn Leu Arg Asp Leu Leu His Leu Leu Ala Ala Ser Lys Ser Cys
                85                  90                  95

Pro Leu Pro Gln Val Arg Ala Leu Glu Ser Leu Glu Ser Leu Gly Val
            100                 105                 110

Val Leu Glu Ala Ser Leu Tyr Ser Thr Glu Val Val Ala Leu Ser Arg
        115                 120                 125

Leu Gln Gly Ser Leu Gln Asp Met Leu Arg Gln Leu Asp Leu Ser Pro
    130                 135                 140
```

Gly Cys
145

<210> SEQ ID NO 36
<211> LENGTH: 146
<212> TYPE: PRT
<213> ORGANISM: Pan troglodytes

<400> SEQUENCE: 36

```
Val Pro Ile Gln Lys Val Gln Asp Asp Thr Lys Thr Leu Ile Lys Thr
 1               5                  10                  15
Ile Val Thr Arg Ile Asn Asp Ile Ser His Thr Gln Ser Val Ser Ser
                20                  25                  30
Lys Gln Lys Val Thr Gly Leu Asp Phe Ile Pro Gly Leu His Pro Ile
            35                  40                  45
Leu Thr Leu Ser Lys Met Asp Gln Thr Leu Ala Val Tyr Gln Gln Ile
    50                  55                  60
Leu Thr Ser Met Pro Ser Arg Asn Met Ile Gln Ile Ser Asn Asp Leu
65                  70                  75                  80
Glu Asn Leu Arg Asp Leu Leu His Val Leu Ala Phe Ser Lys Ser Cys
                85                  90                  95
His Leu Pro Trp Ala Ser Gly Leu Glu Thr Leu Asp Ser Leu Gly Gly
            100                 105                 110
Val Leu Glu Ala Ser Gly Tyr Ser Thr Glu Val Val Ala Leu Ser Arg
        115                 120                 125
Leu Gln Gly Ser Leu Gln Asp Met Leu Trp Gln Leu Asp Leu Ser Pro
    130                 135                 140
Gly Cys
145
```

<210> SEQ ID NO 37
<211> LENGTH: 146
<212> TYPE: PRT
<213> ORGANISM: Pongo pygmaeus

<400> SEQUENCE: 37

```
Val Pro Ile Gln Lys Val Gln Asp Asp Thr Lys Thr Leu Ile Lys Thr
 1               5                  10                  15
Val Ile Thr Arg Ile Asn Asp Ile Ser His Thr Gln Ser Val Ser Ser
                20                  25                  30
Lys Gln Lys Val Thr Gly Leu Asp Phe Ile Pro Gly Leu His Pro Ile
            35                  40                  45
Leu Thr Leu Ser Lys Met Asp Gln Thr Leu Ala Val Tyr Gln Gln Ile
    50                  55                  60
Leu Thr Ser Met Pro Ser Arg Asn Val Ile Gln Ile Ser Asn Asp Leu
65                  70                  75                  80
Glu Asn Leu Arg Asp Leu Leu His Val Leu Ala Phe Ser Lys Ser Cys
                85                  90                  95
His Leu Pro Trp Ala Ser Gly Leu Glu Thr Leu Asp Arg Leu Gly Gly
            100                 105                 110
Val Leu Glu Ala Ser Gly Tyr Ser Thr Glu Val Val Ala Leu Ser Arg
        115                 120                 125
Leu Gln Arg Ser Leu Gln Asp Met Leu Trp Gln Leu Asp Leu Ser Pro
    130                 135                 140
Gly Cys
145
```

<210> SEQ ID NO 38
<211> LENGTH: 167
<212> TYPE: PRT
<213> ORGANISM: Rattus norvegicus

<400> SEQUENCE: 38

Met Cys Trp Arg Pro Leu Cys Arg Phe Leu Trp Leu Trp Ser Tyr Leu
1               5                   10                  15

Ser Tyr Val Gln Ala Val Pro Ile His Lys Val Gln Asp Asp Thr Lys
            20                  25                  30

Thr Leu Ile Lys Thr Ile Val Thr Arg Ile Asn Asp Ile Ser His Thr
        35                  40                  45

Gln Ser Val Ser Ala Arg Gln Arg Val Thr Gly Leu Asp Phe Ile Pro
    50                  55                  60

Gly Leu His Pro Ile Leu Ser Leu Ser Lys Met Asp Gln Thr Leu Ala
65                  70                  75                  80

Val Tyr Gln Gln Ile Leu Thr Ser Leu Pro Ser Gln Asn Val Leu Gln
                85                  90                  95

Ile Ala His Asp Leu Glu Asn Leu Arg Asp Leu Leu His Leu Leu Ala
            100                 105                 110

Phe Ser Lys Ser Cys Ser Leu Pro Gln Thr Arg Gly Leu Gln Lys Pro
        115                 120                 125

Glu Ser Leu Asp Gly Val Leu Glu Ala Ser Leu Tyr Ser Thr Glu Val
    130                 135                 140

Val Ala Leu Ser Arg Leu Gln Gly Ser Leu Gln Asp Ile Leu Gln Gln
145                 150                 155                 160

Leu Asp Leu Ser Pro Glu Cys
                165

<210> SEQ ID NO 39
<211> LENGTH: 167
<212> TYPE: PRT
<213> ORGANISM: Sus scrofa

<400> SEQUENCE: 39

Met Arg Cys Gly Pro Leu Cys Arg Phe Leu Trp Leu Trp Pro Tyr Leu
1               5                   10                  15

Ser Tyr Val Glu Ala Val Pro Ile Trp Arg Val Gln Asp Asp Thr Lys
            20                  25                  30

Thr Leu Ile Lys Thr Ile Val Thr Arg Ile Ser Asp Ile Ser His Met
        35                  40                  45

Gln Ser Val Ser Ser Lys Gln Arg Val Thr Gly Leu Asp Phe Ile Pro
    50                  55                  60

Gly Leu His Pro Val Leu Ser Leu Ser Lys Met Asp Gln Thr Leu Ala
65                  70                  75                  80

Ile Tyr Gln Gln Ile Leu Thr Ser Leu Pro Ser Arg Asn Val Ile Gln
                85                  90                  95

Ile Ser Asn Asp Leu Glu Asn Leu Arg Asp Leu Leu His Leu Leu Ala
            100                 105                 110

Ser Ser Lys Ser Cys Pro Leu Pro Gln Ala Arg Ala Leu Glu Thr Leu
        115                 120                 125

Glu Ser Leu Gly Gly Val Leu Glu Ala Ser Leu Tyr Ser Thr Glu Val
    130                 135                 140

Val Ala Leu Ser Arg Leu Gln Gly Ala Leu Gln Asp Met Leu Arg Gln
145                 150                 155                 160

Leu Asp Leu Ser Pro Gly Cys
            165

<210> SEQ ID NO 40
<211> LENGTH: 4
<212> TYPE: PRT
<213> ORGANISM: Homo sapiens

<400> SEQUENCE: 40

Glu Thr Leu Asp
1

<210> SEQ ID NO 41
<211> LENGTH: 4
<212> TYPE: PRT
<213> ORGANISM: Mus musculus

<400> SEQUENCE: 41

Gln Lys Pro Glu
1

<210> SEQ ID NO 42
<211> LENGTH: 6
<212> TYPE: PRT
<213> ORGANISM: Homo sapiens

<400> SEQUENCE: 42

Leu Asp Ser Leu Gly Gly
1               5

<210> SEQ ID NO 43
<211> LENGTH: 4
<212> TYPE: PRT
<213> ORGANISM: Homo sapiens

<400> SEQUENCE: 43

Glu Lys Leu Glu
1

<210> SEQ ID NO 44
<211> LENGTH: 4
<212> TYPE: PRT
<213> ORGANISM: Homo sapiens

<400> SEQUENCE: 44

Glu Lys Pro Glu
1

<210> SEQ ID NO 45
<211> LENGTH: 4
<212> TYPE: PRT
<213> ORGANISM: Homo sapiens

<400> SEQUENCE: 45

Glu Lys Pro Asp
1

<210> SEQ ID NO 46
<211> LENGTH: 5
<212> TYPE: PRT
<213> ORGANISM: Homo sapiens

<400> SEQUENCE: 46

Thr Pro Asp Ser Leu
1               5

```
<210> SEQ ID NO 47
<211> LENGTH: 9
<212> TYPE: PRT
<213> ORGANISM: Homo sapiens

<400> SEQUENCE: 47

Gly Leu Gln Thr Leu Asp Ser Leu Gly
1               5

<210> SEQ ID NO 48
<211> LENGTH: 5
<212> TYPE: PRT
<213> ORGANISM: Homo sapiens

<400> SEQUENCE: 48

Gly Gly Val Leu Glu
1               5

<210> SEQ ID NO 49
<211> LENGTH: 6
<212> TYPE: PRT
<213> ORGANISM: Homo sapiens

<400> SEQUENCE: 49

Thr Pro Asp Ser Leu Gly
1               5

<210> SEQ ID NO 50
<211> LENGTH: 9
<212> TYPE: PRT
<213> ORGANISM: Homo sapiens

<400> SEQUENCE: 50

Ser Leu Gly Gly Val Leu Glu Ala Ser
1               5

<210> SEQ ID NO 51
<211> LENGTH: 6
<212> TYPE: PRT
<213> ORGANISM: Homo sapiens

<400> SEQUENCE: 51

Pro Glu Ser Leu Gly Gly
1               5

<210> SEQ ID NO 52
<211> LENGTH: 6
<212> TYPE: PRT
<213> ORGANISM: Homo sapiens

<400> SEQUENCE: 52

Pro Asp Ser Leu Gly Gly
1               5

<210> SEQ ID NO 53
<211> LENGTH: 7
<212> TYPE: PRT
<213> ORGANISM: Homo sapiens

<400> SEQUENCE: 53

Leu Gly Gly Val Leu Glu Ala
1               5
```

```
<210> SEQ ID NO 54
<211> LENGTH: 22
<212> TYPE: PRT
<213> ORGANISM: Homo sapiens

<400> SEQUENCE: 54

Glu Asn Leu Arg Asp Leu Leu His Val Leu Ala Phe Ser Lys Ser Cys
1               5                   10                  15

His Leu Pro Trp Ala Ser
            20

<210> SEQ ID NO 55
<211> LENGTH: 22
<212> TYPE: PRT
<213> ORGANISM: Homo sapiens

<400> SEQUENCE: 55

Leu Leu His Val Leu Ala Phe Ser Lys Ser Cys His Leu Pro Trp Ala
1               5                   10                  15

Ser Gly Leu Glu Thr Leu
            20

<210> SEQ ID NO 56
<211> LENGTH: 22
<212> TYPE: PRT
<213> ORGANISM: Homo sapiens

<400> SEQUENCE: 56

Ala Phe Ser Lys Ser Cys His Leu Pro Trp Ala Ser Gly Leu Glu Thr
1               5                   10                  15

Leu Asp Ser Leu Gly Gly
            20

<210> SEQ ID NO 57
<211> LENGTH: 22
<212> TYPE: PRT
<213> ORGANISM: Homo sapiens

<400> SEQUENCE: 57

Cys His Leu Pro Trp Ala Ser Gly Leu Glu Thr Leu Asp Ser Leu Gly
1               5                   10                  15

Gly Val Leu Glu Ala Ser
            20

<210> SEQ ID NO 58
<211> LENGTH: 18
<212> TYPE: PRT
<213> ORGANISM: Homo sapiens

<400> SEQUENCE: 58

Leu Pro Trp Ala Ser Gly Leu Glu Thr Leu Asp Ser Leu Gly Gly Val
1               5                   10                  15

Leu Glu

<210> SEQ ID NO 59
<211> LENGTH: 14
<212> TYPE: PRT
<213> ORGANISM: Homo sapiens

<400> SEQUENCE: 59

Trp Ala Ser Gly Leu Glu Thr Leu Asp Ser Leu Gly Gly Val
1               5                   10
```

<210> SEQ ID NO 60
<211> LENGTH: 21
<212> TYPE: PRT
<213> ORGANISM: Homo sapiens

<400> SEQUENCE: 60

Ala Ser Gly Leu Glu Thr Asp Ser Leu Gly Gly Val Leu Glu Ala Ser
1               5                   10                  15

Gly Tyr Ser Thr Glu
            20

<210> SEQ ID NO 61
<211> LENGTH: 10
<212> TYPE: PRT
<213> ORGANISM: Homo sapiens

<400> SEQUENCE: 61

Ser Gly Leu Glu Thr Leu Asp Ser Leu Gly
1               5                   10

<210> SEQ ID NO 62
<211> LENGTH: 22
<212> TYPE: PRT
<213> ORGANISM: Homo sapiens

<400> SEQUENCE: 62

Thr Leu Asp Ser Leu Gly Gly Val Leu Glu Ala Ser Gly Tyr Ser Thr
1               5                   10                  15

Glu Val Val Ala Leu Ser
            20

<210> SEQ ID NO 63
<211> LENGTH: 22
<212> TYPE: PRT
<213> ORGANISM: Homo sapiens

<400> SEQUENCE: 63

Gly Gly Val Leu Glu Ala Ser Gly Tyr Ser Thr Glu Val Val Ala Leu
1               5                   10                  15

Ser Arg Gly Gln Gly Ser
            20

<210> SEQ ID NO 64
<211> LENGTH: 22
<212> TYPE: PRT
<213> ORGANISM: Mus musculus

<400> SEQUENCE: 64

Glu Asn Leu Arg Asp Leu Leu His Leu Leu Ala Phe Ser Lys Ser Cys
1               5                   10                  15

Ser Leu Pro Gln Thr Ser
            20

<210> SEQ ID NO 65
<211> LENGTH: 22
<212> TYPE: PRT
<213> ORGANISM: Mus musculus

<400> SEQUENCE: 65

Leu Leu His Leu Leu Ala Phe Ser Lys Ser Cys Ser Leu Pro Gln Thr
1               5                   10                  15

Ser Gly Leu Gln Lys Pro

-continued

```
            20

<210> SEQ ID NO 66
<211> LENGTH: 22
<212> TYPE: PRT
<213> ORGANISM: Mus musculus

<400> SEQUENCE: 66

Ala Phe Ser Lys Ser Cys Ser Leu Pro Gln Thr Ser Gly Leu Gln Lys
1               5                   10                  15

Pro Glu Ser Leu Asp Gly
            20

<210> SEQ ID NO 67
<211> LENGTH: 22
<212> TYPE: PRT
<213> ORGANISM: Mus musculus

<400> SEQUENCE: 67

Cys Ser Leu Pro Gln Thr Ser Gly Leu Gln Lys Pro Glu Ser Leu Asp
1               5                   10                  15

Gly Val Leu Glu Ala Ser
            20

<210> SEQ ID NO 68
<211> LENGTH: 18
<212> TYPE: PRT
<213> ORGANISM: Mus musculus

<400> SEQUENCE: 68

Leu Pro Gln Thr Ser Gly Leu Gln Lys Pro Glu Ser Leu Asp Gly Val
1               5                   10                  15

Leu Glu

<210> SEQ ID NO 69
<211> LENGTH: 14
<212> TYPE: PRT
<213> ORGANISM: Mus musculus

<400> SEQUENCE: 69

Gln Thr Ser Gly Leu Gln Lys Pro Glu Ser Leu Asp Gly Val
1               5                   10

<210> SEQ ID NO 70
<211> LENGTH: 22
<212> TYPE: PRT
<213> ORGANISM: Mus musculus

<400> SEQUENCE: 70

Thr Ser Gly Leu Gln Lys Pro Glu Ser Leu Asp Gly Val Leu Glu Ala
1               5                   10                  15

Ser Leu Tyr Ser Thr Glu
            20

<210> SEQ ID NO 71
<211> LENGTH: 10
<212> TYPE: PRT
<213> ORGANISM: Mus musculus

<400> SEQUENCE: 71

Ser Gly Leu Gln Lys Pro Glu Ser Leu Asp
1               5                   10
```

```
<210> SEQ ID NO 72
<211> LENGTH: 22
<212> TYPE: PRT
<213> ORGANISM: Mus musculus

<400> SEQUENCE: 72

Lys Pro Glu Ser Leu Asp Gly Val Leu Glu Ala Ser Leu Tyr Ser Thr
1               5                   10                  15

Glu Val Val Ala Leu Ser
            20

<210> SEQ ID NO 73
<211> LENGTH: 22
<212> TYPE: PRT
<213> ORGANISM: Mus musculus

<400> SEQUENCE: 73

Asp Gly Val Leu Glu Ala Ser Leu Tyr Ser Thr Glu Val Val Ala Leu
1               5                   10                  15

Ser Arg Leu Gln Gly Ser
            20

<210> SEQ ID NO 74
<211> LENGTH: 67
<212> TYPE: DNA
<213> ORGANISM: Artificial Sequence
<220> FEATURE:
<223> OTHER INFORMATION: oligonucleotide Chimeric oligonucleotides

<400> SEQUENCE: 74
atgcaacagg acggacttgg agtagttttc uacuccaagt cagtccuguu gcaugcgcgt      60
ttcgcgc                                                                67

<210> SEQ ID NO 75
<211> LENGTH: 20
<212> TYPE: DNA
<213> ORGANISM: Artificial Sequence
<220> FEATURE:
<223> OTHER INFORMATION: oligonucleotide Forward Primer

<400> SEQUENCE: 75
tgtccacgtc gtttacgctc                                                  20

<210> SEQ ID NO 76
<211> LENGTH: 20
<212> TYPE: DNA
<213> ORGANISM: Artificial Sequence
<220> FEATURE:
<223> OTHER INFORMATION: oligonucleotide Reverse Primer

<400> SEQUENCE: 76
tcccacttcc gttccttgtc                                                  20

<210> SEQ ID NO 77
<211> LENGTH: 27
<212> TYPE: DNA
<213> ORGANISM: Artificial Sequence
<220> FEATURE:
<223> OTHER INFORMATION: oligonucleotide Probes endogenous/mutant

<400> SEQUENCE: 77
cctactccaa gtcmgtcctg ttgcatt                                          27
```

```
<210> SEQ ID NO 78
<211> LENGTH: 67
<212> TYPE: DNA
<213> ORGANISM: Artificial Sequence
<220> FEATURE:
<223> OTHER INFORMATION: oligonucleotide Chimeric oligonucleotides

<400> SEQUENCE: 78
gaccctgccc tgtacctacc taccagatgt tttcaucugg uaggttcagg gcagggucgc    60
gcgtttt                                                              67

<210> SEQ ID NO 79
<211> LENGTH: 21
<212> TYPE: DNA
<213> ORGANISM: Artificial Sequence
<220> FEATURE:
<223> OTHER INFORMATION: oligonucleotide Forward Primer

<400> SEQUENCE: 79
gtggtgatcc tcttccagcc t                                              21

<210> SEQ ID NO 80
<211> LENGTH: 19
<212> TYPE: DNA
<213> ORGANISM: Artificial Sequence
<220> FEATURE:
<223> OTHER INFORMATION: oligonucleotide Reverse Primer

<400> SEQUENCE: 80
ccagatgacg atgggttgc                                                 19

<210> SEQ ID NO 81
<211> LENGTH: 25
<212> TYPE: DNA
<213> ORGANISM: Artificial Sequence
<220> FEATURE:
<223> OTHER INFORMATION: oligonucleotide Probes endogenous/mutant

<400> SEQUENCE: 81
accctgccct gwcctaccag atgac                                          25

<210> SEQ ID NO 82
<211> LENGTH: 68
<212> TYPE: DNA
<213> ORGANISM: Artificial Sequence
<220> FEATURE:
<223> OTHER INFORMATION: oligonucleotide Chimeric oligonucleotides

<400> SEQUENCE: 82
tggctgagct cttacctggt tttcattttt gaaaaccagg tcagagctca gccagcgcgt    60
tttcgcgc                                                             68

<210> SEQ ID NO 83
<211> LENGTH: 20
<212> TYPE: DNA
<213> ORGANISM: Artificial Sequence
<220> FEATURE:
<223> OTHER INFORMATION: oligonucleotide Forward Primer

<400> SEQUENCE: 83
gagctcatcg tccttgggag                                                20

<210> SEQ ID NO 84
<211> LENGTH: 19
<212> TYPE: DNA
```

```
<213> ORGANISM: Artificial Sequence
<220> FEATURE:
<223> OTHER INFORMATION: oligonucleotide Reverse Primer

<400> SEQUENCE: 84
agtcttctat gggccccgc                                                      19

<210> SEQ ID NO 85
<211> LENGTH: 27
<212> TYPE: DNA
<213> ORGANISM: Artificial Sequence
<220> FEATURE:
<223> OTHER INFORMATION: oligonucleotide Probes endogenous/mutant

<400> SEQUENCE: 85
caccgactcg agamtggacc aaaagtc                                             27

<210> SEQ ID NO 86
<211> LENGTH: 68
<212> TYPE: DNA
<213> ORGANISM: Artificial Sequence
<220> FEATURE:
<223> OTHER INFORMATION: oligonucleotide Chimeric oligonucleotides

<400> SEQUENCE: 86
ggttgtggta tgcctggctg ccttcttttg aaggcagcca gtcataccac aaccgcgcgt         60
tttcgcgc                                                                  68

<210> SEQ ID NO 87
<211> LENGTH: 20
<212> TYPE: DNA
<213> ORGANISM: Artificial Sequence
<220> FEATURE:
<223> OTHER INFORMATION: oligonucleotide Forward Primer

<400> SEQUENCE: 87
acgcagagct catcgtcctt                                                     20

<210> SEQ ID NO 88
<211> LENGTH: 20
<212> TYPE: DNA
<213> ORGANISM: Artificial Sequence
<220> FEATURE:
<223> OTHER INFORMATION: oligonucleotide Reverse Primer

<400> SEQUENCE: 88
gatgcccagg aggaggaaga                                                     20

<210> SEQ ID NO 89
<211> LENGTH: 23
<212> TYPE: DNA
<213> ORGANISM: Artificial Sequence
<220> FEATURE:
<223> OTHER INFORMATION: oligonucleotide Probes endogenous/mutant

<400> SEQUENCE: 89
caacaccata ckgaccgacg gaa                                                 23

<210> SEQ ID NO 90
<211> LENGTH: 18
<212> TYPE: DNA
<213> ORGANISM: Artificial Sequence
<220> FEATURE:
<223> OTHER INFORMATION: oligonucleotide mouse LSR specific primer

<400> SEQUENCE: 90
```
acgcatggga atcatggc                                              18

<210> SEQ ID NO 91
<211> LENGTH: 18
<212> TYPE: DNA
<213> ORGANISM: Artificial Sequence
<220> FEATURE:
<223> OTHER INFORMATION: oligonucleotide Zinc finger nuclotides of
      SEQID1

<400> SEQUENCE: 91
taggggtgag cggcgggg                                              18

<210> SEQ ID NO 92
<211> LENGTH: 21
<212> TYPE: DNA
<213> ORGANISM: Artificial Sequence
<220> FEATURE:
<223> OTHER INFORMATION: oligonucleotide Zinc finger nuclotides of
      SEQID1
<220> FEATURE:
<221> NAME/KEY: misc_feature
<222> LOCATION: 10..12
<223> OTHER INFORMATION: n=a, g, c or t

<400> SEQUENCE: 92
gagggctggn nntagggtg a                                           21

<210> SEQ ID NO 93
<211> LENGTH: 20
<212> TYPE: DNA
<213> ORGANISM: Artificial Sequence
<220> FEATURE:
<223> OTHER INFORMATION: oligonucleotide Zinc finger nuclotides of
      SEQID1
<220> FEATURE:
<221> NAME/KEY: misc_feature
<222> LOCATION: 10..11
<223> OTHER INFORMATION: n=a, g, c or t

<400> SEQUENCE: 93
agggctgggn ntagggtga                                             20

<210> SEQ ID NO 94
<211> LENGTH: 18
<212> TYPE: DNA
<213> ORGANISM: Artificial Sequence
<220> FEATURE:
<223> OTHER INFORMATION: oligonucleotide Zinc finger nuclotides of
      SEQID1

<400> SEQUENCE: 94
gtgggagccg agggctgg                                              18

<210> SEQ ID NO 95
<211> LENGTH: 19
<212> TYPE: DNA
<213> ORGANISM: Artificial Sequence
<220> FEATURE:
<223> OTHER INFORMATION: oligonucleotide Zinc finger nuclotides of
      SEQID1
<220> FEATURE:
<221> NAME/KEY: misc_feature
<222> LOCATION: 10
<223> OTHER INFORMATION: n=a, g, c or t

<400> SEQUENCE: 95
gtgggagccn agggctggg                                             19

```
<210> SEQ ID NO 96
<211> LENGTH: 18
<212> TYPE: DNA
<213> ORGANISM: Artificial Sequence
<220> FEATURE:
<223> OTHER INFORMATION: oligonucleotide Zinc finger nuclotides of
      SEQID1

<400> SEQUENCE: 96
gcggcggccg ggtgggag                                                 18

<210> SEQ ID NO 97
<211> LENGTH: 18
<212> TYPE: DNA
<213> ORGANISM: Artificial Sequence
<220> FEATURE:
<223> OTHER INFORMATION: oligonucleotide Zinc finger nuclotides of
      SEQID1

<400> SEQUENCE: 97
ttggccggag cagatggg                                                 18

<210> SEQ ID NO 98
<211> LENGTH: 20
<212> TYPE: DNA
<213> ORGANISM: Artificial Sequence
<220> FEATURE:
<223> OTHER INFORMATION: oligonucleotide Zinc finger nuclotides of
      SEQID1
<220> FEATURE:
<221> NAME/KEY: misc_feature
<222> LOCATION: 10..11
<223> OTHER INFORMATION: n=a, g, c or t

<400> SEQUENCE: 98
gcagatgggn nccggaaggg                                               20

<210> SEQ ID NO 99
<211> LENGTH: 21
<212> TYPE: DNA
<213> ORGANISM: Artificial Sequence
<220> FEATURE:
<223> OTHER INFORMATION: oligonucleotide Zinc finger nuclotides of
      SEQID1
<220> FEATURE:
<221> NAME/KEY: misc_feature
<222> LOCATION: 10..12
<223> OTHER INFORMATION: n=a, g, c or t

<400> SEQUENCE: 99
agggctgggn nnaggggtga g                                             21

<210> SEQ ID NO 100
<211> LENGTH: 21
<212> TYPE: DNA
<213> ORGANISM: Artificial Sequence
<220> FEATURE:
<223> OTHER INFORMATION: oligonucleotide Zinc finger nuclotides of
      SEQID1
<220> FEATURE:
<221> NAME/KEY: misc_feature
<222> LOCATION: 10..12
<223> OTHER INFORMATION: n=a, g, c or t

<400> SEQUENCE: 100
aggggtgagn nncggggagg g                                             21
```

```
<210> SEQ ID NO 101
<211> LENGTH: 18
<212> TYPE: DNA
<213> ORGANISM: Artificial Sequence
<220> FEATURE:
<223> OTHER INFORMATION: oligonucleotide Zinc finger nuclotides of
      SEQID1

<400> SEQUENCE: 101
aagtgggtct cggttgca                                                 18

<210> SEQ ID NO 102
<211> LENGTH: 21
<212> TYPE: DNA
<213> ORGANISM: Artificial Sequence
<220> FEATURE:
<223> OTHER INFORMATION: oligonucleotide zinc finger LSR sequences

<400> SEQUENCE: 102
aaggtcgcct atggtgcaga c                                             21

<210> SEQ ID NO 103
<211> LENGTH: 20
<212> TYPE: DNA
<213> ORGANISM: Artificial Sequence
<220> FEATURE:
<223> OTHER INFORMATION: oligonucleotide zinc finger LSR sequences

<400> SEQUENCE: 103
gtgggagccc ggggctgga                                                20

<210> SEQ ID NO 104
<211> LENGTH: 18
<212> TYPE: DNA
<213> ORGANISM: Artificial Sequence
<220> FEATURE:
<223> OTHER INFORMATION: oligonucleotide zinc finger LSR sequences

<400> SEQUENCE: 104
tgggggtggg cggcgggg                                                 18

<210> SEQ ID NO 105
<211> LENGTH: 20
<212> TYPE: DNA
<213> ORGANISM: Artificial Sequence
<220> FEATURE:
<223> OTHER INFORMATION: oligonucleotide zinc finger LSR sequences

<400> SEQUENCE: 105
ccgggagtgc gcaggggta                                                20

<210> SEQ ID NO 106
<211> LENGTH: 19
<212> TYPE: DNA
<213> ORGANISM: Artificial Sequence
<220> FEATURE:
<223> OTHER INFORMATION: oligonucleotide zinc finger LSR sequences

<400> SEQUENCE: 106
gtggctgcac aaggtcgcc                                                19
```

We claim:
1. An isolated polypeptide comprising:
a) a leptin polypeptide fragment that modulates an activity of the Lipolysis Stimulated Receptor (LSR) and comprises at least 22 but not more than 50 contiguous amino acids of SEQ ID NO: 32 and contains amino acid residues 117-138 of SEQ ID NO: 32, wherein said activity of the LSR is selected from the group consisting of binding of lipoproteins, uptake of lipoproteins, degradation of lipoproteins, binding of leptin, uptake of leptin, and degradation of leptin;
b) a leptin polypeptide fragment that modulates an activity of the LSR and comprises at least 22 but not more than 40 contiguous amino acids of SEQ ID NO: 32 and contains amino acid residues 117-138 of SEQ ID NO: 32, wherein said activity of the LSR is selected from the group consisting of binding of lipoproteins, uptake of lipoproteins, degradation of lipoproteins, binding of leptin, uptake of leptin, and degradation of leptin;
c) a leptin polypeptide fragment that modulates an activity of the LSR and comprises at least 22 but not more than 30 contiguous amino acids of SEQ ID NO: 32 and contains amino acid residues 117-138 of SEQ ID NO: 32, wherein said activity of the LSR is selected from the group consisting of binding of lipoproteins, uptake of lipoproteins, degradation of lipoproteins, binding of leptin, uptake of leptin, and degradation of leptin;
d) a leptin polypeptide fragment that modulates an activity of the LSR, said leptin polypeptide fragment comprising an amino acid sequence that is at least 85% identical to a polypeptide that comprises at least 22 but not more than 50 contiguous amino acids of SEQ ID NO: 32 wherein said fragment contains amino acid residues 117-138 of SEQ ID NO: 32, wherein said activity of the LSR is selected from the group consisting of binding of lipoproteins, uptake of lipoproteins, degradation of lipoproteins, binding of leptin, uptake of leptin, and degradation of leptin;
e) a leptin polypeptide fragment that modulates an activity of the LSR, said leptin polypeptide fragment comprising an amino acid sequence that is at least 95% identical to a polypeptide that comprises at least 22 but not more than 50 contiguous amino acids of SEQ ID NO: 32 wherein said fragment contains amino acid residues 117-138 of SEQ ID NO: 32, wherein said activity of the LSR is selected from the group consisting of binding of lipoproteins, uptake of lipoproteins, degradation of lipoproteins, binding of leptin, uptake of leptin, and degradation of leptin; or
f) a leptin polypeptide fragment of at least 22 but not more than 50 contiguous amino acids of SEQ ID NO:32 wherein said fragment contains amino acid residues 117-138 of SEQ ID NO: 32.

2. A composition comprising a polypeptide according to claim 1 and a pharmaceutically acceptable diluent.

3. The isolated polypeptide according to claim 1, wherein said polypeptide is a leptin polypeptide fragment that modulates an activity of the Lipolysis Stimulated Receptor (LSR) and comprises at least 22 but not more than 50 contiguous amino acids of SEQ ID NO: 32 and contains amino acid residues 117-138 of SEQ ID NO: 32, wherein said activity of the LSR is selected from the group consisting of binding of lipoproteins, uptake of lipoproteins, degradation of lipoproteins, binding of leptin, uptake of leptin, and degradation of leptin.

4. The isolated polypeptide according to claim 1, wherein said polypeptide is a leptin polypeptide fragment that modulates an activity of the LSR and comprises at least 22 but not more than 40 contiguous amino acids of SEQ ID NO: 32 and contains amino acid residues 117-138 of SEQ ID NO: 32, wherein said activity of the LSR is selected from the group consisting of binding of lipoproteins, uptake of lipoproteins, degradation of lipoproteins, binding of leptin, uptake of leptin, and degradation of leptin.

5. The isolated polypeptide according to claim 1, wherein said polypeptide is a leptin polypeptide fragment that modulates an activity of the LSR and comprises at least 22 but not more than 30 contiguous amino acids of SEQ ID NO: 32 and contains amino acid residues 117-138 of SEQ ID NO: 32, wherein said activity of the LSR is selected from the group consisting of binding of lipoproteins, uptake of lipoproteins, degradation of lipoproteins, binding of leptin, uptake of leptin, and degradation of leptin.

6. The isolated polypeptide according to claim 1, wherein said polypeptide is a leptin polypeptide fragment that modulates an activity of the LSR and comprises an amino acid sequence that is at least 85% identical to a polypeptide that comprises at least 22 but not more than 50 contiguous amino acids of SEQ ID NO: 32 wherein said fragment contains amino acid residues 117-138 of SEQ ID NO: 32, wherein said activity of the LSR is selected from the group consisting of binding of lipoproteins, uptake of lipoproteins, degradation of lipoproteins, binding of leptin, uptake of leptin, and degradation of leptin.

7. The isolated polypeptide according to claim 1, wherein said polypeptide is a leptin polypeptide fragment that modulates an activity of the LSR and comprises an amino acid sequence that is at least 95% identical to a polypeptide that comprises at least 22 but not more than 50 contiguous amino acids of SEQ ID NO: 32 wherein said fragment contains amino acid residues 117-138 of SEQ ID NO: 32, wherein said activity of the LSR is selected from the group consisting of binding of lipoproteins, uptake of lipoproteins, degradation of lipoproteins, binding of leptin, uptake of leptin, and degradation of leptin.

8. The isolated polypeptide according to claim 1, wherein said polypeptide is a leptin polypeptide fragment of at least 22 but not more than 50 contiguous amino acids of SEQ ID NO: 32 wherein said fragment contains amino acid residues 117-138 of SEQ ID NO: 32.

9. The isolated polypeptide according to claim 1, wherein said polypeptide is a leptin polypeptide fragment that modulates an activity of the Lipolysis Stimulated Receptor (LSR) and consists of at least 22 but not more than 50 contiguous amino acids of SEQ ID NO: 32 and contains amino acid residues 117-138 of SEQ ID NO: 32, wherein said activity of the LSR is selected from the group consisting of binding of lipoproteins, uptake of lipoproteins, degradation of lipoproteins, binding of leptin, uptake of leptin, and degradation of leptin.

10. The isolated polypeptide according to claim 1, wherein said polypeptide is a leptin polypeptide fragment that modulates an activity of the LSR and consists of at least 22 but not more than 40 contiguous amino acids of SEQ ID NO: 32 and contains amino acid residues 117-138 of SEQ ID NO: 32, wherein said activity of the LSR is selected from the group consisting of binding of lipoproteins, uptake of lipoproteins, degradation of lipoproteins, binding of leptin, uptake of leptin, and degradation of leptin.

11. The isolated polypeptide according to claim 1, wherein said polypeptide is a leptin polypeptide fragment that modulates an activity of the LSR and consists of at least 22 but not more than 30 contiguous amino acids of SEQ ID NO: 32 and contains amino acid residues 117-138 of SEQ ID NO: 32, wherein said activity of the LSR is selected from the group consisting of binding of lipoproteins, uptake of lipoproteins, degradation of lipoproteins, binding of leptin, uptake of leptin, and degradation of leptin.

12. The isolated polypeptide according to claim 1, wherein said polypeptide is a leptin polypeptide fragment that modulates an activity of the LSR and consists of an amino acid sequence that is at least 85% identical to a polypeptide that consists of at least 22 but not more than 50 contiguous amino acids of SEQ ID NO: 32 wherein said fragment contains amino acid residues 117-138 of SEQ ID NO: 32, wherein said activity of the LSR is selected from the group consisting of binding of lipoproteins, uptake of lipoproteins, degradation of lipoproteins, binding of leptin, uptake of leptin, and degradation of leptin.

13. The isolated polypeptide according to claim 1, wherein said polypeptide is a leptin polypeptide fragment that modulates an activity of the LSR and consists of an amino acid sequence that is at least 95% identical to a polypeptide that consists of least 22 but not more than 50 contiguous amino acids of SEQ ID NO: 32 wherein said fragment contains amino acid residues 117-138 of SEQ ID NO: 32, wherein said activity of the LSR is selected from the group consisting of binding of lipoproteins, uptake of lipoproteins, degradation of lipoproteins, binding of leptin, uptake of leptin, and degradation of leptin.

14. The isolated polypeptide according to claim 1, wherein said polypeptide is a leptin polypeptide fragment consisting of SEQ ID NO:32.

15. The isolated polypeptide according to claim 1, wherein said polypeptide is a leptin polypeptide fragment that comprises at least 22 but not more than 50 contiguous amino acids of SEQ ID NO: 32 wherein said fragment contains amino acid residues 117-138 of SEQ ID NO:32.

16. An isolated leptin polypeptide fragment consisting of amino acid residues 117-138 of SEQ ID NO:32.

17. A composition comprising a pharmaceutically acceptable diluent and a leptin polypeptide fragment consisting of amino acid residues 117-138 of SEQ ID NO:32.

* * * * *

UNITED STATES PATENT AND TRADEMARK OFFICE
CERTIFICATE OF CORRECTION

PATENT NO. : 7,470,669 B2  
APPLICATION NO. : 11/236198  
DATED : December 30, 2008  
INVENTOR(S) : Frances Yen et al.

It is certified that error appears in the above-identified patent and that said Letters Patent is hereby corrected as shown below:

Column 5,
Line 12, "a amino acid" should read --an amino acid--.

Column 6,
Lines 42-43, "SEQ ID NO: 1" should read --SEQ ID NO: 11--.

Column 15,
Lines 37-38, "a (N—N) bound" should read --a (N—N) bond--.

Column 17,
Line 31, "80, 90, 10, 110" should read --80, 90, 100, 110--.

Column 25,
Line 33, "al the site" should read --at the site--.
Line 35, "endogenous TSR gene" should read --endogenous LSR gene--.

Column 29,
Line 29, "the book or" should read --the book of--.

Column 34,
Line 3, "; No. 1651)" should read --; No. CRL1651)--.

Column 35,
Line 56, "a LULL" should read --a LI/LL--.

Column 37,
Line 35, "Van der Waal s forces" should read --Van der Waals forces--.
Lines 39-40, "the now-leptin compounds" should read --the non-leptin compounds--.

Column 47,
Line 55, "zinc linger" should read --zinc finger--.

Signed and Sealed this

Ninth Day of November, 2010

David J. Kappos  
*Director of the United States Patent and Trademark Office*

CERTIFICATE OF CORRECTION (continued)
U.S. Pat. No. 7,470,669 B2

Column 49,
Line 65, "Fir FIG. 6C" should read --For FIG. 6C--.

Column 51,
Line 14, "125I-LDL" should read --$^{125}$I-LDL--.

Column 56,
Line 13, "125I-leptin" should read --$^{125}$I-leptin--.
Lines 13-14, "After six 10 mm washes" should read --After six 10 min washes--.

Column 61,
Line 25, "the amino terminal end" should read --the amino terminal end.--.

Column 62,
Lines 60-61, "Plasma TG 2-3 hours nafter test meal (mg/mL)" should read
    --Plasma TG 2-3 hours after test meal (mg/mL)--.

Column 71,
Line 15, "Reverse Primer: AGTGTTCTATGGGCCCCGC (SEQ ID NO: 84)" should
    read --Reverse Primer: AGTCTTCTATGGGCCCCGC (SEQ ID NO: 84)--.
Lines 50-51, "5'-GGTTGTGGTATGCCTGGCTGGGTTCTTTTgaaggcagccAGTCA
    taccacaaccGCGCGTTTTCGCGC-3'" should read
        --5'-GGTTGTGGTATGCCTGGCTGCCTTCTTTTgaaggcagccAGTCA
    taccacaaccGCGCGTTTTCGCGC-3'--.

Column 78,
Line 17, "e.g. 0, 0.1 mM 0.2 mM," should read --e.g. 0, 0.1 mM, 0.2 mM,--.

Column 80,
Line 17, "$^{125}$labelled LDL" should read --$^{125}$I labelled LDL--.

Column 82,
Table 1, Row "GAPDH", column "Probe",
    "ACTCACGGCAAATTTCAACGGCACAG" should read
    --ACTCACGGCAAATTCAACGGCACAG--.

Column 83,

SEQUENCE LISTING

<110> Yen, Frances
      Bihain, Bernard
      Erickson, Mary Ruth
      Fruebis, Joachim <120> Methods of Screening for Compounds that Modulate the
LSR-Leptin Interaction and Their Use in the Prevention
and Treatment of Obesity-Related Diseases

<130> G-070US03CON

<140> US 11/236,198
<141> 2005-09-07

<150> 60/155,506
<151> 1999-09-22

<160> 129

<170> Patent.pm

<210> 1
<211> 23187
<212> DNA
<213> Homo sapiens

<220>
<221> exon
<222> 2001..2356
<223> exon1

<220>
<221> exon
<222> 3540..3884
<223> exon2

<220>
<221> exon
<222> 12163..12282
<223> exon3

<220>
<221> exon
<222> 15144..15200
<223> exon4

<220>
<221> exon
<222> 15765..15911
<223> exon5

<220>
<221> exon
<222> 19579..19752
<223> exon6

```
<220>
<221> exon
<222> 19899..19958
<223> exon7

<220>
<221> exon
<222> 20056..20187
<223> exon8

<220>
<221> exon
<222> 20329..20957
<223> exon9

<220>
<221> exon
<222> 21047..21187
<223> exon10

<220>
<221> polyA_signal
<222> 21168..21173
<223> AATAAA

<220>
<221> misc_feature
<222> 1..2000
<223> potential  5'regulatory  region

<220>
<221> misc_feature
<222> 22324..23187
<223> homology  with  USF2  gene  in  ref:  embl  Y07661

<220>
<221> primer_bind
<222> 523..544
<223> upstream amplification primer 17-2

<220>
<221> primer_bind
<222> 1047..1068
<223> downstream amplification primer 17-2 , complement <220>
<221> primer_bind
<222> 946..963
<223> upstream amplification primer 99-4576

<220>
<221> primer_bind
<222> 1385..1402
<223> downstream amplification primer 99-4576 , complement <220>
<221> primer_bind
<222> 1096..1115
<223> upstream amplification primer 9-19
```

```
<220>
<221> primer_bind
<222> 1616..1635
<223> downstream amplification primer 9-19 , complement <220>
<221> primer_bind
<222> 1602..1621
<223> upstream amplification primer 9-20

<220>
<221> primer_bind
<222> 2074..2093
<223> downstream amplification primer 9-20 , complement <220>
<221> primer_bind
<222> 2036..2053
<223> upstream amplification primer 99-4557

<220>
<221> primer_bind
<222> 2563..2580
<223> downstream amplification primer 99-4557 , complement <220>
<221> primer_bind
<222> 2084..2102
<223> upstream amplification primer 9-1

<220>
<221> primer_bind
<222> 2483..2500
<223> downstream amplification primer 9-1 , complement <220>
<221> primer_bind
<222> 2470..2489
<223> upstream amplification primer 9-21 , complement <220>
<221> primer_bind
<222> 2062..2081
<223> downstream amplification primer 9-21

<220>
<221> primer_bind
<222> 3455..3474
<223> upstream amplification primer 9-3

<220>
<221> primer_bind
<222> 3882..3901
<223> downstream amplification primer 9-3 , complement <220>
<221> primer_bind
<222> 3775..3792
```

<223> upstream amplification primer 99-4558

<220>
<221> primer_bind
<222> 4336..4356
<223> downstream amplification primer 99-4558 , complement <220>
<221> primer_bind
<222> 4902..4920
<223> upstream amplification primer 99-14419 , complement <220>
<221> primer_bind
<222> 4444..4463
<223> downstream amplification primer 99-14419

<220>
<221> primer_bind
<222> 6638..6655
<223> upstream amplification primer 99-4577

<220>
<221> primer_bind
<222> 7072..7089
<223> downstream amplification primer 99-4577 , complement <220>
<221> primer_bind
<222> 7995..8012
<223> upstream amplification primer 99-4559

<220>
<221> primer_bind
<222> 8576..8593
<223> downstream amplification primer 99-4559 , complement <220>
<221> primer_bind
<222> 9622..9639
<223> upstream amplification primer 99-3148

<220>
<221> primer_bind
<222> 10023..10040
<223> downstream amplification primer 99-3148 , complement <220>
<221> primer_bind
<222> 9964..9981
<223> upstream amplification primer 99-4560

<220>
<221> primer_bind
<222> 10546..10563
<223> downstream amplification primer 99-4560 , complement <220>
<221> primer_bind <222> 10996..11015
<223> upstream amplification primer 99-14411 , complement <220>
<221> primer_bind
<222> 10492..10512
<223> downstream amplification primer 99-14411

<220>
<221> primer_bind
<222> 11972..11990
<223> upstream amplification primer 99-4561

<220>
<221> primer_bind
<222> 12481..12501
<223> downstream amplification primer 99-4561 , complement <220>
<221> primer_bind
<222> 12005..12023
<223> upstream amplification primer 9-4

<220>
<221> primer_bind
<222> 12417..12436
<223> downstream amplification primer 9-4 , complement <220>
<221> primer_bind
<222> 14102..14119
<223> upstream amplification primer 99-4562

<220>
<221> primer_bind
<222> 14543..14563
<223> downstream amplification primer 99-4562 , complement <220>
<221> primer_bind
<222> 14431..14448
<223> upstream amplification primer 99-3149

<220>
<221> primer_bind
<222> 14848..14865
<223> downstream amplification primer 99-3149 , complement <220>
<221> primer_bind
<222> 14748..14767
<223> upstream amplification primer 9-22

<220>
<221> primer_bind
<222> 15198..15218
<223> downstream amplification primer 9-22 , complement

<220>

<221> primer_bind
<222> 14748..14767
<223> upstream amplification primer 9-24

<220>
<221> primer_bind
<222> 15333..15351
<223> downstream amplification primer 9-24 , complement <220>
<221> primer_bind
<222> 15002..15019
<223> upstream amplification primer 9-5

<220>
<221> primer_bind
<222> 15333..15351
<223> downstream amplification primer 9-5 , complement <220>
<221> primer_bind
<222> 15640..15657
<223> upstream amplification primer 9-6

<220>
<221> primer_bind
<222> 16072..16089
<223> downstream amplification primer 9-6 , complement <220>
<221> primer_bind
<222> 15800..15817
<223> upstream amplification primer 99-4563

<220>
<221> primer_bind
<222> 16179..16199
<223> downstream amplification primer 99-4563 , complement <220>
<221> primer_bind
<222> 19295..19312
<223> upstream amplification primer 99-3150

<220>
<221> primer_bind
<222> 19729..19746
<223> downstream amplification primer 99-3150 , complement <220>
<221> primer_bind
<222> 19420..19438
<223> upstream amplification primer 9-7

<220>
<221> primer_bind
<222> 19824..19841
<223> downstream amplification primer 9-7 , complement <220>
<221> primer_bind
<222> 19798..19815
<223> upstream amplification primer 9-8

<220>
<221> primer_bind
<222> 20137..20155
<223> downstream amplification primer 9-8 , complement <220>
<221> primer_bind
<222> 19913..19931
<223> upstream amplification primer 9-9

<220>
<221> primer_bind
<222> 20329..20346
<223> downstream amplification primer 9-9 , complement <220>
<221> primer_bind
<222> 20139..20157
<223> upstream amplification primer 99-4564

<220>
<221> primer_bind
<222> 20582..20599
<223> downstream amplification primer 99-4564 , complement <220>
<221> primer_bind
<222> 20238..20256
<223> upstream amplification primer 9-10

<220>
<221> primer_bind
<222> 20645..20662
<223> downstream amplification primer 9-10 , complement <220>
<221> primer_bind
<222> 20410..20424
<223> upstream amplification primer 9-26

<220>
<221> primer_bind
<222> 20690..20706
<223> downstream amplification primer 9-26 , complement <220>
<221> primer_bind
<222> 20569..20588
<223> upstream amplification primer 9-23

<220>
<221> primer_bind
<222> 21243..21262
<223> downstream amplification primer 9-23 , complement <220>
<221> primer_bind
<222> 20583..20604
<223> upstream amplification primer 9-11

<220>
<221> primer_bind
<222> 21015..21034
<223> downstream amplification primer 9-11 , complement <220>
<221> primer_bind
<222> 20584..20601
<223> upstream amplification primer 99-15285 , complement <220>
<221> primer_bind
<222> 20139..20158
<223> downstream amplification primer 99-15285

<220>
<221> primer_bind
<222> 20642..20659
<223> upstream amplification primer 99-15287 , complement <220>
<221> primer_bind
<222> 20207..20227
<223> downstream amplification primer 99-15287

<220>
<221> primer_bind
<222> 20691..20709
<223> upstream amplification primer 99-15286 , complement <220>
<221> primer_bind
<222> 20238..20257
<223> downstream amplification primer 99-15286

<220>
<221> primer_bind
<222> 20943..20960
<223> upstream amplification primer 9-2

<220>
<221> primer_bind
<222> 21295..21312
<223> downstream amplification primer 9-2 , complement <220>
<221> primer_bind
<222> 21013..21031
<223> upstream amplification primer 99-15284 , complement <220>
<221> primer_bind
<222> 20582..20602

<223> downstream amplification primer 99-15284

<220>
<221> primer_bind
<222> 21019..21038
<223> upstream amplification primer 99-14407 , complement <220>
<221> primer_bind
<222> 20571..20589
<223> downstream amplification primer 99-14407

<220>
<221> primer_bind
<222> 21079..21097
<223> upstream amplification primer 99-15283 , complement <220>
<221> primer_bind
<222> 20638..20655
<223> downstream amplification primer 99-15283

<220>
<221> primer_bind
<222> 21013..21032
<223> upstream amplification primer LSRi9f15s <220>
<221> primer_bind
<222> 21195..21214
<223> downstream amplification primer LSRi10r14s , complement <220>
<221> primer_bind
<222> 20354..20372
<223> upstream amplification primer LSRx9f13s <220>
<221> primer_bind
<222> 20570..20591
<223> upstream amplification primer LSRx9f14s <220>
<221> primer_bind
<222> 20811..20832
<223> downstream amplification primer LSRx9r13s , complement <220>
<221> allele
<222> 818
<223> 17-2-297  :  polymorphic  base  G  or  C <220>
<221> allele
<222> 1243
<223> 9-19-148  :  polymorphic  base  C  or  T <220>
<221> allele

```
<222> 1374
<223> 9-19-256  : polymorphic base  A  or  G

<220>
<221> allele
<222> 1401
<223> 9-19-307  : polymorphic base  A  or  T

<220>
<221> allele
<222> 1535
<223> 9-19-442  : polymorphic base  deletion of C

<220>
<221> allele
<222> 1788
<223> 9-20-187  : polymorphic base  A  or  C

<220>
<221> allele
<222> 2391
<223> 9-1-308   : polymorphic base  G  or  C

<220>
<221> allele
<222> 3778
<223> 9-3-324   : polymorphic base  C  or  T

<220>
<221> allele
<222> 4498
<223> 99-14419-424 : polymorphic base  T  or  G

<220>
<221> allele
<222> 15007
<223> 9-24-260  : polymorphic base  A  or  G

<220>
<221> allele
<222> 15233
<223> 9-24-486  : polymorphic base  A  or  G

<220>
<221> allele
<222> 15826
<223> 9-6-187   : polymorphic base  C  or  T

<220>
<221> allele
<222> 19567
<223> 9-7-148   : polymorphic base  A  or  G

<220>
<221> allele
<222> 19744
<223> 9-7-325   : polymorphic base  A  or  G

<220>
```

<221> allele
<222> 19786
<223> 9-7-367 : polymorphic base A or C

<220>
<221> allele
<222> 20158
<223> 9-9-246 : polymorphic base G or C

<220>
<221> allele
<222> 20595
<223> LSRX9-BM (17-1-240) : polymorphic base deletion of AGG <220>
<221> allele
<222> 21108
<223> LSRX10-BM : polymorphic base T or G <220>
<221> allele
<222> 606
<223> potential polymorphic base C or T <220>
<221> allele
<222> 5141
<223> potential polymorphic base insertion of G <220>
<221> allele
<222> 7428
<223> potential polymorphic base insertion of C <220>
<221> allele
<222> 8394
<223> potential polymorphic base C or G <220>
<221> allele
<222> 8704
<223> potential polymorphic base T or C <220>
<221> allele
<222> 9028
<223> potential polymorphic base G or A <220>
<221> allele
<222> 9950
<223> potential polymorphic base deletion of GAATGAAA <220>
<221> allele
<222> 9977
<223> potential polymorphic base T or C

```
<220>
<221> allele
<222> 10021
<223> potential polymorphic base A or G

<220>
<221> allele
<222> 11878
<223> potential polymorphic base C or T

<220>
<221> allele
<222> 19040
<223> potential polymorphic base deletion of G

<220>
<221> allele
<222> 21363
<223> potential polymorphic base A or G

<220>
<221> allele
<222> 21449
<223> potential polymorphic base C or T

<220>
<221> allele
<222> 21451
<223> potential polymorphic base G or C

<220>
<221> allele
<222> 21454
<223> potential polymorphic base A or G

<220>
<221> allele
<222> 21455
<223> potential polymorphic base G or A

<220>
<221> allele
<222> 21569
<223> potential polymorphic base T or A

<220>
<221> allele
<222> 21683
<223> potential polymorphic base deletion of C

<220>
<221> allele
<222> 21694
<223> potential polymorphic base insertion of T

<220>
<221> allele
<222> 21728
<223> potential polymorphic base deletion of G
```

```
<220>
<221> misc_binding
<222> 799..817
<223> 17-2-297.mis1

<220>
<221> misc_binding
<222> 819..837
<223> complement 17-2-297.mis2

<220>
<221> misc_binding
<222> 1224..1242
<223> 9-19-148.mis1

<220>
<221> misc_binding
<222> 1244..1262
<223> complement 9-19-148.mis2

<220>
<221> misc_binding
<222> 1330..1373
<223> 9-19-256.mis1

<220>
<221> misc_binding
<222> 1375..1393
<223> complement 9-19-256.mis2

<220>
<221> misc_binding
<222> 1382..1400
<223> 9-19-307.mis1

<220>
<221> misc_binding
<222> 1402..1420
<223> complement 9-19-307.mis2

<220>
<221> misc_binding
<222> 1516..1534
<223> 9-19-442.mis1

<220>
<221> misc_binding
<222> 1769..1787
<223> 9-20-187.mis1

<220>
<221> misc_binding
<222> 1789..1807
<223> complement 9-20-187.mis2

<220>
<221> misc_binding
<222> 2372..2390
```

```
<223> 9-1-308.mis1

<220>
<221> misc_binding
<222> 2392..2410
<223> complement 9-1-308.mis2

<220>
<221> misc_binding
<222> 3759..3777
<223> 9-3-324.mis1

<220>
<221> misc_binding
<222> 3779..3797
<223> complement 9-3-324.mis2

<220>
<221> misc_binding
<222> 4979..4997
<223> 99-14419-424.mis2

<220>
<221> misc_binding
<222> 4999..5017
<223> complement 99-14419-424.mis1

<220>
<221> misc_binding
<222> 14988..15006
<223> 9-24-260.mis1

<220>
<221> misc_binding
<222> 15008..15026
<223> complement 9-24-260.mis2

<220>
<221> misc_binding
<222> 15214..15232
<223> 9-24-486.mis1

<220>
<221> misc_binding
<222> 15234..15252
<223> complement 9-24-486.mis2

<220>
<221> misc_binding
<222> 15807..15825
<223> 9-6-187.mis1

<220>
<221> misc_binding
<222> 15827..15845
<223> complement 9-6-187.mis2

<220>
<221> misc_binding
```

```
<222> 19548..19566
<223> 9-7-148.mis1

<220>
<221> misc_binding
<222> 19568..19586
<223> complement 9-7-148.mis2

<220>
<221> misc_binding
<222> 19725..19743
<223> 9-7-325.mis1

<220>
<221> misc_binding
<222> 19745..19763
<223> complement 9-7-325.mis2

<220>
<221> misc_binding
<222> 19767..19785
<223> 9-7-367.mis1

<220>
<221> misc_binding
<222> 19787..19805
<223> complement 9-7-367.mis2

<220>
<221> misc_binding
<222> 20139..20157
<223> 9-9-246.mis1

<220>
<221> misc_binding
<222> 20159..20177
<223> complement 9-9-246.mis2

<220>
<221> misc_binding
<222> 20576..20594
<223> LSRX9-BM.mis1(17-1-240)

<220>
<221> misc_binding
<222> 20596..20614
<223> complement LSRX9-BM.mis2(17-1-240)

<220>
<221> misc_binding
<222> 21089..21107
<223> LSRX10-BM.mis1

<220>
<221> misc_binding
<222> 21109..21127
<223> complement LSRX10-BM.mis2

<220>
```

```
<221> misc_binding
<222> 587..605
<223> potentialsite606.mis1   potential

<220>
<221> misc_binding
<222> 607..625
<223> complement potentialsite606.mis2   potential <220>
<221> misc_binding
<222> 5122..5140
<223> potentialsite5141.mis1   potential <220>
<221> misc_binding
<222> 5142..5160
<223> complement potentialsite5141.mis2   potential <220>
<221> misc_binding
<222> 7409..7427
<223> potentialsite7428.mis1   potential <220>
<221> misc_binding
<222> 7429..7447
<223> complement potentialsite7428.mis2   potential <220>
<221> misc_binding
<222> 8375..8393
<223> potentialsite8394.mis1   potential <220>
<221> misc_binding
<222> 8395..8413
<223> complement potentialsite8394.mis2   potential <220>
<221> misc_binding
<222> 8685..8703
<223> potentialsite8704.mis1   potential <220>
<221> misc_binding
<222> 8705..8723
<223> complement potentialsite8704.mis2   potential <220>
<221> misc_binding
<222> 9009..9027
<223> potentialsite9028.mis1   potential <220>
<221> misc_binding
<222> 9029..9047
<223> complement potentialsite9028.mis2   potential
```

```
<220>
<221> misc_binding
<222> 9931..9949
<223> potentialsite9950.mis1  potential <220>
<221> misc_binding
<222> 9951..9969
<223> complement potentialsite9950.mis2  potential <220>
<221> misc_binding
<222> 9958..9976
<223> potentialsite9977.mis1  potential <220>
<221> misc_binding
<222> 9978..9996
<223> complement potentialsite9977.mis2  potential <220>
<221> misc_binding
<222> 10002..10020
<223> potentialsite10021.mis1  potential <220>
<221> misc_binding
<222> 10022..10040
<223> complement potentialsite10021.mis2  potential <220>
<221> misc_binding
<222> 11859..11877
<223> potentialsite11878.mis1  potential <220>
<221> misc_binding
<222> 11879..11897
<223> complement potentialsite11878.mis2  potential <220>
<221> misc_binding
<222> 19021..19039
<223> potentialsite19040.mis1  potential <220>
<221> misc_binding
<222> 19041..19059
<223> complement potentialsite19040.mis2  potential <220>
<221> misc_binding
<222> 21344..21362
<223> potentialsite21363.mis1  potential <220>
<221> misc_binding
<222> 21364..21382
<223> complement potentialsite21363.mis2  potential
```

```
<220>
<221> misc_binding
<222> 21430..21448
<223> potentialsite21449.mis1   potential <220>
<221> misc_binding
<222> 21450..21468
<223> complement potentialsite21449.mis2   potential <220>
<221> misc_binding
<222> 21432..21450
<223> potentialsite21451.mis1   potential <220>
<221> misc_binding
<222> 21452..21470
<223> complement potentialsite21451.mis2   potential <220>
<221> misc_binding
<222> 21435..21453
<223> potentialsite21454.mis1   potential <220>
<221> misc_binding
<222> 21455..21473
<223> complement potentialsite21454.mis2   potential <220>
<221> misc_binding
<222> 21436..21454
<223> potentialsite21455.mis1   potential <220>
<221> misc_binding
<222> 21456..21474
<223> complement potentialsite21455.mis2   potential <220>
<221> misc_binding
<222> 21550..21568
<223> potentialsite21569.mis1   potential <220>
<221> misc_binding
<222> 21570..21588
<223> complement potentialsite21569.mis2   potential <220>
<221> misc_binding
<222> 21664..21682
<223> potentialsite21683.mis1   potential <220>
<221> misc_binding
<222> 21684..21702
```

<223> complement potentialsite21683.mis2  potential

<220>
<221> misc_binding
<222> 21675..21693
<223> potentialsite21694.mis1  potential <220>
<221> misc_binding
<222> 21695..21713
<223> complement potentialsite21694.mis2  potential <220>
<221> misc_binding
<222> 21709..21727
<223> potentialsite21728.mis1  potential <220>
<221> misc_binding
<222> 21729..21747
<223> complement potentialsite21728.mis2  potential <220>
<221> misc_feature
<222> 22113,22122,22227,22264,22268
<223> n=a, g, c or t

<400> 1

```
ccataatcaa gaaaatggat aataagtttt ggtggggatg tggagaaatt ggaatcctcc    60
gtgcattgct ggtgggaatg tacaatagtg cagtcattgg ggaaaacagt ttggcagttc   120
ctcaaaaggt taaaaataga actaccaagt cacccagcaa ttccattctt aggcatatat   180
tcaaaagaaa tgaaagcaga tatttgtaca ccagtgttca cagctgcact atttacaata   240
gtcaaaaggt agaaacaacc taggtccatc cacaaatgaa tggataaata aaacgtagca   300
tatacataca atggtacact agtccgctgt aaaaagaaat tttgatctta ctgcatgcta   360
catggcttcg acatactaca acatggatgg accttgaaaa cattattctt tgtgaaataa   420
actagacaca ggacaaatgt tagcgattc cacttatatg aggcacctag aatgggcaat   480
ttggtaagca aagtagaata gaaattacta ggggcacagg tagcagggaa tggggagtta   540
ctgtttaatg gtcacagagt ttatgttggg gatgatgaaa cagtttcggg gataaagagt   600
ggtgactggt acacgacatt gtgaatatac ttaatgccac tgaattttac acttgaagtg   660
gttaaagcga taaatattat agtttgcata ttttatcata aaaatatttt tttaaacgat   720
gaagggacgt gaacgggttg aaattttata aaaagtggcc agggaaggtg tcactgcaat   780
ggtgtcctac aggaggagga agatcatgtg gacatctscg ggaagggtgt tctggcagag   840
ggagtagcac gggcgatggc tctgaggact gtgagaagta tagttggaaa cagcgaggag   900
gccagggtgt ccgaagctga gtaagccaga gagagtggga ggaggtgaga taagagggg    960
aaggtcagtt tctgctgaga gtgaggagga gccacaggag ggctgtgagc aggtggacgt  1020
gatctggctt gagttttaac agggccagta gaacaaagca cgcctgggta ccgaaaccag  1080
ccactggcca gttgcaacc tggggagtc taacgcgagg aagcgcccag ggttccccca    1140
ggatgcgctt tccctcgccg ccacctggag acagcagagt cacgcccagc gctgcgcagg  1200
ctgatcgccg cgccgcgccc ccgccctcgg tcgcaggtgg ctygttccgg gaattcctaa  1260
gcggaaaccg gtcccaagcc ccgcgccttc gctcggcccc tttaagagcc agaatttccg  1320
gagggctgac ccggggctag ggatgcccag gggccgaacc acaagttggg aacrggtggg  1380
ggaggtggcg aaaacttccg wagtggaatt ccaacttttc ctggccctga ttccccttgg  1440
gcatccctga gggggcagag cttcccttcc ggggacttta gagggttcct caggtcatct  1500
aactgggaga cacaggaggc ccgaagcgcc cccctccac ccggtccgga ggaacccag    1560
tggaagtgga gaagtcaggc gccaccaaca agcctctccc agccaggact ttgcttagac  1620
tcgctcctcc cggcagggcg cacctaggcg ggtccatcgc cagccgggga gagggtttg   1680
ggcagggagg gaacaggtgc gcggcgggac ccgccctatc tcaacaggtg aatcgctcca  1740
agtgggtctc ggttgcatgg atctcggtgc gcttggtttg gccggagmag atgggggccg  1800
gaagggacct gtggtccgca ggcgccctcc cagcgggcca gtcacttggt tcgggccctg  1860
```

```
ggggacggag cgcacctggg tcagcccact tccggggagg gaggcagagg aacccctccc    1920
cgccgctcac ccctaagccc agccctcggc tcccacccLt gtgtacctgg gccgaaccat    1980
tcaccggagc gcgcagcggg tggagtgtgg ctcggaggac cgcggcgggt caagcacctt    2040
tctcccccat atctgaaagc atgcccLttg tccacgtcgt ttacgctcat taaaacttcc    2100
agaatgcaac aggacggact tggagtaggg acaaggaacg gaagtgggaa ggggaggagc    2160
gtgcacccct cctggccttg gtgcgcgccg cgcccctaa ggtactttgg aagggacgcg     2220
cgggccagac gcgcccagac ggccgcgatg gcgctgttgg ccggcgggct ctccagaggg    2280
ctgggctccc acccggccgc cgcaggccgg gacgcggtcg tcttcgtgtg gcttctgctt    2340
agcacctggt gcacaggtac ggggcacggg gcctctgacg ctgcggaacg scggagggaa    2400
ctgtagaggg ggatggatgg agttggaggc ggcgggaagc gggaagcggg ggtctcagag    2460
gctgggacct tccgatcccc tgggtcttgg gcgatctgtt gcgcgcggga gtgagaggaa    2520
ttccccattt gtgccgggga gcgctccccg cgccctLatc tggaagatag caggaagtga    2580
aactccctgg acggtgagac ccggagcggc agggagaatg gaactctttg tggggaggga    2640
gtggaagacc gcccgatctc tgggaaaaga aaagccggga tgggacttgg gcgcacccgg    2700
ggatttctaa gttttggagt aacggggaga gggcacggga gggctggatc agacgcttcc    2760
tagagggaca gagacgaagg aacaatgcct aggcctcggg tgggtgtggg actggggact    2820
ccccatcccc cgcacccac ccacctcccg cgggctccgg attatacgtg cgtaagagtc     2880
tggtgggatg gatttacgga cttgaaaccg acttctgctg gcaggctttc acctggatgg    2940
gatatttggg tggtgatgag gtctttcccg agacactttt ggttcagtca tttgaaatga    3000
ctttagagta gggtgaggtg gtgggaggct gatggagata ttgtggggggc tttagtccct   3060
ccatggcaaa gcagttcagg caaacaactc catggttttc cctccaaatt caaaaggccc    3120
cgggtaacct ggaatccttc gtagtcggtt ttgaagtggg gccttgggcg ctgggggcat    3180
caacatggcc atcLgggctt gcctgcccag gccacacaga ggcccttgt tgtgggtgaa     3240
tggcaaaggg aagaggggac tggtgtggtt cagaggccac aggctgggaa gagggatggc    3300
gggcgagtcc aaggaaactg gccgtgtcac cgtgcacctg ccacttcagc cccacgggtc    3360
tataaaatgg gcatgattat cgtggctacc tcactggtcc tggcaattaa ggaacaatgt    3420
gtgccaggca ctctgtaaac cacatacttg cgagtgtcaa gctggtgaca ggtggcgttc    3480
ctgttgaagc·acctccctga gctcacagca acccttgctg tctctcctct tgccctcagc    3540
tcctgccagg gccatccagg tgaccgtgtc caacccctac cacgtggtga tcctcttcca    3600
gcctgtgacc ctgccctgta cctaccagat gacctcgacc cccacgcaac ccatcgtcat    3660
cLggaagtac aagtctttct gccgggaccg catcgccgat gccttctccc cggccagcgt    3720
cgacaaccag ctcaatgccc agctggcagc cgggaaccca ggctacaacc cctacgtyga    3780
gtgccaggac agcgtgcgca ccgtcagggt cgtggccacc aagcagggca acgctgtgac    3840
cctgggagat tactaccagg gccggaggat taccatcacc ggaagtatgt tgggcagggc    3900
agggggatga ggctgggctt gcccgggtgg tgggactggc gtccttgtgc gggacctgga    3960
gtccccatct gaaagctctt gagtgccagt gtctgaaagg accattgaag ggagcaattc    4020
tttttttttt tttttttgaa gatggagtct tgctctggac tccaggctgg agtgcagtgg    4080
tgcgatctca gctcactgca acctccacct cccaggttca agcaattctc ttgcctcagc    4140
ctcccgagta gctgggactc caggtgcgtg ccaccacgcc cagttaattt ttgtattttt    4200
agtagagatg gggtttcacc atgttggcca ggctggtctc aaactcctga cctcaaatga    4260
tctgccgcc ttggcctcgc aaagtctga gagacaccat acccagccta aagggagcga      4320
ttctattcta ctattcttcc ttctgctaat ccttccattc tttaatttaa taacgaagat    4380
ttttgagta cctgtcatat accaggtgct gttctgggcc ctgggaatac agctgttaac     4440
aaaatcatca aaccacttcc ctcgtggagc ccacattgca gtgagagaga caaacackac    4500
acacactctc aagtccttga agataaagaa aactgggtaa cggagagaag aggccagggt    4560
ttgttctata atcattaata acacgagcag taagaagtaa aatttatcta agtaacaact    4620
tataaagggt ctactgtgtg ctaagctctc atccaggttc ccaaggatta actcagacca    4680
cacagtaatt gaatagattc tatcattgtc atcttacaga ggcccagaga gagaaagtga    4740
cttgcctagt gtcatagctg gtaacggggc tgggattcta actcagccac tttgggtcta    4800
gtggccaagc tcctaatccc tttgcttgcc tagggtggtc cgcagaggac tcacagagga    4860
gatggcagga gtgaactgca ggggcaagag agcttaatgg agaaagcctg tgacatgcca    4920
ggaactgcac acatattctc ccattgagtc ctcccctcta ccctcctgac agctgaggca    4980
cagagaggtt accttgttca aatgggtgca taggaagtca aagtctggag ctggggtttg    5040
aacccaggca gccctgagaa ccttgttctt ttttttgag acggagtctc gctctgtcgc     5100
ccaggctgga gtgcagtggc gggatctcgg ctcactgcaa gctccgcctc ccgggttcac    5160
gccattctcc tgcctcagcc tcccaagtag ctgggactac aggcgcccgc cactacgcct    5220
ggctaatttt ttgtattttt agtagagacg gggtttcacc gttttagccg gatggtctc    5280
gatctcctga cctcgtgatc cgcccgcctc ggcctcccaa agtgctggga ttacaggcgt    5340
gagccaccgc gccggccc ttgttcttaa ctgtaatgct gcctcctgat aggatgtgcc      5400
```

```
tgttgggact aagtaagggg cagtcattca ttcattcatt tggtatttat caagcatcga   5460
ctatgtgtcg ttggtgctgg ggatagaggt gattgggatg gctgaagttt ctgtcgtcaa   5520
ggagatgaca ttctggtgga gtgagactgg cagtaaataa gcagataaag aaagagtatg   5580
agaatttcaa agtctgggca cggtggctca cgtctgtaat ctcagcactt gggaggcca    5640
aggtgggtgg atcacctgag gtcaggagtt ccagaccagc ctggccaaca tggtgaaacc   5700
ccgtctctac taaaaataca aagattagcc aggcatggtg gcacatgcct gtaatcccag   5760
ctactcagga ggctgaggca tgagaatcgc ttgaacccag gaggcagagg ttgcagtgag   5820
ctgagatcgc accactgtac tgcagtctgg gcgacagagt gagactctgt ctcaaaaaaa   5880
aaaaaaaaaa aaaagactcc gtcaaggtat aagaatgtca gagagtacta agtgttgcaa   5940
agaaaataac accaggctgg gtgcattggc tcatgcctgt aaatttcagc actttgggag   6000
gccaaggcag gaggatcact tgagcctagg agtttgagac cagcctggac aacaaaatga   6060
gaccccatgt ctacaaaaat tttaaaaatt taaaaattag ctgggcatgg tggcatgtgc   6120
ctgtggtccc ggctgctcag gaggctgagg tgggaggatt gcttgggctt gagaggtcaa   6180
ggcttcagtg agtcatgatc gtgccactgc attccagcct ggtgacaga gtgagaccct    6240
gtcttgaaat gaaagaaaa taggctgggc gcagtggctc acacctgtaa tcccagcact   6300
ttgggaggcc gaggtgggtg gatcacctga ggtcaggaga tcgagaccag cctggccaac   6360
atggtgaaat cccatctcta ctaaaaatac aaaatttagc cgggcgtggt ggtgggcgcc   6420
tgtaatccca gctactcggg aggctgaggc aggagaatcg cttgaacctg ggaggcgaag   6480
gttgcggtgc gccaagattg cgccactgca ctctagcctg ggaaacagtg agactccgtc   6540
ttaaaaaaaa aagaaaaaag aaaatagcac tgggtgatgt gctacatgga atgacttggg   6600
ctgtgaatat gatttgagga gggcctgggc ctgggcctta cagaacctag aaggcagaga   6660
ggaagggggag gggcagggtg ccagggatga aggctcacgt acctcatgtc ttagtgtgtg   6720
ttcactgtct taaacaagaa tttaaagttg ggcatggggc agagcgggga agggagcatc   6780
cctttgcaga ccccaagaag ccaggaactg gagcacattc tgctagagga tcgatgggaa   6840
gcagggttcc aggggctgag cctatgtcag tcctgtttca gaggaggcac caggcttgct   6900
tgccctgaat ttctgtgggc agctcagcca tgagcatcct actgttattg aggtcacagg   6960
gctgcttagg cccccctcct tctaacccag ggattgtgcc tgcctggacc aggcgtgact   7020
gctaagcttc tgccaggaca agccaaatac tgagggtgct tcctctgctg gacgcaaaag   7080
tccaggatga ccccccaggc tctgtctcgg ggaaggggcc ctgcatgctc cagggcctc    7140
acaggcctgg gtctttcaaa ccaccccac ctgggcctgt gtttgatcaa ggccctgagt    7200
gtaaacatcc attgtgtgtg tcctttcagg aaatcccata gccataggag cttcctctgt   7260
ttcagctttg aggatgggga aaagtggact ccccgtggtg ttcctaggggt cacccactgt   7320
gctgggggttt ttctgttgtt gttgtttttt ttctgttgcc caggctggag tgcagtggtg   7380
caatctcagc tcactgcaac ctctgcctcg caagttcaag tgattctccc gcctcagcct   7440
cctgagtagc tgggattaca ggtgcacacc accacacctg gctaatttt gtatcttttt    7500
ggtagagatg ggattcgcc atgttggcca ggctggtctc aaactcctga cctcaggtga    7560
tctgcctgcc ttggcctccc aaagttctgg gattacagat gtgagccacc atgcccggcc   7620
tatcctggtt tcaaaagtga aaatagtcct ggataaggta gaaggctgtc cactccaggc   7680
atccctccgg tccggtggct cattccctgc tttgtccttc catgctttgg gtgatggacc   7740
agcacctgga caggaggccc tgttccacct cctcgggctc cttggggtcc aagtgccccc   7800
acctccagct gcactgcagc agagagccca tgggacctct gaaatcatga aggtcacctt   7860
tgcggtgtat aaagaaggaa ccagaggttg gagatgtgga ggaggcctgg ctgctgttcc   7920
cactggagac ctgcatcttc tccccgacc taaaacaatg aaagcagtgc tcagcccgga   7980
tgagatcacg gccagcccaa gaccaggaac agggtacgcc ctgcaggaag aaggtgtgcc   8040
cagaccttag gatggatcaa aagaagccgg aaaactatat tttttgtgag ttttgaaaat   8100
gtcagacagg tcaaacaaaa cacagtgagg tccagcctcg gcctacaaga tgccagattt   8160
caaccctgg cctatatgat ctgtttgcca tggcaggcgg ttcctgtcca cctctttgt     8220
ttatagcagg gaccagctct tgagctccag tgttgaagag gcacggtcag ggtctgatct   8280
gaagacactg gtggctcatg cctgtaatcc cagcacttca ggaggccgag gcaggaggat   8340
tgcttgagga caggagctgg gagaccagcc tgggcaacac agtgagaccc agacactaca   8400
aaaaaataaa tttagcgggg catgatggca caccctgcta ctctggagat gggaagattg   8460
cttgagccta ggagttcgaa gctgcagtga cccatgatcg caccactgca ctccagcctg   8520
ggcgaccaag ctaggccctc tcaaaaaaga tacaggtgga aaaatgatgg acgaagaggg   8580
cattgtggca aacctgggga tttaggagaa cctagtttgg aattctatga ggattcaatg   8640
aaagaatgtg tgtagagggg cccagcacat agtaagagct caataaacgg tgggggctag   8700
gggtggtggc tcatgcctgt aatcccagca ctttgggagg ctgaggcagg tggatcactt   8760
gagccctgga gttcaagatc aacctggaca acaaagcaag atcccatctc aaaattaaaa   8820
aacaacacca acaacaaaaa aacagtggct tagatgcctg atcattaggg taagtcgtgt   8880
cctcaacccc ttcacatctg ctctgaaggt caccatatcc ggaagccttc cctggcctcc   8940
```

```
ttgtttaaaa tggcacagcc cccactccac gcctggcact ctctgctgtc cctgattcgt   9000
tttctccata cagcttatct ttgtctggta tgtgacatag ttaacatttt atatttgtct   9060
ttctttccta gttagaatct gaactctaga agggcaaggg caaggattta taactcaaag   9120
attccgggct taggcctctt ttatattctt gattttgagg ttaattaaga gctcaggcct   9180
agcgaggtgg ctcatgcctg gaatcccagc actttgggag gcccaggcgg gcagatcact   9240
tgaggtcagg agttccagac ctgcctggcc aacacagtga aaaacctgtc tctactaaaa   9300
atacaaaaat tagccagtta tgttggcagg cgcctataat cccagctact caagaggctg   9360
aggcaggaga atcgcttgaa cccaggaggc agaggctgca gtgagccaag atcgtgccac   9420
tgcactccag cctgggcaac agagcgagac tccatctcaa aaaaaaaaaa aaaattaaga   9480
gctcaaagag tttgttttca taggcagcag aatgagaaaa gtttacaaaa tagtttaaat   9540
gacaataaag tcattataga ttaacataaa taaaatacct tttatgaaaa aaataatcat   9600
tttctgaaat cagacaaaac attgtgaatg agaaggtggc atggttttat ttttttgcaa   9660
gtctccgaag cctggctgga tagaagagcc tggcttctca gagctgcttc agtctgttgt   9720
gatatctatt gtatgtcacg tagcctctgg aaaactccac agttagtatt gttgggaaaa   9780
taactttgac ctcaggatct cctgaaaacg tcttggggaa ccccagggtc tagaggctgc   9840
agtttgagaa ctgttgctgt ggtatcccag gtgtctcaaa tactgcctag aacataggtg   9900
gtactcagta attattgttg aaggatgaat gaatgaatga atgaatgaat gaaagaaaga   9960
aatgtgtctt tgaatctagc catgtgccca gaatgatgag acagatgaca aaagctaagg  10020
gactttagca tgaggagagg gggttcgttt cctttttttt ctttttttt tgagatggag   10080
tctcactcta ctcccaggc tagagtgcag tggtgcaatc tcagctcact gcaatctctg    10140
cctcctgagt tcaagcaatt ctcctgcctc agcctccagg gtagctggga ctacaggtgc   10200
gtgccaccat gcctagctaa ttttttacat ttttggtaga gatggggttt taccatgttg   10260
gccgggctgg tctggaactc ctgacctcaa gtgatccacc tgcctcagcc tcccaaagtg   10320
ttaggattac aggtgtgagc caccatgtcc ggccaagagg gtgttcattt ctgctccttg   10380
ccaggtattg tgtcaggcac tggggaccca gcagtggctg agacagacag ggctctgcct   10440
cacggagccc acattttcac caggcaaagg atggtcggcc cctaagctgg gagataagac   10500
ttcagcagtt gggtggggga gccgtgggag aagcccagcc cacaggggga cagtgcaaat   10560
ctagaaccaa ggcgatggca ggggtgaggc tggcacggta gctagagacc acgtcgtgcc   10620
aagggccttg gggaccatgg gactatggga ccttagggaa ggcgtctgga atgctgtagc   10680
cagacactgt tgcaaggagg attttctgt agacatgagg ccttccttat gaagaaagca    10740
agggttcttt cattcctggg ggtgccaggt gctgtggact gcagcacgcg tggttgctgc   10800
cgtcacagag ctgtcatgca ggagggcagc gcgtccttgg gaaggtggca ggcaggtcag   10860
gctaggagga aagaggccgg gaagctgagg gcatttcctg cccgagatgc caatgtagc    10920
ctacttctgt ccccagtggc ttaaggcaga gttgcctggt aggtgccctg gtcccaccct   10980
ggtgaaaggc tgaaggtatt taattagtgc ctgagaagca gagaggaaac aggatgtgcc   11040
aaaacacttt gatggatggt agagttaaca ggctccttgc ctgcagctgc ttcagacaag   11100
agcgtcccca agccctgggc ctgacctgga atgtggggat ggaagggag ggggaggaac    11160
caaggcactg ggagggtaag tctctctctc ccacatagac acaccactc cttatgggtg    11220
cctggcatc tcctggtacc tagaatctgg cctgtttatc tccacaccca tccctggggt    11280
ctacactagg ccctgtgggt ggcagttcac atcaggggag ttctgacttt ggctctgaga   11340
ggtggttcag agatggctgt aagttgagaa gcacagactg ctgggtgtgg tggttcacgc   11400
ctgtaatccc agcactttgg gaggctgagg tggggtgga tcacctgagg tctggagttc    11460
aaaaccaact tggtcaacat ggcgaaactc catctctact aaaaatgcaa aaattagcca   11520
ggtgtggtgg caggtgccta taatcccagc tacatgggag gctgaggcag gagaatcgct   11580
tgaatctggg aggcgaagat tgtagtgagc cgagattagt tcgccatt gcatgccagc     11640
ctgggcaaca agagtgaaac tccgattcaa acaaacaaaa aaaaaagct gggcatggtg    11700
gagtgcctgt agtcctaact actcaggtgg gaggattgct tgagtccagg aggttgaagt   11760
tgcagtgggc tataattaca ccactgcact ccagccaggg ccacagagtg agaccctgtc   11820
tctaaagaaa gaaaaaaaaa aacaacctca ggctccgagg gcaccattac tgctctacac   11880
tgaagagctg tgcagctttt ccagacccga aatgtcatcc acaaaacaga agtgataatg   11940
gtcctgcctc acagacttct tgcagtagtc caggtgttta gaacggggtg taaaaggccg   12000
tgtgcccttg gtaggaatct ttgcatatgc atttgatcat ctgcagcctg cccagcccac   12060
tgcttgcccc ctcctgggtg tgctgggaag gggtctttgg ccctccaggg gttaggtgcc   12120
ccagcctcca aggtgccctc acgccttttc atcccgactc agatgctgac ctgacctttg   12180
accagacggc gtgggggac agtggtgtgt attactgctc cgtggtctca gcccaggacc    12240
tccagggaa caatgaggcc tacgcagagc tcatcgtcct tggtgagtgg gcctgggaag    12300
ggggaggcat ggcccttcct tttgtccgct tctgttctgt ctgccctccc ctgtgtccgc   12360
cctctgccct ccagcttacc ctctgggctc tgtcgcctgc tctgctctcc ccaggctct   12420
gccagtcact taggctcccc tgtgccctgc accccaggca gggaccactg gcccacagtg   12480
```

```
cctccaatca cccaagccaa actaagagaa gagtggagac aattggagac tctgccttrt   12540
caaagtctca tttttaaaaa aaatccagac ttggggtccg ggtgcggtag ttcatgcctg   12600
taatcccagc actttgggag gccgaggcgg gtggatcact tgaggccagg agttcgagac   12660
tagcctggcc aacgtggcaa aatcccgtct ctataaaaaa tataaaagcc aggcgtggtg   12720
gtgcacatgc ctgtaatccc agttactcag aaggctgagg catgaggatt gcttgaacct   12780
gggaggcaga ggatgcagta agccaagatc aagccactgc actccagcct gggcgacaga   12840
gtgagactct gtccaaaaaa aaaaaaaatc cagacgtggt cagagtccat gggcagtgaa   12900
tgaggacagt tgatggtgtg caaaatcgac ccacctcttg ctacatcccc aaggcctcat   12960
ctcacccgag tccctcgcca aagcacagcg gttttgccgt gtgccctgct gggatggcgc   13020
tgcatggcac acacactgtg taagtttgag tgcagctgaa acgaagccga ttccagacac   13080
ccaggggcag ggcggggtgt ccgtgtggct gggaggcctc cttgtgttag ggggatgttg   13140
ccatcggcca ggtgccctgc tgtaagccaa cacatggagt cttgtatgac atgtgctctg   13200
catgagtgat gccgctgggc tgtacactgc catcttcaca tgtgtgaatg agcacgtgac   13260
tgggggtac ttgggctgca agacagagtt catgtgtggg ggatggaaca cgtgcaccag   13320
tgacccagga acctctgcct gttcttcggt aaaatgcacc atttgcatca gcagttccca   13380
aaattagtct ccaggtctat ttacactcta aaacattatc gagggtctcc aagagctttt   13440
gtttgtttct gtgggtttta tgtctatctg ttgcttaaca tattaggaat taaaatgggg   13500
agattttcct ttttttttt ttttttttga gatggagtct cgttctgtcg cccaggctgg   13560
agtgcagtgg ctcgatctcg gctcactgca agcttcacct cctgggttca cgccattctc   13620
ctgcctcagc ctcccaagta gctgggacta caggcacccg ccaccacacc cggctaattt   13680
tttttgtatt tttagtagag actgggtttc accatgttag ccaggatggt ctcgatctcc   13740
tgacctcgtg atccacccac ctgggcctcc caaagtgctg ggattacagg catgagccac   13800
tgcccggcct taaatgggg agatttttca agcccaagat acacaaggaa gactgggcaa   13860
catgcaaga ccctgactct acaaaaaatt ttaaaattaa ccaggcatgg tggcatgcac   13920
ctgtgagccc agcttcttgg gaggctgagg caggagtatc gcttgcaccc aggaggtcaa   13980
ggctgcagtg agccatgact atgctactgc actctagcat gagtgacaga gaccctggct   14040
caagaaacac aaacacacac acacacacac acacgcatat agtccattag gcatcaggc   14100
gatgatggca tcagggagcc tgggaaactc tactggacat tcatgggaga acaagtgaaa   14160
aagqcaaata acatcttagt gttattctaa aatttcttct tttggccttg tggacaggac   14220
cacgctttga gagctgtgac tgacatgcct ctgtcctgtt gcgagggcct atagtgccaa   14280
gtgcatgagc tctgggagg gcttcgtggg tgcagagctg ggcctgtgga ggcccctcag   14340
acacaacact ggtggggctc agagctccag gggcactcga gggaagacaa gaaccggctc   14400
tgagatgcgt gaatgtgaca gtgcatgagt agagatggag accttgtggg tcccagaacc   14460
aggactgcat atgactttca tatgtgggta tttttgcctt catgggtccc ttcctgtttt   14520
aaaaaaaatg tgtgattatg ttgtcacaaa gagtttattc ctgtatattg tgttaatttg   14580
tgttcagatt tgtaaagtaa aattaaacca tttcagccag gtgtggtgac acatgcctgt   14640
agccctagct acttacccca gaggctgagg tgggaggatc gcctgagccc acgaggttga   14700
agctgcagtg agccatgatc acaccctgc actccagact gggcgacaga gctgagatcc   14760
tatttcgtgg gccctaggtc cctgtgcctg ctggaacagg acatccctat caccgtggtt   14820
ggagcccttt ggggtgctaa gacctatgaa tgagggaaac ttagggtgcc caagctgagg   14880
tagagccctc agaaccccct gggatttgta ttggagccct cgtggcataa cacaggtgga   14940
ttatgcaatg ggagtttctt acctataagc acccacatgt gggcgggtgg agggtaggag   15000
ccatgcrcta gggcttcagc ccccagcccc ttcccgcttc agggcacacc ttgcacttgg   15060
ccagcctgga gctgggcttt cgggggtggc acagcctggg ctggctctgg ccagcataat   15120
ctgtttctct tttgtccctc cagggaggac ctcaggggtg gctgagctct tacctggttt   15180
tcaggcgggg cccatagaag gtacgggggg tggatcctga gttgggcttc tcrggagctc   15240
ccatacatca cctactgctt ctgactctag ttagtatccc cttccccact aaaccctgct   15300
cactgtggac ccctcactaa cctggcctga ctgtggctct gaggcatcta gtggtctggc   15360
gctgggccta ggctaggctg ggctgaggag agcctggggt gcaggccagg gctctgtgac   15420
tggcacctgc ggtgctcttg agggtgtggc gtctgggcag ctggctctct ctttggtctg   15480
ggggctgcag tctgtctccc tctgtgcaag ctgcctcgtt ttctgccttg tgttttttgc   15540
acctggggga gggccgtaac tgggaatgg ccggatggt agaatgggga gtgtgctgtg   15600
cccagcctct ggcacaaaaa atccagccag ggctgcaggt tccttggtga gctttgcaaa   15660
tcgtccccga cctcagtgct ggctccgcac catgtacccc tgctgtgccg ttagccctgt   15720
tccctcccag gcctccgggc tcagggcctg ttgtctttct gcagactggc tcttcgtggt   15780
tgtggtatgc ctggctgcct tcctcatctt cctcctcctg ggcatytgct ggtgccagtg   15840
ctgcccgcac acttgctgct gctacgtcag gtgcccctgc tgcccagaca agtgctgctg   15900
ccccgaggcc cgtaagtgtc ccgctcatgg ccaccctggt ttgggcaaca tcctgcatcc   15960
aagggaagga ggtggccatc cacctgcccc caggacagtg gcgttggtct ggagggtgtg   16020
```

```
aatttagcca gtggggagaa agtaggctga ggagggtctg ctgtttagat tgtcgtttac 16080
ttcctccaac ttttagttta tttttatttta tgttgttctt ttcttttgta agtataatcc 16140
atacacatgg taaaaatgtc caacagtaca agatactagt cacatggaag taaagccctc 16200
taaaaaaacc aaatcttggc taggcgcagt gattacgcct gtaatcccag cactttggga 16260
ggccaagacg agtggatcac ttgaggtcag gagttccaga tcagcctggc caacatggta 16320
aaacccagtt ctctactaaa aatacaaaaa ttagctgggc atggtggtga tcgcctgtaa 16380
tcccagctac tcaggagact gaggcatgag aatcgcttaa acccaagaag tggaggttgc 16440
agtgagctga gatcacgcca ctgcactcca gcctgggcga cagagtgaga ctctgtctca 16500
aaaaaaaaag aaaaaaaaat gttaagtgaa aaagttaaga aaccaaacaa ggtttacaac 16560
actacatgat ttaagcaaaa aaaatttttt ttgttttaga gaaagggtct cattctgtca 16620
tccaggcagt gcagtgcgat catagctctc tgcagcctca aactcccggg ttcaagcagt 16680
cctcccgcct cagcctctgg agcagctggg actgtaggca cacaccacca tgcccagcta 16740
atttttttgat ttttgttttt tgtagagacg gggtctcagt atgttgccca gcctgatctc 16800
aaactcctgg cctcaggtga tcctccgaag tcagcctccc caaagtgctg ggattacagg 16860
catgtgccac catgctggcc aatttttaaa aattttctgt agagacaggg tcttgctatg 16920
ttgcccaggc tggtcttgaa ctcttgacct caagtgatcc tgcctcaggc tcccaaagtg 16980
atgggattac aggcatgaac taccacacct ggccttaaac ttaagcaaat ttttttttt 17040
ttttggagac agtttcactc tgtcgcccag gctggagtaa agtggcgtga tctctgctca 17100
ctgcaacctc cgccccggg gtttaagcta ttctcctgcc tcagcctccc gagtagctgg 17160
gatataggcg cctgccacca cgcctgacta attttttgtat ttttagtaga cacggggttt 17220
tgccatgttg gccaggctgg tctcgaactc ctgacctcag gcaatccgct ccccgcacc 17280
cctaccttgg cctcccaaag tgttaggact acaggtgtga gccaccatgc ctggccaaat 17340
ttaagcaaat gtttgaaaac acatacccac aggaatgctg cacattttac ccagctacta 17400
tgtctagggt cgtatctagc acaccagcat ggctactgtg gagagctggg actggatgtg 17460
agatgagagc taaaggggaa gtaagcaaac caagcagggg aaggtaagag aagacagaag 17520
acagagagag agggacctaa ctctatgaga ggagtcagac atgtgcaatt gaaaaagact 17580
tgctcctgtc tctcttctgt gaatgtttgt gaatatccca acgggacact ttcacagagg 17640
agctgattga cgtggtcaca gccatcagcc ttgggacacc agaccacagt gtgtacacta 17700
agtggcactg atggacactt cagcatccct ctagctgctg tcccgtttcc cctcctcggg 17760
gaccacagct gttgccagtc cttggtttcc ttcaggaggg tgtctgggta gaccagcctg 17820
tgtgcacaca gtccaagata catgaacagt gaagtgccag gcaatccttg caagcatggg 17880
caggtggaga gctgaggcct gcttgacacc ttcctgctca gaagcccagt gagcagtttc 17940
cctccctagg gctcagtgtc atcccctata aaatggggct tatggcagag ctcaccacac 18000
tgggtgcatc tggggatttg gcgagctcat gtgcacacca ttgagcatgg ggcccaacct 18060
atataaaata ttctacgtct gtcagctgct gggcactgcc actatcagcc tcagtagtga 18120
ctgagggaca gggcaccagt cagagccctg gtgcacacag agtgacccca gagaagcagc 18180
cttccctctc tgagtcctgt ttccttctgt taggtcctga cttcatgggt tgttgttagc 18240
attaaggaag tcgctggcta attttatagt cattgaagtc agtggtgtgc aacctggttc 18300
ctcaaaggat cacttccctg aaaaaattcc actgctccct ggaggcttat gcaggccatc 18360
ccatcccctc cctcttgttg tgttcagctg acagcttttt gctcagtgag taagtgttag 18420
gtccatttca cagatggct gcaaccaagt ttgcagtgaa cccactaaga ccagagctag 18480
ggccaggact aaatgctggt cccaatgcca cattccctg tccccacacc acatttcctc 18540
catccggaga ccctgttacc ccaacccagg gccccattaa ctccctggca gaggccctgt 18600
tacatctgct gctgccacag cctccgccca ccttcagga ggcagcaggt cccactgctg 18660
atgataaagt tgcaggctgc ctgagctaat gaagggctt cctctaggct gtgcacttag 18720
tcttctgctt ccaaaccaaa tcagaggtga ggcaccctct ctgggcccat ctctctcctc 18780
cattttcctg ttggggtccc agggaggaag ccacttgcct agggcccagg aattttgcaa 18840
gcctcttgcc ctaggagga aggaagggag gaggatctta ccttgaactg tcaagcctag 18900
agcctggtgg ggcaggcaga aatgggtgca gtccatgagt tagaaacact agaggagaca 18960
ctttgctgct tggccggggc aggcaagtta attcccgagg ctcctgccac tgcatctcaa 19020
tctggaaggt gaccaggtgg ggcaggaccc acgtctccca gatgactcat ttttctaga 19080
acagggctt ggctgccaaa gaggatactt gatttcggct tgtggggaca gtggtggacc 19140
cagcatctgg gcttttatata aagggcagct ttgttgccct gtaaacacac agaccatggg 19200
tggccacttc ttccagtaag ttagctgggg agttggaagt ttaggtaaaa ccttttgatt 19260
gacaaatgtt ggcgaattac catgctgtta aatgaaacat tgttctgcca ccctgggct 19320
gtgggtgcct gcgtgcaccc tctgaaaaat cacacaggaa gtggggtggg gtctctgtga 19380
agctggtgtc ccccagcctc agggatgctg cagaaatgga atgaggacca acagggactc 19440
agatgtccaa ggaagctcta cagcggagag gacggcttgg gaaggaggtc caggcccagg 19500
tccctccgga acccaatggg tatgggcag cctggctcct gcctcatccc ccttctcctg 19560
```

```
ttgattrtgt cctcacagtg tatgccgccg gcaaagcagc cacctcaggt gttcccagca 19620
tttatgcccc cagcacctat gcccacctgt ctcccgccaa gacccaccc ccaccagcta 19680
tgattcccat gggccctgcc tacaacgggt accctggagg ataccctgga gacgttgaca 19740
ggartagctc aggtgaggcc gggggaagca ggaacagctg gtgggmgtgt gctgggcatc 19800
tggacactga ggggcagggg ctggaaggaa gagtgtcttg ggagccgagg aggggctctg 19860
ctcctggtgc gcggccactg acagccactc tcccccagct ggtggccaag gctcctatgt 19920
accccctgctt cgggacacgg acagcagtgt ggcctctggt gagaatccat cgtcccgaag 19980
ttggatgtgc ctgtaaggga gaggggtggg ccaggatcca tcctcccaaa ccgaccacca 20040
ccccctgtc cctagaagtc cgcagtggct acaggattca ggccagccag caggacgact 20100
ccatgcgggt cctgtactac atggagaagg agctggccaa cttcgaccct tctcgacstg 20160
gccccccag tggccgtgtg gagcggggta agcaggagcc ttggggtctg agggcttta 20220
aggtgggggg gtgaaacatg tctccctgat acctgccgca gggactcttg gtgcaaaccc 20280
tggaccccgg gctcctccag cagtcagtga cacccccctt ccctgcagcc atgagtgaag 20340
tcacctccct ccacgaggac gactggcgat ctcggccttc cggggccct gccctcaccc 20400
cgatccggga tgaggagtgg ggtggccact cccccggag tccaggga tgggaccagg 20460
agcccgccag ggagcaggca ggcggggct ggcgggccag gcggccccgg gcccgctccg 20520
tggacgccct ggacgacctc accccgccga gcaccgccga gtcagggagc aggtctccca 20580
cgagtaatgg tgggaggaga agccgggcct acatgccccc gcggagccgc agccgggacg 20640
acctctatga ccaagacgac tcgagggact tcccacgctc ccgggacccc cactacgacg 20700
acttcaggtc tcgggagcgc cctcctgccg accccaggtc ccaccaccac cgtacccggg 20760
accctcggga caacggctcc aggtccgggg acctcccta tgatgggcgg ctactggagg 20820
aggctgtgag gaagaagggg tcggaggaga ggaggagacc ccacaaggag gaggaggaag 20880
aggcctacta cccgcccgcg ccgcccccgt actcggagac cgactcgcag gcgtcccgag 20940
agcgcaggct caagaaggtg agggcgccc tccctggcgt ccagaccgtc cctgggcccc 21000
cagccggtcc ccgcggctca tacccttctt tctttctccc ttgcagaact tggccctgag 21060
tcgggaaagt ttagtcgtct gatctgacgt tttctacgta gcttttgkat ttttttttt 21120
aatttgaagg aacactgatg aagccctgcc ataccctcc cgagtctaat aaaacgtata 21180
atcacaagct ctggagagaa ccatttgttc ggccgcgcgg ggcgggggac cggggctgct 21240
cccgtatgcg tctgtaaagc gccgcgtccc gggggcaccg gagtccgggg ccgggaggaa 21300
gagacccagc ctggcccggc ccgcgccgc gccgccggcc ggagaacgtg ccccgcgcag 21360
ccaccgcccg cctgcgtgcg cgccccggcc ccgcccaggc gtgcgcatgc gccccggccc 21420
tccgccttcg cgcaccgcag gctggccgcc gggagcgcgc gcgcgctcct ctcccttcc 21480
agcccatccc ccccagcccc ccaccgacct actttactgt ctccaaactc gggcagccca 21540
cctggccccc gacgacccca gcccctgctc cgggtacccc gacgttccat ccagacccgc 21600
gtttcaccag ggcggcgcgc ggcgacctcg cgcccgcgg agcccgggc tcgcgcgcgc 21660
ccgccgccc ccggagacag acagcgcgcg cgctcccggg ccgcctcccc cagcgcgcg 21720
tccgccccgg gctcgcgccg ccgccgccgc cgccgccgcg cgcgcgcagc tcaagtaaag 21780
gaggaaaaaa aaaagggga aaaatagaaa gcggcggcgg ctgcagcagc gatccgccgc 21840
cggactgggc caagccgggc ggcggccgcg cgagccggcg atccagggca ctggcggcgg 21900
ccagccaggg cgggccgtgt tcaaaaaaaa aagtcgcggc ggcggcggct gctcagggaa 21960
ggaggcctga gggccgcgtg cagcgggcgg gcagctgggt gggctggggg cggccgcgcg 22020
gcgtccggga gcctcgggcc gcccggagcc ggcgggcggg cggaggcgga ggcggcggcg 22080
gctgcagcgg ctgcaggagc ggcggcggct gcngcggcgg cngcggcatc tcctcctcac 22140
atgaccccac tgtttgtccc cgtgatcagc gcgagcggct cccgtatctc ctccgtcccc 22200
tcctgccgcg cggcgtgagc gccgggnctc ggggcccccc cggccgcccg ccccctcccc 22260
tccntccntc ccctcccctc ccctccccnc cgggccccgc gccccccccg ccccgcccc 22320
cccatggac atgctggacc cgggtctgga tcccgctgcc tcggccaccg ctgctgccgc 22380
cgccaggtaa gatccccggc ccggccgtgc cccgcgccc cggccccggc cccggccccg 22440
cggcctgcag gccggggccg ccatgatccc gagcggccgc gggccccgct caaaatggag 22500
gccgccggcg cggggggac ctggcgcctc ccgccccgg ccccggcct cggcggcgcc 22560
cccggcctca ggcgcggccg ggtgggactg gggccctgca gctggcgcg ggggcggggg 22620
ccgggcgcg ggccgcgctg accctgctcc ctcctgtgcc cctggcagcc acgacaaggg 22680
acccgaggcg gaggagggcg tcgagctgca ggaaggtgag tgcttgccgg gccggccgcg 22740
cccggggagg gctggggcg ctcggcgcgg ccctgaccgt gccccgaccc tcctcggccc 22800
caggcgggga cggccagga gcggaggagc agacagcggt ggccatcacc agcgtccagc 22860
aggcggcgtt cggcgaccac aacatccagt accagttccg cacagagaca aatggaggac 22920
aggtgagcgg cgggccgcga gagcgaacgg gcgggcgggc gggcgcgcc ggaaggctcg 22980
gacctggccc cagcgccggc ctcgccgctc tgccgccccc tgcaggtgac ataccgcgta 23040
gtccaggtga ctgatggtca gctggacggc cagggcgaca cagctggcgc cgtcagcgtc 23100
```

```
gtgtccaccg ctgccttcgc ggggggggcag caggctgtga cccaggtggg tgtggacggg    23160
gcagcccagc gcccgggccc cgccgct                                         23187

<210> 2
<211> 2158
<212> DNA
<213> Homo sapiens

<220>
<221> allele
<222> 595
<223> 9-3-324  : polymorphic  base  C  or  T

<220>
<221> allele
<222> 940
<223> 9-6-187  : polymorphic  base  C  or  T

<220>
<221> allele
<222> 1191
<223> 9-7-325  : polymorphic  base  A  or  G

<220>
<221> allele
<222> 1362
<223> 9-9-246  : polymorphic  base  G  or  C

<220>
<221> allele
<222> 1658
<223> LSRX9f13-BM  : polymorphic  base  deletion  of  AGG <220>
<221> allele
<222> 2079
<223> LSRX9f14-BM  : polymorphic  base  T  or  G
<400> 2
tggagtgtgg ctcggaggac cgcggcgggt caagcacctt tctcccccat atctgaaagc    60
atgcccttttg tccacgtcgt ttacgctcat taaaacttcc aga atg caa cag gac     115
                                             Met Gln Gln Asp
                                              1
gga ctt gga gta ggg aca agg aac gga agt ggg aag ggg agg agc gtg      163
Gly Leu Gly Val Gly Thr Arg Asn Gly Ser Gly Lys Gly Arg Ser Val
 5               10                  15                  20
cac ccc tcc tgg cct tgg tgc gcg ccg cgc ccc cta agg tac ttt gga      211
His Pro Ser Trp Pro Trp Cys Ala Pro Arg Pro Leu Arg Tyr Phe Gly
             25                  30                  35
agg gac gcg cgg gcc aga cgc gcc cag acg gcc gcg atg gcg ctg ttg      259
Arg Asp Ala Arg Ala Arg Arg Ala Gln Thr Ala Ala Met Ala Leu Leu
         40                  45                  50
gcc ggc ggg ctc tcc aga ggg ctg ggc tcc cac ccg gcc gcc gca ggc      307
Ala Gly Gly Leu Ser Arg Gly Leu Gly Ser His Pro Ala Ala Ala Gly
     55                  60                  65
cgg gac gcg gtc gtc ttc gtg tgg ctt ctg ctt agc acc tgg tgc aca      355
Arg Asp Ala Val Val Phe Val Trp Leu Leu Leu Ser Thr Trp Cys Thr
 70                  75                  80
gct cct gcc agg gcc atc cag gtg acc gtg tcc aac ccc tac cac gtg      403
```

```
Ala Pro Ala Arg Ala Ile Gln Val Thr Val Ser Asn Pro Tyr His Val
85                  90                  95                  100
gtg atc ctc ttc cag cct gtg acc ctg ccc tgt acc tac cag atg acc      451
Val Ile Leu Phe Gln Pro Val Thr Leu Pro Cys Thr Tyr Gln Met Thr
                105                 110                 115
tcg acc ccc acg caa ccc atc gtc atc tgg aag tac aag tct ttc tgc      499
Ser Thr Pro Thr Gln Pro Ile Val Ile Trp Lys Tyr Lys Ser Phe Cys
                120                 125                 130
cgg gac cgc atc gcc gat gcc ttc tcc ccg gcc agc gtc gac aac cag      547
Arg Asp Arg Ile Ala Asp Ala Phe Ser Pro Ala Ser Val Asp Asn Gln
                135                 140                 145
ctc aat gcc cag ctg gca gcc ggg aac cca ggc tac aac ccc tac gty      595
Leu Asn Ala Gln Leu Ala Ala Gly Asn Pro Gly Tyr Asn Pro Tyr Val
                150                 155                 160
gag tgc cag gac agc gtg cgc acc gtc agg gtc gtg gcc acc aag cag      643
Glu Cys Gln Asp Ser Val Arg Thr Val Arg Val Val Ala Thr Lys Gln
165                 170                 175                 180
ggc aac gct gtg acc ctg gga gat tac tac cag ggc cgg agg att acc      691
Gly Asn Ala Val Thr Leu Gly Asp Tyr Tyr Gln Gly Arg Arg Ile Thr
                185                 190                 195
atc acc gga aat gct gac ctg acc ttt gac cag acg gcg tgg ggg gac      739
Ile Thr Gly Asn Ala Asp Leu Thr Phe Asp Gln Thr Ala Trp Gly Asp
                200                 205                 210
agt ggt gtg tat tac tgc tcc gtg gtc tca gcc cag gac ctc cag ggg      787
Ser Gly Val Tyr Tyr Cys Ser Val Val Ser Ala Gln Asp Leu Gln Gly
                215                 220                 225
aac aat gag gcc tac gca gag ctc atc gtc ctt ggg agg acc tca ggg      835
Asn Asn Glu Ala Tyr Ala Glu Leu Ile Val Leu Gly Arg Thr Ser Gly
                230                 235                 240
gtg gct gag ctc tta cct ggt ttt cag gcg ggg ccc ata gaa gac tgg      883
Val Ala Glu Leu Leu Pro Gly Phe Gln Ala Gly Pro Ile Glu Asp Trp
245                 250                 255                 260
ctc ttc gtg gtt gtg gta tgc ctg gct gcc ttc ctc atc ttc ctc ctc      931
Leu Phe Val Val Val Val Cys Leu Ala Ala Phe Leu Ile Phe Leu Leu
                265                 270                 275
ctg ggc aty tgc tgg tgc cag tgc tgc ccg cac act tgc tgc tgc tac      979
Leu Gly Ile Cys Trp Cys Gln Cys Cys Pro His Thr Cys Cys Cys Tyr
                280                 285                 290
gtc agg tgc ccc tgc tgc cca gac aag tgc tgc tgc ccc gag gcc ctg     1027
Val Arg Cys Pro Cys Cys Pro Asp Lys Cys Cys Cys Pro Glu Ala Leu
                295                 300                 305
tat gcc gcc ggc aaa gca gcc acc tca ggt gtt ccc agc att tat gcc     1075
Tyr Ala Ala Gly Lys Ala Ala Thr Ser Gly Val Pro Ser Ile Tyr Ala
310                 315                 320
ccc agc acc tat gcc cac ctg tct ccc gcc aag acc cca ccc cca cca     1123
Pro Ser Thr Tyr Ala His Leu Ser Pro Ala Lys Thr Pro Pro Pro Pro
325                 330                 335                 340
gct atg att ccc atg ggc cct gcc tac aac ggg tac cct gga gga tac     1171
Ala Met Ile Pro Met Gly Pro Ala Tyr Asn Gly Tyr Pro Gly Gly Tyr
                345                 350                 355
cct gga gac gtt gac agg art agc tca gct ggt ggc caa ggc tcc tat     1219
Pro Gly Asp Val Asp Arg Xaa Ser Ser Ala Gly Gly Gln Gly Ser Tyr
                360                 365                 370
gta ccc ctg ctt cgg gac acg gac agc agt gtg gcc tct gaa gtc cgc     1267
Val Pro Leu Leu Arg Asp Thr Asp Ser Ser Val Ala Ser Glu Val Arg
                375                 380                 385
agt ggc tac agg att cag gcc agc cag cag gac gac tcc atg cgg gtc     1315
Ser Gly Tyr Arg Ile Gln Ala Ser Gln Gln Asp Asp Ser Met Arg Val
                390                 395                 400
```

```
ctg tac tac atg gag aag gag ctg gcc aac ttc gac cct tct cga cst    1363
Leu Tyr Tyr Met Glu Lys Glu Leu Ala Asn Phe Asp Pro Ser Arg Xaa
405                 410                 415                 420
ggc ccc ccc agt ggc cgt gtg gag cgg gcc atg agt gaa gtc acc tcc    1411
Gly Pro Pro Ser Gly Arg Val Glu Arg Ala Met Ser Glu Val Thr Ser
                425                 430                 435
ctc cac gag gac gac tgg cga tct cgg cct tcc cgg ggc cct gcc ctc    1459
Leu His Glu Asp Asp Trp Arg Ser Arg Pro Ser Arg Gly Pro Ala Leu
                440                 445                 450
acc ccg atc cgg gat gag gag tgg ggt ggc cac tcc ccc cgg agt ccc    1507
Thr Pro Ile Arg Asp Glu Glu Trp Gly Gly His Ser Pro Arg Ser Pro
            455                 460                 465
agg gga tgg gac cag gag ccc gcc agg gag cag gca ggc ggg ggc tgg    1555
Arg Gly Trp Asp Gln Glu Pro Ala Arg Glu Gln Ala Gly Gly Gly Trp
        470                 475                 480
cgg gcc agg cgg ccc cgg gcc cgc tcc gtg gac gcc ctg gac gac ctc    1603
Arg Ala Arg Arg Pro Arg Ala Arg Ser Val Asp Ala Leu Asp Asp Leu
485                 490                 495                 500
acc ccg ccg agc acc gcc gag tca ggg agc agg tct ccc acg agt aat    1651
Thr Pro Pro Ser Thr Ala Glu Ser Gly Ser Arg Ser Pro Thr Ser Asn
                505                 510                 515
ggt ggg aga agc cgg gcc tac atg ccc ccg cgg agc cgc agc cgg gac    1699
Gly Gly Arg Ser Arg Ala Tyr Met Pro Pro Arg Ser Arg Ser Arg Asp
                520                 525                 530
gac ctc tat gac caa gac gac tcg agg gac ttc cca cgc tcc cgg gac    1747
Asp Leu Tyr Asp Gln Asp Asp Ser Arg Asp Phe Pro Arg Ser Arg Asp
            535                 540                 545
ccc cac tac gac gac ttc agg tct cgg gag cgc cct cct gcc gac ccc    1795
Pro His Tyr Asp Asp Phe Arg Ser Arg Glu Arg Pro Pro Ala Asp Pro
        550                 555                 560
agg tcc cac cac cac cgt acc cgg gac cct cgg gac aac ggc tcc agg    1843
Arg Ser His His His Arg Thr Arg Asp Pro Arg Asp Asn Gly Ser Arg
565                 570                 575                 580
tcc ggg gac ctc ccc tat gat ggg cgg cta ctg gag gag gct gtg agg    1891
Ser Gly Asp Leu Pro Tyr Asp Gly Arg Leu Leu Glu Glu Ala Val Arg
                585                 590                 595
aag aag ggg tcg gag gag agg agg aga ccc cac aag gag gag gag gaa    1939
Lys Lys Gly Ser Glu Glu Arg Arg Arg Pro His Lys Glu Glu Glu Glu
                600                 605                 610
gag gcc tac tac ccg ccc gcg ccg ccc ccg tac tcg gag acc gac tcg    1987
Glu Ala Tyr Tyr Pro Pro Ala Pro Pro Pro Tyr Ser Glu Thr Asp Ser
            615                 620                 625
cag gcg tcc cga gag cgc agg ctc aag aag aac ttg gcc ctg agt cgg    2035
Gln Ala Ser Arg Glu Arg Arg Leu Lys Lys Asn Leu Ala Leu Ser Arg
        630                 635                 640
gaa agt tta gtc gtc tga tctgacgttt tctacgtagc ttttgkattt           2083
Glu Ser Leu Val Val *
645                 650
ttttttttaa tttgaaggaa cactgatgaa gccctgccat acccctcccg agtctaataa  2143
aacgtataat cacaa                                                   2158

<210> 3
<211> 649
<212> PRT
<213> Homo sapiens

<220>
<221> VARIANT
<222> 363
```

<223> 9-7-325 : polymorphic amino acid Ser or Asn

<220>
<221> VARIANT
<222> 420
<223> 9-9-246 : polymorphic amino acid Pro or Arg

<220>
<221> VARIANT
<222> 519
<223> LSRX9f13-BM : polymorphic amino acid deletion of Arg

<400> 3

```
Met Gln Gln Asp Gly Leu Gly Val Gly Thr Arg Asn Gly Ser Gly Lys
1               5                   10                  15
Gly Arg Ser Val His Pro Ser Trp Pro Trp Cys Ala Pro Arg Pro Leu
            20                  25                  30
Arg Tyr Phe Gly Arg Asp Ala Arg Ala Arg Arg Ala Gln Thr Ala Ala
        35                  40                  45
Met Ala Leu Leu Ala Gly Gly Leu Ser Arg Gly Leu Gly Ser His Pro
    50                  55                  60
Ala Ala Ala Gly Arg Asp Ala Val Val Phe Val Trp Leu Leu Leu Ser
65                  70                  75                  80
Thr Trp Cys Thr Ala Pro Ala Arg Ala Ile Gln Val Thr Val Ser Asn
                85                  90                  95
Pro Tyr His Val Val Ile Leu Phe Gln Pro Val Thr Leu Pro Cys Thr
                100                 105                 110
Tyr Gln Met Thr Ser Thr Pro Thr Gln Pro Ile Val Ile Trp Lys Tyr
            115                 120                 125
Lys Ser Phe Cys Arg Asp Arg Ile Ala Asp Ala Phe Ser Pro Ala Ser
        130                 135                 140
Val Asp Asn Gln Leu Asn Ala Gln Leu Ala Ala Gly Asn Pro Gly Tyr
145                 150                 155                 160
Asn Pro Tyr Val Glu Cys Gln Asp Ser Val Arg Thr Val Arg Val Val
                165                 170                 175
Ala Thr Lys Gln Gly Asn Ala Val Thr Leu Gly Asp Tyr Tyr Gln Gly
            180                 185                 190
Arg Arg Ile Thr Ile Thr Gly Asn Ala Asp Leu Thr Phe Asp Gln Thr
        195                 200                 205
Ala Trp Gly Asp Ser Gly Val Tyr Tyr Cys Ser Val Val Ser Ala Gln
    210                 215                 220
Asp Leu Gln Gly Asn Asn Glu Ala Tyr Ala Glu Leu Ile Val Leu Gly
225                 230                 235                 240
Arg Thr Ser Gly Val Ala Glu Leu Leu Pro Gly Phe Gln Ala Gly Pro
                245                 250                 255
Ile Glu Asp Trp Leu Phe Val Val Val Cys Leu Ala Ala Phe Leu
                260                 265                 270
Ile Phe Leu Leu Leu Gly Ile Cys Trp Cys Gln Cys Cys Pro His Thr
        275                 280                 285
Cys Cys Cys Tyr Val Arg Cys Pro Cys Cys Pro Asp Lys Cys Cys Cys
    290                 295                 300
Pro Glu Ala Leu Tyr Ala Ala Gly Lys Ala Ala Thr Ser Gly Val Pro
305                 310                 315                 320
Ser Ile Tyr Ala Pro Ser Thr Tyr Ala His Leu Ser Pro Ala Lys Thr
                325                 330                 335
Pro Pro Pro Pro Ala Met Ile Pro Met Gly Pro Ala Tyr Asn Gly Tyr
                340                 345                 350
Pro Gly Gly Tyr Pro Gly Asp Val Asp Arg Ser Ser Ser Ala Gly Gly
            355                 360                 365
```

```
Gln Gly Ser Tyr Val Pro Leu Leu Arg Asp Thr Asp Ser Ser Val Ala
    370                 375                 380
Ser Glu Val Arg Ser Gly Tyr Arg Ile Gln Ala Ser Gln Gln Asp Asp
385                 390                 395                 400
Ser Met Arg Val Leu Tyr Tyr Met Glu Lys Glu Leu Ala Asn Phe Asp
            405                 410                 415
Pro Ser Arg Pro Gly Pro Pro Ser Gly Arg Val Glu Arg Ala Met Ser
            420                 425                 430
Glu Val Thr Ser Leu His Glu Asp Asp Trp Arg Ser Arg Pro Ser Arg
        435                 440                 445
Gly Pro Ala Leu Thr Pro Ile Arg Asp Glu Glu Trp Gly Gly His Ser
        450                 455                 460
Pro Arg Ser Pro Arg Gly Trp Asp Gln Glu Pro Ala Arg Glu Gln Ala
465                 470                 475                 480
Gly Gly Gly Trp Arg Ala Arg Arg Pro Arg Ala Arg Ser Val Asp Ala
            485                 490                 495
Leu Asp Asp Leu Thr Pro Pro Ser Thr Ala Glu Ser Gly Ser Arg Ser
            500                 505                 510
Pro Thr Ser Asn Gly Gly Arg Ser Arg Ala Tyr Met Pro Pro Arg Ser
        515                 520                 525
Arg Ser Arg Asp Asp Leu Tyr Asp Gln Asp Asp Ser Arg Asp Phe Pro
    530                 535                 540
Arg Ser Arg Asp Pro His Tyr Asp Asp Phe Arg Ser Arg Glu Arg Pro
545                 550                 555                 560
Pro Ala Asp Pro Arg Ser His His His Arg Thr Arg Asp Pro Arg Asp
            565                 570                 575
Asn Gly Ser Arg Ser Gly Asp Leu Pro Tyr Asp Gly Arg Leu Leu Glu
            580                 585                 590
Glu Ala Val Arg Lys Lys Gly Ser Glu Glu Arg Arg Arg Pro His Lys
        595                 600                 605
Glu Glu Glu Glu Glu Ala Tyr Tyr Pro Pro Ala Pro Pro Pro Tyr Ser
610                 615                 620
Glu Thr Asp Ser Gln Ala Ser Arg Glu Arg Arg Leu Lys Lys Asn Leu
625                 630                 635                 640
Ala Leu Ser Arg Glu Ser Leu Val Val
            645

<210> 4
<211> 2101
<212> DNA
<213> Homo sapiens

<220>
<221> allele
<222> 595
<223> 9-3-324 : polymorphic base C or T

<220>
<221> allele
<222> 883
<223> 9-6-187 : polymorphic base C or T

<220>
<221> allele
<222> 1134
<223> 9-7-325 : polymorphic base A or G

<220>
<221> allele
```

<222> 1305
<223> 9-9-246 : polymorphic base G or C

<220>
<221> allele
<222> 1601
<223> LSRX9f13-BM : polymorphic base deletion of AGG <220>
<221> allele
<222> 2022
<223> LSRX9f14-BM : polymorphic base T or G

<400> 4

```
tggagtgtgg ctcggaggac cgcggcgggt caagcacctt tctcccccat atctgaaagc      60
atgcccttg tccacgtcgt ttacgtcat taaaacttcc aga atg caa cag gac         115
                                              Met Gln Gln Asp
                                               1
gga ctt gga gta ggg aca agg aac gga agt ggg aag ggg agg agc gtg       163
Gly Leu Gly Val Gly Thr Arg Asn Gly Ser Gly Lys Gly Arg Ser Val
 5                  10                  15                  20
cac ccc tcc tgg cct tgg tgc gcg ccg cgc ccc cta agg tac ttt gga       211
His Pro Ser Trp Pro Trp Cys Ala Pro Arg Pro Leu Arg Tyr Phe Gly
                25                  30                  35
agg gac gcg cgg gcc aga cgc gcc cag acg gcc gcg atg gcg ctg ttg       259
Arg Asp Ala Arg Ala Arg Arg Ala Gln Thr Ala Ala Met Ala Leu Leu
            40                  45                  50
gcc ggc ggg ctc tcc aga ggg ctg ggc tcc cac ccg gcc gcc gca ggc       307
Ala Gly Gly Leu Ser Arg Gly Leu Gly Ser His Pro Ala Ala Ala Gly
            55                  60                  65
cgg gac gcg gtc gtc ttc gtg tgg ctt ctg ctt agc acc tgg tgc aca       355
Arg Asp Ala Val Val Phe Val Trp Leu Leu Leu Ser Thr Trp Cys Thr
 70                  75                  80
gct cct gcc agg gcc atc cag gtg acc gtg tcc aac ccc tac cac gtg       403
Ala Pro Ala Arg Ala Ile Gln Val Thr Val Ser Asn Pro Tyr His Val
 85                  90                  95                 100
gtg atc ctc ttc cag cct gtg acc ctg ccc tgt acc tac cag atg acc       451
Val Ile Leu Phe Gln Pro Val Thr Leu Pro Cys Thr Tyr Gln Met Thr
                105                 110                 115
tcg acc ccc acg caa ccc atc gtc atc tgg aag tac aag tct ttc tgc       499
Ser Thr Pro Thr Gln Pro Ile Val Ile Trp Lys Tyr Lys Ser Phe Cys
            120                 125                 130
cgg gac cgc atc gcc gat gcc ttc tcc ccg gcc agc gtc gac aac cag       547
Arg Asp Arg Ile Ala Asp Ala Phe Ser Pro Ala Ser Val Asp Asn Gln
            135                 140                 145
ctc aat gcc cag ctg gca gcc ggg aac cca ggc tac aac ccc tac gty       595
Leu Asn Ala Gln Leu Ala Ala Gly Asn Pro Gly Tyr Asn Pro Tyr Val
        150                 155                 160
gag tgc cag gac agc gtg cgc acc gtc agg gtc gtg gcc acc aag cag       643
Glu Cys Gln Asp Ser Val Arg Thr Val Arg Val Val Ala Thr Lys Gln
165                 170                 175                 180
ggc aac gct gtg acc ctg gga gat tac tac cag ggc cgg agg att acc       691
Gly Asn Ala Val Thr Leu Gly Asp Tyr Tyr Gln Gly Arg Arg Ile Thr
                185                 190                 195
atc acc gga aat gct gac ctg acc ttt gac cag acg gcg tgg ggg gac       739
Ile Thr Gly Asn Ala Asp Leu Thr Phe Asp Gln Thr Ala Trp Gly Asp
            200                 205                 210
agt ggt gtg tat tac tgc tcc gtg gtc tca gcc cag gac ctc cag ggg       787
Ser Gly Val Tyr Tyr Cys Ser Val Val Ser Ala Gln Asp Leu Gln Gly
```

```
              215                      220                      225
aac aat gag gcc tac gca gag ctc atc gtc ctt gac tgg ctc ttc gtg       835
Asn Asn Glu Ala Tyr Ala Glu Leu Ile Val Leu Asp Trp Leu Phe Val
            230                      235                      240
gtt gtg gta tgc ctg gct gcc ttc ctc atc ttc ctc ctc ctg ggc aty       883
Val Val Val Cys Leu Ala Ala Phe Leu Ile Phe Leu Leu Leu Gly Ile
245                      250                      255                      260
tgc tgg tgc cag tgc tgc ccg cac act tgc tgc tgc tac gtc agg tgc       931
Cys Trp Cys Gln Cys Cys Pro His Thr Cys Cys Cys Tyr Val Arg Cys
                    265                      270                      275
ccc tgc tgc cca gac aag tgc tgc tgc ccc gag gcc ctg tat gcc gcc       979
Pro Cys Cys Pro Asp Lys Cys Cys Cys Pro Glu Ala Leu Tyr Ala Ala
                280                      285                      290
ggc aaa gca gcc acc tca ggt gtt ccc agc att tat gcc ccc agc acc      1027
Gly Lys Ala Ala Thr Ser Gly Val Pro Ser Ile Tyr Ala Pro Ser Thr
            295                      300                      305
tat gcc cac ctg tct ccc gcc aag acc cca ccc cca cca gct atg att      1075
Tyr Ala His Leu Ser Pro Ala Lys Thr Pro Pro Pro Pro Ala Met Ile
310                      315                      320
ccc atg ggc cct gcc tac aac ggg tac cct gga gga tac cct gga gac      1123
Pro Met Gly Pro Ala Tyr Asn Gly Tyr Pro Gly Gly Tyr Pro Gly Asp
325                      330                      335                      340
gtt gac agg art agc tca gct ggt ggc caa ggc tcc tat gta ccc ctg      1171
Val Asp Arg Xaa Ser Ser Ala Gly Gly Gln Gly Ser Tyr Val Pro Leu
                    345                      350                      355
ctt cgg gac acg gac agc agt gtg gcc tct gaa gtc cgc agt ggc tac      1219
Leu Arg Asp Thr Asp Ser Ser Val Ala Ser Glu Val Arg Ser Gly Tyr
                360                      365                      370
agg att cag gcc agc cag cag gac gac tcc atg cgg gtc ctg tac tac      1267
Arg Ile Gln Ala Ser Gln Gln Asp Asp Ser Met Arg Val Leu Tyr Tyr
            375                      380                      385
atg gag aag gag ctg gcc aac ttc gac cct tct cga cst ggc ccc ccc      1315
Met Glu Lys Glu Leu Ala Asn Phe Asp Pro Ser Arg Xaa Gly Pro Pro
390                      395                      400
agt ggc cgt gtg gag cgg gcc atg agt gaa gtc acc tcc ctc cac gag      1363
Ser Gly Arg Val Glu Arg Ala Met Ser Glu Val Thr Ser Leu His Glu
405                      410                      415                      420
gac gac tgg cga tct cgg cct tcc cgg ggc cct gcc ctc acc ccg atc      1411
Asp Asp Trp Arg Ser Arg Pro Ser Arg Gly Pro Ala Leu Thr Pro Ile
                    425                      430                      435
cgg gat gag gag tgg ggt ggc cac tcc ccc cgg agt ccc agg gga tgg      1459
Arg Asp Glu Glu Trp Gly Gly His Ser Pro Arg Ser Pro Arg Gly Trp
                440                      445                      450
gac cag gag ccc gcc agg gag cag gca ggc ggg ggc tgg cgg gcc agg      1507
Asp Gln Glu Pro Ala Arg Glu Gln Ala Gly Gly Gly Trp Arg Ala Arg
            455                      460                      465
cgg ccc cgg gcc cgc tcc gtg gac gcc ctg gac gac ctc acc ccg ccg      1555
Arg Pro Arg Ala Arg Ser Val Asp Ala Leu Asp Asp Leu Thr Pro Pro
470                      475                      480
agc acc gcc gag tca ggg agc agg tct ccc acg agt aat ggt ggg aga      1603
Ser Thr Ala Glu Ser Gly Ser Arg Ser Pro Thr Ser Asn Gly Gly Arg
485                      490                      495                      500
agc cgg gcc tac atg ccc ccg cgg agc cgc agc cgg gac gac ctc tat      1651
Ser Arg Ala Tyr Met Pro Pro Arg Ser Arg Ser Arg Asp Asp Leu Tyr
                    505                      510                      515
gac caa gac gac tcg agg gac ttc cca cgc tcc cgg gac ccc cac tac      1699
Asp Gln Asp Asp Ser Arg Asp Phe Pro Arg Ser Arg Asp Pro His Tyr
                520                      525                      530
gac gac ttc agg tct cgg gag cgc cct cct gcc gac ccc agg tcc cac      1747
```

```
Asp Asp Phe Arg Ser Arg Glu Arg Pro Pro Ala Asp Pro Arg Ser His
        535                 540                 545
cac cac cgt acc cgg gac cct cgg gac aac ggc tcc agg tcc ggg gac        1795
His His Arg Thr Arg Asp Pro Arg Asp Asn Gly Ser Arg Ser Gly Asp
550                 555                 560
ctc ccc tat gat ggg cgg cta ctg gag gag gct gtg agg aag aag ggg        1843
Leu Pro Tyr Asp Gly Arg Leu Leu Glu Glu Ala Val Arg Lys Lys Gly
565                 570                 575                 580
tcg gag gag agg agg aga ccc cac aag gag gag gag gaa gag gcc tac        1891
Ser Glu Glu Arg Arg Arg Pro His Lys Glu Glu Glu Glu Glu Ala Tyr
            585                 590                 595
tac ccg ccc gcg ccg ccc ccg tac tcg gag acc gac tcg cag gcg tcc        1939
Tyr Pro Pro Ala Pro Pro Pro Tyr Ser Glu Thr Asp Ser Gln Ala Ser
                600                 605                 610
cga gag cgc agg ctc aag aag aac ttg gcc ctg agt cgg gaa agt tta        1987
Arg Glu Arg Arg Leu Lys Lys Asn Leu Ala Leu Ser Arg Glu Ser Leu
            615                 620                 625
gtc gtc tga tctgacgttt tctacgtagc ttttgkattt ttttttttaa                2036
Val Val *
630 tttgaaggaa cactgatgaa gccctgccat accccctcccg agtctaataa aacgtataat     2096
cacaa                                                                  2101

<210> 5
<211> 630
<212> PRT
<213> Homo sapiens

<220>
<221> VARIANT
<222> 344
<223> 9-7-325  :  polymorphic  amino  acid  Ser  or  Asn <220>
<221> VARIANT
<222> 401
<223> 9-9-246  :  polymorphic  amino  acid  Pro  or  Arg <220>
<221> VARIANT
<222> 500
<223> LSRX9f13-BM  :  polymorphic  amino  acid  deletion  of  Arg
<400> 5
Met Gln Gln Asp Gly Leu Gly Val Gly Thr Arg Asn Gly Ser Gly Lys
1               5                   10                  15
Gly Arg Ser Val His Pro Ser Trp Pro Trp Cys Ala Pro Arg Pro Leu
            20                  25                  30
Arg Tyr Phe Gly Arg Asp Ala Arg Ala Arg Arg Ala Gln Thr Ala Ala
        35                  40                  45
Met Ala Leu Leu Ala Gly Gly Leu Ser Arg Gly Leu Gly Ser His Pro
    50                  55                  60
Ala Ala Ala Gly Arg Asp Ala Val Val Phe Val Trp Leu Leu Leu Ser
65                  70                  75                  80
Thr Trp Cys Thr Ala Pro Ala Arg Ala Ile Gln Val Thr Val Ser Asn
                85                  90                  95
Pro Tyr His Val Val Ile Leu Phe Gln Pro Val Thr Leu Pro Cys Thr
                100                 105                 110
Tyr Gln Met Thr Ser Thr Pro Thr Gln Pro Ile Val Ile Trp Lys Tyr
```

```
              115                     120                     125
Lys Ser Phe Cys Arg Asp Arg Ile Ala Asp Ala Phe Ser Pro Ala Ser
        130                     135                     140
Val Asp Asn Gln Leu Asn Ala Gln Leu Ala Ala Gly Asn Pro Gly Tyr
145                     150                     155                     160
Asn Pro Tyr Val Glu Cys Gln Asp Ser Val Arg Thr Val Arg Val Val
                165                     170                     175
Ala Thr Lys Gln Gly Asn Ala Val Thr Leu Gly Asp Tyr Tyr Gln Gly
                180                     185                     190
Arg Arg Ile Thr Ile Thr Gly Asn Ala Asp Leu Thr Phe Asp Gln Thr
            195                     200                     205
Ala Trp Gly Asp Ser Gly Val Tyr Tyr Cys Ser Val Val Ser Ala Gln
        210                     215                     220
Asp Leu Gln Gly Asn Asn Glu Ala Tyr Ala Glu Leu Ile Val Leu Asp
225                     230                     235                     240
Trp Leu Phe Val Val Val Val Cys Leu Ala Ala Phe Leu Ile Phe Leu
                245                     250                     255
Leu Leu Gly Ile Cys Trp Cys Gln Cys Cys Pro His Thr Cys Cys Cys
                260                     265                     270
Tyr Val Arg Cys Pro Cys Cys Pro Asp Lys Cys Cys Cys Pro Glu Ala
            275                     280                     285
Leu Tyr Ala Ala Gly Lys Ala Ala Thr Ser Gly Val Pro Ser Ile Tyr
        290                     295                     300
Ala Pro Ser Thr Tyr Ala His Leu Ser Pro Ala Lys Thr Pro Pro Pro
305                     310                     315                     320
Pro Ala Met Ile Pro Met Gly Pro Ala Tyr Asn Gly Tyr Pro Gly Gly
                325                     330                     335
Tyr Pro Gly Asp Val Asp Arg Ser Ser Ser Ala Gly Gly Gln Gly Ser
                340                     345                     350
Tyr Val Pro Leu Leu Arg Asp Thr Asp Ser Ser Val Ala Ser Glu Val
            355                     360                     365
Arg Ser Gly Tyr Arg Ile Gln Ala Ser Gln Gln Asp Asp Ser Met Arg
        370                     375                     380
Val Leu Tyr Tyr Met Glu Lys Glu Leu Ala Asn Phe Asp Pro Ser Arg
385                     390                     395                     400
Pro Gly Pro Pro Ser Gly Arg Val Glu Arg Ala Met Ser Glu Val Thr
                405                     410                     415
Ser Leu His Glu Asp Asp Trp Arg Ser Arg Pro Ser Arg Gly Pro Ala
                420                     425                     430
Leu Thr Pro Ile Arg Asp Glu Glu Trp Gly Gly His Ser Pro Arg Ser
        435                     440                     445
Pro Arg Gly Trp Asp Gln Glu Pro Ala Arg Glu Gln Ala Gly Gly Gly
        450                     455                     460
Trp Arg Ala Arg Arg Pro Arg Ala Arg Ser Val Asp Ala Leu Asp Asp
465                     470                     475                     480
Leu Thr Pro Pro Ser Thr Ala Glu Ser Gly Ser Arg Ser Pro Thr Ser
                485                     490                     495
Asn Gly Gly Arg Ser Arg Ala Tyr Met Pro Pro Arg Ser Arg Ser Arg
                500                     505                     510
Asp Asp Leu Tyr Asp Gln Asp Asp Ser Arg Asp Phe Pro Arg Ser Arg
            515                     520                     525
Asp Pro His Tyr Asp Asp Phe Arg Ser Arg Glu Arg Pro Pro Ala Asp
        530                     535                     540
Pro Arg Ser His His His Arg Thr Arg Asp Pro Arg Asp Asn Gly Ser
545                     550                     555                     560
Arg Ser Gly Asp Leu Pro Tyr Asp Gly Arg Leu Leu Glu Glu Ala Val
                565                     570                     575
Arg Lys Lys Gly Ser Glu Glu Arg Arg Arg Pro His Lys Glu Glu Glu
                580                     585                     590
```

```
Glu Glu Ala Tyr Tyr Pro Pro Ala Pro Pro Tyr Ser Glu Thr Asp
        595             600             605
Ser Gln Ala Ser Arg Glu Arg Arg Leu Lys Lys Asn Leu Ala Leu Ser
        610             615             620
Arg Glu Ser Leu Val Val
625             630

<210> 6
<211> 1954
<212> DNA
<213> Homo sapiens

<220>
<221> allele
<222> 595
<223> 9-3-324  :  polymorphic  base  C  or  T

<220>
<221> allele
<222> 987
<223> 9-7-325  :  polymorphic  base  A  or  G

<220>
<221> allele
<222> 1158
<223> 9-9-246  :  polymorphic  base  G  or  C

<220>
<221> allele
<222> 1454
<223> LSRX9f13-BM  :  polymorphic  base  deletion  of  AGG <220>
<221> allele
<222> 1875
<223> LSRX9f14-BM  :  polymorphic  base  T  or  G
<400> 6
tggagtgtgg ctcggaggac cgcggcgggt caagcacctt tctcccccat atctgaaagc    60
atgccctttg tccacgtcgt ttacgctcat taaaacttcc aga atg caa cag gac    115
                                            Met Gln Gln Asp
                                             1
gga ctt gga gta ggg aca agg aac gga agt ggg aag ggg agg agc gtg    163
Gly Leu Gly Val Gly Thr Arg Asn Gly Ser Gly Lys Gly Arg Ser Val
5               10              15                  20
cac ccc tcc tgg cct tgg tgc gcg ccg cgc ccc cta agg tac ttt gga    211
His Pro Ser Trp Pro Trp Cys Ala Pro Arg Pro Leu Arg Tyr Phe Gly
            25              30                  35
agg gac gcg cgg gcc aga cgc gcc cag acg gcg gcg atg gcg ctg ttg    259
Arg Asp Ala Arg Ala Arg Arg Ala Gln Thr Ala Ala Met Ala Leu Leu
            40              45              50
gcc ggc ggg ctc tcc aga ggg ctg ggc tcc cac ccg gcc gcc gca ggc    307
Ala Gly Gly Leu Ser Arg Gly Leu Gly Ser His Pro Ala Ala Ala Gly
        55              60              65
cgg gac gcg gtc gtc ttc gtg tgg ctt ctg ctt agc acc tgg tgc aca    355
Arg Asp Ala Val Val Phe Val Trp Leu Leu Leu Ser Thr Trp Cys Thr
    70              75              80
gct cct gcc agg gcc atc cag gtg acc gtg tcc aac ccc tac cac gtg    403
Ala Pro Ala Arg Ala Ile Gln Val Thr Val Ser Asn Pro Tyr His Val
```

```
           85                      90                      95                     100
gtg atc ctc ttc cag cct gtg acc ctg ccc tgt acc tac cag atg acc          451
Val Ile Leu Phe Gln Pro Val Thr Leu Pro Cys Thr Tyr Gln Met Thr
                    105                     110                     115
tcg acc ccc acg caa ccc atc gtc atc tgg aag tac aag tct ttc tgc          499
Ser Thr Pro Thr Gln Pro Ile Val Ile Trp Lys Tyr Lys Ser Phe Cys
                120                     125                     130
cgg gac cgc atc gcc gat gcc ttc tcc ccg gcc agc gtc gac aac cag          547
Arg Asp Arg Ile Ala Asp Ala Phe Ser Pro Ala Ser Val Asp Asn Gln
            135                     140                     145
ctc aat gcc cag ctg gca gcc ggg aac cca ggc tac aac ccc tac gty          595
Leu Asn Ala Gln Leu Ala Ala Gly Asn Pro Gly Tyr Asn Pro Tyr Val
            150                     155                     160
gag tgc cag gac agc gtg cgc acc gtc agg gtc gtg gcc acc aag cag          643
Glu Cys Gln Asp Ser Val Arg Thr Val Arg Val Val Ala Thr Lys Gln
165                     170                     175                     180
ggc aac gct gtg acc ctg gga gat tac tac cag ggc cgg agg att acc          691
Gly Asn Ala Val Thr Leu Gly Asp Tyr Tyr Gln Gly Arg Arg Ile Thr
                    185                     190                     195
atc acc gga aat gct gac ctg acc ttt gac cag acg gcg tgg ggg gac          739
Ile Thr Gly Asn Ala Asp Leu Thr Phe Asp Gln Thr Ala Trp Gly Asp
                200                     205                     210
agt ggt gtg tat tac tgc tcc gtg gtc tca gcc cag gac ctc cag ggg          787
Ser Gly Val Tyr Tyr Cys Ser Val Val Ser Ala Gln Asp Leu Gln Gly
            215                     220                     225
aac aat gag gcc tac gca gag ctc atc gtc ctt gtg tat gcc gcc ggc          835
Asn Asn Glu Ala Tyr Ala Glu Leu Ile Val Leu Val Tyr Ala Ala Gly
            230                     235                     240
aaa gca gcc acc tca ggt gtt ccc agc att tat gcc ccc agc acc tat          883
Lys Ala Ala Thr Ser Gly Val Pro Ser Ile Tyr Ala Pro Ser Thr Tyr
245                     250                     255                     260
gcc cac ctg tct ccc gcc aag acc cca ccc cca gct atg att ccc              931
Ala His Leu Ser Pro Ala Lys Thr Pro Pro Pro Ala Met Ile Pro
                    265                     270                     275
atg ggc cct gcc tac aac ggg tac cct gga gga tac cct gga gac gtt          979
Met Gly Pro Ala Tyr Asn Gly Tyr Pro Gly Gly Tyr Pro Gly Asp Val
                280                     285                     290
gac agg art agc tca gct ggt ggc caa ggc tcc tat gta ccc ctg ctt         1027
Asp Arg Xaa Ser Ser Ala Gly Gly Gln Gly Ser Tyr Val Pro Leu Leu
            295                     300                     305
cgg gac acg gac agc agt gtg gcc tct gaa gtc cgc agt ggc tac agg         1075
Arg Asp Thr Asp Ser Ser Val Ala Ser Glu Val Arg Ser Gly Tyr Arg
310                     315                     320
att cag gcc agc cag cag gac gac tcc atg cgg gtc ctg tac tac atg         1123
Ile Gln Ala Ser Gln Gln Asp Asp Ser Met Arg Val Leu Tyr Tyr Met
325                     330                     335                     340
gag aag gag ctg gcc aac ttc gac cct tct cga cst ggc ccc ccc agt         1171
Glu Lys Glu Leu Ala Asn Phe Asp Pro Ser Arg Xaa Gly Pro Pro Ser
                    345                     350                     355
ggc cgt gtg gag cgg gcc atg agt gaa gtc acc tcc ctc cac gag gac         1219
Gly Arg Val Glu Arg Ala Met Ser Glu Val Thr Ser Leu His Glu Asp
                360                     365                     370
gac tgg cga tct cgg cct tcc cgg ggc cct gcc ctc acc ccg atc cgg         1267
Asp Trp Arg Ser Arg Pro Ser Arg Gly Pro Ala Leu Thr Pro Ile Arg
        375                     380                     385
gat gag gag tgg ggt ggc cac tcc ccc cgg agt ccc agg gga tgg gac         1315
Asp Glu Glu Trp Gly Gly His Ser Pro Arg Ser Pro Arg Gly Trp Asp
390                     395                     400
cag gag ccc gcc agg gag cag gca ggc ggg tgg cgg gcc agg cgg             1363
```

```
Gln Glu Pro Ala Arg Glu Gln Ala Gly Gly Gly Trp Arg Ala Arg Arg
405                 410                 415                 420
ccc cgg gcc cgc tcc gtg gac gcc ctg gac gac ctc acc ccg ccg agc      1411
Pro Arg Ala Arg Ser Val Asp Ala Leu Asp Asp Leu Thr Pro Pro Ser
                425                 430                 435
acc gcc gag tca ggg agc agg tct ccc acg agt aat ggt ggg aga agc      1459
Thr Ala Glu Ser Gly Ser Arg Ser Pro Thr Ser Asn Gly Gly Arg Ser
                440                 445                 450
cgg gcc tac atg ccc ccg cgg agc cgc agc cgg gac gac ctc tat gac      1507
Arg Ala Tyr Met Pro Pro Arg Ser Arg Ser Arg Asp Asp Leu Tyr Asp
                455                 460                 465
caa gac gac tcg agg gac ttc cca cgc tcc cgg gac ccc cac tac gac      1555
Gln Asp Asp Ser Arg Asp Phe Pro Arg Ser Arg Asp Pro His Tyr Asp
                470                 475                 480
gac ttc agg tct cgg gag cgc cct cct gcc gac ccc agg tcc cac cac      1603
Asp Phe Arg Ser Arg Glu Arg Pro Pro Ala Asp Pro Arg Ser His His
485                 490                 495                 500
cac cgt acc cgg gac cct cgg gac aac ggc tcc agg tcc ggg gac ctc      1651
His Arg Thr Arg Asp Pro Arg Asp Asn Gly Ser Arg Ser Gly Asp Leu
                505                 510                 515
ccc tat gat ggg cgg cta ctg gag gag gct gtg agg aag aag ggg tcg      1699
Pro Tyr Asp Gly Arg Leu Leu Glu Glu Ala Val Arg Lys Lys Gly Ser
                520                 525                 530
gag gag agg agg aga ccc cac aag gag gag gag gaa gag gcc tac tac      1747
Glu Glu Arg Arg Arg Pro His Lys Glu Glu Glu Glu Glu Ala Tyr Tyr
                535                 540                 545
ccg ccc gcg ccg ccc ccg tac tcg gag acc gac tcg cag gcg tcc cga      1795
Pro Pro Ala Pro Pro Pro Tyr Ser Glu Thr Asp Ser Gln Ala Ser Arg
                550                 555                 560
gag cgc agg ctc aag aag aac ttg gcc ctg agt cgg gaa agt tta gtc      1843
Glu Arg Arg Leu Lys Lys Asn Leu Ala Leu Ser Arg Glu Ser Leu Val
565                 570                 575                 580
gtc tga tctgacgttt tctacgtagc ttttgkattt ttttttttaa tttgaaggaa       1899
Val *
cactgatgaa gccctgccat acccctcccg agtctaataa aacgtataat cacaa         1954

<210> 7
<211> 581
<212> PRT
<213> Homo sapiens

<220>
<221> VARIANT
<222> 295
<223> 9-7-325   :   polymorphic   amino   acid   Ser   or   Asn <220>
<221> VARIANT
<222> 352
<223> 9-9-246   :   polymorphic   amino   acid   Pro   or   Arg <220>
<221> VARIANT
<222> 451
<223> LSRX9f13-BM   :   polymorphic   amino   acid   deletion   of   Arg
<400> 7
Met Gln Gln Asp Gly Leu Gly Val Gly Thr Arg Asn Gly Ser Gly Lys
1               5                   10                  15
```

```
Gly Arg Ser Val His Pro Ser Trp Pro Trp Cys Ala Pro Arg Pro Leu
         20                  25                  30
Arg Tyr Phe Gly Arg Asp Ala Arg Ala Arg Arg Ala Gln Thr Ala Ala
         35                  40                  45
Met Ala Leu Leu Ala Gly Gly Leu Ser Arg Gly Leu Gly Ser His Pro
         50              55                  60
Ala Ala Ala Gly Arg Asp Ala Val Val Phe Val Trp Leu Leu Leu Ser
65               70                  75                      80
Thr Trp Cys Thr Ala Pro Ala Arg Ala Ile Gln Val Thr Val Ser Asn
                 85                  90                  95
Pro Tyr His Val Ile Leu Phe Gln Pro Val Thr Leu Pro Cys Thr
             100                 105             110
Tyr Gln Met Thr Ser Thr Pro Thr Gln Pro Ile Val Ile Trp Lys Tyr
             115                 120             125
Lys Ser Phe Cys Arg Asp Arg Ile Ala Asp Ala Phe Ser Pro Ala Ser
         130                 135             140
Val Asp Asn Gln Leu Asn Ala Gln Leu Ala Ala Gly Asn Pro Gly Tyr
145                 150                 155                 160
Asn Pro Tyr Val Glu Cys Gln Asp Ser Val Arg Thr Val Arg Val Val
                 165                 170                 175
Ala Thr Lys Gln Gly Asn Ala Val Thr Leu Gly Asp Tyr Tyr Gln Gly
             180                 185                 190
Arg Arg Ile Thr Ile Thr Gly Asn Ala Asp Leu Thr Phe Asp Gln Thr
         195                 200                 205
Ala Trp Gly Asp Ser Gly Val Tyr Tyr Cys Ser Val Val Ser Ala Gln
         210                 215                 220
Asp Leu Gln Gly Asn Asn Glu Ala Tyr Ala Glu Leu Ile Val Leu Val
225                 230                 235                 240
Tyr Ala Ala Gly Lys Ala Ala Thr Ser Gly Val Pro Ser Ile Tyr Ala
                 245                 250                 255
Pro Ser Thr Tyr Ala His Leu Ser Pro Ala Lys Thr Pro Pro Pro Pro
                 260                 265             270
Ala Met Ile Pro Met Gly Pro Ala Tyr Asn Gly Tyr Pro Gly Gly Tyr
         275                 280                 285
Pro Gly Asp Val Asp Arg Ser Ser Ser Ala Gly Gly Gln Gly Ser Tyr
     290                 295                 300
Val Pro Leu Leu Arg Asp Thr Asp Ser Ser Val Ala Ser Glu Val Arg
305                 310                 315                 320
Ser Gly Tyr Arg Ile Gln Ala Ser Gln Gln Asp Asp Ser Met Arg Val
                 325                 330                 335
Leu Tyr Tyr Met Glu Lys Glu Leu Ala Asn Phe Asp Pro Ser Arg Pro
             340                 345                 350
Gly Pro Pro Ser Gly Arg Val Glu Arg Ala Met Ser Glu Val Thr Ser
         355                 360                 365
Leu His Glu Asp Asp Trp Arg Ser Arg Pro Ser Arg Gly Pro Ala Leu
         370                 375                 380
Thr Pro Ile Arg Asp Glu Glu Trp Gly Gly His Ser Pro Arg Ser Pro
385                 390                 395                 400
Arg Gly Trp Asp Gln Glu Pro Ala Arg Glu Gln Ala Gly Gly Gly Trp
                 405                 410                 415
Arg Ala Arg Arg Pro Arg Ala Arg Ser Val Asp Ala Leu Asp Asp Leu
                 420                 425                 430
Thr Pro Pro Ser Thr Ala Glu Ser Gly Ser Arg Ser Pro Thr Ser Asn
         435                 440                 445
Gly Gly Arg Ser Arg Ala Tyr Met Pro Pro Arg Ser Arg Ser Arg Asp
         450                 455                 460
Asp Leu Tyr Asp Gln Asp Asp Ser Arg Asp Phe Pro Arg Ser Arg Asp
465                 470                 475                 480
Pro His Tyr Asp Asp Phe Arg Ser Arg Glu Arg Pro Pro Ala Asp Pro
```

```
                      485                 490                  495
Arg Ser His His His Arg Thr Arg Asp Pro Arg Asp Asn Gly Ser Arg
            500                 505                 510
Ser Gly Asp Leu Pro Tyr Asp Gly Arg Leu Leu Glu Glu Ala Val Arg
        515                 520                 525
Lys Lys Gly Ser Glu Glu Arg Arg Arg Pro His Lys Glu Glu Glu Glu
    530                 535                 540
Glu Ala Tyr Tyr Pro Pro Ala Pro Pro Pro Tyr Ser Glu Thr Asp Ser
545                 550                 555                 560
Gln Ala Ser Arg Glu Arg Arg Leu Lys Lys Asn Leu Ala Leu Ser Arg
                565                 570                 575
Glu Ser Leu Val Val
                580

<210> 8
<211> 2097
<212> DNA
<213> Rattus norvegicus

<400> 8
accgctcacc aggtcagttg tccccggaaa gccgaaggca tgagcttcgc ccaagttctt    60
tttatgggtt agaactcctc cagagcgggg gaaaaaggac ttggaatagg ggcgggacgg   120
agcacgcacc cttctccgcc ttggttctcg ccgcgccccc tactctcggg atacttggga   180
ggggacgcgc gggcaccgtc gctgctagac ggccgcg atg gcg ccg gcg gcc ggc   235
                                        Met Ala Pro Ala Ala Gly
                                          1                   5
gcg tgt gct ggg gcg cct gac tcc cac cca gct acc gtg gtc ttc gtg    283
Ala Cys Ala Gly Ala Pro Asp Ser His Pro Ala Thr Val Val Phe Val
                10                  15                  20
tgt ctc ttt ctc atc att ttc tgc cca gac cct gcc agt gcc atc cag    331
Cys Leu Phe Leu Ile Ile Phe Cys Pro Asp Pro Ala Ser Ala Ile Gln
            25                  30                  35
gtg act gtg tct gac ccc tac cac gta gtg atc ctg ttc cag cca gtg    379
Val Thr Val Ser Asp Pro Tyr His Val Val Ile Leu Phe Gln Pro Val
    40                  45                  50
acc ctg ccc tgc acc tat cag atg agc aac act ctc aca gtc ccc atc    427
Thr Leu Pro Cys Thr Tyr Gln Met Ser Asn Thr Leu Thr Val Pro Ile
55                  60                  65                  70
gtg atc tgg aag tac aag tca ttc tgc cgg gac cgt att gcc gat gcc    475
Val Ile Trp Lys Tyr Lys Ser Phe Cys Arg Asp Arg Ile Ala Asp Ala
                75                  80                  85
ttc tct cct gcc agt gtg gac aac cag cta aat gcc cag ttg gca gct    523
Phe Ser Pro Ala Ser Val Asp Asn Gln Leu Asn Ala Gln Leu Ala Ala
            90                  95                  100
ggc aac ccc ggc tac aac ccc tat gtg gag tgc cag gac agt gta cgc    571
Gly Asn Pro Gly Tyr Asn Pro Tyr Val Glu Cys Gln Asp Ser Val Arg
    105                 110                 115
act gtc agg gtg gtg gcc acc aaa cag ggc aat gcg gtg acc ctg gga    619
Thr Val Arg Val Val Ala Thr Lys Gln Gly Asn Ala Val Thr Leu Gly
    120                 125                 130
gac tac tac caa ggc agg agg atc acc ata aca gga aat gct gac ctg    667
Asp Tyr Tyr Gln Gly Arg Arg Ile Thr Ile Thr Gly Asn Ala Asp Leu
135                 140                 145                 150
acc ttc gag cag aca gcc tgg gga gac agt gga gtg tat tac tgc tct    715
Thr Phe Glu Gln Thr Ala Trp Gly Asp Ser Gly Val Tyr Tyr Cys Ser
                155                 160                 165
gtg gtc tcg gcc caa gat ctg gat gga aac aac gag gcg tac gca gag    763
Val Val Ser Ala Gln Asp Leu Asp Gly Asn Asn Glu Ala Tyr Ala Glu
            170                 175                 180
```

```
ctc atc gtc ctt ggc agg acc tca gag gcc cct gag ctc cta cct ggt       811
Leu Ile Val Leu Gly Arg Thr Ser Glu Ala Pro Glu Leu Leu Pro Gly
        185                 190                 195
ttt cgg gcg ggg ccc ttg gaa gat tgg ctc ttt gtg gtc gtg gtc tgc       859
Phe Arg Ala Gly Pro Leu Glu Asp Trp Leu Phe Val Val Val Val Cys
    200                 205                 210
ctg gcg agc ctc ctc ctc ttc ctc ctc ctg ggc atc tgc tgg tgc cag       907
Leu Ala Ser Leu Leu Leu Phe Leu Leu Leu Gly Ile Cys Trp Cys Gln
215                 220                 225                 230
tgc tgt cct cac acc tgc tgc tgc tat gtc cga tgt ccc tgc tgc cca       955
Cys Cys Pro His Thr Cys Cys Cys Tyr Val Arg Cys Pro Cys Cys Pro
                235                 240                 245
gac aag tgc tgt tgc cct gag gct ctt tat gct gct ggc aaa gca gcc      1003
Asp Lys Cys Cys Cys Pro Glu Ala Leu Tyr Ala Ala Gly Lys Ala Ala
            250                 255                 260
acc tca ggt gtc ccg agc atc tat gcc ccc agc atc tat acc cac ctc      1051
Thr Ser Gly Val Pro Ser Ile Tyr Ala Pro Ser Ile Tyr Thr His Leu
        265                 270                 275
tca cct gcc aag acc cca cca cct ccg cct gcc atg att ccc atg ggc      1099
Ser Pro Ala Lys Thr Pro Pro Pro Pro Ala Met Ile Pro Met Gly
280                 285                 290
cct ccc tat ggg tac cct gga gac ttt gac aga cat agc tca gtt ggt      1147
Pro Pro Tyr Gly Tyr Pro Gly Asp Phe Asp Arg His Ser Ser Val Gly
295                 300                 305                 310
ggc cac agc tcc caa gta ccc ctg ctg cgt gac gtg gat ggc agt gta      1195
Gly His Ser Ser Gln Val Pro Leu Leu Arg Asp Val Asp Gly Ser Val
                315                 320                 325
tct tca gaa gta cga agt ggc tac agg atc cag gct aac cag caa gat      1243
Ser Ser Glu Val Arg Ser Gly Tyr Arg Ile Gln Ala Asn Gln Gln Asp
            330                 335                 340
gac tcc atg agg gtc cta tac tat atg gag aaa gag cta gcc aac ttt      1291
Asp Ser Met Arg Val Leu Tyr Tyr Met Glu Lys Glu Leu Ala Asn Phe
        345                 350                 355
gac cct tcc cga cct ggc cct ccc aat ggc aga gtg gaa cgg gcc atg      1339
Asp Pro Ser Arg Pro Gly Pro Pro Asn Gly Arg Val Glu Arg Ala Met
    360                 365                 370
agt gaa gta acc tcc ctc cat gaa gat gac tgg cga tcg agg cct tcc      1387
Ser Glu Val Thr Ser Leu His Glu Asp Asp Trp Arg Ser Arg Pro Ser
375                 380                 385                 390
agg gct cct gcc ctc acc ccc atc agg gat gag gag tgg aat cgc cac      1435
Arg Ala Pro Ala Leu Thr Pro Ile Arg Asp Glu Glu Trp Asn Arg His
                395                 400                 405
tcc cca cag agt ccc aga aca tgg gag cag gaa ccc ctt caa gaa caa      1483
Ser Pro Gln Ser Pro Arg Thr Trp Glu Gln Glu Pro Leu Gln Glu Gln
            410                 415                 420
cca agg ggt ggt tgg ggg tct gga cgc cct cgg gcc cgc tct gtg gat      1531
Pro Arg Gly Gly Trp Gly Ser Gly Arg Pro Arg Ala Arg Ser Val Asp
        425                 430                 435
gct cta gat gat atc aac cgg cct ggc tcc act gaa tca gga cgg tct      1579
Ala Leu Asp Asp Ile Asn Arg Pro Gly Ser Thr Glu Ser Gly Arg Ser
    440                 445                 450
tct ccc cca agt agt gga cgg aga gga cgg gcc tat gca cct cca aga      1627
Ser Pro Pro Ser Ser Gly Arg Arg Gly Arg Ala Tyr Ala Pro Pro Arg
455                 460                 465                 470
agt cgc agc cgg gat gac ctc tat gac ccg gac gat cct agg gac ttg      1675
Ser Arg Ser Arg Asp Asp Leu Tyr Asp Pro Asp Asp Pro Arg Asp Leu
                475                 480                 485
cca cat tcc cga gat ccc cac tat tat gac gac atc agg tct aga gat      1723
Pro His Ser Arg Asp Pro His Tyr Tyr Asp Asp Ile Arg Ser Arg Asp
```

```
                  490                   495                   500
cca cgt gct gac ccc aga tcc cgt cag cga tcc cga gat cct cgg gat    1771
Pro Arg Ala Asp Pro Arg Ser Arg Gln Arg Ser Arg Asp Pro Arg Asp
            505                   510                   515
gct ggc ttc agg tca agg gac cct cag tat gat ggg cga cta tta gaa    1819
Ala Gly Phe Arg Ser Arg Asp Pro Gln Tyr Asp Gly Arg Leu Leu Glu
        520                   525                   530
gag gct tta aag aaa aag ggg tcg ggc gag aga agg agg gtt tac agg    1867
Glu Ala Leu Lys Lys Lys Gly Ser Gly Glu Arg Arg Arg Val Tyr Arg
535                   540                   545                   550
gag gaa gaa gag gaa gag gag ggc caa tac ccc cca gca cct cca cct    1915
Glu Glu Glu Glu Glu Glu Glu Gly Gln Tyr Pro Pro Ala Pro Pro Pro
                555                   560                   565
tac tca gag act gac tcg cag gcc tca cgg gag agg agg ctg aaa aag    1963
Tyr Ser Glu Thr Asp Ser Gln Ala Ser Arg Glu Arg Arg Leu Lys Lys
            570                   575                   580
aat ttg gcc ctg agt cgg gaa agt tta gtc gtc tga tccacgtttt         2009
Asn Leu Ala Leu Ser Arg Glu Ser Leu Val Val *
        585                   590
gtatgtagct tttgtacttt ttttttaatt ggaatcaata ttgatgaaac ttcaagccta  2069
ataaaatgtc taatcacaaa aaaaaaaa                                     2097

<210> 9
<211> 593
<212> PRT
<213> Rattus norvegicus

<400> 9
Met Ala Pro Ala Ala Gly Ala Cys Ala Gly Ala Pro Asp Ser His Pro
1               5                   10                  15
Ala Thr Val Val Phe Val Cys Leu Phe Leu Ile Ile Phe Cys Pro Asp
                20                  25                  30
Pro Ala Ser Ala Ile Gln Val Thr Val Ser Asp Pro Tyr His Val Val
            35                  40                  45
Ile Leu Phe Gln Pro Val Thr Leu Pro Cys Thr Tyr Gln Met Ser Asn
        50                  55                  60
Thr Leu Thr Val Pro Ile Val Ile Trp Lys Tyr Lys Ser Phe Cys Arg
65                  70                  75                  80
Asp Arg Ile Ala Asp Ala Phe Ser Pro Ala Ser Val Asp Asn Gln Leu
                85                  90                  95
Asn Ala Gln Leu Ala Ala Gly Asn Pro Gly Tyr Asn Pro Tyr Val Glu
            100                 105                 110
Cys Gln Asp Ser Val Arg Thr Val Arg Val Val Ala Thr Lys Gln Gly
        115                 120                 125
Asn Ala Val Thr Leu Gly Asp Tyr Tyr Gln Gly Arg Arg Ile Thr Ile
    130                 135                 140
Thr Gly Asn Ala Asp Leu Thr Phe Glu Gln Thr Ala Trp Gly Asp Ser
145                 150                 155                 160
Gly Val Tyr Tyr Cys Ser Val Val Ser Ala Gln Asp Leu Asp Gly Asn
                165                 170                 175
Asn Glu Ala Tyr Ala Glu Leu Ile Val Leu Gly Arg Thr Ser Glu Ala
            180                 185                 190
Pro Glu Leu Leu Pro Gly Phe Arg Ala Gly Pro Leu Glu Asp Trp Leu
        195                 200                 205
Phe Val Val Val Val Cys Leu Ala Ser Leu Leu Leu Phe Leu Leu Leu
    210                 215                 220
Gly Ile Cys Trp Cys Gln Cys Cys Pro His Thr Cys Cys Cys Tyr Val
225                 230                 235                 240
Arg Cys Pro Cys Cys Pro Asp Lys Cys Cys Cys Pro Glu Ala Leu Tyr
```

|  |  |  | 245 |  |  |  |  | 250 |  |  |  | 255 |  |  |
|---|---|---|---|---|---|---|---|---|---|---|---|---|---|---|
| Ala | Ala | Gly | Lys | Ala | Ala | Thr | Ser | Gly | Val | Pro | Ser | Ile | Tyr | Ala | Pro |
|  |  |  | 260 |  |  |  |  | 265 |  |  |  | 270 |  |  |
| Ser | Ile | Tyr | Thr | His | Leu | Ser | Pro | Ala | Lys | Thr | Pro | Pro | Pro | Pro | Pro |
|  |  |  | 275 |  |  |  |  | 280 |  |  |  | 285 |  |  |
| Ala | Met | Ile | Pro | Met | Gly | Pro | Pro | Tyr | Gly | Tyr | Pro | Gly | Asp | Phe | Asp |
|  |  |  | 290 |  |  |  |  | 295 |  |  |  | 300 |  |  |
| Arg | His | Ser | Ser | Val | Gly | Gly | His | Ser | Ser | Gln | Val | Pro | Leu | Leu | Arg |
| 305 |  |  |  |  | 310 |  |  |  |  | 315 |  |  |  |  | 320 |
| Asp | Val | Asp | Gly | Ser | Val | Ser | Ser | Glu | Val | Arg | Ser | Gly | Tyr | Arg | Ile |
|  |  |  |  | 325 |  |  |  |  | 330 |  |  |  |  | 335 |  |
| Gln | Ala | Asn | Gln | Gln | Asp | Asp | Ser | Met | Arg | Val | Leu | Tyr | Tyr | Met | Glu |
|  |  |  | 340 |  |  |  |  | 345 |  |  |  | 350 |  |  |
| Lys | Glu | Leu | Ala | Asn | Phe | Asp | Pro | Ser | Arg | Pro | Gly | Pro | Pro | Asn | Gly |
|  |  |  | 355 |  |  |  |  | 360 |  |  |  | 365 |  |  |
| Arg | Val | Glu | Arg | Ala | Met | Ser | Glu | Val | Thr | Ser | Leu | His | Glu | Asp | Asp |
|  |  |  | 370 |  |  |  |  | 375 |  |  |  | 380 |  |  |
| Trp | Arg | Ser | Arg | Pro | Ser | Arg | Ala | Pro | Ala | Leu | Thr | Pro | Ile | Arg | Asp |
| 385 |  |  |  |  | 390 |  |  |  |  | 395 |  |  |  |  | 400 |
| Glu | Glu | Trp | Asn | Arg | His | Ser | Pro | Gln | Ser | Pro | Arg | Thr | Trp | Glu | Gln |
|  |  |  |  | 405 |  |  |  |  | 410 |  |  |  |  | 415 |  |
| Glu | Pro | Leu | Gln | Glu | Gln | Pro | Arg | Gly | Gly | Trp | Gly | Ser | Gly | Arg | Pro |
|  |  |  | 420 |  |  |  |  | 425 |  |  |  | 430 |  |  |
| Arg | Ala | Arg | Ser | Val | Asp | Ala | Leu | Asp | Asp | Ile | Asn | Arg | Pro | Gly | Ser |
|  |  |  | 435 |  |  |  |  | 440 |  |  |  | 445 |  |  |
| Thr | Glu | Ser | Gly | Arg | Ser | Ser | Pro | Pro | Ser | Ser | Gly | Arg | Arg | Gly | Arg |
|  |  |  | 450 |  |  |  |  | 455 |  |  |  | 460 |  |  |
| Ala | Tyr | Ala | Pro | Pro | Arg | Ser | Arg | Ser | Arg | Asp | Asp | Leu | Tyr | Asp | Pro |
| 465 |  |  |  |  | 470 |  |  |  |  | 475 |  |  |  |  | 480 |
| Asp | Asp | Pro | Arg | Asp | Leu | Pro | His | Ser | Arg | Asp | Pro | His | Tyr | Tyr | Asp |
|  |  |  |  | 485 |  |  |  |  | 490 |  |  |  |  | 495 |  |
| Asp | Ile | Arg | Ser | Arg | Asp | Pro | Arg | Ala | Asp | Pro | Arg | Ser | Arg | Gln | Arg |
|  |  |  |  | 500 |  |  |  |  | 505 |  |  |  |  | 510 |  |
| Ser | Arg | Asp | Pro | Arg | Asp | Ala | Gly | Phe | Arg | Ser | Arg | Asp | Pro | Gln | Tyr |
|  |  |  |  | 515 |  |  |  |  | 520 |  |  |  |  | 525 |  |
| Asp | Gly | Arg | Leu | Leu | Glu | Glu | Ala | Leu | Lys | Lys | Lys | Gly | Ser | Gly | Glu |
|  |  |  | 530 |  |  |  |  | 535 |  |  |  | 540 |  |  |
| Arg | Arg | Arg | Val | Tyr | Arg | Glu | Glu | Glu | Glu | Glu | Glu | Gly | Gln | Tyr |  |
| 545 |  |  |  |  | 550 |  |  |  |  | 555 |  |  |  |  | 560 |
| Pro | Pro | Ala | Pro | Pro | Pro | Tyr | Ser | Glu | Thr | Asp | Ser | Gln | Ala | Ser | Arg |
|  |  |  |  | 565 |  |  |  |  | 570 |  |  |  |  | 575 |  |
| Glu | Arg | Arg | Leu | Lys | Lys | Asn | Leu | Ala | Leu | Ser | Arg | Glu | Ser | Leu | Val |
|  |  |  | 580 |  |  |  |  | 585 |  |  |  | 590 |  |  |
| Val |  |  |  |  |  |  |  |  |  |  |  |  |  |  |  |

```
<210> 10
<211> 2040
<212> DNA
<213> Rattus norvegicus

<400> 10
accgctcacc aggtcagttg tccccggaaa gccgaaggca tgagcttcgc ccaagttctt     60
tttatggqtt agaactcctc cagagcgggg gaaaaaggac ttggaatagg ggcgggacgg    120
agcacgcacc cttctccgcc ttggttctcg ccgcgccccc tactctcggg atacttggga    180
gggacgcgc gggcaccgtc gctgctagac ggccgcg atg gcg ccg gcg gcc ggc     235
                                            Met Ala Pro Ala Ala Gly
                                              1               5
gcg tgt gct ggg gcg cct gac tcc cac cca gct acc gtg gtc ttc gtg     283
Ala Cys Ala Gly Ala Pro Asp Ser His Pro Ala Thr Val Val Phe Val
```

```
                    10                      15                      20
tgt ctc ttt ctc atc att ttc tgc cca gac cct gcc agt gcc atc cag      331
Cys Leu Phe Leu Ile Ile Phe Cys Pro Asp Pro Ala Ser Ala Ile Gln
            25                      30                      35
gtg act gtg tct gac ccc tac cac gta gtg atc ctg ttc cag cca gtg      379
Val Thr Val Ser Asp Pro Tyr His Val Val Ile Leu Phe Gln Pro Val
        40                      45                      50
acc ctg ccc tgc acc tat cag atg agc aac act ctc aca gtc ccc atc      427
Thr Leu Pro Cys Thr Tyr Gln Met Ser Asn Thr Leu Thr Val Pro Ile
55                      60                      65                  70
gtg atc tgg aag tac aag tca ttc tgc cgg gac cgt att gcc gat gcc      475
Val Ile Trp Lys Tyr Lys Ser Phe Cys Arg Asp Arg Ile Ala Asp Ala
                75                      80                      85
ttc tct cct gcc agt gtg gac aac cag cta aat gcc cag ttg gca gct      523
Phe Ser Pro Ala Ser Val Asp Asn Gln Leu Asn Ala Gln Leu Ala Ala
            90                      95                      100
ggc aac ccc ggc tac aac ccc tat gtg gag tgc cag gac agt gta cgc      571
Gly Asn Pro Gly Tyr Asn Pro Tyr Val Glu Cys Gln Asp Ser Val Arg
        105                     110                     115
act gtc agg gtg gtg gcc acc aaa cag ggc aat gcg gtg acc ctg gga      619
Thr Val Arg Val Val Ala Thr Lys Gln Gly Asn Ala Val Thr Leu Gly
    120                     125                     130
gac tac tac caa ggc agg agg atc acc ata aca gga aat gct gac ctg      667
Asp Tyr Tyr Gln Gly Arg Arg Ile Thr Ile Thr Gly Asn Ala Asp Leu
135                     140                     145                 150
acc ttc gag cag aca gcc tgg gga gac agt gga gtg tat tac tgc tct      715
Thr Phe Glu Gln Thr Ala Trp Gly Asp Ser Gly Val Tyr Tyr Cys Ser
                155                     160                     165
gtg gtc tcg gcc caa gat ctg gat gga aac aac gag gcg tac gca gag      763
Val Val Ser Ala Gln Asp Leu Asp Gly Asn Asn Glu Ala Tyr Ala Glu
            170                     175                     180
ctc atc gtc ctt gat tgg ctc ttt gtg gtc gtg gtc tgc ctg gcg agc      811
Leu Ile Val Leu Asp Trp Leu Phe Val Val Val Val Cys Leu Ala Ser
        185                     190                     195
ctc ctc ctc ttc ctc ctg ggc atc tgc tgg tgc cag tgc tgt cct          859
Leu Leu Leu Phe Leu Leu Leu Gly Ile Cys Trp Cys Gln Cys Cys Pro
    200                     205                     210
cac acc tgc tgc tgc tat gtc cga tgt ccc tgc tgc cca gac aag tgc      907
His Thr Cys Cys Cys Tyr Val Arg Cys Pro Cys Cys Pro Asp Lys Cys
215                     220                     225                 230
tgt tgc cct gag gct ctt tat gct gct ggc aaa gca gcc acc tca ggt      955
Cys Cys Pro Glu Ala Leu Tyr Ala Ala Gly Lys Ala Ala Thr Ser Gly
                235                     240                     245
gtc ccg agc atc tat gcc ccc agc atc tat acc cac ctc tca cct gcc     1003
Val Pro Ser Ile Tyr Ala Pro Ser Ile Tyr Thr His Leu Ser Pro Ala
            250                     255                     260
aag acc cca cca cct ccg cct gcc atg att ccc atg ggc cct ccc tat     1051
Lys Thr Pro Pro Pro Pro Pro Ala Met Ile Pro Met Gly Pro Pro Tyr
        265                     270                     275
ggg tac cct gga gac ttt gac aga cat agc tca gtt ggt ggc cac agc     1099
Gly Tyr Pro Gly Asp Phe Asp Arg His Ser Ser Val Gly Gly His Ser
    280                     285                     290
tcc caa gta ccc ctg ctg cgt gac gtg gat ggc agt gta tct tca gaa     1147
Ser Gln Val Pro Leu Leu Arg Asp Val Asp Gly Ser Val Ser Ser Glu
295                     300                     305                 310
gta cga agt ggc tac agg atc cag gct aac cag caa gat gac tcc atg     1195
Val Arg Ser Gly Tyr Arg Ile Gln Ala Asn Gln Gln Asp Asp Ser Met
                315                     320                     325
agg gtc cta tac tat atg gag aaa gag cta gcc aac ttt gac cct tcc     1243
```

```
Arg Val Leu Tyr Tyr Met Glu Lys Glu Leu Ala Asn Phe Asp Pro Ser
            330                 335                 340
cga cct ggc cct ccc aat ggc aga gtg gaa cgg gcc atg agt gaa gta      1291
Arg Pro Gly Pro Pro Asn Gly Arg Val Glu Arg Ala Met Ser Glu Val
            345                 350                 355
acc tcc ctc cat gaa gat gac tgg cga tcg agg cct tcc agg gct cct      1339
Thr Ser Leu His Glu Asp Asp Trp Arg Ser Arg Pro Ser Arg Ala Pro
    360                 365                 370
gcc ctc acc ccc atc agg gat gag gag tgg aat cgc cac tcc cca cag      1387
Ala Leu Thr Pro Ile Arg Asp Glu Glu Trp Asn Arg His Ser Pro Gln
375                 380                 385                 390
agt ccc aga aca tgg gag cag gaa ccc ctt caa gaa caa cca agg ggt      1435
Ser Pro Arg Thr Trp Glu Gln Glu Pro Leu Gln Glu Gln Pro Arg Gly
            395                 400                 405
ggt tgg ggg tct gga cgc cct cgg gcc cgc tct gtg gat gct cta gat      1483
Gly Trp Gly Ser Gly Arg Pro Arg Ala Arg Ser Val Asp Ala Leu Asp
            410                 415                 420
gat atc aac cgg cct ggc tcc act gaa tca gga cgg tct tct ccc cca      1531
Asp Ile Asn Arg Pro Gly Ser Thr Glu Ser Gly Arg Ser Ser Pro Pro
            425                 430                 435
agt agt gga cgg aga gga cgg gcc tat gca cct cca aga agt cgc agc      1579
Ser Ser Gly Arg Arg Gly Arg Ala Tyr Ala Pro Pro Arg Ser Arg Ser
    440                 445                 450
cgg gat gac ctc tat gac ccg gac gat cct agg gac ttg cca cat tcc      1627
Arg Asp Asp Leu Tyr Asp Pro Asp Asp Pro Arg Asp Leu Pro His Ser
455                 460                 465                 470
cga gat ccc cac tat tat gac gac atc agg tct aga gat cca cgt gct      1675
Arg Asp Pro His Tyr Tyr Asp Asp Ile Arg Ser Arg Asp Pro Arg Ala
            475                 480                 485
gac ccc aga tcc cgt cag cga tcc cga gat cct cgg gat gct ggc ttc      1723
Asp Pro Arg Ser Arg Gln Arg Ser Arg Asp Pro Arg Asp Ala Gly Phe
            490                 495                 500
agg tca agg gac cct cag tat gat ggg cga cta tta gaa gag gct tta      1771
Arg Ser Arg Asp Pro Gln Tyr Asp Gly Arg Leu Leu Glu Glu Ala Leu
            505                 510                 515
aag aaa aag ggg tcg ggc gag aga agg agg gtt tac agg gag gaa gaa      1819
Lys Lys Lys Gly Ser Gly Glu Arg Arg Arg Val Tyr Arg Glu Glu Glu
    520                 525                 530
gag gaa gag gag ggc caa tac ccc cca gca cct cca cct tac tca gag      1867
Glu Glu Glu Glu Gly Gln Tyr Pro Pro Ala Pro Pro Pro Tyr Ser Glu
535                 540                 545                 550
act gac tcg cag gcc tca cgg gag agg agg ctg aaa aag aat ttg gcc      1915
Thr Asp Ser Gln Ala Ser Arg Glu Arg Arg Leu Lys Lys Asn Leu Ala
            555                 560                 565
ctg agc cgg gaa agt tta gtc gtc tga tccacgtttt gtatgtagct            1962
Leu Ser Arg Glu Ser Leu Val Val  *
            570                 575
tttgtacttt tttttttaatt ggaatcaata ttgatgaaac ttcaagccta ataaaatgtc   2022
taatcacaaa aaaaaaaa                                                  2040

<210> 11
<211> 574
<212> PRT
<213> Rattus norvegicus

<400> 11
Met Ala Pro Ala Ala Gly Ala Cys Ala Gly Ala Pro Asp Ser His Pro
1               5                   10                  15
Ala Thr Val Val Phe Val Cys Leu Phe Leu Ile Ile Phe Cys Pro Asp
```

```
                    20                      25                      30
Pro Ala Ser Ala Ile Gln Val Thr Val Ser Asp Pro Tyr His Val Val
        35                      40                      45
Ile Leu Phe Gln Pro Val Thr Leu Pro Cys Thr Tyr Gln Met Ser Asn
    50                      55                      60
Thr Leu Thr Val Pro Ile Val Ile Trp Lys Tyr Lys Ser Phe Cys Arg
65                      70                      75                  80
Asp Arg Ile Ala Asp Ala Phe Ser Pro Ala Ser Val Asp Asn Gln Leu
                85                      90                      95
Asn Ala Gln Leu Ala Ala Gly Asn Pro Gly Tyr Asn Pro Tyr Val Glu
                100                     105                     110
Cys Gln Asp Ser Val Arg Thr Val Arg Val Val Ala Thr Lys Gln Gly
            115                     120                     125
Asn Ala Val Thr Leu Gly Asp Tyr Tyr Gln Gly Arg Arg Ile Thr Ile
        130                     135                     140
Thr Gly Asn Ala Asp Leu Thr Phe Glu Gln Thr Ala Trp Gly Asp Ser
145                     150                     155                 160
Gly Val Tyr Tyr Cys Ser Val Val Ser Ala Gln Asp Leu Asp Gly Asn
                165                     170                     175
Asn Glu Ala Tyr Ala Glu Leu Ile Val Leu Asp Trp Leu Phe Val Val
                180                     185                     190
Val Val Cys Leu Ala Ser Leu Leu Leu Phe Leu Leu Leu Gly Ile Cys
            195                     200                     205
Trp Cys Gln Cys Cys Pro His Thr Cys Cys Cys Tyr Val Arg Cys Pro
        210                     215                     220
Cys Cys Pro Asp Lys Cys Cys Cys Pro Glu Ala Leu Tyr Ala Ala Gly
225                     230                     235                 240
Lys Ala Ala Thr Ser Gly Val Pro Ser Ile Tyr Ala Pro Ser Ile Tyr
                245                     250                     255
Thr His Leu Ser Pro Ala Lys Thr Pro Pro Pro Pro Ala Met Ile
                260                     265                     270
Pro Met Gly Pro Pro Tyr Gly Tyr Pro Gly Asp Phe Asp Arg His Ser
        275                     280                     285
Ser Val Gly Gly His Ser Ser Gln Val Pro Leu Leu Arg Asp Val Asp
        290                     295                     300
Gly Ser Val Ser Ser Glu Val Arg Ser Gly Tyr Arg Ile Gln Ala Asn
305                     310                     315                 320
Gln Gln Asp Asp Ser Met Arg Val Leu Tyr Tyr Met Glu Lys Glu Leu
                325                     330                     335
Ala Asn Phe Asp Pro Ser Arg Pro Gly Pro Pro Asn Gly Arg Val Glu
                340                     345                     350
Arg Ala Met Ser Glu Val Thr Ser Leu His Glu Asp Asp Trp Arg Ser
            355                     360                     365
Arg Pro Ser Arg Ala Pro Ala Leu Thr Pro Ile Arg Asp Glu Glu Trp
        370                     375                     380
Asn Arg His Ser Pro Gln Ser Pro Arg Thr Trp Glu Gln Glu Pro Leu
385                     390                     395                 400
Gln Glu Gln Pro Arg Gly Gly Trp Gly Ser Gly Arg Pro Arg Ala Arg
                405                     410                     415
Ser Val Asp Ala Leu Asp Asp Ile Asn Arg Pro Gly Ser Thr Glu Ser
                420                     425                     430
Gly Arg Ser Ser Pro Pro Ser Ser Gly Arg Arg Gly Arg Ala Tyr Ala
            435                     440                     445
Pro Pro Arg Ser Arg Ser Arg Asp Asp Leu Tyr Asp Pro Asp Asp Pro
        450                     455                     460
Arg Asp Leu Pro His Ser Arg Asp Pro His Tyr Tyr Asp Asp Ile Arg
465                     470                     475                 480
Ser Arg Asp Pro Arg Ala Asp Pro Arg Ser Arg Gln Arg Ser Arg Asp
                485                     490                     495
```

```
Pro Arg Asp Ala Gly Phe Arg Ser Arg Asp Pro Gln Tyr Asp Gly Arg
            500                     505                 510
Leu Leu Glu Glu Ala Leu Lys Lys Lys Gly Ser Gly Glu Arg Arg Arg
        515                 520                 525
Val Tyr Arg Glu Glu Glu Glu Glu Glu Gly Gln Tyr Pro Pro Ala
    530                 535                 540
Pro Pro Pro Tyr Ser Glu Thr Asp Ser Gln Ala Ser Arg Glu Arg Arg
545                 550                 555                 560
Leu Lys Lys Asn Leu Ala Leu Ser Arg Glu Ser Leu Val Val
                565                 570
```

<210> 12
<211> 1893
<212> DNA
<213> Rattus norvegicus

<400> 12

```
accgctcacc aggtcagttg tccccggaaa gccgaaggca tgagcttcgc ccaagttctt     60
tttatgggtt agaactcctc cagagcgggg gaaaaaggac ttggaatagg ggcgggacgg    120
agcacgcacc cttctccgcc ttggttctcg ccgcgccccc tactctcggg atacttggga    180
ggggacgcgc gggcaccgtc gctgctagac ggccgcg atg gcg ccg gcg gcc ggc    235
                                          Met Ala Pro Ala Ala Gly
                                            1               5
gcg tgt gct ggg gcg cct gac tcc cac cca gct acc gtg gtc ttc gtg    283
Ala Cys Ala Gly Ala Pro Asp Ser His Pro Ala Thr Val Val Phe Val
             10                  15                  20
tgt ctc ttt ctc atc att ttc tgc cca gac cct gcc agt gcc atc cag    331
Cys Leu Phe Leu Ile Ile Phe Cys Pro Asp Pro Ala Ser Ala Ile Gln
         25                  30                  35
gtg act gtg tct gac ccc tac cac gta gtg atc ctg ttc cag cca gtg    379
Val Thr Val Ser Asp Pro Tyr His Val Val Ile Leu Phe Gln Pro Val
     40                  45                  50
acc ctg ccc tgc acc tat cag atg agc aac act ctc aca gtc ccc atc    427
Thr Leu Pro Cys Thr Tyr Gln Met Ser Asn Thr Leu Thr Val Pro Ile
55                  60                  65                  70
gtg atc tgg aag tac aag tca ttc tgc cgg gac cgt att gcc gat gcc    475
Val Ile Trp Lys Tyr Lys Ser Phe Cys Arg Asp Arg Ile Ala Asp Ala
                 75                  80                  85
ttc tct cct gcc agt gtg gac aac cag cta aat gcc cag ttg gca gct    523
Phe Ser Pro Ala Ser Val Asp Asn Gln Leu Asn Ala Gln Leu Ala Ala
             90                  95                 100
ggc aac ccc ggc tac aac ccc tat gtg gag tgc cag gac agt gta cgc    571
Gly Asn Pro Gly Tyr Asn Pro Tyr Val Glu Cys Gln Asp Ser Val Arg
        105                 110                 115
act gtc agg gtg gtg gcc acc aaa cag ggc aat gcg gtg acc ctg gga    619
Thr Val Arg Val Val Ala Thr Lys Gln Gly Asn Ala Val Thr Leu Gly
    120                 125                 130
gac tac tac caa ggc agg agg atc acc ata aca gga aat gct gac ctg    667
Asp Tyr Tyr Gln Gly Arg Arg Ile Thr Ile Thr Gly Asn Ala Asp Leu
135                 140                 145                 150
acc ttc gag cag aca gcc tgg gga gac agt gga gtg tat tac tgc tct    715
Thr Phe Glu Gln Thr Ala Trp Gly Asp Ser Gly Val Tyr Tyr Cys Ser
                155                 160                 165
gtg gtc tcg gcc caa gat ctg gat gga aac aac gag gcg tac gca gag    763
Val Val Ser Ala Gln Asp Leu Asp Gly Asn Asn Glu Ala Tyr Ala Glu
            170                 175                 180
ctc atc gtc ctt gtt tat gct gct ggc aaa gca gcc acc tca ggt gtc    811
Leu Ile Val Leu Val Tyr Ala Ala Gly Lys Ala Ala Thr Ser Gly Val
        185                 190                 195
```

```
ccg agc atc tat gcc ccc agc atc tat acc cac ctc tca cct gcc aag        859
Pro Ser Ile Tyr Ala Pro Ser Ile Tyr Thr His Leu Ser Pro Ala Lys
200                 205                 210
acc cca cca cct ccg cct gcc atg att ccc atg ggc cct ccc tat ggg        907
Thr Pro Pro Pro Pro Ala Met Ile Pro Met Gly Pro Pro Tyr Gly
215                 220                 225                 230
tac cct gga gac ttt gac aga cat agc tca gtt ggt ggc cac agc tcc        955
Tyr Pro Gly Asp Phe Asp Arg His Ser Ser Val Gly Gly His Ser Ser
                235                 240                 245
caa gta ccc ctg ctg cgt gac gtg gat ggc agt gta tct tca gaa gta       1003
Gln Val Pro Leu Leu Arg Asp Val Asp Gly Ser Val Ser Ser Glu Val
            250                 255                 260
cga agt ggc tac agg atc cag gct aac cag caa gat gac tcc atg agg       1051
Arg Ser Gly Tyr Arg Ile Gln Ala Asn Gln Gln Asp Asp Ser Met Arg
        265                 270                 275
gtc cta tac tat atg gag aaa gag cta gcc aac ttt gac cct tcc cga       1099
Val Leu Tyr Tyr Met Glu Lys Glu Leu Ala Asn Phe Asp Pro Ser Arg
    280                 285                 290
cct ggc cct ccc aat ggc aga gtg gaa cgg gcc atg agt gaa gta acc       1147
Pro Gly Pro Pro Asn Gly Arg Val Glu Arg Ala Met Ser Glu Val Thr
295                 300                 305                 310
tcc ctc cat gaa gat gac tgg cga tcg agg cct tcc agg gct cct gcc       1195
Ser Leu His Glu Asp Asp Trp Arg Ser Arg Pro Ser Arg Ala Pro Ala
                315                 320                 325
ctc acc ccc atc agg gat gag gag tgg aat cgc cac tcc cca cag agt       1243
Leu Thr Pro Ile Arg Asp Glu Glu Trp Asn Arg His Ser Pro Gln Ser
            330                 335                 340
ccc aga aca tgg gag cag gaa ccc ctt caa gaa caa cca agg ggt ggt       1291
Pro Arg Thr Trp Glu Gln Glu Pro Leu Gln Glu Gln Pro Arg Gly Gly
        345                 350                 355
tgg ggg tct gga cgc cct cgg gcc cgc tct gtg gat gct cta gat gat       1339
Trp Gly Ser Gly Arg Pro Arg Ala Arg Ser Val Asp Ala Leu Asp Asp
    360                 365                 370
atc aac cgg cct ggc tcc act gaa tca gga cgg tct tct ccc cca agt       1387
Ile Asn Arg Pro Gly Ser Thr Glu Ser Gly Arg Ser Ser Pro Pro Ser
375                 380                 385                 390
agt gga cgg aga gga cgg gcc tat gca cct cca aga agt cgc agc cgg       1435
Ser Gly Arg Arg Gly Arg Ala Tyr Ala Pro Pro Arg Ser Arg Ser Arg
                395                 400                 405
gat gac ctc tat gac ccg gac gat cct agg gac ttg cca cat tcc cga       1483
Asp Asp Leu Tyr Asp Pro Asp Asp Pro Arg Asp Leu Pro His Ser Arg
            410                 415                 420
gat ccc cac tat tat gac gac atc agg tct aga gat cca cgt gct gac       1531
Asp Pro His Tyr Tyr Asp Asp Ile Arg Ser Arg Asp Pro Arg Ala Asp
        425                 430                 435
ccc aga tcc cgt cag cga tcc cga gat cct cgg gat gct ggc ttc agg       1579
Pro Arg Ser Arg Gln Arg Ser Arg Asp Pro Arg Asp Ala Gly Phe Arg
    440                 445                 450
tca agg gac cct cag tat gat ggg cga cta tta gaa gag gct tta aag       1627
Ser Arg Asp Pro Gln Tyr Asp Gly Arg Leu Leu Glu Glu Ala Leu Lys
455                 460                 465                 470
aaa aag ggg tcg ggc gag aga agg agg gtt tac agg gag gaa gaa gag       1675
Lys Lys Gly Ser Gly Glu Arg Arg Arg Val Tyr Arg Glu Glu Glu Glu
                475                 480                 485
gaa gag gag ggc caa tac ccc cca gca cct cca cct tac tca gag act       1723
Glu Glu Glu Gly Gln Tyr Pro Pro Ala Pro Pro Pro Tyr Ser Glu Thr
            490                 495                 500
gac tcg cag gcc tca cgg gag agg agg ctg aaa aag aat ttg gcc ctg       1771
Asp Ser Gln Ala Ser Arg Glu Arg Arg Leu Lys Lys Asn Leu Ala Leu
```

```
                   505                 510                 515
agt cgg gaa agt tta gtc gtc tga tccacgtttt gtatgtagct tttgtacttt         1825
Ser Arg Glu Ser Leu Val Val  *
520                 525
ttttttaatt ggaatcaata ttgatgaaac ttcaagccta ataaaatgtc taatcacaaa        1885
aaaaaaaa                                                                  1893
```

<210> 13
<211> 525
<212> PRT
<213> Rattus norvegicus

<400> 13

```
Met Ala Pro Ala Ala Gly Ala Cys Ala Gly Ala Pro Asp Ser His Pro
1               5                   10                  15
Ala Thr Val Val Phe Val Cys Leu Phe Leu Ile Ile Phe Cys Pro Asp
                20                  25                  30
Pro Ala Ser Ala Ile Gln Val Thr Val Ser Asp Pro Tyr His Val Val
                35                  40                  45
Ile Leu Phe Gln Pro Val Thr Leu Pro Cys Thr Tyr Gln Met Ser Asn
        50                  55                  60
Thr Leu Thr Val Pro Ile Val Ile Trp Lys Tyr Lys Ser Phe Cys Arg
65                  70                  75                  80
Asp Arg Ile Ala Asp Ala Phe Ser Pro Ala Ser Val Asp Asn Gln Leu
                85                  90                  95
Asn Ala Gln Leu Ala Ala Gly Asn Pro Gly Tyr Asn Pro Tyr Val Glu
                100                 105                 110
Cys Gln Asp Ser Val Arg Thr Val Arg Val Val Ala Thr Lys Gln Gly
                115                 120                 125
Asn Ala Val Thr Leu Gly Asp Tyr Tyr Gln Gly Arg Arg Ile Thr Ile
        130                 135                 140
Thr Gly Asn Ala Asp Leu Thr Phe Glu Gln Thr Ala Trp Gly Asp Ser
145                 150                 155                 160
Gly Val Tyr Tyr Cys Ser Val Val Ser Ala Gln Asp Leu Asp Gly Asn
                165                 170                 175
Asn Glu Ala Tyr Ala Glu Leu Ile Val Leu Val Tyr Ala Ala Gly Lys
                180                 185                 190
Ala Ala Thr Ser Gly Val Pro Ser Ile Tyr Ala Pro Ser Ile Tyr Thr
        195                 200                 205
His Leu Ser Pro Ala Lys Thr Pro Pro Pro Pro Ala Met Ile Pro
210                 215                 220
Met Gly Pro Pro Tyr Gly Tyr Pro Gly Asp Phe Asp Arg His Ser Ser
225                 230                 235                 240
Val Gly Gly His Ser Ser Gln Val Pro Leu Leu Arg Asp Val Asp Gly
                245                 250                 255
Ser Val Ser Ser Glu Val Arg Ser Gly Tyr Arg Ile Gln Ala Asn Gln
                260                 265                 270
Gln Asp Asp Ser Met Arg Val Leu Tyr Tyr Met Glu Lys Glu Leu Ala
        275                 280                 285
Asn Phe Asp Pro Ser Arg Pro Gly Pro Pro Asn Gly Arg Val Glu Arg
        290                 295                 300
Ala Met Ser Glu Val Thr Ser Leu His Glu Asp Asp Trp Arg Ser Arg
305                 310                 315                 320
Pro Ser Arg Ala Pro Ala Leu Thr Pro Ile Arg Asp Glu Glu Trp Asn
                325                 330                 335
Arg His Ser Pro Gln Ser Pro Arg Thr Trp Glu Gln Glu Pro Leu Gln
                340                 345                 350
Glu Gln Pro Arg Gly Gly Trp Gly Ser Gly Arg Pro Arg Ala Arg Ser
        355                 360                 365
```

```
Val Asp Ala Leu Asp Asp Ile Asn Arg Pro Gly Ser Thr Glu Ser Gly
    370             375                 380
Arg Ser Ser Pro Pro Ser Ser Gly Arg Arg Gly Arg Ala Tyr Ala Pro
385             390                 395                 400
Pro Arg Ser Arg Ser Arg Asp Asp Leu Tyr Asp Pro Asp Asp Pro Arg
            405                 410                 415
Asp Leu Pro His Ser Arg Asp Pro His Tyr Tyr Asp Asp Ile Arg Ser
            420                 425                 430
Arg Asp Pro Arg Ala Asp Pro Arg Ser Arg Gln Arg Ser Arg Asp Pro
        435                 440                 445
Arg Asp Ala Gly Phe Arg Ser Arg Asp Pro Gln Tyr Asp Gly Arg Leu
    450                 455                 460
Leu Glu Glu Ala Leu Lys Lys Lys Gly Ser Gly Glu Arg Arg Arg Val
465                 470                 475                 480
Tyr Arg Glu Glu Glu Glu Glu Glu Gly Gln Tyr Pro Pro Ala Pro
            485                 490                 495
Pro Pro Tyr Ser Glu Thr Asp Ser Gln Ala Ser Arg Glu Arg Arg Leu
            500                 505                 510
Lys Lys Asn Leu Ala Leu Ser Arg Glu Ser Leu Val Val
            515                 520                 525

<210> 14
<211> 1886
<212> DNA
<213> Mus musculus

<400> 14
gcaccgtcgc tgctagacgg ccgcg atg gcg ccg gcg gcc agc gcg tgt gct        52
                            Met Ala Pro Ala Ala Ser Ala Cys Ala
                            1               5
ggg gcg cct ggc tcc cac ccg gcc acc acg atc ttc gtg tgt ctt ttt       100
Gly Ala Pro Gly Ser His Pro Ala Thr Thr Ile Phe Val Cys Leu Phe
10              15                  20                  25
ctc atc att tac tgc cca gac cgt gcc agt gcc atc cag gtg acc gtg       148
Leu Ile Ile Tyr Cys Pro Asp Arg Ala Ser Ala Ile Gln Val Thr Val
                30                  35                  40
cct gac ccc tac cac gta gtg atc ctg ttc cag cca gtg aca cta cac       196
Pro Asp Pro Tyr His Val Val Ile Leu Phe Gln Pro Val Thr Leu His
            45                  50                  55
tgc acc tac cag atg agc aat acc ctc aca gcc cct atc gtg atc tgg       244
Cys Thr Tyr Gln Met Ser Asn Thr Leu Thr Ala Pro Ile Val Ile Trp
            60                  65                  70
aag tat aag tcg ttc tgt cgg gac cgt gtt gcc gac gcc ttc tcc cct       292
Lys Tyr Lys Ser Phe Cys Arg Asp Arg Val Ala Asp Ala Phe Ser Pro
75              80                  85
gcc agc gtg gac aac cag ctc aac gcc cag ctg gcg gct ggc aac ccc       340
Ala Ser Val Asp Asn Gln Leu Asn Ala Gln Leu Ala Ala Gly Asn Pro
90              95                  100                 105
ggc tac aac ccc tat gtg gag tgc cag gac agc gta cgc act gtc agg       388
Gly Tyr Asn Pro Tyr Val Glu Cys Gln Asp Ser Val Arg Thr Val Arg
            110                 115                 120
gtg gtg gcc acc aaa cag ggc aat gct gtg acc ctg gga gac tac tac       436
Val Val Ala Thr Lys Gln Gly Asn Ala Val Thr Leu Gly Asp Tyr Tyr
            125                 130                 135
cag ggc agg aga atc acc atc aca gga aat gct ggc ctg acc ttc gag       484
Gln Gly Arg Arg Ile Thr Ile Thr Gly Asn Ala Gly Leu Thr Phe Glu
        140                 145                 150
cag acg gcc tgg gga gac agt gga gtg tat tac tgc tcc gtg gtc tca       532
Gln Thr Ala Trp Gly Asp Ser Gly Val Tyr Tyr Cys Ser Val Val Ser
```

```
              155                    160                      165
gcc caa gat ctg gat ggg aac aac gag gcg tac gca gag ctc att gtc    580
Ala Gln Asp Leu Asp Gly Asn Asn Glu Ala Tyr Ala Glu Leu Ile Val
170                     175                    180                     185
ctt ggc agg acc tca gaa gcc cct gag ctc cta cct ggt ttt cgg gcg    628
Leu Gly Arg Thr Ser Glu Ala Pro Glu Leu Leu Pro Gly Phe Arg Ala
                    190                    195                    200
ggg ccc ttg gaa gat tgg ctc ttt gtg gtc gtg gtc tgc ctg gca agc    676
Gly Pro Leu Glu Asp Trp Leu Phe Val Val Val Val Cys Leu Ala Ser
                205                    210                    215
ctc ctc ttc ttc ctc ctc ctg ggc atc tgc tgg tgc cag tgc tgt ccc    724
Leu Leu Phe Phe Leu Leu Leu Gly Ile Cys Trp Cys Gln Cys Cys Pro
            220                    225                    230
cac acc tgc tgc tat gtc aga tgt ccc tgc tgc cca gac aag tgc        772
His Thr Cys Cys Cys Tyr Val Arg Cys Pro Cys Cys Pro Asp Lys Cys
        235                    240                    245
tgt tgc cct gag gcc ctt tat gct gct ggc aaa gca gcc acc tca ggt    820
Cys Cys Pro Glu Ala Leu Tyr Ala Ala Gly Lys Ala Ala Thr Ser Gly
250                    255                    260                    265
gtg cca agc atc tat gcc ccc agc atc tat acc cac ctc tct cct gcc    868
Val Pro Ser Ile Tyr Ala Pro Ser Ile Tyr Thr His Leu Ser Pro Ala
                    270                    275                    280
aag act ccg cca cct ccg cct gcc atg att ccc atg cgt cct ccc tat    916
Lys Thr Pro Pro Pro Pro Ala Met Ile Pro Met Arg Pro Pro Tyr
                285                    290                    295
ggg tac cct gga gac ttt gac agg acc agc tca gtt ggt ggc cac agc    964
Gly Tyr Pro Gly Asp Phe Asp Arg Thr Ser Ser Val Gly Gly His Ser
            300                    305                    310
tcc cag gtg ccc ctg ctg cgt gaa gtg gat ggg agc gta tct tca gaa    1012
Ser Gln Val Pro Leu Leu Arg Glu Val Asp Gly Ser Val Ser Ser Glu
        315                    320                    325
gta cga agt ggc tac agg atc cag gct aac cag caa gat gac tcc atg    1060
Val Arg Ser Gly Tyr Arg Ile Gln Ala Asn Gln Gln Asp Asp Ser Met
330                    335                    340                    345
agg gtc cta tac tat atg gag aag gag cta gcc aac ttc gat cct tcc    1108
Arg Val Leu Tyr Tyr Met Glu Lys Glu Leu Ala Asn Phe Asp Pro Ser
                    350                    355                    360
cgg cct ggc cct ccc aat ggc cga gtg gaa cgg gcc atg agt gaa gta    1156
Arg Pro Gly Pro Pro Asn Gly Arg Val Glu Arg Ala Met Ser Glu Val
                365                    370                    375
acc tcc ctc cat gaa gat gac tgg cga tct cgg cct tcc agg gct cct    1204
Thr Ser Leu His Glu Asp Asp Trp Arg Ser Arg Pro Ser Arg Ala Pro
            380                    385                    390
gcc ctc aca ccc atc agg gat gag gag tgg aat cgc cac tcc cct cgg    1252
Ala Leu Thr Pro Ile Arg Asp Glu Glu Trp Asn Arg His Ser Pro Arg
        395                    400                    405
agt ccc aga aca tgg gag cag gaa ccc ctt caa gaa cag cca agg ggt    1300
Ser Pro Arg Thr Trp Glu Gln Glu Pro Leu Gln Glu Gln Pro Arg Gly
410                    415                    420                    425
ggt tgg ggg tct ggg cgg cct cgg gcc cgc tct gtg gat gct cta gat    1348
Gly Trp Gly Ser Gly Arg Pro Arg Ala Arg Ser Val Asp Ala Leu Asp
                    430                    435                    440
gac atc aac cgg cct ggc tcc act gaa tca gga agg tct tct ccc cca    1396
Asp Ile Asn Arg Pro Gly Ser Thr Glu Ser Gly Arg Ser Ser Pro Pro
                445                    450                    455
agt agt gga cgg aga ggg cgg gcc tat gca cct ccg aga agt cgc agc    1444
Ser Ser Gly Arg Arg Gly Arg Ala Tyr Ala Pro Pro Arg Ser Arg Ser
            460                    465                    470
cgg gat gac ctc tat gac ccc gac gat cct aga gac ttg cca cat tcc    1492
```

```
        Arg Asp Asp Leu Tyr Asp Pro Asp Asp Pro Arg Asp Leu Pro His Ser
            475                 480                 485
        cga gat ccc cac tat tat gat gat ttg agg tct agg gat cca cgt gct       1540
        Arg Asp Pro His Tyr Tyr Asp Asp Leu Arg Ser Arg Asp Pro Arg Ala
        490                 495                 500                 505
        gac ccc aga tcc cgt cag cga tcc cac gat cct cgg gat gct ggc ttc       1588
        Asp Pro Arg Ser Arg Gln Arg Ser His Asp Pro Arg Asp Ala Gly Phe
                        510                 515                 520
        agg tca cgg gac cct cag tat gat ggg cga ctc tta gaa gag gct tta       1636
        Arg Ser Arg Asp Pro Gln Tyr Asp Gly Arg Leu Leu Glu Glu Ala Leu
                        525                 530                 535
        aag aaa aaa ggg gct ggg gag aga aga cgc gtt tac agg gag gaa gaa       1684
        Lys Lys Lys Gly Ala Gly Glu Arg Arg Arg Val Tyr Arg Glu Glu Glu
                    540                 545                 550
        gaa gaa gaa gag gag ggc cac tat ccc cca gca cct ccg cct tac tct       1732
        Glu Glu Glu Glu Glu Gly His Tyr Pro Pro Ala Pro Pro Pro Tyr Ser
                    555                 560                 565
        gag act gac tcg cag gcc tcg agg gag cgg agg atg aaa aag aat ttg       1780
        Glu Thr Asp Ser Gln Ala Ser Arg Glu Arg Arg Met Lys Lys Asn Leu
        570                 575                 580                 585
        gcc ctg agt cgg gaa agt tta gtc gtc tga tcccacgttt tgttatgtag         1830
        Ala Leu Ser Arg Glu Ser Leu Val Val  *
                        590                 595
        cttttatact tttttaattg gaatattgat gaaactcttc accaagccta ataaaa         1886

<210> 15
<211> 1829
<212> DNA
<213> Mus musculus

<400> 15
gcaccgtcgc tgctagacgg ccgcg atg gcg ccg gcg gcc agc gcg tgt gct             52
                            Met Ala Pro Ala Ala Ser Ala Cys Ala
                              1               5
ggg gcg cct ggc tcc cac ccg gcc acg acg atc ttc gtg tgt ctt ttt            100
Gly Ala Pro Gly Ser His Pro Ala Thr Thr Ile Phe Val Cys Leu Phe
10                  15                  20                  25
ctc atc att tac tgc cca gac cgt gcc agt gcc atc cag gtg acc gtg            148
Leu Ile Ile Tyr Cys Pro Asp Arg Ala Ser Ala Ile Gln Val Thr Val
                30                  35                  40
cct gac ccc tac cac gta gtg atc ctg ttc cag cca gtg aca cta cac            196
Pro Asp Pro Tyr His Val Val Ile Leu Phe Gln Pro Val Thr Leu His
                    45                  50                  55
tgc acc tac cag atg agc aat acc ctc aca gcc cct atc gtg atc tgg            244
Cys Thr Tyr Gln Met Ser Asn Thr Leu Thr Ala Pro Ile Val Ile Trp
                60                  65                  70
aag tat aag tcg ttc tgt cgg gac cgt gtt gcc gac gcc ttc tcc cct            292
Lys Tyr Lys Ser Phe Cys Arg Asp Arg Val Ala Asp Ala Phe Ser Pro
75                  80                  85
gcc agc gtg gac aac cag ctc aac gcc cag ctg gcg gct ggc aac ccc            340
Ala Ser Val Asp Asn Gln Leu Asn Ala Gln Leu Ala Ala Gly Asn Pro
90                  95                  100                 105
ggc tac aac ccc tat gtg gag tgc cag gac agc gta cgc act gtc agg            388
Gly Tyr Asn Pro Tyr Val Glu Cys Gln Asp Ser Val Arg Thr Val Arg
                    110                 115                 120
gtg gtg gcc acc aaa cag ggc aat gct gtg acc ctg gga gac tac tac            436
Val Val Ala Thr Lys Gln Gly Asn Ala Val Thr Leu Gly Asp Tyr Tyr
                125                 130                 135
cag ggc agg aga atc acc atc aca gga aat gct ggc ctg acc ttc gag            484
```

```
        Gln Gly Arg Arg Ile Thr Ile Thr Gly Asn Ala Gly Leu Thr Phe Glu
                140                 145                 150
cag acg gcc tgg gga gac agt gga gtg tat tac tgc tcc gtg gtc tca        532
Gln Thr Ala Trp Gly Asp Ser Gly Val Tyr Tyr Cys Ser Val Val Ser
    155                 160                 165
gcc caa gat ctg gat ggg aac aac gag gcg tac gca gag ctc att gtc        580
Ala Gln Asp Leu Asp Gly Asn Asn Glu Ala Tyr Ala Glu Leu Ile Val
170                 175                 180                     185
ctt gat tgg ctc ttt gtg gtc gtg gtc tgc ctg gca agc ctc ctc ttc        628
Leu Asp Trp Leu Phe Val Val Val Val Cys Leu Ala Ser Leu Leu Phe
                190                 195                 200
ttc ctc ctc ctg ggc atc tgc tgg tgc cag tgc tgt ccc cac acc tgc        676
Phe Leu Leu Leu Gly Ile Cys Trp Cys Gln Cys Cys Pro His Thr Cys
            205                 210                 215
tgc tgc tat gtc aga tgt ccc tgc tgc cca gac aag tgc tgt tgc cct        724
Cys Cys Tyr Val Arg Cys Pro Cys Cys Pro Asp Lys Cys Cys Cys Pro
                220                 225                 230
gag gcc ctt tat gct gct ggc aaa gca gcc acc tca ggt gtg cca agc        772
Glu Ala Leu Tyr Ala Ala Gly Lys Ala Ala Thr Ser Gly Val Pro Ser
    235                 240                 245
atc tat gcc ccc agc atc tat acc cac ctc tct cct gcc aag act ccg        820
Ile Tyr Ala Pro Ser Ile Tyr Thr His Leu Ser Pro Ala Lys Thr Pro
250                 255                 260                     265
cca cct ccg cct gcc atg att ccc atg cgt cct ccc tat ggg tac cct        868
Pro Pro Pro Pro Ala Met Ile Pro Met Arg Pro Pro Tyr Gly Tyr Pro
                270                 275                 280
gga gac ttt gac agg acc agc tca gtt ggt ggc cac agc tcc cag gtg        916
Gly Asp Phe Asp Arg Thr Ser Ser Val Gly Gly His Ser Ser Gln Val
            285                 290                 295
ccc ctg ctg cgt gaa gtg gat ggg agc gta tct tca gaa gta cga agt        964
Pro Leu Leu Arg Glu Val Asp Gly Ser Val Ser Ser Glu Val Arg Ser
        300                 305                 310
ggc tac agg atc cag gct aac cag caa gat gac tcc atg agg gtc cta       1012
Gly Tyr Arg Ile Gln Ala Asn Gln Gln Asp Asp Ser Met Arg Val Leu
    315                 320                 325
tac tat atg gag aag gag cta gcc aac ttc gat cct tcc cgg cct ggc       1060
Tyr Tyr Met Glu Lys Glu Leu Ala Asn Phe Asp Pro Ser Arg Pro Gly
330                 335                 340                     345
cct ccc aat ggc cga gtg gaa cgg gcc atg agt gaa gta acc tcc ctc       1108
Pro Pro Asn Gly Arg Val Glu Arg Ala Met Ser Glu Val Thr Ser Leu
                350                 355                 360
cat gaa gat gac tgg cga tct cgg cct tcc agg gct cct gcc ctc aca       1156
His Glu Asp Asp Trp Arg Ser Arg Pro Ser Arg Ala Pro Ala Leu Thr
            365                 370                 375
ccc atc agg gat gag gag tgg aat cgc cac tcc cct cgg agt ccc aga       1204
Pro Ile Arg Asp Glu Glu Trp Asn Arg His Ser Pro Arg Ser Pro Arg
        380                 385                 390
aca tgg gag cag gaa ccc ctt caa gaa cag cca agg ggt ggt tgg ggg       1252
Thr Trp Glu Gln Glu Pro Leu Gln Glu Gln Pro Arg Gly Gly Trp Gly
    395                 400                 405
tct ggg cgg cct cgg gcc cgc tct gtg gat gct cta gat gac atc aac       1300
Ser Gly Arg Pro Arg Ala Arg Ser Val Asp Ala Leu Asp Asp Ile Asn
410                 415                 420                     425
cgg cct ggc tcc act gaa tca gga agg tct tct ccc cca agt agt gga       1348
Arg Pro Gly Ser Thr Glu Ser Gly Arg Ser Ser Pro Pro Ser Ser Gly
                430                 435                 440
cgg aga ggg cgg gcc tat gca cct ccg aga agt cgc agc cgg gat gac       1396
Arg Arg Gly Arg Ala Tyr Ala Pro Pro Arg Ser Arg Ser Arg Asp Asp
            445                 450                 455
```

```
ctc tat gac ccc gac gat cct aga gac ttg cca cat tcc cga gat ccc      1444
Leu Tyr Asp Pro Asp Asp Pro Arg Asp Leu Pro His Ser Arg Asp Pro
        460                 465                 470
cac tat tat gat gat ttg agg tct agg gat cca cgt gct gac ccc aga      1492
His Tyr Tyr Asp Asp Leu Arg Ser Arg Asp Pro Arg Ala Asp Pro Arg
    475                 480                 485
tcc cgt cag cga tcc cac gat cct cgg gat gct ggc ttc agg tca cgg      1540
Ser Arg Gln Arg Ser His Asp Pro Arg Asp Ala Gly Phe Arg Ser Arg
490                 495                 500                 505
gac cct cag tat gat ggg cga ctc tta gaa gag gct tta aag aaa aaa      1588
Asp Pro Gln Tyr Asp Gly Arg Leu Leu Glu Glu Ala Leu Lys Lys Lys
                510                 515                 520
ggg gct ggg gag aga aga cgc gtt tac agg gag gaa gaa gaa gaa gaa      1636
Gly Ala Gly Glu Arg Arg Arg Val Tyr Arg Glu Glu Glu Glu Glu Glu
            525                 530                 535
gag gag ggc cac tat ccc cca gca cct ccg cct tac tct gag act gac      1684
Glu Glu Gly His Tyr Pro Pro Ala Pro Pro Pro Tyr Ser Glu Thr Asp
        540                 545                 550
tcg cag gcc tcg agg gag cgg agg atg aaa aag aat ttg gcc ctg agt      1732
Ser Gln Ala Ser Arg Glu Arg Arg Met Lys Lys Asn Leu Ala Leu Ser
    555                 560                 565
cgg gaa agt tta gtc gtc tga tcccacgttt tgttatgtag cttttatact        1783
Arg Glu Ser Leu Val Val  *
570                 575
tctttaattg gaatattgat gaaactcttc accaagccta ataaaa                  1829

<210> 16
<211> 1682
<212> DNA
<213> Mus musculus

<400> 16
gcaccgtcgc tgctagacgg ccgcg atg gcg ccg gcg gcc agc gcg tgt gct       52
                            Met Ala Pro Ala Ala Ser Ala Cys Ala
                            1               5
ggg gcg cct ggc tcc cac ccg gcc acc acg atc ttc gtg tgt ctt ttt      100
Gly Ala Pro Gly Ser His Pro Ala Thr Thr Ile Phe Val Cys Leu Phe
10                  15                  20                  25
ctc atc att tac tgc cca gac cgt gcc agt gcc atc cag gtg acc gtg     148
Leu Ile Ile Tyr Cys Pro Asp Arg Ala Ser Ala Ile Gln Val Thr Val
                30                  35                  40
cct gac ccc tac cac gta gtg atc ctg ttc cag cca gtg aca cta cac     196
Pro Asp Pro Tyr His Val Val Ile Leu Phe Gln Pro Val Thr Leu His
            45                  50                  55
tgc acc tac cag atg agc aat acc ctc aca gcc cct atc gtg atc tgg     244
Cys Thr Tyr Gln Met Ser Asn Thr Leu Thr Ala Pro Ile Val Ile Trp
        60                  65                  70
aag tat aag tcg ttc tgt cgg gac cgt gtt gcc gac gcc ttc tcc cct     292
Lys Tyr Lys Ser Phe Cys Arg Asp Arg Val Ala Asp Ala Phe Ser Pro
    75                  80                  85
gcc agc gtg gac aac cag ctc aac gcc cag ctg gcg gct ggc aac ccc     340
Ala Ser Val Asp Asn Gln Leu Asn Ala Gln Leu Ala Ala Gly Asn Pro
90                  95                  100                 105
ggc tac aac ccc tat gtg gag tgc cag gac agc gta cgc act gtc agg     388
Gly Tyr Asn Pro Tyr Val Glu Cys Gln Asp Ser Val Arg Thr Val Arg
                110                 115                 120
gtg gtg gcc acc aaa cag ggc aat gct gtg acc ctg gga gac tac tac     436
Val Val Ala Thr Lys Gln Gly Asn Ala Val Thr Leu Gly Asp Tyr Tyr
            125                 130                 135
```

```
cag ggc agg aga atc acc atc aca gga aat gct ggc ctg acc ttc gag        484
Gln Gly Arg Arg Ile Thr Ile Thr Gly Asn Ala Gly Leu Thr Phe Glu
        140             145             150
cag acg gcc tgg gga gac agt gga gtg tat tac tgc tcc gtg gtc tca        532
Gln Thr Ala Trp Gly Asp Ser Gly Val Tyr Tyr Cys Ser Val Val Ser
    155             160             165
gcc caa gat ctg gat ggg aac aac gag gcg tac gca gag ctc att gtc        580
Ala Gln Asp Leu Asp Gly Asn Asn Glu Ala Tyr Ala Glu Leu Ile Val
170             175             180                 185
ctt gtt tat gct gct ggc aaa gca gcc acc tca ggt gtg cca agc atc        628
Leu Val Tyr Ala Ala Gly Lys Ala Ala Thr Ser Gly Val Pro Ser Ile
                190             195             200
tat gcc ccc agc atc tat acc cac ctc tct cct gcc aag act ccg cca        676
Tyr Ala Pro Ser Ile Tyr Thr His Leu Ser Pro Ala Lys Thr Pro Pro
            205             210             215
cct ccg cct gcc atg att ccc atg cgt cct ccc tat ggg tac cct gga        724
Pro Pro Pro Ala Met Ile Pro Met Arg Pro Pro Tyr Gly Tyr Pro Gly
        220             225             230
gac ttt gac agg acc agc tca gtt ggt ggc cac agc tcc cag gtg ccc        772
Asp Phe Asp Arg Thr Ser Ser Val Gly Gly His Ser Ser Gln Val Pro
    235             240             245
ctg ctg cgt gaa gtg gat ggg agc gta tct tca gaa gta cga agt ggc        820
Leu Leu Arg Glu Val Asp Gly Ser Val Ser Ser Glu Val Arg Ser Gly
250             255             260             265
tac agg atc cag gct aac cag caa gat gac tcc atg agg gtc cta tac        868
Tyr Arg Ile Gln Ala Asn Gln Gln Asp Asp Ser Met Arg Val Leu Tyr
                270             275             280
tat atg gag aag gag cta gcc aac ttc gat cct tcc cgg cct ggc cct        916
Tyr Met Glu Lys Glu Leu Ala Asn Phe Asp Pro Ser Arg Pro Gly Pro
            285             290             295
ccc aat ggc cga gtg gaa cgg gcc atg agt gaa gta acc tcc ctc cat        964
Pro Asn Gly Arg Val Glu Arg Ala Met Ser Glu Val Thr Ser Leu His
        300             305             310
gaa gat gac tgg cga tct cgg cct tcc agg gct cct gcc ctc aca ccc       1012
Glu Asp Asp Trp Arg Ser Arg Pro Ser Arg Ala Pro Ala Leu Thr Pro
    315             320             325
atc agg gat gag gag tgg aat cgc cac tcc cct cgg agt ccc aga aca       1060
Ile Arg Asp Glu Glu Trp Asn Arg His Ser Pro Arg Ser Pro Arg Thr
330             335             340             345
tgg gag cag gaa ccc ctt caa gaa cag cca agg ggt ggt tgg ggg tct       1108
Trp Glu Gln Glu Pro Leu Gln Glu Gln Pro Arg Gly Gly Trp Gly Ser
                350             355             360
ggg cgg cct cgg gcc cgc tct gtg gat gct cta gat gac atc aac cgg       1156
Gly Arg Pro Arg Ala Arg Ser Val Asp Ala Leu Asp Asp Ile Asn Arg
            365             370             375
cct ggc tcc act gaa tca gga agg tct tct ccc cca agt agt gga cgg       1204
Pro Gly Ser Thr Glu Ser Gly Arg Ser Ser Pro Pro Ser Ser Gly Arg
        380             385             390
aga ggg cgg gcc tat gca cct ccg aga agt cgc agc cgg gat gac ctc       1252
Arg Gly Arg Ala Tyr Ala Pro Pro Arg Ser Arg Ser Arg Asp Asp Leu
    395             400             405
tat gac ccc gac gat cct aga gac ttg cca cat tcc cga gat ccc cac       1300
Tyr Asp Pro Asp Asp Pro Arg Asp Leu Pro His Ser Arg Asp Pro His
410             415             420             425
tat tat gat gat ttg agg tct agg gat cca cgt gct gac ccc aga tcc       1348
Tyr Tyr Asp Asp Leu Arg Ser Arg Asp Pro Arg Ala Asp Pro Arg Ser
                430             435             440
cgt cag cga tcc cac gat cct cgg gat gct ggc ttc agg tca cgg gac       1396
Arg Gln Arg Ser His Asp Pro Arg Asp Ala Gly Phe Arg Ser Arg Asp
```

```
                    445                  450                  455
cct cag tat gat ggg cga ctc tta gaa gag gct tta aag aaa aaa ggg      1444
Pro Gln Tyr Asp Gly Arg Leu Leu Glu Glu Ala Leu Lys Lys Lys Gly
            460                  465                  470
gct ggg gag aga aga cgc gtt tac agg gag gaa gaa gaa gaa gag          1492
Ala Gly Glu Arg Arg Arg Val Tyr Arg Glu Glu Glu Glu Glu Glu
        475                  480                  485
gag ggc cac tat ccc cca gca cct ccg cct tac tct gag act gac tcg      1540
Glu Gly His Tyr Pro Pro Ala Pro Pro Pro Tyr Ser Glu Thr Asp Ser
490                  495                  500                  505
cag gcc tcg agg gag cgg agg atg aaa aag aat ttg gcc ctg agt cgg      1588
Gln Ala Ser Arg Glu Arg Arg Met Lys Lys Asn Leu Ala Leu Ser Arg
                510                  515                  520
gaa agt tta gtc gtc tga tcccacgttt tgttatgtag cttttatact             1636
Glu Ser Leu Val Val *
                525
tttttaattg gaatattgat gaaactcttc accaagccta ataaaa                   1682
```

<210> 17
<211> 594
<212> PRT
<213> Mus musculus

<400> 17

```
Met Ala Pro Ala Ala Ser Ala Cys Ala Gly Ala Pro Gly Ser His Pro
1               5                   10                  15
Ala Thr Thr Ile Phe Val Cys Leu Phe Leu Ile Ile Tyr Cys Pro Asp
                20                  25                  30
Arg Ala Ser Ala Ile Gln Val Thr Val Pro Asp Pro Tyr His Val Val
            35                  40                  45
Ile Leu Phe Gln Pro Val Thr Leu His Cys Thr Tyr Gln Met Ser Asn
    50                  55                  60
Thr Leu Thr Ala Pro Ile Val Ile Trp Lys Tyr Lys Ser Phe Cys Arg
65                  70                  75                  80
Asp Arg Val Ala Asp Ala Phe Ser Pro Ala Ser Val Asp Asn Gln Leu
                85                  90                  95
Asn Ala Gln Leu Ala Ala Gly Asn Pro Gly Tyr Asn Pro Tyr Val Glu
            100                 105                 110
Cys Gln Asp Ser Val Arg Thr Val Arg Val Val Ala Thr Lys Gln Gly
        115                 120                 125
Asn Ala Val Thr Leu Gly Asp Tyr Tyr Gln Gly Arg Arg Ile Thr Ile
    130                 135                 140
Thr Gly Asn Ala Gly Leu Thr Phe Glu Gln Thr Ala Trp Gly Asp Ser
145                 150                 155                 160
Gly Val Tyr Tyr Cys Ser Val Val Ser Ala Gln Asp Leu Asp Gly Asn
                165                 170                 175
Asn Glu Ala Tyr Ala Glu Leu Ile Val Leu Gly Arg Thr Ser Glu Ala
            180                 185                 190
Pro Glu Leu Leu Pro Gly Phe Arg Ala Gly Pro Leu Glu Asp Trp Leu
        195                 200                 205
Phe Val Val Val Cys Leu Ala Ser Leu Leu Phe Phe Leu Leu Leu
    210                 215                 220
Gly Ile Cys Trp Cys Gln Cys Cys Pro His Thr Cys Cys Cys Tyr Val
225                 230                 235                 240
Arg Cys Pro Cys Cys Pro Asp Lys Cys Cys Cys Pro Glu Ala Leu Tyr
                245                 250                 255
Ala Ala Gly Lys Ala Ala Thr Ser Gly Val Pro Ser Ile Tyr Ala Pro
            260                 265                 270
Ser Ile Tyr Thr His Leu Ser Pro Ala Lys Thr Pro Pro Pro Pro
```

```
                    275                 280                 285
Ala Met Ile Pro Met Arg Pro Pro Tyr Gly Tyr Pro Gly Asp Phe Asp
            290                 295                 300
Arg Thr Ser Ser Val Gly Gly His Ser Ser Gln Val Pro Leu Leu Arg
305                 310                 315                 320
Glu Val Asp Gly Ser Val Ser Ser Glu Val Arg Ser Gly Tyr Arg Ile
                325                 330                 335
Gln Ala Asn Gln Gln Asp Asp Ser Met Arg Val Leu Tyr Tyr Met Glu
            340                 345                 350
Lys Glu Leu Ala Asn Phe Asp Pro Ser Arg Pro Gly Pro Pro Asn Gly
            355                 360                 365
Arg Val Glu Arg Ala Met Ser Glu Val Thr Ser Leu His Glu Asp Asp
            370                 375                 380
Trp Arg Ser Arg Pro Ser Arg Ala Pro Ala Leu Thr Pro Ile Arg Asp
385                 390                 395                 400
Glu Glu Trp Asn Arg His Ser Pro Arg Ser Pro Arg Thr Trp Glu Gln
                405                 410                 415
Glu Pro Leu Gln Glu Gln Pro Arg Gly Gly Trp Gly Ser Gly Arg Pro
            420                 425                 430
Arg Ala Arg Ser Val Asp Ala Leu Asp Asp Ile Asn Arg Pro Gly Ser
            435                 440                 445
Thr Glu Ser Gly Arg Ser Ser Pro Pro Ser Ser Gly Arg Arg Gly Arg
            450                 455                 460
Ala Tyr Ala Pro Pro Arg Ser Arg Ser Arg Asp Asp Leu Tyr Asp Pro
465                 470                 475                 480
Asp Asp Pro Arg Asp Leu Pro His Ser Arg Asp Pro His Tyr Tyr Asp
                485                 490                 495
Asp Leu Arg Ser Arg Asp Pro Arg Ala Asp Pro Arg Ser Arg Gln Arg
                500                 505                 510
Ser His Asp Pro Arg Asp Ala Gly Phe Arg Ser Arg Asp Pro Gln Tyr
            515                 520                 525
Asp Gly Arg Leu Leu Glu Glu Ala Leu Lys Lys Lys Gly Ala Gly Glu
            530                 535                 540
Arg Arg Arg Val Tyr Arg Glu Glu Glu Glu Glu Glu Glu Gly His
545                 550                 555                 560
Tyr Pro Pro Ala Pro Pro Tyr Ser Glu Thr Asp Ser Gln Ala Ser
                565                 570                 575
Arg Glu Arg Arg Met Lys Lys Asn Leu Ala Leu Ser Arg Glu Ser Leu
            580                 585                 590
Val Val

<210> 18
<211> 575
<212> PRT
<213> Mus musculus

<400> 18
Met Ala Pro Ala Ala Ser Ala Cys Ala Gly Ala Pro Gly Ser His Pro
1               5                   10                  15
Ala Thr Thr Ile Phe Val Cys Leu Phe Leu Ile Ile Tyr Cys Pro Asp
            20                  25                  30
Arg Ala Ser Ala Ile Gln Val Thr Val Pro Asp Pro Tyr His Val Val
            35                  40                  45
Ile Leu Phe Gln Pro Val Thr Leu His Cys Thr Tyr Gln Met Ser Asn
        50                  55                  60
Thr Leu Thr Ala Pro Ile Val Ile Trp Lys Tyr Lys Ser Phe Cys Arg
65                  70                  75                  80
Asp Arg Val Ala Asp Ala Phe Ser Pro Ala Ser Val Asp Asn Gln Leu
                85                  90                  95
```

```
Asn Ala Gln Leu Ala Ala Gly Asn Pro Gly Tyr Asn Pro Tyr Val Glu
        100                     105                 110
Cys Gln Asp Ser Val Arg Thr Val Arg Val Val Ala Thr Lys Gln Gly
            115                 120             125
Asn Ala Val Thr Leu Gly Asp Tyr Tyr Gln Gly Arg Arg Ile Thr Ile
130                     135                 140
Thr Gly Asn Ala Gly Leu Thr Phe Glu Gln Thr Ala Trp Gly Asp Ser
145                 150                 155                 160
Gly Val Tyr Tyr Cys Ser Val Val Ser Ala Gln Asp Leu Asp Gly Asn
                165                 170                 175
Asn Glu Ala Tyr Ala Glu Leu Ile Val Leu Asp Trp Leu Phe Val Val
            180                 185                 190
Val Val Cys Leu Ala Ser Leu Leu Phe Phe Leu Leu Leu Gly Ile Cys
        195                 200                 205
Trp Cys Gln Cys Cys Pro His Thr Cys Cys Cys Tyr Val Arg Cys Pro
    210                 215                 220
Cys Cys Pro Asp Lys Cys Cys Cys Pro Glu Ala Leu Tyr Ala Ala Gly
225             230                 235                 240
Lys Ala Ala Thr Ser Gly Val Pro Ser Ile Tyr Ala Pro Ser Ile Tyr
                245                 250                 255
Thr His Leu Ser Pro Ala Lys Thr Pro Pro Pro Pro Ala Met Ile
            260                 265                 270
Pro Met Arg Pro Pro Tyr Gly Tyr Pro Gly Asp Phe Asp Arg Thr Ser
        275                 280                 285
Ser Val Gly Gly His Ser Ser Gln Val Pro Leu Leu Arg Glu Val Asp
    290                 295                 300
Gly Ser Val Ser Ser Glu Val Arg Ser Gly Tyr Arg Ile Gln Ala Asn
305                 310                 315                 320
Gln Gln Asp Asp Ser Met Arg Val Leu Tyr Tyr Met Glu Lys Glu Leu
            325                 330                 335
Ala Asn Phe Asp Pro Ser Arg Pro Gly Pro Pro Asn Gly Arg Val Glu
            340                 345                 350
Arg Ala Met Ser Glu Val Thr Ser Leu His Glu Asp Asp Trp Arg Ser
        355                 360                 365
Arg Pro Ser Arg Ala Pro Ala Leu Thr Pro Ile Arg Asp Glu Glu Trp
    370                 375                 380
Asn Arg His Ser Pro Arg Ser Pro Arg Thr Trp Glu Gln Glu Pro Leu
385                 390                 395                 400
Gln Glu Gln Pro Arg Gly Gly Trp Gly Ser Gly Arg Pro Arg Ala Arg
            405                 410                 415
Ser Val Asp Ala Leu Asp Asp Ile Asn Arg Pro Gly Ser Thr Glu Ser
            420                 425                 430
Gly Arg Ser Ser Pro Pro Ser Ser Gly Arg Arg Gly Arg Ala Tyr Ala
        435                 440                 445
Pro Pro Arg Ser Arg Ser Arg Asp Asp Leu Tyr Asp Pro Asp Asp Pro
    450                 455                 460
Arg Asp Leu Pro His Ser Arg Asp Pro His Tyr Tyr Asp Asp Leu Arg
465                 470                 475                 480
Ser Arg Asp Pro Arg Ala Asp Pro Arg Ser Arg Gln Arg Ser His Asp
                485                 490                 495
Pro Arg Asp Ala Gly Phe Arg Ser Arg Asp Pro Gln Tyr Asp Gly Arg
            500                 505                 510
Leu Leu Glu Glu Ala Leu Lys Lys Lys Gly Ala Gly Glu Arg Arg Arg
        515                 520                 525
Val Tyr Arg Glu Glu Glu Glu Glu Glu Glu Gly His Tyr Pro Pro
    530                 535                 540
Ala Pro Pro Pro Tyr Ser Glu Thr Asp Ser Gln Ala Ser Arg Glu Arg
545                 550                 555                 560
Arg Met Lys Lys Asn Leu Ala Leu Ser Arg Glu Ser Leu Val Val
```

565 570 575

<210> 19
<211> 526
<212> PRT
<213> Mus musculus

<400> 19

| Met | Ala | Pro | Ala | Ala | Ser | Ala | Cys | Ala | Gly | Ala | Pro | Gly | Ser | His | Pro |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Ala | Thr | Thr | Ile | Phe | Val | Cys | Leu | Phe | Leu | Ile | Ile | Tyr | Cys | Pro | Asp |
|     |     |     | 20  |     |     |     |     | 25  |     |     |     |     | 30  |     |     |
| Arg | Ala | Ser | Ala | Ile | Gln | Val | Thr | Val | Pro | Asp | Pro | Tyr | His | Val | Val |
|     |     | 35  |     |     |     |     | 40  |     |     |     |     | 45  |     |     |     |
| Ile | Leu | Phe | Gln | Pro | Val | Thr | Leu | His | Cys | Thr | Tyr | Gln | Met | Ser | Asn |
|     | 50  |     |     |     |     | 55  |     |     |     |     | 60  |     |     |     |     |
| Thr | Leu | Thr | Ala | Pro | Ile | Val | Ile | Trp | Lys | Tyr | Lys | Ser | Phe | Cys | Arg |
| 65  |     |     |     |     | 70  |     |     |     | 75  |     |     |     |     |     | 80  |
| Asp | Arg | Val | Ala | Asp | Ala | Phe | Ser | Pro | Ala | Ser | Val | Asp | Asn | Gln | Leu |
|     |     |     |     | 85  |     |     |     |     | 90  |     |     |     |     | 95  |     |
| Asn | Ala | Gln | Leu | Ala | Ala | Gly | Asn | Pro | Gly | Tyr | Asn | Pro | Tyr | Val | Glu |
|     |     |     | 100 |     |     |     |     | 105 |     |     |     |     | 110 |     |     |
| Cys | Gln | Asp | Ser | Val | Arg | Thr | Val | Arg | Val | Val | Ala | Thr | Lys | Gln | Gly |
|     |     | 115 |     |     |     |     | 120 |     |     |     |     | 125 |     |     |     |
| Asn | Ala | Val | Thr | Leu | Gly | Asp | Tyr | Tyr | Gln | Gly | Arg | Arg | Ile | Thr | Ile |
|     | 130 |     |     |     |     | 135 |     |     |     |     | 140 |     |     |     |     |
| Thr | Gly | Asn | Ala | Gly | Leu | Thr | Phe | Glu | Gln | Thr | Ala | Trp | Gly | Asp | Ser |
| 145 |     |     |     |     | 150 |     |     |     |     | 155 |     |     |     |     | 160 |
| Gly | Val | Tyr | Tyr | Cys | Ser | Val | Val | Ser | Ala | Gln | Asp | Leu | Asp | Gly | Asn |
|     |     |     |     | 165 |     |     |     |     | 170 |     |     |     |     | 175 |     |
| Asn | Glu | Ala | Tyr | Ala | Glu | Leu | Ile | Val | Leu | Val | Tyr | Ala | Ala | Gly | Lys |
|     |     |     | 180 |     |     |     |     | 185 |     |     |     |     | 190 |     |     |
| Ala | Ala | Thr | Ser | Gly | Val | Pro | Ser | Ile | Tyr | Ala | Pro | Ser | Ile | Tyr | Thr |
|     |     | 195 |     |     |     |     | 200 |     |     |     |     | 205 |     |     |     |
| His | Leu | Ser | Pro | Ala | Lys | Thr | Pro | Pro | Pro | Pro | Ala | Met | Ile | Pro |     |
|     | 210 |     |     |     |     | 215 |     |     |     |     | 220 |     |     |     |     |
| Met | Arg | Pro | Pro | Tyr | Gly | Tyr | Pro | Gly | Asp | Phe | Asp | Arg | Thr | Ser | Ser |
| 225 |     |     |     |     | 230 |     |     |     |     | 235 |     |     |     |     | 240 |
| Val | Gly | Gly | His | Ser | Ser | Gln | Val | Pro | Leu | Leu | Arg | Glu | Val | Asp | Gly |
|     |     |     |     | 245 |     |     |     |     | 250 |     |     |     |     | 255 |     |
| Ser | Val | Ser | Ser | Glu | Val | Arg | Ser | Gly | Tyr | Arg | Ile | Gln | Ala | Asn | Gln |
|     |     |     | 260 |     |     |     |     | 265 |     |     |     |     | 270 |     |     |
| Gln | Asp | Asp | Ser | Met | Arg | Val | Leu | Tyr | Tyr | Met | Glu | Lys | Glu | Leu | Ala |
|     |     | 275 |     |     |     |     | 280 |     |     |     |     | 285 |     |     |     |
| Asn | Phe | Asp | Pro | Ser | Arg | Pro | Gly | Pro | Pro | Asn | Gly | Arg | Val | Glu | Arg |
|     | 290 |     |     |     |     | 295 |     |     |     |     | 300 |     |     |     |     |
| Ala | Met | Ser | Glu | Val | Thr | Ser | Leu | His | Glu | Asp | Asp | Trp | Arg | Ser | Arg |
| 305 |     |     |     |     | 310 |     |     |     |     | 315 |     |     |     |     | 320 |
| Pro | Ser | Arg | Ala | Pro | Ala | Leu | Thr | Pro | Ile | Arg | Asp | Glu | Glu | Trp | Asn |
|     |     |     |     | 325 |     |     |     |     | 330 |     |     |     |     | 335 |     |
| Arg | His | Ser | Pro | Arg | Ser | Pro | Arg | Thr | Trp | Glu | Gln | Glu | Pro | Leu | Gln |
|     |     |     | 340 |     |     |     |     | 345 |     |     |     |     | 350 |     |     |
| Glu | Gln | Pro | Arg | Gly | Gly | Trp | Gly | Ser | Gly | Arg | Pro | Arg | Ala | Arg | Ser |
|     |     | 355 |     |     |     |     | 360 |     |     |     |     | 365 |     |     |     |
| Val | Asp | Ala | Leu | Asp | Asp | Ile | Asn | Arg | Pro | Gly | Ser | Thr | Glu | Ser | Gly |
|     | 370 |     |     |     |     | 375 |     |     |     |     | 380 |     |     |     |     |
| Arg | Ser | Ser | Pro | Pro | Ser | Ser | Gly | Arg | Arg | Gly | Arg | Ala | Tyr | Ala | Pro |
| 385 |     |     |     |     | 390 |     |     |     |     | 395 |     |     |     |     | 400 |
| Pro | Arg | Ser | Arg | Ser | Arg | Asp | Asp | Leu | Tyr | Asp | Pro | Asp | Asp | Pro | Arg |

```
                      405                     410                     415
Asp Leu Pro His Ser Arg Asp Pro His Tyr Tyr Asp Asp Leu Arg Ser
              420                     425                     430
Arg Asp Pro Arg Ala Asp Pro Arg Ser Arg Gln Arg Ser His Asp Pro
              435                     440                     445
Arg Asp Ala Gly Phe Arg Ser Arg Asp Pro Gln Tyr Asp Gly Arg Leu
    450                     455                     460
Leu Glu Glu Ala Leu Lys Lys Lys Gly Ala Gly Glu Arg Arg Arg Val
465                     470                     475                     480
Tyr Arg Glu Glu Glu Glu Glu Glu Glu Gly His Tyr Pro Pro Ala
                  485                     490                     495
Pro Pro Pro Tyr Ser Glu Thr Asp Ser Gln Ala Ser Arg Glu Arg Arg
              500                     505                     510
Met Lys Lys Asn Leu Ala Leu Ser Arg Glu Ser Leu Val Val
              515                     520                     525

<210> 20
<211> 18
<212> DNA
<213> Homo Sapiens

<220>
<221> misc_binding
<222> 1..18
<223> sequencing oligonucleotide PrimerPU

<400> 20
tgtaaaacga cggccagt                                                    18

<210> 21
<211> 18
<212> DNA
<213> Homo Sapiens

<220>
<221> misc_binding
<222> 1..18
<223> sequencing oligonucleotide PrimerRP

<400> 21
caggaaacag ctatgacc                                                    18

<210> 22
<211> 20
<212> DNA
<213> Artificial Sequence

<220>
<223> oligonucleotide sense primer

<400> 22
ctacaacccc tacgtcgagt                                                  20

<210> 23
<211> 20
<212> DNA
<213> Artificial Sequence

<220>
```

<223> oligonucleotide anti sense primer

<400> 23
aggcggagat cgccagtcgt                    20

<210> 24
<211> 24
<212> DNA
<213> Artificial Sequence

<220>
<223> oligonucleotide sense primer

<400> 24
cctttgtcca cgtcgtttac gctc               24

<210> 25
<211> 20
<212> DNA
<213> Artificial Sequence

<220>
<223> oligonucleotide anti sense primer

<400> 25
tcacagcgtt gccctgcttg                    20

<210> 26
<211> 21
<212> DNA
<213> Artificial Sequence

<220>
<223> oligonucleotide sense primer

<400> 26
ttactgctcc gtggtctcag c                  21

<210> 27
<211> 22
<212> DNA
<213> Artificial Sequence

<220>
<223> oligonucleotide anti sense primer

<400> 27
agctactcct gtcaacgtct cc                 22

<210> 28
<211> 167
<212> PRT
<213> Bos taurus

<400> 28
Met Arg Cys Gly Pro Leu Tyr Arg Phe Leu Trp Leu Trp Pro Tyr Leu
1               5                   10                  15
Ser Tyr Val Glu Ala Val Pro Ile Arg Lys Val Gln Asp Asp Thr Lys
            20                  25                  30

```
Thr Leu Ile Lys Thr Ile Val Thr Arg Ile Asn Asp Ile Ser His Thr
        35                  40                  45
Gln Ser Val Ser Ser Lys Gln Arg Val Thr Gly Leu Asp Phe Ile Pro
    50                  55                  60
Gly Leu His Pro Leu Leu Ser Leu Ser Lys Met Asp Gln Thr Leu Ala
65                  70                  75                  80
Ile Tyr Gln Gln Ile Leu Thr Ser Leu Pro Ser Arg Asn Val Val Gln
                85                  90                  95
Ile Ser Asn Asp Leu Glu Asn Leu Arg Asp Leu Leu His Leu Leu Ala
            100                 105                 110
Ala Ser Lys Ser Cys Pro Leu Pro Gln Val Arg Ala Leu Glu Ser Leu
        115                 120                 125
Glu Ser Leu Gly Val Val Leu Glu Ala Ser Leu Tyr Ser Thr Glu Val
    130                 135                 140
Val Ala Leu Ser Arg Leu Gln Gly Ser Leu Gln Asp Met Leu Arg Gln
145                 150                 155                 160
Leu Asp Leu Ser Pro Gly Cys
                165

<210> 29
<211> 146
<212> PRT
<213> Canis familiaris

<400> 29
Val Pro Ile Arg Lys Val Gln Asp Asp Thr Lys Thr Leu Ile Lys Thr
1               5                   10                  15
Ile Val Ala Arg Ile Asn Asp Ile Ser His Thr Gln Ser Val Ser Ser
                20                  25                  30
Lys Gln Arg Val Ala Gly Leu Asp Phe Ile Pro Gly Leu Gln Pro Val
            35                  40                  45
Leu Ser Leu Ser Arg Met Asp Gln Thr Leu Ala Ile Tyr Gln Gln Ile
        50                  55                  60
Leu Asn Ser Leu His Ser Arg Asn Val Val Gln Ile Ser Asn Asp Leu
65                  70                  75                  80
Glu Asn Leu Arg Asp Leu Leu His Leu Leu Ala Ser Ser Lys Ser Cys
                85                  90                  95
Pro Leu Pro Arg Ala Arg Gly Leu Glu Thr Phe Glu Ser Leu Gly Gly
            100                 105                 110
Val Leu Glu Ala Ser Leu Tyr Ser Thr Glu Val Val Ala Leu Ser Arg
        115                 120                 125
Leu Gln Ala Ala Leu Gln Asp Met Leu Arg Arg Leu Asp Leu Ser Pro
    130                 135                 140
Gly Cys
145

<210> 30
<211> 163
<212> PRT
<213> Gallus gallus

<400> 30
Met Cys Trp Arg Pro Leu Cys Arg Leu Trp Ser Tyr Leu Val Tyr Val
1               5                   10                  15
Gln Ala Val Pro Cys Gln Ile Phe Gln Asp Asp Thr Lys Thr Leu Ile
                20                  25                  30
Lys Thr Ile Val Thr Arg Ile Asn Asp Ile Ser His Thr Ser Val Ser
            35                  40                  45
Ala Lys Gln Arg Val Thr Gly Leu Asp Phe Ile Pro Gly Leu His Pro
```

```
            50                  55                  60
Ile Leu Ser Leu Ser Lys Met Asp Gln Thr Leu Ala Val Tyr Gln Gln
 65                  70                  75                  80
Val Leu Thr Ser Leu Pro Ser Gln Asn Val Leu Gln Ile Ala Asn Asp
                85                  90                  95
Leu Glu Asn Leu Arg Asp Leu Leu His Leu Leu Ala Phe Ser Lys Ser
            100                 105                 110
Cys Ser Leu Pro Gln Thr Ser Gly Leu Gln Lys Pro Glu Ser Leu Asp
        115                 120                 125
Gly Val Leu Glu Ala Ser Leu Tyr Ser Thr Glu Val Ala Leu Ser
    130                 135                 140
Arg Leu Gln Gly Ser Leu Gln Asp Ile Leu Gln Gln Leu Asp Ile Ser
145                 150                 155                 160
Pro Glu Cys
```

<210> 31
<211> 146
<212> PRT
<213> Gorilla gorilla

<400> 31
```
Val Pro Ile Gln Lys Val Gln Asp Asp Thr Lys Thr Leu Ile Lys Thr
 1                   5                  10                  15
Ile Val Thr Arg Ile Ser Asp Ile Ser His Thr Gln Ser Val Ser Ser
                20                  25                  30
Lys Gln Lys Val Thr Gly Leu Asp Phe Ile Pro Gly Leu His Pro Ile
            35                  40                  45
Leu Thr Leu Ser Lys Met Asp Gln Thr Leu Ala Val Tyr Gln Gln Ile
        50                  55                  60
Leu Thr Ser Met Pro Ser Arg Asn Met Ile Gln Ile Ser Asn Asp Leu
 65                  70                  75                  80
Glu Asn Leu Arg Asp Leu Leu His Val Leu Ala Phe Ser Lys Ser Cys
                85                  90                  95
His Leu Pro Trp Ala Ser Gly Leu Glu Thr Leu Asp Ser Leu Gly Gly
            100                 105                 110
Val Leu Glu Ala Ser Gly Tyr Ser Thr Glu Val Val Ala Leu Ser Arg
        115                 120                 125
Leu Gln Gly Ser Leu Gln Asp Met Leu Trp Gln Leu Asp Leu Ser Pro
    130                 135                 140
Gly Cys
145
```

<210> 32
<211> 167
<212> PRT
<213> Homo sapiens

<400> 32
```
Met His Trp Gly Thr Leu Cys Gly Phe Leu Trp Leu Trp Pro Tyr Leu
 1                   5                  10                  15
Phe Tyr Val Gln Ala Val Pro Ile Gln Lys Val Gln Asp Asp Thr Lys
                20                  25                  30
Thr Leu Ile Lys Thr Ile Val Thr Arg Ile Asn Asp Ile Ser His Thr
            35                  40                  45
Gln Ser Val Ser Ser Lys Gln Lys Val Thr Gly Leu Asp Phe Ile Pro
        50                  55                  60
Gly Leu His Pro Ile Leu Thr Leu Ser Lys Met Asp Gln Thr Leu Ala
 65                  70                  75                  80
Val Tyr Gln Gln Ile Leu Thr Ser Met Pro Ser Arg Asn Val Ile Gln
```

```
                        85                      90                       95
Ile Ser Asn Asp Leu Glu Asn Leu Arg Asp Leu Leu His Val Leu Ala
                100                 105                 110
Phe Ser Lys Ser Cys His Leu Pro Trp Ala Ser Gly Leu Glu Thr Leu
        115                 120                 125
Asp Ser Leu Gly Gly Val Leu Glu Ala Ser Gly Tyr Ser Thr Glu Val
    130                 135                 140
Val Ala Leu Ser Arg Leu Gln Gly Ser Leu Gln Asp Met Leu Trp Gln
145                 150                 155                 160
Leu Asp Leu Ser Pro Gly Cys
                165

<210> 33
<211> 167
<212> PRT
<213> Macaca mulatta

<400> 33
Met Tyr Trp Arg Thr Leu Trp Gly Phe Leu Trp Leu Trp Pro Tyr Leu
1               5                   10                  15
Phe Tyr Ile Gln Ala Val Pro Ile Gln Lys Val Gln Ser Asp Thr Lys
                20                  25                  30
Thr Leu Ile Lys Thr Ile Val Thr Arg Ile Asn Asp Ile Ser His Thr
            35                  40                  45
Gln Ser Val Ser Ser Lys Gln Arg Val Thr Gly Leu Asp Phe Ile Pro
    50                  55                  60
Gly Leu His Pro Val Leu Thr Leu Ser Gln Met Asp Gln Thr Leu Ala
65                  70                  75                  80
Ile Tyr Gln Gln Ile Leu Ile Asn Leu Pro Ser Arg Asn Val Ile Gln
                85                  90                  95
Ile Ser Asn Asp Leu Glu Asn Leu Arg Asp Leu Leu His Leu Leu Ala
                100                 105                 110
Phe Ser Lys Ser Cys His Leu Pro Leu Ala Ser Gly Leu Glu Thr Leu
        115                 120                 125
Glu Ser Leu Gly Asp Val Leu Glu Ala Ser Leu Tyr Ser Thr Glu Val
    130                 135                 140
Val Ala Leu Ser Arg Leu Gln Gly Ser Leu Gln Asp Met Leu Trp Gln
145                 150                 155                 160
Leu Asp Leu Ser Pro Gly Cys
                165

<210> 34
<211> 167
<212> PRT
<213> Mus musculus

<400> 34
Met Cys Trp Arg Pro Leu Cys Arg Phe Leu Trp Leu Trp Ser Tyr Leu
1               5                   10                  15
Ser Tyr Val Gln Ala Val Pro Ile Gln Lys Val Gln Asp Asp Thr Lys
                20                  25                  30
Thr Leu Ile Lys Thr Ile Val Thr Arg Ile Asn Asp Ile Ser His Thr
            35                  40                  45
Gln Ser Val Ser Ala Lys Gln Arg Val Thr Gly Leu Asp Phe Ile Pro
    50                  55                  60
Gly Leu His Pro Ile Leu Ser Leu Ser Lys Met Asp Gln Thr Leu Ala
65                  70                  75                  80
Val Tyr Gln Gln Val Leu Thr Ser Leu Pro Ser Gln Asn Val Leu Gln
                85                  90                  95
```

Ile Ala Asn Asp Leu Glu Asn Leu Arg Asp Leu Leu His Leu Leu Ala
            100                 105                 110
Phe Ser Lys Ser Cys Ser Leu Pro Gln Thr Ser Gly Leu Gln Lys Pro
        115                 120                 125
Glu Ser Leu Asp Gly Val Leu Glu Ala Ser Leu Tyr Ser Thr Glu Val
    130                 135                 140
Val Ala Leu Ser Arg Leu Gln Gly Ser Leu Gln Asp Ile Leu Gln Gln
145                 150                 155                 160
Leu Asp Val Ser Pro Glu Cys
                165

<210> 35
<211> 146
<212> PRT
<213> Ovus aries

<400> 35
Val Pro Ile Arg Lys Val Gln Asp Asp Thr Lys Thr Leu Ile Lys Thr
1               5                   10                  15
Ile Val Thr Arg Ile Asn Asp Ile Ser His Thr Gln Ser Val Ser Ser
            20                  25                  30
Lys Gln Arg Val Thr Gly Leu Asp Phe Ile Pro Gly Leu His Pro Leu
        35                  40                  45
Leu Ser Leu Ser Lys Met Asp Gln Thr Leu Ala Ile Tyr Gln Gln Ile
    50                  55                  60
Leu Ala Ser Leu Pro Ser Arg Asn Val Ile Gln Ile Ser Asn Asp Leu
65                  70                  75                  80
Glu Asn Leu Arg Asp Leu Leu His Leu Leu Ala Ala Ser Lys Ser Cys
                85                  90                  95
Pro Leu Pro Gln Val Arg Ala Leu Glu Ser Leu Glu Ser Leu Gly Val
            100                 105                 110
Val Leu Glu Ala Ser Leu Tyr Ser Thr Glu Val Val Ala Leu Ser Arg
        115                 120                 125
Leu Gln Gly Ser Leu Gln Asp Met Leu Arg Gln Leu Asp Leu Ser Pro
    130                 135                 140
Gly Cys
145

<210> 36
<211> 146
<212> PRT
<213> Pan troglodytes

<400> 36
Val Pro Ile Gln Lys Val Gln Asp Asp Thr Lys Thr Leu Ile Lys Thr
1               5                   10                  15
Ile Val Thr Arg Ile Asn Asp Ile Ser His Thr Gln Ser Val Ser Ser
            20                  25                  30
Lys Gln Lys Val Thr Gly Leu Asp Phe Ile Pro Gly Leu His Pro Ile
        35                  40                  45
Leu Thr Leu Ser Lys Met Asp Gln Thr Leu Ala Val Tyr Gln Gln Ile
    50                  55                  60
Leu Thr Ser Met Pro Ser Arg Asn Met Ile Gln Ile Ser Asn Asp Leu
65                  70                  75                  80
Glu Asn Leu Arg Asp Leu Leu His Val Leu Ala Phe Ser Lys Ser Cys
                85                  90                  95
His Leu Pro Trp Ala Ser Gly Leu Glu Thr Leu Asp Ser Leu Gly Gly
            100                 105                 110
Val Leu Glu Ala Ser Gly Tyr Ser Thr Glu Val Val Ala Leu Ser Arg

```
            115                 120                 125
Leu Gln Gly Ser Leu Gln Asp Met Leu Trp Gln Leu Asp Leu Ser Pro
        130                 135                 140
Gly Cys
145

<210> 37
<211> 146
<212> PRT
<213> Pongo pygmaeus

<400> 37
Val Pro Ile Gln Lys Val Gln Asp Asp Thr Lys Thr Leu Ile Lys Thr
1               5                   10                  15
Val Ile Thr Arg Ile Asn Asp Ile Ser His Thr Gln Ser Val Ser Ser
            20                  25                  30
Lys Gln Lys Val Thr Gly Leu Asp Phe Ile Pro Gly Leu His Pro Ile
        35                  40                  45
Leu Thr Leu Ser Lys Met Asp Gln Thr Leu Ala Val Tyr Gln Gln Ile
    50                  55                  60
Leu Thr Ser Met Pro Ser Arg Asn Val Ile Gln Ile Ser Asn Asp Leu
65                  70                  75                  80
Glu Asn Leu Arg Asp Leu Leu His Val Leu Ala Phe Ser Lys Ser Cys
                85                  90                  95
His Leu Pro Trp Ala Ser Gly Leu Glu Thr Leu Asp Arg Leu Gly Gly
            100                 105                 110
Val Leu Glu Ala Ser Gly Tyr Ser Thr Glu Val Val Ala Leu Ser Arg
        115                 120                 125
Leu Gln Arg Ser Leu Gln Asp Met Leu Trp Gln Leu Asp Leu Ser Pro
    130                 135                 140
Gly Cys
145

<210> 38
<211> 167
<212> PRT
<213> Rattus norvegicus

<400> 38
Met Cys Trp Arg Pro Leu Cys Arg Phe Leu Trp Leu Trp Ser Tyr Leu
1               5                   10                  15
Ser Tyr Val Gln Ala Val Pro Ile His Lys Val Gln Asp Asp Thr Lys
            20                  25                  30
Thr Leu Ile Lys Thr Ile Val Thr Arg Ile Asn Asp Ile Ser His Thr
        35                  40                  45
Gln Ser Val Ser Ala Arg Gln Arg Val Thr Gly Leu Asp Phe Ile Pro
    50                  55                  60
Gly Leu His Pro Ile Leu Ser Leu Ser Lys Met Asp Gln Thr Leu Ala
65                  70                  75                  80
Val Tyr Gln Gln Ile Leu Thr Ser Leu Pro Ser Gln Asn Val Leu Gln
                85                  90                  95
Ile Ala His Asp Leu Glu Asn Leu Arg Asp Leu Leu His Leu Leu Ala
            100                 105                 110
Phe Ser Lys Ser Cys Ser Leu Pro Gln Thr Arg Gly Leu Gln Lys Pro
        115                 120                 125
Glu Ser Leu Asp Gly Val Leu Glu Ala Ser Leu Tyr Ser Thr Glu Val
    130                 135                 140
Val Ala Leu Ser Arg Leu Gln Gly Ser Leu Gln Asp Ile Leu Gln Gln
145                 150                 155                 160
```

```
Leu Asp Leu Ser Pro Glu Cys
                165

<210> 39
<211> 167
<212> PRT
<213> Sus scrofa

<400> 39
Met Arg Cys Gly Pro Leu Cys Arg Phe Leu Trp Leu Trp Pro Tyr Leu
1               5                   10                  15
Ser Tyr Val Glu Ala Val Pro Ile Trp Arg Val Gln Asp Asp Thr Lys
            20                  25                  30
Thr Leu Ile Lys Thr Ile Val Thr Arg Ile Ser Asp Ile Ser His Met
        35                  40                  45
Gln Ser Val Ser Ser Lys Gln Arg Val Thr Gly Leu Asp Phe Ile Pro
    50                  55                  60
Gly Leu His Pro Val Leu Ser Leu Ser Lys Met Asp Gln Thr Leu Ala
65                  70                  75                  80
Ile Tyr Gln Gln Ile Leu Thr Ser Leu Pro Ser Arg Asn Val Ile Gln
                85                  90                  95
Ile Ser Asn Asp Leu Glu Asn Leu Arg Asp Leu Leu His Leu Leu Ala
            100                 105                 110
Ser Ser Lys Ser Cys Pro Leu Pro Gln Ala Arg Ala Leu Glu Thr Leu
        115                 120                 125
Glu Ser Leu Gly Gly Val Leu Glu Ala Ser Leu Tyr Ser Thr Glu Val
    130                 135                 140
Val Ala Leu Ser Arg Leu Gln Gly Ala Leu Gln Asp Met Leu Arg Gln
145                 150                 155                 160
Leu Asp Leu Ser Pro Gly Cys
                165

<210> 40
<211> 4
<212> PRT
<213> Homo sapiens

<400> 40
Glu Thr Leu Asp
1

<210> 41
<211> 4
<212> PRT
<213> Mus musculus

<400> 41
Gln Lys Pro Glu
1

<210> 42
<211> 6
<212> PRT
<213> Homo sapiens

<400> 42
Leu Asp Ser Leu Gly Gly
1               5
```

<210> 43
<211> 4
<212> PRT
<213> Homo sapiens

<400> 43
Glu Lys Leu Glu
1

<210> 44
<211> 4
<212> PRT
<213> Homo sapiens

<400> 44
Glu Lys Pro Glu
1

<210> 45
<211> 4
<212> PRT
<213> Homo sapiens

<400> 45
Glu Lys Pro Asp
1

<210> 46
<211> 5
<212> PRT
<213> Homo sapiens

<400> 46
Thr Pro Asp Ser Leu
1               5

<210> 47
<211> 9
<212> PRT
<213> Homo sapiens

<400> 47
Gly Leu Gln Thr Leu Asp Ser Leu Gly
1               5

<210> 48
<211> 5
<212> PRT
<213> Homo sapiens

<400> 48
Gly Gly Val Leu Glu
1               5

<210> 49
<211> 6
<212> PRT
<213> Homo sapiens

<400> 49
Thr Pro Asp Ser Leu Gly
1               5

<210> 50
<211> 9
<212> PRT
<213> Homo sapiens

<400> 50
Ser Leu Gly Gly Val Leu Glu Ala Ser
1               5

<210> 51
<211> 6
<212> PRT
<213> Homo sapiens

<400> 51
Pro Glu Ser Leu Gly Gly
1               5

<210> 52
<211> 6
<212> PRT
<213> Homo sapiens

<400> 52
Pro Asp Ser Leu Gly Gly
1               5

<210> 53
<211> 7
<212> PRT
<213> Homo sapiens

<400> 53
Leu Gly Gly Val Leu Glu Ala
1               5

<210> 54
<211> 22
<212> PRT
<213> Homo sapiens

<400> 54
Glu Asn Leu Arg Asp Leu Leu His Val Leu Ala Phe Ser Lys Ser Cys
1               5                   10                  15
His Leu Pro Trp Ala Ser
            20

<210> 55
<211> 22
<212> PRT
<213> Homo sapiens

<400> 55
Leu Leu His Val Leu Ala Phe Ser Lys Ser Cys His Leu Pro Trp Ala
1               5                   10                  15

Ser Gly Leu Glu Thr Leu
            20

<210> 56
<211> 22
<212> PRT
<213> Homo sapiens

<400> 56
Ala Phe Ser Lys Ser Cys His Leu Pro Trp Ala Ser Gly Leu Glu Thr
1               5                   10                  15
Leu Asp Ser Leu Gly Gly
            20

<210> 57
<211> 22
<212> PRT
<213> Homo sapiens

<400> 57
Cys His Leu Pro Trp Ala Ser Gly Leu Glu Thr Leu Asp Ser Leu Gly
1               5                   10                  15
Gly Val Leu Glu Ala Ser
            20

<210> 58
<211> 18
<212> PRT
<213> Homo sapiens

<400> 58
Leu Pro Trp Ala Ser Gly Leu Glu Thr Leu Asp Ser Leu Gly Gly Val
1               5                   10                  15
Leu Glu

<210> 59
<211> 14
<212> PRT
<213> Homo sapiens

<400> 59
Trp Ala Ser Gly Leu Glu Thr Leu Asp Ser Leu Gly Gly Val
1               5                   10

<210> 60
<211> 21
<212> PRT
<213> Homo sapiens

<400> 60
Ala Ser Gly Leu Glu Thr Asp Ser Leu Gly Gly Val Leu Glu Ala Ser
1               5                   10                  15
Gly Tyr Ser Thr Glu
            20

<210> 61
<211> 10
<212> PRT
<213> Homo sapiens

```
<400> 61
Ser Gly Leu Glu Thr Leu Asp Ser Leu Gly
1               5                   10

<210> 62
<211> 22
<212> PRT
<213> Homo sapiens

<400> 62
Thr Leu Asp Ser Leu Gly Gly Val Leu Glu Ala Ser Gly Tyr Ser Thr
1               5                   10                  15
Glu Val Val Ala Leu Ser
            20

<210> 63
<211> 22
<212> PRT
<213> Homo sapiens

<400> 63
Gly Gly Val Leu Glu Ala Ser Gly Tyr Ser Thr Glu Val Val Ala Leu
1               5                   10                  15
Ser Arg Gly Gln Gly Ser
            20

<210> 64
<211> 22
<212> PRT
<213> Mus musculus

<400> 64
Glu Asn Leu Arg Asp Leu Leu His Leu Leu Ala Phe Ser Lys Ser Cys
1               5                   10                  15
Ser Leu Pro Gln Thr Ser
            20

<210> 65
<211> 22
<212> PRT
<213> Mus musculus

<400> 65
Leu Leu His Leu Leu Ala Phe Ser Lys Ser Cys Ser Leu Pro Gln Thr
1               5                   10                  15
Ser Gly Leu Gln Lys Pro
            20

<210> 66
<211> 22
<212> PRT
<213> Mus musculus

<400> 66
Ala Phe Ser Lys Ser Cys Ser Leu Pro Gln Thr Ser Gly Leu Gln Lys
1               5                   10                  15
Pro Glu Ser Leu Asp Gly
            20
```

```
<210> 67
<211> 22
<212> PRT
<213> Mus musculus

<400> 67
Cys Ser Leu Pro Gln Thr Ser Gly Leu Gln Lys Pro Glu Ser Leu Asp
1               5                   10                  15
Gly Val Leu Glu Ala Ser
            20

<210> 68
<211> 18
<212> PRT
<213> Mus musculus

<400> 68
Leu Pro Gln Thr Ser Gly Leu Gln Lys Pro Glu Ser Leu Asp Gly Val
1               5                   10                  15
Leu Glu

<210> 69
<211> 14
<212> PRT
<213> Mus musculus

<400> 69
Gln Thr Ser Gly Leu Gln Lys Pro Glu Ser Leu Asp Gly Val
1               5                   10

<210> 70
<211> 22
<212> PRT
<213> Mus musculus

<400> 70
Thr Ser Gly Leu Gln Lys Pro Glu Ser Leu Asp Gly Val Leu Glu Ala
1               5                   10                  15
Ser Leu Tyr Ser Thr Glu
            20

<210> 71
<211> 10
<212> PRT
<213> Mus musculus

<400> 71
Ser Gly Leu Gln Lys Pro Glu Ser Leu Asp
1               5                   10

<210> 72
<211> 22
<212> PRT
<213> Mus musculus

<400> 72
Lys Pro Glu Ser Leu Asp Gly Val Leu Glu Ala Ser Leu Tyr Ser Thr
1               5                   10                  15
```

Glu Val Val Ala Leu Ser
            20

<210> 73
<211> 22
<212> PRT
<213> Mus musculus

<400> 73
Asp Gly Val Leu Glu Ala Ser Leu Tyr Ser Thr Glu Val Val Ala Leu
1               5                   10                  15
Ser Arg Leu Gln Gly Ser
            20

<210> 74
<211> 67
<212> DNA
<213> Artificial Sequence

<220>
<223> oligonucleotide Chimeric oligonucleotides

<400> 74
atgcaacagg acggacttgg agtagttttc uacuccaagt cagtccuguu gcaugcgcgt    60
ttcgcgc                                                             67

<210> 75
<211> 20
<212> DNA
<213> Artificial Sequence

<220>
<223> oligonucleotide Forward Primer

<400> 75
tgtccacgtc gtttacgctc                                                20

<210> 76
<211> 20
<212> DNA
<213> Artificial Sequence

<220>
<223> oligonucleotide Reverse Primer

<400> 76
tcccacttcc gttccttgtc                                                20

<210> 77
<211> 27
<212> DNA
<213> Artificial Sequence

<220>
<223> oligonucleotide Probes endogenous/mutant

<400> 77
cctactccaa gtcmgtcctg ttgcatt                                        27

<210> 78
<211> 67
<212> DNA
<213> Artificial Sequence

<220>
<223> oligonucleotide Chimeric oligonucleotides

<400> 78
gaccctgccc tgtacctacc taccagatgt tttcaucugg uaggttcagg gcagggucgc    60
gcgtttt                                                              67

<210> 79
<211> 21
<212> DNA
<213> Artificial Sequence

<220>
<223> oligonucleotide Forward Primer

<400> 79
gtggtgatcc tcttccagcc t                                              21

<210> 80
<211> 19
<212> DNA
<213> Artificial Sequence

<220>
<223> oligonucleotide Reverse Primer

<400> 80
ccagatgacg atgggttgc                                                 19

<210> 81
<211> 25
<212> DNA
<213> Artificial Sequence

<220>
<223> oligonucleotide Probes endogenous/mutant

<400> 81
accctgccct gwcctaccag atgac                                          25

<210> 82
<211> 68
<212> DNA
<213> Artificial Sequence

<220>
<223> oligonucleotide Chimeric oligonucleotides

<400> 82
tggctgagct cttacctggt tttcattttt gaaaaccagg tcagagctca gccagcgcgt    60
tttcgcgc                                                             68

<210> 83
<211> 20

```
<212> DNA
<213> Artificial Sequence

<220>
<223> oligonucleotide Forward Primer

<400> 83
gagctcatcg tccttgggag                                                    20

<210> 84
<211> 19
<212> DNA
<213> Artificial Sequence

<220>
<223> oligonucleotide Reverse Primer

<400> 84
agtcttctat gggccccgc                                                     19

<210> 85
<211> 27
<212> DNA
<213> Artificial Sequence

<220>
<223> oligonucleotide Probes endogenous/mutant

<400> 85
caccgactcg agamtggacc aaaagtc                                            27

<210> 86
<211> 68
<212> DNA
<213> Artificial Sequence

<220>
<223> oligonucleotide Chimeric oligonucleotides

<400> 86
ggttgtggta tgcctggctg ccttcttttg aaggcagcca gtcataccac aaccgcgcgt        60
tttcgcgc                                                                 68

<210> 87
<211> 20
<212> DNA
<213> Artificial Sequence

<220>
<223> oligonucleotide Forward Primer

<400> 87
acgcagagct catcgtcctt                                                    20

<210> 88
<211> 20
<212> DNA
<213> Artificial Sequence
```

```
<220>
<223> oligonucleotide Reverse Primer

<400> 88
gatgcccagg aggaggaaga                                           20

<210> 89
<211> 23
<212> DNA
<213> Artificial Sequence

<220>
<223> oligonucleotide Probes endogenous/mutant

<400> 89
caacaccata ckgaccgacg gaa                                       23

<210> 90
<211> 18
<212> DNA
<213> Artificial Sequence

<220>
<223> oligonucleotide mouse LSR specific primer

<400> 90
acgcatggga atcatggc                                             18

<210> 91
<211> 18
<212> DNA
<213> Artificial Sequence

<220>
<223> oligonucleotide Zinc finger nuclotides of SEQID1

<400> 91
tagggtgag cggcgggg                                              18

<210> 92
<211> 21
<212> DNA
<213> Artificial Sequence

<220>
<223> oligonucleotide Zinc finger nuclotides of SEQID1

<220>
<221> misc_feature
<222> 10..12
<223> n=a, g, c or t

<400> 92
gagggctggn nntagggtg a                                         21

<210> 93
<211> 20
<212> DNA
<213> Artificial Sequence
```

```
<220>
<223> oligonucleotide Zinc finger nuclotides of SEQID1

<220>
<221> misc_feature
<222> 10..11
<223> n=a, g, c or t

<400> 93
agggctgggn ntagggtga                                              20

<210> 94
<211> 18
<212> DNA
<213> Artificial Sequence

<220>
<223> oligonucleotide Zinc finger nuclotides of SEQID1

<400> 94
gtgggagccg agggctgg                                               18

<210> 95
<211> 19
<212> DNA
<213> Artificial Sequence

<220>
<223> oligonucleotide Zinc finger nuclotides of SEQID1

<220>
<221> misc_feature
<222> 10
<223> n=a, g, c or t

<400> 95
gtgggagccn agggctggg                                              19

<210> 96
<211> 18
<212> DNA
<213> Artificial Sequence

<220>
<223> oligonucleotide Zinc finger nuclotides of SEQID1

<400> 96
gcggcggccg ggtgggag                                               18

<210> 97
<211> 18
<212> DNA
<213> Artificial Sequence

<220>
<223> oligonucleotide Zinc finger nuclotides of SEQID1

<400> 97
```
ttggccggag cagatggg                                                     18

<210> 98
<211> 20
<212> DNA
<213> Artificial Sequence

<220>
<223> oligonucleotide Zinc finger nuclotides of SEQID1

<220>
<221> misc_feature
<222> 10..11
<223> n=a, g, c or t

<400> 98
gcagatgggn nccggaaggg                                                   20

<210> 99
<211> 21
<212> DNA
<213> Artificial Sequence

<220>
<223> oligonucleotide Zinc finger nuclotides of SEQID1

<220>
<221> misc_feature
<222> 10..12
<223> n=a, g, c or t

<400> 99
agggctgggn nnaggggtga g                                                 21

<210> 100
<211> 21
<212> DNA
<213> Artificial Sequence

<220>
<223> oligonucleotide Zinc finger nuclotides of SEQID1

<220>
<221> misc_feature
<222> 10..12
<223> n=a, g, c or t

<400> 100
aggggtgagn nncggggagg g                                                 21

<210> 101
<211> 18
<212> DNA
<213> Artificial Sequence

<220>
<223> oligonucleotide Zinc finger nuclotides of SEQID1

<400> 101

```
aagtgggtct cggttgca                                                    18

<210> 102
<211> 21
<212> DNA
<213> Artificial Sequence

<220>
<223> oligonucleotide zinc finger LSR sequences

<400> 102
aaggtcgcct atggtgcaga c                                                21

<210> 103
<211> 20
<212> DNA
<213> Artificial Sequence

<220>
<223> oligonucleotide zinc finger LSR sequences

<400> 103
gtgggagccc gggggctgga                                                  20

<210> 104
<211> 18
<212> DNA
<213> Artificial Sequence

<220>
<223> oligonucleotide zinc finger LSR sequences

<400> 104
tgggggtggg cggcgggg                                                    18

<210> 105
<211> 20
<212> DNA
<213> Artificial Sequence

<220>
<223> oligonucleotide zinc finger LSR sequences

<400> 105
ccgggagtgc gcaggggggta                                                 20

<210> 106
<211> 19
<212> DNA
<213> Artificial Sequence

<220>
<223> oligonucleotide zinc finger LSR sequences

<400> 106
gtggctgcac aaggtcgcc                                                   19

<210> 107
```

<211> 6319
<212> DNA
<213> Artificial sequence

<220>
<223> LSR zinc finger plasmid

<400> 107

```
gacggatcgg gagatctccc gatcccctat ggtcgactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180
ttagggttag gcgttttgcg ctgcttcgcg atgtacgggc cagatatacg cgttgacatt     240
gattattgac tagttattaa tagtaatcaa ttacggggtc attagttcat agcccatata     300
tggagttccg cgttacataa cttacggtaa atggcccgcc tggctgaccg cccaacgacc     360
cccgcccatt gacgtcaata atgacgtatg ttcccatagt aacgccaata gggactttcc     420
attgacgtca atgggtggac tatttacggt aaactgccca cttggcagta catcaagtgt     480
atcatatgcc aagtacgccc cctattgacg tcaatgacgg taaatggccc gcctggcatt     540
atgcccagta catgacctta tgggactttc ctacttggca gtacatctac gtattagtca     600
tcgctattac catggtgatg cggttttggc agtacatcaa tgggcgtgga tagcggtttg     660
actcacgggg atttccaagt ctccacccca ttgacgtcaa tgggagtttg ttttggcacc     720
aaaatcaacg ggactttcca aatgtcgta acaactccgc cccattgacg caaatgggcg      780
gtaggcgtgt acggtgggag gtctatataa gcagagctct ctggctaact agagaaccca     840
ctgcttactg gcttatcgaa attaatacga ctcactatag ggagacccaa gctggctagc     900
gtttaaactt aagctgatcc actagtccag tgtggtggaa ttcgctagcg ccaccatggc     960
ccccaagaag aagaggaagg tgggaatcca tgggtaccg ggcaagaaga agcagcacat    1020
ctgccacatc cagggctgtg gtaaagttta cggcgaccgc tccaacctga cccgccacct    1080
gcgctggcac accggcgaga ggcctttcat gtgtacatgg tcctactgtg gtaaacgctt    1140
cacccagtcc ggcgacctga cccgccacaa gcgtacccac accggtgaga agaaatttgc    1200
ttgtccggaa tgtccgaagc gcttcatgat gtccaccac ctgtcccgcc acatcaagac    1260
ccaccagaac aagaagggtg gatctggtga tggtggccgt cgcggtgccg gttctggcaa    1320
gaagaagcag cacatctgcc acatccaggg ctgtggtaaa gtttacggcg agcgcggcga    1380
cctgacccgc cacctgcgct ggcacaccgg cgagaggcct tcatgtgta catggtccta    1440
ctgtggtaaa cgcttcaccg acccgggcgc cctggtgcgc cacaagcgta cccacaccgg    1500
tgagaagaaa tttgcttgtc cggaatgtcc gaagcgcttc atgcgctccg acaacctgac    1560
```

| | | | | | |
|---|---|---|---|---|---|
| ccagcacatc | aagacccacc | agaacaagaa | gggtggatcc | gccccccga | ccgatgtcag | 1620
| cctgggggac | gagctccact | tagacggcga | ggacgtggcg | atggcgcatg | ccgacgcgct | 1680
| agacgatttc | gatctggaca | tgttggggga | cggggattcc | ccggggccgg | gatttacccc | 1740
| ccacgactcc | gcccctacg | gcgctctgga | tatggccggc | ttcgagtttg | agcagatgtt | 1800
| taccgatgcc | cttggaattg | acgagtacgg | tgggggcagc | gactacaagg | acgacgatga | 1860
| caagtaagct | tctcgagtct | agagggcccg | tttaaacccg | ctgatcagcc | tcgactgtgc | 1920
| cttctagttg | ccagccatct | gttgtttgcc | cctccccgt | gccttccttg | accctggaag | 1980
| gtgccactcc | cactgtcctt | tcctaataaa | atgaggaaat | tgcatcgcat | tgtctgagta | 2040
| ggtgtcattc | tattctgggg | ggtggggtgg | ggcaggacag | caagggggag | gattgggaag | 2100
| acaatagcag | gcatgctggg | gatgcggtgg | gctctatggc | ttctgaggcg | gaaagaacca | 2160
| gctggggctc | taggggtat | ccccacgcgc | cctgtagcgg | cgcattaagc | gcggcgggtg | 2220
| tggtggttac | gcgcagcgtg | accgctacac | ttgccagcgc | cctagcgccc | gctcctttcg | 2280
| ctttcttccc | ttcctttctc | gccacgttcg | ccggctttcc | ccgtcaagct | ctaaatcggg | 2340
| gcatcccttt | agggttccga | tttagtgctt | tacggcacct | cgaccccaaa | aaacttgatt | 2400
| agggtgatgg | ttcacgtagt | gggccatcgc | cctgatagac | ggttttcgc | cctttgacgt | 2460
| tggagtccac | gttctttaat | agtggactct | tgttccaaac | tggaacaaca | ctcaaccta | 2520
| tctcggtcta | ttcttttgat | ttataaggga | ttttggggat | ttcggcctat | tggttaaaaa | 2580
| atgagctgat | ttaacaaaaa | tttaacgcga | attaattctg | tggaatgtgt | gtcagttagg | 2640
| gtgtggaaag | tccccaggct | ccccaggcag | gcagaagtat | gcaaagcatg | catctcaatt | 2700
| agtcagcaac | caggtgtgga | aagtccccag | gctccccagc | aggcagaagt | atgcaaagca | 2760
| tgcatctcaa | ttagtcagca | accatagtcc | cgcccctaac | tccgcccatc | ccgcccctaa | 2820
| ctccgcccag | ttccgcccat | tctccgcccc | atggctgact | aatttttttt | atttatgcag | 2880
| aggccgaggc | cgcctctgcc | tctgagctat | tccagaagta | gtgaggaggc | ttttttggag | 2940
| gcctaggctt | ttgcaaaaag | ctcccgggag | cttgtatatc | cattttcgga | tctgatcaag | 3000
| agacaggatg | aggatcgttt | cgcatgattg | aacaagatgg | attgcacgca | ggttctccgg | 3060
| ccgcttgggt | ggagaggcta | ttcggctatg | actgggcaca | acagacaatc | ggctgctctg | 3120
| atgccgccgt | gttccggctg | tcagcgcagg | ggcgcccggt | tctttttgtc | aagaccgacc | 3180
| tgtccggtgc | cctgaatgaa | ctgcaggacg | aggcagcgcg | gctatcgtgg | ctggccacga | 3240
| cgggcgttcc | ttgcgcagct | gtgctcgacg | ttgtcactga | agcgggaagg | gactggctgc | 3300

```
tattgggcga agtgccgggg caggatctcc tgtcatctca ccttgctcct gccgagaaag    3360
tatccatcat ggctgatgca atgcggcggc tgcatacgct tgatccggct acctgcccat    3420
tcgaccacca agcgaaacat cgcatcgagc gagcacgtac tcggatggaa gccggtcttg    3480
tcgatcagga tgatctggac gaagagcatc aggggctcgc gccagccgaa ctgttcgcca    3540
ggctcaaggc gcgcatgccc gacggcgagg atctcgtcgt gacccatggc gatgcctgct    3600
tgccgaatat catggtggaa aatggccgct tttctggatt catcgactgt ggccggctgg    3660
gtgtggcgga ccgctatcag gacatagcgt tggctacccg tgatattgct gaagagcttg    3720
gcggcgaatg ggctgaccgc ttcctcgtgc tttacggtat cgccgctccc gattcgcagc    3780
gcatcgcctt ctatcgcctt cttgacgagt tcttctgagc gggactctgg ggttcgaaat    3840
gaccgaccaa gcgacgccca acctgccatc acgagatttc gattccaccg ccgccttcta    3900
tgaaaggttg ggcttcggaa tcgtttttccg ggacgccggc tggatgatcc tccagcgcgg    3960
ggatctcatg ctggagttct tcgcccaccc caacttgttt attgcagctt ataatggtta    4020
caaataaagc aatagcatca caaatttcac aaataaagca ttttttttcac tgcattctag    4080 ttgtggtttg tccaaactca tcaatgtatc ttatcatgtc tgtataccgt cgacctctag    4140
ctagagcttg gcgtaatcat ggtcatagct gtttcctgtg tgaaattgtt atccgctcac    4200
aattccacac aacatacgag ccggaagcat aaagtgtaaa gcctggggtg cctaatgagt    4260
gagctaactc acattaattg cgttgcgctc actgcccgct ttccagtcgg gaaacctgtc    4320
gtgccagctg cattaatgaa tcggccaacg cgcggggaga ggcggtttgc gtattgggcg    4380
ctcttccgct tcctcgctca ctgactcgct gcgctcggtc gttcggctgc ggcgagcggt    4440
atcagctcac tcaaaggcgg taatacggtt atccacagaa tcagggaata cgcaggaaa    4500 gaacatgtga gcaaaaggcc agcaaaaggc caggaaccgt aaaaaggccg cgttgctggc    4560 gttttttccat aggctccgcc ccctgacga gcatcacaaa atcgacgct caagtcagag    4620 gtggcgaaac ccgacaggac tataaagata ccaggcgttt ccccctggaa gctccctcgt    4680
gcgctctcct gttccgaccc tgccgcttac cggatacctg tccgcctttc tcccttcggg    4740
aagcgtggcg ctttctcaat gctcacgctg taggtatctc agttcggtgt aggtcgttcg    4800
ctccaagctg ggctgtgtgc acgaacccc cgttcagccc gaccgctgcg ccttatccgg    4860
taactatcgt cttgagtcca acccggtaag acacgactta tcgccactgg cagcagccac    4920
tggtaacagg attagcagag cgaggtatgt aggcggtgct acagagttct tgaagtggtg    4980
gcctaactac ggctacacta aaggacagt atttggtatc tgcgctctgc tgaagccagt    5040
taccttcgga aaaagagttg gtagctcttg atccggcaaa caaaccaccg ctggtagcgg    5100
```

| | | | | |
|---|---|---|---|---|
| tggttttttt | gtttgcaagc | agcagattac | gcgcagaaaa | aaaggatctc aagaagatcc | 5160 |
| tttgatcttt | tctacggggt | ctgacgctca | gtggaacgaa | aactcacgtt aagggatttt | 5220 |
| ggtcatgaga | ttatcaaaaa | ggatcttcac | ctagatcctt | ttaaattaaa aatgaagttt | 5280 |
| taaatcaatc | taaagtatat | atgagtaaac | ttggtctgac | agttaccaat gcttaatcag | 5340 |
| tgaggcacct | atctcagcga | tctgtctatt | tcgttcatcc | atagttgcct gactccccgt | 5400 |
| cgtgtagata | actacgatac | gggagggctt | accatctggc | cccagtgctg caatgatacc | 5460 |
| gcgagaccca | cgctcaccgg | ctccagattt | atcagcaata | aaccagccag ccggaagggc | 5520 |
| cgagcgcaga | agtggtcctg | caactttatc | cgcctccatc | cagtctatta attgttgccg | 5580 |
| ggaagctaga | gtaagtagtt | cgccagttaa | tagtttgcgc | aacgttgttg ccattgctac | 5640 |
| aggcatcgtg | gtgtcacgct | cgtcgtttgg | tatggcttca | ttcagctccg gttcccaacg | 5700 |
| atcaaggcga | gttacatgat | cccccatgtt | gtgcaaaaaa | gcggttagct ccttcggtcc | 5760 |
| tccgatcgtt | gtcagaagta | agttggccgc | agtgttatca | ctcatggtta tggcagcact | 5820 |
| gcataattct | cttactgtca | tgccatccgt | aagatgcttt | tctgtgactg gtgagtactc | 5880 |
| aaccaagtca | ttctgagaat | agtgtatgcg | gcgaccgagt | tgctcttgcc cggcgtcaat | 5940 |
| acgggataat | accgcgccac | atagcagaac | tttaaaagtg | ctcatcattg gaaaacgttc | 6000 |
| ttcggggcga | aaactctcaa | ggatcttacc | gctgttgaga | tccagttcga tgtaacccac | 6060 |
| tcgtgcaccc | aactgatctt | cagcatcttt | tactttcacc | agcgtttctg ggtgagcaaa | 6120 |
| aacaggaagg | caaaatgccg | caaaaaaggg | aataagggcg | acacggaaat gttgaatact | 6180 |
| catactcttc | ctttttcaat | attattgaag | catttatcag | ggttattgtc tcatgagcgg | 6240 |
| atacatattt | gaatgtattt | agaaaaataa | acaaataggg | gttccgcgca catttccccg | 6300 |
| aaaagtgcca | cctgacgtc | | | | 6319 |

<210> 108
<211> 6319
<212> DNA
<213> Artificial sequence

<220>
<223> LSR zinc finger plasmid

<400> 108
| | | | | |
|---|---|---|---|---|
| gacggatcgg | gagatctccc | gatcccctat | ggtcgactct | cagtacaatc tgctctgatg | 60 |
| ccgcatagtt | aagccagtat | ctgctccctg | cttgtgtgtt | ggaggtcgct gagtagtgcg | 120 |
| cgagcaaaat | ttaagctaca | acaaggcaag | gcttgaccga | caattgcatg aagaatctgc | 180 |

```
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggac tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
gtttaaactt aagctgatcc actagtccag tgtggtggaa ttcgctagcg ccaccatggc    960
ccccaagaag aagaggaagg tgggaatcca tgggtaccg ggcaagaaga agcagcacat   1020
ctgccacatc cagggctgtg gtaaagttta cggccagtcc ggccacctgg cccgccacct   1080
gcgctggcac accggcgaga ggcctttcat gtgtacatgg tcctactgtg gtaaacgctt   1140
caccacctcc ggcgagctgg tgcgccacaa gcgtacccac accggtgaga gaaatttgc    1200 ttgtccggaa tgtccgaagc gcttcatgcg ttccgaccac ctgtcccgtc acatcaagac   1260
ccaccagaac aagaagggtg gatctggtga tggtggccgt cgcggtggcg gttctggcaa   1320
gaagaagcag cacatctgcc acatccaggg ctgtggtaaa gtttacggcg agcgcggcga   1380
cctgacccgc cacctgcgct ggcacaccgg cgagaggcct ttcatgtgta catggtccta   1440
ctgtgctaaa cgcttcaccc agcgcgccca cctggagcgc cacaagcgta cccacaccgg   1500
tgagaagaaa tttgcttgtc cggaatgtcc gaagcgcttc atgcgctccg acgccctgac   1560
ccgccacatc aagacccacc agaacaagaa gggtggatcc gcccccccga ccgatgtcag   1620 cctggggga gagctccact tagacggcga ggacgtggcg atggcgcatg ccgacgcgct   1680
agacgatttc gatctggaca tgttggggga cggggattcc ccggggccgg gatttacccc   1740
ccacgactcc gcccctacg gcgctctgga tatggccggc ttcgagtttg agcagatgtt   1800
taccgatgcc cttggaattg acgagtacgg tgggggcagc gactacaagg acgacgatga   1860
caagtaagct tctcgagtct agagggcccg tttaaacccg ctgatcagcc tcgactgtgc   1920
cttctagttg ccagccatct gttgtttgcc cctcccccgt gccttccttg accctggaag   1980
```

```
gtgccactcc cactgtcctt tcctaataaa atgaggaaat tgcatcgcat tgtctgagta    2040
ggtgtcattc tattctgggg ggtggggtgg ggcaggacag caaggggggag gattgggaag   2100 acaatagcag gcatgctggg gatgcggtgg gctctatggc ttctgaggcg gaaagaacca   2160
gctggggctc taggggtat ccccacgcgc cctgtagcgg cgcattaagc gcggcgggtg    2220
tggtggttac gcgcagcgtg accgctacac ttgccagcgc cctagcgccc gctcctttcg   2280
ctttcttccc ttcctttctc gccacgttcg ccggctttcc ccgtcaagct ctaaatcggg   2340
gcatcccttt agggttccga tttagtgctt tacggcacct cgaccccaaa aaacttgatt   2400
agggtgatgg ttcacgtagt gggccatcgc cctgatagac ggttttcgc cctttgacgt    2460 tggagtccac gttctttaat agtggactct tgttccaaac tggaacaaca ctcaacccta   2520
tctcggtcta ttctttgat ttataaggga ttttggggat ttcggcctat tggttaaaaa    2580
atgagctgat ttaacaaaaa tttaacgcga attaattctg tggaatgtgt gtcagttagg   2640
gtgtggaaag tccccaggct ccccaggcag gcagaagtat gcaaagcatg catctcaatt   2700
agtcagcaac caggtgtgga aagtccccag gctccccagc aggcagaagt atgcaaagca   2760
tgcatctcaa ttagtcagca accatagtcc cgccctaac tccgcccatc ccgcccctaa    2820
ctccgcccag ttccgcccat tctccgcccc atggctgact aattttttt atttatgcag    2880 aggccgaggc cgcctctgcc tctgagctat tccagaagta gtgaggaggc ttttttggag   2940
gcctaggctt ttgcaaaaag ctcccgggag cttgtatatc cattttcgga tctgatcaag   3000
agacaggatg aggatcgttt cgcatgattg aacaagatgg attgcacgca ggttctccgg   3060
ccgcttgggt ggagaggcta ttcggctatg actgggcaca acagacaatc ggctgctctg   3120
atgccgccgt gttccggctg tcagcgcagg ggcgcccggt tctttttgtc aagaccgacc   3180
tgtccggtgc cctgaatgaa ctgcaggacg aggcagcgcg gctatcgtgg ctggccacga   3240
cgggcgttcc ttgcgcagct gtgctcgacg ttgtcactga agcgggaagg gactggctgc   3300
tattgggcga agtgccgggg caggatctcc tgtcatctca ccttgctcct gccgagaaag   3360
tatccatcat ggctgatgca atgcggcggc tgcatacgct tgatccggct acctgcccat   3420
tcgaccacca agcgaaacat cgcatcgagc gagcacgtac tcggatggaa gccggtcttg   3480
tcgatcagga tgatctggac gaagagcatc aggggctcgc gccagccgaa ctgttcgcca   3540
ggctcaaggc gcgcatgccc gacggcgagg atctcgtcgt gacccatggc gatgcctgct   3600
tgccgaatat catggtggaa aatggccgct tttctggatt catcgactgt ggccggctgg   3660
gtgtggcgga ccgctatcag gacatagcgt tggctacccg tgatattgct gaagagcttg   3720
```

```
gcggcgaatg ggctgaccgc ttcctcgtgc tttacggtat cgccgctccc gattcgcagc    3780
gcatcgcctt ctatcgcctt cttgacgagt tcttctgagc gggactctgg ggttcgaaat    3840
gaccgaccaa gcgacgccca acctgccatc acgagatttc gattccaccg ccgccttcta    3900
tgaaaggttg ggcttcggaa tcgttttccg ggacgccggc tggatgatcc tccagcgcgg    3960
ggatctcatg ctggagttct tcgcccaccc caacttgttt attgcagctt ataatggtta    4020
caaataaagc aatagcatca caaatttcac aaataaagca ttttttcac tgcattctag     4080 ttgtggtttg tccaaactca tcaatgtatc ttatcatgtc tgtataccgt cgacctctag    4140
ctagagcttg gcgtaatcat ggtcatagct gtttcctgtg tgaaattgtt atccgctcac    4200
aattccacac aacatacgag ccggaagcat aaagtgtaaa gcctggggtg cctaatgagt    4260
gagctaactc acattaattg cgttgcgctc actgcccgct ttccagtcgg gaaacctgtc    4320
gtgccagctg cattaatgaa tcggccaacg cgcggggaga ggcggtttgc gtattgggcg    4380
ctcttccgct tcctcgctca ctgactcgct gcgctcggtc gttcggctgc ggcgagcggt    4440
atcagctcac tcaaaggcgg taatacggtt atccacagaa tcagggggata acgcaggaaa    4500 gaacatgtga gcaaaaggcc agcaaaaggc caggaaccgt aaaaaggccg cgttgctggc    4560
gtttttccat aggctccgcc cccctgacga gcatcacaaa aatcgacgct caagtcagag    4620
gtggcgaaac ccgacaggac tataaagata ccaggcgttt ccccctggaa gctccctcgt    4680
gcgctctcct gttccgaccc tgccgcttac cggatacctg tccgcctttc tcccttcggg    4740
aagcgtggcg ctttctcaat gctcacgctg taggtatctc agttcggtgt aggtcgttcg    4800
ctccaagctg ggctgtgtgc acgaaccccc cgttcagccc gaccgctgcg ccttatccgg    4860
taactatcgt cttgagtcca acccggtaag acacgactta tcgccactgg cagcagccac    4920
tggtaacagg attagcagag cgaggtatgt aggcggtgct acagagttct tgaagtggtg    4980
gcctaactac ggctacacta aaggacagt atttggtatc tgcgctctgc tgaagccagt     5040
taccttcgga aaaagagttg gtagctcttg atccggcaaa caaaccaccg ctggtagcgg    5100 tggtttttt gtttgcaagc agcagattac gcgcagaaaa aaaggatctc aagaagatcc     5160
tttgatcttt tctacggggt ctgacgctca gtggaacgaa aactcacgtt aagggatttt    5220
ggtcatgaga ttatcaaaaa ggatcttcac ctagatcctt ttaaattaaa aatgaagttt    5280
taaatcaatc taaagtatat atgagtaaac ttggtctgac agttaccaat gcttaatcag    5340
tgaggcacct atctcagcga tctgtctatt tcgttcatcc atagttgcct gactccccgt    5400
cgtgtagata actacgatac gggagggctt accatctggc cccagtgctg caatgatacc    5460
gcgagaccca cgctcaccgg ctccagattt atcagcaata accagccag ccggaagggc     5520
```

```
cgagcgcaga agtggtcctg caactttatc cgcctccatc cagtctatta attgttgccg    5580
ggaagctaga gtaagtagtt cgccagttaa tagtttgcgc aacgttgttg ccattgctac    5640
aggcatcgtg gtgtcacgct cgtcgtttgg tatggcttca ttcagctccg gttcccaacg    5700
atcaaggcga gttacatgat cccccatgtt gtgcaaaaaa gcggttagct ccttcggtcc    5760
tccgatcgtt gtcagaagta agttggccgc agtgttatca ctcatggtta tggcagcact    5820
gcataattct cttactgtca tgccatccgt aagatgcttt tctgtgactg gtgagtactc    5880
aaccaagtca ttctgagaat agtgtatgcg gcgaccgagt tgctcttgcc cggcgtcaat    5940
acgggataat accgcgccac atagcagaac tttaaaagtg ctcatcattg gaaaacgttc    6000
ttcggggcga aaactctcaa ggatcttacc gctgttgaga tccagttcga tgtaacccac    6060
tcgtgcaccc aactgatctt cagcatcttt tactttcacc gcgtttctg ggtgagcaaa     6120
aacaggaagg caaaatgccg caaaaaaggg aataagggcg acacggaaat gttgaatact    6180
catactcttc cttttcaat attattgaag catttatcag ggttattgtc tcatgagcgg     6240
atacatattt gaatgtattt agaaaaataa acaatagggg gttccgcgca catttccccg    6300
aaaagtgcca cctgacgtc                                                 6319

<210> 109
<211> 6295
<212> DNA
<213> Artificial sequence

<220>
<223> LSR zinc finger plasmid

<400> 109
gacggatcgg gagatctccc gatcccctat ggtcgactct cagtacaatc tgctctgatg     60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggac tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
```

```
tcgctattac catggtgatg cggttttggc agtacatcaa tgggcgtgga tagcggtttg     660
actcacgggg atttccaagt ctccacccca ttgacgtcaa tgggagtttg ttttggcacc     720
aaaatcaacg ggactttcca aatgtcgta acaactccgc cccattgacg caaatgggcg     780
gtaggcgtgt acggtgggag gtctatataa gcagagctct ctggctaact agagaaccca     840
ctgcttactg gcttatcgaa attaatacga ctcactatag ggagacccaa gctggctagc     900
gtttaaactt aagctgatcc actagtccag tgtggtggaa ttcgctagcg ccaccatggc     960
ccccaagaag aagaggaagg tgggaatcca tggggtaccg ggcaagaaga agcagcacat    1020
ctgccacatc cagggctgtg gtaaagttta cggccgctcc gaccacctgg cccgccacct    1080
gcgctggcac accggcgaga ggcctttcat gtgtacatgg tcctactgtg gtaaacgctt    1140
cacccgctcc gacgagctgc agcgccacaa gcgtacccac accggtgaga agaaatttgc    1200
ttgtccggaa tgtccgaagc gcttcatgcg ctccgacgag cgcaagcgcc acatcaagac    1260
ccaccagaac aagaaggtg gatctggtga tggcaagaag aagcagcaca tctgccacat    1320
ccagggctgt ggtaaagttt acggccgctc cgaccacctg accacccacc tgcgctggca    1380
caccggcgag aggcctttca tgtgtacatg gtcctactgt ggtaaacgct tcacccgctc    1440
cgaccacctg acccgccaca agcgtaccca caccggtgag aagaaatttg cttgtccgga    1500
atgtccgaag cgcttcatgc gctccgacca cctgaccacc cacatcaaga cccaccagaa    1560
caagaaggt ggatccgccc ccccgaccga tgtcagcctg ggggacgagc tccacttaga    1620
cggcgaggac gtggcgatgg cgcatgccga cgcgctagac gatttcgatc tggacatgtt    1680
ggggacggg gattccccgg ggccgggatt taccccccac gactccgccc cctacggcgc    1740
tctggatatg gccggcttcg agtttgagca gatgtttacc gatgcccttg gaattgacga    1800
gtacggtggg ggcagcgact acaaggacga cgatgacaag taagcttctc gagtctagag    1860
ggcccgttta aacccgctga tcagcctcga ctgtgccttc tagttgccag ccatctgttg    1920
tttgccctc ccccgtgcct tccttgaccc tggaaggtgc cactcccact gtcctttcct    1980
aataaaatga ggaaattgca tcgcattgtc tgagtaggtg tcattctatt ctggggggtg    2040
gggtggggca ggacagcaag ggggaggatt gggaagacaa tagcaggcat gctggggatg    2100
cggtgggctc tatggcttct gaggcggaaa gaaccagctg gggctctagg gggtatcccc    2160
acgcgccctg tagcggcgca ttaagcgcgg cgggtgtggt ggttacgcgc agcgtgaccg    2220
ctacacttgc cagcgcccta gcgcccgctc ctttcgcttt cttcccttcc tttctcgcca    2280
cgttcgccgg ctttccccgt caagctctaa atcggggcat ccctttaggg ttccgattta    2340
gtgctttacg gcacctcgac cccaaaaaac ttgattaggg tgatggttca cgtagtgggc    2400
```

```
catcgccctg atagacggtt tttcgccctt tgacgttgga gtccacgttc tttaatagtg    2460
gactcttgtt ccaaactgga acaacactca accctatctc ggtctattct tttgatttat    2520
aagggatttt ggggatttcg gcctattggt taaaaaatga gctgatttaa caaaaattta    2580
acgcgaatta attctgtgga atgtgtgtca gttagggtgt ggaaagtccc caggctcccc    2640
aggcaggcag aagtatgcaa agcatgcatc tcaattagtc agcaaccagg tgtggaaagt    2700
ccccaggctc cccagcaggc agaagtatgc aaagcatgca tctcaattag tcagcaacca    2760
tagtcccgcc cctaactccg cccatcccgc cctaactcc gcccagttcc gcccattctc    2820
cgccccatgg ctgactaatt tttttattt atgcagaggc cgaggccgcc tctgcctctg    2880
agctattcca gaagtagtga ggaggctttt ttggaggcct aggcttttgc aaaaagctcc    2940
cgggagcttg tatatccatt ttcggatctg atcaagagac aggatgagga tcgtttcgca    3000
tgattgaaca agatggattg cacgcaggtt ctccggccgc ttgggtggag aggctattcg    3060
gctatgactg ggcacaacag acaatcggct gctctgatgc cgccgtgttc cggctgtcag    3120 cgcagggcg cccggttctt tttgtcaaga ccgacctgtc cggtgccctg aatgaactgc    3180
aggacgaggc agcgcggcta tcgtggctgg ccacgacggg cgttccttgc gcagctgtgc    3240
tcgacgttgt cactgaagcg ggaagggact ggctgctatt gggcgaagtg ccggggcagg    3300
atctcctgtc atctcacctt gctcctgccg agaaagtatc catcatggct gatgcaatgc    3360
ggcggctgca tacgcttgat ccggctacct gcccattcga ccaccaagcg aaacatcgca    3420
tcgagcgagc acgtactcgg atggaagccg gtcttgtcga tcaggatgat ctggacgaag    3480
agcatcaggg gctcgcgcca gccgaactgt tcgccaggct caaggcgcgc atgcccgacg    3540
gcgaggatct cgtcgtgacc catggcgatg cctgcttgcc gaatatcatg gtggaaaatg    3600
gccgcttttc tggattcatc gactgtggcc ggctgggtgt ggcggaccgc tatcaggaca    3660
tagcgttggc tacccgtgat attgctgaag agcttggcgg cgaatgggct gaccgcttcc    3720
tcgtgcttta cggtatcgcc gctcccgatt cgcagcgcat cgccttctat cgccttcttg    3780
acgagttctt ctgagcggga ctctggggtt cgaaatgacc gaccaagcga cgcccaacct    3840
gccatcacga gatttcgatt ccaccgccgc cttctatgaa aggttgggct tcggaatcgt    3900
tttccgggac gccggctgga tgatcctcca gcgcgggat ctcatgctgg agttcttcgc    3960 ccacccaac ttgtttattg cagcttataa tggttacaaa taaagcaata gcatcacaa    4020 tttcacaaat aaagcatttt tttcactgca ttctagttgt ggtttgtcca aactcatcaa    4080
tgtatcttat catgtctgta taccgtcgac ctctagctag agcttggcgt aatcatggtc    4140
```

```
atagctgttt cctgtgtgaa attgttatcc gctcacaatt ccacacaaca tacgagccgg    4200
aagcataaag tgtaaagcct ggggtgccta atgagtgagc taactcacat taattgcgtt    4260
gcgctcactg cccgctttcc agtcgggaaa cctgtcgtgc cagctgcatt aatgaatcgg    4320
ccaacgcgcg gggagaggcg gtttgcgtat tgggcgctct tccgcttcct cgctcactga    4380
ctcgctgcgc tcggtcgttc ggctgcggcg agcggtatca gctcactcaa aggcggtaat    4440
acggttatcc acagaatcag gggataacgc aggaaagaac atgtgagcaa aaggccagca    4500
aaaggccagg aaccgtaaaa aggccgcgtt gctggcgttt ttccataggc tccgcccccc    4560
tgacgagcat cacaaaaatc gacgctcaag tcagaggtgg cgaaacccga caggactata    4620
aagataccag gcgtttcccc ctggaagctc cctcgtgcgc tctcctgttc cgaccctgcc    4680
gcttaccgga tacctgtccg cctttctccc ttcgggaagc gtggcgcttt ctcaatgctc    4740
acgctgtagg tatctcagtt cggtgtaggt cgttcgctcc aagctgggct gtgtgcacga    4800
accccccgtt cagcccgacc gctgcgcctt atccggtaac tatcgtcttg agtccaaccc    4860
ggtaagacac gacttatcgc cactggcagc agccactggt aacaggatta gcagagcgag    4920
gtatgtaggc ggtgctacag agttcttgaa gtggtggcct aactacggct acactagaag    4980
gacagtattt ggtatctgcg ctctgctgaa gccagttacc ttcggaaaaa gagttggtag    5040
ctcttgatcc ggcaaacaaa ccaccgctgg tagcggtggt ttttttgttt gcaagcagca    5100
gattacgcgc agaaaaaaag gatctcaaga agatcctttg atctttccta cggggtctga    5160
cgctcagtgg aacgaaaact cacgttaagg gattttggtc atgagattat caaaaaggat    5220
cttcacctag atccttttaa attaaaaatg aagttttaaa tcaatctaaa gtatatatga    5280
gtaaacttgg tctgacagtt accaatgctt aatcagtgag gcacctatct cagcgatctg    5340
tctatttcgt tcatccatag ttgcctgact ccccgtcgtg tagataacta cgatacggga    5400
gggcttacca tctggcccca gtgctgcaat gataccgcga gacccacgct caccggctcc    5460
agatttatca gcaataaacc agccagccgg aagggccgag cgcagaagtg gtcctgcaac    5520
tttatccgcc tccatccagt ctattaattg ttgccgggaa gctagagtaa gtagttcgcc    5580
agttaatagt ttgcgcaacg ttgttgccat tgctacaggc atcgtggtgt cacgctcgtc    5640
gtttggtatg gcttcattca gctccggttc ccaacgatca aggcgagtta catgatcccc    5700
catgttgtgc aaaaaagcgg ttagctcctt cggtcctccg atcgttgtca gaagtaagtt    5760
ggccgcagtg ttatcactca tggttatggc agcactgcat aattctctta ctgtcatgcc    5820
atccgtaaga tgcttttctg tgactggtga gtactcaacc aagtcattct gagaatagtg    5880
tatgcggcga ccgagttgct cttgcccggc gtcaatacgg gataataccg cgccacatag    5940
```

```
cagaacttta aaagtgctca tcattggaaa acgttcttcg gggcgaaaac tctcaaggat    6000
cttaccgctg ttgagatcca gttcgatgta acccactcgt gcacccaact gatcttcagc    6060
atcttttact ttcaccagcg tttctgggtg agcaaaaaca ggaaggcaaa atgccgcaaa    6120
aaagggaata agggcgacac ggaaatgttg aatactcata ctcttccttt ttcaatatta    6180
ttgaagcatt tatcagggtt attgtctcat gagcggatac atatttgaat gtatttagaa    6240
aaataaacaa atagggggttc cgcgcacatt tccccgaaaa gtgccacctg acgtc          6295
```

<210> 110
<211> 6319
<212> DNA
<213> Artificial sequence

<220>
<223> LSR zinc finger plasmid

<400> 110
```
gacggatcgg gagatctccc gatccccta  ggtcgactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180
ttagggttag gcgttttgcg ctgcttcgcg atgtacgggc cagatatacg cgttgacatt     240
gattattgac tagttattaa tagtaatcaa ttacggggtc attagttcat agcccatata     300
tggagttccg cgttacataa cttacggtaa atggcccgcc tggctgaccg cccaacgacc     360
cccgcccatt gacgtcaata atgacgtatg ttcccatagt aacgccaata gggactttcc     420
attgacgtca atgggtggac tatttacggt aaactgccca cttggcagta catcaagtgt     480
atcatatgcc aagtacgccc cctattgacg tcaatgacgg taaatggccc gcctggcatt     540
atgcccagta catgacctta tgggactttc ctacttggca gtacatctac gtattagtca     600
tcgctattac catggtgatg cggttttggc agtacatcaa tgggcgtgga tagcggtttg     660
actcacgggg atttccaagt ctccacccca ttgacgtcaa tgggagtttg ttttggcacc     720
aaaatcaacg ggactttcca aatgtcgta acaactccgc cccattgacg caaatgggcg     780
gtaggcgtgt acggtgggag gtctatataa gcagagctct ctggctaact agagaaccca     840
ctgcttactg gcttatcgaa attaatacga ctcactatag ggagacccaa gctggctagc     900
gtttaaactt aagctgatcc actagtccag tgtggtggaa ttcgctagcg ccaccatggc     960
ccccaagaag aagaggaagg tgggaatcca tggggtaccg ggcaagaaga agcagcacat    1020
ctgccacatc cagggctgtg gtaaagttta cggccagtcc ggcgccctga cccgccacct    1080
```

| | | | | | |
|---|---|---|---|---|---|
| gcgctggcac | accggcgaga | ggcctttcat | gtgtacatgg | tcctactgtg | gtaaacgctt | 1140 |
| cacccgctcc | gaccacctga | cccgccacaa | gcgtacccac | accggtgaga | agaaatttgc | 1200 |
| ttgtccggaa | tgtccgaagc | gcttcatgcg | ctccgacaac | ctgcgcgagc | acaacaagac | 1260 |
| ccaccagaac | aagaagggtg | gatctggtga | tggtggccgt | cgcggtggcg | gttctggcaa | 1320 |
| gaagaagcag | cacatctgcc | acatccaggg | ctgtggtaaa | gtttacggcc | gctcctccgc | 1380 |
| cctgacccgc | cacctgcgct | ggcacaccgg | cgagaggcct | tcatgtgta | catggtccta | 1440 |
| ctgtggtaaa | cgcttcaccc | agcgcgccca | cctggagcgc | cacaagcgta | cccacaccgg | 1500 |
| tgagaagaaa | tttgcttgtc | cggaatgtcc | gaagcgcttc | atgcgctccg | acaccctgcg | 1560 |
| cgagcacatc | aagacccacc | agaacaagaa | gggtggatcc | gccccccga | ccgatgtcag | 1620 |
| cctgggggac | gagctccact | agacggcga | ggacgtggcg | atggcgcatg | ccgacgcgct | 1680 |
| agacgatttc | gatctggaca | tgttggggga | cggggattcc | ccggggccgg | gatttacccc | 1740 |
| ccacgactcc | gcccctacg | gcgctctgga | tatggccggc | ttcgagtttg | agcagatgtt | 1800 |
| taccgatgcc | cttggaattg | acgagtacgg | tgggggcagc | gactacaagg | acgacgatga | 1860 |
| caagtaagct | tctcgagtct | agagggcccg | tttaaacccg | ctgatcagcc | tcgactgtgc | 1920 |
| cttctagttg | ccagccatct | gttgtttgcc | cctcccccgt | gccttccttg | accctggaag | 1980 |
| gtgccactcc | cactgtcctt | tcctaataaa | atgaggaaat | tgcatcgcat | tgtctgagta | 2040 |
| ggtgtcattc | tattctgggg | ggtggggtgg | ggcaggacag | caagggggag | gattgggaag | 2100 |
| acaatagcag | gcatgctggg | gatgcggtgg | gctctatggc | ttctgaggcg | gaaagaacca | 2160 |
| gctggggctc | taggggggtat | ccccacgcgc | cctgtagcgg | cgcattaagc | gcggcgggtg | 2220 |
| tggtggttac | gcgcagcgtg | accgctacac | ttgccagcgc | cctagcgccc | gctcctttcg | 2280 |
| ctttcttccc | ttcctttctc | gccacgttcg | ccggctttcc | ccgtcaagct | ctaaatcggg | 2340 |
| gcatcccttt | agggttccga | tttagtgctt | tacggcacct | cgaccccaaa | aaacttgatt | 2400 |
| agggtgatgg | ttcacgtagt | gggccatcgc | cctgatagac | ggttttcgc | cctttgacgt | 2460 |
| tggagtccac | gttctttaat | agtggactct | tgttccaaac | tggaacaaca | ctcaaccta | 2520 |
| tctcggtcta | ttcttttgat | ttataaggga | ttttggggat | ttcggcctat | tggttaaaaa | 2580 |
| atgagctgat | ttaacaaaaa | tttaacgcga | attaattctg | tggaatgtgt | gtcagttagg | 2640 |
| gtgtggaaag | tccccaggct | ccccaggcag | gcagaagtat | gcaaagcatg | catctcaatt | 2700 |
| agtcagcaac | caggtgtgga | aagtccccag | gctccccagc | aggcagaagt | atgcaaagca | 2760 |
| tgcatctcaa | ttagtcagca | accatagtcc | cgcccctaac | tccgcccatc | cgcccctaa | 2820 |
| ctccgcccag | ttccgcccat | tctccgcccc | atggctgact | aatttttttt | atttatgcag | 2880 |

```
aggccgaggc cgcctctgcc tctgagctat tccagaagta gtgaggaggc ttttttggag   2940
gcctaggctt ttgcaaaaag ctcccgggag cttgtatatc cattttcgga tctgatcaag   3000
agacaggatg aggatcgttt cgcatgattg aacaagatgg attgcacgca ggttctccgg   3060
ccgcttgggt ggagaggcta ttcggctatg actgggcaca acagacaatc ggctgctctg   3120
atgccgccgt gttccggctg tcagcgcagg ggcgcccggt tctttttgtc aagaccgacc   3180
tgtccggtgc cctgaatgaa ctgcaggacg aggcagcgcg gctatcgtgg ctggccacga   3240
cgggcgttcc ttgcgcagct gtgctcgacg ttgtcactga agcgggaagg gactggctgc   3300
tattgggcga agtgccgggg caggatctcc tgtcatctca ccttgctcct gccgagaaag   3360
tatccatcat ggctgatgca atgcggcggc tgcatacgct tgatccggct acctgcccat   3420
tcgaccacca agcgaaacat cgcatcgagc gagcacgtac tcggatggaa gccggtcttg   3480
tcgatcagga tgatctggac gaagagcatc aggggctcgc gccagccgaa ctgttcgcca   3540
ggctcaaggc gcgcatgccc gacggcgagg atctcgtcgt gacccatggc gatgcctgct   3600
tgccgaatat catggtggaa aatggccgct ttctggatt catcgactgt ggccggctgg   3660
gtgtggcgga ccgctatcag gacatagcgt tggctacccg tgatattgct gaagagcttg   3720
gcggcgaatg ggctgaccgc ttcctcgtgc tttacggtat cgccgctccc gattcgcagc   3780
gcatcgcctt ctatcgcctt cttgacgagt tcttctgagc gggactctgg ggttcgaaat   3840
gaccgaccaa gcgacgccca acctgccatc acgagatttc gattccaccg ccgccttcta   3900
tgaaaggttg ggcttcggaa tcgttttccg gacgccggc tggatgatcc tccagcgcgg   3960
ggatctcatg ctggagttct tcgcccaccc caacttgttt attgcagctt ataatggtta   4020
caaataaagc aatagcatca caaatttcac aaataaagca tttttttcac tgcattctag   4080
ttgtggtttg tccaaactca tcaatgtatc ttatcatgtc tgtataccgt cgacctctag   4140
ctagagcttg gcgtaatcat ggtcatagct gtttcctgtg tgaaattgtt atccgctcac   4200
aattccacac aacatacgag ccggaagcat aaagtgtaaa gcctggggtg cctaatgagt   4260
gagctaactc acattaattg cgttgcgctc actgcccgct ttccagtcgg gaaacctgtc   4320
gtgccagctg cattaatgaa tcggccaacg cgcgggaga ggcggtttgc gtattgggcg   4380
ctcttccgct tcctcgctca ctgactcgct gcgctcggtc gttcggctgc ggcgagcggt   4440
atcagctcac tcaaaggcgg taatacggtt atccacagaa tcaggggata acgcaggaaa   4500
gaacatgtga gcaaaaggcc agcaaaggc caggaaccgt aaaaaggccg cgttgctggc   4560
gtttttccat aggctccgcc ccctgacga gcatcacaaa atcgacgct caagtcagag   4620
```

```
gtggcgaaac ccgacaggac tataaagata ccaggcgttt ccccctggaa gctccctcgt    4680
gcgctctcct gttccgaccc tgccgcttac cggatacctg tccgcctttc tcccttcggg    4740
aagcgtggcg ctttctcaat gctcacgctg taggtatctc agttcggtgt aggtcgttcg    4800
ctccaagctg ggctgtgtgc acgaaccccc cgttcagccc gaccgctgcg ccttatccgg    4860
taactatcgt cttgagtcca acccggtaag acacgactta tcgccactgg cagcagccac    4920
tggtaacagg attagcagag cgaggtatgt aggcggtgct acagagttct tgaagtggtg    4980
gcctaactac ggctacacta gaaggacagt atttggtatc tgcgctctgc tgaagccagt    5040
taccttcgga aaagagttg gtagctcttg atccggcaaa caaaccaccg ctggtagcgg    5100
tggttttttt gtttgcaagc agcagattac gcgcagaaaa aaggatctc aagaagatcc    5160
tttgatcttt tctacggggt ctgacgctca gtggaacgaa aactcacgtt aagggatttt    5220
ggtcatgaga ttatcaaaaa ggatcttcac ctagatcctt ttaaattaaa aatgaagttt    5280
taaatcaatc taaagtatat atgagtaaac ttggtctgac agttaccaat gcttaatcag    5340
tgaggcacct atctcagcga tctgtctatt tcgttcatcc atagttgcct gactccccgt    5400
cgtgtagata actacgatac gggagggctt accatctggc cccagtgctg caatgatacc    5460
gcgagaccca cgctcaccgg ctccagattt atcagcaata aaccagccag ccggaagggc    5520
cgagcgcaga agtggtcctg caactttatc cgcctccatc cagtctatta attgttgccg    5580
ggaagctaga gtaagtagtt cgccagttaa tagtttgcgc aacgttgttg ccattgctac    5640
aggcatcgtg gtgtcacgct cgtcgtttgg tatggcttca ttcagctccg gttcccaacg    5700
atcaaggcga gttacatgat cccccatgtt gtgcaaaaaa gcggttagct ccttcggtcc    5760
tccgatcgtt gtcagaagta agttggccgc agtgttatca ctcatggtta tggcagcact    5820
gcataattct cttactgtca tgccatccgt aagatgcttt tctgtgactg gtgagtactc    5880
aaccaagtca ttctgagaat agtgtatgcg gcgaccgagt tgctcttgcc cggcgtcaat    5940
acgggataat accgcgccac atagcagaac tttaaaagtg ctcatcattg gaaaacgttc    6000
ttcggggcga aaactctcaa ggatcttacc gctgttgaga tccagttcga tgtaacccac    6060
tcgtgcaccc aactgatctt cagcatcttt tactttcacc agcgtttctg ggtgagcaaa    6120
aacaggaagg caaaatgccg caaaaaaggg aataaggcg acacggaaat gttgaatact    6180
catactcttc ctttttcaat attattgaag catttatcag ggttattgtc tcatgagcgg    6240
atacatattt gaatgtattt agaaaaataa acaataggg gttccgcgca catttccccg    6300
aaaagtgcca cctgacgtc                                                6319
```

<210> 111
<211> 6295
<212> DNA
<213> Artificial sequence

<220>
<223> LSR zinc finger plasmid

<400> 111

| | | | | | |
|---|---|---|---|---|---|
| gacggatcgg | gagatctccc | gatccoctat | ggtcgactct | cagtacaatc | tgctctgatg | 60 |
| ccgcatagtt | aagccagtat | ctgctccctg | cttgtgtgtt | ggaggtcgct | gagtagtgcg | 120 |
| cgagcaaaat | ttaagctaca | acaaggcaag | gcttgaccga | caattgcatg | aagaatctgc | 180 |
| ttagggttag | gcgttttgcg | ctgcttcgcg | atgtacgggc | cagatatacg | cgttgacatt | 240 |
| gattattgac | tagttattaa | tagtaatcaa | ttacggggtc | attagttcat | agcccatata | 300 |
| tggagttccg | cgttacataa | cttacggtaa | atggcccgcc | tggctgaccg | cccaacgacc | 360 |
| cccgcccatt | gacgtcaata | atgacgtatg | ttcccatagt | aacgccaata | gggactttcc | 420 |
| attgacgtca | atgggtggac | tatttacggt | aaactgccca | cttggcagta | catcaagtgt | 480 |
| atcatatgcc | aagtacgccc | cctattgacg | tcaatgacgg | taaatggccc | gcctggcatt | 540 |
| atgcccagta | catgacctta | tgggactttc | ctacttggca | gtacatctac | gtattagtca | 600 |
| tcgctattac | catggtgatg | cggttttggc | agtacatcaa | tgggcgtgga | tagcggtttg | 660 |
| actcacgggg | atttccaagt | ctccacccca | ttgacgtcaa | tgggagtttg | ttttggcacc | 720 |
| aaaatcaacg | ggactttcca | aaatgtcgta | acaactccgc | cccattgacg | caaatgggcg | 780 |
| gtaggcgtgt | acggtgggag | gtctatataa | gcagagctct | ctggctaact | agagaaccca | 840 |
| ctgcttactg | gcttatcgaa | attaatacga | ctcactatag | ggagacccaa | gctggctagc | 900 |
| gtttaaactt | aagctgatcc | actagtccag | tgtggtggaa | ttcgctagcg | ccaccatggc | 960 |
| ccccaagaag | aagaggaagg | tgggaatcca | tgggtaccg | ggcaagaaga | agcagcacat | 1020 |
| ctgccacatc | cagggctgtg | gtaaagttta | cggcgagcgc | ggcgacctga | ccgccacct | 1080 |
| gcgctggcac | accggcgaga | ggcctttcat | gtgtacatgg | tcctactgtg | gtaaacgctt | 1140 |
| caccgacccg | ggcgccctgg | tgcgccacaa | gcgtacccac | accggtgaga | agaaatttgc | 1200 |
| ttgtccggaa | tgtccgaagc | gcttcatgcg | ctccgacaac | ctgacccagc | acatcaagac | 1260 |
| ccaccagaac | aagaagggtg | gatctggtga | tggcaagaag | aagcagcaca | tctgccacat | 1320 |
| ccagggctgt | ggtaaagttt | acggccagtc | cggcaccctg | acccgccacc | tgcgctggca | 1380 |
| caccggcgag | aggcctttca | tgtgtacatg | gtcctactgt | ggtaaacgct | tcacccagtc | 1440 |
| ctccgacctg | cagcgccaca | gcgtaccca | caccggtgag | aagaaatttg | cttgtccgga | 1500 |

```
atgtccgaag cgcttcatgc gctccgacgc cctggcccgc cacatcaaga cccaccagaa   1560
caagaagggt ggatccgccc ccccgaccga tgtcagcctg ggggacgagc tccacttaga   1620
cggcgaggac gtggcgatgg cgcatgccga cgcgctagac gatttcgatc tggacatgtt   1680
gggggacggg gattccccgg ggccgggatt tacccccac gactccgccc cctacggcgc    1740
tctggatatg gccggcttcg agtttgagca gatgtttacc gatgcccttg gaattgacga   1800
gtacggtggg ggcagcgact acaaggacga cgatgacaag taagcttctc gagtctagag   1860
ggcccgttta acccgctga tcagcctcga ctgtgccttc tagttgccag ccatctgttg     1920 tttgccccte cccegtgcct tccttgaccc tggaaggtgc cactcccact gtcctttcct    1980
aataaaatga ggaaattgca tcgcattgtc tgagtaggtg tcattctatt ctggggggtg   2040
gggtggggca ggacagcaag ggggaggatt gggaagacaa tagcaggcat gctgggatg    2100 cggtgggctc tatggcttct gaggcggaaa gaaccagctg gggctctagg gggtatcccc   2160
acgcgccctg tagcggcgca ttaagcgcgg cgggtgtggt ggttacgcgc agcgtgaccg   2220
ctacacttgc cagcgcccta gcgcccgctc ctttcgcttt cttcccttcc tttctcgcca   2280
cgttcgccgg ctttccccgt caagctctaa atcggggcat ccctttaggg ttccgattta   2340
gtgctttacg gcacctcgac cccaaaaaac ttgattaggg tgatggttca cgtagtgggc   2400
catcgccctg atagacggtt tttcgccctt tgacgttgga gtccacgttc tttaatagtg   2460
gactcttgtt ccaaactgga acaacactca accctatctc ggtctattct tttgatttat    2520
aagggatttt ggggatttcg gcctattggt taaaaaatga gctgatttaa caaaaattta    2580
acgcgaatta attctgtgga atgtgtgtca gttagggtgt ggaaagtccc caggctcccc   2640
aggcaggcag aagtatgcaa agcatgcatc tcaattagtc agcaaccagg tgtggaaagt   2700
ccccaggctc cccagcaggc agaagtatgc aaagcatgca tctcaattag tcagcaacca   2760
tagtcccgcc cctaactccg cccatcccgc cctaactcc gcccagttcc gcccattctc     2820
cgccccatgg ctgactaatt ttttttattt atgcagaggc cgaggccgcc tctgcctctg    2880
agctattcca gaagtagtga ggaggctttt ttggaggcct aggcttttgc aaaaagctcc   2940
cgggagcttg tatatccatt ttcggatctg atcaagagac aggatgagga tcgtttcgca   3000
tgattgaaca agatggattg cacgcaggtt ctccggccgc ttgggtggag aggctattcg   3060
gctatgactg ggcacaacag acaatcggct gctctgatgc cgccgtgttc cggctgtcag   3120 cgcagggcg cccggttctt tttgtcaaga ccgacctgtc cggtgccctg aatgaactgc     3180
aggacgaggc agcgcggcta tcgtggctgg ccacgacggg cgttccttgc gcagctgtgc   3240
tcgacgttgt cactgaagcg ggaagggact ggctgctatt gggcgaagtg ccggggcagg   3300
```

```
atctcctgtc atctcacctt gctcctgccg agaaagtatc catcatggct gatgcaatgc   3360
ggcggctgca tacgcttgat ccggctacct gcccattcga ccaccaagcg aaacatcgca   3420
tcgagcgagc acgtactcgg atggaagccg gtcttgtcga tcaggatgat ctggacgaag   3480
agcatcaggg gctcgcgcca gccgaactgt tcgccaggct caaggcgcgc atgcccgacg   3540
gcgaggatct cgtcgtgacc catggcgatg cctgcttgcc gaatatcatg gtggaaaatg   3600
gccgcttttc tggattcatc gactgtggcc ggctgggtgt ggcggaccgc tatcaggaca   3660
tagcgttggc tacccgtgat attgctgaag agcttggcgg cgaatgggct gaccgcttcc   3720
tcgtgcttta cggtatcgcc gctcccgatt cgcagcgcat cgccttctat cgccttcttg   3780
acgagttctt ctgagcggga ctctggggtt cgaaatgacc gaccaagcga cgcccaacct   3840
gccatcacga gatttcgatt ccaccgccgc cttctatgaa aggttgggct tcggaatcgt   3900
tttccgggac gccggctgga tgatcctcca gcgcgggat ctcatgctgg agttcttcgc   3960
ccacccaac ttgtttattg cagcttataa tggttacaaa taaagcaata gcatcacaaa   4020
tttcacaaat aaagcatttt tttcactgca ttctagttgt ggtttgtcca aactcatcaa   4080
tgtatcttat catgtctgta taccgtcgac ctctagctag agcttggcgt aatcatggtc   4140
atagctgttt cctgtgtgaa attgttatcc gctcacaatt ccacacaaca tacgagccgg   4200
aagcataaag tgtaaagcct ggggtgccta atgagtgagc taactcacat taattgcgtt   4260
gcgctcactg cccgctttcc agtcgggaaa cctgtcgtgc cagctgcatt aatgaatcgg   4320
ccaacgcgcg gggagaggcg gtttgcgtat tgggcgctct tccgcttcct cgctcactga   4380
ctcgctgcgc tcggtcgttc ggctgcggcg agcggtatca gctcactcaa aggcggtaat   4440
acggttatcc acagaatcag gggataacgc aggaaagaac atgtgagcaa aaggccagca   4500
aaaggccagg aaccgtaaaa aggccgcgtt gctggcgttt ttccataggc tccgcccccc   4560
tgacgagcat cacaaaaatc gacgctcaag tcagaggtgg cgaaacccga caggactata   4620
aagataccag gcgtttcccc ctggaagctc cctcgtgcgc tctcctgttc cgaccctgcc   4680
gcttaccgga tacctgtccg cctttctccc ttcgggaagc gtggcgcttt ctcaatgctc   4740
acgctgtagg tatctcagtt cggtgtaggt cgttcgctcc aagctgggct gtgtgcacga   4800
accccccgtt cagcccgacc gctgcgcctt atccggtaac tatcgtcttg agtccaaccc   4860
ggtaagacac gacttatcgc cactggcagc agccactggt aacaggatta gcagagcgag   4920
gtatgtaggc ggtgctacag agttcttgaa gtggtggcct aactacggct acactagaag   4980
gacagtattt ggtatctgcg ctctgctgaa gccagttacc ttcggaaaaa gagttggtag   5040
```

| | | | | |
|---|---|---|---|---|
| ctcttgatcc | ggcaaacaaa | ccaccgctgg | tagcggtggt | ttttttgttt gcaagcagca | 5100
| gattacgcgc | agaaaaaaag | gatctcaaga | agatcctttg | atcttttcta cggggtctga | 5160
| cgctcagtgg | aacgaaaact | cacgttaagg | gattttggtc | atgagattat caaaaaggat | 5220
| cttcacctag | atccttttaa | attaaaaatg | aagttttaaa | tcaatctaaa gtatatatga | 5280
| gtaaacttgg | tctgacagtt | accaatgctt | aatcagtgag | gcacctatct cagcgatctg | 5340
| tctatttcgt | tcatccatag | ttgcctgact | ccccgtcgtg | tagataacta cgatacggga | 5400
| gggcttacca | tctggcccca | gtgctgcaat | gataccgcga | gacccacgct caccggctcc | 5460
| agatttatca | gcaataaacc | agccagccgg | aagggccgag | cgcagaagtg gtcctgcaac | 5520
| tttatccgcc | tccatccagt | ctattaattg | ttgccgggaa | gctagagtaa gtagttcgcc | 5580
| agttaatagt | ttgcgcaacg | ttgttgccat | tgctacaggc | atcgtggtgt cacgctcgtc | 5640
| gtttggtatg | gcttcattca | gctccggttc | ccaacgatca | aggcgagtta catgatcccc | 5700
| catgttgtgc | aaaaaagcgg | ttagctcctt | cggtcctccg | atcgttgtca gaagtaagtt | 5760
| ggccgcagtg | ttatcactca | tggttatggc | agcactgcat | aattctctta ctgtcatgcc | 5820
| atccgtaaga | tgcttttctg | tgactggtga | gtactcaacc | aagtcattct gagaatagtg | 5880
| tatgcggcga | ccgagttgct | cttgcccggc | gtcaatacgg | gataataccg cgccacatag | 5940
| cagaacttta | aaagtgctca | tcattggaaa | acgttcttcg | gggcgaaaac tctcaaggat | 6000
| cttaccgctg | ttgagatcca | gttcgatgta | acccactcgt | gcacccaact gatcttcagc | 6060
| atcttttact | ttcaccagcg | tttctgggtg | agcaaaaaca | ggaaggcaaa atgccgcaaa | 6120
| aaagggaata | agggcgacac | ggaaatgttg | aatactcata | ctcttccttt ttcaatatta | 6180
| ttgaagcatt | tatcagggtt | attgtctcat | gagcggatac | atatttgaat gtatttagaa | 6240
| aaataaacaa | ataggggttc | cgcgcacatt | tccccgaaaa | gtgccacctg acgtc | 6295

<210> 112
<211> 9
<212> PRT
<213> Mus musculus

<400> 112

Cys Pro Asp Arg Ala Ser Ala Ile Gln
1               5

<210> 113
<211> 14
<212> PRT
<213> Mus musculus

<400> 113

Glu Glu Gly His Tyr Pro Pro Ala Pro Pro Tyr Ser Glu Thr
1               5                   10

<210> 114
<211> 21
<212> DNA
<213> Artificial sequence

<220>
<223> GAPDH forward primer

<400> 114
aacgacccct tcattgacct c                                    21

<210> 115
<211> 19
<212> DNA
<213> Artificial sequence

<220>
<223> GAPDH reverse primer

<400> 115
cttcccattc tcggccttg                                       19

<210> 116
<211> 25
<212> DNA
<213> Artificial sequence

<220>
<223> GAPDH probe

<400> 116
actcacggca aattcaacgg cacag                                25

<210> 117
<211> 21
<212> DNA
<213> Artificial sequence

<220>
<223> LSR complete forward primer

<400> 117
ggcaggagaa tcaccatcac a                                    21

<210> 118
<211> 20
<212> DNA
<213> Artificial sequence

```
<220>
<223>  LSR complete reverse primer

<400>  118
gatcttgggc tgagaccacg                                                      20

<210>  119
<211>  24
<212>  DNA
<213>  Artificial sequence

<220>
<223>  LSR complete probe

<400>  119
tgctggcctg accttcgagc agac                                                 24

<210>  120
<211>  20
<212>  DNA
<213>  Artificial sequence

<220>
<223>  LSR alpha forward primer

<400>  120
gcccttggaa gattggctct                                                      20

<210>  121
<211>  20
<212>  DNA
<213>  Artificial sequence

<220>
<223>  LSR alpha reverse primer

<400>  121
atgcttggca cacctgaggt                                                      20

<210>  122
<211>  23
<212>  DNA
<213>  Artificial sequence

<220>
<223>  LSR alpha probe

<400>  122
ccagtgctgt ccccacacct gct                                                  23

<210>  123
<211>  20
<212>  DNA
<213>  Artificial sequence
```

```
<220>
<223>  LSR alpha' forward primer

<400>  123
accagggcag gagaatcacc                                              20

<210>  124
<211>  21
<212>  DNA
<213>  Artificial sequence

<220>
<223>  LSR alpha' reverse primer

<400>  124
ggaggaagaa gaggaggctt g                                            21

<210>  125
<211>  29
<212>  DNA
<213>  Artificial sequence

<220>
<223>  LSR alpha' probe

<400>  125
agctcattgt ccttgattgg ctctttgtg                                    29

<210>  126
<211>  22
<212>  DNA
<213>  Artificial sequence

<220>
<223>  LSR beta forward primer

<400>  126
ttgtccttgt ttatgctgct gg                                           22

<210>  127
<211>  24
<212>  DNA
<213>  Artificial sequence

<220>
<223>  LSR beta reverse primer

<400>  127
caggagagag gtgggtatag atgc                                         24

<210>  128
<211>  23
<212>  DNA
```

CERTIFICATE OF CORRECTION (continued)
U.S. Pat. No. 7,470,669 B2

```
<213>  Artificial sequence

<220>
<223>  LSR beta probe

<400>  128
agcagccacc tcaggtgtgc caa                                              23

<210>  129
<211>  8
<212>  PRT
<213>  Homo sapiens

<400>  129

Leu Gly Gly Val Leu Glu Ala Ser
1               5
```

UNITED STATES PATENT AND TRADEMARK OFFICE
CERTIFICATE OF CORRECTION

| | |
|---|---|
| PATENT NO. | : 7,470,669 B2 |
| APPLICATION NO. | : 11/236198 |
| DATED | : December 30, 2008 |
| INVENTOR(S) | : Frances Yen et al. |

It is certified that error appears in the above-identified patent and that said Letters Patent is hereby corrected as shown below:

Column 5,
Line 12, "a amino acid" should read --an amino acid--.

Column 6,
Lines 42-43, "SEQ ID NO: 1" should read --SEQ ID NO: 11--.

Column 15,
Lines 37-38, "a (N—N) bound" should read --a (N—N) bond--.

Column 17,
Line 31, "80, 90, 10, 110" should read --80, 90, 100, 110--.

Column 25,
Line 33, "al the site" should read --at the site--.
Line 35, "endogenous TSR gene" should read --endogenous LSR gene--.

Column 29,
Line 29, "the book or" should read --the book of--.

Column 34,
Line 3, "; No. 1651)" should read --; No. CRL1651)--.

Column 35,
Line 56, "a LULL" should read --a LI/LL--.

This certificate supersedes the Certificate of Correction issued November 9, 2010.

Signed and Sealed this
Fifteenth Day of February, 2011

David J. Kappos
*Director of the United States Patent and Trademark Office*

Column 37,
Line 35, "Van der Waal s forces" should read --Van der Waals forces--.
Lines 39-40, "the now-leptin compounds" should read --the non-leptin compounds--.

Column 47,
Line 55, "zinc linger" should read --zinc finger--.

Column 49,
Line 65, "Fir FIG. 6C" should read --For FIG. 6C--.

Column 51,
Line 14, "125I-LDL" should read --$^{125}$I-LDL--.

Column 56,
Line 13, "125I-leptin" should read --$^{125}$I-leptin--.
Lines 13-14, "After six 10 mm washes" should read --After six 10 min washes--.

Column 61,
Line 25, "the amino terminal end" should read --the amino terminal end.--.

Column 62,
Lines 60-61, "Plasma TG 2-3 hours nafter test meal (mg/mL)" should read
--Plasma TG 2-3 hours after test meal (mg/mL)--.

Column 71,
Line 15, "Reverse Primer: AGTGTTCTATGGGCCCCGC (SEQ ID NO: 84)" should
read --Reverse Primer: AGTCTTCTATGGGCCCCGC (SEQ ID NO: 84)--.
Lines 50-51, "5'-GGTTGTGGTATGCCTGGCTGGGTTCTTTTgaaggcagccAGTCA
taccacaaccGCGCGTTTTCGCGC-3'" should read
--5'-GGTTGTGGTATGCCTGGCTGCCTTCTTTTgaaggcagccAGTCA
taccacaaccGCGCGTTTTCGCGC-3'--.

Column 78,
Line 17, "e.g. 0, 0.1 mM 0.2 mM," should read --e.g. 0, 0.1 mM, 0.2 mM,--.

Column 80,
Line 17, ""$^{125}$labelled LDL" should read --$^{125}$I labelled LDL--.

Column 82,
Table 1, Row "GAPDH", column "Probe",
"ACTCACGGCAAATTTCAACGGCACAG" should read
--ACTCACGGCAAATTCAACGGCACAG--.

CERTIFICATE OF CORRECTION (continued)
U.S. Pat. No. 7,470,669 B2

Column 83,
Table 1, Row "NZB normal", column "LSR-alpha",
  "SEM 44.46" should read --SEM 4446--.

Column 88,
Line 40, "embodiments of the invention has been" should read
  --embodiments of the invention have been--.

Columns 91-238,
Delete sequence listing and replace with attached sequence listing.

SEQUENCE LISTING

```
<110> Yen, Frances
      Bihain, Bernard
      Erickson, Mary Ruth
      Fruebis, Joachim <120> Methods of Screening for Compounds that Modulate the
LSR-Leptin Interaction and Their Use in the Prevention
and Treatment of Obesity-Related Diseases

<130> G-070US03CON

<140> US 11/236,198
<141> 2005-09-07

<150> 60/155,506
<151> 1999-09-22

<160> 129

<170> Patent.pm

<210> 1
<211> 23187
<212> DNA
<213> Homo sapiens

<220>
<221> exon
<222> 2001..2356
<223> exon1

<220>
<221> exon
<222> 3540..3884
<223> exon2

<220>
<221> exon
<222> 12163..12282
<223> exon3

<220>
<221> exon
<222> 15144..15200
<223> exon4

<220>
<221> exon
<222> 15765..15911
<223> exon5

<220>
<221> exon
<222> 19579..19752
<223> exon6
```

```
<220>
<221> exon
<222> 19899..19958
<223> exon7

<220>
<221> exon
<222> 20056..20187
<223> exon8

<220>
<221> exon
<222> 20329..20957
<223> exon9

<220>
<221> exon
<222> 21047..21187
<223> exon10

<220>
<221> polyA_signal
<222> 21168..21173
<223> AATAAA

<220>
<221> misc_feature
<222> 1..2000
<223> potential  5'regulatory  region

<220>
<221> misc_feature
<222> 22324..23187
<223> homology  with  USF2  gene  in  ref:  embl  Y07661

<220>
<221> primer_bind
<222> 523..544
<223> upstream amplification primer 17-2

<220>
<221> primer_bind
<222> 1047..1068
<223> downstream amplification primer 17-2 , complement <220>
<221> primer_bind
<222> 946..963
<223> upstream amplification primer 99-4576

<220>
<221> primer_bind
<222> 1385..1402
<223> downstream amplification primer 99-4576 , complement <220>
<221> primer_bind
<222> 1096..1115
<223> upstream amplification primer 9-19
```

```
<220>
<221> primer_bind
<222> 1616..1635
<223> downstream amplification primer 9-19 , complement <220>
<221> primer_bind
<222> 1602..1621
<223> upstream amplification primer 9-20

<220>
<221> primer_bind
<222> 2074..2093
<223> downstream amplification primer 9-20 , complement <220>
<221> primer_bind
<222> 2036..2053
<223> upstream amplification primer 99-4557

<220>
<221> primer_bind
<222> 2563..2580
<223> downstream amplification primer 99-4557 , complement <220>
<221> primer_bind
<222> 2084..2102
<223> upstream amplification primer 9-1

<220>
<221> primer_bind
<222> 2483..2500
<223> downstream amplification primer 9-1 , complement <220>
<221> primer_bind
<222> 2470..2489
<223> upstream amplification primer 9-21 , complement <220>
<221> primer_bind
<222> 2062..2081
<223> downstream amplification primer 9-21

<220>
<221> primer_bind
<222> 3455..3474
<223> upstream amplification primer 9-3

<220>
<221> primer_bind
<222> 3882..3901
<223> downstream amplification primer 9-3 , complement <220>
<221> primer_bind
<222> 3775..3792
```

<223> upstream amplification primer 99-4558

<220>
<221> primer_bind
<222> 4336..4356
<223> downstream amplification primer 99-4558 , complement <220>
<221> primer_bind
<222> 4902..4920
<223> upstream amplification primer 99-14419 , complement <220>
<221> primer_bind
<222> 4444..4463
<223> downstream amplification primer 99-14419

<220>
<221> primer_bind
<222> 6638..6655
<223> upstream amplification primer 99-4577

<220>
<221> primer_bind
<222> 7072..7089
<223> downstream amplification primer 99-4577 , complement <220>
<221> primer_bind
<222> 7995..8012
<223> upstream amplification primer 99-4559

<220>
<221> primer_bind
<222> 8576..8593
<223> downstream amplification primer 99-4559 , complement <220>
<221> primer_bind
<222> 9622..9639
<223> upstream amplification primer 99-3148

<220>
<221> primer_bind
<222> 10023..10040
<223> downstream amplification primer 99-3148 , complement <220>
<221> primer_bind
<222> 9964..9981
<223> upstream amplification primer 99-4560

<220>
<221> primer_bind
<222> 10546..10563
<223> downstream amplification primer 99-4560 , complement <220>
<221> primer_bind <222> 10996..11015
<223> upstream amplification primer 99-14411 , complement <220>
<221> primer_bind
<222> 10492..10512
<223> downstream amplification primer 99-14411

<220>
<221> primer_bind
<222> 11972..11990
<223> upstream amplification primer 99-4561

<220>
<221> primer_bind
<222> 12481..12501
<223> downstream amplification primer 99-4561 , complement <220>
<221> primer_bind
<222> 12005..12023
<223> upstream amplification primer 9-4

<220>
<221> primer_bind
<222> 12417..12436
<223> downstream amplification primer 9-4 , complement <220>
<221> primer_bind
<222> 14102..14119
<223> upstream amplification primer 99-4562

<220>
<221> primer_bind
<222> 14543..14563
<223> downstream amplification primer 99-4562 , complement <220>
<221> primer_bind
<222> 14431..14448
<223> upstream amplification primer 99-3149

<220>
<221> primer_bind
<222> 14848..14865
<223> downstream amplification primer 99-3149 , complement <220>
<221> primer_bind
<222> 14748..14767
<223> upstream amplification primer 9-22

<220>
<221> primer_bind
<222> 15198..15218
<223> downstream amplification primer 9-22 , complement

<220>

```
<221> primer_bind
<222> 14748..14767
<223> upstream amplification primer 9-24

<220>
<221> primer_bind
<222> 15333..15351
<223> downstream amplification primer 9-24 , complement <220>
<221> primer_bind
<222> 15002..15019
<223> upstream amplification primer 9-5

<220>
<221> primer_bind
<222> 15333..15351
<223> downstream amplification primer 9-5 , complement <220>
<221> primer_bind
<222> 15640..15657
<223> upstream amplification primer 9-6

<220>
<221> primer_bind
<222> 16072..16089
<223> downstream amplification primer 9-6 , complement <220>
<221> primer_bind
<222> 15800..15817
<223> upstream amplification primer 99-4563

<220>
<221> primer_bind
<222> 16179..16199
<223> downstream amplification primer 99-4563 , complement <220>
<221> primer_bind
<222> 19295..19312
<223> upstream amplification primer 99-3150

<220>
<221> primer_bind
<222> 19729..19746
<223> downstream amplification primer 99-3150 , complement <220>
<221> primer_bind
<222> 19420..19438
<223> upstream amplification primer 9-7

<220>
<221> primer_bind
<222> 19824..19841
<223> downstream amplification primer 9-7 , complement
```

```
<220>
<221> primer_bind
<222> 19798..19815
<223> upstream amplification primer 9-8

<220>
<221> primer_bind
<222> 20137..20155
<223> downstream amplification primer 9-8 , complement <220>
<221> primer_bind
<222> 19913..19931
<223> upstream amplification primer 9-9

<220>
<221> primer_bind
<222> 20329..20346
<223> downstream amplification primer 9-9 , complement <220>
<221> primer_bind
<222> 20139..20157
<223> upstream amplification primer 99-4564

<220>
<221> primer_bind
<222> 20582..20599
<223> downstream amplification primer 99-4564 , complement <220>
<221> primer_bind
<222> 20238..20256
<223> upstream amplification primer 9-10

<220>
<221> primer_bind
<222> 20645..20662
<223> downstream amplification primer 9-10 , complement <220>
<221> primer_bind
<222> 20410..20424
<223> upstream amplification primer 9-26

<220>
<221> primer_bind
<222> 20690..20706
<223> downstream amplification primer 9-26 , complement <220>
<221> primer_bind
<222> 20569..20588
<223> upstream amplification primer 9-23

<220>
<221> primer_bind
<222> 21243..21262
<223> downstream amplification primer 9-23 , complement
```

```
<220>
<221> primer_bind
<222> 20583..20604
<223> upstream amplification primer 9-11

<220>
<221> primer_bind
<222> 21015..21034
<223> downstream amplification primer 9-11 , complement <220>
<221> primer_bind
<222> 20584..20601
<223> upstream amplification primer 99-15285 , complement <220>
<221> primer_bind
<222> 20139..20158
<223> downstream amplification primer 99-15285

<220>
<221> primer_bind
<222> 20642..20659
<223> upstream amplification primer 99-15287 , complement <220>
<221> primer_bind
<222> 20207..20227
<223> downstream amplification primer 99-15287

<220>
<221> primer_bind
<222> 20691..20709
<223> upstream amplification primer 99-15286 , complement <220>
<221> primer_bind
<222> 20238..20257
<223> downstream amplification primer 99-15286

<220>
<221> primer_bind
<222> 20943..20960
<223> upstream amplification primer 9-2

<220>
<221> primer_bind
<222> 21295..21312
<223> downstream amplification primer 9-2 , complement <220>
<221> primer_bind
<222> 21013..21031
<223> upstream amplification primer 99-15284 , complement <220>
<221> primer_bind
<222> 20582..20602
```

```
<223> downstream amplification primer 99-15284

<220>
<221> primer_bind
<222> 21019..21038
<223> upstream amplification primer 99-14407 , complement <220>
<221> primer_bind
<222> 20571..20589
<223> downstream amplification primer 99-14407

<220>
<221> primer_bind
<222> 21079..21097
<223> upstream amplification primer 99-15283 , complement <220>
<221> primer_bind
<222> 20638..20655
<223> downstream amplification primer 99-15283

<220>
<221> primer_bind
<222> 21013..21032
<223> upstream amplification primer LSRi9f15s <220>
<221> primer_bind
<222> 21195..21214
<223> downstream amplification primer LSRi10r14s , complement <220>
<221> primer_bind
<222> 20354..20372
<223> upstream amplification primer LSRx9f13s <220>
<221> primer_bind
<222> 20570..20591
<223> upstream amplification primer LSRx9f14s <220>
<221> primer_bind
<222> 20811..20832
<223> downstream amplification primer LSRx9r13s , complement <220>
<221> allele
<222> 818
<223> 17-2-297 : polymorphic base G or C <220>
<221> allele
<222> 1243
<223> 9-19-148 : polymorphic base C or T <220>
<221> allele
```

```
<222> 1374
<223> 9-19-256  :  polymorphic base  A  or  G

<220>
<221> allele
<222> 1401
<223> 9-19-307  :  polymorphic base  A  or  T

<220>
<221> allele
<222> 1535
<223> 9-19-442  :  polymorphic base  deletion  of  C <220>
<221> allele
<222> 1788
<223> 9-20-187  :  polymorphic base  A  or  C <220>
<221> allele
<222> 2391
<223> 9-1-308  :  polymorphic base  G  or  C <220>
<221> allele
<222> 3778
<223> 9-3-324  :  polymorphic base  C  or  T <220>
<221> allele
<222> 4498
<223> 99-14419-424  :  polymorphic base  T  or  G <220>
<221> allele
<222> 15007
<223> 9-24-260  :  polymorphic base  A  or  G <220>
<221> allele
<222> 15233
<223> 9-24-486  :  polymorphic base  A  or  G <220>
<221> allele
<222> 15826
<223> 9-6-187  :  polymorphic base  C  or  T <220>
<221> allele
<222> 19567
<223> 9-7-148  :  polymorphic base  A  or  G <220>
<221> allele
<222> 19744
<223> 9-7-325  :  polymorphic base  A  or  G

<220>
```

```
<221> allele
<222> 19786
<223> 9-7-367 : polymorphic base A or C

<220>
<221> allele
<222> 20158
<223> 9-9-246 : polymorphic base G or C

<220>
<221> allele
<222> 20595
<223> LSRX9-BM (17-1-240) : polymorphic base deletion of AGG <220>
<221> allele
<222> 21108
<223> LSRX10-BM : polymorphic base T or G <220>
<221> allele
<222> 606
<223> potential polymorphic base C or T <220>
<221> allele
<222> 5141
<223> potential polymorphic base insertion of G <220>
<221> allele
<222> 7428
<223> potential polymorphic base insertion of C <220>
<221> allele
<222> 8394
<223> potential polymorphic base C or G <220>
<221> allele
<222> 8704
<223> potential polymorphic base T or C <220>
<221> allele
<222> 9028
<223> potential polymorphic base G or A <220>
<221> allele
<222> 9950
<223> potential polymorphic base deletion of GAATGAAA <220>
<221> allele
<222> 9977
<223> potential polymorphic base T or C
```

```
<220>
<221> allele
<222> 10021
<223> potential  polymorphic  base  A  or  G

<220>
<221> allele
<222> 11878
<223> potential  polymorphic  base  C  or  T

<220>
<221> allele
<222> 19040
<223> potential  polymorphic  base  deletion  of  G <220>
<221> allele
<222> 21363
<223> potential  polymorphic  base  A  or  G <220>
<221> allele
<222> 21449
<223> potential  polymorphic  base  C  or  T <220>
<221> allele
<222> 21451
<223> potential  polymorphic  base  G  or  C <220>
<221> allele
<222> 21454
<223> potential  polymorphic  base  A  or  G <220>
<221> allele
<222> 21455
<223> potential  polymorphic  base  G  or  A <220>
<221> allele
<222> 21569
<223> potential  polymorphic  base  T  or  A <220>
<221> allele
<222> 21683
<223> potential  polymorphic  base  deletion  of  C <220>
<221> allele
<222> 21694
<223> potential  polymorphic  base  insertion  of  T <220>
<221> allele
<222> 21728
<223> potential  polymorphic  base  deletion  of  G
```

```
<220>
<221> misc_binding
<222> 799..817
<223> 17-2-297.mis1

<220>
<221> misc_binding
<222> 819..837
<223> complement 17-2-297.mis2

<220>
<221> misc_binding
<222> 1224..1242
<223> 9-19-148.mis1

<220>
<221> misc_binding
<222> 1244..1262
<223> complement 9-19-148.mis2

<220>
<221> misc_binding
<222> 1330..1373
<223> 9-19-256.mis1

<220>
<221> misc_binding
<222> 1375..1393
<223> complement 9-19-256.mis2

<220>
<221> misc_binding
<222> 1382..1400
<223> 9-19-307.mis1

<220>
<221> misc_binding
<222> 1402..1420
<223> complement 9-19-307.mis2

<220>
<221> misc_binding
<222> 1516..1534
<223> 9-19-442.mis1

<220>
<221> misc_binding
<222> 1769..1787
<223> 9-20-187.mis1

<220>
<221> misc_binding
<222> 1789..1807
<223> complement 9-20-187.mis2

<220>
<221> misc_binding
<222> 2372..2390
```

```
<223> 9-1-308.mis1

<220>
<221> misc_binding
<222> 2392..2410
<223> complement 9-1-308.mis2

<220>
<221> misc_binding
<222> 3759..3777
<223> 9-3-324.mis1

<220>
<221> misc_binding
<222> 3779..3797
<223> complement 9-3-324.mis2

<220>
<221> misc_binding
<222> 4979..4997
<223> 99-14419-424.mis2

<220>
<221> misc_binding
<222> 4999..5017
<223> complement 99-14419-424.mis1

<220>
<221> misc_binding
<222> 14988..15006
<223> 9-24-260.mis1

<220>
<221> misc_binding
<222> 15008..15026
<223> complement 9-24-260.mis2

<220>
<221> misc_binding
<222> 15214..15232
<223> 9-24-486.mis1

<220>
<221> misc_binding
<222> 15234..15252
<223> complement 9-24-486.mis2

<220>
<221> misc_binding
<222> 15807..15825
<223> 9-6-187.mis1

<220>
<221> misc_binding
<222> 15827..15845
<223> complement 9-6-187.mis2

<220>
<221> misc_binding
```

```
<222> 19548..19566
<223> 9-7-148.mis1

<220>
<221> misc_binding
<222> 19568..19586
<223> complement 9-7-148.mis2

<220>
<221> misc_binding
<222> 19725..19743
<223> 9-7-325.mis1

<220>
<221> misc_binding
<222> 19745..19763
<223> complement 9-7-325.mis2

<220>
<221> misc_binding
<222> 19767..19785
<223> 9-7-367.mis1

<220>
<221> misc_binding
<222> 19787..19805
<223> complement 9-7-367.mis2

<220>
<221> misc_binding
<222> 20139..20157
<223> 9-9-246.mis1

<220>
<221> misc_binding
<222> 20159..20177
<223> complement 9-9-246.mis2

<220>
<221> misc_binding
<222> 20576..20594
<223> LSRX9-BM.mis1(17-1-240)

<220>
<221> misc_binding
<222> 20596..20614
<223> complement LSRX9-BM.mis2(17-1-240)

<220>
<221> misc_binding
<222> 21089..21107
<223> LSRX10-BM.mis1

<220>
<221> misc_binding
<222> 21109..21127
<223> complement LSRX10-BM.mis2

<220>
```

```
<221> misc_binding
<222> 587..605
<223> potentialsite606.mis1   potential

<220>
<221> misc_binding
<222> 607..625
<223> complement potentialsite606.mis2   potential <220>
<221> misc_binding
<222> 5122..5140
<223> potentialsite5141.mis1   potential <220>
<221> misc_binding
<222> 5142..5160
<223> complement potentialsite5141.mis2   potential <220>
<221> misc_binding
<222> 7409..7427
<223> potentialsite7428.mis1   potential <220>
<221> misc_binding
<222> 7429..7447
<223> complement potentialsite7428.mis2   potential <220>
<221> misc_binding
<222> 8375..8393
<223> potentialsite8394.mis1   potential <220>
<221> misc_binding
<222> 8395..8413
<223> complement potentialsite8394.mis2   potential <220>
<221> misc_binding
<222> 8685..8703
<223> potentialsite8704.mis1   potential <220>
<221> misc_binding
<222> 8705..8723
<223> complement potentialsite8704.mis2   potential <220>
<221> misc_binding
<222> 9009..9027
<223> potentialsite9028.mis1   potential <220>
<221> misc_binding
<222> 9029..9047
<223> complement potentialsite9028.mis2   potential
```

```
<220>
<221> misc_binding
<222> 9931..9949
<223> potentialsite9950.mis1   potential <220>
<221> misc_binding
<222> 9951..9969
<223> complement potentialsite9950.mis2  potential <220>
<221> misc_binding
<222> 9958..9976
<223> potentialsite9977.mis1   potential <220>
<221> misc_binding
<222> 9978..9996
<223> complement potentialsite9977.mis2  potential <220>
<221> misc_binding
<222> 10002..10020
<223> potentialsite10021.mis1   potential <220>
<221> misc_binding
<222> 10022..10040
<223> complement potentialsite10021.mis2  potential <220>
<221> misc_binding
<222> 11859..11877
<223> potentialsite11878.mis1   potential <220>
<221> misc_binding
<222> 11879..11897
<223> complement potentialsite11878.mis2  potential <220>
<221> misc_binding
<222> 19021..19039
<223> potentialsite19040.mis1   potential <220>
<221> misc_binding
<222> 19041..19059
<223> complement potentialsite19040.mis2  potential <220>
<221> misc_binding
<222> 21344..21362
<223> potentialsite21363.mis1   potential <220>
<221> misc_binding
<222> 21364..21382
<223> complement potentialsite21363.mis2  potential
```

```
<220>
<221> misc_binding
<222> 21430..21448
<223> potentialsite21449.mis1  potential <220>
<221> misc_binding
<222> 21450..21468
<223> complement potentialsite21449.mis2  potential <220>
<221> misc_binding
<222> 21432..21450
<223> potentialsite21451.mis1  potential <220>
<221> misc_binding
<222> 21452..21470
<223> complement potentialsite21451.mis2  potential <220>
<221> misc_binding
<222> 21435..21453
<223> potentialsite21454.mis1  potential <220>
<221> misc_binding
<222> 21455..21473
<223> complement potentialsite21454.mis2  potential <220>
<221> misc_binding
<222> 21436..21454
<223> potentialsite21455.mis1  potential <220>
<221> misc_binding
<222> 21456..21474
<223> complement potentialsite21455.mis2  potential <220>
<221> misc_binding
<222> 21550..21568
<223> potentialsite21569.mis1  potential <220>
<221> misc_binding
<222> 21570..21588
<223> complement potentialsite21569.mis2  potential <220>
<221> misc_binding
<222> 21664..21682
<223> potentialsite21683.mis1  potential <220>
<221> misc_binding
<222> 21684..21702
```

<223> complement potentialsite21683.mis2 potential

<220>
<221> misc_binding
<222> 21675..21693
<223> potentialsite21694.mis1 potential <220>
<221> misc_binding
<222> 21695..21713
<223> complement potentialsite21694.mis2 potential <220>
<221> misc_binding
<222> 21709..21727
<223> potentialsite21728.mis1 potential <220>
<221> misc_binding
<222> 21729..21747
<223> complement potentialsite21728.mis2 potential <220>
<221> misc_feature
<222> 22113,22122,22227,22264,22268
<223> n=a, g, c or t

<400> 1

```
ccataatcaa gaaaatggat aataagtttt ggtggggatg tggagaaatt ggaatcctcc      60
gtgcattgct ggtgggaatg tacaatagtg cagtcattgg ggaaaacagt ttggcagttc     120
ctcaaaaggt taaaaataga actaccaagt cacccagcaa ttccattctt aggcatatat     180
tcaaaagaaa tgaaagcaga tatttgtaca ccagtgttca cagctgcact atttacaata     240
gtcaaaaggt agaaacaacc taggtccatc cacaaatgaa tggataaata aaacgtagca     300
tatacataca atggtacact agtccgctgt aaaaagaaat tttgatctta ctgcatgcta     360
catggcttcg acatactaca acatggatgg acttgaaaaa cattattctt tgtgaaataa     420
actagacaca ggacaaatgt tagacgattc cacttatatg aggcacctag aatgggcaat     480
ttggtaagca aagtagaata gaattacta ggggcacagg tagcagggaa tggggagtta     540
ctgtttaatg gtcacagagt ttatgttggg gatgatgaaa cagtttcggg gataaagagt     600
ggtgactggt acacgacatt gtaatatac ttaatgccac tgaattttac acttgaagtg      660
gttaaagcga taaatattat agtttgcata ttttatcata aaaatatttt tttaaacgat     720
gaagggacgt gaacgggttg aaatttttata aaaagtggcc agggaaggtg tcactgcaat     780
ggtgtcctac aggaggagga agatcatgtg gacatctccg ggaagggtgt tctggcagag     840
ggagtagcac gggcgatggc tctgaggact gtgagaagta tagttggaaa cagcgaggag     900
gccagggtgt ccgaagctga gtaagccaga gagagtggga ggaggtgaga taagaggggg     960
aaggtcagtt tctgctgaga gtgaggagga gccacaggag ggctgtgagc aggtggacgt    1020
gatctggctt gagttttaac agggccagta gaacaaagca cgcctgggta ccgaaaccag    1080
ccactggcca gttggcaacc tgggggagtc taacgcgagg aagcgcccag ggttccccca    1140
ggatgcgctt tccctcgccg ccacctggag acagcagagt cacgcccagc gctgcgcagg    1200
ctgatcgccg cgccgcgccc ccgccctcgg tcgcaggtgg ctygttccgg gaattcctaa    1260
gcggaaaccg gtcccaagcc ccgcgccttc gctcggcccc tttaagagcc agaatttccg    1320
gagggctgac ccggggctag ggatgcccag gggccgaacc acaagttggg aacrggtggg    1380
ggaggtggcg aaaacttccg wagtggaatt ccaactttc ctggccctga ttccccttgg     1440
gcatccctga gggggcagag cttcccttcc ggggacttta gagggttcct caggtcatct    1500
aactgggaga cacaggaggc ccgaagcgcc cccctccac ccggtccgga ggaacccag       1560
tggaagtgga gaagtcaggc gccaccaaca agcctctccc agccaggact ttgcttagac    1620
tcgctcctcc cggcagggcg cacctaggcg ggtccatcgc cagccgggga gagggtttg     1680
ggcagggagg gaacaggtgc gcggcgggac ccgccctatc tcaacaggtg aatcgctcca    1740
agtgggtctc ggttgcatgg atctcggtgc gcttggtttg gccggagmag atgggggccg    1800
gaagggacct gtggtccgca ggcgccctcc cagcgggcca gtcacttggt tcgggccctg    1860
```

```
ggggacggag cgcacctggg tcagcccact tccggggagg gaggcagagg aacccctccc   1920
cgccgctcac ccctaagccc agccctcggc tcccaccctt gtgtacctgg gccgaaccat   1980
tcaccggagc gcgcagcggg tggagtgtgg ctcggaggac cgcggcgggt caagcacctt   2040
tctccccat  atctgaaagc atgcccttty tccacgtcgt ttacgctcat taaaacttcc   2100
agaatgcaac aggacggact tggagtaggg acaaggaacg gaagtgggaa ggggaggagc   2160
gtgcacccct cctggccttg gtgcgcgccg cgcccctaa  ggtactttgg aagggacgcg   2220
cgggccagac gcgcccagac ggccgcgatg gcgctgttgg ccggcgggct ctccagaggg   2280
ctgggctccc acccggccgc cgcaggccgg gacgcggtcg tcttcgtgtg gcttctgctt   2340
agcacctggt gcacaggtac ggggcacggg gcctctgacg ctgcggaacg acggagggaa   2400
ctgtagaggg ggatggatgg agttggaggc ggcgggaagc gggaagcggg ggtctcagag   2460
gctgggacct tccgatcccc tgggtcttgg gcgatctgtt gcgcgcggga gtgagaggaa   2520
ttccccattt gtgccgggga gcgctccccg cgcccttatc tggaagatag caggaagtga   2580
aactccctgg acggtgagac ccggagcggc agggagaatg gaactctttg tggggaggga   2640
gtggaagacc gcccgatctc tgggaaaaga aaagccggga tgggacttgg gcgcacccgg   2700
ggatttctaa gttttggagt aacggggaga gggcacggga gggctggatc agacgcttcc   2760
tagagggaca gagacgaagg aacaatgcct aggcctcggg tgggtgtggg actggggact   2820
ccccatcccc cgcaccccac ccacctcccg cgggctccgg attatacgtg cgtaagagtc   2880
tggtgggatg gatttacgga cttgaaaccg acttctgctg gcaggctttc acctggatgg   2940
gatatttggg tggtgatgag gtctttcccg agacactttt ggttcagtca tttgaaatga   3000
ctttagagta gggtgaggtg gtgggaggct gatggagata ttgtgggggc tttagtccct   3060
ccatggcaaa gcagttcagg caaacaactc catggttttc cctccaaatt caaaaggccc   3120
cgggtaacct ggaatccttc gtagtcggtt ttgaagtggg gccttggcg  ctgggggcat   3180
caacatggcc atctgcccag gccacacaga ggcccttgt  tgtgggtgaa              3240
tggcaaaggg aagaggggac tggtgtggtt cagaggccac aggctgggaa gagggatggc   3300
gggcgagtcc aaggaaactg gccgtgtcac cgtgcacctg ccacttcagc cccacgggtc   3360
tataaaatgg gcatgattat cgtggctacc tcactggtcc tggcaattaa ggaacaatgt   3420
gtgccaggca ctctgtaaac cacatacttg cgagtgtcaa gctggtgaca ggtggcgttc   3480
ctgttgaagc acctccctga gctcacagca acccttgctg tctctcctct tgccctcagc   3540
tcctgccagg gccatccagg tgaccgtgtc caacccctac cacgtggtga tcctcttcca   3600
gcctgtgacc ctgcctgta  cctaccagat gacctcgacc cccacgcaac ccatcgtcat   3660
ctggaagtac aagtctttct gccgggaccg catcgccgat gccttctccc cggccagcgt   3720
cgacaaccag ctcaatgccc agctggcagc cgggaaccca ggctacaacc cctacgtyga   3780
gtgccaggac agcgtgcgca ccgtcagggt cgtggccacc aagcagggca acgctgtgac   3840
cctgggagat tactaccagg gccggaggat taccatcacc ggaagtatgt tgggcagggc   3900
aggggatga  ggctgggctt gcccgggtgg tgggactggc gtccttgtgc gggacctgga   3960
gtccccatct gaaagctctt gagtgccagt gtctgaaagg accattgaag ggagcagttc   4020
tttttttt   tttttttgaa gatggagtct tgctctggac tccaggctgg agtgcagtgg   4080
tgcgatctca gctcactgca acctccacct cccaggttca agcaattctc ttgcctcagc   4140
ctcccgagta gctgggactc caggtgcgtg ccaccacgcc cagttaattt ttgtatttt   4200
agtagagatg gggtttcacc atgttggcca ggctggtctc aaactcctga cctcaaatga   4260
tctgccgcc  ttggcctcgc aaagtgctga gagacaccat acccagccta aagggagcga   4320
ttctattcta ctattcttcc ttctgctaat ccttccattc tttaatttaa taacgaagat   4380
ttttgagta  cctgtcatat accaggtgct gttctgggcc ctgggaatac agctgttaac   4440
aaaatcatca aaccacttcc ctcgtggagc ccacattgca gtgagagaga caaacackac   4500
acacactctc aagtccttga agataaagaa aactgggtaa cggagagaag aggccagggt   4560
ttgttctata atcattaata acacgagcag taagaagtaa aatttatcta agtaacaact   4620
tataaagggt ctactgtgtg ctaagctctc atccaggttc ccaaggatta actcagacca   4680
cacagtaatt gaatagattc tatcattgtc atcttacaga ggcccagaga gagaaagtga   4740
cttgcctagt gtcatagctg gtaacggggc tgggattcta actcagccac tttgggtcta   4800
gtggccaagc tcctaatccc tttgcttgcc tagggtggtc cgcagaggac tcacagagga   4860
gatggcagga gtgaactgca ggggcaagag agcttaatgg agaaagcctg tgacatgcca   4920
ggaactgcac acatattctc ccattgagtc ctctcctcta ccctcctgac agctgaggca   4980
cagagaggtt accttgttca aatgggtgca taggaagtca aagtctggag ctggggtttg   5040
aacccaggca gccctgagaa ccttgttctt ttttcttgag acgagtctc  gctctgtcgc   5100
ccaggctgga gtgcagtggc gggatctcgg ctcactgcaa gtccgcctc  ccgggttcac   5160
gccattctcc tgcctcagcc tcccaagtag ctgggactac aggcgcccgc cactacgcct   5220
ggctaatttt ttgtattttt aytagagacg gggtttcacc gttttagccg ggatggtctc   5280
gatctcctga cctcgtgatc cgcccgcctc ggcctcccaa agtgctggga ttacaggcgt   5340
gagccaccgc gcccggcccc ttgttcttaa ctgtaatgct gcctcctgat aggatgtgcc   5400
```

```
tgttgggact aagtaagggg cagtcattca ttcattcatt tggtatttat caagcatcga    5460
ctatgtgtcg ttggtgctgg ggatagaggt gattgggatg gctgaagttt ctgtcgtcaa    5520
ggagatgaca ttctggtgga gtgagactgg cagtaaataa gcagataaag aaagagtatg    5580
agaatttcaa agtctgggca cggtggctca cgtctgtaat ctcagcactt gggaggcca     5640
aggtgggtgg atcacctgag gtcaggagtt ccagaccagc ctggccaaca tggtgaaacc    5700
ccgtctctac taaaaataca aagattagcc aggcatggtg gcacatgcct gtaatcccag    5760
ctactcagga ggctgaggca tgagaatcgc ttgaacccag gaggcagagg ttgcagtgag    5820
ctgagatcgc accactgtac tgcagtctgg gcgacagagt gagactctgt ctcaaaaaaa    5880
aaaaaaaaaa aaaagactcc gtcaaggtat aagaatgtca gagagtacta agtgttgcaa    5940
agaaaataac accaggctgg gtgcattggc tcatgcctgt aaatttcagc actttgggag    6000
gccaaggcag gaggatcact tgagcctagg agtttgagac cagcctggac aacaaaatga    6060
gaccccatgt ctacaaaaat tttaaaaatt taaaaattag ctgggcatgg tggcatgtgc    6120
ctgtggtccc ggctgctcag gaggctgagg tgggaggatt gcttgggctt gagaggtcaa    6180
ggcttcagtg agtcatgatc gtgccactgc attccagcct gggtgacaga gtgagaccct    6240
gtcttgaaat gaaaagaaaa taggctgggc gcagtggctc acacctgtaa tcccagcact    6300
ttgggaggcc gaggtgggtg gatcacctga ggtcaggaga tcgagaccag cctggccaac    6360
atggtgaaat cccatctcta ctaaaaatac aaaatttagc cgggcgtggt ggtgggcgcc    6420
tgtaatccca gctactcggg aggctgaggc aggagaatcg cttgaacctg ggaggcgaag    6480
gttgcggtgc gccaagattg cgccactgca ctctagcctg ggaaacagtg agactccgtc    6540
ttaaaaaaaa aagaaaaaag aaaatagcac tgggtgatgt gctacatgga atgacttggg    6600
ctgtgaatat gatttgagga gggcctgggc ctggcctta cagaacctag aaggcagaga     6660
ggaaggggag gggcagggtg ccagggatga aggctcacgt acctcatgtc ttagtgtgtg    6720
ttcactgtct taaacaagaa tttaaagttg ggcatgggc agagcgggga agggagcatc     6780
cctttgcaga ccccaagaag ccaggaactg gagcacattc tgctagagga tcgatgggaa    6840
gcagggttcc aggggctgag cctatgtcag tcctgtttca gaggaggcac caggcttgct    6900
tgccctgaat ttctgtgggc agctcagcca tgagcatcct actgttattg aggtcacagg    6960
gctgcttagg cccctcctc tctaaccag ggattgtgcc tgcctggacc aggcgtgact       7020
gctaagcttc tgccaggaca agccaaatac tgagggtgct tcctctgctg gacgcaaaag    7080
tccaggatga ccccccaggc tctgtctcgg ggaaggggcc ctgcatgctc cagggcctc     7140
acaggcctgg gtctttcaaa ccaccccccac ctgggcctgt gtttgatcaa ggccctgagt   7200
gtaaacatcc attgtgtgtg tcctttcagg aaatcccata gccataggag cttcctctgt    7260
ttcagctttg aggatgggga aaagtggact cccgtggtg ttcctagggt cacccactgt     7320
gctggggttt ttctgttgtt gttgtttttt ttctgttgcc caggctggag tgcagtggtg    7380
caatctcagc tcactgcaac ctctgcctcg caagttcaag tgattctccc gcctcagcct    7440
cctgagtagc tgggattaca ggtgcacacc accacctg gctaattttt gtatcttttt      7500
ggtagagatg ggatttcgcc atgttggcca ggctggtctc aaactcctga cctcaggtga    7560
tctgcctgcc ttggcctccc aaagtctgg gattacagat gtgagccacc atgcccggcc    7620
tatcctggtt tcaaaagtga aaatagtcct ggataaggta gaaggctgtc cactccaggc    7680
atccctccgg tccggtgggct cattccctgc tttgtccttc catgctttgg gtgatggacc   7740
agcacctgga caggaggccc tgttccacct cctcgggctc cttggggtcc aagtgccccc    7800
acctccagct gcactgcagc agagagccca tgggacctct gaaatcatga aggtcacctt    7860
tgcggtgtat aaagaaggaa ccagaggttg gagatgtgga ggaggcctgg ctgctgttcc    7920
cactggagac ctggcatctt ctcccgacc taaacaatg aaagcagtgc tcagcccgga      7980
tgagatcacg gccagccaa gaccaggaac agggtacgcc ctgcaggaag aaggtgtgcc     8040
cagaccttag gatggatcaa aagaagccgg aaaactatat tttttgtgag ttttgaaaat    8100
gtcagacagg tcaaacaaaa cacagtgagg tccagcctcg gcctacaaga tgccagattt    8160
caaccctgg cctatatgat ctgtttgcca tggcaggcgg ttcctgtcca cctcttttgt     8220
ttatagcagg gaccagctct tgagctccag tgttgaagag gcacggtcag ggtctgatct    8280
gaagacactg gtggctcatg cctgtaatcc cagcacttca ggaggccgag gcaggaggat    8340
tgcttgagga caggagctgg gagaccagcc tgggcaacac agtgagaccc agacactaca    8400
aaaaaataaa tttagcgggg catgatggca caccctgcta ctctggagat gggaagattg    8460
cttgagccta ggagttcgaa gctgcagtga cccatgatcg caccactgca ctccagcctg    8520
ggcgaccaag ctaggccctc tcaaaaaaga tacaggtgga aaaatgatgg acgaagaggg    8580
cattgtggca aacctgggga tttaggagaa cctagtttgg aattctatga ggattcaatg    8640
aaagaatgtg tgtagagggg cccagcacat agtaagagct caataaacgg tggggctag     8700
gggtggtggc tcatgcctgt aatcccagca ctttggaggg ctgaggcagg tggatcactt    8760
gagcctggga gttcaagatc aacctggaca acaaagcaag atcccatctc aaaattaaaa    8820
aacaacacca acaacaaaaa aacagtggct tagatgcctg atcattaggg taagtcgtgt    8880
cctcaaccc ttcacatctg ctctgaaggt caccatatcc ggaagccttc cctggcctcc    8940
```

```
ttgtttaaaa tggcacagcc cccactccac gcctggcact ctctgctgtc cctgattcgt   9000
tttctccata cagcttatct ttgtctggta tgtgacatag ttaacatttt atatttgtct   9060
ttctttccta gttagaatct gaactctaga agggcaaggg oaaggattta taactcaaag   9120
attccgggct taggcctctt ttatattctt gattttgagg ttaattaaga gctcaggcct   9180
agcgaggtgg ctcatgcctg gaatcccagc actttgggag gccaggcgg gcagatcact   9240
tgaggtcagg agttccagac ctgcctggcc aacacagtga aaaacctgtc tctactaaaa   9300
atacaaaaat tagccagtta tgttggcagg cgcctataat cccagctact caagaggctg   9360
aggcaggaga atcgcttgaa cccaggaggc agaggctgca gtgagccaag atcgtgccac   9420
tgcactccag cctgggcaac agagcgagac tccatctcaa aaaaaaaaaa aaaattaaga   9480
gctcaaagag tttgttttca taggcagcag aatgagaaaa gtttacaaaa tagtttaaat   9540
gacaataaag tcattataga ttaacataaa taaaatacct tttatgaaaa aataatcat    9600
tttctgaaat cagacaaaac attgtgaatg agaaggtggc atggttttat tttttttgcaa  9660
gtctccgaag cctggctgga tagaagagcc tggcttctca gagctgcttc agtctgttgt   9720
gatatctatt gtatgtcacg tagcctctgg aaaactccac agttagtatt gttgggaaaa   9780
taactttgac ctcaggatct cctgaaaacg tcttggggaa cccagggtc tagaggctgc    9840
agtttgagaa ctgttgctgt ggtatcccag gtgtctcaaa tactgcctag aacataggtg   9900
gtactcagta attattgttg aaggatgaat gaatgaatga atgaatgaat gaaagaaaga   9960
aatgtgtctt tgaatctagc catgtgccca gaatgatgag acagatgaca aaagctaagg  10020
gactttagca tgaggagagg gggttcgttt cctttttttt cttttttttt tgagatggag  10080
tctcactcta ctgcccaggc tagagtgcag tggtgcaatc tcagctcact gcaatctctg  10140
cctcctgagt tcaagcaatt ctcctgcctc agcctccagg gtagctggga ctacaggtgc  10200
gtgccaccat gcctagctaa ttttttacat ttttggtaga gatgggggtt taccatgttg  10260
gccgggctgg tctggaactc ctgacctcaa gtgatccacc tgcctcagcc tcccaaagtg  10320
ttaggattac aggtgtgagc caccatgtcc ggccaagagg gtgttcattt ctgctccttg  10380
ccaggtattg tgtcaggcac tggggaccca gcagtggctg agacagacag ggctctgcct  10440
cacggagccc acatttttcac caggcaaagg atggtcggcc cctaagctgg gagataagac  10500
ttcagcagtt gggtggggga gccgtgggag aagcccagcc cacaggggga cagtgcaaat  10560
ctagaaccaa ggcgatggca ggggtgaggc tggcacggta gctagagacc acgtcgtgcc  10620
aagggccttg gggaccatgg gactatggga ccttagggaa ggcgtctgga atgctgtagc  10680
cagacactgt tgcaaggagg attttttctgt agacatgagg ccttccttat gaagaaagca  10740
agggttcttt cattcctggg ggtgccaggt gctgtggact gcagcacgcg tggttgctgc  10800
cgtcacagag ctgtcatgca ggagggcagc gcgtccttgg gaaggtggca ggcaggtcag  10860
gctaggagga aagaggccgg gaagctgagg gcatttcctg cccgagatgc ccaatgtagc  10920
ctactrctgt cccagtggc ttaaggcaga gttgcctgt aggtgccctg gtcccaccct    10980
ggtgaaaggc tgaaggtatt taattagtgc ctgagaagca gagaggaaac aggatgtgcc  11040
aaaacacttt gatggatggt agagttaaca ggctccttgc ctgcagctgc ttcagacaag  11100
agcgtcccca agccctgggc ctgacctgga atgtggggat ggaaggggag ggggaggaac  11160
caaggcactg ggagggtaag tctctctctc ccacatagac acacccactc cttatgggtg  11220
cctgggcatc tcctggtacc tagaatctgg cctgtttatc tccacaccca tccctggggt  11280
ctacactagg ccctgtgggt ggcagttcac atcaggggag ttctgacttt ggctctgaga  11340
ggtggttcag agatggctgt aagttgagaa gcacagactg ctgggtgtgg tggttcacgc  11400
ctgtaatccc agcactttgg gaggctgagg tggggtgga tcacctgagg tctggagttc   11460
aaaaccaact tggtcaacat ggcgaaactc catctctact aaaaatgcaa aaattagcca  11520
ggtgtggtgg caggtgccta taatcccagc tacatgggag gctgaggcag gagaatcgct  11580
tgaatctggg aggcgaagat tgtagtgagc cgagattagt tcgcaccatt gcatgccagc  11640
ctgggcaaca agagtgaaac tccgattcaa acaaacaaaa aaaaaagct gggcatggtg   11700
gagtgcctgt agtcctaact actcaggtgg gaggattgct tgagtccagg aggttgaagt  11760
tgcagtgggc tataattaca ccactgcact ccagccaggg ccacagagtg agaccctgtc  11820
tctaaagaaa gaaaaaaaaa aacaacctca ggctccgagg gcaccattac tgctctacac  11880
tgaagagctg tgcagctttt ccagacccga aatgtcatcc acaaaacaga agtgataatg  11940
gtcctgcctc acagacttct tgcagtagtc caggtgttta gaacggggtg taaaaggccg  12000
tgtgcccttg gtaggaatct ttgcatatgc atttgatcat ctgcagcctg cccagcccgc  12060
tgcttgcccc ctcctgggtg tgctgggaag gggtctttgg ccctccaggg gttaggtgcc  12120
ccagcctcca aggtgccctc acgccttttc atcccgactc agatgctgac ctgaccttg   12180
accagacggc gtgggggac agtggtgtgt attactgctc cgtggtctca gcccaggacc   12240
tccaggggaa caatgaggcc tacgcagagc tcatcgtcct tggtgagtgg gcctgggaag  12300
ggggaggcat ggcccttcct tttgtccgct tctgttctgt ctgccctccc ctgtgtccgc  12360
cctctgccct ccagcttacc ctctgggctc tgtcgcctgc tctgctctcc cccaggctct  12420
gccagtcact taggctcccc tgtgccctgc accccaggca gggaccactg gcccacagtg  12480
```

```
cctccaatca cccaagccaa actaagagaa gagtggagac aattggagac tctgccttt    12540
caaagtctca tttttaaaaa aaatccagac ttggggtccg ggtgcggtag ttcatgcctg    12600
taatcccagc actttgggag gccgaggcgg gtggatcact tgaggccagg agttcgagac    12660
tagcctggcc aacgtggcaa aatcccgtct ctataaaaaa tataaaagcc aggcgtggtg    12720
gtgcacatgc ctgtaatccc agttactcag aaggctgagg catgaggatt gcttgaacct    12780
gggaggcaga ggatgcagta agccaagatc aagccactgc actccagcct gggcgacaga    12840
gtgagactct gtccaaaaaa aaaaaaaatc cagacgtggt cagagtccat gggcagtgaa    12900
tgaggacagt tgatggtgtg caaaatcgac ccacctcttg ctacatccca aaggcctcat    12960
ctcacccgag tccctcgcca aagcacagcg gttttgccgt gtgcctgct gggatggcgc    13020
tgcatggcac acacactgtg taagtttgag tgcagctgaa acgaagccga ttccagacac    13080
ccaggggcag ggcggggtgt ccgtgtggct gggaggcctc cttgtgttag ggggatgttg    13140
ccatcggcca ggtgccctgc tgtaagccaa cacatggagt cttgtatgac atgtgctctg    13200
catgagtgat gccgctgggc tgtacactgc catcttcaca tgtgtgaatg agcacgtgac    13260
tgggggtac ttgggctgca agacagagtt catgtgtggg ggatggaaca cgtgcaccag    13320
tgacccagga acctctgcct gttcttcggt aaaatgcacc atttgcatca gcagttccca    13380
aaattagtct ccaggtctat ttacactcta aaacattatc gagggtctcc aagagctttt    13440
gtttgtttct gtgggtttta tgtctatctg ttgcttaaca tattaggaat taaaatgggg    13500
agattttcct tttttttttt tttttttga gatggagtct cgttctgtcg cccaggctgg    13560
agtgcagtgg ctcgatctcg gctcactgca agcttcacct cctgggttca cgccattctc    13620
ctgcctcagc ctcccaagta gctgggacta caggcacccg ccaccacacc cggctaattt    13680
tttttgtatt tttagtagag actgggtttc accatgttag ccaggatggt ctcgatctcc    13740
tgacctcgtg atccacccac ctggcctcc caaagtgctg ggattacagg catgagccac    13800
tgcccggcct aaaatggggg agattttca agcccaagat acacaaggaa gactgggcaa    13860
catggcaaga ccctgactct acaaaaaatt ttaaaattaa ccaggcatgg tggcatgcac    13920
ctgtgagccc agcttcttgg gaggctgagg caggagtatc gcttgcaccc aggaggtcaa    13980
ggctgcagtg agccatgact atgctactgc actctagcat gagtgacaga gaccctggct    14040
caagaaacac aaacacacac acacacacac acacgcatat agtccattag gcatcagggc    14100
gatgatggca tcagggagcc tgggaaactc tactggacat tcatgggaga acaagtgaaa    14160
aaggcaaata acatcttagt gttattctaa aatttcttct tttggccttg tggacaggac    14220
cacgctttga gagctgtgac tgacatgcct ctgtcctgtt gcgagggcct atagtgccaa    14280
gtgcatgagc tctggggagg gcttcgtggg tgcagagctg ggcctgtgga ggcccctcag    14340
acacaacact ggtggggctc agagctccag gggcactcga gggaagacaa gaaccggctc    14400
tgagatgcgt gaatgtgaca gtgcatgagt agagatggag accttgtggg tcccagaacc    14460
aggactgcat atgactttca tatgtgggta ttttgccctt catgggtccc ttcctgttt    14520
aaaaaaaatg tgtgattatg ttgtcacaaa gagtttattc ctgtatattg tgttaatttg    14580
tgttcagatt tgtaaagtaa aattaaacca tttcagccag gtgtggtgac acatgcctgt    14640
agccctagct acttacccca gaggctgagg tgggaggatc gcctgagccc acgaggttga    14700
agctgcagtg agccatgatc acaccctgc actccagact gggcgacaga gctgagatcc    14760
tatttcgtgg gccctaggtc cctgtgcctg ctggaacagg acatccctat caccgtggtt    14820
ggagcccttt ggggtgctaa gacctatgaa tgagggaaac ttagggtgcc caagctgagg    14880
tagagccctc agaaccccct gggatttgta ttggagccct cgtggcataa cacaggtgga    14940
ttatgcaatg ggagtttctt acctataagc acccacatgt gggcgggtgg agggtaggag    15000
ccatgcrcta gggcttcagc ccccagcccc ttccgcttc agggcacacc ttgcacttgg    15060
ccagcctgga gctgggcttt cggggtggc acagcctggg ctggctctgg ccagcataat    15120
ctgtttctct tttgtccctc cagggaggac ctcaggggtg gctgagctct tacctggttt    15180
tcaggcgggg cccatagaag gtacggggg tggatcctga gttgggcttc tcggagctc    15240
ccatacatca cctactgctt ctgactctag ttagtatccc ctcccccact aaaccctgct    15300
cactgtggac ccctcactaa cctggcctga ctgtggctct gaggcatcta gtggtctggc    15360
gctgggccta ggctaggctg ggctgaggag agcctgggt gcaggccagg gctctgtgac    15420
tggcacctgc ggtgctcttg agggtgtggc gtctgggcag ctggctctct ctttggtctg    15480
ggggctgcag tctgtctccc tctgtgcagg ctgcctcgtt ttctgccttg tgttttttgc    15540
acctggggga gggccgtaac tggggaatgg ccgggatggt agaatgggga gtgtgctgtg    15600
cccagcctct ggcacaaaaa atccagccag ggctgcaggt tccttggtga gctttgcaaa    15660
tcgtcccga cctcagtgct ggctccgcac catgtacccc tgctgtgccg ttagccctgt    15720
tcctcccag gcctccgggc tcagggcctg ttgtctttct gcagactggc tcttcgtggt    15780
tgtggtatgc ctggctgcct tcctcatctt cctcctcctg ggcatytgct ggtgccagtg    15840
ctgcccgcac acttgctgct gctacgtcag gtgccctgc tgcccagaca agtgctgctg    15900
ccccgaggcc cgtaagtgtc ccgctcatgg ccacctggt tgggcaaca tcctgcatcc    15960
aagggaagga ggtggccatc caccctgcccc caggacagtg gcgttggtct ggagggtgtg    16020
```

```
aatttagcca gtgggagaa agtaggctga ggagggtctg ctgtttagat tgtcgtttac 16080
ttcctccaac ttttagttta ttttttattta tgttgttctt ttcttttgta agtataatcc 16140
atacacatgg taaaaatgtc caacagtaca agatactagt cacatggaag taaagccctc 16200
taaaaaaacc aaatcttggc taggcgcagt gattacgcct gtaatccag cactttggga 16260
ggccaagacg agtggatcac ttgaggtcag gagttccaga tcagcctggc caacatggta 16320
aaacccagtt ctctactaaa aatacaaaaa ttagctgggc atggtggtga tgcctgtaa 16380
tcccagctac tcaggagact gaggcatgag aatcgcttaa acccaagaag tggaggttgc 16440
agtgagctga gatcacgcca ctgcactcca gcctgggcga cagagtgaga ctctgtctca 16500
aaaaaaaaag aaaaaaaaat gttaagtgaa aaagttaaga aaccaaacaa ggtttacaac 16560
actacatgat ttaagcaaaa aaaattttt ttgttttaga gaaagggtct cattctgtca 16620
tccaggcagt gcagtgcgat catagctctc tgcagcctca aactcccggg ttcaagcagt 16680
cctcccgcct cagcctctgg agcagctggg actgtaggca cacaccacca tgcccagcta 16740
attttttgat ttttgttttt tgtagagacg gggtctcagt atgttgccca gcctgatctc 16800
aaactcctgg cctcaggtga tcctccgaag tcagcctccc caaagtgctg ggattacagg 16860
catgtgccac catgctggcc aattttaaa aattttctgt agagacaggg tcttgctatg 16920
ttgcccaggc tggtcttgaa ctcttgacct caagtgatcc tgcctcaggc tcccaaagtg 16980
atgggattac aggcatgaac taccacacct ggccttaaac ttaagcaaat ttttttttt 17040
ttttggagac agtttcactc tgtcgcccag gctggagtaa agtggcgtga tctctgctca 17100
ctgcaacctc cgccccccgg gtttaagcta ttctcctgcc tcagcctccc gagtagctgg 17160
gatataggcg cctgccacca cgcctgacta attttgtat ttttagtaga gacgggttt 17220
tgccatgttg gccaggctgg tctcgaactc ctgacctcag gcaatccgct cccccgcacc 17280
cctaccttgg cctcccaaag tgttaggact acaggtgtga gccaccatgc ctggccaaat 17340
ttaagcaaat gtttgaaaac atacccac aggaatgctg cacatttac ccagctacta 17400
tgtctagggt cgtatctagc acaccagcat ggctactgtg gagagctggg actggatgtg 17460
agatgagagc taaaggggaa gtaagcaaac caagcagggg aaggtaagag aagacagaag 17520
acagagagag agggacctaa ctctatgaga ggagtcagac atgtgcaatt gaaaaagact 17580
tgctcctgtc tctcttctgt gaatgtttgt gaatatccca acgggacact ttcacagagg 17640
agctgattga cgtggtcaca gccatcagcc ttgggacacc agaccacagt gtgtacacta 17700
agtggcactg atggacactt cagcatccct ctagctgctg tcccgtttcc cctcctcggg 17760
gaccacagct gttgccagtc cttggtttcc ttcaggaggg tgtctgggta gaccagcctg 17820
tgtgcacaca gtccaagata catgaacagt gaagtgccag gcaatccttg caagcatggg 17880
caggtggaga gctgaggcct gcttgacacc ttcctgctca gaagcccagt gagcagtttc 17940
cctccctagg gctcagtgtc atcccctata aaatggggct tatggcagag ctcaccacac 18000
tgggtgcatc tgggatttg gcgagctcat gtgcacacca ttgagcatgg ggcccaacct 18060
atataaaata ttctacgtct gtcagctgct gggcactgcc actatcagcc tcagtagtga 18120
ctgagggaca gggcaccagt cagagccctg gtgcacacag agtgacccca gagaagcagc 18180
cttccctctc tgagtcctgt ttccttctgt taggtcctga cttcatgggt tgttgttagc 18240
attaaggaag tcgctggcta attttatagt cattgaagtc agtggtgtgc aacctggttc 18300
ctcaaaggat cacttccctg aaaaaattcc actgctcct ggaggcttat gcaggccatc 18360
ccatcccctc cctcttgttg tgttcagctg acagcttttt gctcagtgag taagtgttag 18420
gtccatttca cagatgggct gcaaccaagt ttgcagtgaa cccactaaga ccagagctag 18480
ggccaggact aaatgctggt cccaatgcca cattcccctg tccccacacc acatttcctc 18540
catccggaga ccctgttacc ccaacccagg gccccattaa ctccctggca gaggccctgt 18600
tacatctgct gctgccacag cctccgccca cccttcagga ggcagcaggt cccactgctg 18660
atgataaagt tgcaggctgc ctgagctaat gaaggggctt cctctaggct gtgcacttag 18720
tcttctgctt ccaaaccaaa tcagaggtga ggcaccctct ctgggcccat ctctctcctc 18780
catttttcctg ttgggtccc agggaggaag ccattgcct agggccagg aatttgcaa 18840
gcctcttgcc ctagggagga aggaagggag gaggatctta ccttgaactg tcaagcctag 18900
agcctggtgg ggcaggcaga aatgggtgca gtccatgagt tagaaacact agaggagaca 18960
ctttgctgct tggccggggc aggcaagtta attcccgagg ctcctgccac tgcatctcaa 19020
tctggaaggt gaccaggtgg ggcaggaccc acgtctccca gatgactcat tttttctaga 19080
acagggcttt ggctgccaaa gaggatactt gatttcggct tgtggggaca gtggtggacc 19140
cagcatctgg gctttatata aagggcagct ttgttgccct gtaaacacac agaccatggg 19200
tggccacttc ttccagtaag ttagctgggg agttggaagt ttaggtaaaa ccttttgatt 19260
gacaaatgtt ggcgaattac catgctgtta aatgaaacat tgttctgcca ccctggggct 19320
gtgggtgcct gcgtgcaccc tctgaaaaat cacacaggaa gtgggtggg gtctctgtga 19380
agctggtgtc ccccagcctc agggatgctg cagaaatgga atgaggacca acagggactc 19440
agatgtccaa ggaagctcta cagcggagag gacggcttgg gaaggaggtc caggcccagg 19500
tccctccgga acccaatggg tatgggcag cctggctcct gcctcatccc ccttctcctg 19560
```

```
ttgattrtgt cctcacagtg tatgccgccg gcaaagcagc cacctcaggt gttcccagca 19620
tttatgcccc cagcacctat gcccacctgt ctcccgccaa gacccccaccc ccaccagcta 19680
tgattcccat gggccctgcc tacaacgggt accctggagg ataccctgga gacgttgaca 19740
ggartagctc aggtgaggcc gggggaagca ggaacagctg gtgggmgtgt gctgggcatc 19800
tggacactga ggggcagggg ctggaaggaa gagtgtcttg ggagccgagg aggggctctg 19860
ctcctggtgc gcggccactg acagccactc tcccccagct ggtggccaag gctcctatgt 19920
accoctgctt cgggacacgg acagcagtgt ggcctctggt gagaatccat cgtcccgaag 19980
ttggatgtgc ctgtaaggga gaggggtggg ccaggatcca tcctcccaaa ccgaccacca 20040
cccccctgtc cctagaagtc cgcagtggct acaggattca ggccagccag caggacgact 20100
ccatgcgggt cctgtactac atggagaagg agctggccaa cttcgaccct tctcgacstg 20160
gccccccccag tggccgtgtg gagcggggta agcaggagcc ttggggtctg agggcttta 20220
aggtggggg gtgaaacatg tctccctgat acctgccgca gggactcttg gtgcaaaccc 20280
tggacccgg gctcctccag cagtcagtga cacccccctt ccctgcagcc atgagtgaag 20340
tcacctccct ccacgaggac gactggcgat ctcggccttc ccggggccct gccctcaccc 20400
cgatccggga tgaggagtgg ggtggccact ccccccggag tccagggga tggaccagg 20460
agcccgccag ggagcaggca ggcggggct ggcgggccag gcggccccgg gcccgctccg 20520
tggacgccct ggacgacctc accccgccga gcaccgccga gtcagggagc aggtctccca 20580
cgagtaatgg tgggaggaga agccgggcct acatgccccc gcggagccgc agccgggacg 20640
acctctatga ccaagacgac tcgagggact tcccacgctc ccgggacccc cactacgacg 20700
acttcaggtc tcgggagcgc cctcctgccg accccaggtc ccaccaccac cgtaccgggg 20760
accctcggga caacggctcc aggtccgggg acctcccta tgatgggcgg ctactggagg 20820
aggctgtgag gaagaagggg tcggaggaga ggaggagacc ccacaaggag gaggaggaag 20880
aggcctacta cccgcccgcg ccgccccgt actcggagac cgactcgcag gcgtcccgag 20940
agcgcaggct caagaaggtg agggccgcc tccctggcgt ccagaccgtc cctgggcccc 21000
cagccggtcc ccgcggctca taccettctt tctttctccc ttgcagaact tggccctgag 21060
tcgggaaagt ttagtcgtct gatctgacgt tttctacgta gcttttgkat ttttttttt 21120
aatttgaagg aacactgatg aagccctgcc ataccctcc cgagtctaat aaaacgtata 21180
atcacaagct ctggagagaa ccatttgttc ggccgcgcgg ggcggggac cgggctgct 21240
ccgtatgcg tctgtaaagc gccgcgtccc ggggcaccg gagtccgggg ccggaggaa 21300
gagaccagc ctggcccggc ccgcgcccgc gccgccggcc ggagaacgtg ccccgcgcag 21360
ccaccgcccg cctgcgtgcg cgccccggcc ccgcccaggc gtgcgcatgc gccccggccc 21420
tccgccttcg cgcaccgcag gctggccgcc gggagcgcgc gcgcgctcct ctcccttcc 21480
agcccatccc ccccagcccc ccaccgacct actttactgt ctccaaactc gggcagccca 21540
cctggccccc gacgacccca gcccctgctc cgggtacccc gacgttccat ccagacccgc 21600
gtttcaccag ggcggcgcgc ggcgacctcg cgcccgcgg agcccgggc tcgcgcgcgc 21660
ccgcccgccc ccggagacag acagcgcgcg cgctcccggg ccgcctcccc ccagcgcgcg 21720
tccgcccgg gctcgcgccg ccgccgccgc cgccgccgcg cgcgcgcagc tcaagtaaag 21780
gaggaaaaaa aaaggggga aaaatagaaa gcggcggcgg ctgcagcagc gatccgccgc 21840
cggactgggc caagccgggc ggcggccgcg cgagccggcg atccagggca ctggcggcgg 21900
ccagccaggg cgggccgtgt tcaaaaaaaa aagtcgcggc ggcggcggct gctcagggaa 21960
ggaggcctga gggccgcgtg cagcgggcgg gcagctgggt gggctggggg cggccgcgcg 22020
gcgtcccgga gcctcgggcc gcccggagcc ggcgggcggg cggaggcgga ggcggcggcg 22080
gctgcagcgg ctgcaggagc ggcggcggct gcngcggcgg cngcggcatc tcctcctcac 22140
atgacccac tgtttgtccc cgtgatcagc gcgagcggct cccgtatctc ctccgtcccc 22200
tcctgccgcg cggcgtgagc gccgggnctc ggggcccccc cggccgcccg cccctcccc 22260
tccntccntc ccctccctc ccctccccc cgggcccgc gccccccg ccccgcccc 22320
cccatggac atgctggacc cgggtctgga tccgctgcc tggccaccg ctgctgccgc 22380
cgccaggtaa gatccccggc ccggccgtgc cccgcgccc cggccccggc cccggcccg 22440
cggcctgcag gccggggccg ccatgatccc gagcggccgc gggccccgct caaaatggag 22500
gccgccggcg cgggggggac ctggcgcctc ccgccccgg ccccggcct cggcggcgcc 22560
cccggcctca ggcgcggccg ggtgggactg gggccctgca gctggcgcg ggggcggggg 22620
cgcgggcgcg ggccgcgctg accctgctcc ctcctgtgcc cctggcagcc acgacaaggg 22680
acccgaggcg gaggagggcg tcgagctgca ggaaggtgag tgcttgccgg gccggccgcg 22740
cccggggagg gctgggggcg ctcggcgcgg ccctgaccgt gccccgaccc tcctcggccc 22800
caggcgggga cggcccagga gcggaggagc agacagcggt ggccatcacc agcgtccagc 22860
aggcggcgtt cggcgaccac aacatccagt accagttccg cacagagaca aatggaggac 22920
aggtgagcgg cgggccgcga gagcgaacgg gcgggcgggc gggcgcgccg ggaaggctcg 22980
gacctggccc cagcgccggc ctcgccgctc tgccgccccc tgcaggtgac ataccgcgta 23040
gtccaggtga ctgatggtca gctggacggc cagggcgaca cagctggcgc cgtcagcgtc 23100
```

```
gtgtccaccg ctgccttcgc ggggggggcag caggctgtga cccaggtggg tgtggacggg    23160
gcagcccagc gcccgggccc cgccgct                                          23187
```

<210> 2
<211> 2158
<212> DNA
<213> Homo sapiens

<220>
<221> allele
<222> 595
<223> 9-3-324   :  polymorphic  base  C  or  T

<220>
<221> allele
<222> 940
<223> 9-6-187   :  polymorphic  base  C  or  T

<220>
<221> allele
<222> 1191
<223> 9-7-325   :  polymorphic  base  A  or  G

<220>
<221> allele
<222> 1362
<223> 9-9-246   :  polymorphic  base  G  or  C

<220>
<221> allele
<222> 1658
<223> LSRX9f13-BM  :  polymorphic  base  deletion  of  AGG <220>
<221> allele
<222> 2079
<223> LSRX9f14-BM  :  polymorphic  base  T  or  G

```
<400> 2
tggagtgtgg ctcggaggac cgcggcgggt caagcacctt tctcccccat atctgaaagc    60
atgcccttttg tccacgtcgt ttacgctcat taaaacttcc aga atg caa cag gac     115
                                                 Met Gln Gln Asp
                                                  1
gga ctt gga gta ggg aca agg aac gga agt ggg aag ggg agg agc gtg     163
Gly Leu Gly Val Gly Thr Arg Asn Gly Ser Gly Lys Gly Arg Ser Val
 5              10                  15                  20
cac ccc tcc tgg cct tgg tgc gcg ccg cgc ccc cta agg tac ttt gga     211
His Pro Ser Trp Pro Trp Cys Ala Pro Arg Pro Leu Arg Tyr Phe Gly
                25                  30                  35
agg gac gcg cgg gcc aga cgc gcc cag acg gcc gcg atg gcg ctg ttg     259
Arg Asp Ala Arg Ala Arg Ala Gln Thr Ala Ala Met Ala Leu Leu
            40                  45                  50
gcc ggc ggg ctc tcc aga ggg ctg ggc tcc cac ccg gcc gcc gca ggc     307
Ala Gly Gly Leu Ser Arg Gly Leu Gly Ser His Pro Ala Ala Ala Gly
        55                  60                  65
cgg gac gcg gtc gtc ttc gtg tgg ctt ctg ctt agc acc tgg tgc aca     355
Arg Asp Ala Val Val Phe Val Trp Leu Leu Leu Ser Thr Trp Cys Thr
    70                  75                  80
gct cct gcc agg gcc atc cag gtg acc gtg tcc aac ccc tac cac gtg     403
```

```
Ala Pro Ala Arg Ala Ile Gln Val Thr Val Ser Asn Pro Tyr His Val
85              90                  95                 100
gtg atc ctc ttc cag cct gtg acc ctg ccc tgt acc tac cag atg acc      451
Val Ile Leu Phe Gln Pro Val Thr Leu Pro Cys Thr Tyr Gln Met Thr
                105                 110                115
tcg acc ccc acg caa ccc atc gtc atc tgg aag tac aag tct ttc tgc      499
Ser Thr Pro Thr Gln Pro Ile Val Ile Trp Lys Tyr Lys Ser Phe Cys
                120                 125                130
cgg gac cgc atc gcc gat gcc ttc tcc ccg gcc agc gtc gac aac cag      547
Arg Asp Arg Ile Ala Asp Ala Phe Ser Pro Ala Ser Val Asp Asn Gln
                135                 140                145
ctc aat gcc cag ctg gca gcc ggg aac cca ggc tac aac ccc tac gty      595
Leu Asn Ala Gln Leu Ala Ala Gly Asn Pro Gly Tyr Asn Pro Tyr Val
    150                 155                 160
gag tgc cag gac agc gtg cgc acc gtc agg gtc gtg gcc acc aag cag      643
Glu Cys Gln Asp Ser Val Arg Thr Val Arg Val Val Ala Thr Lys Gln
165                 170                 175                180
ggc aac gct gtg acc ctg gga gat tac tac cag ggc cgg agg att acc      691
Gly Asn Ala Val Thr Leu Gly Asp Tyr Tyr Gln Gly Arg Arg Ile Thr
                185                 190                195
atc acc gga aat gct gac ctg acc ttt gac cag acg gcg tgg ggg gac      739
Ile Thr Gly Asn Ala Asp Leu Thr Phe Asp Gln Thr Ala Trp Gly Asp
                200                 205                210
agt ggt gtg tat tac tgc tcc gtg gtc tca gcc cag gac ctc cag ggg      787
Ser Gly Val Tyr Tyr Cys Ser Val Val Ser Ala Gln Asp Leu Gln Gly
                215                 220                225
aac aat gag gcc tac gca gag ctc atc gtc ctt ggg agg acc tca ggg      835
Asn Asn Glu Ala Tyr Ala Glu Leu Ile Val Leu Gly Arg Thr Ser Gly
        230                 235                 240
gtg gct gag ctc tta cct ggt ttt cag gcg ggg ccc ata gaa gac tgg      883
Val Ala Glu Leu Leu Pro Gly Phe Gln Ala Gly Pro Ile Glu Asp Trp
245                 250                 255                260
ctc ttc gtg gtt gtg gta tgc ctg gct gcc ttc ctc atc ttc ctc ctc      931
Leu Phe Val Val Val Val Cys Leu Ala Ala Phe Leu Ile Phe Leu Leu
                265                 270                275
ctg ggc aty tgc tgg tgc cag tgc tgc ccg cac act tgc tgc tgc tac      979
Leu Gly Ile Cys Trp Cys Gln Cys Cys Pro His Thr Cys Cys Cys Tyr
                280                 285                290
gtc agg tgc ccc tgc tgc cca gac aag tgc tgc tgc ccc gag gcc ctg     1027
Val Arg Cys Pro Cys Cys Pro Asp Lys Cys Cys Cys Pro Glu Ala Leu
                295                 300                305
tat gcc gcc ggc aaa gca gcc acc tca ggt gtt ccc agc att tat gcc     1075
Tyr Ala Ala Gly Lys Ala Ala Thr Ser Gly Val Pro Ser Ile Tyr Ala
                310                 315                320
ccc agc acc tat gcc cac ctg tct ccc gcc aag acc cca ccc cca cca     1123
Pro Ser Thr Tyr Ala His Leu Ser Pro Ala Lys Thr Pro Pro Pro Pro
325                 330                 335                340
gct atg att ccc atg ggc cct gcc tac aac ggg tac cct gga gga tac     1171
Ala Met Ile Pro Met Gly Pro Ala Tyr Asn Gly Tyr Pro Gly Gly Tyr
                345                 350                355
cct gga gac gtt gac agg art agc tca gct ggt ggc caa ggc tcc tat     1219
Pro Gly Asp Val Asp Arg Xaa Ser Ser Ala Gly Gly Gln Gly Ser Tyr
                360                 365                370
gta ccc ctg ctt cgg gac acg gac agc agt gtg gcc tct gaa gtc cgc     1267
Val Pro Leu Leu Arg Asp Thr Asp Ser Ser Val Ala Ser Glu Val Arg
                375                 380                385
agt ggc tac agg att cag gcc agc cag cag gac gac tcc atg cgg gtc     1315
Ser Gly Tyr Arg Ile Gln Ala Ser Gln Gln Asp Asp Ser Met Arg Val
                390                 395                400
```

```
ctg tac tac atg gag aag gag ctg gcc aac ttc gac cct tct cga cst      1363
Leu Tyr Tyr Met Glu Lys Glu Leu Ala Asn Phe Asp Pro Ser Arg Xaa
405                 410                 415                 420
ggc ccc ccc agt ggc cgt gtg gag cgg gcc atg agt gaa gtc acc tcc      1411
Gly Pro Pro Ser Gly Arg Val Glu Arg Ala Met Ser Glu Val Thr Ser
                425                 430                 435
ctc cac gag gac gac tgg cga tct cgg cct tcc cgg ggc cct gcc ctc      1459
Leu His Glu Asp Asp Trp Arg Ser Arg Pro Ser Arg Gly Pro Ala Leu
                440                 445                 450
acc ccg atc cgg gat gag gag tgg ggt ggc cac tcc ccc cgg agt ccc      1507
Thr Pro Ile Arg Asp Glu Glu Trp Gly Gly His Ser Pro Arg Ser Pro
            455                 460                 465
agg gga tgg gac cag gag ccc gcc agg gag cag gca ggc ggg ggc tgg      1555
Arg Gly Trp Asp Gln Glu Pro Ala Arg Glu Gln Ala Gly Gly Gly Trp
        470                 475                 480
cgg gcc agg cgg ccc cgg gcc cgc tcc gtg gac gcc ctg gac gac ctc      1603
Arg Ala Arg Arg Pro Arg Ala Arg Ser Val Asp Ala Leu Asp Asp Leu
485                 490                 495                 500
acc ccg ccg agc acc gcc gag tca ggg agc agg tct ccc acg agt aat      1651
Thr Pro Pro Ser Thr Ala Glu Ser Gly Ser Arg Ser Pro Thr Ser Asn
                505                 510                 515
ggt ggg aga agc cgg gcc tac atg ccc ccg cgg agc cgc agc cgg gac      1699
Gly Gly Arg Ser Arg Ala Tyr Met Pro Pro Arg Ser Arg Ser Arg Asp
                520                 525                 530
gac ctc tat gac caa gac gac tcg agg gac ttc cca cgc tcc cgg gac      1747
Asp Leu Tyr Asp Gln Asp Asp Ser Arg Asp Phe Pro Arg Ser Arg Asp
            535                 540                 545
ccc cac tac gac gac ttc agg tct cgg gag cgc cct cct gcc gac ccc      1795
Pro His Tyr Asp Asp Phe Arg Ser Arg Glu Arg Pro Pro Ala Asp Pro
550                 555                 560
agg tcc cac cac cac cgt acc cgg gac cct cgg gac aac ggc tcc agg      1843
Arg Ser His His His Arg Thr Arg Asp Pro Arg Asp Asn Gly Ser Arg
565                 570                 575                 580
tcc ggg gac ctc ccc tat gat ggg cgg cta ctg gag gag gct gtg agg      1891
Ser Gly Asp Leu Pro Tyr Asp Gly Arg Leu Leu Glu Glu Ala Val Arg
                585                 590                 595
aag aag ggg tcg gag gag agg agg aga ccc cac aag gag gag gag gaa      1939
Lys Lys Gly Ser Glu Glu Arg Arg Arg Pro His Lys Glu Glu Glu Glu
                600                 605                 610
gag gcc tac tac ccg ccc gcg ccg ccc ccg tac tcg gag acc gac tcg      1987
Glu Ala Tyr Tyr Pro Pro Ala Pro Pro Pro Tyr Ser Glu Thr Asp Ser
            615                 620                 625
cag gcg tcc cga gag cgc agg ctc aag aag aac ttg gcc ctg agt cgg      2035
Gln Ala Ser Arg Glu Arg Arg Leu Lys Lys Asn Leu Ala Leu Ser Arg
        630                 635                 640
gaa agt tta gtc gtc tga tctgacgttt tctacgtagc ttttgkattt             2083
Glu Ser Leu Val Val  *
645             650
tttttttttaa tttgaaggaa cactgatgaa gccctgccat acccctcccg agtctaataa   2143
aacgtataat cacaa                                                     2158

<210> 3
<211> 649
<212> PRT
<213> Homo sapiens

<220>
<221> VARIANT
<222> 363
```

<223> 9-7-325 : polymorphic amino acid Ser or Asn

<220>
<221> VARIANT
<222> 420
<223> 9-9-246 : polymorphic amino acid Pro or Arg

<220>
<221> VARIANT
<222> 519
<223> LSRX9f13-BM : polymorphic amino acid deletion of Arg

<400> 3

```
Met Gln Gln Asp Gly Leu Gly Val Gly Thr Arg Asn Gly Ser Gly Lys
1               5                   10                  15
Gly Arg Ser Val His Pro Ser Trp Pro Trp Cys Ala Pro Arg Pro Leu
                20                  25                  30
Arg Tyr Phe Gly Arg Asp Ala Arg Arg Ala Gln Thr Ala Ala
            35                  40                  45
Met Ala Leu Leu Ala Gly Gly Leu Ser Arg Gly Leu Gly Ser His Pro
        50                  55                  60
Ala Ala Ala Gly Arg Asp Ala Val Val Phe Val Trp Leu Leu Leu Ser
65                  70                  75                  80
Thr Trp Cys Thr Ala Pro Ala Arg Ala Ile Gln Val Thr Val Ser Asn
                85                  90                  95
Pro Tyr His Val Val Ile Leu Phe Gln Pro Val Thr Leu Pro Cys Thr
                100                 105                 110
Tyr Gln Met Thr Ser Thr Pro Thr Gln Pro Ile Val Ile Trp Lys Tyr
            115                 120                 125
Lys Ser Phe Cys Arg Asp Arg Ile Ala Asp Ala Phe Ser Pro Ala Ser
        130                 135                 140
Val Asp Asn Gln Leu Asn Ala Gln Leu Ala Ala Gly Asn Pro Gly Tyr
145                 150                 155                 160
Asn Pro Tyr Val Glu Cys Gln Asp Ser Val Arg Thr Val Arg Val Val
                165                 170                 175
Ala Thr Lys Gln Gly Asn Ala Val Thr Leu Gly Asp Tyr Tyr Gln Gly
                180                 185                 190
Arg Arg Ile Thr Ile Thr Gly Asn Ala Asp Leu Thr Phe Asp Gln Thr
            195                 200                 205
Ala Trp Gly Asp Ser Gly Val Tyr Tyr Cys Ser Val Val Ser Ala Gln
        210                 215                 220
Asp Leu Gln Gly Asn Asn Glu Ala Tyr Ala Glu Leu Ile Val Leu Gly
225                 230                 235                 240
Arg Thr Ser Gly Val Ala Glu Leu Leu Pro Gly Phe Gln Ala Gly Pro
                245                 250                 255
Ile Glu Asp Trp Leu Phe Val Val Val Cys Leu Ala Ala Phe Leu
            260                 265                 270
Ile Phe Leu Leu Leu Gly Ile Cys Trp Cys Gln Cys Cys Pro His Thr
        275                 280                 285
Cys Cys Cys Tyr Val Arg Cys Pro Cys Cys Pro Asp Lys Cys Cys Cys
        290                 295                 300
Pro Glu Ala Leu Tyr Ala Ala Gly Lys Ala Ala Thr Ser Gly Val Pro
305                 310                 315                 320
Ser Ile Tyr Ala Pro Ser Thr Tyr Ala His Leu Ser Pro Ala Lys Thr
                325                 330                 335
Pro Pro Pro Pro Ala Met Ile Pro Met Gly Pro Ala Tyr Asn Gly Tyr
                340                 345                 350
Pro Gly Gly Tyr Pro Gly Asp Val Asp Arg Ser Ser Ser Ala Gly Gly
            355                 360                 365
```

```
Gln Gly Ser Tyr Val Pro Leu Leu Arg Asp Thr Asp Ser Ser Val Ala
    370                 375                 380
Ser Glu Val Arg Ser Gly Tyr Arg Ile Gln Ala Ser Gln Gln Asp Asp
385                 390                 395                 400
Ser Met Arg Val Leu Tyr Tyr Met Glu Lys Glu Leu Ala Asn Phe Asp
                405                 410                 415
Pro Ser Arg Pro Gly Pro Pro Ser Gly Arg Val Glu Arg Ala Met Ser
            420                 425                 430
Glu Val Thr Ser Leu His Glu Asp Asp Trp Arg Ser Arg Pro Ser Arg
        435                 440                 445
Gly Pro Ala Leu Thr Pro Ile Arg Asp Glu Glu Trp Gly Gly His Ser
    450                 455                 460
Pro Arg Ser Pro Arg Gly Trp Asp Gln Glu Pro Ala Arg Glu Gln Ala
465                 470                 475                 480
Gly Gly Gly Trp Arg Ala Arg Arg Pro Arg Ala Arg Ser Val Asp Ala
                485                 490                 495
Leu Asp Asp Leu Thr Pro Pro Ser Thr Ala Glu Ser Gly Ser Arg Ser
            500                 505                 510
Pro Thr Ser Asn Gly Gly Arg Ser Arg Ala Tyr Met Pro Pro Arg Ser
        515                 520                 525
Arg Ser Arg Asp Asp Leu Tyr Asp Gln Asp Asp Ser Arg Asp Phe Pro
    530                 535                 540
Arg Ser Arg Asp Pro His Tyr Asp Asp Phe Arg Ser Arg Glu Arg Pro
545                 550                 555                 560
Pro Ala Asp Pro Arg Ser His His His Arg Thr Arg Asp Pro Arg Asp
                565                 570                 575
Asn Gly Ser Arg Ser Gly Asp Leu Pro Tyr Asp Gly Arg Leu Leu Glu
            580                 585                 590
Glu Ala Val Arg Lys Lys Gly Ser Glu Glu Arg Arg Arg Pro His Lys
        595                 600                 605
Glu Glu Glu Glu Glu Ala Tyr Tyr Pro Pro Ala Pro Pro Pro Tyr Ser
    610                 615                 620
Glu Thr Asp Ser Gln Ala Ser Arg Glu Arg Arg Leu Lys Lys Asn Leu
625                 630                 635                 640
Ala Leu Ser Arg Glu Ser Leu Val Val
                645

<210> 4
<211> 2101
<212> DNA
<213> Homo sapiens

<220>
<221> allele
<222> 595
<223> 9-3-324 : polymorphic base C or T

<220>
<221> allele
<222> 883
<223> 9-6-187 : polymorphic base C or T

<220>
<221> allele
<222> 1134
<223> 9-7-325 : polymorphic base A or G

<220>
<221> allele
```

```
<222> 1305
<223> 9-9-246 : polymorphic base G or C

<220>
<221> allele
<222> 1601
<223> LSRX9f13-BM : polymorphic base deletion of AGG <220>
<221> allele
<222> 2022
<223> LSRX9f14-BM : polymorphic base T or G
<400> 4
tggagtgtgg ctcggaggac cgcggcgggt caagcacctt tctccccat atctgaaagc      60
atgcccttg tccacgtcgt ttacgctcat taaaacttcc aga atg caa cag gac       115
                                              Met Gln Gln Asp
                                               1
gga ctt gga gta ggg aca agg aac gga agt ggg aag ggg agg agc gtg       163
Gly Leu Gly Val Gly Thr Arg Asn Gly Ser Gly Lys Gly Arg Ser Val
 5                  10                  15                  20
cac ccc tcc tgg cct tgg tgc gcg ccg cgc ccc cta agg tac ttt gga       211
His Pro Ser Trp Pro Trp Cys Ala Pro Arg Pro Leu Arg Tyr Phe Gly
                 25                  30                  35
agg gac gcg cgg gcc aga cgc gcc cag acg gcc gcg atg gcg ctg ttg       259
Arg Asp Ala Arg Ala Arg Arg Ala Gln Thr Ala Ala Met Ala Leu Leu
             40                  45                  50
gcc ggc ggg ctc tcc aga ggg ctg ggc tcc cac ccg gcc gcc gca ggc       307
Ala Gly Gly Leu Ser Arg Gly Leu Gly Ser His Pro Ala Ala Ala Gly
         55                  60                  65
cgg gac gcg gtc gtc ttc gtg tgg ctt ctg ctt agc acc tgg tgc aca       355
Arg Asp Ala Val Val Phe Val Trp Leu Leu Leu Ser Thr Trp Cys Thr
 70                  75                  80
gct cct gcc agg gcc atc cag gtg acc gtg tcc aac ccc tac cac gtg       403
Ala Pro Ala Arg Ala Ile Gln Val Thr Val Ser Asn Pro Tyr His Val
 85                  90                  95                 100
gtg atc ctc ttc cag cct gtg acc ctg ccc tgt acc tac cag atg acc       451
Val Ile Leu Phe Gln Pro Val Thr Leu Pro Cys Thr Tyr Gln Met Thr
                105                 110                 115
tcg acc ccc acg caa ccc atc gtc atc tgg aag tac aag tct ttc tgc       499
Ser Thr Pro Thr Gln Pro Ile Val Ile Trp Lys Tyr Lys Ser Phe Cys
            120                 125                 130
cgg gac cgc atc gcc gat gcc ttc tcc ccg gcc agc gtc gac aac cag       547
Arg Asp Arg Ile Ala Asp Ala Phe Ser Pro Ala Ser Val Asp Asn Gln
        135                 140                 145
ctc aat gcc cag ctg gca gcc ggg aac cca ggc tac aac ccc tac gty       595
Leu Asn Ala Gln Leu Ala Ala Gly Asn Pro Gly Tyr Asn Pro Tyr Val
    150                 155                 160
gag tgc cag gac agc gtg cgc acc gtc agg gtc gtg gcc acc aag cag       643
Glu Cys Gln Asp Ser Val Arg Thr Val Arg Val Val Ala Thr Lys Gln
165                 170                 175                 180
ggc aac gct gtg acc ctg gga gat tac tac cag ggc cgg agg att acc       691
Gly Asn Ala Val Thr Leu Gly Asp Tyr Tyr Gln Gly Arg Arg Ile Thr
                185                 190                 195
atc acc gga aat gct gac ctg acc ttt gac cag acg gcg tgg ggg gac       739
Ile Thr Gly Asn Ala Asp Leu Thr Phe Asp Gln Thr Ala Trp Gly Asp
            200                 205                 210
agt ggt gtg tat tac tgc tcc gtg gtc tca gcc cag gac ctc cag ggg       787
Ser Gly Val Tyr Tyr Cys Ser Val Val Ser Ala Gln Asp Leu Gln Gly
```

```
              215                      220                       225
aac aat gag gcc tac gca gag ctc atc gtc ctt gac tgg ctc ttc gtg     835
Asn Asn Glu Ala Tyr Ala Glu Leu Ile Val Leu Asp Trp Leu Phe Val
        230                      235                       240
gtt gtg gta tgc ctg gct gcc ttc ctc atc ttc ctc ctc ctg ggc aty     883
Val Val Val Cys Leu Ala Ala Phe Leu Ile Phe Leu Leu Leu Gly Ile
245                      250                      255                      260
tgc tgg tgc cag tgc tgc ccg cac act tgc tgc tgc tac gtc agg tgc     931
Cys Trp Cys Gln Cys Cys Pro His Thr Cys Cys Cys Tyr Val Arg Cys
                    265                      270                      275
ccc tgc tgc cca gac aag tgc tgc tgc ccc gag gcc ctg tat gcc gcc     979
Pro Cys Cys Pro Asp Lys Cys Cys Cys Pro Glu Ala Leu Tyr Ala Ala
                280                      285                      290
ggc aaa gca gcc acc tca ggt gtt ccc agc att tat gcc ccc agc acc    1027
Gly Lys Ala Ala Thr Ser Gly Val Pro Ser Ile Tyr Ala Pro Ser Thr
            295                      300                      305
tat gcc cac ctg tct ccc gcc aag acc cca ccc cca cca gct atg att    1075
Tyr Ala His Leu Ser Pro Ala Lys Thr Pro Pro Pro Pro Ala Met Ile
    310                      315                      320
ccc atg ggc cct gcc tac aac ggg tac cct gga gga tac cct gga gac    1123
Pro Met Gly Pro Ala Tyr Asn Gly Tyr Pro Gly Gly Tyr Pro Gly Asp
325                      330                      335                      340
gtt gac agg art agc tca gct ggt ggc caa ggc tcc tat gta ccc ctg    1171
Val Asp Arg Xaa Ser Ser Ala Gly Gly Gln Gly Ser Tyr Val Pro Leu
                    345                      350                      355
ctt cgg gac acg gac agc agt gtg gcc tct gaa gtc cgc agt ggc tac    1219
Leu Arg Asp Thr Asp Ser Ser Val Ala Ser Glu Val Arg Ser Gly Tyr
                360                      365                      370
agg att cag gcc agc cag cag gac gac tcc atg cgg gtc ctg tac tac    1267
Arg Ile Gln Ala Ser Gln Gln Asp Asp Ser Met Arg Val Leu Tyr Tyr
            375                      380                      385
atg gag aag gag ctg gcc aac ttc gac cct tct cga cst ggc ccc ccc    1315
Met Glu Lys Glu Leu Ala Asn Phe Asp Pro Ser Arg Xaa Gly Pro Pro
    390                      395                      400
agt ggc cgt gtg gag cgg gcc atg agt gaa gtc acc tcc ctc cac gag    1363
Ser Gly Arg Val Glu Arg Ala Met Ser Glu Val Thr Ser Leu His Glu
405                      410                      415                      420
gac gac tgg cga tct cgg cct tcc cgg ggc cct gcc ctc acc ccg atc    1411
Asp Asp Trp Arg Ser Arg Pro Ser Arg Gly Pro Ala Leu Thr Pro Ile
                    425                      430                      435
cgg gat gag gag tgg ggt ggc cac tcc ccc cgg agt ccc agg gga tgg    1459
Arg Asp Glu Glu Trp Gly Gly His Ser Pro Arg Ser Pro Arg Gly Trp
                440                      445                      450
gac cag gag ccc gcc agg gag cag gca ggc ggg ggc tgg cgg gcc agg    1507
Asp Gln Glu Pro Ala Arg Glu Gln Ala Gly Gly Gly Trp Arg Ala Arg
            455                      460                      465
cgg ccc cgg gcc cgc tcc gtg gac gcc ctg gac gac ctc acc ccg ccg    1555
Arg Pro Arg Ala Arg Ser Val Asp Ala Leu Asp Asp Leu Thr Pro Pro
    470                      475                      480
agc acc gcc gag tca ggg agc agg tct ccc acg agt aat ggt ggg aga    1603
Ser Thr Ala Glu Ser Gly Ser Arg Ser Pro Thr Ser Asn Gly Gly Arg
485                      490                      495                      500
agc cgg gcc tac atg ccc ccg cgg agc cgc agc cgg gac gac ctc tat    1651
Ser Arg Ala Tyr Met Pro Pro Arg Ser Arg Ser Arg Asp Asp Leu Tyr
                    505                      510                      515
gac caa gac gac tcg agg gac ttc cca cgc tcc cgg gac ccc cac tac    1699
Asp Gln Asp Asp Ser Arg Asp Phe Pro Arg Ser Arg Asp Pro His Tyr
                520                      525                      530
gac gac ttc agg tct cgg gag cgc cct cct gcc gac ccc agg tcc cac    1747
```

```
            Asp Asp Phe Arg Ser Arg Glu Arg Pro Pro Ala Asp Pro Arg Ser His
                    535                 540                 545
            cac cac cgt acc cgg gac cct cgg gac aac ggc tcc agg tcc ggg gac      1795
            His His Arg Thr Arg Asp Pro Arg Asp Asn Gly Ser Arg Ser Gly Asp
                550                     555                 560
            ctc ccc tat gat ggg cgg cta ctg gag gag gct gtg agg aag aag ggg      1843
            Leu Pro Tyr Asp Gly Arg Leu Leu Glu Glu Ala Val Arg Lys Lys Gly
            565                 570                 575                 580
            tcg gag gag agg agg aga ccc cac aag gag gag gag gaa gag gcc tac      1891
            Ser Glu Glu Arg Arg Arg Pro His Lys Glu Glu Glu Glu Glu Ala Tyr
                            585                 590                 595
            tac ccg ccc gcg ccg ccc ccg tac tcg gag acc gac tcg cag gcg tcc      1939
            Tyr Pro Pro Ala Pro Pro Pro Tyr Ser Glu Thr Asp Ser Gln Ala Ser
                            600                 605                 610
            cga gag cgc agg ctc aag aag aac ttg gcc ctg agt cgg gaa agt tta      1987
            Arg Glu Arg Arg Leu Lys Lys Asn Leu Ala Leu Ser Arg Glu Ser Leu
                            615                 620                 625
            gtc gtc tga tctgacgttt tctacgtagc ttttgkattt ttttttttaa              2036
            Val Val *
                    630
            tttgaaggaa cactgatgaa gccctgccat acccctcccg agtctaataa aacgtataat    2096
            cacaa                                                                2101

<210> 5
<211> 630
<212> PRT
<213> Homo sapiens

<220>
<221> VARIANT
<222> 344
<223> 9-7-325 : polymorphic amino acid Ser or Asn

<220>
<221> VARIANT
<222> 401
<223> 9-9-246 : polymorphic amino acid Pro or Arg

<220>
<221> VARIANT
<222> 500
<223> LSRX9f13-BM : polymorphic amino acid deletion of Arg
<400> 5
Met Gln Gln Asp Gly Leu Gly Val Gly Thr Arg Asn Gly Ser Gly Lys
1               5                   10                  15
Gly Arg Ser Val His Pro Ser Trp Pro Trp Cys Ala Pro Arg Pro Leu
                20                  25                  30
Arg Tyr Phe Gly Arg Asp Ala Arg Ala Arg Arg Ala Gln Thr Ala Ala
            35                  40                  45
Met Ala Leu Leu Ala Gly Gly Leu Ser Arg Gly Leu Gly Ser His Pro
        50                  55                  60
Ala Ala Ala Gly Arg Asp Ala Val Val Phe Val Trp Leu Leu Leu Ser
65                  70                  75                  80
Thr Trp Cys Thr Ala Pro Ala Arg Ala Ile Gln Val Thr Val Ser Asn
                85                  90                  95
Pro Tyr His Val Val Ile Leu Phe Gln Pro Val Thr Leu Pro Cys Thr
                100                 105                 110
Tyr Gln Met Thr Ser Thr Pro Thr Gln Pro Ile Val Ile Trp Lys Tyr
```

```
                    115                 120                 125
Lys Ser Phe Cys Arg Asp Arg Ile Ala Asp Ala Phe Ser Pro Ala Ser
        130                 135                 140
Val Asp Asn Gln Leu Asn Ala Gln Leu Ala Ala Gly Asn Pro Gly Tyr
145                 150                 155                 160
Asn Pro Tyr Val Glu Cys Gln Asp Ser Val Arg Thr Val Arg Val Val
                165                 170                 175
Ala Thr Lys Gln Gly Asn Ala Val Thr Leu Gly Asp Tyr Tyr Gln Gly
            180                 185                 190
Arg Arg Ile Thr Ile Thr Gly Asn Ala Asp Leu Thr Phe Asp Gln Thr
        195                 200                 205
Ala Trp Gly Asp Ser Gly Val Tyr Tyr Cys Ser Val Val Ser Ala Gln
    210                 215                 220
Asp Leu Gln Gly Asn Asn Glu Ala Tyr Ala Glu Leu Ile Val Leu Asp
225                 230                 235                 240
Trp Leu Phe Val Val Val Val Cys Leu Ala Ala Phe Leu Ile Phe Leu
                245                 250                 255
Leu Leu Gly Ile Cys Trp Cys Gln Cys Cys Pro His Thr Cys Cys Cys
            260                 265                 270
Tyr Val Arg Cys Pro Cys Cys Pro Asp Lys Cys Cys Cys Pro Glu Ala
        275                 280                 285
Leu Tyr Ala Ala Gly Lys Ala Ala Thr Ser Gly Val Pro Ser Ile Tyr
    290                 295                 300
Ala Pro Ser Thr Tyr Ala His Leu Ser Pro Ala Lys Thr Pro Pro Pro
305                 310                 315                 320
Pro Ala Met Ile Pro Met Gly Pro Ala Tyr Asn Gly Tyr Pro Gly Gly
                325                 330                 335
Tyr Pro Gly Asp Val Asp Arg Ser Ser Ser Ala Gly Gly Gln Gly Ser
            340                 345                 350
Tyr Val Pro Leu Leu Arg Asp Thr Asp Ser Ser Val Ala Ser Glu Val
        355                 360                 365
Arg Ser Gly Tyr Arg Ile Gln Ala Ser Gln Gln Asp Asp Ser Met Arg
    370                 375                 380
Val Leu Tyr Tyr Met Glu Lys Glu Leu Ala Asn Phe Asp Pro Ser Arg
385                 390                 395                 400
Pro Gly Pro Pro Ser Gly Arg Val Glu Arg Ala Met Ser Glu Val Thr
                405                 410                 415
Ser Leu His Glu Asp Asp Trp Arg Ser Arg Pro Ser Arg Gly Pro Ala
            420                 425                 430
Leu Thr Pro Ile Arg Asp Glu Glu Trp Gly Gly His Ser Pro Arg Ser
        435                 440                 445
Pro Arg Gly Trp Asp Gln Glu Pro Ala Arg Glu Gln Ala Gly Gly Gly
    450                 455                 460
Trp Arg Ala Arg Arg Pro Arg Ala Arg Ser Val Asp Ala Leu Asp Asp
465                 470                 475                 480
Leu Thr Pro Pro Ser Thr Ala Glu Ser Gly Ser Arg Ser Pro Thr Ser
                485                 490                 495
Asn Gly Gly Arg Ser Arg Ala Tyr Met Pro Pro Arg Ser Arg Ser Arg
            500                 505                 510
Asp Asp Leu Tyr Asp Gln Asp Asp Ser Arg Asp Phe Pro Arg Ser Arg
        515                 520                 525
Asp Pro His Tyr Asp Asp Phe Arg Ser Arg Glu Arg Pro Pro Ala Asp
    530                 535                 540
Pro Arg Ser His His His Arg Thr Arg Asp Pro Arg Asp Asn Gly Ser
545                 550                 555                 560
Arg Ser Gly Asp Leu Pro Tyr Asp Gly Arg Leu Leu Glu Glu Ala Val
                565                 570                 575
Arg Lys Lys Gly Ser Glu Glu Arg Arg Arg Pro His Lys Glu Glu Glu
            580                 585                 590
```

```
            Glu Glu Ala Tyr Tyr Pro Pro Ala Pro Pro Pro Tyr Ser Glu Thr Asp
                    595                 600                 605
            Ser Gln Ala Ser Arg Glu Arg Arg Leu Lys Lys Asn Leu Ala Leu Ser
                610                 615                 620
            Arg Glu Ser Leu Val Val
            625                 630
```

<210> 6
<211> 1954
<212> DNA
<213> Homo sapiens

<220>
<221> allele
<222> 595
<223> 9-3-324 : polymorphic base C or T

<220>
<221> allele
<222> 987
<223> 9-7-325 : polymorphic base A or G

<220>
<221> allele
<222> 1158
<223> 9-9-246 : polymorphic base G or C

<220>
<221> allele
<222> 1454
<223> LSRX9f13-BM : polymorphic base deletion of AGG <220>
<221> allele
<222> 1875
<223> LSRX9f14-BM : polymorphic base T or G

```
<400> 6
tggagtgtgg ctcggaggac cgcggcgggt caagcacctt tctcccccat atctgaaagc         60
atgcccttig tccacgtcgt ttacgctcat taaaacttcc aga atg caa cag gac        115
                                              Met Gln Gln Asp
                                              1
gga ctt gga gta ggg aca agg aac gga agt ggg aag ggg agg agc gtg        163
Gly Leu Gly Val Gly Thr Arg Asn Gly Ser Gly Lys Gly Arg Ser Val
5                   10                  15                  20
cac ccc tcc tgg cct tgg tgc gcg ccg cgc ccc cta agg tac ttt gga        211
His Pro Ser Trp Pro Trp Cys Ala Pro Arg Pro Leu Arg Tyr Phe Gly
                25                  30                  35
agg gac gcg cgg gcc aga cgc gcc cag acg gcc gcg atg gcg ctg ttg        259
Arg Asp Ala Arg Ala Arg Arg Ala Gln Thr Ala Ala Met Ala Leu Leu
            40                  45                  50
gcc ggc ggg ctc tcc aga ggg ctg ggc tcc cac ccg gcc gcc gca ggc        307
Ala Gly Gly Leu Ser Arg Gly Leu Gly Ser His Pro Ala Ala Ala Gly
                55                  60                  65
cgg gac gcg gtc gtc ttc gtg tgg ctt ctg ctt agc acc tgg tgc aca        355
Arg Asp Ala Val Val Phe Val Trp Leu Leu Leu Ser Thr Trp Cys Thr
        70                  75                  80
gct cct gcc agg gcc atc cag gtg acc gtg tcc aac ccc tac cac gtg        403
Ala Pro Ala Arg Ala Ile Gln Val Thr Val Ser Asn Pro Tyr His Val
```

```
          85                  90                  95                 100
gtg atc ctc ttc cag cct gtg acc ctg ccc tgt acc tac cag atg acc          451
Val Ile Leu Phe Gln Pro Val Thr Leu Pro Cys Thr Tyr Gln Met Thr
                    105                 110                 115
tcg acc ccc acg caa ccc atc gtc atc tgg aag tac aag tct ttc tgc          499
Ser Thr Pro Thr Gln Pro Ile Val Ile Trp Lys Tyr Lys Ser Phe Cys
            120                 125                 130
cgg gac cgc atc gcc gat gcc ttc tcc ccg gcc agc gtc gac aac cag          547
Arg Asp Arg Ile Ala Asp Ala Phe Ser Pro Ala Ser Val Asp Asn Gln
            135                 140                 145
ctc aat gcc cag ctg gca gcc ggg aac cca ggc tac aac ccc tac gty          595
Leu Asn Ala Gln Leu Ala Ala Gly Asn Pro Gly Tyr Asn Pro Tyr Val
        150                 155                 160
gag tgc cag gac agc gtg cgc acc gtc agg gtc gtg gcc acc aag cag          643
Glu Cys Gln Asp Ser Val Arg Thr Val Arg Val Val Ala Thr Lys Gln
165                 170                 175                 180
ggc aac gct gtg acc ctg gga gat tac tac cag ggc cgg agg att acc          691
Gly Asn Ala Val Thr Leu Gly Asp Tyr Tyr Gln Gly Arg Arg Ile Thr
                    185                 190                 195
atc acc gga aat gct gac ctg acc ttt gac cag acg gcg tgg ggg gac          739
Ile Thr Gly Asn Ala Asp Leu Thr Phe Asp Gln Thr Ala Trp Gly Asp
                    200                 205                 210
agt ggt gtg tat tac tgc tcc gtg gtc tca gcc cag gac ctc cag ggg          787
Ser Gly Val Tyr Tyr Cys Ser Val Val Ser Ala Gln Asp Leu Gln Gly
            215                 220                 225
aac aat gag gcc tac gca gag ctc atc gtc ctt gtg tat gcc gcc ggc          835
Asn Asn Glu Ala Tyr Ala Glu Leu Ile Val Leu Val Tyr Ala Ala Gly
        230                 235                 240
aaa gca gcc acc tca ggt gtt ccc agc att tat gcc ccc agc acc tat          883
Lys Ala Ala Thr Ser Gly Val Pro Ser Ile Tyr Ala Pro Ser Thr Tyr
245                 250                 255                 260
gcc cac ctg tct ccc gcc aag acc cca ccc cca gct atg att ccc          931
Ala His Leu Ser Pro Ala Lys Thr Pro Pro Pro Ala Met Ile Pro
                265                 270                 275
atg ggc cct gcc tac aac ggg tac cct gga gga tac cct gga gac gtt          979
Met Gly Pro Ala Tyr Asn Gly Tyr Pro Gly Gly Tyr Pro Gly Asp Val
                    280                 285                 290
gac agg art agc tca gct ggt ggc caa ggc tcc tat gta ccc ctg ctt         1027
Asp Arg Xaa Ser Ser Ala Gly Gly Gln Gly Ser Tyr Val Pro Leu Leu
            295                 300                 305
cgg gac acg gac agc agt gtg gcc tct gaa gtc cgc agt ggc tac agg         1075
Arg Asp Thr Asp Ser Ser Val Ala Ser Glu Val Arg Ser Gly Tyr Arg
    310                 315                 320
att cag gcc agc cag cag gac gac tcc atg cgg gtc ctg tac tac atg         1123
Ile Gln Ala Ser Gln Gln Asp Asp Ser Met Arg Val Leu Tyr Tyr Met
325                 330                 335                 340
gag aag gag ctg gcc aac ttc gac cct tct cga cst ggc ccc ccc agt         1171
Glu Lys Glu Leu Ala Asn Phe Asp Pro Ser Arg Xaa Gly Pro Pro Ser
                345                 350                 355
ggc cgt gtg gag cgg gcc atg agt gaa gtc acc tcc ctc cac gag gac         1219
Gly Arg Val Glu Arg Ala Met Ser Glu Val Thr Ser Leu His Glu Asp
                360                 365                 370
gac tgg cga tct cgg cct tcc cgg ggc cct gcc ctc acc ccg atc cgg         1267
Asp Trp Arg Ser Arg Pro Ser Arg Gly Pro Ala Leu Thr Pro Ile Arg
            375                 380                 385
gat gag gag tgg ggt ggc cac tcc ccc cgg agt ccc agg gga tgg gac         1315
Asp Glu Glu Trp Gly Gly His Ser Pro Arg Ser Pro Arg Gly Trp Asp
        390                 395                 400
cag gag ccc gcc agg gag cag gca ggc ggg tgg cgg gcc agg cgg         1363
```

```
Gln Glu Pro Ala Arg Glu Gln Ala Gly Gly Gly Trp Arg Ala Arg Arg
405                 410                 415                 420
ccc cgg gcc cgc tcc gtg gac gcc ctg gac gac ctc acc ccg ccg agc    1411
Pro Arg Ala Arg Ser Val Asp Ala Leu Asp Asp Leu Thr Pro Pro Ser
                425                 430                 435
acc gcc gag tca ggg agc agg tct ccc acg agt aat ggt ggg aga agc    1459
Thr Ala Glu Ser Gly Ser Arg Ser Pro Thr Ser Asn Gly Gly Arg Ser
                440                 445                 450
cgg gcc tac atg ccc ccg cgg agc cgc agc cgg gac gac ctc tat gac    1507
Arg Ala Tyr Met Pro Pro Arg Ser Arg Ser Arg Asp Asp Leu Tyr Asp
                455                 460                 465
caa gac gac tcg agg gac ttc cca cgc tcc cgg gac ccc cac tac gac    1555
Gln Asp Asp Ser Arg Asp Phe Pro Arg Ser Arg Asp Pro His Tyr Asp
    470                 475                 480
gac ttc agg tct cgg gag cgc cct cct gcc gac ccc agg tcc cac cac    1603
Asp Phe Arg Ser Arg Glu Arg Pro Pro Ala Asp Pro Arg Ser His His
485                 490                 495                 500
cac cgt acc cgg gac cct cgg gac aac ggc tcc agg tcc ggg gac ctc    1651
His Arg Thr Arg Asp Pro Arg Asp Asn Gly Ser Arg Ser Gly Asp Leu
                505                 510                 515
ccc tat gat ggg cgg cta ctg gag gag gct gtg agg aag aag ggg tcg    1699
Pro Tyr Asp Gly Arg Leu Leu Glu Glu Ala Val Arg Lys Lys Gly Ser
                520                 525                 530
gag gag agg agg aga ccc cac aag gag gag gag gaa gag gcc tac tac    1747
Glu Glu Arg Arg Arg Pro His Lys Glu Glu Glu Glu Glu Ala Tyr Tyr
                535                 540                 545
ccg ccc gcg ccg ccc ccg tac tcg gag acg gac tcg cag gcg tcc cga    1795
Pro Pro Ala Pro Pro Pro Tyr Ser Glu Thr Asp Ser Gln Ala Ser Arg
550                 555                 560
gag cgc agg ctc aag aag aac ttg gcc ctg agt cgg gaa agt tta gtc    1843
Glu Arg Arg Leu Lys Lys Asn Leu Ala Leu Ser Arg Glu Ser Leu Val
565                 570                 575                 580
gtc tga tctgacgttt tctacgtagc ttttgkattt ttttttttaa tttgaaggaa    1899
Val *
cactgatgaa gccctgccat acccctcccg agtctaataa aacgtataat cacaa       1954

<210> 7
<211> 581
<212> PRT
<213> Homo sapiens

<220>
<221> VARIANT
<222> 295
<223> 9-7-325 : polymorphic amino acid Ser or Asn

<220>
<221> VARIANT
<222> 352
<223> 9-9-246 : polymorphic amino acid Pro or Arg

<220>
<221> VARIANT
<222> 451
<223> LSRX9f13-BM : polymorphic amino acid deletion of Arg
<400> 7
Met Gln Gln Asp Gly Leu Gly Val Gly Thr Arg Asn Gly Ser Gly Lys
1               5                   10                  15
```

```
Gly Arg Ser Val His Pro Ser Trp Pro Trp Cys Ala Pro Arg Pro Leu
         20                  25                  30
Arg Tyr Phe Gly Arg Asp Ala Arg Ala Arg Arg Ala Gln Thr Ala Ala
         35                  40                  45
Met Ala Leu Leu Ala Gly Gly Leu Ser Arg Gly Leu Gly Ser His Pro
         50                  55                  60
Ala Ala Ala Gly Arg Asp Ala Val Val Phe Val Trp Leu Leu Leu Ser
65                   70                  75                   80
Thr Trp Cys Thr Ala Pro Ala Arg Ala Ile Gln Val Thr Val Ser Asn
                 85                  90                  95
Pro Tyr His Val Val Ile Leu Phe Gln Pro Val Thr Leu Pro Cys Thr
             100                 105                 110
Tyr Gln Met Thr Ser Thr Pro Thr Gln Pro Ile Val Ile Trp Lys Tyr
         115                 120                 125
Lys Ser Phe Cys Arg Asp Arg Ile Ala Asp Ala Phe Ser Pro Ala Ser
         130                 135                 140
Val Asp Asn Gln Leu Asn Ala Gln Leu Ala Ala Gly Asn Pro Gly Tyr
145                 150                 155                 160
Asn Pro Tyr Val Glu Cys Gln Asp Ser Val Arg Thr Val Arg Val Val
                 165                 170                 175
Ala Thr Lys Gln Gly Asn Ala Val Thr Leu Gly Asp Tyr Tyr Gln Gly
             180                 185                 190
Arg Arg Ile Thr Ile Thr Gly Asn Ala Asp Leu Thr Phe Asp Gln Thr
         195                 200                 205
Ala Trp Gly Asp Ser Gly Val Tyr Tyr Cys Ser Val Val Ser Ala Gln
         210                 215                 220
Asp Leu Gln Gly Asn Asn Glu Ala Tyr Ala Glu Leu Ile Val Leu Val
225                 230                 235                 240
Tyr Ala Ala Gly Lys Ala Ala Thr Ser Gly Val Pro Ser Ile Tyr Ala
                 245                 250                 255
Pro Ser Thr Tyr Ala His Leu Ser Pro Ala Lys Thr Pro Pro Pro Pro
             260                 265                 270
Ala Met Ile Pro Met Gly Pro Ala Tyr Asn Gly Tyr Pro Gly Gly Tyr
         275                 280                 285
Pro Gly Asp Val Asp Arg Ser Ser Ser Ala Gly Gly Gln Gly Ser Tyr
         290                 295                 300
Val Pro Leu Leu Arg Asp Thr Asp Ser Ser Val Ala Ser Glu Val Arg
305                 310                 315                 320
Ser Gly Tyr Arg Ile Gln Ala Ser Gln Gln Asp Asp Ser Met Arg Val
                 325                 330                 335
Leu Tyr Tyr Met Glu Lys Glu Leu Ala Asn Phe Asp Pro Ser Arg Pro
             340                 345                 350
Gly Pro Pro Ser Gly Arg Val Glu Arg Ala Met Ser Glu Val Thr Ser
         355                 360                 365
Leu His Glu Asp Asp Trp Arg Ser Arg Pro Ser Arg Gly Pro Ala Leu
         370                 375                 380
Thr Pro Ile Arg Asp Glu Glu Trp Gly Gly His Ser Pro Arg Ser Pro
385                 390                 395                 400
Arg Gly Trp Asp Gln Glu Pro Ala Arg Glu Gln Ala Gly Gly Gly Trp
                 405                 410                 415
Arg Ala Arg Arg Pro Arg Ala Arg Ser Val Asp Ala Leu Asp Asp Leu
             420                 425                 430
Thr Pro Pro Ser Thr Ala Glu Ser Gly Ser Arg Ser Pro Thr Ser Asn
         435                 440                 445
Gly Gly Arg Ser Arg Ala Tyr Met Pro Pro Arg Ser Arg Ser Arg Asp
         450                 455                 460
Asp Leu Tyr Asp Gln Asp Asp Ser Arg Asp Phe Pro Arg Ser Arg Asp
465                 470                 475                 480
Pro His Tyr Asp Asp Phe Arg Ser Arg Glu Arg Pro Pro Ala Asp Pro
```

```
                                485                   490                   495
    Arg Ser His His His Arg Thr Arg Asp Pro Arg Asp Asn Gly Ser Arg
                    500                   505                   510
    Ser Gly Asp Leu Pro Tyr Asp Gly Arg Leu Leu Glu Glu Ala Val Arg
                    515                   520                   525
    Lys Lys Gly Ser Glu Glu Arg Arg Arg Pro His Lys Glu Glu Glu Glu
                    530                   535                   540
    Glu Ala Tyr Tyr Pro Pro Ala Pro Pro Pro Tyr Ser Glu Thr Asp Ser
    545                   550                   555                   560
    Gln Ala Ser Arg Glu Arg Arg Leu Lys Lys Asn Leu Ala Leu Ser Arg
                    565                   570                   575
    Glu Ser Leu Val Val
                    580

<210> 8
<211> 2097
<212> DNA
<213> Rattus norvegicus

<400> 8
accgctcacc aggtcagttg tccccggaaa gccgaaggca tgagcttcgc ccaagttctt    60
tttatgggtt agaactcctc cagagcgggg gaaaaaggac ttggaatagg ggcgggacgg   120
agcacgcacc cttctccgcc ttggttctcg ccgcgccccc tactctcggg atacttggga   180
ggggacgcgc gggcaccgtc gctgctagac ggccgcg atg gcg ccg gcg gcc ggc   235
                                           Met Ala Pro Ala Ala Gly
                                             1               5 gcg tgt gct ggg gcg cct gac tcc cac cca gct acc gtg gtc ttc gtg    283
Ala Cys Ala Gly Ala Pro Asp Ser His Pro Ala Thr Val Val Phe Val
            10                  15                  20 tgt ctc ttt ctc atc att ttc tgc cca gac cct gcc agt gcc atc cag    331
Cys Leu Phe Leu Ile Ile Phe Cys Pro Asp Pro Ala Ser Ala Ile Gln
        25                  30                  35 gtg act gtg tct gac ccc tac cac gta gtg atc ctg ttc cag cca gtg    379
Val Thr Val Ser Asp Pro Tyr His Val Val Ile Leu Phe Gln Pro Val
    40                  45                  50 acc ctg ccc tgc acc tat cag atg agc aac act ctc aca gtc ccc atc    427
Thr Leu Pro Cys Thr Tyr Gln Met Ser Asn Thr Leu Thr Val Pro Ile
55                  60                  65                  70 gtg atc tgg aag tac aag tca ttc tgc cgg gac cgt att gcc gat gcc    475
Val Ile Trp Lys Tyr Lys Ser Phe Cys Arg Asp Arg Ile Ala Asp Ala
                75                  80                  85 ttc tct cct gcc agt gtg gac aac cag cta aat gcc cag ttg gca gct    523
Phe Ser Pro Ala Ser Val Asp Asn Gln Leu Asn Ala Gln Leu Ala Ala
            90                  95                 100 ggc aac ccc ggc tac aac ccc tat gtg gag tgc cag gac agt gta cgc    571
Gly Asn Pro Gly Tyr Asn Pro Tyr Val Glu Cys Gln Asp Ser Val Arg
        105                 110                 115 act gtc agg gtg gtg gcc acc aaa cag ggc aat gcg gtg acc ctg gga    619
Thr Val Arg Val Val Ala Thr Lys Gln Gly Asn Ala Val Thr Leu Gly
    120                 125                 130 gac tac tac caa ggc agg agg atc acc ata aca gga aat gct gac ctg    667
Asp Tyr Tyr Gln Gly Arg Arg Ile Thr Ile Thr Gly Asn Ala Asp Leu
135                 140                 145                 150 acc ttc gag cag aca gcc tgg gga gac agt gga gtg tat tac tgc tct    715
Thr Phe Glu Gln Thr Ala Trp Gly Asp Ser Gly Val Tyr Tyr Cys Ser
                155                 160                 165 gtg gtc tcg gcc caa gat ctg gat gga aac aac gag gcg tac gca gag    763
Val Val Ser Ala Gln Asp Leu Asp Gly Asn Asn Glu Ala Tyr Ala Glu
            170                 175                 180
```

```
ctc atc gtc ctt ggc agg acc tca gag gcc cct gag ctc cta cct ggt      811
Leu Ile Val Leu Gly Arg Thr Ser Glu Ala Pro Glu Leu Leu Pro Gly
        185                 190                 195
ttt cgg gcg ggg ccc ttg gaa gat tgg ctc ttt gtg gtc gtg gtc tgc      859
Phe Arg Ala Gly Pro Leu Glu Asp Trp Leu Phe Val Val Val Val Cys
        200                 205                 210
ctg gcg agc ctc ctc ctc ttc ctc ctc ctg ggc atc tgc tgg tgc cag      907
Leu Ala Ser Leu Leu Leu Phe Leu Leu Leu Gly Ile Cys Trp Cys Gln
215                 220                 225                 230
tgc tgt cct cac acc tgc tgc tgc tat gtc cga tgt ccc tgc tgc cca      955
Cys Cys Pro His Thr Cys Cys Cys Tyr Val Arg Cys Pro Cys Cys Pro
                235                 240                 245
gac aag tgc tgt tgc cct gag gct ctt tat gct gct ggc aaa gca gcc     1003
Asp Lys Cys Cys Cys Pro Glu Ala Leu Tyr Ala Ala Gly Lys Ala Ala
        250                 255                 260
acc tca ggt gtc ccg agc atc tat gcc ccc agc atc tat acc cac ctc     1051
Thr Ser Gly Val Pro Ser Ile Tyr Ala Pro Ser Ile Tyr Thr His Leu
        265                 270                 275
tca cct gcc aag acc cca cca cct ccg cct gcc atg att ccc atg ggc     1099
Ser Pro Ala Lys Thr Pro Pro Pro Pro Ala Met Ile Pro Met Gly
280                 285                 290
cct ccc tat ggg tac cct gga gac ttt gac aga cat agc tca gtt ggt     1147
Pro Pro Tyr Gly Tyr Pro Gly Asp Phe Asp Arg His Ser Ser Val Gly
295                 300                 305                 310
ggc cac agc tcc caa gta ccc ctg ctg cgt gac gtg gat ggc agt gta     1195
Gly His Ser Ser Gln Val Pro Leu Leu Arg Asp Val Asp Gly Ser Val
                315                 320                 325
tct tca gaa gta cga agt ggc tac agg atc cag gct aac cag caa gat     1243
Ser Ser Glu Val Arg Ser Gly Tyr Arg Ile Gln Ala Asn Gln Gln Asp
                330                 335                 340
gac tcc atg agg gtc cta tac tat atg gag aaa gag cta gcc aac ttt     1291
Asp Ser Met Arg Val Leu Tyr Tyr Met Glu Lys Glu Leu Ala Asn Phe
        345                 350                 355
gac cct tcc cga cct ggc cct ccc aat ggc aga gtg gaa cgg gcc atg     1339
Asp Pro Ser Arg Pro Gly Pro Pro Asn Gly Arg Val Glu Arg Ala Met
        360                 365                 370
agt gaa gta acc tcc ctc cat gaa gat gac tgg cga tcg agg cct tcc     1387
Ser Glu Val Thr Ser Leu His Glu Asp Asp Trp Arg Ser Arg Pro Ser
375                 380                 385                 390
agg gct cct gcc ctc acc ccc atc agg gat gag gag tgg aat cgc cac     1435
Arg Ala Pro Ala Leu Thr Pro Ile Arg Asp Glu Glu Trp Asn Arg His
                395                 400                 405
tcc cca cag agt ccc aga aca tgg gag cag gaa ccc ctt caa gaa caa     1483
Ser Pro Gln Ser Pro Arg Thr Trp Glu Gln Glu Pro Leu Gln Glu Gln
                410                 415                 420
cca agg ggt ggt tgg ggg tct gga cgc cct cgg gcc cgc tct gtg gat     1531
Pro Arg Gly Gly Trp Gly Ser Gly Arg Pro Arg Ala Arg Ser Val Asp
        425                 430                 435
gct cta gat gat atc aac cgg cct ggc tcc act gaa tca gga cgg tct     1579
Ala Leu Asp Asp Ile Asn Arg Pro Gly Ser Thr Glu Ser Gly Arg Ser
440                 445                 450
tct ccc cca agt agt gga cgg aga gga cgg gcc tat gca cct cca aga     1627
Ser Pro Pro Ser Ser Gly Arg Arg Gly Arg Ala Tyr Ala Pro Pro Arg
455                 460                 465                 470
agt cgc agc cgg gat gac ctc tat gac ccg gac gat cct agg gac ttg     1675
Ser Arg Ser Arg Asp Asp Leu Tyr Asp Pro Asp Asp Pro Arg Asp Leu
                475                 480                 485
cca cat tcc cga gat ccc cac tat tat gac gac atc agg tct aga gat     1723
Pro His Ser Arg Asp Pro His Tyr Tyr Asp Asp Ile Arg Ser Arg Asp
```

```
              490                      495                      500
cca cgt gct gac ccc aga tcc cgt cag cga tcc cga gat cct cgg gat    1771
Pro Arg Ala Asp Pro Arg Ser Arg Gln Arg Ser Arg Asp Pro Arg Asp
        505                      510                     515
gct ggc ttc agg tca agg gac cct cag tat gat ggg cga cta tta gaa    1819
Ala Gly Phe Arg Ser Arg Asp Pro Gln Tyr Asp Gly Arg Leu Leu Glu
    520                      525                      530
gag gct tta aag aaa aag ggg tcg ggc gag aga agg agg gtt tac agg    1867
Glu Ala Leu Lys Lys Lys Gly Ser Gly Glu Arg Arg Arg Val Tyr Arg
535                      540                      545              550
gag gaa gaa gag gaa gag gag ggc caa tac ccc cca gca cct cca cct    1915
Glu Glu Glu Glu Glu Glu Glu Gly Gln Tyr Pro Pro Ala Pro Pro Pro
                    555                      560                  565
tac tca gag act gac tcg cag gcc tca cgg gag agg agg ctg aaa aag    1963
Tyr Ser Glu Thr Asp Ser Gln Ala Ser Arg Glu Arg Arg Leu Lys Lys
            570                      575                   580
aat ttg gcc ctg agt cgg gaa agt tta gtc gtc tga tccacgtttt          2009
Asn Leu Ala Leu Ser Arg Glu Ser Leu Val Val *
            585                      590
gtatgtagct tttgtacttt ttttttaatt ggaatcaata ttgatgaaac ttcaagccta   2069
ataaaatgtc taatcacaaa aaaaaaaa                                      2097

<210> 9
<211> 593
<212> PRT
<213> Rattus norvegicus

<400> 9
Met Ala Pro Ala Ala Gly Ala Cys Ala Gly Ala Pro Asp Ser His Pro
1               5                   10                  15
Ala Thr Val Val Phe Val Cys Leu Phe Leu Ile Ile Phe Cys Pro Asp
                20                  25                  30
Pro Ala Ser Ala Ile Gln Val Thr Val Ser Asp Pro Tyr His Val Val
            35                  40                  45
Ile Leu Phe Gln Pro Val Thr Leu Pro Cys Thr Tyr Gln Met Ser Asn
        50                  55                  60
Thr Leu Thr Val Pro Ile Val Ile Trp Lys Tyr Lys Ser Phe Cys Arg
65                  70                  75                  80
Asp Arg Ile Ala Asp Ala Phe Ser Pro Ala Ser Val Asp Asn Gln Leu
                85                  90                  95
Asn Ala Gln Leu Ala Ala Gly Asn Pro Gly Tyr Asn Pro Tyr Val Glu
                100                 105                 110
Cys Gln Asp Ser Val Arg Thr Val Arg Val Val Ala Thr Lys Gln Gly
            115                 120                 125
Asn Ala Val Thr Leu Gly Asp Tyr Tyr Gln Gly Arg Arg Ile Thr Ile
        130                 135                 140
Thr Gly Asn Ala Asp Leu Thr Phe Glu Gln Thr Ala Trp Gly Asp Ser
145                 150                 155                 160
Gly Val Tyr Tyr Cys Ser Val Val Ser Ala Gln Asp Leu Asp Gly Asn
                165                 170                 175
Asn Glu Ala Tyr Ala Glu Leu Ile Val Leu Gly Arg Thr Ser Glu Ala
                180                 185                 190
Pro Glu Leu Leu Pro Gly Phe Arg Ala Gly Pro Leu Glu Asp Trp Leu
            195                 200                 205
Phe Val Val Val Cys Leu Ala Ser Leu Leu Leu Phe Leu Leu Leu
        210                 215                 220
Gly Ile Cys Trp Cys Gln Cys Cys Pro His Thr Cys Cys Cys Tyr Val
225                 230                 235                 240
Arg Cys Pro Cys Cys Pro Asp Lys Cys Cys Cys Pro Glu Ala Leu Tyr
```

```
                      245                  250                    255
    Ala Ala Gly Lys Ala Ala Thr Ser Gly Val Pro Ser Ile Tyr Ala Pro
                260                  265                  270
    Ser Ile Tyr Thr His Leu Ser Pro Ala Lys Thr Pro Pro Pro Pro Pro
                275                  280                  285
    Ala Met Ile Pro Met Gly Pro Pro Tyr Gly Tyr Pro Gly Asp Phe Asp
                290                  295                  300
    Arg His Ser Ser Val Gly Gly His Ser Ser Gln Val Pro Leu Leu Arg
    305                  310                  315                  320
    Asp Val Asp Gly Ser Val Ser Ser Glu Val Arg Ser Gly Tyr Arg Ile
                325                  330                  335
    Gln Ala Asn Gln Gln Asp Asp Ser Met Arg Val Leu Tyr Tyr Met Glu
                340                  345                  350
    Lys Glu Leu Ala Asn Phe Asp Pro Ser Arg Pro Gly Pro Pro Asn Gly
                355                  360                  365
    Arg Val Glu Arg Ala Met Ser Glu Val Thr Ser Leu His Glu Asp Asp
                370                  375                  380
    Trp Arg Ser Arg Pro Ser Arg Ala Pro Ala Leu Thr Pro Ile Arg Asp
    385                  390                  395                  400
    Glu Glu Trp Asn Arg His Ser Pro Gln Ser Pro Arg Thr Trp Glu Gln
                        405                  410                  415
    Glu Pro Leu Gln Glu Gln Pro Arg Gly Gly Trp Gly Ser Gly Arg Pro
                420                  425                  430
    Arg Ala Arg Ser Val Asp Ala Leu Asp Asp Ile Asn Arg Pro Gly Ser
                435                  440                  445
    Thr Glu Ser Gly Arg Ser Ser Pro Pro Ser Ser Gly Arg Arg Gly Arg
    450                  455                  460
    Ala Tyr Ala Pro Pro Arg Ser Arg Ser Arg Asp Asp Leu Tyr Asp Pro
    465                  470                  475                  480
    Asp Asp Pro Arg Asp Leu Pro His Ser Arg Asp Pro His Tyr Tyr Asp
                        485                  490                  495
    Asp Ile Arg Ser Arg Asp Pro Arg Ala Asp Pro Arg Ser Arg Gln Arg
                500                  505                  510
    Ser Arg Asp Pro Arg Asp Ala Gly Phe Arg Ser Arg Asp Pro Gln Tyr
                515                  520                  525
    Asp Gly Arg Leu Leu Glu Glu Ala Leu Lys Lys Lys Gly Ser Gly Glu
    530                  535                  540
    Arg Arg Arg Val Tyr Arg Glu Glu Glu Glu Glu Glu Gly Gln Tyr
    545                  550                  555                  560
    Pro Pro Ala Pro Pro Pro Tyr Ser Glu Thr Asp Ser Gln Ala Ser Arg
                        565                  570                  575
    Glu Arg Arg Leu Lys Lys Asn Leu Ala Leu Ser Arg Glu Ser Leu Val
                580                  585                  590
    Val

<210> 10
<211> 2040
<212> DNA
<213> Rattus norvegicus

<400> 10
accgctcacc aggtcagttg tccccggaaa gccgaaggca tgagcttcgc ccaagttctt    60
tttatgggtt agaactcctc cagagcgggg gaaaaaggac ttggaatagg ggcgggacgg   120
agcacgcacc cttctccgcc ttggttctcg ccgcgccccc tactctcggg atacttggga   180
ggggacgcgc gggcaccgtc gctgctagac ggccgcg atg gcg ccg gcg gcc ggc   235
                                           Met Ala Pro Ala Ala Gly
                                             1               5
gcg tgt gct ggg gcg cct gac tcc cac cca gct acc gtg gtc ttc gtg   283
Ala Cys Ala Gly Ala Pro Asp Ser His Pro Ala Thr Val Val Phe Val
```

```
                    10                    15                    20
tgt ctc ttt ctc atc att ttc tgc cca gac cct gcc agt gcc atc cag    331
Cys Leu Phe Leu Ile Ile Phe Cys Pro Asp Pro Ala Ser Ala Ile Gln
        25                    30                    35
gtg act gtg tct gac ccc tac cac gta gtg atc ctg ttc cag cca gtg    379
Val Thr Val Ser Asp Pro Tyr His Val Val Ile Leu Phe Gln Pro Val
    40                    45                    50
acc ctg ccc tgc acc tat cag atg agc aac act ctc aca gtc ccc atc    427
Thr Leu Pro Cys Thr Tyr Gln Met Ser Asn Thr Leu Thr Val Pro Ile
55                    60                    65                    70
gtg atc tgg aag tac aag tca ttc tgc cgg gac cgt att gcc gat gcc    475
Val Ile Trp Lys Tyr Lys Ser Phe Cys Arg Asp Arg Ile Ala Asp Ala
                75                    80                    85
ttc tct cct gcc agt gtg gac aac cag cta aat gcc cag ttg gca gct    523
Phe Ser Pro Ala Ser Val Asp Asn Gln Leu Asn Ala Gln Leu Ala Ala
            90                    95                    100
ggc aac ccc ggc tac aac ccc tat gtg gag tgc cag gac agt gta cgc    571
Gly Asn Pro Gly Tyr Asn Pro Tyr Val Glu Cys Gln Asp Ser Val Arg
        105                   110                   115
act gtc agg gtg gtg gcc acc aaa cag ggc aat gcg gtg acc ctg gga    619
Thr Val Arg Val Val Ala Thr Lys Gln Gly Asn Ala Val Thr Leu Gly
    120                   125                   130
gac tac tac caa ggc agg agg atc acc ata aca gga aat gct gac ctg    667
Asp Tyr Tyr Gln Gly Arg Arg Ile Thr Ile Thr Gly Asn Ala Asp Leu
135                   140                   145                   150
acc ttc gag cag aca gcc tgg gga gac agt gga gtg tat tac tgc tct    715
Thr Phe Glu Gln Thr Ala Trp Gly Asp Ser Gly Val Tyr Tyr Cys Ser
                155                   160                   165
gtg gtc tcg gcc caa gat ctg gat gga aac aac gag gcg tac gca gag    763
Val Val Ser Ala Gln Asp Leu Asp Gly Asn Asn Glu Ala Tyr Ala Glu
            170                   175                   180
ctc atc gtc ctt gat tgg ctc ttt gtg gtc gtg gtc tgc ctg gcg agc    811
Leu Ile Val Leu Asp Trp Leu Phe Val Val Val Val Cys Leu Ala Ser
        185                   190                   195
ctc ctc ctc ttc ctc ctg ggc atc tgc tgg tgc cag tgc tgt cct    859
Leu Leu Leu Phe Leu Leu Leu Gly Ile Cys Trp Cys Gln Cys Cys Pro
    200                   205                   210
cac acc tgc tgc tgc tat gtc cga tgt ccc tgc tgc cca gac aag tgc    907
His Thr Cys Cys Cys Tyr Val Arg Cys Pro Cys Cys Pro Asp Lys Cys
215                   220                   225                   230
tgt tgc cct gag gct ctt tat gct gct ggc aaa gca gcc acc tca ggt    955
Cys Cys Pro Glu Ala Leu Tyr Ala Ala Gly Lys Ala Ala Thr Ser Gly
                235                   240                   245
gtc ccg agc atc tat gcc ccc agc atc tat acc cac ctc tca cct gcc   1003
Val Pro Ser Ile Tyr Ala Pro Ser Ile Tyr Thr His Leu Ser Pro Ala
            250                   255                   260
aag acc cca cca cct ccg cct gcc atg att ccc atg ggc cct ccc tat   1051
Lys Thr Pro Pro Pro Pro Pro Ala Met Ile Pro Met Gly Pro Pro Tyr
        265                   270                   275
ggg tac cct gga gac ttt gac aga cat agc tca gtt ggt ggc cac agc   1099
Gly Tyr Pro Gly Asp Phe Asp Arg His Ser Ser Val Gly Gly His Ser
    280                   285                   290
tcc caa gta ccc ctg ctg cgt gac gtg gat ggc agt gta tct tca gaa   1147
Ser Gln Val Pro Leu Leu Arg Asp Val Asp Gly Ser Val Ser Ser Glu
295                   300                   305                   310
gta cga agt ggc tac agg atc cag gct aac cag caa gat gac tcc atg   1195
Val Arg Ser Gly Tyr Arg Ile Gln Ala Asn Gln Gln Asp Asp Ser Met
                315                   320                   325
agg gtc cta tac tat atg gag aaa gag cta gcc aac ttt gac cct tcc   1243
```

```
                Arg Val Leu Tyr Tyr Met Glu Lys Glu Leu Ala Asn Phe Asp Pro Ser
                            330                 335                 340
cga cct ggc cct ccc aat ggc aga gtg gaa cgg gcc atg agt gaa gta                 1291
Arg Pro Gly Pro Pro Asn Gly Arg Val Glu Arg Ala Met Ser Glu Val
            345                 350                 355
acc tcc ctc cat gaa gat gac tgg cga tcg agg cct tcc agg gct cct                 1339
Thr Ser Leu His Glu Asp Asp Trp Arg Ser Arg Pro Ser Arg Ala Pro
360                 365                 370
gcc ctc acc ccc atc agg gat gag gag tgg aat cgc cac tcc cca cag                 1387
Ala Leu Thr Pro Ile Arg Asp Glu Glu Trp Asn Arg His Ser Pro Gln
375                 380                 385                 390
agt ccc aga aca tgg gag cag gaa ccc ctt caa gaa caa cca agg ggt                 1435
Ser Pro Arg Thr Trp Glu Gln Glu Pro Leu Gln Glu Gln Pro Arg Gly
                395                 400                 405
ggt tgg ggg tct gga cgc cct cgg gcc cgc tct gtg gat gct cta gat                 1483
Gly Trp Gly Ser Gly Arg Pro Arg Ala Arg Ser Val Asp Ala Leu Asp
            410                 415                 420
gat atc aac cgg cct ggc tcc act gaa tca gga cgg tct tct ccc cca                 1531
Asp Ile Asn Arg Pro Gly Ser Thr Glu Ser Gly Arg Ser Ser Pro Pro
        425                 430                 435
agt agt gga cgg aga gga cgg gcc tat gca cct cca aga agt cgc agc                 1579
Ser Ser Gly Arg Arg Gly Arg Ala Tyr Ala Pro Pro Arg Ser Arg Ser
    440                 445                 450
cgg gat gac ctc tat gac ccg gac gat cct agg gac ttg cca cat tcc                 1627
Arg Asp Asp Leu Tyr Asp Pro Asp Asp Pro Arg Asp Leu Pro His Ser
455                 460                 465                 470
cga gat ccc cac tat tat gac gac atc agg tct aga gat cca cgt gct                 1675
Arg Asp Pro His Tyr Tyr Asp Asp Ile Arg Ser Arg Asp Pro Arg Ala
                475                 480                 485
gac ccc aga tcc cgt cag cga tcc cga gat cct cgg gat gct ggc ttc                 1723
Asp Pro Arg Ser Arg Gln Arg Ser Arg Asp Pro Arg Asp Ala Gly Phe
            490                 495                 500
agg tca agg gac cct cag tat gat ggg cga cta tta gaa gag gct tta                 1771
Arg Ser Arg Asp Pro Gln Tyr Asp Gly Arg Leu Leu Glu Glu Ala Leu
        505                 510                 515
aag aaa aag ggg tcg ggc gag aga agg agg gtt tac agg gag gaa gaa                 1819
Lys Lys Lys Gly Ser Gly Glu Arg Arg Arg Val Tyr Arg Glu Glu Glu
    520                 525                 530
gag gaa gag gag ggc caa tac ccc cca gca cct cca cct tac tca gag                 1867
Glu Glu Glu Glu Gly Gln Tyr Pro Pro Ala Pro Pro Pro Tyr Ser Glu
535                 540                 545                 550
act gac tcg cag gcc tca cgg gag agg agg ctg aaa aag aat ttg gcc                 1915
Thr Asp Ser Gln Ala Ser Arg Glu Arg Arg Leu Lys Lys Asn Leu Ala
                555                 560                 565
ctg agc cgg gaa agt tta gtc gtc tga tccacgtttt gtatgtagct                       1962
Leu Ser Arg Glu Ser Leu Val Val *
            570                 575
tttgtacttt tttttttaatt ggaatcaata ttgatgaaac ttcaagccta ataaaatgtc              2022
taatcacaaa aaaaaaaa                                                             2040

<210> 11
<211> 574
<212> PRT
<213> Rattus norvegicus

<400> 11
Met Ala Pro Ala Ala Gly Ala Cys Ala Gly Ala Pro Asp Ser His Pro
1               5                   10                  15
Ala Thr Val Val Phe Val Cys Leu Phe Leu Ile Ile Phe Cys Pro Asp
```

```
                    20                      25                      30
Pro Ala Ser Ala Ile Gln Val Thr Val Ser Asp Pro Tyr His Val Val
            35                      40                      45
Ile Leu Phe Gln Pro Val Thr Leu Pro Cys Thr Tyr Gln Met Ser Asn
            50                      55                      60
Thr Leu Thr Val Pro Ile Val Ile Trp Lys Tyr Lys Ser Phe Cys Arg
 65                      70                      75                  80
Asp Arg Ile Ala Asp Ala Phe Ser Pro Ala Ser Val Asp Asn Gln Leu
                    85                      90                      95
Asn Ala Gln Leu Ala Ala Gly Asn Pro Gly Tyr Asn Pro Tyr Val Glu
                    100                     105                     110
Cys Gln Asp Ser Val Arg Thr Val Arg Val Val Ala Thr Lys Gln Gly
                    115                     120                     125
Asn Ala Val Thr Leu Gly Asp Tyr Tyr Gln Gly Arg Arg Ile Thr Ile
                    130                     135                     140
Thr Gly Asn Ala Asp Leu Thr Phe Glu Gln Thr Ala Trp Gly Asp Ser
 145                     150                     155                 160
Gly Val Tyr Tyr Cys Ser Val Val Ser Ala Gln Asp Leu Asp Gly Asn
                    165                     170                     175
Asn Glu Ala Tyr Ala Glu Leu Ile Val Leu Asp Trp Leu Phe Val Val
                    180                     185                     190
Val Val Cys Leu Ala Ser Leu Leu Leu Phe Leu Leu Leu Gly Ile Cys
                    195                     200                     205
Trp Cys Gln Cys Cys Pro His Thr Cys Cys Cys Tyr Val Arg Cys Pro
            210                     215                     220
Cys Cys Pro Asp Lys Cys Cys Cys Pro Glu Ala Leu Tyr Ala Ala Gly
 225                     230                     235                 240
Lys Ala Ala Thr Ser Gly Val Pro Ser Ile Tyr Ala Pro Ser Ile Tyr
                    245                     250                     255
Thr His Leu Ser Pro Ala Lys Thr Pro Pro Pro Pro Ala Met Ile
                    260                     265                     270
Pro Met Gly Pro Pro Tyr Gly Tyr Pro Gly Asp Phe Asp Arg His Ser
            275                     280                     285
Ser Val Gly Gly His Ser Ser Gln Val Pro Leu Leu Arg Asp Val Asp
            290                     295                     300
Gly Ser Val Ser Ser Glu Val Arg Ser Gly Tyr Arg Ile Gln Ala Asn
 305                     310                     315                 320
Gln Gln Asp Asp Ser Met Arg Val Leu Tyr Tyr Met Glu Lys Glu Leu
                    325                     330                     335
Ala Asn Phe Asp Pro Ser Arg Pro Gly Pro Pro Asn Gly Arg Val Glu
                    340                     345                     350
Arg Ala Met Ser Glu Val Thr Ser Leu His Glu Asp Asp Trp Arg Ser
            355                     360                     365
Arg Pro Ser Arg Ala Pro Ala Leu Thr Pro Ile Arg Asp Glu Glu Trp
 370                     375                     380
Asn Arg His Ser Pro Gln Ser Pro Arg Thr Trp Glu Gln Glu Pro Leu
 385                     390                     395                 400
Gln Glu Gln Pro Arg Gly Gly Trp Gly Ser Gly Arg Pro Arg Ala Arg
                    405                     410                     415
Ser Val Asp Ala Leu Asp Asp Ile Asn Arg Pro Gly Ser Thr Glu Ser
                    420                     425                     430
Gly Arg Ser Ser Pro Pro Ser Ser Gly Arg Arg Gly Arg Ala Tyr Ala
            435                     440                     445
Pro Pro Arg Ser Arg Ser Arg Asp Asp Leu Tyr Asp Pro Asp Asp Pro
            450                     455                     460
Arg Asp Leu Pro His Ser Arg Asp Pro His Tyr Tyr Asp Asp Ile Arg
 465                     470                     475                 480
Ser Arg Asp Pro Arg Ala Asp Pro Arg Ser Arg Gln Arg Ser Arg Asp
                    485                     490                     495
```

```
        Pro Arg Asp Ala Gly Phe Arg Ser Arg Asp Pro Gln Tyr Asp Gly Arg
                    500                 505                 510
        Leu Leu Glu Glu Ala Leu Lys Lys Lys Gly Ser Gly Glu Arg Arg Arg
                    515                 520                 525
        Val Tyr Arg Glu Glu Glu Glu Glu Glu Gly Gln Tyr Pro Pro Ala
                    530                 535             540
        Pro Pro Pro Tyr Ser Glu Thr Asp Ser Gln Ala Ser Arg Glu Arg Arg
        545                 550                 555                 560
        Leu Lys Lys Asn Leu Ala Leu Ser Arg Glu Ser Leu Val Val
                        565                 570

<210> 12
<211> 1893
<212> DNA
<213> Rattus norvegicus

<400> 12
accgctcacc aggtcagttg tccccggaaa gccgaaggca tgagcttcgc ccaagttctt        60
tttatgggtt agaactcctc cagagcgggg gaaaaaggac ttggaatagg ggcgggacgg       120
agcacgcacc cttctccgcc ttggttctcg ccgcgccccc tactctcggg atacttggga       180
ggggacgcgc gggcaccgtc gctgctagac ggccgcg atg gcg ccg gcg gcc ggc       235
                                        Met Ala Pro Ala Ala Gly
                                          1               5
gcg tgt gct ggg gcg cct gac tcc cac cca gct acc gtg gtc ttc gtg       283
Ala Cys Ala Gly Ala Pro Asp Ser His Pro Ala Thr Val Val Phe Val
              10                  15                  20
tgt ctc ttt ctc atc att ttc tgc cca gac cct gcc agt gcc atc cag       331
Cys Leu Phe Leu Ile Ile Phe Cys Pro Asp Pro Ala Ser Ala Ile Gln
          25                  30                  35
gtg act gtg tct gac ccc tac cac gta gtg atc ctg ttc cag cca gtg       379
Val Thr Val Ser Asp Pro Tyr His Val Val Ile Leu Phe Gln Pro Val
      40                  45                  50
acc ctg ccc tgc acc tat cag atg agc aac act ctc aca gtc ccc atc       427
Thr Leu Pro Cys Thr Tyr Gln Met Ser Asn Thr Leu Thr Val Pro Ile
55                  60                  65                  70
gtg atc tgg aag tac aag tca ttc tgc cgg gac cgt att gcc gat gcc       475
Val Ile Trp Lys Tyr Lys Ser Phe Cys Arg Asp Arg Ile Ala Asp Ala
              75                  80                  85
ttc tct cct gcc agt gtg gac aac cag cta aat gcc cag ttg gca gct       523
Phe Ser Pro Ala Ser Val Asp Asn Gln Leu Asn Ala Gln Leu Ala Ala
          90                  95                  100
ggc aac ccc ggc tac aac ccc tat gtg gag tgc cag gac agt gta cgc       571
Gly Asn Pro Gly Tyr Asn Pro Tyr Val Glu Cys Gln Asp Ser Val Arg
      105                 110                 115
act gtc agg gtg gtg gcc acc aaa cag ggc aat gcg gtg acc ctg gga       619
Thr Val Arg Val Val Ala Thr Lys Gln Gly Asn Ala Val Thr Leu Gly
120                 125                 130
gac tac tac caa ggc agg agg atc acc ata aca gga aat gct gac ctg       667
Asp Tyr Tyr Gln Gly Arg Arg Ile Thr Ile Thr Gly Asn Ala Asp Leu
135                 140                 145                 150
acc ttc gag cag aca gcc tgg gga gac agt gga gtg tat tac tgc tct       715
Thr Phe Glu Gln Thr Ala Trp Gly Asp Ser Gly Val Tyr Tyr Cys Ser
              155                 160                 165
gtg gtc tcg gcc caa gat ctg gat gga aac aac gag gcg tac gca gag       763
Val Val Ser Ala Gln Asp Leu Asp Gly Asn Asn Glu Ala Tyr Ala Glu
          170                 175                 180
ctc atc gtc ctt gtt tat gct gct ggc aaa gca gcc acc tca ggt gtc       811
Leu Ile Val Leu Val Tyr Ala Ala Gly Lys Ala Ala Thr Ser Gly Val
          185                 190                 195
```

```
ccg agc atc tat gcc ccc agc atc tat acc cac ctc tca cct gcc aag    859
Pro Ser Ile Tyr Ala Pro Ser Ile Tyr Thr His Leu Ser Pro Ala Lys
    200             205             210
acc cca cca cct ccg cct gcc atg att ccc atg ggc cct ccc tat ggg    907
Thr Pro Pro Pro Pro Pro Ala Met Ile Pro Met Gly Pro Pro Tyr Gly
215             220             225             230
tac cct gga gac ttt gac aga cat agc tca gtt ggt ggc cac agc tcc    955
Tyr Pro Gly Asp Phe Asp Arg His Ser Ser Val Gly Gly His Ser Ser
            235             240             245
caa gta ccc ctg ctg cgt gac gtg gat ggc agt gta tct tca gaa gta   1003
Gln Val Pro Leu Leu Arg Asp Val Asp Gly Ser Val Ser Ser Glu Val
        250             255             260
cga agt ggc tac agg atc cag gct aac cag caa gat gac tcc atg agg   1051
Arg Ser Gly Tyr Arg Ile Gln Ala Asn Gln Gln Asp Asp Ser Met Arg
        265             270             275
gtc cta tac tat atg gag aaa gag cta gcc aac ttt gac cct tcc cga   1099
Val Leu Tyr Tyr Met Glu Lys Glu Leu Ala Asn Phe Asp Pro Ser Arg
    280             285             290
cct ggc cct ccc aat ggc aga gtg gaa cgg gcc atg agt gaa gta acc   1147
Pro Gly Pro Pro Asn Gly Arg Val Glu Arg Ala Met Ser Glu Val Thr
295             300             305             310
tcc ctc cat gaa gat gac tgg cga tcg agg cct tcc agg gct cct gcc   1195
Ser Leu His Glu Asp Asp Trp Arg Ser Arg Pro Ser Arg Ala Pro Ala
            315             320             325
ctc acc ccc atc agg gat gag gag tgg aat cgc cac tcc cca cag agt   1243
Leu Thr Pro Ile Arg Asp Glu Glu Trp Asn Arg His Ser Pro Gln Ser
        330             335             340
ccc aga aca tgg gag cag gaa ccc ctt caa gaa caa cca agg ggt ggt   1291
Pro Arg Thr Trp Glu Gln Glu Pro Leu Gln Glu Gln Pro Arg Gly Gly
        345             350             355
tgg ggg tct gga cgc cct cgg gcc cgc tct gtg gat gct cta gat gat   1339
Trp Gly Ser Gly Arg Pro Arg Ala Arg Ser Val Asp Ala Leu Asp Asp
    360             365             370
atc aac cgg cct ggc tcc act gaa tca gga cgg tct tct ccc cca agt   1387
Ile Asn Arg Pro Gly Ser Thr Glu Ser Gly Arg Ser Ser Pro Pro Ser
375             380             385             390
agt gga cgg aga gga cgg gcc tat gca cct cca aga agt cgc agc cgg   1435
Ser Gly Arg Arg Gly Arg Ala Tyr Ala Pro Pro Arg Ser Arg Ser Arg
            395             400             405
gat gac ctc tat gac ccg gac gat cct agg gac ttg cca cat tcc cga   1483
Asp Asp Leu Tyr Asp Pro Asp Asp Pro Arg Asp Leu Pro His Ser Arg
        410             415             420
gat ccc cac tat tat gac gac atc agg tct aga gat cca cgt gct gac   1531
Asp Pro His Tyr Tyr Asp Asp Ile Arg Ser Arg Asp Pro Arg Ala Asp
        425             430             435
ccc aga tcc cgt cag cga tcc cga gat cct cgg gat gct ggc ttc agg   1579
Pro Arg Ser Arg Gln Arg Ser Arg Asp Pro Arg Asp Ala Gly Phe Arg
    440             445             450
tca agg gac cct cag tat gat ggg cga cta tta gaa gag gct tta aag   1627
Ser Arg Asp Pro Gln Tyr Asp Gly Arg Leu Leu Glu Glu Ala Leu Lys
455             460             465             470
aaa aag ggg tcg ggc gag aga agg agg gtt tac agg gag gaa gaa gag   1675
Lys Lys Gly Ser Gly Glu Arg Arg Arg Val Tyr Arg Glu Glu Glu Glu
            475             480             485
gaa gag gag ggc caa tac ccc cca gca cct cca cct tac tca gag act   1723
Glu Glu Glu Gly Gln Tyr Pro Pro Ala Pro Pro Pro Tyr Ser Glu Thr
        490             495             500
gac tcg cag gcc tca cgg gag agg agg ctg aaa aag aat ttg gcc ctg   1771
Asp Ser Gln Ala Ser Arg Glu Arg Arg Leu Lys Lys Asn Leu Ala Leu
```

CERTIFICATE OF CORRECTION (continued)

U.S. Pat. No. 7,470,669 B2

```
              505                 510                515
      agt cgg gaa agt tta gtc gtc tga tccacgtttt gtatgtagct tttgtacttt    1825
      Ser Arg Glu Ser Leu Val Val *
          520                 525
      tttttaatt ggaatcaata ttgatgaaac ttcaagccta ataaaatgtc taatcacaa     1885
      aaaaaaaa                                                            1893
```

<210> 13
<211> 525
<212> PRT
<213> Rattus norvegicus

<400> 13

```
Met Ala Pro Ala Ala Gly Ala Cys Ala Gly Ala Pro Asp Ser His Pro
1               5                   10                  15
Ala Thr Val Val Phe Val Cys Leu Phe Leu Ile Ile Phe Cys Pro Asp
            20                  25                  30
Pro Ala Ser Ala Ile Gln Val Thr Val Ser Asp Pro Tyr His Val Val
            35                  40                  45
Ile Leu Phe Gln Pro Val Thr Leu Pro Cys Thr Tyr Gln Met Ser Asn
        50                  55                  60
Thr Leu Thr Val Pro Ile Val Ile Trp Lys Tyr Lys Ser Phe Cys Arg
65                  70                  75                  80
Asp Arg Ile Ala Asp Ala Phe Ser Pro Ala Ser Val Asp Asn Gln Leu
                85                  90                  95
Asn Ala Gln Leu Ala Ala Gly Asn Pro Gly Tyr Asn Pro Tyr Val Glu
                100                 105                 110
Cys Gln Asp Ser Val Arg Thr Val Arg Val Val Ala Thr Lys Gln Gly
            115                 120                 125
Asn Ala Val Thr Leu Gly Asp Tyr Tyr Gln Gly Arg Arg Ile Thr Ile
        130                 135                 140
Thr Gly Asn Ala Asp Leu Thr Phe Glu Gln Thr Ala Trp Gly Asp Ser
145                 150                 155                 160
Gly Val Tyr Tyr Cys Ser Val Val Ser Ala Gln Asp Leu Asp Gly Asn
                165                 170                 175
Asn Glu Ala Tyr Ala Glu Leu Ile Val Leu Val Tyr Ala Ala Gly Lys
            180                 185                 190
Ala Ala Thr Ser Gly Val Pro Ser Ile Tyr Ala Pro Ser Ile Tyr Thr
        195                 200                 205
His Leu Ser Pro Ala Lys Thr Pro Pro Pro Pro Ala Met Ile Pro
    210                 215                 220
Met Gly Pro Pro Tyr Gly Tyr Pro Gly Asp Phe Asp Arg His Ser Ser
225                 230                 235                 240
Val Gly Gly His Ser Ser Gln Val Pro Leu Leu Arg Asp Val Asp Gly
                245                 250                 255
Ser Val Ser Ser Glu Val Arg Ser Gly Tyr Arg Ile Gln Ala Asn Gln
            260                 265                 270
Gln Asp Asp Ser Met Arg Val Leu Tyr Tyr Met Glu Lys Glu Leu Ala
        275                 280                 285
Asn Phe Asp Pro Ser Arg Pro Gly Pro Pro Asn Gly Arg Val Glu Arg
    290                 295                 300
Ala Met Ser Glu Val Thr Ser Leu His Glu Asp Asp Trp Arg Ser Arg
305                 310                 315                 320
Pro Ser Arg Ala Pro Ala Leu Thr Pro Ile Arg Asp Glu Glu Trp Asn
                325                 330                 335
Arg His Ser Pro Gln Ser Pro Arg Thr Trp Glu Gln Glu Pro Leu Gln
            340                 345                 350
Glu Gln Pro Arg Gly Gly Trp Gly Ser Gly Arg Pro Arg Ala Arg Ser
        355                 360                 365
```

```
Val Asp Ala Leu Asp Asp Ile Asn Arg Pro Gly Ser Thr Glu Ser Gly
    370                 375                 380
Arg Ser Ser Pro Pro Ser Ser Gly Arg Arg Gly Arg Ala Tyr Ala Pro
385                 390                 395                 400
Pro Arg Ser Arg Ser Arg Asp Asp Leu Tyr Asp Pro Asp Asp Pro Arg
                405                 410                 415
Asp Leu Pro His Ser Arg Asp Pro His Tyr Tyr Asp Asp Ile Arg Ser
            420                 425                 430
Arg Asp Pro Arg Ala Asp Pro Arg Ser Arg Gln Arg Ser Arg Asp Pro
        435                 440                 445
Arg Asp Ala Gly Phe Arg Ser Arg Asp Pro Gln Tyr Asp Gly Arg Leu
    450                 455                 460
Leu Glu Glu Ala Leu Lys Lys Lys Gly Ser Gly Glu Arg Arg Arg Val
465                 470                 475                 480
Tyr Arg Glu Glu Glu Glu Glu Glu Gly Gln Tyr Pro Pro Ala Pro
                485                 490                 495
Pro Pro Tyr Ser Glu Thr Asp Ser Gln Ala Ser Arg Glu Arg Arg Leu
            500                 505                 510
Lys Lys Asn Leu Ala Leu Ser Arg Glu Ser Leu Val Val
            515                 520                 525

<210> 14
<211> 1886
<212> DNA
<213> Mus musculus

<400> 14
gcaccgtcgc tgctagacgg ccgcg atg gcg ccg gcg gcc agc gcg tgt gct    52
                            Met Ala Pro Ala Ala Ser Ala Cys Ala
                            1               5
ggg gcg cct ggc tcc cac ccg gcc acc acg atc ttc gtg tgt ctt ttt    100
Gly Ala Pro Gly Ser His Pro Ala Thr Thr Ile Phe Val Cys Leu Phe
10              15                  20                  25
ctc atc att tac tgc cca gac cgt gcc agt gcc atc cag gtg acc gtg    148
Leu Ile Ile Tyr Cys Pro Asp Arg Ala Ser Ala Ile Gln Val Thr Val
                30                  35                  40
cct gac ccc tac cac gta gtg atc ctg ttc cag cca gtg aca cta cac    196
Pro Asp Pro Tyr His Val Val Ile Leu Phe Gln Pro Val Thr Leu His
            45                  50                  55
tgc acc tac cag atg agc aat acc ctc aca gcc cct atc gtg atc tgg    244
Cys Thr Tyr Gln Met Ser Asn Thr Leu Thr Ala Pro Ile Val Ile Trp
        60                  65                  70
aag tat aag tcg ttc tgt cgg gac cgt gtt gcc gac gcc ttc tcc cct    292
Lys Tyr Lys Ser Phe Cys Arg Asp Arg Val Ala Asp Ala Phe Ser Pro
    75                  80                  85
gcc agc gtg gac aac cag ctc aac gcc cag ctg gcg gct ggc aac ccc    340
Ala Ser Val Asp Asn Gln Leu Asn Ala Gln Leu Ala Ala Gly Asn Pro
90                  95                  100                 105
ggc tac aac ccc tat gtg gag tgc cag gac agc gta cgc act gtc agg    388
Gly Tyr Asn Pro Tyr Val Glu Cys Gln Asp Ser Val Arg Thr Val Arg
                110                 115                 120
gtg gtg gcc acc aaa cag ggc aat gct gtg acc ctg gga gac tac tac    436
Val Val Ala Thr Lys Gln Gly Asn Ala Val Thr Leu Gly Asp Tyr Tyr
            125                 130                 135
cag ggc agg aga atc acc atc aca gga aat gct ggc ctg acc ttc gag    484
Gln Gly Arg Arg Ile Thr Ile Thr Gly Asn Ala Gly Leu Thr Phe Glu
        140                 145                 150
cag acg gcc tgg gga gac agt gga gtg tat tac tgc tcc gtg gtc tca    532
Gln Thr Ala Trp Gly Asp Ser Gly Val Tyr Tyr Cys Ser Val Val Ser
```

```
              155                    160                      165
gcc caa gat ctg gat ggg aac aac gag gcg tac gca gag ctc att gtc    580
Ala Gln Asp Leu Asp Gly Asn Asn Glu Ala Tyr Ala Glu Leu Ile Val
170                      175                      180              185
ctt ggc agg acc tca gaa gcc cct gag ctc cta cct ggt ttt cgg gcg    628
Leu Gly Arg Thr Ser Glu Ala Pro Glu Leu Leu Pro Gly Phe Arg Ala
                190                      195                 200
ggg ccc ttg gaa gat tgg ctc ttt gtg gtc gtg gtc tgc ctg gca agc    676
Gly Pro Leu Glu Asp Trp Leu Phe Val Val Val Val Cys Leu Ala Ser
            205                      210                      215
ctc ctc ttc ttc ctc ctc ctg ggc atc tgc tgg tgc cag tgc tgt ccc    724
Leu Leu Phe Phe Leu Leu Leu Gly Ile Cys Trp Cys Gln Cys Cys Pro
        220                      225                      230
cac acc tgc tgc tgc tat gtc aga tgt ccc tgc tgc cca gac aag tgc    772
His Thr Cys Cys Cys Tyr Val Arg Cys Pro Cys Cys Pro Asp Lys Cys
    235                      240                      245
tgt tgc cct gag gcc ctt tat gct gct ggc aaa gca gcc acc tca ggt    820
Cys Cys Pro Glu Ala Leu Tyr Ala Ala Gly Lys Ala Ala Thr Ser Gly
250                      255                      260              265
gtg cca agc atc tat gcc ccc agc atc tat acc cac ctc tct cct gcc    868
Val Pro Ser Ile Tyr Ala Pro Ser Ile Tyr Thr His Leu Ser Pro Ala
                270                      275                 280
aag act ccg cca cct ccg cct gcc atg att ccc atg cgt cct ccc tat    916
Lys Thr Pro Pro Pro Pro Ala Met Ile Pro Met Arg Pro Pro Tyr
            285                      290                      295
ggg tac cct gga gac ttt gac agg acc agc tca gtt ggt ggc cac agc    964
Gly Tyr Pro Gly Asp Phe Asp Arg Thr Ser Ser Val Gly Gly His Ser
        300                      305                      310
tcc cag gtg ccc ctg ctg cgt gaa gtg gat ggg agc gta tct tca gaa   1012
Ser Gln Val Pro Leu Leu Arg Glu Val Asp Gly Ser Val Ser Ser Glu
    315                      320                      325
gta cga agt ggc tac agg atc cag gct aac cag caa gat gac tcc atg   1060
Val Arg Ser Gly Tyr Arg Ile Gln Ala Asn Gln Gln Asp Asp Ser Met
330                      335                      340              345
agg gtc cta tac tat atg gag aag gag cta gcc aac ttc gat cct tcc   1108
Arg Val Leu Tyr Tyr Met Glu Lys Glu Leu Ala Asn Phe Asp Pro Ser
                350                      355                 360
cgg cct ggc cct ccc aat ggc cga gtg gaa cgg gcc atg agt gaa gta   1156
Arg Pro Gly Pro Pro Asn Gly Arg Val Glu Arg Ala Met Ser Glu Val
            365                      370                      375
acc tcc ctc cat gaa gat gac tgg cga tct cgg cct tcc agg gct cct   1204
Thr Ser Leu His Glu Asp Asp Trp Arg Ser Arg Pro Ser Arg Ala Pro
        380                      385                      390
gcc ctc aca ccc atc agg gat gag gag tgg aat cgc cac tcc cct cgg   1252
Ala Leu Thr Pro Ile Arg Asp Glu Glu Trp Asn Arg His Ser Pro Arg
    395                      400                      405
agt ccc aga aca tgg gag cag gaa ccc ctt caa gaa cag cca agg ggt   1300
Ser Pro Arg Thr Trp Glu Gln Glu Pro Leu Gln Glu Gln Pro Arg Gly
410                      415                      420              425
ggt tgg ggg tct ggg cgg cct cgg gcc cgc tct gtg gat gct cta gat   1348
Gly Trp Gly Ser Gly Arg Pro Arg Ala Arg Ser Val Asp Ala Leu Asp
                430                      435                 440
gac atc aac cgg cct ggc tcc act gaa tca gga agg tct tct ccc cca   1396
Asp Ile Asn Arg Pro Gly Ser Thr Glu Ser Gly Arg Ser Ser Pro Pro
            445                      450                      455
agt agt gga cgg aga ggg cgg gcc tat gca cct ccg aga agt cgc agc   1444
Ser Ser Gly Arg Arg Gly Arg Ala Tyr Ala Pro Pro Arg Ser Arg Ser
        460                      465                      470
cgg gat gac ctc tat gac ccc gac gat cct aga gac ttg cca cat tcc   1492
```

```
Arg Asp Asp Leu Tyr Asp Pro Asp Asp Pro Arg Asp Leu Pro His Ser
    475             480                 485
cga gat ccc cac tat tat gat gat ttg agg tct agg gat cca cgt gct      1540
Arg Asp Pro His Tyr Tyr Asp Asp Leu Arg Ser Arg Asp Pro Arg Ala
490             495                 500                 505
gac ccc aga tcc cgt cag cga tcc cac gat cct cgg gat gct ggc ttc      1588
Asp Pro Arg Ser Arg Gln Arg Ser His Asp Pro Arg Asp Ala Gly Phe
                510                 515                 520
agg tca cgg gac cct cag tat gat ggg cga ctc tta gaa gag gct tta      1636
Arg Ser Arg Asp Pro Gln Tyr Asp Gly Arg Leu Leu Glu Glu Ala Leu
            525                 530                 535
aag aaa aaa ggg gct ggg gag aga aga cgc gtt tac agg gag gaa gaa      1684
Lys Lys Lys Gly Ala Gly Glu Arg Arg Arg Val Tyr Arg Glu Glu Glu
        540                 545                 550
gaa gaa gaa gag gag ggc cac tat ccc cca gca cct ccg cct tac tct      1732
Glu Glu Glu Glu Glu Gly His Tyr Pro Pro Ala Pro Pro Pro Tyr Ser
    555                 560                 565
gag act gac tcg cag gcc tcg agg gag cgg agg atg aaa aag aat ttg      1780
Glu Thr Asp Ser Gln Ala Ser Arg Glu Arg Arg Met Lys Lys Asn Leu
570                 575                 580                 585
gcc ctg agt cgg gaa agt tta gtc gtc tga tcccacgttt tgttatgtag        1830
Ala Leu Ser Arg Glu Ser Leu Val Val  *
                590                 595
cttttatact tttttaattg gaatattgat gaaactcttc accaagccta ataaaa        1886

<210> 15
<211> 1829
<212> DNA
<213> Mus musculus

<400> 15
gcaccgtcgc tgctagacgg ccgcg atg gcg ccg gcg gcc agc gcg tgt gct       52
                            Met Ala Pro Ala Ala Ser Ala Cys Ala
                            1               5
ggg gcg cct ggc tcc cac ccg gcc acc acg atc ttc gtg tgt ctt ttt      100
Gly Ala Pro Gly Ser His Pro Ala Thr Thr Ile Phe Val Cys Leu Phe
10              15                  20                  25
ctc atc att tac tgc cca gac cgt gcc agt gcc atc cag gtg acc gtg      148
Leu Ile Ile Tyr Cys Pro Asp Arg Ala Ser Ala Ile Gln Val Thr Val
                30                  35                  40
cct gac ccc tac cac gta gtg atc ctg ttc cag cca gtg aca cta cac      196
Pro Asp Pro Tyr His Val Val Ile Leu Phe Gln Pro Val Thr Leu His
            45                  50                  55
tgc acc tac cag atg agc aat acc ctc aca gcc cct atc gtg atc tgg      244
Cys Thr Tyr Gln Met Ser Asn Thr Leu Thr Ala Pro Ile Val Ile Trp
        60                  65                  70
aag tat aag tcg ttc tgt cgg gac cgt gtt gcc gac gcc ttc tcc cct      292
Lys Tyr Lys Ser Phe Cys Arg Asp Arg Val Ala Asp Ala Phe Ser Pro
75                  80                  85
gcc agc gtg gac aac cag ctc aac gcc cag ctg gcg gct ggc aac ccc      340
Ala Ser Val Asp Asn Gln Leu Asn Ala Gln Leu Ala Ala Gly Asn Pro
90                  95                  100                 105
ggc tac aac ccc tat gtg gag tgc cag gac agc gta cgc act gtc agg      388
Gly Tyr Asn Pro Tyr Val Glu Cys Gln Asp Ser Val Arg Thr Val Arg
                110                 115                 120
gtg gtg gcc acc aaa cag ggc aat gct gtg acc ctg gga gac tac tac      436
Val Val Ala Thr Lys Gln Gly Asn Ala Val Thr Leu Gly Asp Tyr Tyr
            125                 130                 135
cag ggc agg aga atc acc atc aca gga aat gct ggc ctg acc ttc gag      484
```

```
             Gln Gly Arg Arg Ile Thr Ile Thr Gly Asn Ala Gly Leu Thr Phe Glu
                         140                 145                 150
cag acg gcc tgg gga gac agt gga gtg tat tac tgc tcc gtg gtc tca           532
Gln Thr Ala Trp Gly Asp Ser Gly Val Tyr Tyr Cys Ser Val Val Ser
        155                 160                 165
gcc caa gat ctg gat ggg aac aac gag gcg tac gca gag ctc att gtc           580
Ala Gln Asp Leu Asp Gly Asn Asn Glu Ala Tyr Ala Glu Leu Ile Val
170                 175                 180                 185
ctt gat tgg ctc ttt gtg gtc gtg gtc tgc ctg gca agc ctc ctc ttc           628
Leu Asp Trp Leu Phe Val Val Val Val Cys Leu Ala Ser Leu Leu Phe
                    190                 195                 200
ttc ctc ctc ctg ggc atc tgc tgg tgc cag tgc tgt ccc cac acc tgc           676
Phe Leu Leu Leu Gly Ile Cys Trp Cys Gln Cys Cys Pro His Thr Cys
                205                 210                 215
tgc tgc tat gtc aga tgt ccc tgc tgc cca gac aag tgc tgt tgc cct           724
Cys Cys Tyr Val Arg Cys Pro Cys Cys Pro Asp Lys Cys Cys Cys Pro
            220                 225                 230
gag gcc ctt tat gct gct ggc aaa gca gcc acc tca ggt gtg cca agc           772
Glu Ala Leu Tyr Ala Ala Gly Lys Ala Ala Thr Ser Gly Val Pro Ser
        235                 240                 245
atc tat gcc ccc agc atc tat acc cac ctc tct cct gcc aag act ccg           820
Ile Tyr Ala Pro Ser Ile Tyr Thr His Leu Ser Pro Ala Lys Thr Pro
250                 255                 260                 265
cca cct ccg cct gcc atg att ccc atg cgt cct ccc tat ggg tac cct           868
Pro Pro Pro Pro Ala Met Ile Pro Met Arg Pro Pro Tyr Gly Tyr Pro
                    270                 275                 280
gga gac ttt gac agg acc agc tca gtt ggt ggc cac agc tcc cag gtg           916
Gly Asp Phe Asp Arg Thr Ser Ser Val Gly Gly His Ser Ser Gln Val
                285                 290                 295
ccc ctg ctg cgt gaa gtg gat ggg agc gta tct tca gaa gta cga agt           964
Pro Leu Leu Arg Glu Val Asp Gly Ser Val Ser Ser Glu Val Arg Ser
            300                 305                 310
ggc tac agg atc cag gct aac cag caa gat gac tcc atg agg gtc cta          1012
Gly Tyr Arg Ile Gln Ala Asn Gln Gln Asp Asp Ser Met Arg Val Leu
        315                 320                 325
tac tat atg gag aag gag cta gcc aac ttc gat cct tcc cgg cct ggc          1060
Tyr Tyr Met Glu Lys Glu Leu Ala Asn Phe Asp Pro Ser Arg Pro Gly
330                 335                 340                 345
cct ccc aat ggc cga gtg gaa cgg gcc atg agt gaa gta acc tcc ctc          1108
Pro Pro Asn Gly Arg Val Glu Arg Ala Met Ser Glu Val Thr Ser Leu
                    350                 355                 360
cat gaa gat gac tgg cga tct cgg cct tcc agg gct cct gcc ctc aca          1156
His Glu Asp Asp Trp Arg Ser Arg Pro Ser Arg Ala Pro Ala Leu Thr
                365                 370                 375
ccc atc agg gat gag gag tgg aat cgc cac tcc cct cgg agt ccc aga          1204
Pro Ile Arg Asp Glu Glu Trp Asn Arg His Ser Pro Arg Ser Pro Arg
            380                 385                 390
aca tgg gag cag gaa ccc ctt caa gaa cag cca agg ggt ggt tgg ggg          1252
Thr Trp Glu Gln Glu Pro Leu Gln Glu Gln Pro Arg Gly Gly Trp Gly
        395                 400                 405
tct ggg cgg cct cgg gcc cgc tct gtg gat gct cta gat gac atc aac          1300
Ser Gly Arg Pro Arg Ala Arg Ser Val Asp Ala Leu Asp Asp Ile Asn
410                 415                 420                 425
cgg cct ggc tcc act gaa tca gga agg tct ccc cca agt agt gga          1348
Arg Pro Gly Ser Thr Glu Ser Gly Arg Ser Ser Pro Pro Ser Ser Gly
                    430                 435                 440
cgg aga ggg cgg gcc tat gca cct ccg aga agt cgc agc cgg gat gac          1396
Arg Arg Gly Arg Ala Tyr Ala Pro Pro Arg Ser Arg Ser Arg Asp Asp
                445                 450                 455
```

```
ctc tat gac ccc gac gat cct aga gac ttg cca cat tcc cga gat ccc    1444
Leu Tyr Asp Pro Asp Asp Pro Arg Asp Leu Pro His Ser Arg Asp Pro
        460                 465                 470
cac tat tat gat gat ttg agg tct agg gat cca cgt gct gac ccc aga    1492
His Tyr Tyr Asp Asp Leu Arg Ser Arg Asp Pro Arg Ala Asp Pro Arg
        475                 480                 485
tcc cgt cag cga tcc cac gat cct cgg gat gct ggc ttc agg tca cgg    1540
Ser Arg Gln Arg Ser His Asp Pro Arg Asp Ala Gly Phe Arg Ser Arg
490                 495                 500                 505
gac cct cag tat gat ggg cga ctc tta gaa gag gct tta aag aaa aaa    1588
Asp Pro Gln Tyr Asp Gly Arg Leu Leu Glu Glu Ala Leu Lys Lys Lys
                510                 515                 520
ggg gct ggg gag aga aga cgc gtt tac agg gag gaa gaa gaa gaa gaa    1636
Gly Ala Gly Glu Arg Arg Arg Val Tyr Arg Glu Glu Glu Glu Glu Glu
            525                 530                 535
gag gag ggc cac tat ccc cca gca cct ccg cct tac tct gag act gac    1684
Glu Glu Gly His Tyr Pro Pro Ala Pro Pro Pro Tyr Ser Glu Thr Asp
            540                 545                 550
tcg cag gcc tcg agg gag cgg agg atg aaa aag aat ttg gcc ctg agt    1732
Ser Gln Ala Ser Arg Glu Arg Arg Met Lys Lys Asn Leu Ala Leu Ser
        555                 560                 565
cgg gaa agt tta gtc gtc tga tcccacgttt tgttatgtag cttttatact       1783
Arg Glu Ser Leu Val Val *
570                 575
tttttaattg gaatattgat gaaactcttc accaagccta ataaaa                 1829

<210> 16
<211> 1682
<212> DNA
<213> Mus musculus

<400> 16
gcaccgtcgc tgctagacgg ccgcg atg gcg ccg gcg gcc agc gcg tgt gct    52
                            Met Ala Pro Ala Ala Ser Ala Cys Ala
                            1               5
ggg gcg cct ggc tcc cac ccg gcc acc acg atc ttc gtg tgt ctt ttt    100
Gly Ala Pro Gly Ser His Pro Ala Thr Thr Ile Phe Val Cys Leu Phe
10              15                  20                  25
ctc atc att tac tgc cca gac cgt gcc agt gcc atc cag gtg acc gtg    148
Leu Ile Ile Tyr Cys Pro Asp Arg Ala Ser Ala Ile Gln Val Thr Val
                30                  35                  40
cct gac ccc tac cac gta gtg atc ctg ttc cag cca gtg aca cta cac    196
Pro Asp Pro Tyr His Val Val Ile Leu Phe Gln Pro Val Thr Leu His
            45                  50                  55
tgc acc tac cag atg agc aat acc ctc aca gcc cct atc gtg atc tgg    244
Cys Thr Tyr Gln Met Ser Asn Thr Leu Thr Ala Pro Ile Val Ile Trp
        60                  65                  70
aag tat aag tcg ttc tgt cgg gac cgt gtt gcc gac gcc ttc tcc cct    292
Lys Tyr Lys Ser Phe Cys Arg Asp Arg Val Ala Asp Ala Phe Ser Pro
    75                  80                  85
gcc agc gtg gac aac cag ctc aac gcc cag ctg gcg gct ggc aac ccc    340
Ala Ser Val Asp Asn Gln Leu Asn Ala Gln Leu Ala Ala Gly Asn Pro
90                  95                  100                 105
ggc tac aac ccc tat gtg gag tgc cag gac agc gta cgc act gtc agg    388
Gly Tyr Asn Pro Tyr Val Glu Cys Gln Asp Ser Val Arg Thr Val Arg
                110                 115                 120
gtg gtg gcc acc aaa cag ggc aat gct gtg acc ctg gga gac tac tac    436
Val Val Ala Thr Lys Gln Gly Asn Ala Val Thr Leu Gly Asp Tyr Tyr
            125                 130                 135
```

```
cag ggc agg aga atc acc atc aca gga aat gct ggc ctg acc ttc gag      484
Gln Gly Arg Arg Ile Thr Ile Thr Gly Asn Ala Gly Leu Thr Phe Glu
        140             145             150
cag acg gcc tgg gga gac agt gga gtg tat tac tgc tcc gtg gtc tca      532
Gln Thr Ala Trp Gly Asp Ser Gly Val Tyr Tyr Cys Ser Val Val Ser
    155             160             165
gcc caa gat ctg gat ggg aac aac gag gcg tac gca gag ctc att gtc      580
Ala Gln Asp Leu Asp Gly Asn Asn Glu Ala Tyr Ala Glu Leu Ile Val
170             175             180             185
ctt gtt tat gct gct ggc aaa gca gcc acc tca ggt gtg cca agc atc      628
Leu Val Tyr Ala Ala Gly Lys Ala Ala Thr Ser Gly Val Pro Ser Ile
            190             195             200
tat gcc ccc agc atc tat acc cac ctc tct cct gcc aag act ccg cca      676
Tyr Ala Pro Ser Ile Tyr Thr His Leu Ser Pro Ala Lys Thr Pro Pro
        205             210             215
cct ccg cct gcc atg att ccc atg cgt cct ccc tat ggg tac cct gga      724
Pro Pro Pro Ala Met Ile Pro Met Arg Pro Pro Tyr Gly Tyr Pro Gly
        220             225             230
gac ttt gac agg acc agc tca gtt ggt ggc cac agc tcc cag gtg ccc      772
Asp Phe Asp Arg Thr Ser Ser Val Gly Gly His Ser Ser Gln Val Pro
    235             240             245
ctg ctg cgt gaa gtg gat ggg agc gta tct tca gaa gta cga agt ggc      820
Leu Leu Arg Glu Val Asp Gly Ser Val Ser Ser Glu Val Arg Ser Gly
250             255             260             265
tac agg atc cag gct aac cag caa gat gac tcc atg agg gtc cta tac      868
Tyr Arg Ile Gln Ala Asn Gln Gln Asp Asp Ser Met Arg Val Leu Tyr
            270             275             280
tat atg gag aag gag cta gcc aac ttc gat cct tcc cgg cct ggc cct      916
Tyr Met Glu Lys Glu Leu Ala Asn Phe Asp Pro Ser Arg Pro Gly Pro
        285             290             295
ccc aat ggc cga gtg gaa cgg gcc atg agt gaa gta acc tcc ctc cat      964
Pro Asn Gly Arg Val Glu Arg Ala Met Ser Glu Val Thr Ser Leu His
        300             305             310
gaa gat gac tgg cga tct cgg cct tcc agg gct cct gcc ctc aca ccc     1012
Glu Asp Asp Trp Arg Ser Arg Pro Ser Arg Ala Pro Ala Leu Thr Pro
        315             320             325
atc agg gat gag gag tgg aat cgc cac tcc cct cgg agt ccc aga aca     1060
Ile Arg Asp Glu Glu Trp Asn Arg His Ser Pro Arg Ser Pro Arg Thr
330             335             340             345
tgg gag cag gaa ccc ctt caa gaa cag cca agg ggt ggt tgg ggg tct     1108
Trp Glu Gln Glu Pro Leu Gln Glu Gln Pro Arg Gly Gly Trp Gly Ser
            350             355             360
ggg cgg cct cgg gcc cgc tct gtg gat gct cta gat gac atc aac cgg     1156
Gly Arg Pro Arg Ala Arg Ser Val Asp Ala Leu Asp Asp Ile Asn Arg
        365             370             375
cct ggc tcc act gaa tca gga agg tct tct ccc cca agt agt gga cgg     1204
Pro Gly Ser Thr Glu Ser Gly Arg Ser Ser Pro Pro Ser Ser Gly Arg
        380             385             390
aga ggg cgg gcc tat gca cct ccg aga agt cgc agc cgg gat gac ctc     1252
Arg Gly Arg Ala Tyr Ala Pro Pro Arg Ser Arg Ser Arg Asp Asp Leu
    395             400             405
tat gac ccc gac gat cct aga gac ttg cca cat tcc cga gat ccc cac     1300
Tyr Asp Pro Asp Asp Pro Arg Asp Leu Pro His Ser Arg Asp Pro His
410             415             420             425
tat tat gat gat ttg agg tct agg gat cca cgt gct gac ccc aga tcc     1348
Tyr Tyr Asp Asp Leu Arg Ser Arg Asp Pro Arg Ala Asp Pro Arg Ser
            430             435             440
cgt cag cga tcc cac gat cct cgg gat gct ggc ttc agg tca cgg gac     1396
Arg Gln Arg Ser His Asp Pro Arg Asp Ala Gly Phe Arg Ser Arg Asp
```

```
                    445                    450                    455
    cct cag tat gat ggg cga ctc tta gaa gag gct tta aag aaa aaa ggg      1444
    Pro Gln Tyr Asp Gly Arg Leu Leu Glu Glu Ala Leu Lys Lys Lys Gly
            460                    465                    470
    gct ggg gag aga aga cgc gtt tac agg gag gaa gaa gaa gaa gaa gag      1492
    Ala Gly Glu Arg Arg Arg Val Tyr Arg Glu Glu Glu Glu Glu Glu Glu
        475                    480                    485
    gag ggc cac tat ccc cca gca cct ccg cct tac tct gag act gac tcg      1540
    Glu Gly His Tyr Pro Pro Ala Pro Pro Pro Tyr Ser Glu Thr Asp Ser
    490                    495                    500                505
    cag gcc tcg agg gag cgg agg atg aaa aag aat ttg gcc ctg agt cgg      1588
    Gln Ala Ser Arg Glu Arg Arg Met Lys Lys Asn Leu Ala Leu Ser Arg
                510                    515                    520
    gaa agt tta gtc gtc tga tcccacgttt tgttatgtag cttttatact             1636
    Glu Ser Leu Val Val  *
                525
    tttttaattg gaatattgat gaaactcttc accaagccta ataaaa                    1682

<210> 17
<211> 594
<212> PRT
<213> Mus musculus

<400> 17
Met Ala Pro Ala Ala Ser Ala Cys Ala Gly Ala Pro Gly Ser His Pro
1               5                   10                  15
Ala Thr Thr Ile Phe Val Cys Leu Phe Leu Ile Ile Tyr Cys Pro Asp
            20                  25                  30
Arg Ala Ser Ala Ile Gln Val Thr Val Pro Asp Pro Tyr His Val Val
        35                  40                  45
Ile Leu Phe Gln Pro Val Thr Leu His Cys Thr Tyr Gln Met Ser Asn
    50                  55                  60
Thr Leu Thr Ala Pro Ile Val Ile Trp Lys Tyr Lys Ser Phe Cys Arg
65                  70                  75                  80
Asp Arg Val Ala Asp Ala Phe Ser Pro Ala Ser Val Asp Asn Gln Leu
                85                  90                  95
Asn Ala Gln Leu Ala Ala Gly Asn Pro Gly Tyr Asn Pro Tyr Val Glu
            100                 105                 110
Cys Gln Asp Ser Val Arg Thr Val Arg Val Val Ala Thr Lys Gln Gly
        115                 120                 125
Asn Ala Val Thr Leu Gly Asp Tyr Tyr Gln Gly Arg Arg Ile Thr Ile
    130                 135                 140
Thr Gly Asn Ala Gly Leu Thr Phe Glu Gln Thr Ala Trp Gly Asp Ser
145                 150                 155                 160
Gly Val Tyr Tyr Cys Ser Val Val Ser Ala Gln Asp Leu Asp Gly Asn
                165                 170                 175
Asn Glu Ala Tyr Ala Glu Leu Ile Val Leu Gly Arg Thr Ser Glu Ala
            180                 185                 190
Pro Glu Leu Leu Pro Gly Phe Arg Ala Gly Pro Leu Glu Asp Trp Leu
        195                 200                 205
Phe Val Val Val Cys Leu Ala Ser Leu Leu Phe Phe Leu Leu Leu
    210                 215                 220
Gly Ile Cys Trp Cys Gln Cys Cys Pro His Thr Cys Cys Cys Tyr Val
225                 230                 235                 240
Arg Cys Pro Cys Cys Pro Asp Lys Cys Cys Cys Pro Glu Ala Leu Tyr
                245                 250                 255
Ala Ala Gly Lys Ala Ala Thr Ser Gly Val Pro Ser Ile Tyr Ala Pro
            260                 265                 270
Ser Ile Tyr Thr His Leu Ser Pro Ala Lys Thr Pro Pro Pro Pro
```

```
                275                    280                    285
Ala Met Ile Pro Met Arg Pro Pro Tyr Gly Tyr Pro Gly Asp Phe Asp
        290                    295                    300
Arg Thr Ser Ser Val Gly Gly His Ser Ser Gln Val Pro Leu Leu Arg
305                    310                    315                    320
Glu Val Asp Gly Ser Val Ser Ser Glu Val Arg Ser Gly Tyr Arg Ile
                325                    330                    335
Gln Ala Asn Gln Gln Asp Asp Ser Met Arg Val Leu Tyr Tyr Met Glu
                340                    345                    350
Lys Glu Leu Ala Asn Phe Asp Pro Ser Arg Pro Gly Pro Pro Asn Gly
                355                    360                    365
Arg Val Glu Arg Ala Met Ser Glu Val Thr Ser Leu His Glu Asp Asp
        370                    375                    380
Trp Arg Ser Arg Pro Ser Arg Ala Pro Ala Leu Thr Pro Ile Arg Asp
385                    390                    395                    400
Glu Glu Trp Asn Arg His Ser Pro Arg Ser Pro Arg Thr Trp Glu Gln
                405                    410                    415
Glu Pro Leu Gln Glu Gln Pro Arg Gly Gly Trp Gly Ser Gly Arg Pro
                420                    425                    430
Arg Ala Arg Ser Val Asp Ala Leu Asp Asp Ile Asn Arg Pro Gly Ser
                435                    440                    445
Thr Glu Ser Gly Arg Ser Ser Pro Pro Ser Ser Gly Arg Arg Gly Arg
        450                    455                    460
Ala Tyr Ala Pro Pro Arg Ser Arg Ser Arg Asp Asp Leu Tyr Asp Pro
465                    470                    475                    480
Asp Asp Pro Arg Asp Leu Pro His Ser Arg Asp Pro His Tyr Tyr Asp
                485                    490                    495
Asp Leu Arg Ser Arg Asp Pro Arg Ala Asp Pro Arg Ser Arg Gln Arg
                500                    505                    510
Ser His Asp Pro Arg Asp Ala Gly Phe Arg Ser Arg Asp Pro Gln Tyr
                515                    520                    525
Asp Gly Arg Leu Leu Glu Glu Ala Leu Lys Lys Lys Gly Ala Gly Glu
        530                    535                    540
Arg Arg Arg Val Tyr Arg Glu Glu Glu Glu Glu Glu Glu Glu Gly His
545                    550                    555                    560
Tyr Pro Pro Ala Pro Pro Tyr Ser Glu Thr Asp Ser Gln Ala Ser
                565                    570                    575
Arg Glu Arg Arg Met Lys Lys Asn Leu Ala Leu Ser Arg Glu Ser Leu
                580                    585                    590
Val Val

<210> 18
<211> 575
<212> PRT
<213> Mus musculus

<400> 18
Met Ala Pro Ala Ala Ser Ala Cys Ala Gly Ala Pro Gly Ser His Pro
1               5                   10                  15
Ala Thr Thr Ile Phe Val Cys Leu Phe Leu Ile Ile Tyr Cys Pro Asp
                20                  25                  30
Arg Ala Ser Ala Ile Gln Val Thr Val Pro Asp Pro Tyr His Val Val
        35                  40                  45
Ile Leu Phe Gln Pro Val Thr Leu His Cys Thr Tyr Gln Met Ser Asn
        50                  55                  60
Thr Leu Thr Ala Pro Ile Val Ile Trp Lys Tyr Lys Ser Phe Cys Arg
65                  70                  75                  80
Asp Arg Val Ala Asp Ala Phe Ser Pro Ala Ser Val Asp Asn Gln Leu
                85                  90                  95
```

```
Asn Ala Gln Leu Ala Ala Gly Asn Pro Gly Tyr Asn Pro Tyr Val Glu
            100                 105                 110
Cys Gln Asp Ser Val Arg Thr Val Arg Val Val Ala Thr Lys Gln Gly
        115                 120                 125
Asn Ala Val Thr Leu Gly Asp Tyr Tyr Gln Gly Arg Arg Ile Thr Ile
    130                 135                 140
Thr Gly Asn Ala Gly Leu Thr Phe Glu Gln Thr Ala Trp Gly Asp Ser
145                 150                 155                 160
Gly Val Tyr Tyr Cys Ser Val Val Ser Ala Gln Asp Leu Asp Gly Asn
                165                 170                 175
Asn Glu Ala Tyr Ala Glu Leu Ile Val Leu Asp Trp Leu Phe Val Val
            180                 185                 190
Val Val Cys Leu Ala Ser Leu Leu Phe Phe Leu Leu Leu Gly Ile Cys
        195                 200                 205
Trp Cys Gln Cys Cys Pro His Thr Cys Cys Cys Tyr Val Arg Cys Pro
    210                 215                 220
Cys Cys Pro Asp Lys Cys Cys Cys Pro Glu Ala Leu Tyr Ala Ala Gly
225                 230                 235                 240
Lys Ala Ala Thr Ser Gly Val Pro Ser Ile Tyr Ala Pro Ser Ile Tyr
                245                 250                 255
Thr His Leu Ser Pro Ala Lys Thr Pro Pro Pro Pro Ala Met Ile
            260                 265                 270
Pro Met Arg Pro Pro Tyr Gly Tyr Pro Gly Asp Phe Asp Arg Thr Ser
        275                 280                 285
Ser Val Gly Gly His Ser Ser Gln Val Pro Leu Leu Arg Glu Val Asp
    290                 295                 300
Gly Ser Val Ser Ser Glu Val Arg Ser Gly Tyr Arg Ile Gln Ala Asn
305                 310                 315                 320
Gln Gln Asp Asp Ser Met Arg Val Leu Tyr Tyr Met Glu Lys Glu Leu
                325                 330                 335
Ala Asn Phe Asp Pro Ser Arg Pro Gly Pro Pro Asn Gly Arg Val Glu
            340                 345                 350
Arg Ala Met Ser Glu Val Thr Ser Leu His Glu Asp Asp Trp Arg Ser
        355                 360                 365
Arg Pro Ser Arg Ala Pro Ala Leu Thr Pro Ile Arg Asp Glu Glu Trp
    370                 375                 380
Asn Arg His Ser Pro Arg Ser Pro Arg Thr Trp Glu Gln Glu Pro Leu
385                 390                 395                 400
Gln Glu Gln Pro Arg Gly Gly Trp Gly Ser Gly Arg Pro Arg Ala Arg
                405                 410                 415
Ser Val Asp Ala Leu Asp Asp Ile Asn Arg Pro Gly Ser Thr Glu Ser
            420                 425                 430
Gly Arg Ser Ser Pro Pro Ser Ser Gly Arg Arg Gly Arg Ala Tyr Ala
        435                 440                 445
Pro Pro Arg Ser Arg Ser Arg Asp Asp Leu Tyr Asp Pro Asp Asp Pro
    450                 455                 460
Arg Asp Leu Pro His Ser Arg Asp Pro His Tyr Tyr Asp Asp Leu Arg
465                 470                 475                 480
Ser Arg Asp Pro Arg Ala Asp Pro Arg Ser Arg Gln Arg Ser His Asp
                485                 490                 495
Pro Arg Asp Ala Gly Phe Arg Ser Arg Asp Pro Gln Tyr Asp Gly Arg
            500                 505                 510
Leu Leu Glu Glu Ala Leu Lys Lys Lys Gly Ala Gly Glu Arg Arg Arg
        515                 520                 525
Val Tyr Arg Glu Glu Glu Glu Glu Glu Glu Gly His Tyr Pro Pro
    530                 535                 540
Ala Pro Pro Pro Tyr Ser Glu Thr Asp Ser Gln Ala Ser Arg Glu Arg
545                 550                 555                 560
Arg Met Lys Lys Asn Leu Ala Leu Ser Arg Glu Ser Leu Val Val
```

565 570 575

<210> 19
<211> 526
<212> PRT
<213> Mus musculus

<400> 19
Met Ala Pro Ala Ala Ser Ala Cys Ala Gly Ala Pro Gly Ser His Pro
1               5                   10                  15
Ala Thr Thr Ile Phe Val Cys Leu Phe Leu Ile Ile Tyr Cys Pro Asp
                20                  25                  30
Arg Ala Ser Ala Ile Gln Val Thr Val Pro Asp Pro Tyr His Val Val
            35                  40                  45
Ile Leu Phe Gln Pro Val Thr Leu His Cys Thr Tyr Gln Met Ser Asn
        50                  55                  60
Thr Leu Thr Ala Pro Ile Val Ile Trp Lys Tyr Lys Ser Phe Cys Arg
65                  70                  75                  80
Asp Arg Val Ala Asp Ala Phe Ser Pro Ala Ser Val Asp Asn Gln Leu
                85                  90                  95
Asn Ala Gln Leu Ala Ala Gly Asn Pro Gly Tyr Asn Pro Tyr Val Glu
            100                 105                 110
Cys Gln Asp Ser Val Arg Thr Val Arg Val Val Ala Thr Lys Gln Gly
        115                 120                 125
Asn Ala Val Thr Leu Gly Asp Tyr Tyr Gln Gly Arg Arg Ile Thr Ile
    130                 135                 140
Thr Gly Asn Ala Gly Leu Thr Phe Glu Gln Thr Ala Trp Gly Asp Ser
145                 150                 155                 160
Gly Val Tyr Tyr Cys Ser Val Val Ser Ala Gln Asp Leu Asp Gly Asn
                165                 170                 175
Asn Glu Ala Tyr Ala Glu Leu Ile Val Leu Val Tyr Ala Ala Gly Lys
            180                 185                 190
Ala Ala Thr Ser Gly Val Pro Ser Ile Tyr Ala Pro Ser Ile Tyr Thr
        195                 200                 205
His Leu Ser Pro Ala Lys Thr Pro Pro Pro Pro Ala Met Ile Pro
    210                 215                 220
Met Arg Pro Pro Tyr Gly Tyr Pro Gly Asp Phe Asp Arg Thr Ser Ser
225                 230                 235                 240
Val Gly Gly His Ser Ser Gln Val Pro Leu Leu Arg Glu Val Asp Gly
                245                 250                 255
Ser Val Ser Ser Glu Val Arg Ser Gly Tyr Arg Ile Gln Ala Asn Gln
            260                 265                 270
Gln Asp Asp Ser Met Arg Val Leu Tyr Tyr Met Glu Lys Glu Leu Ala
        275                 280                 285
Asn Phe Asp Pro Ser Arg Pro Gly Pro Pro Asn Gly Arg Val Glu Arg
    290                 295                 300
Ala Met Ser Glu Val Thr Ser Leu His Glu Asp Asp Trp Arg Ser Arg
305                 310                 315                 320
Pro Ser Arg Ala Pro Ala Leu Thr Pro Ile Arg Asp Glu Glu Trp Asn
                325                 330                 335
Arg His Ser Pro Arg Ser Pro Arg Thr Trp Glu Gln Glu Pro Leu Gln
            340                 345                 350
Glu Gln Pro Arg Gly Gly Trp Gly Ser Gly Arg Pro Arg Ala Arg Ser
        355                 360                 365
Val Asp Ala Leu Asp Asp Ile Asn Arg Pro Gly Ser Thr Glu Ser Gly
    370                 375                 380
Arg Ser Ser Pro Pro Ser Ser Gly Arg Arg Gly Arg Ala Tyr Ala Pro
385                 390                 395                 400
Pro Arg Ser Arg Ser Arg Asp Asp Leu Tyr Asp Pro Asp Asp Pro Arg

```
                        405                     410                     415
Asp Leu Pro His Ser Arg Asp Pro His Tyr Tyr Asp Asp Leu Arg Ser
                420                     425                 430
Arg Asp Pro Arg Ala Asp Pro Arg Ser Arg Gln Arg Ser His Asp Pro
            435                     440                  445
Arg Asp Ala Gly Phe Arg Ser Arg Asp Pro Gln Tyr Asp Gly Arg Leu
        450                     455                 460
Leu Glu Glu Ala Leu Lys Lys Lys Gly Ala Gly Glu Arg Arg Arg Val
465                     470                     475                 480
Tyr Arg Glu Glu Glu Glu Glu Glu Glu Gly His Tyr Pro Pro Ala
                    485                     490                 495
Pro Pro Pro Tyr Ser Glu Thr Asp Ser Gln Ala Ser Arg Glu Arg Arg
                500                     505                 510
Met Lys Lys Asn Leu Ala Leu Ser Arg Glu Ser Leu Val Val
            515                     520                 525
```

<210> 20
<211> 18
<212> DNA
<213> Homo Sapiens

<220>
<221> misc_binding
<222> 1..18
<223> sequencing oligonucleotide PrimerPU

<400> 20
tgtaaaacga cggccagt                                                 18

<210> 21
<211> 18
<212> DNA
<213> Homo Sapiens

<220>
<221> misc_binding
<222> 1..18
<223> sequencing oligonucleotide PrimerRP

<400> 21
caggaaacag ctatgacc                                                 18

<210> 22
<211> 20
<212> DNA
<213> Artificial Sequence

<220>
<223> oligonucleotide sense primer

<400> 22
ctacaaccoc tacgtcgagt                                               20

<210> 23
<211> 20
<212> DNA
<213> Artificial Sequence

<220>

<223> oligonucleotide anti sense primer

<400> 23
aggcggagat cgccagtcgt                    20

<210> 24
<211> 24
<212> DNA
<213> Artificial Sequence

<220>
<223> oligonucleotide sense primer

<400> 24
cctttgtcca cgtcgtttac gctc               24

<210> 25
<211> 20
<212> DNA
<213> Artificial Sequence

<220>
<223> oligonucleotide anti sense primer

<400> 25
tcacagcgtt gccctgcttg                    20

<210> 26
<211> 21
<212> DNA
<213> Artificial Sequence

<220>
<223> oligonucleotide sense primer

<400> 26
ttactgctcc gtggtctcag c                  21

<210> 27
<211> 22
<212> DNA
<213> Artificial Sequence

<220>
<223> oligonucleotide anti sense primer

<400> 27
agctactcct gtcaacgtct cc                 22

<210> 28
<211> 167
<212> PRT
<213> Bos taurus

<400> 28
Met Arg Cys Gly Pro Leu Tyr Arg Phe Leu Trp Leu Trp Pro Tyr Leu
1               5                   10                  15
Ser Tyr Val Glu Ala Val Pro Ile Arg Lys Val Gln Asp Asp Thr Lys
            20                  25                  30

```
Thr Leu Ile Lys Thr Ile Val Thr Arg Ile Asn Asp Ile Ser His Thr
        35                  40                  45
Gln Ser Val Ser Ser Lys Gln Arg Val Thr Gly Leu Asp Phe Ile Pro
    50                  55                  60
Gly Leu His Pro Leu Leu Ser Leu Ser Lys Met Asp Gln Thr Leu Ala
65                  70                  75                  80
Ile Tyr Gln Gln Ile Leu Thr Ser Leu Pro Ser Arg Asn Val Val Gln
                85                  90                  95
Ile Ser Asn Asp Leu Glu Asn Leu Arg Asp Leu Leu His Leu Leu Ala
            100                 105                 110
Ala Ser Lys Ser Cys Pro Leu Pro Gln Val Arg Ala Leu Glu Ser Leu
        115                 120                 125
Glu Ser Leu Gly Val Val Leu Glu Ala Ser Leu Tyr Ser Thr Glu Val
    130                 135                 140
Val Ala Leu Ser Arg Leu Gln Gly Ser Leu Gln Asp Met Leu Arg Gln
145                 150                 155                 160
Leu Asp Leu Ser Pro Gly Cys
                165

<210> 29
<211> 146
<212> PRT
<213> Canis familiaris

<400> 29
Val Pro Ile Arg Lys Val Gln Asp Asp Thr Lys Thr Leu Ile Lys Thr
1               5                   10                  15
Ile Val Ala Arg Ile Asn Asp Ile Ser His Thr Gln Ser Val Ser Ser
            20                  25                  30
Lys Gln Arg Val Ala Gly Leu Asp Phe Ile Pro Gly Leu Gln Pro Val
        35                  40                  45
Leu Ser Leu Ser Arg Met Asp Gln Thr Leu Ala Ile Tyr Gln Gln Ile
    50                  55                  60
Leu Asn Ser Leu His Ser Arg Asn Val Val Gln Ile Ser Asn Asp Leu
65                  70                  75                  80
Glu Asn Leu Arg Asp Leu Leu His Leu Leu Ala Ser Ser Lys Ser Cys
                85                  90                  95
Pro Leu Pro Arg Ala Arg Gly Leu Glu Thr Phe Glu Ser Leu Gly Gly
            100                 105                 110
Val Leu Glu Ala Ser Leu Tyr Ser Thr Glu Val Val Ala Leu Ser Arg
        115                 120                 125
Leu Gln Ala Ala Leu Gln Asp Met Leu Arg Arg Leu Asp Leu Ser Pro
    130                 135                 140
Gly Cys
145

<210> 30
<211> 163
<212> PRT
<213> Gallus gallus

<400> 30
Met Cys Trp Arg Pro Leu Cys Arg Leu Trp Ser Tyr Leu Val Tyr Val
1               5                   10                  15
Gln Ala Val Pro Cys Gln Ile Phe Gln Asp Asp Thr Lys Thr Leu Ile
            20                  25                  30
Lys Thr Ile Val Thr Arg Ile Asn Asp Ile Ser His Thr Ser Val Ser
        35                  40                  45
Ala Lys Gln Arg Val Thr Gly Leu Asp Phe Ile Pro Gly Leu His Pro
```

```
              50                  55                  60
Ile Leu Ser Leu Ser Lys Met Asp Gln Thr Leu Ala Val Tyr Gln Gln
65                  70                  75                  80
Val Leu Thr Ser Leu Pro Ser Gln Asn Val Leu Gln Ile Ala Asn Asp
                85                  90                  95
Leu Glu Asn Leu Arg Asp Leu Leu His Leu Leu Ala Phe Ser Lys Ser
            100                 105                 110
Cys Ser Leu Pro Gln Thr Ser Gly Leu Gln Lys Pro Glu Ser Leu Asp
        115                 120                 125
Gly Val Leu Glu Ala Ser Leu Tyr Ser Thr Glu Val Val Ala Leu Ser
    130                 135                 140
Arg Leu Gln Gly Ser Leu Gln Asp Ile Leu Gln Gln Leu Asp Ile Ser
145                 150                 155                 160
Pro Glu Cys
```

<210> 31
<211> 146
<212> PRT
<213> Gorilla gorilla

<400> 31
```
Val Pro Ile Gln Lys Val Gln Asp Asp Thr Lys Thr Leu Ile Lys Thr
1               5                   10                  15
Ile Val Thr Arg Ile Ser Asp Ile Ser His Thr Gln Ser Val Ser Ser
                20                  25                  30
Lys Gln Lys Val Thr Gly Leu Asp Phe Ile Pro Gly Leu His Pro Ile
            35                  40                  45
Leu Thr Leu Ser Lys Met Asp Gln Thr Leu Ala Val Tyr Gln Gln Ile
        50                  55                  60
Leu Thr Ser Met Pro Ser Arg Asn Met Ile Gln Ile Ser Asn Asp Leu
65                  70                  75                  80
Glu Asn Leu Arg Asp Leu Leu His Val Leu Ala Phe Ser Lys Ser Cys
                85                  90                  95
His Leu Pro Trp Ala Ser Gly Leu Glu Thr Leu Asp Ser Leu Gly Gly
            100                 105                 110
Val Leu Glu Ala Ser Gly Tyr Ser Thr Glu Val Val Ala Leu Ser Arg
        115                 120                 125
Leu Gln Gly Ser Leu Gln Asp Met Leu Trp Gln Leu Asp Leu Ser Pro
    130                 135                 140
Gly Cys
145
```

<210> 32
<211> 167
<212> PRT
<213> Homo sapiens

<400> 32
```
Met His Trp Gly Thr Leu Cys Gly Phe Leu Trp Leu Trp Pro Tyr Leu
1               5                   10                  15
Phe Tyr Val Gln Ala Val Pro Ile Gln Lys Val Gln Asp Asp Thr Lys
                20                  25                  30
Thr Leu Ile Lys Thr Ile Val Thr Arg Ile Asn Asp Ile Ser His Thr
            35                  40                  45
Gln Ser Val Ser Ser Lys Gln Lys Val Thr Gly Leu Asp Phe Ile Pro
        50                  55                  60
Gly Leu His Pro Ile Leu Thr Leu Ser Lys Met Asp Gln Thr Leu Ala
65                  70                  75                  80
Val Tyr Gln Gln Ile Leu Thr Ser Met Pro Ser Arg Asn Val Ile Gln
```

```
                         85                      90                      95
    Ile Ser Asn Asp Leu Glu Asn Leu Arg Asp Leu Leu His Val Leu Ala
                    100                 105                 110
    Phe Ser Lys Ser Cys His Leu Pro Trp Ala Ser Gly Leu Glu Thr Leu
                115                 120                 125
    Asp Ser Leu Gly Gly Val Leu Glu Ala Ser Gly Tyr Ser Thr Glu Val
            130                 135                 140
    Val Ala Leu Ser Arg Leu Gln Gly Ser Leu Gln Asp Met Leu Trp Gln
    145                 150                 155                 160
    Leu Asp Leu Ser Pro Gly Cys
                    165
```

<210> 33
<211> 167
<212> PRT
<213> Macaca mulatta

<400> 33
```
Met Tyr Trp Arg Thr Leu Trp Gly Phe Leu Trp Leu Trp Pro Tyr Leu
1               5                   10                  15
Phe Tyr Ile Gln Ala Val Pro Ile Gln Lys Val Gln Ser Asp Thr Lys
                20                  25                  30
Thr Leu Ile Lys Thr Ile Val Thr Arg Ile Asn Asp Ile Ser His Thr
            35                  40                  45
Gln Ser Val Ser Ser Lys Gln Arg Val Thr Gly Leu Asp Phe Ile Pro
        50                  55                  60
Gly Leu His Pro Val Leu Thr Leu Ser Gln Met Asp Gln Thr Leu Ala
65                  70                  75                  80
Ile Tyr Gln Gln Ile Leu Ile Asn Leu Pro Ser Arg Asn Val Ile Gln
                85                  90                  95
Ile Ser Asn Asp Leu Glu Asn Leu Arg Asp Leu Leu His Leu Leu Ala
                100                 105                 110
Phe Ser Lys Ser Cys His Leu Pro Leu Ala Ser Gly Leu Glu Thr Leu
            115                 120                 125
Glu Ser Leu Gly Asp Val Leu Glu Ala Ser Leu Tyr Ser Thr Glu Val
        130                 135                 140
Val Ala Leu Ser Arg Leu Gln Gly Ser Leu Gln Asp Met Leu Trp Gln
145                 150                 155                 160
Leu Asp Leu Ser Pro Gly Cys
                165
```

<210> 34
<211> 167
<212> PRT
<213> Mus musculus

<400> 34
```
Met Cys Trp Arg Pro Leu Cys Arg Phe Leu Trp Leu Trp Ser Tyr Leu
1               5                   10                  15
Ser Tyr Val Gln Ala Val Pro Ile Gln Lys Val Gln Asp Asp Thr Lys
                20                  25                  30
Thr Leu Ile Lys Thr Ile Val Thr Arg Ile Asn Asp Ile Ser His Thr
            35                  40                  45
Gln Ser Val Ser Ala Lys Gln Arg Val Thr Gly Leu Asp Phe Ile Pro
        50                  55                  60
Gly Leu His Pro Ile Leu Ser Leu Ser Lys Met Asp Gln Thr Leu Ala
65                  70                  75                  80
Val Tyr Gln Gln Val Leu Thr Ser Leu Pro Ser Gln Asn Val Leu Gln
                85                  90                  95
```

```
Ile Ala Asn Asp Leu Glu Asn Leu Arg Asp Leu Leu His Leu Leu Ala
            100                 105                 110
Phe Ser Lys Ser Cys Ser Leu Pro Gln Thr Ser Gly Leu Gln Lys Pro
        115                 120                 125
Glu Ser Leu Asp Gly Val Leu Glu Ala Ser Leu Tyr Ser Thr Glu Val
130                     135                 140
Val Ala Leu Ser Arg Leu Gln Gly Ser Leu Gln Asp Ile Leu Gln Gln
145                 150                 155                 160
Leu Asp Val Ser Pro Glu Cys
                165

<210> 35
<211> 146
<212> PRT
<213> Ovus aries

<400> 35
Val Pro Ile Arg Lys Val Gln Asp Asp Thr Lys Thr Leu Ile Lys Thr
1               5                   10                  15
Ile Val Thr Arg Ile Asn Asp Ile Ser His Thr Gln Ser Val Ser Ser
            20                  25                  30
Lys Gln Arg Val Thr Gly Leu Asp Phe Ile Pro Gly Leu His Pro Leu
        35                  40                  45
Leu Ser Leu Ser Lys Met Asp Gln Thr Leu Ala Ile Tyr Gln Gln Ile
    50                  55                  60
Leu Ala Ser Leu Pro Ser Arg Asn Val Ile Gln Ile Ser Asn Asp Leu
65                  70                  75                  80
Glu Asn Leu Arg Asp Leu Leu His Leu Leu Ala Ala Ser Lys Ser Cys
                85                  90                  95
Pro Leu Pro Gln Val Arg Ala Leu Glu Ser Leu Glu Ser Leu Gly Val
            100                 105                 110
Val Leu Glu Ala Ser Leu Tyr Ser Thr Glu Val Val Ala Leu Ser Arg
            115                 120                 125
Leu Gln Gly Ser Leu Gln Asp Met Leu Arg Gln Leu Asp Leu Ser Pro
        130                 135                 140
Gly Cys
145

<210> 36
<211> 146
<212> PRT
<213> Pan troglodytes

<400> 36
Val Pro Ile Gln Lys Val Gln Asp Asp Thr Lys Thr Leu Ile Lys Thr
1               5                   10                  15
Ile Val Thr Arg Ile Asn Asp Ile Ser His Thr Gln Ser Val Ser Ser
            20                  25                  30
Lys Gln Lys Val Thr Gly Leu Asp Phe Ile Pro Gly Leu His Pro Ile
        35                  40                  45
Leu Thr Leu Ser Lys Met Asp Gln Thr Leu Ala Val Tyr Gln Gln Ile
    50                  55                  60
Leu Thr Ser Met Pro Ser Arg Asn Met Ile Gln Ile Ser Asn Asp Leu
65                  70                  75                  80
Glu Asn Leu Arg Asp Leu Leu His Val Leu Ala Phe Ser Lys Ser Cys
                85                  90                  95
His Leu Pro Trp Ala Ser Gly Leu Glu Thr Leu Asp Ser Leu Gly Gly
            100                 105                 110
Val Leu Glu Ala Ser Gly Tyr Ser Thr Glu Val Val Ala Leu Ser Arg
```

```
                115                 120                 125
Leu Gln Gly Ser Leu Gln Asp Met Leu Trp Gln Leu Asp Leu Ser Pro
        130                 135                 140
Gly Cys
145

<210> 37
<211> 146
<212> PRT
<213> Pongo pygmaeus

<400> 37
Val Pro Ile Gln Lys Val Gln Asp Asp Thr Lys Thr Leu Ile Lys Thr
1               5                   10                  15
Val Ile Thr Arg Ile Asn Asp Ile Ser His Thr Gln Ser Val Ser Ser
                20                  25                  30
Lys Gln Lys Val Thr Gly Leu Asp Phe Ile Pro Gly Leu His Pro Ile
            35                  40                  45
Leu Thr Leu Ser Lys Met Asp Gln Thr Leu Ala Val Tyr Gln Gln Ile
        50                  55                  60
Leu Thr Ser Met Pro Ser Arg Asn Val Ile Gln Ile Ser Asn Asp Leu
65                  70                  75                  80
Glu Asn Leu Arg Asp Leu Leu His Val Leu Ala Phe Ser Lys Ser Cys
                85                  90                  95
His Leu Pro Trp Ala Ser Gly Leu Glu Thr Leu Asp Arg Leu Gly Gly
                100                 105                 110
Val Leu Glu Ala Ser Gly Tyr Ser Thr Glu Val Val Ala Leu Ser Arg
            115                 120                 125
Leu Gln Arg Ser Leu Gln Asp Met Leu Trp Gln Leu Asp Leu Ser Pro
        130                 135                 140
Gly Cys
145

<210> 38
<211> 167
<212> PRT
<213> Rattus norvegicus

<400> 38
Met Cys Trp Arg Pro Leu Cys Arg Phe Leu Trp Leu Trp Ser Tyr Leu
1               5                   10                  15
Ser Tyr Val Gln Ala Val Pro Ile His Lys Val Gln Asp Asp Thr Lys
                20                  25                  30
Thr Leu Ile Lys Thr Ile Val Thr Arg Ile Asn Asp Ile Ser His Thr
            35                  40                  45
Gln Ser Val Ser Ala Arg Gln Arg Val Thr Gly Leu Asp Phe Ile Pro
        50                  55                  60
Gly Leu His Pro Ile Leu Ser Leu Ser Lys Met Asp Gln Thr Leu Ala
65                  70                  75                  80
Val Tyr Gln Gln Ile Leu Thr Ser Leu Pro Ser Gln Asn Val Leu Gln
                85                  90                  95
Ile Ala His Asp Leu Glu Asn Leu Arg Asp Leu Leu His Leu Leu Ala
                100                 105                 110
Phe Ser Lys Ser Cys Ser Leu Pro Gln Thr Arg Gly Leu Gln Lys Pro
            115                 120                 125
Glu Ser Leu Asp Gly Val Leu Glu Ala Ser Leu Tyr Ser Thr Glu Val
        130                 135                 140
Val Ala Leu Ser Arg Leu Gln Gly Ser Leu Gln Asp Ile Leu Gln Gln
145                 150                 155                 160
```

```
Leu Asp Leu Ser Pro Glu Cys
                165

<210> 39
<211> 167
<212> PRT
<213> Sus scrofa

<400> 39
Met Arg Cys Gly Pro Leu Cys Arg Phe Leu Trp Leu Trp Pro Tyr Leu
1               5                   10                  15
Ser Tyr Val Glu Ala Val Pro Ile Trp Arg Val Gln Asp Asp Thr Lys
            20                  25                  30
Thr Leu Ile Lys Thr Ile Val Thr Arg Ile Ser Asp Ile Ser His Met
        35                  40                  45
Gln Ser Val Ser Ser Lys Gln Arg Val Thr Gly Leu Asp Phe Ile Pro
    50                  55                  60
Gly Leu His Pro Val Leu Ser Leu Ser Lys Met Asp Gln Thr Leu Ala
65                  70                  75                  80
Ile Tyr Gln Gln Ile Leu Thr Ser Leu Pro Ser Arg Asn Val Ile Gln
                85                  90                  95
Ile Ser Asn Asp Leu Glu Asn Leu Arg Asp Leu Leu His Leu Leu Ala
            100                 105                 110
Ser Ser Lys Ser Cys Pro Leu Pro Gln Ala Arg Ala Leu Glu Thr Leu
        115                 120                 125
Glu Ser Leu Gly Gly Val Leu Glu Ala Ser Leu Tyr Ser Thr Glu Val
    130                 135                 140
Val Ala Leu Ser Arg Leu Gln Gly Ala Leu Gln Asp Met Leu Arg Gln
145                 150                 155                 160
Leu Asp Leu Ser Pro Gly Cys
                165

<210> 40
<211> 4
<212> PRT
<213> Homo sapiens

<400> 40
Glu Thr Leu Asp
1

<210> 41
<211> 4
<212> PRT
<213> Mus musculus

<400> 41
Gln Lys Pro Glu
1

<210> 42
<211> 6
<212> PRT
<213> Homo sapiens

<400> 42
Leu Asp Ser Leu Gly Gly
1               5
```

<210> 43
<211> 4
<212> PRT
<213> Homo sapiens

<400> 43
Glu Lys Leu Glu
1

<210> 44
<211> 4
<212> PRT
<213> Homo sapiens

<400> 44
Glu Lys Pro Glu
1

<210> 45
<211> 4
<212> PRT
<213> Homo sapiens

<400> 45
Glu Lys Pro Asp
1

<210> 46
<211> 5
<212> PRT
<213> Homo sapiens

<400> 46
Thr Pro Asp Ser Leu
1               5

<210> 47
<211> 9
<212> PRT
<213> Homo sapiens

<400> 47
Gly Leu Gln Thr Leu Asp Ser Leu Gly
1               5

<210> 48
<211> 5
<212> PRT
<213> Homo sapiens

<400> 48
Gly Gly Val Leu Glu
1               5

<210> 49
<211> 6
<212> PRT
<213> Homo sapiens

<400> 49
Thr Pro Asp Ser Leu Gly
1               5

<210> 50
<211> 9
<212> PRT
<213> Homo sapiens

<400> 50
Ser Leu Gly Gly Val Leu Glu Ala Ser
1               5

<210> 51
<211> 6
<212> PRT
<213> Homo sapiens

<400> 51
Pro Glu Ser Leu Gly Gly
1               5

<210> 52
<211> 6
<212> PRT
<213> Homo sapiens

<400> 52
Pro Asp Ser Leu Gly Gly
1               5

<210> 53
<211> 7
<212> PRT
<213> Homo sapiens

<400> 53
Leu Gly Gly Val Leu Glu Ala
1               5

<210> 54
<211> 22
<212> PRT
<213> Homo sapiens

<400> 54
Glu Asn Leu Arg Asp Leu Leu His Val Leu Ala Phe Ser Lys Ser Cys
1               5                   10                  15
His Leu Pro Trp Ala Ser
            20

<210> 55
<211> 22
<212> PRT
<213> Homo sapiens

<400> 55
Leu Leu His Val Leu Ala Phe Ser Lys Ser Cys His Leu Pro Trp Ala
1               5                   10                  15

Ser Gly Leu Glu Thr Leu
            20

<210> 56
<211> 22
<212> PRT
<213> Homo sapiens

<400> 56
Ala Phe Ser Lys Ser Cys His Leu Pro Trp Ala Ser Gly Leu Glu Thr
1               5                   10                  15
Leu Asp Ser Leu Gly Gly
            20

<210> 57
<211> 22
<212> PRT
<213> Homo sapiens

<400> 57
Cys His Leu Pro Trp Ala Ser Gly Leu Glu Thr Leu Asp Ser Leu Gly
1               5                   10                  15
Gly Val Leu Glu Ala Ser
            20

<210> 58
<211> 18
<212> PRT
<213> Homo sapiens

<400> 58
Leu Pro Trp Ala Ser Gly Leu Glu Thr Leu Asp Ser Leu Gly Gly Val
1               5                   10                  15
Leu Glu

<210> 59
<211> 14
<212> PRT
<213> Homo sapiens

<400> 59
Trp Ala Ser Gly Leu Glu Thr Leu Asp Ser Leu Gly Gly Val
1               5                   10

<210> 60
<211> 21
<212> PRT
<213> Homo sapiens

<400> 60
Ala Ser Gly Leu Glu Thr Asp Ser Leu Gly Gly Val Leu Glu Ala Ser
1               5                   10                  15
Gly Tyr Ser Thr Glu
            20

<210> 61
<211> 10
<212> PRT
<213> Homo sapiens

<400> 61
Ser Gly Leu Glu Thr Leu Asp Ser Leu Gly
1               5                   10

<210> 62
<211> 22
<212> PRT
<213> Homo sapiens

<400> 62
Thr Leu Asp Ser Leu Gly Gly Val Leu Glu Ala Ser Gly Tyr Ser Thr
1               5                   10                  15
Glu Val Val Ala Leu Ser
            20

<210> 63
<211> 22
<212> PRT
<213> Homo sapiens

<400> 63
Gly Gly Val Leu Glu Ala Ser Gly Tyr Ser Thr Glu Val Val Ala Leu
1               5                   10                  15
Ser Arg Gly Gln Gly Ser
            20

<210> 64
<211> 22
<212> PRT
<213> Mus musculus

<400> 64
Glu Asn Leu Arg Asp Leu Leu His Leu Leu Ala Phe Ser Lys Ser Cys
1               5                   10                  15
Ser Leu Pro Gln Thr Ser
            20

<210> 65
<211> 22
<212> PRT
<213> Mus musculus

<400> 65
Leu Leu His Leu Leu Ala Phe Ser Lys Ser Cys Ser Leu Pro Gln Thr
1               5                   10                  15
Ser Gly Leu Gln Lys Pro
            20

<210> 66
<211> 22
<212> PRT
<213> Mus musculus

<400> 66
Ala Phe Ser Lys Ser Cys Ser Leu Pro Gln Thr Ser Gly Leu Gln Lys
1               5                   10                  15
Pro Glu Ser Leu Asp Gly
            20

<210> 67
<211> 22
<212> PRT
<213> Mus musculus

<400> 67
Cys Ser Leu Pro Gln Thr Ser Gly Leu Gln Lys Pro Glu Ser Leu Asp
1               5                   10                  15
Gly Val Leu Glu Ala Ser
            20

<210> 68
<211> 18
<212> PRT
<213> Mus musculus

<400> 68
Leu Pro Gln Thr Ser Gly Leu Gln Lys Pro Glu Ser Leu Asp Gly Val
1               5                   10                  15
Leu Glu

<210> 69
<211> 14
<212> PRT
<213> Mus musculus

<400> 69
Gln Thr Ser Gly Leu Gln Lys Pro Glu Ser Leu Asp Gly Val
1               5                   10

<210> 70
<211> 22
<212> PRT
<213> Mus musculus

<400> 70
Thr Ser Gly Leu Gln Lys Pro Glu Ser Leu Asp Gly Val Leu Glu Ala
1               5                   10                  15
Ser Leu Tyr Ser Thr Glu
            20

<210> 71
<211> 10
<212> PRT
<213> Mus musculus

<400> 71
Ser Gly Leu Gln Lys Pro Glu Ser Leu Asp
1               5                   10

<210> 72
<211> 22
<212> PRT
<213> Mus musculus

<400> 72
Lys Pro Glu Ser Leu Asp Gly Val Leu Glu Ala Ser Leu Tyr Ser Thr
1               5                   10                  15

Glu Val Val Ala Leu Ser
            20

<210> 73
<211> 22
<212> PRT
<213> Mus musculus

<400> 73
Asp Gly Val Leu Glu Ala Ser Leu Tyr Ser Thr Glu Val Val Ala Leu
1               5                   10                  15
Ser Arg Leu Gln Gly Ser
            20

<210> 74
<211> 67
<212> DNA
<213> Artificial Sequence

<220>
<223> oligonucleotide Chimeric oligonucleotides

<400> 74
atgcaacagg acggacttgg agtagttttc uacuccaagt cagtccuguu gcaugcgcgt     60
ttcgcgc                                                               67

<210> 75
<211> 20
<212> DNA
<213> Artificial Sequence

<220>
<223> oligonucleotide Forward Primer

<400> 75
tgtccacgtc gtttacgctc                                                 20

<210> 76
<211> 20
<212> DNA
<213> Artificial Sequence

<220>
<223> oligonucleotide Reverse Primer

<400> 76
tcccacttcc gttccttgtc                                                 20

<210> 77
<211> 27
<212> DNA
<213> Artificial Sequence

<220>
<223> oligonucleotide Probes endogenous/mutant

<400> 77
cctactccaa gtcmgtcctg ttgcatt                                         27

<210> 78
<211> 67
<212> DNA
<213> Artificial Sequence

<220>
<223> oligonucleotide Chimeric oligonucleotides

<400> 78
gaccctgccc tgtacctacc taccagatgt tttcaucugg uaggttcagg gcagggucgc    60
gcgtttt                                                              67

<210> 79
<211> 21
<212> DNA
<213> Artificial Sequence

<220>
<223> oligonucleotide Forward Primer

<400> 79
gtggtgatcc tcttccagcc t                                              21

<210> 80
<211> 19
<212> DNA
<213> Artificial Sequence

<220>
<223> oligonucleotide Reverse Primer

<400> 80
ccagatgacg atgggttgc                                                 19

<210> 81
<211> 25
<212> DNA
<213> Artificial Sequence

<220>
<223> oligonucleotide Probes endogenous/mutant

<400> 81
accctgccct gwcctaccag atgac                                          25

<210> 82
<211> 68
<212> DNA
<213> Artificial Sequence

<220>
<223> oligonucleotide Chimeric oligonucleotides

<400> 82
tggctgagct cttacctggt tttcattttt gaaaaccagg tcagagctca gccagcgcgt    60
tttcgcgc                                                             68

<210> 83
<211> 20

<212> DNA
<213> Artificial Sequence

<220>
<223> oligonucleotide Forward Primer

<400> 83
gagctcatcg tccttgggag                                              20

<210> 84
<211> 19
<212> DNA
<213> Artificial Sequence

<220>
<223> oligonucleotide Reverse Primer

<400> 84
agtcttctat gggccccgc                                               19

<210> 85
<211> 27
<212> DNA
<213> Artificial Sequence

<220>
<223> oligonucleotide Probes endogenous/mutant

<400> 85
caccgactcg agamtggacc aaaagtc                                      27

<210> 86
<211> 68
<212> DNA
<213> Artificial Sequence

<220>
<223> oligonucleotide Chimeric oligonucleotides

<400> 86
ggttgtggta tgcctggctg ccttcttttg aaggcagcca gtcataccac aaccgcgcgt   60
tttcgcgc                                                           68

<210> 87
<211> 20
<212> DNA
<213> Artificial Sequence

<220>
<223> oligonucleotide Forward Primer

<400> 87
acgcagagct catcgtcctt                                              20

<210> 88
<211> 20
<212> DNA
<213> Artificial Sequence

```
<220>
<223> oligonucleotide Reverse Primer

<400> 88
gatgcccagg aggaggaaga                                              20

<210> 89
<211> 23
<212> DNA
<213> Artificial Sequence

<220>
<223> oligonucleotide Probes endogenous/mutant

<400> 89
caacaccata ckgaccgacg gaa                                          23

<210> 90
<211> 18
<212> DNA
<213> Artificial Sequence

<220>
<223> oligonucleotide mouse LSR specific primer

<400> 90
acgcatggga atcatggc                                                18

<210> 91
<211> 18
<212> DNA
<213> Artificial Sequence

<220>
<223> oligonucleotide Zinc finger nuclotides of SEQID1

<400> 91
tagggtgag cggcgggg                                                 18

<210> 92
<211> 21
<212> DNA
<213> Artificial Sequence

<220>
<223> oligonucleotide Zinc finger nuclotides of SEQID1

<220>
<221> misc_feature
<222> 10..12
<223> n=a, g, c or t

<400> 92
gagggctggn nntaggggtg a                                            21

<210> 93
<211> 20
<212> DNA
<213> Artificial Sequence
```

```
<220>
<223> oligonucleotide Zinc finger nuclotides of SEQID1

<220>
<221> misc_feature
<222> 10..11
<223> n=a, g, c or t

<400> 93
agggctgggn ntagggtga                                                    20

<210> 94
<211> 18
<212> DNA
<213> Artificial Sequence

<220>
<223> oligonucleotide Zinc finger nuclotides of SEQID1

<400> 94
gtgggagccg agggctgg                                                     18

<210> 95
<211> 19
<212> DNA
<213> Artificial Sequence

<220>
<223> oligonucleotide Zinc finger nuclotides of SEQID1

<220>
<221> misc_feature
<222> 10
<223> n=a, g, c or t

<400> 95
gtgggagccn agggctggg                                                    19

<210> 96
<211> 18
<212> DNA
<213> Artificial Sequence

<220>
<223> oligonucleotide Zinc finger nuclotides of SEQID1

<400> 96
gcggcggccg ggtgggag                                                     18

<210> 97
<211> 18
<212> DNA
<213> Artificial Sequence

<220>
<223> oligonucleotide Zinc finger nuclotides of SEQID1

<400> 97
```

```
ttggccggag cagatggg                                              18

<210> 98
<211> 20
<212> DNA
<213> Artificial Sequence

<220>
<223> oligonucleotide Zinc finger nuclotides of SEQID1

<220>
<221> misc_feature
<222> 10..11
<223> n=a, g, c or t

<400> 98
gcagatgggn nccggaaggg                                            20

<210> 99
<211> 21
<212> DNA
<213> Artificial Sequence

<220>
<223> oligonucleotide Zinc finger nuclotides of SEQID1

<220>
<221> misc_feature
<222> 10..12
<223> n=a, g, c or t

<400> 99
agggctgggn nnaggggtga g                                          21

<210> 100
<211> 21
<212> DNA
<213> Artificial Sequence

<220>
<223> oligonucleotide Zinc finger nuclotides of SEQID1

<220>
<221> misc_feature
<222> 10..12
<223> n=a, g, c or t

<400> 100
aggggtgagn nncggggagg g                                          21

<210> 101
<211> 18
<212> DNA
<213> Artificial Sequence

<220>
<223> oligonucleotide Zinc finger nuclotides of SEQID1

<400> 101
```
aagtgggtct cggttgca					18

<210> 102
<211> 21
<212> DNA
<213> Artificial Sequence

<220>
<223> oligonucleotide zinc finger LSR sequences

<400> 102
aaggtcgcct atggtgcaga c					21

<210> 103
<211> 20
<212> DNA
<213> Artificial Sequence

<220>
<223> oligonucleotide zinc finger LSR sequences

<400> 103
gtgggagccc gggggctgga					20

<210> 104
<211> 18
<212> DNA
<213> Artificial Sequence

<220>
<223> oligonucleotide zinc finger LSR sequences

<400> 104
tgggggtggg cggcgggg					18

<210> 105
<211> 20
<212> DNA
<213> Artificial Sequence

<220>
<223> oligonucleotide zinc finger LSR sequences

<400> 105
ccgggagtgc gcaggggta					20

<210> 106
<211> 19
<212> DNA
<213> Artificial Sequence

<220>
<223> oligonucleotide zinc finger LSR sequences

<400> 106
gtggctgcac aaggtcgcc					19

<210> 107

<211> 6319
<212> DNA
<213> Artificial sequence

<220>
<223> LSR zinc finger plasmid

<400> 107

```
gacggatcgg gagatctccc gatcccctat ggtcgactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180
ttagggttag gcgttttgcg ctgcttcgcg atgtacgggc cagatatacg cgttgacatt     240
gattattgac tagttattaa tagtaatcaa ttacggggtc attagttcat agcccatata     300
tggagttccg cgttacataa cttacggtaa atggcccgcc tggctgaccg cccaacgacc     360
cccgcccatt gacgtcaata atgacgtatg ttcccatagt aacgccaata gggactttcc     420
attgacgtca atgggtggac tatttacggt aaactgccca cttggcagta catcaagtgt     480
atcatatgcc aagtacgccc cctattgacg tcaatgacgg taaatggccc gcctggcatt     540
atgcccagta catgacctta tgggactttc ctacttggca gtacatctac gtattagtca     600
tcgctattac catggtgatg cggttttggc agtacatcaa tgggcgtgga tagcggtttg     660
actcacgggg atttccaagt ctccacccca ttgacgtcaa tgggagtttg ttttggcacc     720
aaaatcaacg ggactttcca aaatgtcgta acaactccgc cccattgacg caaatgggcg     780
gtaggcgtgt acggtgggag gtctatataa gcagagctct ctggctaact agagaaccca     840
ctgcttactg gcttatcgaa attaatacga ctcactatag ggagacccaa gctggctagc     900
gtttaaactt aagctgatcc actagtccag tgtggtggaa ttcgctagcg ccaccatggc     960
ccccaagaag aagaggaagg tgggaatcca tgggtaccg ggcaagaaga agcagcacat    1020
ctgccacatc cagggctgtg gtaaagttta cggcgaccgc tccaacctga cccgccacct    1080
gcgctggcac accggcgaga ggcctttcat gtgtacatgg tcctactgtg gtaaacgctt    1140
cacccagtcc ggcgacctga cccgccacaa gcgtacccac accggtgaga agaaatttgc    1200
ttgtccggaa tgtccaaagc gcttcatgat gtcccaccac ctgtcccgcc acatcaagac    1260
ccaccagaac aagaagggtg gatctggtga tggtggccgt cgcggtgccg gttctggcaa    1320
gaagaagcag cacatctgcc acatccaggg ctgtggtaaa gtttacggcg agcgcggcga    1380
cctgacccgc cacctgcgct ggcacaccgg cgagaggcct tcatgtgta catggtccta    1440
ctgtggtaaa cgcttcaccg acccgggcgc cctggtgcgc cacaagcgta cccacaccgg    1500
tgagaagaaa tttgcttgtc cggaatgtcc gaagcgcttc atgcgctccg acaacctgac    1560
```

```
ccagcacatc aagacccacc agaacaagaa gggtggatcc gccccccga ccgatgtcag   1620 cctgggggac gagctccact tagacggcga ggacgtggcg atggcgcatg ccgacgcgct   1680
agacgatttc gatctggaca tgttggggga cggggattcc ccggggccgg gatttacccc   1740
ccacgactcc gccccctacg gcgctctgga tatggccggc ttcgagtttg agcagatgtt   1800
taccgatgcc cttggaattg acgagtacgg tgggggcagc gactacaagg acgacgatga   1860
caagtaagct tctcgagtct agagggcccg tttaaacccg ctgatcagcc tcgactgtgc   1920
cttctagttg ccagccatct gttgtttgcc cctcccccgt gccttccttg accctggaag   1980
gtgccactcc cactgtcctt tcctaataaa atgaggaaat tgcatcgcat tgtctgagta   2040
ggtgtcattc tattctgggg ggtggggtgg ggcaggacag caaggggggag gattgggaag   2100 acaatagcag gcatgctggg gatgcggtgg gctctatggc ttctgaggcg gaaagaacca   2160 gctgggctc tagggggtat ccccacgcgc cctgtagcgg cgcattaagc gcggcgggtg   2220
tggtggttac gcgcagcgtg accgctacac ttgccagcgc cctagcgccc gctcctttcg   2280
ctttcttccc ttcctttctc gccacgttcg ccggctttcc ccgtcaagct ctaaatcggg   2340
gcatcccttt agggttccga tttagtgctt tacggcacct cgaccccaaa aaacttgatt   2400
agggtgatgg ttcacgtagt gggccatcgc cctgatagac ggtttttcgc cctttgacgt   2460
tggagtccac gttctttaat agtggactct tgttccaaac tggaacaaca ctcaacccta   2520
tctcggtcta ttcttttgat ttataaggga ttttggggat ttcggcctat tggttaaaaa   2580
atgagctgat ttaacaaaaa tttaacgcga attaattctg tggaatgtgt gtcagttagg   2640
gtgtggaaag tccccaggct ccccaggcag gcagaagtat gcaaagcatg catctcaatt   2700
agtcagcaac caggtgtgga aagtccccag gctccccagc aggcagaagt atgcaaagca   2760
tgcatctcaa ttagtcagca accatagtcc cgcccctaac tccgcccatc ccgcccctaa   2820
ctccgcccag ttccgcccat tctccgcccc atggctgact aatttttttt atttatgcag   2880
aggccgaggc cgcctctgcc tctgagctat tccagaagta gtgaggaggc ttttttggag   2940
gcctaggctt ttgcaaaaag ctcccgggag cttgtatatc cattttcgga tctgatcaag   3000
agacaggatg aggatcgttt cgcatgattg aacaagatgg attgcacgca ggttctccgg   3060
ccgcttgggt ggagaggcta ttcggctatg actgggcaca acagacaatc ggctgctctg   3120
atgccgccgt gttccggctg tcagcgcagg ggcgcccggt tctttttgtc aagaccgacc   3180
tgtccggtgc cctgaatgaa ctgcaggacg aggcagcgcg gctatcgtgg ctggccacga   3240
cgggcgttcc ttgcgcagct gtgctcgacg ttgtcactga agcgggaagg gactggctgc   3300
```

```
tattgggcga agtgccgggg caggatctcc tgtcatctca ccttgctcct gccgagaaag   3360
tatccatcat ggctgatgca atgcggcggc tgcatacgct tgatccggct acctgcccat   3420
tcgaccacca agcgaaacat cgcatcgagc gagcacgtac tcggatggaa gccggtcttg   3480
tcgatcagga tgatctggac gaagagcatc aggggctcgc gccagccgaa ctgttcgcca   3540
ggctcaaggc gcgcatgccc gacggcgagg atctcgtcgt gacccatggc gatgcctgct   3600
tgccgaatat catggtggaa aatggccgct tttctggatt catcgactgt ggccggctgg   3660
gtgtggcgga ccgctatcag gacatagcgt tggctacccg tgatattgct gaagagcttg   3720
gcggcgaatg ggctgaccgc ttcctcgtgc tttacggtat cgccgctccc gattcgcagc   3780
gcatcgcctt ctatcgcctt cttgacgagt tcttctgagc gggactctgg ggttcgaaat   3840
gaccgaccaa gcgacgccca acctgccatc acgagatttc gattccaccg ccgccttcta   3900
tgaaaggttg ggcttcggaa tcgtttccg ggacgccggc tggatgatcc tccagcgcgg   3960
ggatctcatg ctggagttct tcgcccaccc caacttgttt attgcagctt ataatggtta   4020
caaataaagc aatagcatca caaatttcac aaataaagca ttttttcac tgcattctag   4080
ttgtggtttg tccaaactca tcaatgtatc ttatcatgtc tgtataccgt cgacctctag   4140
ctagagcttg gcgtaatcat ggtcatagct gtttcctgtg tgaaattgtt atccgctcac   4200
aattccacac aacatacgag ccggaagcat aaagtgtaaa gcctggggtg cctaatgagt   4260
gagctaactc acattaattg cgttgcgctc actgcccgct ttccagtcgg gaaacctgtc   4320
gtgccagctg cattaatgaa tcggccaacg cgcggggaga ggcggtttgc gtattgggcg   4380
ctcttccgct tcctcgctca ctgactcgct gcgctcggtc gttcggctgc ggcgagcggt   4440
atcagctcac tcaaaggcgg taatacggtt atccacagaa tcaggggata acgcaggaaa   4500
gaacatgtga gcaaaaggcc agcaaaaggc caggaaccgt aaaaaggccg cgttgctggc   4560
gtttttccat aggctccgcc ccctgacga gcatcacaaa aatcgacgct caagtcagag   4620
gtggcgaaac ccgacaggac tataaagata ccaggcgttt ccccctggaa gctccctcgt   4680
gcgctctcct gttccgaccc tgccgcttac cggatacctg tccgcctttc tcccttcggg   4740
aagcgtggcg ctttctcaat gctcacgctg taggtatctc agttcggtgt aggtcgttcg   4800
ctccaagctg ggctgtgtgc acgaaccccc cgttcagccc gaccgctgcg ccttatccgg   4860
taactatcgt cttgagtcca acccggtaag acacgactta tcgccactgg cagcagccac   4920
tggtaacagg attagcagag cgaggtatgt aggcggtgct acagagttct tgaagtggtg   4980
gcctaactac ggctacacta aaggacagt atttggtatc tgcgctctgc tgaagccagt   5040
taccttcgga aaagagttg gtagctcttg atccggcaaa caaaccaccg ctggtagcgg   5100
```

```
tggtttttttt gtttgcaagc agcagattac gcgcagaaaa aaaggatctc aagaagatcc    5160
tttgatcttt tctacggggt ctgacgctca gtggaacgaa aactcacgtt aagggatttt    5220
ggtcatgaga ttatcaaaaa ggatcttcac ctagatcctt ttaaattaaa aatgaagttt    5280
taaatcaatc taaagtatat atgagtaaac ttggtctgac agttaccaat gcttaatcag    5340
tgaggcacct atctcagcga tctgtctatt tcgttcatcc atagttgcct gactccccgt    5400
cgtgtagata actacgatac gggagggctt accatctggc cccagtgctg caatgatacc    5460
gcgagaccca cgctcaccgg ctccagattt atcagcaata accagccag ccggaagggc    5520 cgagcgcaga gtggtcctg caactttatc cgcctccatc cagtctatta attgttgccg    5580
ggaagctaga gtaagtagtt cgccagttaa tagtttgcgc aacgttgttg ccattgctac    5640
aggcatcgtg gtgtcacgct cgtcgtttgg tatggcttca ttcagctccg gttcccaacg    5700
atcaaggcga gttacatgat cccccatgtt gtgcaaaaaa gcggttagct ccttcggtcc    5760
tccgatcgtt gtcagaagta agttggccgc agtgttatca ctcatggtta tggcagcact    5820
gcataattct cttactgtca tgccatccgt aagatgcttt tctgtgactg gtgagtactc    5880
aaccaagtca ttctgagaat agtgtatgcg gcgaccgagt tgctcttgcc cggcgtcaat    5940
acgggataat accgcgccac atagcagaac tttaaaagtg ctcatcattg gaaaacgttc    6000
ttcggggcga aaactctcaa ggatcttacc gctgttgaga tccagttcga tgtaacccac    6060
tcgtgcaccc aactgatctt cagcatcttt tactttcacc agcgtttctg ggtgagcaaa    6120
aacaggaagg caaaatgccg caaaaaaggg aataaggcg acacggaaat gttgaatact    6180
catactcttc cttttcaat attattgaag cattatcag ggttattgtc tcatgagcgg    6240
atacatattt gaatgtattt agaaaaataa acaaataggg gttccgcgca catttccccg    6300
aaaagtgcca cctgacgtc                                                 6319
```

<210> 108  
<211> 6319  
<212> DNA  
<213> Artificial sequence

<220>  
<223> LSR zinc finger plasmid

<400> 108
```
gacggatcgg gagatctccc gatcccctat ggtcgactct cagtacaatc tgctctgatg     60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
```

```
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggac tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
gtttaaactt aagctgatcc actagtccag tgtggtggaa ttcgctagcg ccaccatggc    960
ccccaagaag aagaggaagg tgggaatcca tgggtaccg ggcaagaaga agcagcacat   1020
ctgccacatc cagggctgtg gtaaagttta cggccagtcc ggccacctgg ccgccacct   1080
gcgctggcac accggcgaga ggcctttcat gtgtacatgg tcctactgtg gtaaacgctt   1140
caccacctcc ggcgagctgg tgcgccacaa gcgtacccac accggtgaga agaaatttgc   1200
ttgtccggaa tgtccgaagc gcttcatgcg ttccgaccac ctgtcccgtc acatcaagac   1260
ccaccagaac aagaagggtg gatctggtga tggtggccgt cgcggtggcg gttctggcaa   1320
gaagaagcag cacatctgcc acatccaggg ctgtggtaaa gtttacggcg agcgcggcga   1380
cctgacccgc cacctgcgct ggcacaccgg cgagaggcct tcatgtgta catggtccta   1440
ctgtgctaaa cgcttcaccc agcgcgccca cctggagcgc acaagcgta cccacaccgg   1500
tgagaagaaa tttgcttgtc cggaatgtcc gaagcgcttc atgcgctccg acgcctgac   1560
ccgccacatc aagacccacc agaacaagaa gggtggatcc gccccccga ccgatgtcag   1620
cctgggggac gagctccact tagacggcga ggacgtggcg atggcgcatg ccgacgcgct   1680
agacgatttc gatctggaca tgttggggga cggggattcc ccggggccgg gatttacccc   1740
ccacgactcc gcccctacg gcgctctgga tatggccggc ttcgagtttg agcagatgtt   1800
taccgatgcc cttggaattg acgagtacgg tggggcagc gactacaagg acgacgatga   1860
caagtaagct tctcgagtct agagggcccg tttaaacccg ctgatcagcc tcgactgtgc   1920
cttctagttg ccagccatct gttgtttgcc cctcccccgt gccttccttg accctggaag   1980
```

```
gtgccactcc cactgtcctt tcctaataaa atgaggaaat tgcatcgcat tgtctgagta  2040
ggtgtcattc tattctgggg ggtggggtgg ggcaggacag caaggggag gattgggaag   2100
acaatagcag gcatgctggg gatgcggtgg gctctatggc ttctgaggcg gaaagaacca  2160
gctggggctc taggggtat ccccacgcgc cctgtagcgg cgcattaagc gcggcgggtg   2220
tggtggttac gcgcagcgtg accgctacac ttgccagcgc cctagcgccc gctcctttcg  2280
ctttcttccc ttcctttctc gccacgttcg ccggctttcc ccgtcaagct ctaaatcggg  2340
gcatcccttt agggttccga tttagtgctt tacggcacct cgacccaaa aaacttgatt   2400
agggtgatgg ttcacgtagt gggccatcgc cctgatagac ggtttttcgc cctttgacgt  2460
tggagtccac gttctttaat agtggactct tgttccaaac tggaacaaca ctcaaccccta 2520
tctcggtcta ttcttttgat ttataaggga ttttggggat ttcggcctat tggttaaaaa  2580
atgagctgat ttaacaaaaa tttaacgcga attaattctg tggaatgtgt gtcagttagg  2640
gtgtggaaag tccccaggct ccccaggcag gcagaagtat gcaaagcatg catctcaatt  2700
agtcagcaac caggtgtgga aagtccccag gctccccagc aggcagaagt atgcaaagca  2760
tgcatctcaa ttagtcagca accatagtcc cgccctaac tccgccatc ccgccctaa    2820
ctccgcccag ttccgcccat tctccgcccc atggctgact aatttttttt atttatgcag  2880
aggccgaggc cgcctctgcc tctgagctat tccagaagta gtgaggaggc ttttttggag  2940
gcctaggctt ttgcaaaaag ctcccgggag cttgtatatc catttcgga tctgatcaag   3000
agacaggatg aggatcgttt cgcatgattg aacaagatgg attgcacgca ggttctccgg  3060
ccgcttgggt ggagaggcta ttcggctatg actgggcaca acagacaatc ggctgctctg  3120
atgccgccgt gttccggctg tcagcgcagg ggcgcccggt tctttttgtc aagaccgacc  3180
tgtccggtgc cctgaatgaa ctgcaggacg aggcagcgcg gctatcgtgg ctggccacga  3240
cgggcgttcc ttgcgcagct gtgctcgacg ttgtcactga agcgggaagg gactggctgc  3300
tattgggcga agtgccgggg caggatctcc tgtcatctca ccttgctcct gccgagaaag  3360
tatccatcat ggctgatgca atgcggcggc tgcatacgct tgatccggct acctgcccat  3420
tcgaccacca agcgaaacat cgcatcgagc gagcacgtac tcggatggaa gccggtcttg  3480
tcgatcagga tgatctggac gaagagcatc aggggctcgc gccagccgaa ctgttcgcca  3540
ggctcaaggc gcgcatgccc gacggcgagg atctcgtcgt gacccatggc gatgcctgct  3600
tgccgaatat catggtggaa aatggccgct tttctggatt catcgactgt ggccggctgg  3660
gtgtggcgga ccgctatcag gacatagcgt tggctacccg tgatattgct gaagagcttg  3720
```

```
gcggcgaatg ggctgaccgc ttcctcgtgc tttacggtat cgccgctccc gattcgcagc    3780
gcatcgcctt ctatcgcctt cttgacgagt tcttctgagc gggactctgg ggttcgaaat    3840
gaccgaccaa gcgacgccca acctgccatc acgagatttc gattccaccg ccgccttcta    3900
tgaaaggttg ggcttcggaa tcgtttttccg ggacgccggc tggatgatcc tccagcgcgg   3960
ggatctcatg ctggagttct tcgcccaccc caacttgttt attgcagctt ataatggtta    4020
caaataaagc aatagcatca caaatttcac aaataaagca ttttttcac tgcattctag     4080
ttgtggtttg tccaaactca tcaatgtatc ttatcatgtc tgtataccgt cgacctctag    4140
ctagagcttg gcgtaatcat ggtcatagct gtttcctgtg tgaaattgtt atccgctcac    4200
aattccacac aacatacgag ccggaagcat aaagtgtaaa gcctggggtg cctaatgagt    4260
gagctaactc acattaattg cgttgcgctc actgcccgct ttccagtcgg gaaacctgtc    4320
gtgccagctg cattaatgaa tcggccaacg cgcggggaga ggcggtttgc gtattgggcg    4380
ctcttccgct tcctcgctca ctgactcgct gcgctcggtc gttcggctgc ggcgagcggt    4440
atcagctcac tcaaaggcgg taatacggtt atccacagaa tcagggata acgcaggaaa     4500
gaacatgtga gcaaaaggcc agcaaaaggc caggaaccgt aaaaaggccg cgttgctggc    4560
gtttttccat aggctccgcc cccctgacga gcatcacaaa aatcgacgct caagtcagag    4620
gtggcgaaac ccgacaggac tataaagata ccaggcgttt ccccctggaa gctccctcgt    4680
gcgctctcct gttccgaccc tgccgcttac cggatacctg tccgcctttc tcccttcggg    4740
aagcgtggcg ctttctcaat gctcacgctg taggtatctc agttcggtgt aggtcgttcg    4800
ctccaagctg ggctgtgtgc acgaaccccc cgttcagccc gaccgctgcg ccttatccgg    4860
taactatcgt cttgagtcca acccggtaag acacgactta tcgccactgg cagcagccac    4920
tggtaacagg attagcagag cgaggtatgt aggcggtgct acagagttct tgaagtggtg    4980
gcctaactac ggctacacta aaggacagt atttggtatc tgcgctctgc tgaagccagt     5040
taccttcgga aaaagagttg gtagctcttg atccggcaaa caaaccaccg ctggtagcgg    5100
tggtttttt gtttgcaagc agcagattac gcgcagaaaa aaggatctc aagaagatcc      5160
tttgatcttt tctacggggt ctgacgctca gtggaacgaa aactcacgtt aagggatttt    5220
ggtcatgaga ttatcaaaaa ggatcttcac ctagatcctt ttaaattaaa aatgaagttt    5280
taaatcaatc taaagtatat atgagtaaac ttggtctgac agttaccaat gcttaatcag    5340
tgaggcacct atctcagcga tctgtctatt tcgttcatcc atagttgcct gactccccgt    5400
cgtgtagata actacgatac gggagggctt accatctggc cccagtgctg caatgatacc    5460
gcgagaccca cgctcaccgg ctccagattt atcagcaata aaccagccag ccggaagggc    5520
```

```
cgagcgcaga agtggtcctg caactttatc cgcctccatc cagtctatta attgttgccg    5580
ggaagctaga gtaagtagtt cgccagttaa tagtttgcgc aacgttgttg ccattgctac    5640
aggcatcgtg gtgtcacgct cgtcgtttgg tatggcttca ttcagctccg gttcccaacg    5700
atcaaggcga gttacatgat cccccatgtt gtgcaaaaaa gcggttagct ccttcggtcc    5760
tccgatcgtt gtcagaagta agttggccgc agtgttatca ctcatggtta tggcagcact    5820
gcataattct cttactgtca tgccatccgt aagatgcttt tctgtgactg gtgagtactc    5880
aaccaagtca ttctgagaat agtgtatgcg gcgaccgagt tgctcttgcc cggcgtcaat    5940
acgggataat accgcgccac atagcagaac tttaaaagtg ctcatcattg gaaaacgttc    6000
ttcggggcga aaactctcaa ggatcttacc gctgttgaga tccagttcga tgtaacccac    6060
tcgtgcaccc aactgatctt cagcatcttt tactttcacc gcgtttctg ggtgagcaaa    6120 aacaggaagg caaaatgccg caaaaaaggg aataagggcg acacggaaat gttgaatact    6180
catactcttc ctttttcaat attattgaag catttatcag ggttattgtc tcatgagcgg    6240
atacatattt gaatgtattt agaaaaataa acaaataggg gttccgcgca catttccccg    6300
aaaagtgcca cctgacgtc                                                  6319

<210> 109
<211> 6295
<212> DNA
<213> Artificial sequence

<220>
<223> LSR zinc finger plasmid

<400> 109
gacggatcgg gagatctccc gatcccctat ggtcgactct cagtacaatc tgctctgatg    60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggac tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
```

```
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
gtttaaactt aagctgatcc actagtccag tgtggtggaa ttcgctagcg ccaccatggc    960
ccccaagaag aagaggaagg tgggaatcca tggggtaccg ggcaagaaga agcagcacat   1020
ctgccacatc cagggctgtg gtaaagttta cggccgctcc gaccacctgg cccgccacct   1080
gcgctggcac accggcgaga ggcctttcat gtgtacatgg tcctactgtg gtaaacgctt   1140
cacccgctcc gacgagctgc agcgccacaa gcgtacccac accggtgaga agaaatttgc   1200
ttgtccggaa tgtccgaagc gcttcatgcg ctccgacgag cgcaagcgcc acatcaagac   1260
ccaccagaac aagaagggtg gatctggtga tggcaagaag aagcagcaca tctgccacat   1320
ccagggctgt ggtaaagttt acggccgctc cgaccacctg accacccacc tgcgctggca   1380
caccggcgag aggcctttca tgtgtacatg gtcctactgt ggtaaacgct tcacccgctc   1440
cgaccacctg acccgccaca gcgtaccca caccggtgag aagaaatttg cttgtccgga   1500
atgtccgaag cgcttcatgc gctccgacca cctgaccacc cacatcaaga cccaccagaa   1560
caagaaggt ggatccgccc ccccgaccga tgtcagcctg ggggacgagc tccacttaga   1620
cggcgaggac gtggcgatgg cgcatgccga cgcgctagac gatttcgatc tggacatgtt   1680
gggggacggg gattccccgg ggccgggatt taccccccac gactccgccc cctacggcgc   1740
tctggatatg gccggcttcg agtttgagca gatgtttacc gatgcccttg gaattgacga   1800
gtacggtggg ggcagcgact acaaggacga cgatgacaag taagcttctc gagtctagag   1860
ggcccgttta acccgctga tcagcctcga ctgtgccttc tagttgccag ccatctgttg   1920
tttgccctc ccccgtgcct tccttgaccc tggaaggtgc cactcccact gtcctttcct   1980
aataaaatga ggaaattgca tcgcattgtc tgagtaggtg tcattctatt ctggggggtg   2040
gggtggggca ggacagcaag ggggaggatt gggaagacaa tagcaggcat gctggggatg   2100
cggtgggctc tatggcttct gaggcggaaa gaaccagctg gggctctagg gggtatcccc   2160
acgcgcctg tagcggcgca ttaagcgcgg cgggtgtggt ggttacgcgc agcgtgaccg   2220
ctacacttgc cagcgcccta gcgcccgctc ctttcgcttt cttcccttcc tttctcgcca   2280
cgttcgccgg ctttccccgt caagctctaa atcggggcat ccctttaggg ttccgattta   2340
gtgctttacg gcacctcgac cccaaaaaac ttgattaggg tgatggttca cgtagtgggc   2400
```

| | | | | | |
|---|---|---|---|---|---|
| catcgccctg | atagacggtt | tttcgccctt | tgacgttgga | gtccacgttc | tttaatagtg | 2460
| gactcttgtt | ccaaactgga | acaacactca | acctatctc | ggtctattct | tttgatttat | 2520
| aagggatttt | ggggatttcg | gcctattggt | taaaaaatga | gctgatttaa | caaaaattta | 2580
| acgcgaatta | attctgtgga | atgtgtgtca | gttagggtgt | ggaaagtccc | caggctcccc | 2640
| aggcaggcag | aagtatgcaa | agcatgcatc | tcaattagtc | agcaaccagg | tgtggaaagt | 2700
| ccccaggctc | cccagcaggc | agaagtatgc | aaagcatgca | tctcaattag | tcagcaacca | 2760
| tagtcccgcc | cctaactccg | cccatcccgc | ccctaactcc | gcccagttcc | gcccattctc | 2820
| cgccccatgg | ctgactaatt | tttttattt | atgcagaggc | cgaggccgcc | tctgcctctg | 2880
| agctattcca | gaagtagtga | ggaggctttt | ttggaggcct | aggcttttgc | aaaaagctcc | 2940
| cgggagcttg | tatatccatt | ttcggatctg | atcaagagac | aggatgagga | tcgtttcgca | 3000
| tgattgaaca | agatggattg | cacgcaggtt | ctccggccgc | ttgggtggag | aggctattcg | 3060
| gctatgactg | ggcacaacag | acaatcggct | gctctgatgc | cgccgtgttc | cggctgtcag | 3120
| cgcaggggcg | cccggttctt | tttgtcaaga | ccgacctgtc | cggtgccctg | aatgaactgc | 3180
| aggacgaggc | agcgcggcta | tcgtggctgg | ccacgacggg | cgttccttgc | gcagctgtgc | 3240
| tcgacgttgt | cactgaagcg | ggaagggact | ggctgctatt | gggcgaagtg | ccggggcagg | 3300
| atctcctgtc | atctcacctt | gctcctgccg | agaaagtatc | catcatggct | gatgcaatgc | 3360
| ggcggctgca | tacgcttgat | ccggctacct | gcccattcga | ccaccaagcg | aaacatcgca | 3420
| tcgagcgagc | acgtactcgg | atggaagccg | gtcttgtcga | tcaggatgat | ctggacgaag | 3480
| agcatcaggg | gctcgcgcca | gccgaactgt | tcgccaggct | caaggcgcgc | atgcccgacg | 3540
| gcgaggatct | cgtcgtgacc | catggcgatg | cctgcttgcc | gaatatcatg | gtggaaaatg | 3600
| gccgcttttc | tggattcatc | gactgtggcc | ggctgggtgt | ggcggaccgc | tatcaggaca | 3660
| tagcgttggc | tacccgtgat | attgctgaag | agcttggcgg | cgaatgggct | gaccgcttcc | 3720
| tcgtgcttta | cggtatcgcc | gctcccgatt | cgcagcgcat | cgccttctat | cgccttcttg | 3780
| acgagttctt | ctgagcggga | ctctggggtt | cgaaatgacc | gaccaagcga | cgcccaacct | 3840
| gccatcacga | gatttcgatt | ccaccgccgc | cttctatgaa | aggttgggct | tcggaatcgt | 3900
| tttccgggac | gccggctgga | tgatcctcca | gcgcggggat | ctcatgctgg | agttcttcgc | 3960
| ccaccccaac | ttgtttattg | cagcttataa | tggttacaaa | taaagcaata | gcatcacaaa | 4020
| tttcacaaat | aaagcatttt | tttcactgca | ttctagttgt | ggtttgtcca | aactcatcaa | 4080
| tgtatcttat | catgtctgta | taccgtcgac | ctctagctag | agcttggcgt | aatcatggtc | 4140

```
atagctgttt cctgtgtgaa attgttatcc gctcacaatt ccacacaaca tacgagccgg  4200
aagcataaag tgtaaagcct ggggtgccta atgagtgagc taactcacat taattgcgtt  4260
gcgctcactg cccgctttcc agtcgggaaa cctgtcgtgc cagctgcatt aatgaatcgg  4320
ccaacgcgcg gggagaggcg gtttgcgtat tgggcgctct tccgcttcct cgctcactga  4380
ctcgctgcgc tcggtcgttc ggctgcggcg agcggtatca gctcactcaa aggcggtaat  4440
acggttatcc acagaatcag gggataacgc aggaaagaac atgtgagcaa aaggccagca  4500
aaaggccagg aaccgtaaaa aggccgcgtt gctggcgttt ttccataggc tccgcccccc  4560
tgacgagcat cacaaaaatc gacgctcaag tcagaggtgg cgaaacccga caggactata  4620
aagataccag gcgtttcccc ctggaagctc cctcgtgcgc tctcctgttc cgaccctgcc  4680
gcttaccgga tacctgtccg cctttctccc ttcgggaagc gtggcgcttt ctcaatgctc  4740
acgctgtagg tatctcagtt cggtgtaggt cgttcgctcc aagctgggct gtgtgcacga  4800
accccccgtt cagcccgacc gctgcgcctt atccggtaac tatcgtcttg agtccaaccc  4860
ggtaagacac gacttatcgc cactggcagc agccactggt aacaggatta gcagagcgag  4920
gtatgtaggc ggtgctacag agttcttgaa gtggtggcct aactacggct acactagaag  4980
gacagtattt ggtatctgcg ctctgctgaa gccagttacc ttcggaaaaa gagttggtag  5040
ctcttgatcc ggcaaacaaa ccaccgctgg tagcggtggt ttttttgttt gcaagcagca  5100
gattacgcgc agaaaaaaag gatctcaaga agatcctttg atcttttcta cggggtctga  5160
cgctcagtgg aacgaaaact cacgttaagg gattttggtc atgagattat caaaaaggat  5220
cttcacctag atcctttaa attaaaaatg aagttttaaa tcaatctaaa gtatatatga  5280
gtaaacttgg tctgacagtt accaatgctt aatcagtgag gcacctatct cagcgatctg  5340
tctatttcgt tcatccatag ttgcctgact ccccgtcgtg tagataacta cgatacggga  5400
gggcttacca tctggcccca gtgctgcaat gataccgcga gacccacgct caccggctcc  5460
agatttatca gcaataaacc agccagccgg aagggccgag cgcagaagtg gtcctgcaac  5520
tttatccgcc tccatccagt ctattaattg ttgccgggaa gctagagtaa gtagttcgcc  5580
agttaatagt ttgcgcaacg ttgttgccat tgctacaggc atcgtggtgt cacgctcgtc  5640
gtttggtatg gcttcattca gctccggttc ccaacgatca aggcgagtta catgatcccc  5700
catgttgtgc aaaaaagcgg ttagctcctt cggtcctccg atcgttgtca gaagtaagtt  5760
ggccgcagtg ttatcactca tggttatggc agcactgcat aattctctta ctgtcatgcc  5820
atccgtaaga tgcttttctg tgactggtga gtactcaacc aagtcattct gagaatagtg  5880
tatgcggcga ccgagttgct cttgcccggc gtcaatacgg gataataccg cgccacatag  5940
```

| | | | | | |
|---|---|---|---|---|---|
| cagaactttta | aaagtgctca | tcattggaaa | acgttcttcg | gggcgaaaac | tctcaaggat | 6000 |
| cttaccgctg | ttgagatcca | gttcgatgta | acccactcgt | gcacccaact | gatcttcagc | 6060 |
| atctttact | ttcaccagcg | tttctgggtg | agcaaaaaca | ggaaggcaaa | atgccgcaaa | 6120 |
| aaagggaata | agggcgacac | ggaaatgttg | aatactcata | ctcttccttt | ttcaatatta | 6180 |
| ttgaagcatt | tatcagggtt | attgtctcat | gagcggatac | atatttgaat | gtatttagaa | 6240 |
| aaataaacaa | atagggggttc | cgcgcacatt | tccccgaaaa | gtgccacctg | acgtc | 6295 |

<210> 110
<211> 6319
<212> DNA
<213> Artificial sequence

<220>
<223> LSR zinc finger plasmid

<400> 110
| | | | | | |
|---|---|---|---|---|---|
| gacggatcgg | gagatctccc | gatcccctat | ggtcgactct | cagtacaatc | tgctctgatg | 60 |
| ccgcatagtt | aagccagtat | ctgctccctg | cttgtgtgtt | ggaggtcgct | gagtagtgcg | 120 |
| cgagcaaaat | ttaagctaca | acaaggcaag | gcttgaccga | caattgcatg | aagaatctgc | 180 |
| ttagggttag | gcgttttgcg | ctgcttcgcg | atgtacgggc | cagatatacg | cgttgacatt | 240 |
| gattattgac | tagttattaa | tagtaatcaa | ttacggggtc | attagttcat | agcccatata | 300 |
| tggagttccg | cgttacataa | cttacggtaa | atggcccgcc | tggctgaccg | cccaacgacc | 360 |
| cccgcccatt | gacgtcaata | atgacgtatg | ttcccatagt | aacgccaata | gggactttcc | 420 |
| attgacgtca | atgggtggac | tatttacggt | aaactgccca | cttggcagta | catcaagtgt | 480 |
| atcatatgcc | aagtacgccc | cctattgacg | tcaatgacgg | taaatggccc | gcctggcatt | 540 |
| atgcccagta | catgacctta | tgggactttc | ctacttggca | gtacatctac | gtattagtca | 600 |
| tcgctattac | catggtgatg | cggttttggc | agtacatcaa | tgggcgtgga | tagcggtttg | 660 |
| actcacgggg | atttccaagt | ctccacccca | ttgacgtcaa | tgggagtttg | ttttggcacc | 720 |
| aaaatcaacg | ggactttcca | aaatgtcgta | acaactccgc | cccattgacg | caaatgggcg | 780 |
| gtaggcgtgt | acggtgggag | gtctatataa | gcagagctct | ctggctaact | agagaaccca | 840 |
| ctgcttactg | gcttatcgaa | attaatacga | ctcactatag | ggagacccaa | gctggctagc | 900 |
| gtttaaactt | aagctgatcc | actagtccag | tgtggtggaa | ttcgctagcg | ccaccatggc | 960 |
| ccccaagaag | aagaggaagg | tgggaatcca | tgggtaccg | ggcaagaaga | agcagcacat | 1020 |
| ctgccacatc | cagggctgtg | gtaaagttta | cggccagtcc | ggcgccctga | cccgccacct | 1080 |

```
gcgctggcac accggcgaga ggcctttcat gtgtacatgg tcctactgtg gtaaacgctt    1140
caccegctcc gaccacctga cccgccacaa gcgtacccac accggtgaga agaaatttgc    1200
ttgtccggaa tgtccgaagc gcttcatgcg ctccgacaac ctgcgcgagc acaacaagac    1260
ccaccagaac aagaagggtg gatctggtga tggtggccgt cgcggtggcg gttctggcaa    1320
gaagaagcag cacatctgcc acatccaggg ctgtggtaaa gtttacggcc gctcctccgc    1380
cctgacccgc cacctgcgct ggcacaccgg cgagaggcct ttcatgtgta catggtccta    1440
ctgtggtaaa cgcttcaccc agcgcgccca cctggagcgc cacaagcgta cccacaccgg    1500
tgagaagaaa tttgcttgtc cggaatgtcc gaagcgcttc atgcgctccg acaccctgcg    1560
cgagcacatc aagacccacc agaacaagaa gggtggatcc gccccccga ccgatgtcag    1620
cctgggggac gagctccact agacggcga ggacgtggcg atggcgcatg ccgacgcgct    1680
agacgatttc gatctggaca tgttggggga cggggattcc ccggggccgg gatttacccc    1740
ccacgactcc gcccctacg gcgctctgga tatggccggc ttcgagtttg agcagatgtt    1800
taccgatgcc cttggaattg acgagtacgg tgggggcagc gactacaagg acgacgatga    1860
caagtaagct tctcgagtct agagggcccg tttaaacccg ctgatcagcc tcgactgtgc    1920
cttctagttg ccagccatct gttgtttgcc cctcccccgt gccttccttg accctggaag    1980
gtgccactcc cactgtcctt tcctaataaa atgaggaaat tgcatcgcat tgtctgagta    2040
ggtgtcattc tattctgggg ggtggggtgg ggcaggacag caaggggga gattgggaag    2100
acaatagcag gcatgctggg gatgcggtgg gctctatggc ttctgaggcg gaaagaacca    2160
gctggggctc taggggtat ccccacgcgc cctgtagcgg cgcattaagc gcggcgggtg    2220
tggtggttac gcgcagcgtg accgctacac ttgccagcgc cctagcgccc gctcctttcg    2280
ctttcttccc ttcctttctc gccacgttcg ccggctttcc ccgtcaagct ctaaatcggg    2340
gcatcccttt agggttccga tttagtgctt tacggcacct cgaccccaaa aaacttgatt    2400
agggtgatgg ttcacgtagt gggccatcgc cctgatagac ggttttttcgc ccttgacgt    2460
tggagtccac gttctttaat agtggactct tgttccaaac tggaacaaca ctcaaccctat    2520
tctcggtcta ttcttttgat ttataaggga ttttggggat ttcggcctat tggttaaaaaa    2580
atgagctgat ttaacaaaaa tttaacgcga attaattctg tggaatgtgt gtcagttagg    2640
gtgtggaaag tccccaggct ccccaggcag gcagaagtat gcaaagcatg catctcaatt    2700
agtcagcaac caggtgtgga aagtccccag gctccccagc aggcagaagt atgcaaagca    2760
tgcatctcaa ttagtcagca accatagtcc cgcccctaac tccgcccatc ccgcccctaa    2820
ctccgcccag ttccgcccat tctccgcccc atggctgact aattttttttt atttatgcag    2880
```

```
aggccgaggc cgcctctgcc tctgagctat tccagaagta gtgaggaggc tttttggag    2940 gcctaggctt ttgcaaaaag ctcccgggag cttgtatatc catttttcgga tctgatcaag  3000 agacaggatg aggatcgttt cgcatgattg aacaagatgg attgcacgca ggttctccgg   3060
ccgcttgggt ggagaggcta ttcggctatg actgggcaca acagacaatc ggctgctctg   3120
atgccgccgt gttccggctg tcagcgcagg ggcgcccggt tctttttgtc aagaccgacc   3180
tgtccggtgc cctgaatgaa ctgcaggacg aggcagcgcg gctatcgtgg ctggccacga   3240
cgggcgttcc ttgcgcagct gtgctcgacg ttgtcactga agcgggaagg gactggctgc   3300
tattgggcga agtgccgggg caggatctcc tgtcatctca ccttgctcct gccgagaaag   3360
tatccatcat ggctgatgca atgcggcggc tgcatacgct tgatccggct acctgcccat   3420
tcgaccacca agcgaaacat cgcatcgagc gagcacgtac tcggatggaa gccggtcttg   3480
tcgatcagga tgatctggac gaagagcatc aggggctcgc gccagccgaa ctgttcgcca   3540
ggctcaaggc gcgcatgccc gacggcgagg atctcgtcgt gacccatggc gatgcctgct   3600
tgccgaatat catggtggaa aatggccgct tttctggatt catcgactgt ggccggctgg   3660
gtgtggcgga ccgctatcag gacatagcgt tggctacccg tgatattgct gaagagcttg   3720
gcggcgaatg ggctgaccgc ttcctcgtgc tttacggtat cgccgctccc gattcgcagc   3780
gcatcgcctt ctatcgcctt cttgacgagt tcttctgagc gggactctgg ggttcgaaat   3840
gaccgaccaa gcgacgccca acctgccatc acgagatttc gattccaccg ccgccttcta   3900
tgaaaggttg ggcttcggaa tcgttttccg gacgccggc tggatgatcc tccagcgcgg   3960
ggatctcatg ctggagttct tcgcccaccc caacttgttt attgcagctt ataatggtta   4020
caaataaagc aatagcatca caaatttcac aaataaagca ttttttcac tgcattctag   4080 ttgtggtttg tccaaactca tcaatgtatc ttatcatgtc tgtataccgt cgacctctag   4140
ctagagcttg gcgtaatcat ggtcatagct gtttcctgtg tgaaattgtt atccgctcac   4200
aattccacac aacatacgag ccggaagcat aaagtgtaaa gcctggggtg cctaatgagt   4260
gagctaactc acattaattg cgttgcgctc actgcccgct ttccagtcgg gaaacctgtc   4320
gtgccagctg cattaatgaa tcggccaacg cgcggggaga ggcggtttgc gtattgggcg   4380
ctcttccgct tcctcgctca ctgactcgct gcgctcggtc gttcggctgc ggcgagcggt   4440
atcagctcac tcaaaggcgg taatacggtt atccacagaa tcaggggata acgcaggaaa   4500
gaacatgtga gcaaaaggcc agcaaaaggc caggaaccgt aaaaaggccg cgttgctggc   4560
gtttttccat aggctccgcc ccctgacga gcatcacaaa aatcgacgct caagtcagag   4620
```

```
gtggcgaaac ccgacaggac tataaagata ccaggcgttt ccccctggaa gctccctcgt    4680
gcgctctcct gttccgaccc tgccgcttac cggatacctg tccgcctttc tcccttcggg    4740
aagcgtggcg ctttctcaat gctcacgctg taggtatctc agttcggtgt aggtcgttcg    4800
ctccaagctg ggctgtgtgc acgaaccccc cgttcagccc gaccgctgcg ccttatccgg    4860
taactatcgt cttgagtcca acccggtaag acacgactta tcgccactgg cagcagccac    4920
tggtaacagg attagcagag cgaggtatgt aggcggtgct acagagttct tgaagtggtg    4980
gcctaactac ggctacacta aaggacagt atttggtatc tgcgctctgc tgaagccagt    5040
taccttcgga aaaagagttg gtagctcttg atccggcaaa caaaccaccg ctggtagcgg    5100
tggttttttt gtttgcaagc agcagattac gcgcagaaaa aaaggatctc aagaagatcc    5160
tttgatcttt tctacggggt ctgacgctca gtggaacgaa aactcacgtt aagggatttt    5220
ggtcatgaga ttatcaaaaa ggatcttcac ctagatcctt ttaaattaaa aatgaagttt    5280
taaatcaatc taaagtatat atgagtaaac ttggtctgac agttaccaat gcttaatcag    5340
tgaggcacct atctcagcga tctgtctatt tcgttcatcc atagttgcct gactccccgt    5400
cgtgtagata actacgatac gggagggctt accatctggc cccagtgctg caatgatacc    5460
gcgagaccca cgctcaccgg ctccagattt atcagcaata aaccagccag ccggaagggc    5520
cgagcgcaga agtggtcctg caactttatc cgcctccatc cagtctatta attgttgccg    5580
ggaagctaga gtaagtagtt cgccagttaa tagtttgcgc aacgttgttg ccattgctac    5640
aggcatcgtg gtgtcacgct cgtcgtttgg tatggcttca ttcagctccg gttcccaacg    5700
atcaaggcga gttacatgat cccccatgtt gtgcaaaaaa gcggttagct ccttcggtcc    5760
tccgatcgtt gtcagaagta agttggccgc agtgttatca ctcatggtta tggcagcact    5820
gcataattct cttactgtca tgccatccgt aagatgcttt tctgtgactg gtgagtactc    5880
aaccaagtca ttctgagaat agtgtatgcg gcgaccgagt tgctcttgcc cggcgtcaat    5940
acgggataat accgcgccac atagcagaac tttaaaagtg ctcatcattg gaaaacgttc    6000
ttcggggcga aaactctcaa ggatcttacc gctgttgaga tccagttcga tgtaacccac    6060
tcgtgcaccc aactgatctt cagcatcttt tactttcacc agcgtttctg ggtgagcaaa    6120
aacaggaagg caaaatgccg caaaaaaggg aataagggcg acacggaaat gttgaatact    6180
catactcttc ctttttcaat attattgaag cattatcag ggttattgtc tcatgagcgg    6240
atacatattt gaatgtattt agaaaaataa acaaataggg gttccgcgca catttccccg    6300
aaaagtgcca cctgacgtc                                                 6319
```

<210> 111
<211> 6295
<212> DNA
<213> Artificial sequence

<220>
<223> LSR zinc finger plasmid

<400> 111
| | | | | | |
|---|---|---|---|---|---|
| gacggatcgg | gagatctccc | gatcccctat | ggtcgactct | cagtacaatc | tgctctgatg | 60 |
| ccgcatagtt | aagccagtat | ctgctccctg | cttgtgtgtt | ggaggtcgct | gagtagtgcg | 120 |
| cgagcaaaat | ttaagctaca | acaaggcaag | gcttgaccga | caattgcatg | aagaatctgc | 180 |
| ttagggttag | gcgttttgcg | ctgcttcgcg | atgtacgggc | cagatatacg | cgttgacatt | 240 |
| gattattgac | tagttattaa | tagtaatcaa | ttacggggtc | attagttcat | agcccatata | 300 |
| tggagttccg | cgttacataa | cttacggtaa | atggcccgcc | tggctgaccg | cccaacgacc | 360 |
| cccgcccatt | gacgtcaata | atgacgtatg | ttcccatagt | aacgccaata | gggactttcc | 420 |
| attgacgtca | atgggtggac | tatttacggt | aaactgccca | cttggcagta | catcaagtgt | 480 |
| atcatatgcc | aagtacgccc | cctattgacg | tcaatgacgg | taaatggccc | gcctggcatt | 540 |
| atgcccagta | catgacctta | tgggactttc | ctacttggca | gtacatctac | gtattagtca | 600 |
| tcgctattac | catggtgatg | cggttttggc | agtacatcaa | tgggcgtgga | tagcggtttg | 660 |
| actcacgggg | atttccaagt | ctccacccca | ttgacgtcaa | tgggagtttg | ttttggcacc | 720 |
| aaaatcaacg | ggactttcca | aaatgtcgta | acaactccgc | cccattgacg | caaatgggcg | 780 |
| gtaggcgtgt | acggtgggag | gtctatataa | gcagagctct | ctggctaact | agagaaccca | 840 |
| ctgcttactg | gcttatcgaa | attaatacga | ctcactatag | ggagacccaa | gctggctagc | 900 |
| gtttaaactt | aagctgatcc | actagtccag | tgtggtggaa | ttcgctagcg | ccaccatggc | 960 |
| ccccaagaag | aagaggaagg | tgggaatcca | tggggtaccg | ggcaagaaga | agcagcacat | 1020 |
| ctgccacatc | cagggctgtg | gtaaagttta | cggcgagcgc | ggcgacctga | ccgccacct | 1080 |
| gcgctggcac | accggcgaga | ggcctttcat | gtgtacatgg | tcctactgtg | gtaaacgctt | 1140 |
| caccgacccg | ggcgccctgg | tgcgccacaa | gcgtacccac | accggtgaga | agaaatttgc | 1200 |
| ttgtccggaa | tgtccgaagc | gcttcatgcg | ctccgacaac | ctgacccagc | acatcaagac | 1260 |
| ccaccagaac | aagaagggtg | gatctggtga | tggcaagaag | aagcagcaca | tctgccacat | 1320 |
| ccagggctgt | ggtaaagttt | acggccagtc | cggcaccctg | acccgccacc | tgcgctggca | 1380 |
| caccggcgag | aggcctttca | tgtgtacatg | gtcctactgt | ggtaaacgct | tcacccagtc | 1440 |
| ctccgacctg | cagcgccaca | agcgtaccca | caccggtgag | aagaaatttg | cttgtccgga | 1500 |

```
atgtccgaag cgcttcatgc gctccgacgc cctggcccgc cacatcaaga cccaccagaa  1560
caagaagggt ggatccgccc ccccgaccga tgtcagcctg ggggacgagc tccacttaga  1620
cggcgaggac gtggcgatgg cgcatgccga cgcgctagac gatttcgatc tggacatgtt  1680
gggggacggg gattccccgg ggccgggatt taccccccac gactccgccc cctacggcgc  1740
tctggatatg gccggcttcg agtttgagca gatgtttacc gatgcccttg gaattgacga  1800
gtacggtggg ggcagcgact acaaggacga cgatgacaag taagcttctc gagtctagag  1860
ggcccgttta aacccgctga tcagcctcga ctgtgccttc tagttgccag ccatctgttg  1920
tttgcccctc ccccgtgcct tccttgaccc tggaaggtgc cactcccact gtcctttcct  1980
aataaaatga ggaaattgca tcgcattgtc tgagtaggtg tcattctatt ctggggggtg  2040
gggtggggca ggacagcaag ggggaggatt gggaagacaa tagcaggcat gctggggatg  2100
cggtgggctc tatggcttct gaggcggaaa gaaccagctg gggctctagg gggtatcccc  2160
acgcgcctg tagcggcgca ttaagcgcgg cgggtgtggt ggttacgcgc agcgtgaccg  2220
ctacacttgc cagcgcccta gcgcccgctc ctttcgcttt cttcccttcc tttctcgcca  2280
cgttcgccgg ctttccccgt caagctctaa atcggggcat ccctttaggg ttccgattta  2340
gtgctttacg gcacctcgac cccaaaaaac ttgattaggg tgatggttca cgtagtgggc  2400
catcgccctg atagacggtt tttcgccctt tgacgttgga gtccacgttc tttaatagtg  2460
gactcttgtt ccaaactgga acaacactca accctatctc ggtctattct tttgatttat  2520
aagggatttt ggggatttcg gcctattggt taaaaaatga gctgatttaa caaaaattta  2580
acgcgaatta attctgtgga atgtgtgtca gttagggtgt ggaaagtccc caggctcccc  2640
aggcaggcag aagtatgcaa agcatgcatc tcaattagtc agcaaccagg tgtggaaagt  2700
ccccaggctc cccagcaggc agaagtatgc aaagcatgca tctcaattag tcagcaacca  2760
tagtcccgcc cctaactccg cccatccgc ccctaactcc gcccagttcc gccattctc   2820
cgccccatgg ctgactaatt ttttttattt atgcagaggc cgaggccgcc tctgcctctg  2880
agctattcca gaagtagtga ggaggctttt ttggaggcct aggcttttgc aaaaagctcc  2940
cgggagcttg tatatccatt ttcggatctg atcaagagac aggatgagga tcgtttcgca  3000
tgattgaaca agatggattg cacgcaggtt ctccggccgc ttgggtggag aggctattcg  3060
gctatgactg ggcacaacag acaatcggct gctctgatgc cgccgtgttc cggctgtcag  3120
cgcaggggcg cccggttctt tttgtcaaga ccgacctgtc cggtgccctg aatgaactgc  3180
aggacgaggc agcgcggcta tcgtggctgg ccacgacggg cgttccttgc gcagctgtgc  3240
tcgacgttgt cactgaagcg ggaagggact ggctgctatt gggcgaagtg ccggggcagg  3300
```

```
atctcctgtc atctcacctt gctcctgccg agaaagtatc catcatggct gatgcaatgc    3360
ggcggctgca tacgcttgat ccggctacct gcccattcga ccaccaagcg aaacatcgca    3420
tcgagcgagc acgtactcgg atggaagccg gtcttgtcga tcaggatgat ctggacgaag    3480
agcatcaggg gctcgcgcca gccgaactgt tcgccaggct caaggcgcgc atgcccgacg    3540
gcgaggatct cgtcgtgacc catggcgatg cctgcttgcc gaatatcatg gtggaaaatg    3600
gccgcttttc tggattcatc gactgtggcc ggctgggtgt ggcggaccgc tatcaggaca    3660
tagcgttggc tacccgtgat attgctgaag agcttggcgg cgaatgggct gaccgcttcc    3720
tcgtgcttta cggtatcgcc gctcccgatt cgcagcgcat cgccttctat cgccttcttg    3780
acgagttctt ctgagcggga ctctggggtt cgaaatgacc gaccaagcga cgcccaacct    3840
gccatcacga gattcgatt ccaccgccgc cttctatgaa aggttgggct tcggaatcgt    3900
tttccgggac gccggctgga tgatcctcca gcgcggggat ctcatgctgg agttcttcgc    3960
ccacccaac ttgtttattg cagcttataa tggttacaaa taaagcaata gcatcacaaa    4020
tttcacaaat aaagcatttt tttcactgca ttctagttgt ggtttgtcca aactcatcaa    4080
tgtatcttat catgtctgta taccgtcgac ctctagctag agcttggcgt aatcatggtc    4140
atagctgttt cctgtgtgaa attgttatcc gctcacaatt ccacacaaca tacgagccgg    4200
aagcataaag tgtaaagcct ggggtgccta atgagtgagc taactcacat taattgcgtt    4260
gcgctcactg cccgctttcc agtcgggaaa cctgtcgtgc cagctgcatt aatgaatcgg    4320
ccaacgcgcg gggagaggcg gtttgcgtat tgggcgctct tccgcttcct cgctcactga    4380
ctcgctgcgc tcggtcgttc ggctgcggcg agcggtatca gctcactcaa aggcggtaat    4440
acggttatcc acagaatcag gggataacgc aggaaagaac atgtgagcaa aaggccagca    4500
aaaggccagg aaccgtaaaa aggccgcgtt gctggcgttt ttccataggc tccgcccccc    4560
tgacgagcat cacaaaaatc gacgctcaag tcagaggtgg cgaaacccga caggactata    4620
aagataccag gcgtttcccc ctggaagctc cctcgtgcgc tctcctgttc cgaccctgcc    4680
gcttaccgga tacctgtccg cctttctccc ttcgggaagc gtggcgcttt ctcaatgctc    4740
acgctgtagg tatctcagtt cggtgtaggt cgttcgctcc aagctgggct gtgtgcacga    4800
accccccgtt cagcccgacc gctgcgcctt atccggtaac tatcgtcttg agtccaaccc    4860
ggtaagacac gacttatcgc cactggcagc agccactggt aacaggatta gcagagcgag    4920
gtatgtaggc ggtgctacag agttcttgaa gtggtggcct aactacggct acactagaag    4980
gacagtattt ggtatctgcg ctctgctgaa gccagttacc ttcggaaaaa gagttggtag    5040
```

```
ctcttgatcc ggcaaacaaa ccaccgctgg tagcggtggt ttttttgttt gcaagcagca    5100
gattacgcgc agaaaaaaag gatctcaaga agatcctttg atctttctta cggggtctga    5160
cgctcagtgg aacgaaaact cacgttaagg gattttggtc atgagattat caaaaaggat    5220
cttcacctag atccttttaa attaaaaatg aagttttaaa tcaatctaaa gtatatatga    5280
gtaaacttgg tctgacagtt accaatgctt aatcagtgag gcacctatct cagcgatctg    5340
tctatttcgt tcatccatag ttgcctgact ccccgtcgtg tagataacta cgatacggga    5400
gggcttacca tctggcccca gtgctgcaat gataccgcga gacccacgct caccggctcc    5460
agatttatca gcaataaacc agccagccgg aagggccgag cgcagaagtg gtcctgcaac    5520
tttatccgcc tccatccagt ctattaattg ttgccgggaa gctagagtaa gtagttcgcc    5580
agttaatagt ttgcgcaacg ttgttgccat tgctacaggc atcgtggtgt cacgctcgtc    5640
gtttggtatg gcttcattca gctccggttc ccaacgatca aggcgagtta catgatcccc    5700
catgttgtgc aaaaaagcgg ttagctcctt cggtcctccg atcgttgtca gaagtaagtt    5760
ggccgcagtg ttatcactca tggttatggc agcactgcat aattctctta ctgtcatgcc    5820
atccgtaaga tgcttttctg tgactggtga gtactcaacc aagtcattct gagaatagtg    5880
tatgcggcga ccgagttgct cttgcccggc gtcaatacgg gataataccg cgccacatag    5940
cagaacttta aaagtgctca tcattggaaa acgttcttcg ggcgaaaac tctcaaggat     6000
cttaccgctg ttgagatcca gttcgatgta acccactcgt gcacccaact gatcttcagc    6060
atcttttact ttcaccagcg tttctgggtg agcaaaaaca ggaaggcaaa atgccgcaaa    6120
aaagggaata agggcgacac ggaaatgttg aatactcata ctcttccttt ttcaatatta    6180
ttgaagcatt tatcagggtt attgtctcat gagcggatac atatttgaat gtatttagaa    6240
aaataaacaa ataggggttc cgcgcacatt tccccgaaaa gtgccacctg acgtc         6295
```

<210> 112  
<211> 9  
<212> PRT  
<213> Mus musculus

<400> 112

Cys Pro Asp Arg Ala Ser Ala Ile Gln  
1               5

<210> 113  
<211> 14  
<212> PRT  
<213> Mus musculus

<400> 113

Glu Glu Gly His Tyr Pro Pro Ala Pro Pro Tyr Ser Glu Thr
1               5                   10

<210> 114
<211> 21
<212> DNA
<213> Artificial sequence

<220>
<223> GAPDH forward primer

<400> 114
aacgacccct tcattgacct c                                    21

<210> 115
<211> 19
<212> DNA
<213> Artificial sequence

<220>
<223> GAPDH reverse primer

<400> 115
cttcccattc tcggccttg                                       19

<210> 116
<211> 25
<212> DNA
<213> Artificial sequence

<220>
<223> GAPDH probe

<400> 116
actcacggca aattcaacgg cacag                                25

<210> 117
<211> 21
<212> DNA
<213> Artificial sequence

<220>
<223> LSR complete forward primer

<400> 117
ggcaggagaa tcaccatcac a                                    21

<210> 118
<211> 20
<212> DNA
<213> Artificial sequence

```
<220>
<223>  LSR complete reverse primer

<400>  118
gatcttgggc tgagaccacg                                                    20

<210>  119
<211>  24
<212>  DNA
<213>  Artificial sequence

<220>
<223>  LSR complete probe

<400>  119
tgctggcctg accttcgagc agac                                               24

<210>  120
<211>  20
<212>  DNA
<213>  Artificial sequence

<220>
<223>  LSR alpha forward primer

<400>  120
gcccttggaa gattggctct                                                    20

<210>  121
<211>  20
<212>  DNA
<213>  Artificial sequence

<220>
<223>  LSR alpha reverse primer

<400>  121
atgcttggca cacctgaggt                                                    20

<210>  122
<211>  23
<212>  DNA
<213>  Artificial sequence

<220>
<223>  LSR alpha probe

<400>  122
ccagtgctgt ccccacacct gct                                                23

<210>  123
<211>  20
<212>  DNA
<213>  Artificial sequence
```

```
<220>
<223>  LSR alpha' forward primer

<400>  123
accagggcag gagaatcacc                                              20

<210>  124
<211>  21
<212>  DNA
<213>  Artificial sequence

<220>
<223>  LSR alpha' reverse primer

<400>  124
ggaggaagaa gaggaggctt g                                            21

<210>  125
<211>  29
<212>  DNA
<213>  Artificial sequence

<220>
<223>  LSR alpha' probe

<400>  125
agctcattgt ccttgattgg ctctttgtg                                    29

<210>  126
<211>  22
<212>  DNA
<213>  Artificial sequence

<220>
<223>  LSR beta forward primer

<400>  126
ttgtccttgt ttatgctgct gg                                           22

<210>  127
<211>  24
<212>  DNA
<213>  Artificial sequence

<220>
<223>  LSR beta reverse primer

<400>  127
caggagagag gtgggtatag atgc                                         24

<210>  128
<211>  23
<212>  DNA
```

```
<213>  Artificial sequence

<220>
<223>  LSR beta probe

<400>  128
agcagccacc tcaggtgtgc caa                                          23

<210>  129
<211>  8
<212>  PRT
<213>  Homo sapiens

<400>  129

Leu Gly Gly Val Leu Glu Ala Ser
1               5
```